US011970536B2

(12) United States Patent
Champion et al.

(10) Patent No.: US 11,970,536 B2
(45) **Date of Patent: *Apr. 30, 2024**

(54) GROUP B ADENOVIRUS ENCODING AN ANTI-TCR-COMPLEX ANTIBODY OR FRAGMENT

(71) Applicant: AKAMIS BIO LIMITED, Abingdon Oxfordshire (GB)

(72) Inventors: Brian Robert Champion, Abingdon (GB); Alice Claire Noel Brown, Abingdon (GB)

(73) Assignee: AKAMIS BIO LIMITED, Abingdon (GB)

( * ) Notice: Subject to any disclaimer, the term of this patent is extended or adjusted under 35 U.S.C. 154(b) by 596 days.

This patent is subject to a terminal disclaimer.

(21) Appl. No.: 16/062,036

(22) PCT Filed: Dec. 19, 2016

(86) PCT No.: PCT/EP2016/081817

§ 371 (c)(1),
(2) Date: Jun. 13, 2018

(87) PCT Pub. No.: WO2017/103290

PCT Pub. Date: Jun. 22, 2017

(65) Prior Publication Data

US 2019/0077865 A1 Mar. 14, 2019

(30) Foreign Application Priority Data

Dec. 17, 2015 (GB) ..................................... 1522334
Apr. 29, 2016 (GB) ..................................... 1607463
Oct. 10, 2016 (GB) ..................................... 1617206
Oct. 10, 2016 (GB) ..................................... 1617207

(51) Int. Cl.

| | |
|---|---|
| ***A61K 35/761*** | (2015.01) |
| ***A61K 35/768*** | (2015.01) |
| ***A61K 38/17*** | (2006.01) |
| ***A61P 35/00*** | (2006.01) |
| ***C07K 14/00*** | (2006.01) |
| ***C07K 14/005*** | (2006.01) |
| ***C07K 14/725*** | (2006.01) |
| ***C07K 16/28*** | (2006.01) |
| ***C07K 16/30*** | (2006.01) |
| ***C12N 7/00*** | (2006.01) |
| ***C12N 15/86*** | (2006.01) |
| *A61K 39/00* | (2006.01) |

(52) U.S. Cl.

CPC ........ *C07K 16/2809* (2013.01); *A61K 35/761* (2013.01); *A61K 35/768* (2013.01); *A61K 38/1774* (2013.01); *A61P 35/00* (2018.01); *C07K 14/00* (2013.01); *C07K 14/005* (2013.01); *C07K 14/7051* (2013.01); *C07K 16/2803* (2013.01); *C07K 16/30* (2013.01); *C12N 7/00* (2013.01); *C12N 15/86* (2013.01); *A61K 2039/505* (2013.01); *C07K 2317/622* (2013.01); *C07K 2317/73* (2013.01); *C12N 2710/10032* (2013.01); *C12N 2710/10041* (2013.01)

(58) Field of Classification Search

CPC .................. C12N 15/86; C12N 15/861; C12N 2710/10032; C07K 16/2809

See application file for complete search history.

(56) References Cited

U.S. PATENT DOCUMENTS

| | | | | |
|---|---|---|---|---|
| 5,358,866 | A | 10/1994 | Mullen et al. | |
| 5,595,756 | A | 1/1997 | Bally et al. | |
| 5,631,236 | A | 5/1997 | Woo et al. | |
| 5,648,478 | A | 7/1997 | Henderson | |
| 5,677,178 | A | 10/1997 | McCormick | |
| 5,843,772 | A | 12/1998 | Devine et al. | |
| 5,972,706 | A | 10/1999 | McCormick | |
| 6,291,214 | B1 | 9/2001 | Richards et al. | |
| 6,294,377 | B1 | 9/2001 | Haddada et al. | |
| 6,420,524 | B1 | 7/2002 | Craig | |
| 7,264,958 | B1 | 9/2007 | Koehl et al. | |
| 7,288,251 | B2 | 10/2007 | Bedian et al. | |
| 7,459,153 | B2 | 12/2008 | Wadell et al. | |
| 7,550,296 | B2 | 6/2009 | Hermiston | |
| 7,858,367 | B2 | 12/2010 | Amalfitano et al. | |
| 8,052,965 | B2 | 8/2011 | Van Beusechem et al. | |
| 8,216,819 | B2 | 7/2012 | Hermiston | |
| 10,548,929 | B2 * | 2/2020 | Champion | C07K 14/523 |
| 2002/0019051 | A1 | 2/2002 | Lusky | |
| 2002/0061592 | A1 | 5/2002 | Blanche et al. | |
| 2003/0017138 | A1 | 1/2003 | Havenga et al. | |
| 2003/0044384 | A1 | 3/2003 | Roberts | |

(Continued)

FOREIGN PATENT DOCUMENTS

| | | | |
|---|---|---|---|
| AU | 2010244348 | A1 | 11/2010 |
| CA | 2244213 | A1 | 8/1997 |

(Continued)

OTHER PUBLICATIONS

International Search Report and Written Opinion for PCT International Application No. PCT/EP2016/081817 dated Mar. 31, 2017.

(Continued)

*Primary Examiner* — Nancy J Leith
*Assistant Examiner* — Khaleda B Hasan
(74) *Attorney, Agent, or Firm* — Debora Plehn-Dujowich; Eckert Seamans Cherin & Mellott, LLC

(57) ABSTRACT

The present disclosure relates to a replication deficient oncolytic viral vector or replication capable group B oncolytic adenovirus selected from the group consisting of Ad11 and enadenotucirev, wherein the virus encodes an antibody or a binding fragment thereof for expression on the surface of a cancer cell, wherein said antibody or binding fragment is specific to a CD3 protein of a T-cell receptor complex (TCR), wherein the virus does not encode a B7 protein or an active fragment thereof, pharmaceutical compositions comprising the same, and use of any one of the same in treatment, particularly in the treatment of cancer.

19 Claims, 107 Drawing Sheets

Specification includes a Sequence Listing.

(56) References Cited

U.S. PATENT DOCUMENTS

| | | | |
|---|---|---|---|
| 2003/0096787 | A1 | 5/2003 | Perricaudet et al. |
| 2004/0136958 | A1 | 7/2004 | Wadell et al. |
| 2004/0151696 | A1 | 8/2004 | Johnson et al. |
| 2004/0213764 | A1 | 10/2004 | Wold et al. |
| 2005/0175589 | A1 | 8/2005 | Iggo et al. |
| 2005/0186225 | A1 | 8/2005 | Evans et al. |
| 2006/0140909 | A1 | 6/2006 | Wickham et al. |
| 2006/0292682 | A1 | 12/2006 | Hawkins et al. |
| 2008/0069836 | A1 | 3/2008 | Nabel et al. |
| 2008/0292592 | A1 | 11/2008 | Chada et al. |
| 2009/0311219 | A1 | 12/2009 | Bonastre et al. |
| 2010/0047208 | A1 | 2/2010 | Ke |
| 2010/0297072 | A1 | 11/2010 | Depinho |
| 2011/0034560 | A1 | 2/2011 | Jacobson et al. |
| 2017/0266243 | A1 | 9/2017 | Champion et al. |
| 2018/0140649 | A1 | 5/2018 | Champion et al. |
| 2018/0311291 | A1 | 11/2018 | Champion et al. |
| 2019/0076493 | A1 | 3/2019 | Champion et al. |
| 2019/0194690 | A1 | 6/2019 | Champion et al. |
| 2019/0233536 | A1 | 8/2019 | Champion et al. |

FOREIGN PATENT DOCUMENTS

| | | | |
|---|---|---|---|
| CN | 1241632 | A | 1/2000 |
| CN | 1242051 | A | 1/2000 |
| CN | 101381742 | A | 3/2009 |
| CN | 1961961 | A | 5/2010 |
| CN | 102586327 | A | 7/2012 |
| DE | 102005055128 | A1 | 5/2007 |
| EP | 1054064 | A1 | 11/2000 |
| EP | 170269 | A1 | 5/2007 |
| JP | 2000504334 | A | 4/2000 |
| JP | 2002531133 | | 9/2002 |
| JP | 2002541792 | A | 12/2002 |
| JP | 2008500051 | A | 1/2008 |
| JP | 2008531700 | A | 8/2008 |
| JP | 2009505680 | A | 2/2009 |
| JP | 2010514418 | A | 5/2010 |
| JP | 2015526450 | A | 8/2015 |
| SE | 0100035-5 | | 1/2001 |
| WO | 1998/022609 | A1 | 5/1998 |
| WO | 1999/018799 | A1 | 4/1999 |
| WO | 2000/15823 | A1 | 3/2000 |
| WO | 00/32754 | A1 | 6/2000 |
| WO | 00/34494 | A1 | 6/2000 |
| WO | 2000061726 | A1 | 10/2000 |
| WO | 00/73478 | A3 | 12/2000 |
| WO | 01/11034 | A2 | 2/2001 |
| WO | 2001/53506 | A2 | 7/2001 |
| WO | 2001/092549 | A2 | 12/2001 |
| WO | 2001/094413 | A2 | 12/2001 |
| WO | 2002/099119 | A2 | 12/2002 |
| WO | 2003/040170 | A2 | 5/2003 |
| WO | 2003/064666 | A1 | 8/2003 |
| WO | 2005/010149 | A1 | 6/2004 |
| WO | 2004/108893 | A2 | 12/2004 |
| WO | 2005/086922 | A2 | 9/2005 |
| WO | 2005/107474 | A2 | 11/2005 |
| WO | 2005/118825 | A2 | 12/2005 |
| WO | 2006060314 | A2 | 6/2006 |
| WO | 2008/080003 | | 7/2008 |
| WO | 2006093924 | A1 | 9/2008 |
| WO | 2009/143610 | A1 | 12/2009 |
| WO | 2010/037835 | A2 | 4/2010 |
| WO | 2012/024351 | A1 | 2/2012 |
| WO | 2013/026833 | A1 | 2/2013 |
| WO | 2013/074507 | A1 | 5/2013 |
| WO | 2013164754 | A2 | 11/2013 |
| WO | 2014029702 | A1 | 2/2014 |
| WO | 2014/138314 | A1 | 9/2014 |
| WO | 2015/059303 | A1 | 4/2015 |
| WO | 2015/059465 | A1 | 4/2015 |
| WO | 2015059303 | A1 | 4/2015 |
| WO | 2015/077624 | A1 | 5/2015 |
| WO | 2015/097220 | A1 | 7/2015 |
| WO | 2015097220 | A1 | 7/2015 |
| WO | 2015153912 | A1 | 10/2015 |
| WO | 2015155370 | A1 | 10/2015 |
| WO | 2016/139463 | A1 | 9/2016 |
| WO | 2016/146894 | A1 | 9/2016 |
| WO | 2016/174200 | A1 | 11/2016 |
| WO | 2017/103290 | A1 | 6/2017 |
| WO | 2017/103291 | A1 | 6/2017 |
| WO | 2017/161360 | A2 | 9/2017 |
| WO | 2018/041827 | A1 | 3/2018 |
| WO | 2018/041838 | | 3/2018 |
| WO | 2018/075978 | A1 | 4/2018 |
| WO | 2018/083257 | A1 | 5/2018 |
| WO | 2018/083258 | A1 | 5/2018 |
| WO | 2018/083259 | A1 | 5/2018 |
| WO | 2019/043020 | A1 | 3/2019 |

OTHER PUBLICATIONS

Paul, et al., The combination of a chemokine, cytokine and TCR-based T cell stimulus for effective gene therapy of cancer, Cancer Immunol Immunother. 51(11-12) ,2002 ,645-654.

Paul, et al., Tumor gene therapy by MVA-mediated expression of T-cell-stimulating antibodies, Cancer Gene Therapy 9 ,2002 ,470-477.

Hoffmann , et al., "Efficient generation of double heterologous promoter controlled oncolytic adenovirus vectors by a single homologous recombination step in *Escherichia coli*", BMC Biotechnol. 6, Aug. 2006, 36.

Janssen , et al., "Development of an AdEasy-based system to produce first- and second-generation adenoviral vectors with tropism for CAR- or CD46-positive cells", J Gene Med. 15(1), Jan. 2013, 1-11.

Li , et al., "A one-step ligation system for rapid generation of armed, conditionally-replicating adenoviruses", Biotechnol Lett. 35, Apr. 2013, 1215-1221.

English abstract for International Publication No. WO2008080003 (corresponding to Japanese Publication No. JP2010514418).

English abstract for Publication No. US2005265973 (corresponding to Japanese Publication No. JP2008500051).

English abstract for International Publication No. WO2007027860 (corresponding to Japanese Publication No. JP2009505680).

Fisicaro et al., Versatile Co-Expression of Graft-Protective Proteins Using 2A-Linked Cassettes, Xenotransplantation (2011), 18(2):121-130.

Hemminki et al., AD3-HTERT-E1A, a Fully Serotype 3 Oncolytic Adenovirus, in Patients With Chemotherapy Refractory Cancer, Molecular Therapy (Aug. 7, 2012), 20(9):1810-1830.

Hotte et al., An Optimized Clinincal Regimen for the Oncolyticvirus PV701, Clinical Cancer Research (Feb. 1, 2007), 13(3):977-985.

Nemunaitis et al., Intravenous Infusion of a Replication-Selective Adenovirus (ONYX-015) in Cancer Patients: Safety, Feasibility and Biological Activity, Gene Therapy (2001), 8:746-759.

Small et al., A Phase I Trial of Intravenous CG7870, a Replication-Selective, Protate-Specific Antigen-Targeted Oncolytic Adenovirus, for the Treatment of Hormone-Refractory, Metastatic Prostate Cancer, Molecular Therapy (Jul. 2006), 14(1):107-117.

European Patent Office, Opposition Division, Decision Revocation of the European Patent No. EP 3007711, Feb. 21, 2023, Munich, Germany.

European Patent Office, Opposition Division, Consolidated List of Cited Opposition Documents, European Patent No. EP 3007711, Dec. 1, 2022, Munich, Germany.

Ahmed et al, Intratumoral expression of a fusogenic membrane glycoprotein enhances the efficacy of replicating adenovirus therapy, Gene Therapy (2003) vol. 10, pp. 1663-1671.

Champion, AACR 106th Annual Meeting, Abstract 295: Delivery ofcheckpoint inhibitor antibodies and other therapeutics directly to tumors by encoding them within the oncolytic adenovirus enadenotucirev, 2015, vol. 75 (15: supple), Apr. 18, 2015, A295.

Alisky et al, Gene transfer to brain and spinal cord using recombinant adenoviral vectors, Methods in Mol Biol, vol. 246, 91-120, 2004.

(56) References Cited

OTHER PUBLICATIONS

Arafat et al, Effective single chain antibody (scFv) concentrations in vivo via adenoviral vector mediated expression of secretory scFv, Gene therapy, vol. 9, 256-262 (2002).
Biery et al, A simple in vitro Tn7-based transposition system with low target site selectivity for genome and gene analysis, Nucleic acids res, 28: 1067-1077 (2000).
Cascone et al, Upregulated stromal EGFR and vascular remodelling in mouse xenograft models of angiogenesis inhibitor-resistant human lung adenocarcinoma, J. clinical invest, vol. 121, No. 4, Apr. 1, 2011, 131-1328.
Casimiro et al, Comparative immunogenicity in rhesus monkeys of DNA plasmid, recombinant vaccinia virus and replication-defective adenovirus vectors, J. Virol 77, 6305-13 (2003).
Database WPI, Week 20267 (See also CN102586327).
Mizuguchi et al, Approaches for generating recombinant adenovirus vectors, Advanced Drug Delivery Reviews, 2001, vol. 52, pp. 165-176.
Champion et al, Jul. 2016, Developing tumor-localized, combination immunotherapies, http://psioxus.com/wp-content/uploads/2016/12/AACR-Poster-Apr-2016.pdf.
Choi, K-J, et al., Concurrent delivery of GM-CSF and B7-1 using an oncolytic adenovirus elicits potent antitumor effect, Gene Ther. Jul. 2006;13(13):1010-20.
Dyer et al, Oncolytic Group B adenovirus Enadenotucirev mediates non-apoptotic cell death with membrane disruption and release of inflammatory mediators, Molecular therapy Oncolytics, vol. 4, Mar. 2017, 18-30.
Dyer A. et al, Antagonism of Glycolysis and Reductive Carboxylation of Glutamine Potentiates Activity of Oncolytic Adenoviruses in Cancer Cells, Cancer Res. 79:331, 2019.
Fajardo et al, Bi-specific T-Cell Engager-Armed oncolytic adenoviruses as a strategy to improve antitumor efficacy, Human Gene Therapy, vol. 26, No. 9, A13-A14, Sep. 2015.
Kuhn, I, et al., Human adenovirus B strain ColoAd1, complete genome, GenBank: EF011630.1.
Kuhn, I., et al., Directed evolution generates a novel oncolytic virus for the treatment of colon cancer, PLoS One. Jun. 18, 2008;3(6):e2409.
Mei et al, Comparative analysis of the genome organization of human adenovirus 11, a member of the human adenovirus species B, and the commonly used human adenovirus 5 vector, a member of species C, J Gen Virol. vol. 84, No. part 8, Aug. 2003, 2061-2071.
Freedman et al, Oncolytic adenovirus expressing bispecific antibody targets T-cell cytotoxicity in cancer biopsies, EMBO molecular med, vol. 9, No. 8, Jun. 20, 2017, 1067-1087.
Freedman J.D. et al, An Oncolytic Virus Expressing a T-cell Engager Simultaneously Targets Cancer and Immunosuppressive Stromal Cells, Cancer Res Nov. 18: 1-14, 2018.
Frentzen et al, Anti-VEGF single=chain antibody GLAF-1 encoded by oncolytic vaccinia virus significantly enhances anti-tumor therapy, Proceedings Nat Aca Sci, vol. 106, No. 31, (Aug. 4, 2009), 12915-12920.
Forrester et al, Serotype-specific inactivation of the cellular DNA damage response during adenovirus infection, J. Vir 85(5), 2011, 2201-2211.
Fountzilas et al, Review: Oncolytic virotherapy, updates and future directions, Oncotarget, vol. 8, No. 60, May 31, 2017.
Fu et al, Expression of a Fusogenic Membrane Glycoprotein by an Oncolytic Herpes Simplex Virus Potentiates the Viral Antitumor Effect, Molecular Therapy, Jun. 2003, vol. 7, No. 6, pp. 748-754.
Galanis et al, Use of Viral Fusogenic Membrane Glycoproteins as Novel Therapeutic Transgenes in Gliomas, Human Sene Therapy, 2001, vol. 12, No. 7, pp. 811-821, Abstract.
Garcia-carbonero et al, Phase I study of intravenous administration of the chimeric adenovirus enadenotucirev in patients undergoing primary tumor resection, J immunotherapy of cancer, Biomed central ltd, vol. 5, No. 19 Sep. 1-13, 2017.
Grill et al, Mol. The organotypic multicellular spheroid is a relevant three-dimensional model to study adenovirus replication and penetration in human tumors in vitro, Therapy, vol. 6, No. 5, 609-614 (2002).
Heise et al, Onyx-015, an E1B gene-attenuated adenovirus, causes tumor-specific cytolysis and antitumoral efficacy that can be augmented by standard chemotherapeutic agents, Nat Met, vol. 3, No. 6, 639-645, 1997.
Champion et al, NG-348: a novel oncolytic virus designed to mediate anti-tumour activity via the potent and selective polyclonal activation of tumor-infiltrating T-cells, Cancer research, vol. 77, No. 13, Jul. 2017.
Hermiston, a demand for next-generation oncolytic adenoviruses, Curr. Op. Mol. Therapeutics 8, 322-30, Aug. 2006.
Machiels J-P. et al, A Phase 1 Dose Escalation Study of the Oncolytic Adenovirus Enadenotucirev, Administered Intravenously to Patients with Epithelial Solid Tumors, (EVOLVE) Journal for ImmunoTherapy of Cancer 7:20, 2019.
Hermiston T., Gene delivery from replication-selective viruses: arming guided missiles in the war against cancer, J Clinical invest, vol. 105, No. 9, (May 1, 2000), 1169-1172.
Ibrahimi et al, Highly efficient multicistronic lentiviral vectors with peptide 2A sequences, Human gene therapy 20: 845-860.
Illingworth et al, Preclinical Safety Studies of Enadenotucirev, a Chimeric Group B Human-Specific Oncolytic Adenovirus, Mol Ther Oncolytics. 5:62, 2017.
Hermiston T. et al, The Discovery and Development of Selectively Replicating Adenoviruses-Anticancer Agents, J Tumor targeting 2000, vol. 4 No. 4, 218-224.
Jolly D et al, Viral vector systems for gene therapy, Cancer gene therapy, vol. 1, No. 1, (1994) 51-64.
Kanerva et al, Gene transfer to ovarian cancer vs normal tisuses with fiber-modified adenoviruses, Molecular Therapy, vol. 5 (6), 2002, 695-704.
Kleinman & Martin, Matrigel: Basement membrane matrix with biological activity, Seminars in cancer biology 15, 378-86, Oct. 1, 2005.
Lai et al, Adenovirus and adeno-associated virus vectors, DNA Cell Bio, vol. 21, No. 12, 895-913 (2002).
Kuhn et al, 319. ColoAd1, a chimeric Ad11p/Ad3 Oncolytic virus for the treatment of colon cancer, Molecular Therapy, vol. 11, Aug. 15, 2005, p. 124.
Lee et al, Replicating adenoviral vector-mediated transfer of a heat-inducible double suicide gene for gene therapy, Cancer gene therapy, vol. 8, No. 6, 397-404 (2001).
Liao et al, Stable expression of chimeric anti-CD3 receptors on mammalian cells for stimulation of anti-tumor immunity, Cancer gene therapy 10, 2003, 779-790.
Kangasniemi, Improving oncolytic adenoviral therapies for gastrointestinal cancers and tumor initiating cells, Cancer Gene Therapy Group, Jan. 1, 2010, 1-70.
Luckow et al, Efficient generation of infectious recombinant baculoviruses by site-specific transposon-mediated insertion of foreign genes into a baculovirus genome propagated in *Esherichia coli*, J. Vorl. 67: 4566-4579 (1993).
Marino et al, Development of a versatile oncolytic virus platform for local intra-tumoral expression of therapeutic transgenes, pLOS One, May 18, 2017, 1-23.
McConnell & Imperiale, Biology of adenovirus and its use as a vector for gene therapy, Human Gene therapy 1022-1033, Nov. 11, 2014.
McVey et al, Rapid construction of adenoviral vectors by lambda phage genetics, J. Virol, vol. 76, No. 8, 3670-3677 (Apr. 2002).
Meinschad & Winnacker, Recombination in adenovirus. I. Analysis of recombinant viruses under non-selective conditions, J of Gen. Virol. 1980, vol. 48, 219-224.
Francini, N. et al, Polyvalent Diazonium Polymers Provide Efficient Protection of Oncolytic Adenovirus Enadenotucirev from Neutralizing Antibodies while Maintaining Biological Activity in Vitro and in Vivo, Bioconjug Chem. 30:1244, 2019.

(56) References Cited

OTHER PUBLICATIONS

Champion, B. R., et al., Arming the chimeric oncolytic adenovirus enadenotucirev to deliver checkpoint inhibitors and other therapeutics directly to tumours, J Immunother Cancer. 2014; 2(Suppl 3): p. 46.
Dias, J. D., et al., Targeted cancer immunotherapy with oncolytic adenovirus coding for a fully human monoclonal antibody specific for CTLA-4, Gene Ther. Oct. 2012;19(10):988-98.
Chia S.L. et al, Group B adenovirus enadenotucirev infects polarised colorectal cancer cells efficiently from the basolateral surface expected to be encountered during intravenous delivery to treat disseminated cancer, Virology 505:162, 2017.
Alemany, R., Oncolytic Adenoviruses in Cancer Treatment, Biomedicines 2014, 2, 36-49.
Nemunaitis, J., et al., Intravenous infusion of a replication-selective adenovirus (ONYX-015) in cancer patients: safety, feasibility and biological activity, Gene Therapy (2001) 8, 746-759.
Hemminki, A., Oncolytic Immunotherapy: Where Are We Clinically?, Scientifica, vol. 2014, Article ID 862925, 7 pages.
Hobbs, W. E., et al., Efficient Activation of Viral Genomes by Levels of Herpes Simplex Virus ICP0 Insufficient to Affect Cellular Gene Expression or Cell Survival, Journal of Virology, Apr. 2001, p. 3391-3403.
Hu, Z-B, et al., A simplified system for generating oncolytic adenovirus vector carrying one or two transgenes, Cancer Gene Therapy vol. 15, pp. 173-182(2008).
Illingworth et al, ColoAd1 a group B oncolytic adenovirus: preclinical assessment of potency, safety and selectivity, Human gene therapy, vol. 23, No. 10, Oct. 2012, p. A19.
Jiang et al, The controlled transgene expression in oncolytic adenoviral vectors with major late promoter for therapy of cancer, Mol. Therapy 13(Supp 1), 2006, S251.
Kwon, O-J, et al., Therapeutic targeting of chitosan-PEG-folate-complexed oncolytic adenovirus for active and systemic cancer gene therapy, J Control Release, Aug. 10, 2013;169(3):257-65.
Lee, Y-S, et al., Enhanced Antitumor Effect of Oncolytic Adenovirus Expressing Interleukin-12 and B7-1 in an Immunocompetent Murine Model, Clin Cancer Res 2006;5859 12(19) Oct. 1, 2006.
Pol, J., et al., Trial Watch Oncolytic viruses for cancer therapy, OncoImmunology 3, e28694; Apr. 2014.
Pützer, B. M., et al., Improved treatment of pancreatic cancer by IL-12 and B7.1 costimulation: antitumor efficacy and immunoregulation in a nonimmunogenic tumor model, Mol Ther. Apr. 2002;5(4):405-12.
Small, E. J., A Phase I Trial of Intravenous CG7870, a Replication-Selective, Prostate-Specific Antigen-Targeted Oncolytic Adenovirus, for the Treatment of Hormone-Refractory, Metastatic Prostate Cancer, Molecular Therapy vol. 14, No. 1, Jul. 2006.
Nakashima, E., et al., A candidate for cancer gene therapy: MIP-1 alpha gene transfer to an adenocarcinoma cell line reduced tumorigenicity and induced protective immunity in immunocompetent mice, Pharm Res. Dec. 1996;13(12):1896-901.
Kaufman, H. L., et al., Oncolytic viruses: a new class of immunotherapy drugs, Nat Rev Drug Discov. Sep. 2015;14(9):642-62.
Ferrantini, M., et al., Interferon-alpha and cancer: mechanisms of action and new perspectives of clinical use, Biochimie. Jun.-Jul. 2007;89(6-7):884-93.
Carlos, A. F., et al., Bi-specific T-Cell engager-armed oncolytic adenoviruses as a strategy to improve antitumor efficacy, Human Gene, vol. 26, No. 9, Sep. 1, 2015, A13-14.
PsiOxus Therapeutics, Ltd, Press Release, PsiOxus Therapeutics to Release Study Results of Oncolytic Vaccine Enadenotucirev in Cancer Patients, Oxford, UK, Apr. 13, 2014.
Ramakrishna, E., et al., Antitumoral immune response by recruitment and expansion of dendritic cells in tumors infected with telomerase-dependent oncolytic viruses, Cancer Res. Feb. 15, 2009;69(4):1448-58.
Liao, K.W., et al., Design of transgenes for efficient expression of active chimeric proteins on mammalian cells, Biotechnol Bioeng. May 20, 2001;73(4):313-23.
Cruise & Lewis, Illustrated Dictionary of Immunology, 2nd Eddition, CRC Press, 1937.
Wüest et al, Construction of a bispecific single chain antibody for recruitment of cytotoxic T cells to the tumor stroma associated antigen fibroblast activation protein, Journal of Biotechnology 92 (2001), 159-168.
Vogels et al, Replication-deficient human adenovirus type 35 vectors for gene transfer and vaccination: efficient human cell infection and bypass of preexisting adenovirus immunity, J of Virology, vol. 77, No. 15, Aug. 2003, 8263-8271.
Reid et al, Intravascular adenoviral agents in cancer patients: lessons from clinical trials, Cancer Gene Therapy (2002), 9, 979-986.
Laurie et al, A phase 1 clinical study of intravenous administration of PV701, an oncolytic virus, using two-step desensitization, Clin Cancer Res 2006; 12(8), Apr. 15, 2006.
Hotte et al, An optimized clinical regimen for the oncolytic virus PV701, Clin Cancer Res, 2007; 13(3), Feb. 1, 2007.
Hemminki et al, Ad3-hTERT-E1A, a fully serotype 3 oncolytic adenovirus, in patients with chemotherapy refractory cancer, Molecular Therapy, vol. 20, No. 9, 1821-1830, Sep. 2012.
Nemunatitis, J., et al., Intravenous infusion of a replication-selective adenovirus (ONYX-015) in cancer patients: safety, feasibility and biological activity, Gene Therapy (2001) 8, 746-759.
Yu, F., et al., Cancer Associated Fibroblasts-Targeted Oncolytic Virus Results in Enhanced Antitumor Activity in Mouse Model, Molecular Therapy vol. 23, Supplement 1, May 2015.
Fajardo, C. A., et al., Oncolytic Adenoviral Delivery of an EGFR-Targeting T-cell Engager Improves Antitumor Efficacy, Cancer Res. Apr. 15, 2017;77(8):2052-2063.
Chang, C-M, et al., Treatment of hepatocellular carcinoma with adeno-associated virus encoding interleukin-15 superagonist, Hum Gene Ther. May 2010;21(5):611-21.
Cheng, L., et al., Hyper-IL-15 suppresses metastatic and autochthonous liver cancer by promoting tumour-specific CD8+ T cell responses, J Hepatol. Dec. 2014;61(6):1297-303.
Guo, Y., et al., Immunobiology of the IL-15/IL-15Rα complex as an antitumor and antiviral agent, Cytokine Growth Factor Rev. Dec. 2017;38:10-21.
Ni, S., et al., Evaluation of biodistribution and safety of adenovirus vectors containing group B fibers after intravenous injection into baboons, Hum Gene Ther. Jun. 2005;16(6):664-77.
Heppner, G. H., et al., Tumor heterogeneity: biological implications and therapeutic consequences, Cancer Metastasis Rev. 1983;2(1):5-23.
Sporn, M. B., et al., Chemoprevention of cancer, Carcinogenesis. Mar. 2000;21(3):525-30.
Auerbach, R., et al., Angiogenesis assays: problems and pitfalls, Cancer Metastasis Rev. 2000; 19(1-2):167-72.
Gura, T., Systems for identifying new drugs are often faulty, Science. Nov. 7, 1997;278(5340):1041-2.
Jain, R. K., Barriers to drug delivery in solid tumors, Sci Am. Jul. 1994;271(1):58-65.
Hait, W. N., Anticancer drug development: the grand challenges, Nat Rev Drug Discov. Apr. 2010;9(4):253-4.
Gravanis, I., et al., The changing world of cancer drug development: the regulatory bodies' perspective, Chin Clin Oncol. Jun. 2014;3(2):22.
Beans, C., News Feature: Targeting metastasis to halt cancer's spread, Proc Natl Acad Sci U S A. Dec. 11, 2018;115(50):12539-12543.
Mukherjee et al, Identification of EpCAM as a Molecular target of prostate cancer stroma, American J of pathology, vol. 175, No. 6, Dec. 1, 2009, 2277-2287.
Demers et al, Pharmacologic indicators of antitumor efficacy for oncolytic virotherapy, Cancer research, vol. 63, No. 14 (Jul. 15, 2003), 4003-4008.
Oorschot et al, Apoptin induces apoptosis in human transformed and malignant cells but not in normal cells, PNAS, May 1997, vol. 94, pp. 5843-5847.
Parks et al, Adenoviral vectors: prospects for gene delivery to the central nervous system, Gene Therapy, 1999, vol. 6, 1349-1350.
Boni et al, A Phase 1 Mechanism of Action Study of Intra-Tumoural (IT) or Intravenous (IV) Administration of Enadenotucirev, an

(56) References Cited

OTHER PUBLICATIONS

Oncolytic AD11/AD3 Chimeric Group B Adenovirus in Colon Cancer Patients Undergoing Resection of Primary Tumour, Annals of Oncology 25 (supplement 4): iv361-iv372, 2014.
Nettelbeck et al, Cellular genetic tools to control oncolytic adenoviruses for virotherapy of cancer, J Mol Med (2008) 86:363-377.
Di, Y., et al, Activity of a Group B Oncolytic Adenovirus (ColoAd1) in Whole Human Blood, Gene Ther. Apr. 2014;21(4):440-3.
Puthupparampil et al, Tumor growth inhibition from tumor targeted delivery of diphtheria toxin gene, Mol Therapy, 2005, vol. 11, supplement No. 1, A124.
Human Vaccines & Immunotherapeutics 8:11, 1550-1553; Nov. 2012, Unique anti-cancer agent ColoAd1 enters the clinic, www.landesbioscience.com.
Fuerer and Iggo, 5-Fluorocytosine increases the toxicity of Wnt-targeting replicating adenoviruses that express cytosine deaminase as a late gene, Gene Therapy (2004), 11, 142-151.
Rancourt et al, Conditionally replicative adenoviruses for cancer therapy, 6th delivery review 27 (1997): 67-81.
Richards et al, The Amid system: Generation of recombinant adenoviruses by Tn7-mediated transposition in *E. coli*, Biotechniques vol. 29, No. 1, 146-154 (2000).
Roshon et al, Gene trap mutagenesis of hnRNP A2/B1: a cryptic 3' splice site in the neomycin resistance gene allows continued expression of the disrupted cellular gene, BMC Genomics, vol. 4, No. 2, 1-11 (2003).
Sirena et al, The nucleotide sequence and a first generation gene transfer vector of species B human adenovirus serotype 3, Virol. 343, 283-98 (2005).
Sood et al, Functional role of matrix metalloproteinases in ovarian tumor cell plasticity, Am. J. Obstetrics Gynecol. 196, 899-909 (2004).
Stellwagan et al, Gain of function mutations in TnsC, an ATP-dependent transposition protein that activates the bacterial transposon Tn7, Genetics 145: 573-585 (1997).
Stevenson et al, Selective targeting of human cells by a chimeric adenovirus vector containing a modified fiber protein, J virol. vol. 71, No. 6, 4782-4790, (1997).
Stone, D., et al, Development and Assessment of Human Adenovirus Type 11 as a Gene Transfer Vector, J Virol. Apr. 2005;79(8):5090-104.
Tedcastle A. et al, Actin-resistant DNAse I Expression From Oncolytic Adenovirus Enadenotucirev Enhances Its Intratumoral Spread and Reduces Tumor Growth, Mol Ther. 24:796, 2014.
Thorne et al, Oncolytic virotherapy: Approaches to tumor targeting and enhancing antitumor effects, Sem oncol. 32, 537-48, Dec. 1, 2005.
Tobias et al, Novel primate-crossreactive BiTE antibodies that eliminate cancer cells expressing cMEt, IGFR-1, FAP-alpha, PSCA, Endosialin, CAIX or Her2/neu, Proceedings of annual meeting of American association for cancer res, vol. 51, p. 590.
Tollefson et al, The Adenovirus Death Protein (E3-11 6K) is Required at Very Late Stages of Infection for Efficient Cell Lysis and Release of Adenovirus from Infected Cells, Journal of Virology, Apr. 1996, vol. 70, No. 4, pp. 2296-2306.
Wang et al, High levels of EGFR expression in tumor stroma are associated with aggressive clinical features in epithelial ovarian cancer, Oncotargets and therapy, vol. 9, Jan. 19, 2016, 377-386.
Yan et al, Developing Novel Oncolytic Adenoviruses through bioselection, J Virol. vol. 77, No. 4, Feb. 2003, 2640-2650.
Plasmids 101: Multicistronic Vectors. Jan. 29, 2015, https://web.archive.org/web/20150129022727/https://blog.addgene.org/plasmids-101-multicistronic-vectors.
Gene Therapy Vaccinia Virus Vectors Explained. Feb. 1, 2015, https://web.archive.org/web/20150201083914/www.genetherapynet.com/viral-vector/vaccinia-viruses.html.
Raki, M., et al, Oncolytic Adenovirus Ad5/3-delta24 and Chemotherapy for Treatment of Orthotopic Ovarian Cancer, Gynecol Oncol Jan. 2008;108(1):166-72.
Russell, S. J., et al, Oncolytic Virotherapy, Nat Biotechnol. Jul. 10, 2012;30(7):658-70.
Vellinga, J., et al, The Adenovirus Capsid: Major Progress in Minor Proteins, J Gen Virol. Jun. 2005;86(Pt 6):1581-1588.
Jin, F., et al., Identification of Novel Insertion Sites in the Ad5 GenomeThat Utilize the Ad Splicing Machinery forTherapeutic Gene Expression, Moleculartherapy vol. 12, No. 6, Dec. 2005.
Hermiston, T.W., et al., Review Armed therapeutic viruses: Strategies and challengesto arming oncolytic viruses with therapeutic genes, Cancer Gene Therapy (2002) 9, 1022-1035.
Funston, G. M., et al., Expression of heterologous genes in oncolytic adenoviruses using picornaviral 2A sequences that trigger ribosome skipping, J Gen Virol . Feb. 2008;89(Pt2):389-396.
Lee, C. H., et al., Tumor-localized ligation of CD3 and CD28 with systemic regulatory T-cell depletion induces potent innate and adaptive antitumor responses, Clin Cancer Res . Apr. 15, 2009;15(8):2756-66.
Liao, K.W., et al., Activation of lymphocytes by anti-CD3 single-chain antibody dimers expressed on the plasma membrane of tumor cells, Gene Ther. Feb. 2000;7(4):339-47.
Garcia-Carbonero et al, ASCO Meeting library Jun. 3, 2014, A phase 1 mechanism of action study of intratumoral or intravenous administration of enadenotucirev, an oncolytic Ad11/AD3 chimeric group B adenovirus in colon cancer patients undergoing resection of primary tumor.
Stone, D., et al., The complete nucleotide sequence, genome organization, and origin of human adenovirus type 11, Virology 309 (2003) 152-165.
Holterman, L., et al., Novel Replication-Incompetent Vector Derived from Adenovirus Type 11 (Ad11) for Vaccination and Gene Therapy: Low Seroprevalence and Non-Cross-Reactivity with Ad5, Journal of Virology, Dec. 2004, p. 13207-13215.
Calvo et al, A First-in-class, a first-in-human phase I study of enadenotucirv an oncolytic Ad11/Ad3 chemeric group B adenovirus, administered intravenously in patients with metastatic epithelial tumors, Journal of Clinical Oncology vol. 32, No. 15 suppl (May 2014), abstract 3103.
Lee, Y-S, et al., Enhanced Antitumor Effect of Oncolytic Adenovirus Expressing Interleukin-12 and B7-1in an Immunocompetent Murine Model, Clin. Cancer Res 2006;12(19) Oct. 1, 2006.
Paul, S., et al., Tumor gene therapy by MVA-mediated expression of T-cell-stimulating antibodies, Cancer Gene Therapy (2002) 9, 470-477.
Raum, T. J., et al., Abstract 2434: Novel primate-crossreactive BiTE antibodies that eliminate cancer cells expressing cMet, IGFR-1, FAP-alpha, PSCA, Endosialin, CAIX or Her2/neu, AACR 101st Annual Meeting 2010—-Apr. 17-21, 2010; Washington, DC.
Yang, Z-M, et al., Anti-CD3 scFv-B7.1 fusion protein expressed on the surface of HeLa cells provokes potent T-lymphocyte activation and cytotoxicity, Biochem Cell Biol. Apr. 2007;85(2):196-202.
International Search Report and Written Opinion of PCT/EP2020/067668, dated Nov. 5, 2020.
Detergents: Triton X-100, Tween-20, and More, Jun. 10, 2020, Mater Methods 2013;3:163.
Clement, N., et al., Construction and production of oncotropic vectors, derived from MVM(p), that share reduced sequence homology with helper plasmids, Cancer Gene Ther Sep. 2002;9(9):762-70.
Shashkova, E., et al., Characterization of human adenovirus serotypes 5, 6, 11, and 35 as anticancer agents, Virology Nov. 25, 2009;394(2):311-20.
Ferguson, M., et al., Systemic delivery of oncolytic viruses: hopes and hurdles, Advances in Virology, V 2012, Article ID 805629.
Carlisle, R.C., et al., Human erythrocytes bind and inactivate type 5 adenovirus by presenting Coxsackie virus-adenovirus receptor and complement receptor 1, Blood Feb. 26, 2009;113(9):1909-18.
Chau, L.A, et al., HuM291(Nuvion), a humanized Fc receptor-nonbinding antibody against CD3, anergizes peripheral blood T cells as partial agonist of the T cell receptor, Transplantation Apr. 15, 2001;71(7):941-50.
Diehl, K-H, et al., A good practice guide to the administration of substances and removal of blood, including routes and volumes, J. Appl. Toxicol, 21, 15-23 (2001).

(56) References Cited

OTHER PUBLICATIONS

Riedmann, Human Vaccines: News, Human Vaccines & Immunotherapeutics (2012), 8(11):1550-1553.
Auerbach et al., Angiogenesis Assays; Problems and Pitfalls, Cancer and Metastasis Reviews (2000), 19:167-172.
Beans, Targeting Metastasis to Halt Cancer's Spread, PNAS (Dec. 11, 2018), 115(50):12539-12543.
Gravanis et al., TPA as a Therapeutic Target in Stroke, Expert Opin Ther Targets (Feb. 2008), 12(2):1-18.
Gura, Systems for Identifying New Drugs Are Often Faulty, Science (Nov. 7, 1997), 278:1041-1042.
Hait, Anticancer Drug Development: the Grand Challenges, Nature Reviews Drug Discovery (Apr. 2010), 9:253-254.
Jain, Barriers to Drug Delivery in Solid Tumors, Scientific American (Jul. 1994), 58-65.
Sporn et al., Chemoprevention of Cancer, Carcinogenesis (2000), 21(3):525-530.

* cited by examiner

Figure 2G ORF cassette for scFv antibody

C

D

Anti-CD3-ScFv and CD80 transgene mRNA expression by NG-348 in HCT-116 tumours

| VIRUS | TITRE (vp/mL) | INFECTIOUS TITRE (IFU/mL) | Infectivity Ratio (P:I) |
|---|---|---|---|
| EnAd (Ref 1) | 3e12 | 7.83e10 | 38.3 |
| EnAd (Ref 2) | 3e12 | 9.37e10 | 32.0 |
| NG-348 | 6.68e12 | 3.31e11 | 20.2 |

Figure 45

SEQ ID NO: 1 Muromonab-CD3 (OKT3) VH

QVQLQQSGAELARPGASVKMSCKASGYTFTRYTMHWVKQRPGQGLEWIGYINPSRGYTNYNQKFKDKAT
LTTDKSSSTAYMQLSSLTSEDSAVYYCARYYDDHYCLDYWGQGTTLTVSS

SEQ ID NO: 2 Muromonab-CD3 (OKT3) VL

DIVLTQSPAIMSASPGEKVTMTCSASSSVSYMNWYQQKSGTSPKRWIYDTSKLASGVPAHFRGSGSGTS
YSLTISGMEAEDAATYYCQQWSSNPFTFGSGTKLEINR

SEQ ID NO: 3 Muromonab –CD3 (OKT3) single chain Fv

QVQLQQSGAELARPGASVKMSCKASGYTFTRYTMHWVKQRPGQGLEWIGYINPSRGYTNYNQKFKDKAT
LTTDKSSSTAYMQLSSLTSEDSAVYYCARYYDDHYCLDYWGQGTTLTVSSGGGGSGGGGSGGGGSDIVL
TQSPAIMSASPGEKVTMTCSASSSVSYMNWYQQKSGTSPKRWIYDTSKLASGVPAHFRGSGSGTSYSLT
ISGMEAEDAATYYCQQWSSNPFTFGSGTKLEINR

SEQ ID NO: 4 Membrane anchored form of the anti-human CD3 single chain Fv

MGWSCIILFLVATATGVHSQVQLQQSGAELARPGASVKMSCKASGYTFTRYTMHWVKQRPGQGLEWIGY
INPSRGYTNYNQKFKDKATLTTDKSSSTAYMQLSSLTSEDSAVYYCARYYDDHYCLDYWGQGTTLTVSS
GGGGSGGGGSGGGGSDIVLTQSPAIMSASPGEKVTMTCSASSSVSYMNWYQQKSGTSPKRWIYDTSKLA
SGVPAHFRGSGSGTSYSLTISGMEAEDAATYYCQQWSSNPFTFGSGTKLEINRGSEQKLISEEDLNAVG
QDTQEVIVVPHSLPFKVVVISAILALVVLTIISLIILIMLWQKKPR

SEQ ID NO: 5 Membrane anchored form of anti-human CD3 single chain Fv with C-terminal V5 tag

MGWSCIILFLVATATGVHSQVQLQQSGAELARPGASVKMSCKASGYTFTRYTMHWVKQRPGQGLEWIGY
INPSRGYTNYNQKFKDKATLTTDKSSSTAYMQLSSLTSEDSAVYYCARYYDDHYCLDYWGQGTTLTVSS
GGGGSGGGGSGGGGSDIVLTQSPAIMSASPGEKVTMTCSASSSVSYMNWYQQKSGTSPKRWIYDTSKLA
SGVPAHFRGSGSGTSYSLTISGMEAEDAATYYCQQWSSNPFTFGSGTKLEINRGSEQKLISEEDLNAVG
QDTQEVIVVPHSLPFKVVVISAILALVVLTIISLIILIMLWQKKPRGSIPNPLLGLD Tag in bold

SEQ ID NO: 6 Teplizumab VH sequence

QVQLVQSGGGVVQPGRSLRLSCKASGYTFTRYTMHWVRQAPGKGLEWIGYINPSRGYTNYNQKVKDRFT
ISRDNSKNTAFLQMDSLRPEDTGVYFCARYYDDHYCLDYWGQGTPVTVSS

Figure 46

SEQ ID NO: 7 Teplizumab VL sequence

DIQMTQSPSSLSASVGDRVTITCSASSSVSYMNWYQQTPGKAPKRWIYDTSKLASGVPSRFSGSGSGTD
YTFTISSLQPEDIATYYCQQWSSNPFTFGQGTKLQITR

SEQ ID NO: 8 Teplizumab Heavy chain sequence

QVQLVQSGGGVVQPGRSLRLSCKASGYTFTRYTMHWVRQAPGKGLEWIGYINPSRGYTNYNQKVKDRFT
ISRDNSKNTAFLQMDSLRPEDTGVYFCARYYDDHYCLDYWGQGTPVTVSSASTKGPSVFPLAPSSKSTS
GGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPEAAGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPGK

SEQ ID NO: 9 Teplizumab Light Chain Sequence

DIQMTQSPSSLSASVGDRVTITCSASSSVSYMNWYQQTPGKAPKRWIYDTSKLASGVPSRFSGSGSGTD
YTFTISSLQPEDIATYYCQQWSSNPFTFGQGTKLQITRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTKS
FNRGEC

SEQ ID NO: 15 PDGFR TM Domain

AVGQDTQEVIVVPHSLPFKVVVISAILALVVLTIISLIILIMLWQKKPR

SEQ ID NO: 18 PDGFR TM Domain with N-terminal c-myc tag gsEQKLISEEDLnAVGQDTQEVIVVPHSLPFKVVVISAILALVVLTIISLIILIMLWQKKPR

Figure 47

SEQ ID NO: 19 HuVH human VH leader sequence
MGWSCIILFLVATATGVHS

SEQ ID NO. 21 EnAd Genome

TCTATCTATATAATATACCTTATAGATGGAATGGTGCCAATATGTAAATGAGGTGATTTTAAAAAGTGT
GGATCGTGTGGTGATTGGCTGTGGGGTTAACGGCTAAAAGGGGCGGTGCGACCGTGGGAAAATGACGTT
TTGTGGGGGTGGAGTTTTTTTGCAAGTTGTCGCGGGAAATGTGACGCATAAAAAGGCTTTTTTCTCACG
GAACTACTTAGTTTTCCCACGGTATTTAACAGGAAATGAGGTAGTTTTGACCGGATGCAAGTGAAAATT
GTTGATTTTCGCGCGAAAACTGAATGAGGAAGTGTTTTTCTGAATAATGTGGTATTTATGGCAGGGTGG
AGTATTTGTTCAGGGCCAGGTAGACTTTGACCCATTACGTGGAGGTTTCGATTACCGTGTTTTTTACCT
GAATTTCCGCGTACCGTGTCAAAGTCTTCTGTTTTTACGTAGGTGTCAGCTGATCGCTAGGGTATTTAT
ACCTCAGGGTTTGTGTCAAGAGGCCACTCTTGAGTGCCAGCGAGAAGAGTTTTCTCCTCTGCGCCGGCA
GTTTAATAATAAAAAAATGAGAGATTTGCGATTTCTGCCTCAGGAAATAATCTCTGCTGAGACTGGAAA
TGAAATATTGGAGCTTGTGGTGCACGCCCTGATGGGAGACGATCCGGAGCCACCTGTGCAGCTTTTTGA
GCCTCCTACGCTTCAGGAACTGTATGATTTAGAGGTAGAGGGATCGGAGGATTCTAATGAGGAAGCTGT
AAATGGCTTTTTTACCGATTCTATGCTTTTAGCTGCTAATGAAGGGTTAGAATTAGATCCGCCTTTGGA
CACTTTTGATACTCCAGGGGTAATTGTGGAAAGCGGTACAGGTGTAAGAAAATTACCTGATTTGAGTTC
CGTGGACTGTGATTTGCACTGCTATGAAGACGGGTTTCCTCCGAGTGATGAGGAGGACCATGAAAAGGA
GCAGTCCATGCAGACTGCAGCGGGTGAGGGAGTGAAGGCTGCCAATGTTGGTTTTCAGTTGGATTGCCC
GGAGCTTCCTGGACATGGCTGTAAGTCTTGTGAATTTCACAGGAAAAATACTGGAGTAAAGGAACTGTT
ATGTTCGCTTTGTTATATGAGAACGCACTGCCACTTTATTTACAGTAAGTGTGTTTAAGTTAAAATTTA
AAGGAATATGCTGTTTTTCACATGTATATTGAGTGTGAGTTTTGTGCTTCTTATTATAGGTCCTGTGTC
TGATGCTGATGAATCACCATCTCCTGATTCTACTACCTCACCTCCTGAGATTCAAGCACCTGTTCCTGT
GGACGTGCGCAAGCCCATTCCTGTGAAGCTTAAGCCTGGGAAACGTCCAGCAGTGGAAAAACTTGAGGA
CTTGTTACAGGGTGGGGACGGACCTTTGGACTTGAGTACACGGAAACGTCCAAGACAATAAGTGTTCCA
TATCCGTGTTTACTTAAGGTGACGTCAATATTTGTGTGACAGTGCAATGTAATAAAAATATGTTAACTG
TTCACTGGTTTTTATTGCTTTTTGGGCGGGGACTCAGGTATATAAGTAGAAGCAGACCTGTGTGGTTAG
CTCATAGGAGCTGGCTTTCATCCATGGAGGTTTGGGCCATTTTGGAAGACCTTAGGAAGACTAGGCAAC
TGTTAGAGAACGCTTCGGACGGAGTCTCCGGTTTTTGGAGATTCTGGTTCGCTAGTGAATTAGCTAGGG
TAGTTTTTAGGATAAAACAGGACTATAAACAAGAATTTGAAAAGTTGTTGGTAGATTGCCCAGGACTTT
TTGAAGCTCTTAATTTGGGCCATCAGGTTCACTTTAAAGAAAAAGTTTTATCAGTTTTAGACTTTTCAA
CCCCAGGTAGAACTGCTGCTGCTGTGGCTTTTCTTACTTTTATATTAGATAAATGGATCCCGCAGACTC
ATTTCAGCAGGGGATACGTTTTGGATTTCATAGCCACAGCATTGTGGAGAACATGGAAGGTTCGCAAGA
TGAGGACAATCTTAGGTTACTGGCCAGTGCAGCCTTTGGGTGTAGCGGGAATCCTGAGGCATCCACCGG
TCATGCCAGCGGTTCTGGAGGAGGAACAGCAAGAGGACAACCCGAGAGCCGGCCTGGACCCTCCAGTGG
AGGAGGCGGAGTAGCTGACTTGTCTCCTGAACTGCAACGGGTGCTTACTGGATCTACGTCCACTGGACG
GGATAGGGGCGTTAAGAGGGAGAGGGCATCTAGTGGTACTGATGCTAGATCTGAGTTGGCTTTAAGTTT
AATGAGTCGCAGACGTCCTGAAACCATTTGGTGGCATGAGGTTCAGAAAGAGGGAAGGGATGAAGTTTC
TGTATTGCAGGAGAAATATTCACTGGAACAGGTGAAAACATGTTGGTTGGAGCCTGAGGATGATTGGGA
GGTGGCCATTAAAAATTATGCCAAGATAGCTTTGAGGCCTGATAAACAGTATAAGATTACTAGACGGAT
TAATATCCGGAATGCTTGTTACATATCTGGAAATGGGGCTGAGGTGGTAATAGATACTCAAGACAAGGC
AGTTATTAGATGCTGCATGATGGATATGTGGCCTGGGGTAGTCGGTATGGAAGCAGTAACTTTTGTAAA
TGTTAAGTTTAGGGGAGATGGTTATAATGGAATAGTGTTTATGGCCAATACCAAACTTATATTGCATGG
TTGTAGCTTTTTTGGTTTCAACAATACCTGTGTAGATGCCTGGGGACAGGTTAGTGTACGGGGATGTAG
TTTCTATGCGTGTTGGATTGCCACAGCTGGCAGAACCAAGAGTCAATTGTCTCTGAAGAAATGCATATT
TCAAAGATGTAACCTGGGCATTCTGAATGAAGGCGAAGCAAGGGTCCGCCACTGCGCTTCTACAGATAC
TGGATGTTTTATTTTGATTAAGGGAAATGCCAGCGTAAAGCATAACATGATTTGCGGTGCTTCCGATGA
GAGGCCTTATCAAATGCTCACTTGTGCTGGTGGGCATTGTAATATGCTGGCTACTGTGCATATTGTTTC
CCATCAACGCAAAAAATGGCCTGTTTTTGATCACAATGTGATGACGAAGTGTACCATGCATGCAGGTGG
GCGTAGAGGAATGTTTATGCCTTACCAGTGTAACATGAATCATGTGAAAGTGTTGTTGGAACCAGATGC
CTTTTCCAGAATGAGCCTAACAGGAATTTTTGACATGAACATGCAAATCTGGAAGATCCTGAGGTATGA

Figure 47 (continued)

TGATACGAGATCGAGGGTACGCGCATGCGAATGCGGAGGCAAGCATGCCAGGTTCCAGCCGGTGTGTGT
AGATGTGACTGAAGATCTCAGACCGGATCATTTGGTTATTGCCCGCACTGGAGCAGAGTTCGGATCCAG
TGGAGAAGAAACTGACTAAGGTGAGTATTGGGAAAACTTTGGGGTGGGATTTTCAGATGGACAGATTGA
GTAAAAATTTGTTTTTTCTGTCTTGCAGCTGTCATGAGTGGAAACGCTTCTTTTAAGGGGGGAGTCTTC
AGCCCTTATCTGACAGGGCGTCTCCCATCCTGGGCAGGAGTTCGTCAGAATGTTATGGGATCTACTGTG
GATGGAAGACCCGTCCAACCCGCCAATTCTTCAACGCTGACCTATGCTACTTTAAGTTCTTCACCTTTG
GACGCAGCTGCAGCTGCCGCCGCCGCTTCTGTTGCCGCTAACACTGTGCTTGGAATGGGTTACTATGGA
AGCATCATGGCTAATTCCACTTCCTCTAATAACCCTTCTACCCTGACTCAGGACAAGTTACTTGTCCTT
TTGGCCCAGCTGGAGGCTTTGACCCAACGTCTGGGTGAACTTTCTCAGCAGGTGGTCGAGTTGCGAGTA
CAAACTGAGTCTGCTGTCGGCACGGCAAAGTCTAAATAAAAAAATCCCAGAATCAATGAATAAATAAAC
AAGCTTGTTGTTGATTTAAAATCAAGTGTTTTTATTTCATTTTTCGCGCACGGTATGCCCTAGACCACC
GATCTCTATCATTGAGAACTCGGTGGATTTTTTCCAGGATCCTATAGAGGTGGGATTGAATGTTTAGAT
ACATGGGCATTAGGCCGTCTTTGGGGTGGAGATAGCTCCATTGAAGGGATTCATGCTCCGGGGTAGTGT
TGTAAATCACCCAGTCATAACAAGGTCGCAGTGCATGGTGTTGCACAATATCTTTTAGAAGTAGGCTGA
TTGCCACAGATAAGCCCTTGGTGTAGGTGTTTACAAACCGGTTGAGCTGGGATGGGTGCATTCGGGGTG
AAATTATGTGCATTTTGGATTGGATTTTTAAGTTGGCAATATTGCCGCCAAGATCCCGTCTTGGGTTCA
TGTTATGAAGGACCACCAAGACGGTGTATCCGGTACATTTAGGAAATTTATCGTGCAGCTTGGATGGAA
AAGCGTGGAAAAATTTGGAGACACCCTTGTGTCCTCCAAGATTTTCCATGCACTCATCCATGATAATAG
CAATGGGGCCGTGGGCAGCGGCGCGGGCAAACACGTTCCGTGGGTCTGACACATCATAGTTATGTTCCT
GAGTTAAATCATCATAAGCCATTTTAATGAATTTGGGGCGGAGAGTACCAGATTGGGGTATGAATGTTC
CTTCGGGCCCCGGAGCATAGTTCCCCTCACAGATTTGCATTTCCCAAGCTTTCAGTTCCGAGGGTGGAA
TCATGTCCACCTGGGGGGCTATGAAAAACACCGTTTCTGGGGCGGGGGTGATTAATTGTGATGATAGCA
AATTTCTGAGCAATTGAGATTTGCCACATCCGGTGGGGCCATAAATGATTCCGATTACGGGTTGCAGGT
GGTAGTTTAGGGAACGGCAACTGCCGTCTTCTCGAAGCAAGGGGGCCACCTCGTTCATCATTTCCCTTA
CATGCATATTTTCCCGCACCAAATCCATTAGGAGGCGCTCTCCTCCTAGTGATAGAAGTTCTTGTAGTG
AGGAAAAGTTTTTCAGCGGTTTCAGACCGTCAGCCATGGGCATTTTGGAGAGAGTTTGCTGCAAAAGTT
CTAGTCTGTTCCACAGTTCAGTGATGTGTTCTATGGCATCTCGATCCAGCAGACCTCCTCGTTTCGCGG
GTTTGGACGGCTCCTGGAATAGGGTATGAGACGATGGGCGTCCAGCGCTGCCAGGGTTCGGTCCTTCCA
GGGTCTCAGTGTTCGAGTCAGGGTTGTTTCCGTCACAGTGAAGGGGTGTGCGCCTGCTTGGGCGCTTGC
CAGGGTGCGCTTCAGACTCATCCTGCTGGTCGAAAACTTCTGTCGCTTGGCGCCCTGTATGTCGGCCAA
GTAGCAGTTTACCATGAGTTCGTAGTTGAGCGCCTCGGCTGCGTGGCCTTTGGCGCGGAGCTTACCTTT
GGAAGTTTTCTTGCATACCGGGCAGTATAGGCATTTCAGCGCATACAACTTGGGCGCAAGGAAAACGGA
TTCTGGGGAGTATGCATCTGCGCCGCAGGAGGCGCAAACAGTTTCACATTCCACCAGCCAGGTTAAATC
CGGTTCATTGGGGTCAAAAACAAGTTTTCCGCCATATTTTTTGATGCGTTTCTTACCTTTGGTCTCCAT
GAGTTCGTGTCCTCGTTGAGTGACAAACAGGCTGTCCGTGTCCCCGTAGACTGATTTTACAGGCCTCTT
CTCCAGTGGAGTGCCTCGGTCTTCTTCGTACAGGAACTCTGACCACTCTGATACAAAGGCGCGCGTCCA
GGCCAGCACAAAGGAGGCTATGTGGGAGGGGTAGCGATCGTTGTCAACCAGGGGGTCCACCTTTTCCAA
AGTATGCAAACACATGTCACCCTCTTCAACATCCAGGAATGTGATTGGCTTGTAGGTGTATTTCACGTG
ACCTGGGGTCCCCGCTGGGGGGGTATAAAAGGGGGCGGTTCTTTGCTCTTCCTCACTGTCTTCCGGATC
GCTGTCCAGGAACGTCAGCTGTTGGGGTAGGTATTCCCTCTCGAAGGCGGGCATGACCTCTGCACTCAG
GTTGTCAGTTTCTAAGAACGAGGAGGATTTGATATTGACAGTGCCGGTTGAGATGCCTTTCATGAGGTT
TTCGTCCATCTGGTCAGAAAACACAATTTTTTTATTGTCAAGTTTGGTGGCAAATGATCCATACAGGGC
GTTGGATAAAAGTTTGGCAATGGATCGCATGGTTTGGTTCTTTTCCTTGTCCGCGCGCTCTTTGGCGGC
GATGTTGAGTTGGACATACTCGCGTGCCAGGCACTTCCATTCGGGGAAGATAGTTGTTAATTCATCTGG
CACGATTCTCACTTGCCACCCTCGATTATGCAAGGTAATTAAATCCACACTGGTGGCCACCTCGCCTCG
AAGGGGTTCATTGGTCCAACAGAGCCTACCTCCTTTCCTAGAACAGAAAGGGGGAAGTGGGTCTAGCAT
AAGTTCATCGGGAGGGTCTGCATCCATGGTAAAGATTCCCGGAAGTAAATCCTTATCAAAATAGCTGAT
GGGAGTGGGGTCATCTAAGGCCATTTGCCATTCTCGAGCTGCCAGTGCGCGCTCATATGGGTTAAGGGG
ACTGCCCCATGGCATGGGATGGGTGAGTGCAGAGGCATACATGCCACAGATGTCATAGACGTAGATGGG
ATCCTCAAAGATGCCTATGTAGGTTGGATAGCATCGCCCCCCTCTGATACTTGCTCGCACATAGTCATA
TAGTTCATGTGATGGCGCTAGCAGCCCCGGACCCAAGTTGGTGCGATTGGGTTTTTCTGTTCTGTAGAC

Figure 47 (continued)

GATCTGGCGAAAGATGGCGTGAGAATTGGAAGAGATGGTGGGTCTTTGAAAAATGTTGAAATGGGCATG
AGGTAGACCTACAGAGTCTCTGACAAAGTGGGCATAAGATTCTTGAAGCTTGGTTACCAGTTCGGCGGT
GACAAGTACGTCTAGGGCGCAGTAGTCAAGTGTTTCTTGAATGATGTCATAACCTGGTTGGTTTTTCTT
TTCCCACAGTTCGCGGTTGAGAAGGTATTCTTCGCGATCCTTCCAGTACTCTTCTAGCGGAAACCCGTC
TTTGTCTGCACGGTAAGATCCTAGCATGTAGAACTGATTAACTGCCTTGTAAGGGCAGCAGCCCTTCTC
TACGGGTAGAGAGTATGCTTGAGCAGCTTTTCGTAGCGAAGCGTGAGTAAGGGCAAAGGTGTCTCTGAC
CATGACTTTGAGGAATTGGTATTTGAAGTCGATGTCGTCACAGGCTCCCTGTTCCCAGAGTTGGAAGTC
TACCCGTTTCTTGTAGGCGGGGTTGGGCAAAGCGAAAGTAACATCATTGAAGAGAATCTTGCCGGCCCT
GGGCATGAAATTGCGAGTGATGCGAAAAGGCTGTGGTACTTCCGCTCGGTTATTGATAACCTGGGCAGC
TAGGACGATCTCGTCGAAACCGTTGATGTTGTGTCCTACGATGTATAATTCTATGAAACGCGGCGTGCC
TCTGACGTGAGGTAGCTTACTGAGCTCATCAAAGGTTAGGTCTGTGGGGTCAGATAAGGCGTAGTGTTC
GAGAGCCCATTCGTGCAGGTGAGGATTCGCTTTAAGGAAGGAGGACCAGAGGTCCACTGCCAGTGCTGT
TTGTAACTGGTCCCGGTACTGACGAAAATGCCGTCCGACTGCCATTTTTTCTGGGGTGACGCAATAGAA
GGTTTGGGGGTCCTGCCGCCAGCGATCCCACTTGAGTTTTATGGCGAGGTCATAGGCGATGTTGACGAG
CCGCTGGTCTCCAGAGAGTTTCATGACCAGCATGAAGGGGATTAGCTGCTTGCCAAAGGACCCCATCCA
GGTGTAGGTTTCCACATCGTAGGTGAGAAAGAGCCTTTCTGTGCGAGGATGAGAGCCAATCGGGAAGAA
CTGGATCTCCTGCCACCAGTTGGAGGAATGGCTGTTGATGTGATGGAAGTAGAACTCCCTGCGACGCGC
CGAGCATTCATGCTTGTGCTTGTACAGACGGCCGCAGTAGTCGCAGCGTTGCACGGGTTGTATCTCGTG
AATGAGTTGTACCTGGCTTCCCTTGACGAGAAATTTCAGTGGGAAGCCGAGGCCTGGCGATTGTATCTC
GTGCTTTACTATGTTGTCTGCATCGGCCTGTTCATCTTCTGTCTCGATGGTGGTCATGCTGACGAGCCC
TCGCGGGAGGCAAGTCCAGACCTCGGCGCGGCAGGGGCGGAGCTCGAGGACGAGAGCGCGCAGGCTGGA
GCTGTCCAGGGTCCTGAGACGCTGCGGACTCAGGTTAGTAGGCAGTGTCAGGAGATTAACTTGCATGAT
CTTTTGGAGGGCGTGCGGGAGGTTCAGATAGTACTTGATCTCAACGGGTCCGTTGGTGGAGATGTCGAT
GGCTTGCAGGGTTCCGTGTCCCTTGGGCGCTACCACCGTGCCCTTGTTTTTCATTTTGGACGGCGGTGG
CTCTGTTGCTTCTTGCATGTTTAGAAGCGGTGTCGAGGGCGCGCACCGGGCGGCAGGGGCGGCTCGGGA
CCCGGCGGCATGGCTGGCAGTGGTACGTCGGCGCCGCGCGCGGGTAGGTTCTGGTACTGCGCCCTGAGA
AGACTCGCATGCGCGACGACGCGGCGGTTGACATCCTGGATCTGACGCCTCTGGGTGAAAGCTACCGGC
CCCGTGAGCTTGAACCTGAAAGAGAGTTCAACAGAATCAATCTCGGTATCGTTGACGGCGGCTTGCCTA
AGGATTTCTTGCACGTCACCAGAGTTGTCCTGGTAGGCGATCTCCGCCATGAACTGCTCGATCTCTTCC
TCTTGAAGATCTCCGCGGCCCGCTCTCTCGACGGTGGCCGCGAGGTCGTTGGAGATGCGCCCAATGAGT
TGAGAGAATGCATTCATGCCCGCCTCGTTCCAGACGCGGCTGTAGACCACGGCCCCCACGGGATCTCTC
GCGCGCATGACCACCTGGGCGAGGTTGAGCTCCACGTGGCGGGTGAAGACCGCATAGTTGCATAGGCGC
TGGAAAAGGTAGTTGAGTGTGGTGGCGATGTGCTCGGTGACGAAGAAATACATGATCCATCGTCTCAGC
GGCATCTCGCTGACATCGCCCAGAGCTTCCAAGCGCTCCATGGCCTCGTAGAAGTCCACGGCAAAATTA
AAAAACTGGGAGTTTCGCGCGGACACGGTCAACTCCTCTTCCAGAAGACGGATAAGTTCGGCGATGGTG
GTGCGCACCTCGCGCTCGAAAGCCCCTGGGATTTCTTCCTCAATCTCTTCTTCTTCCACTAACATCTCT
TCCTCTTCAGGTGGGGCTGCAGGAGGAGGGGGAACGCGGCGACGCCGGCGGCGCACGGGCAGACGGTCG
ATGAATCTTTCAATGACCTCTCCGCGGCGGCGGCGCATGGTTTCAGTGACGGCGCGGCCGTTCTCGCGC
GGTCGCAGAGTAAAAACACCGCCGCGCATCTCCTTAAAGTGGTGACTGGGAGGTTCTCCGTTTGGGAGG
GAGAGGGCGCTGATTATACATTTTATTAATTGGCCCGTAGGGACTGCACGCAGAGATCTGATCGTGTCA
AGATCCACGGGATCTGAAAACCTTTCGACGAAAGCGTCTAACCAGTCACAGTCACAAGGTAGGCTGAGT
ACGGCTTCTTGTGGGCGGGGGTGGTTATGTGTTCGGTCTGGGTCTTCTGTTTCTTCTTCATCTCGGGAA
GGTGAGACGATGCTGCTGGTGATGAAATTAAAGTAGGCAGTTCTAAGACGGCGGATGGTGGCGAGGAGC
ACCAGGTCTTTGGGTCCGGCTTGCTGGATACGCAGGCGATTGGCCATTCCCCAAGCATTATCCTGACAT
CTAGCAAGATCTTTGTAGTAGTCTTGCATGAGCCGTTCTACGGGCACTTCTTCCTCACCCGTTCTGCCA
TGCATACGTGTGAGTCCAAATCCGCGCATTGGTTGTACCAGTGCCAAGTCAGCTACGACTCTTTCGGCG
AGGATGGCTTGCTGTACTTGGGTAAGGGTGGCTTGAAAGTCATCAAAATCCACAAAGCGGTGGTAAGCT
CCTGTATTAATGGTGTAAGCACAGTTGGCCATGACTGACCAGTTAACTGTCTGGTGACCAGGGCGCACG
AGCTCGGTGTATTTAAGGCGCGAATAGGCGCGGGTGTCAAAGATGTAATCGTTGCAGGTGCGCACCAGA
TACTGGTACCCTATAAGAAAATGCGGCGGTGGTTGGCGGTAGAGAGGCCATCGTTCTGTAGCTGGAGCG
CCAGGGGCGAGGTCTTCCAACATAAGGCGGTGATAGCCGTAGATGTACCTGGACATCCAGGTGATTCCT

Figure 47 (continued)

GCGGCGGTAGTAGAAGCCCGAGGAAACTCGCGTACGCGGTTCCAAATGTTGCGTAGCGGCATGAAGTAG
TTCATTGTAGGCACGGTTTGACCAGTGAGGCGCGCGCAGTCATTGATGCTCTATAGACACGGAGAAAAT
GAAAGCGTTCAGCGACTCGACTCCGTAGCCTGGAGGAACGTGAACGGGTTGGGTCGCGGTGTACCCCGG
TTCGAGACTTGTACTCGAGCCGGCCGGAGCCGCGGCTAACGTGGTATTGGCACTCCCGTCTCGACCCAG
CCTACAAAAATCCAGGATACGGAATCGAGTCGTTTTGCTGGTTTCCGAATGGCAGGGAAGTGAGTCCTA
TTTTTTTTTTTTGCCGCTCAGATGCATCCCGTGCTGCGACAGATGCGCCCCCAACAACAGCCCCCCTCG
CAGCAGCAGCAGCAGCAATCACAAAAGGCTGTCCCTGCAACTACTGCAACTGCCGCCGTGAGCGGTGCG
GGACAGCCCGCCTATGATCTGGACTTGGAAGAGGGCGAAGGACTGGCACGTCTAGGTGCGCCTTCACCC
GAGCGGCATCCGCGAGTTCAACTGAAAAAAGATTCTCGCGAGGCGTATGTGCCCCAACAGAACCTATTT
AGAGACAGAAGCGGCGAGGAGCCGGAGGAGATGCGAGCTTCCCGCTTTAACGCGGGTCGTGAGCTGCGT
CACGGTTTGGACCGAAGACGAGTGTTGCGGGACGAGGATTTCGAAGTTGATGAAATGACAGGGATCAGT
CCTGCCAGGGCACACGTGGCTGCAGCCAACCTTGTATCGGCTTACGAGCAGACAGTAAAGGAAGAGCGT
AACTTCCAAAAGTCTTTTAATAATCATGTGCGAACCCTGATTGCCCGCGAAGAAGTTACCCTTGGTTTG
ATGCATTTGTGGGATTTGATGGAAGCTATCATTCAGAACCCTACTAGCAAACCTCTGACCGCCCAGCTG
TTTCTGGTGGTGCAACACAGCAGAGACAATGAGGCTTTCAGAGAGGCGCTGCTGAACATCACCGAACCC
GAGGGGAGATGGTTGTATGATCTTATCAACATTCTACAGAGTATCATAGTGCAGGAGCGGAGCCTGGGC
CTGGCCGAGAAGGTGGCTGCCATCAATTACTCGGTTTTGAGCTTGGGAAAATATTACGCTCGCAAAATC
TACAAGACTCCATACGTTCCCATAGACAAGGAGGTGAAGATAGATGGGTTCTACATGCGCATGACGCTC
AAGGTCTTGACCCTGAGCGATGATCTTGGGGTGTATCGCAATGACAGAATGCATCGCGCGGTTAGCGCC
AGCAGGAGGCGCGAGTTAAGCGACAGGGAACTGATGCACAGTTTGCAAAGAGCTCTGACTGGAGCTGGA
ACCGAGGGTGAGAATTACTTCGACATGGGAGCTGACTTGCAGTGGCAGCCTAGTCGCAGGGCTCTGAGC
GCCGCGACGGCAGGATGTGAGCTTCCTTACATAGAAGAGGCGGATGAAGGCGAGGAGGAAGAGGGCGAG
TACTTGGAAGACTGATGGCACAACCCGTGTTTTTTGCTAGATGGAACAGCAAGCACCGGATCCCGCAAT
GCGGGCGGCGCTGCAGAGCCAGCCGTCCGGCATTAACTCCTCGGACGATTGGACCCAGGCCATGCAACG
TATCATGGCGTTGACGACTCGCAACCCCGAAGCCTTTAGACAGCAACCCCAGGCCAACCGTCTATCGGC
CATCATGGAAGCTGTAGTGCCTTCCCGCTCTAATCCCACTCATGAGAAGGTCCTGGCCATCGTGAACGC
GTTGGTGGAGAACAAAGCTATTCGTCCAGATGAGGCCGGACTGGTATACAACGCTCTCTTAGAACGCGT
GGCTCGCTACAACAGTAGCAATGTGCAAACCAATTTGGACCGTATGATAACAGATGTACGCGAAGCCGT
GTCTCAGCGCGAAAGGTTCCAGCGTGATGCCAACCTGGGTTCGCTGGTGGCGTTAAATGCTTTCTTGAG
TACTCAGCCTGCTAATGTGCCGCGTGGTCAACAGGATTATACTAACTTTTTAAGTGCTTTGAGACTGAT
GGTATCAGAAGTACCTCAGAGCGAAGTGTATCAGTCCGGTCCTGATTACTTCTTTCAGACTAGCAGACA
GGGCTTGCAGACGGTAAATCTGAGCCAAGCTTTTAAAAACCTTAAAGGTTTGTGGGGAGTGCATGCCCC
GGTAGGAGAAAGAGCAACCGTGTCTAGCTTGTTAACTCCGAACTCCCGCCTATTATTACTGTTGGTAGC
TCCTTTCACCGACAGCGGTAGCATCGACCGTAATTCCTATTTGGGTTACCTACTAAACCTGTATCGCGA
AGCCATAGGGCAAAGTCAGGTGGACGAGCAGACCTATCAAGAAATTACCCAAGTCAGTCGCGCTTTGGG
ACAGGAAGACACTGGCAGTTTGGAAGCCACTCTGAACTTCTTGCTTACCAATCGGTCTCAAAAGATCCC
TCCTCAATATGCTCTTACTGCGGAGGAGGAGAGGATCCTTAGATATGTGCAGCAGAGCGTGGGATTGTT
TCTGATGCAAGAGGGGGCAACTCCGACTGCAGCACTGGACATGACAGCGCGAAATATGGAGCCCAGCAT
GTATGCCAGTAACCGACCTTTCATTAACAAACTGCTGGACTACTTGCACAGAGCTGCCGCTATGAACTC
TGATTATTTCACCAATGCCATCTTAAACCCGCACTGGCTGCCCCCACCTGGTTTCTACACGGGCGAATA
TGACATGCCCGACCCTAATGACGGATTTCTGTGGGACGACGTGGACAGCGATGTTTTTTCACCTCTTTC
TGATCATCGCACGTGGAAAAAGGAAGGCGGCGATAGAATGCATTCTTCTGCATCGCTGTCCGGGGTCAT
GGGTGCTACCGCGGCTGAGCCCGAGTCTGCAAGTCCTTTTCCTAGTCTACCCTTTTCTCTACACAGTGT
ACGTAGCAGCGAAGTGGGTAGAATAAGTCGCCCGAGTTTAATGGGCGAAGAGGAGTATCTAAACGATTC
CTTGCTCAGACCGGCAAGAGAAAAAAATTTCCCAAACAATGGAATAGAAAGTTTGGTGGATAAAATGAG
TAGATGGAAGACTTATGCTCAGGATCACAGAGACGAGCCTGGGATCATGGGGATTACAAGTAGAGCGAG
CCGTAGACGCCAGCGCCATGACAGACAGAGGGGTCTTGTGTGGGACGATGAGGATTCGGCCGATGATAG
CAGCGTGCTGGACTTGGGTGGGAGAGGAAGGGGCAACCCGTTTGCTCATTTGCGCCCTCGCTTGGGTGG
TATGTTGTAAAAAAAAATAAAAAAAAAACTCACCAAGGCCATGGCGACGAGCGTACGTTCGTTCTTCTT
TATTATCTGTGTCTAGTATAATGAGGCGAGTCGTGCTAGGCGGAGCGGTGGTGTATCCGGAGGGTCCTC
CTCCTTCGTACGAGAGCGTGATGCAGCAGCAGCAGGCGACGGCGGTGATGCAATCCCCACTGGAGGCTC

Figure 47 (continued)

CCTTTGTGCCTCCGCGATACCTGGCACCTACGGAGGGCAGAAACAGCATTCGTTATTCGGAACTGGCAC
CTCAGTACGATACCACCAGGTTGTATCTGGTGGACAACAAGTCGGCGGACATTGCTTCTCTGAACTATC
AGAATGACCACAGCAACTTCTTGACCACGGTGGTGCAAAACAATGACTTTACCCCTACGGAAGCCAGCA
CCCAGACCATTAACTTTGATGAACGATCGCGGTGGGGCGGTCAGCTAAAGACCATCATGCATACTAACA
TGCCAAACGTGAACGAGTATATGTTTAGTAACAAGTTCAAAGCGCGTGTGATGGTGTCCAGAAAACCTC
CCGACGGTGCTGCAGTTGGGGATACTTATGATCACAAGCAGGATATTTTGAAATATGAGTGGTTCGAGT
TTACTTTGCCAGAAGGCAACTTTTCAGTTACTATGACTATTGATTTGATGAACAATGCCATCATAGATA
ATTACTTGAAAGTGGGTAGACAGAATGGAGTGCTTGAAAGTGACATTGGTGTTAAGTTCGACACCAGGA
ACTTCAAGCTGGGATGGGATCCCGAAACCAAGTTGATCATGCCTGGAGTGTATACGTATGAAGCCTTCC
ATCCTGACATTGTCTTACTGCCTGGCTGCGGAGTGGATTTTACCGAGAGTCGTTTGAGCAACCTTCTTG
GTATCAGAAAAAAACAGCCATTTCAAGAGGGTTTTAAGATTTTGTATGAAGATTTAGAAGGTGGTAATA
TTCCGGCCCTCTTGGATGTAGATGCCTATGAGAACAGTAAGAAAGAACAAAAAGCCAAAATAGAAGCTG
CTACAGCTGCTGCAGAAGCTAAGGCAAACATAGTTGCCAGCGACTCTACAAGGGTTGCTAACGCTGGAG
AGGTCAGAGGAGACAATTTTGCGCCAACACCTGTTCCGACTGCAGAATCATTATTGGCCGATGTGTCTG
AAGGAACGGACGTGAAACTCACTATTCAACCTGTAGAAAAAGATAGTAAGAATAGAAGCTATAATGTGT
TGGAAGACAAAATCAACACAGCCTATCGCAGTTGGTATCTTTCGTACAATTATGGCGATCCCGAAAAAG
GAGTGCGTTCCTGGACATTGCTCACCACCTCAGATGTCACCTGCGGAGCAGAGCAGGTCTACTGGTCGC
TTCCAGACATGATGAAGGATCCTGTCACTTTCCGCTCCACTAGACAAGTCAGTAACTACCCTGTGGTGG
GTGCAGAGCTTATGCCCGTCTTCTCAAAGAGCTTCTACAACGAACAAGCTGTGTACTCCCAGCAGCTCC
GCCAGTCCACCTCGCTTACGCACGTCTTCAACCGCTTTCCTGAGAACCAGATTTTAATCCGTCCGCCGG
CGCCCACCATTACCACCGTCAGTGAAAACGTTCCTGCTCTCACAGATCACGGGACCCTGCCGTTGCGCA
GCAGTATCCGGGGAGTCCAACGTGTGACCGTTACTGACGCCAGACGCCGCACCTGTCCCTACGTGTACA
AGGCACTGGGCATAGTCGCACCGCGCGTCCTTTCAAGCCGCACTTTCTAAAAAAAAAAAAAAATGTCCAT
TCTTATCTCGCCCAGTAATAACACCGGTTGGGGTCTGCGCGCTCCAAGCAAGATGTACGGAGGCGCACG
CAAACGTTCTACCCAACATCCTGTCCGTGTTCGCGGACATTTTCGCGCTCCATGGGGCGCCCTCAAGGG
CCGCACTCGCGTTCGAACCACCGTCGATGATGTAATCGATCAGGTGGTTGCCGACGCCCGTAATTATAC
TCCTACTGCGCCTACATCTACTGTGGATGCAGTTATTGACAGTGTAGTGGCTGACGCTCGCAACTATGC
TCGACGTAAGAGCCGGCGAAGGCGCATTGCCAGACGCCACCGAGCTACCACTGCCATGCGAGCCGCAAG
AGCTCTGCTACGAAGAGCTAGACGCGTGGGGCGAAGAGCCATGCTTAGGGCGGCCAGACGTGCAGCTTC
GGGCGCCAGCGCCGGCAGGTCCCGCAGGCAAGCAGCCGCTGTCGCAGCGGCGACTATTGCCGACATGGC
CCAATCGCGAAGAGGCAATGTATACTGGGTGCGTGACGCTGCCACCGGTCAACGTGTACCCGTGCGCAC
CCGTCCCCCTCGCACTTAGAAGATACTGAGCAGTCTCCGATGTTGTGTCCCAGCGGCGAGGATGTCCAA
GCGCAAATACAAGGAAGAAATGCTGCAGGTTATCGCACCTGAAGTCTACGGCCAACCGTTGAAGGATGA
AAAAAAACCCCGCAAAATCAAGCGGGTTAAAAAGGACAAAAAAGAAGAGGAAGATGGCGATGATGGGCT
GGCGGAGTTTGTGCGCGAGTTTGCCCCACGGCGACGCGTGCAATGGCGTGGGCGCAAAGTTCGACATGT
GTTGAGACCTGGAACTTCGGTGGTCTTTACACCCGGCGAGCGTTCAAGCGCTACTTTTAAGCGTTCCTA
TGATGAGGTGTACGGGGATGATGATATTCTTGAGCAGGCGGCTGACCGATTAGGCGAGTTTGCTTATGG
CAAGCGTAGTAGAATAACTTCCAAGGATGAGACAGTGTCGATACCCTTGGATCATGGAAATCCCACCCC
TAGTCTTAAACCGGTCACTTTGCAGCAAGTGTTACCCGTAACTCCGCGAACAGGTGTTAAACGCGAAGG
TGAAGATTTGTATCCCACTATGCAACTGATGGTACCCAAACGCCAGAAGTTGGAGGACGTTTTGGAGAA
AGTAAAAGTGGATCCAGATATTCAACCTGAGGTTAAAGTGAGACCCATTAAGCAGGTAGCGCCTGGTCT
GGGGGTACAAACTGTAGACATTAAGATTCCCACTGAAAGTATGGAAGTGCAAACTGAACCCGCAAAGCC
TACTGCCACCTCCACTGAAGTGCAAACGGATCCATGGATGCCCATGCCTATTACAACTGACGCCGCCGG
TCCCACTCGAAGATCCCGACGAAAGTACGGTCCAGCAAGTCTGTTGATGCCCAATTATGTTGTACACCC
ATCTATTATTCCTACTCCTGGTTACCGAGGCACTCGCTACTATCGCAGCCGAAACAGTACCTCCCGCCG
TCGCCGCAAGACACCTGCAAATCGCAGTCGTCGCCGTAGACGCACAAGCAAACCGACTCCCGGCGCCCT
GGTGCGGCAAGTGTACCGCAATGGTAGTGCGGAACCTTTGACACTGCCGCGTGCGCGTTACCATCCGAG
TATCATCACTTAATCAATGTTGCCGCTGCCTCCTTGCAGATATGGCCCTCACTTGTCGCCTTCGCGTTC
CCATCACTGGTTACCGAGGAAGAAACTCGCGCCGTAGAAGAGGGATGTTGGGACGCGGAATGCGACGCT
ACAGGCGACGGCGTGCTATCCGCAAGCAATTGCGGGGTGGTTTTTTACCAGCCTTAATTCCAATTATCG
CTGCTGCAATTGGCGCGATACCAGGCATAGCTTCCGTGGCGGTTCAGGCCTCGCAACGACATTGACATT

Figure 47 (continued)

GGAAAAAAACGTATAAATAAAAAAAAAAAAAATACAATGGACTCTGACACTCCTGGTCCTGTGACTATGT
TTTCTTAGAGATGGAAGACATCAATTTTTCATCCTTGGCTCCGCGACACGGCACGAAGCCGTACATGGG
CACCTGGAGCGACATCGGCACGAGCCAACTGAACGGGGGCGCCTTCAATTGGAGCAGTATCTGGAGCGG
GCTTAAAAATTTTGGCTCAACCATAAAAACATACGGGAACAAAGCTTGGAACAGCAGTACAGGACAGGC
GCTTAGAAATAAACTTAAAGACCAGAACTTCCAACAAAAAGTAGTCGATGGGATAGCTTCCGGCATCAA
TGGAGTGGTAGATTTGGCTAACCAGGCTGTGCAGAAAAAGATAAACAGTCGTTTGGACCCGCCGCCAGC
AACCCCAGGTGAAATGCAAGTGGAGGAAGAAATTCCTCCGCCAGAAAAACGAGGCGACAAGCGTCCGCG
TCCCGATTTGGAAGAGACGCTGGTGACGCGCGTAGATGAACCGCCTTCTTATGAGGAAGCAACGAAGCT
TGGAATGCCCACCACTAGACCGATAGCCCCAATGGCCACCGGGGTGATGAAACCTTCTCAGTTGCATCG
ACCCGTCACCTTGGATTTGCCCCCTCCCCCTGCTGCTACTGCTGTACCCGCTTCTAAGCCTGTCGCTGC
CCCGAAACCAGTCGCCGTAGCCAGGTCACGTCCCGGGGGCGCTCCTCGTCCAAATGCGCACTGGCAAAA
TACTCTGAACAGCATCGTGGGTCTAGGCGTGCAAAGTGTAAAACGCCGTCGCTGCTTTTAATTAAATAT
GGAGTAGCGCTTAACTTGCCTATCTGTGTATATGTGTCATTACACGCCGTCACAGCAGCAGAGGAAAAA
AGGAAGAGGTCGTGCGTCGACGCTGAGTTACTTTCAAGATGGCCACCCCATCGATGCTGCCCCAATGGG
CATACATGCACATCGCCGGACAGGATGCTTCGGAGTACCTGAGTCCGGGTCTGGTGCAGTTCGCCCGCG
CCACAGACACCTACTTCAATCTGGGAAATAAGTTTAGAAATCCCACCGTAGCGCCGACCCACGATGTGA
CCACCGACCGTAGCCAGCGGCTCATGTTGCGCTTCGTGCCCGTTGACCGGGAGGACAATACATACTCTT
ACAAAGTGCGGTACACCCTGGCCGTGGGCGACAACAGAGTGCTGGATATGGCCAGCACGTTCTTTGACA
TTAGGGGTGTGTTGGACAGAGGTCCCAGTTTCAAACCCTATTCTGGTACGGCTTACAACTCCCTGGCTC
CTAAAGGCGCTCCAAATACATCTCAGTGGATTGCAGAAGGTGTAAAAAATACAACTGGTGAGGAACACG
TAACAGAAGAGGAAACCAATACTACTACTTACACTTTTGGCAATGCTCCTGTAAAAGCTGAAGCTGAAA
TTACAAAAGAAGGACTCCCAGTAGGTTTGGAAGTTTCAGATGAAGAAAGTAAACCGATTTATGCTGATA
AAACATATCAGCCAGAACCTCAGCTGGGAGATGAAACTTGGACTGACCTTGATGGAAAAACCGAAAAGT
ATGGAGGCAGGGCTCTCAAACCCGATACTAAGATGAAACCATGCTACGGGTCCTTTGCCAAACCTACTA
ATGTGAAAGGCGGTCAGGCAAAACAAAAAACAACGGAGCAGCCAAATCAGAAAGTCGAATATGATATCG
ACATGGAGTTTTTTGATGCGGCATCGCAGAAAACAAACTTAAGTCCTAAAATTGTCATGTATGCAGAAA
ATGTAAATTTGGAAACTCCAGACACTCATGTAGTGTACAAACCTGGAACAGAAGACACAAGTTCCGAAG
CTAATTTGGGACAACAATCTATGCCCAACAGACCCAACTACATTGGCTTCAGAGATAACTTTATTGGAC
TTATGTACTATAACAGTACTGGTAACATGGGGGTGCTGGCTGGTCAAGCGTCTCAGTTAAATGCAGTGG
TTGACTTGCAGGACAGAAACACAGAACTTTCTTACCAACTCTTGCTTGACTCTCTGGGCGACAGAACCA
GATACTTTAGCATGTGGAATCAGGCTGTGGACAGTTATGATCCTGATGTACGTGTTATTGAAAATCATG
GTGTGGAAGATGAACTTCCCAACTACTGTTTTCCACTGGACGGCATAGGTGTTCCAACAACCAGTTACA
AATCAATAGTTCCAAATGGAGACAATGCGCCTAATTGGAAGGAACCTGAAGTAAATGGAACAAGTGAGA
TCGGACAGGGTAATTTGTTTGCCATGGAAATTAACCTTCAAGCCAATCTATGGCGAAGTTTCCTTTATT
CCAATGTGGCTCTATATCTCCCAGACTCGTACAAATACACCCCGTCCAATGTCACTCTTCCAGAAAACA
AAAACACCTACGACTACATGAACGGGCGGGTGGTGCCGCCATCTCTAGTAGACACCTATGTGAACATTG
GTGCCAGGTGGTCTCTGGATGCCATGGACAATGTCAACCCATTCAACCACCACCGTAACGCTGGCTTGC
GTTACCGATCCATGCTTCTGGGTAACGGACGTTATGTGCCTTTCCACATACAAGTGCCTCAAAAATTCT
TCGCTGTTAAAAACCTGCTGCTTCTCCCAGGCTCCTACACTTATGAGTGGAACTTTAGGAAGGATGTGA
ACATGGTTCTACAGAGTTCCCTCGGTAACGACCTGCGGGTAGATGGCGCCAGCATCAGTTTCACGAGCA
TCAACCTCTATGCTACTTTTTTCCCCATGGCTCACAACACCGCTTCCACCCTTGAAGCCATGCTGCGGA
ATGACACCAATGATCAGTCATTCAACGACTACCTATCTGCAGCTAACATGCTCTACCCCATTCCTGCCA
ATGCAACCAATATTCCCATTTCCATTCCTTCTCGCAACTGGGCGGCTTTCAGAGGCTGGTCATTTACCA
GACTGAAAACCAAAGAAACTCCCTCTTTGGGGTCTGGATTTGACCCCTACTTTGTCTATTCTGGTTCTA
TTCCCTACCTGGATGGTACCTTCTACCTGAACCACACTTTTAAGAAGGTTTCCATCATGTTTGACTCTT
CAGTGAGCTGGCCTGGAAATGACAGGTTACTATCTCCTAACGAATTTGAAATAAAGCGCACTGTGGATG
GCGAAGGCTACAACGTAGCCCAATGCAACATGACCAAAGACTGGTTCTTGGTACAGATGCTCGCCAACT
ACAACATCGGCTATCAGGGCTTCTACATTCCAGAAGGATACAAAGATCGCATGTATTCATTTTTCAGAA
ACTTCCAGCCCATGAGCAGGCAGGTGGTTGATGAGGTCAATTACAAAGACTTCAAGGCCGTCGCCATAC
CCTACCAACACAACAACTCTGGCTTTGTGGGTTACATGGCTCCGACCATGCGCCAAGGTCAACCCTATC
CCGCTAACTATCCCTATCCACTCATTGGAACAACTGCCGTAAATAGTGTTACGCAGAAAAAGTTCTTGT

Figure 47 (continued)

GTGACAGAACCATGTGGCGCATACCGTTCTCGAGCAACTTCATGTCTATGGGGGCCCTTACAGACTTGG
GACAGAATATGCTCTATGCCAACTCAGCTCATGCTCTGGACATGACCTTTGAGGTGGATCCCATGGATG
AGCCCACCCTGCTTTATCTTCTCTTCGAAGTTTTCGACGTGGTCAGAGTGCATCAGCCACACCGCGGCA
TCATCGAGGCAGTCTACCTGCGTACACCGTTCTCGGCCGGTAACGCTACCACGTAAGAAGCTTCTTGCT
TCTTGCAAATAGCAGCTGCAACCATGGCCTGCGGATCCCAAAACGGCTCCAGCGAGCAAGAGCTCAGAG
CCATTGTCCAAGACCTGGGTTGCGGACCCTATTTTTTGGGAACCTACGATAAGCGCTTCCCGGGGTTCA
TGGCCCCCGATAAGCTCGCCTGTGCCATTGTAAATACGGCCGGACGTGAGACGGGGGGAGAGCACTGGT
TGGCTTTCGGTTGGAACCCACGTTCTAACACCTGCTACCTTTTTGATCCTTTTGGATTCTCGGATGATC
GTCTCAAACAGATTTACCAGTTTGAATATGAGGGTCTCCTGCGCCGCAGCGCTCTTGCTACCAAGGACC
GCTGTATTACGCTGGAAAAATCTACCCAGACCGTGCAGGGTCCCCGTTCTGCCGCCTGCGGACTTTTCT
GCTGCATGTTCCTTCACGCCTTTGTGCACTGGCCTGACCGTCCCATGGACGGAAACCCCACCATGAAAT
TGCTAACTGGAGTGCCAAACAACATGCTTCATTCTCCTAAAGTCCAGCCCACCCTGTGTGACAATCAAA
AAGCACTCTACCATTTTCTTAATACCCATTCGCCTTATTTTCGCTCCCATCGTACACACATCGAAAGGG
CCACTGCGTTCGACCGTATGGATGTTCAATAATGACTCATGTAAACAACGTGTTCAATAAACATCACTT
TATTTTTTTACATGTATCAAGGCTCTGCATTACTTATTTATTTACAAGTCGAATGGGTTCTGACGAGAA
TCAGAATGACCCGCAGGCAGTGATACGTTGCGGAACTGATACTTGGGTTGCCACTTGAATTCGGGAATC
ACCAACTTGGGAACCGGTATATCGGGCAGGATGTCACTCCACAGCTTTCTGGTCAGCTGCAAAGCTCCA
AGCAGGTCAGGAGCCGAAATCTTGAAATCACAATTAGGACCAGTGCTTTGAGCGCGAGAGTTGCGGTAC
ACCGGATTGCAGCACTGAAACACCATCAGCGACGGATGTCTCACGCTTGCCAGCACGGTGGGATCTGCA
ATCATGCCCACATCCAGATCTTCAGCATTGGCAATGCTGAACGGGGTCATCTTGCAGGTCTGCCTACCC
ATGGCGGGCACCCAATTAGGCTTGTGGTTGCAATCGCAGTGCAGGGGGATCAGTATCATCTTGGCCTGA
TCCTGTCTGATTCCTGGATACACGGCTCTCATGAAAGCATCATATTGCTTGAAAGCCTGCTGGGCTTTA
CTACCCTCGGTATAAAACATCCCGCAGGACCTGCTCGAAAACTGGTTAGCTGCACAGCCGGCATCATTC
ACACAGCAGCGGGCGTCATTGTTAGCTATTTGCACCACACTTCTGCCCCAGCGGTTTTGGGTGATTTTG
GTTCGCTCGGGATTCTCCTTTAAGGCTCGTTGTCCGTTCTCGCTGGCCACATCCATCTCGATAATCTGC
TCCTTCTGAATCATAATATTGCCATGCAGGCACTTCAGCTTGCCCTCATAATCATTGCAGCCATGAGGC
CACAACGCACAGCCTGTACATTCCCAATTATGGTGGGCGATCTGAGAAAAAGAATGTATCATTCCCTGC
AGAAATCTTCCCATCATCGTGCTCAGTGTCTTGTGACTAGTGAAAGTTAACTGGATGCCTCGGTGCTCC
TCGTTTACGTACTGGTGACAGATGCGCTTGTATTGTTCGTGTTGCTCAGGCATTAGTTTAAAAGAGGTT
CTAAGTTCGTTATCCAGCCTGTACTTCTCCATCAGCAGACACATCACTTCCATGCCTTTCTCCCAAGCA
GACACCAGGGGCAAGCTAATCGGATTCTTAACAGTGCAGGCAGCAGCTCCTTTAGCCAGAGGGTCATCT
TTAGCGATCTTCTCAATGCTTCTTTTGCCATCCTTCTCAACGATGCGCACGGGCGGTAGCTGAAACCC
ACTGCTACAAGTTGCGCCTCTTCTCTTTCTTCTTCGCTGTCTTGACTGATGTCTTGCATGGGGATATGT
TTGGTCTTCCTTGGCTTCTTTTTGGGGGGTATCGGAGGAGGAGGACTGTCGCTCCGTTCCGGAGACAGG
GAGGATTGTGACGTTTCGCTCACCATTACCAACTGACTGTCGGTAGAAGAACCTGACCCCACACGGCGA
CAGGTGTTTCTCTTCGGGGGCAGAGGTGGAGGCGATTGCGAAGGGCTGCGGTCCGACCTGGAAGGCGGA
TGACTGGCAGAACCCCTTCCGCGTTCGGGGGTGTGCTCCCTGTGGCGGTCGCTTAACTGATTTCCTTCG
CGGCTGGCCATTGTGTTCTCCTAGGCAGAGAAACAACAGACATGGAAACTCAGCCATTGCTGTCAACAT
CGCCACGAGTGCCATCACATCTCGTCCTCAGCGACGAGGAAAAGGAGCAGAGCTTAAGCATTCCACCGC
CCAGTCCTGCCACCACCTCTACCCTAGAAGATAAGGAGGTCGACGCATCTCATGACATGCAGAATAAAA
AAGCGAAAGAGTCTGAGACAGACATCGAGCAAGACCCGGGCTATGTGACACCGGTGGAACACGAGGAAG
AGTTGAAACGCTTTCTAGAGAGAGAGGATGAAAACTGCCCAAAACAACGAGCAGATAACTATCACCAAG
ATGCTGGAAATAGGGATCAGAACACCGACTACCTCATAGGGCTTGACGGGGAAGACGCGCTCCTTAAAC
ATCTAGCAAGACAGTCGCTCATAGTCAAGGATGCATTATTGGACAGAACTGAAGTGCCCATCAGTGTGG
AAGAGCTCAGCCGCGCCTACGAGCTTAACCTCTTTTCACCTCGTACTCCCCCCAAACGTCAGCCAAACG
GCACCTGCGAGCCAAATCCTCGCTTAAACTTTTATCCAGCTTTTGCTGTGCCAGAAGTACTGGCTACCT
ATCACATCTTTTTTAAAAATCAAAAAATTCCAGTCTCCTGCCGCGCTAATCGCACCCGCGCCGATGCCC
TACTCAATCTGGGACCTGGTTCACGCTTACCTGATATAGCTTCCTTGGAAGAGGTTCCAAAGATCTTCG
AGGGTCTGGGCAATAATGAGACTCGGGCCGCAAATGCTCTGCAAAAGGGAGAAAATGGCATGGATGAGC
ATCACAGCGTTCTGGTGGAATTGGAAGGCGATAATGCCAGACTCGCAGTACTCAAGCGAAGCATCGAGG
TCACACACTTCGCATATCCCGCTGTCAACCTGCCCCCTAAAGTCATGACGGCGGTCATGGACCAGTTAC

Figure 47 (continued)

TCATTAAGCGCGCAAGTCCCCTTTCAGAAGACATGCATGACCCAGATGCCTGTGATGAGGGTAAACCAG
TGGTCAGTGATGAGCAGCTAACCCGATGGCTGGGCACCGACTCTCCCAGGGATTTGGAAGAGCGTCGCA
AGCTTATGATGGCCGTGGTGCTGGTTACCGTAGAACTAGAGTGTCTCCGACGTTTCTTTACCGATTCAG
AAACCTTGCGCAAACTCGAAGAGAATCTGCACTACACTTTTAGACACGGCTTTGTGCGGCAGGCATGCA
AGATATCTAACGTGGAACTCACCAACCTGGTTTCCTACATGGGTATTCTGCATGAGAATCGCCTAGGAC
AAAGCGTGCTGCACAGCACCCTGAAGGGGGAAGCCCGCCGTGATTACATCCGCGATTGTGTCTATCTGT
ACCTGTGCCACACGTGGCAAACCGGCATGGGTGTATGGCAGCAATGTTTAGAAGAACAGAACTTGAAAG
AGCTTGACAAGCTCTTACAGAAATCTCTTAAGGTTCTGTGGACAGGGTTCGACGAGCGCACCGTCGCTT
CCGACCTGGCAGACCTCATCTTCCCAGAGCGTCTCAGGGTTACTTTGCGAAACGGATTGCCTGACTTTA
TGAGCCAGAGCATGCTTAACAATTTTCGCTCTTTCATCCTGGAACGCTCCGGTATCCTGCCCGCCACCT
GCTGCGCACTGCCCTCCGACTTTGTGCCTCTCACCTACCGCGAGTGCCCCCCGCCGCTATGGAGTCACT
GCTACCTGTTCCGTCTGGCCAACTATCTCTCCTACCACTCGGATGTGATCGAGGATGTGAGCGGAGACG
GCTTGCTGGAGTGTCACTGCCGCTGCAATCTGTGCACGCCCCACCGGTCCCTAGCTTGCAACCCCCAGT
TGATGAGCGAAACCCAGATAATAGGCACCTTTGAATTGCAAGGCCCCAGCAGCCAAGGCGATGGGTCTT
CTCCTGGGCAAAGTTTAAAACTGACCCCGGGACTGTGGACCTCCGCCTACTTGCGCAAGTTTGCTCCGG
AAGATTACCACCCCTATGAAATCAAGTTCTATGAGGACCAATCACAGCCTCCAAAGGCCGAACTTTCGG
CCTGCGTCATCACCCAGGGGGCAATTCTGGCCCAATTGCAAGCCATCCAAAAATCCCGCCAAGAATTTC
TACTGAAAAAGGGTAAGGGGGTCTACCTTGACCCCCAGACCGGCGAGGAACTCAACACAAGGTTCCCTC
AGGATGTCCCAACGACGAGAAAACAAGAAGTTGAAGGTGCAGCCGCCGCCCCCAGAAGATATGGAGGAA
GATTGGGACAGTCAGGCAGAGGAGGCGGAGGAGGACAGTCTGGAGGACAGTCTGGAGGAAGACAGTTTG
GAGGAGGAAAACGAGGAGGCAGAGGAGGTGGAAGAAGTAACCGCCGACAAACAGTTATCCTCGGCTGCG
GAGACAAGCAACAGCGCTACCATCTCCGCTCCGAGTCGAGGAACCCGGCGGCGTCCCAGCAGTAGATGG
GACGAGACCGGACGCTTCCCGAACCCAACCAGCGCTTCCAAGACCGGTAAGAAGGATCGGCAGGGATAC
AAGTCCTGGCGGGGGCATAAGAATGCCATCATCTCCTGCTTGCATGAGTGCGGGGGCAACATATCCTTC
ACGCGGCGCTACTTGCTATTCCACCATGGGGTGAACTTTCCGCGCAATGTTTTGCATTACTACCGTCAC
CTCCACAGCCCCTACTATAGCCAGCAAATCCCGGCAGTCTCGACAGATAAAGACAGCGGCGGCGACCTC
CAACAGAAAACCAGCAGCGGCAGTTAGAAAATACACAACAAGTGCAGCAACAGGAGGATTAAAGATTAC
AGCCAACGAGCCAGCGCAAACCCGAGAGTTAAGAAATCGGATCTTTCCAACCCTGTATGCCATCTTCCA
GCAGAGTCGGGGTCAAGAGCAGGAACTGAAAATAAAAAACCGATCTCTGCGTTCGCTCACCAGAAGTTG
TTTGTATCACAAGAGCGAAGATCAACTTCAGCGCACTCTCGAGGACGCCGAGGCTCTCTTCAACAAGTA
CTGCGCGCTGACTCTTAAAGAGTAGGCAGCGACCGCGCTTATTCAAAAAAGGCGGGAATTACATCATCC
TCGACATGAGTAAAGAAATTCCCACGCCTTACATGTGGAGTTATCAACCCCAAATGGGATTGGCGGCAG
GCGCCTCCCAGGACTACTCCACCCGCATGAATTGGCTCAGCGCCGGGCCTTCTATGATTTCTCGAGTTA
ATGATATACGCGCCTACCGAAACCAAATACTTTTGGAACAGTCAGCTCTTACCACCACGCCCCGCCAAC
ACCTTAATCCCAGAAATTGGCCCGCCGCCCTAGTGTACCAGGAAAGTCCCGCTCCCACCACTGTATTAC
TTCCTCGAGACGCCCAGGCCGAAGTCCAAATGACTAATGCAGGTGCGCAGTTAGCTGGCGGCTCCACCC
TATGTCGTCACAGGCCTCGGCATAATATAAAACGCCTGATGATCAGAGGCCGAGGTATCCAGCTCAACG
ACGAGTCGGTGAGCTCTCCGCTTGGTCTACGACCAGACGGAATCTTTCAGATTGCCGGCTGCGGGAGAT
CTTCCTTCACCCCTCGTCAGGCTGTTCTGACTTTGGAAAGTTCGTCTTCGCAACCCCGCTCGGGCGGAA
TCGGGACCGTTCAATTTGTGGAGGAGTTTACTCCCTCTGTCTACTTCAACCCCTTCTCCGGATCTCCTG
GGCATTACCCGGACGAGTTCATACCGAACTTCGACGCGATTAGCGAGTCAGTGGACGGCTACGATTGAT
GTCTGGTGACGCGGCTGAGCTATCTCGGCTGCGACATCTAGACCACTGCCGCCGCTTTCGCTGCTTTGC
CCGGGAACTCATTGAGTTCATCTACTTCGAACTCCCCAAGGATCACCCTCAAGGTCCGGCCCACGGAGT
GCGGATTTCTATCGAAGGCAAAATAGACTCTCGCCTGCAACGAATTTTCTCCCAGCGGCCCGTGCTGAT
CGAGCGAGACCAGGGAAACACCACGGTTTCCATCTACTGCATTTGTAATCACCCCGGATTGCATGAAAG
CCTTTGCTGTCTTATGTGTACTGAGTTTAATAAAAACTGAATTAAGACTCTCCTACGGACTGCCGCTTC
TTCAACCCGGATTTTACAACCAGAAGAACGAAACTTTTCCTGTCGTCCAGGACTCTGTTAACTTCACCT
TTCCTACTCACAAACTAGAAGCTCAACGACTACACCGCTTTTCCAGAAGCATTTTCCCTACTAATACTA
CTTTCAAAACCGGAGGTGAGCTCCAAGGTCTTCCTACAGAAAACCCTTGGGTGGAAGCGGGCCTTGTAG
TGCTAGGAATTCTTGCGGGTGGCTTGTGATTATTCTTTGCTACCTATACACACCTTGCTTCACTTTCT
TAGTGGTGTTGTGGTATTGGTTTAAAAAATGGGGCCCATACTAGTCTTGCTTGTTTTACTTTCGCTTTT

Figure 47 (continued)

GGAACCGGGTTCTGCCAATTACGATCCATGTCTAGACTTCGACCCAGAAAACTGCACACTTACTTTTGC
ACCCGACACAAGCCGCATCTGTGGAGTTCATCGCCTCTCTTACGAACTTGGCCCCCAACGACAAAAATT
TACCTGCATGGTGGGAATCAACCCCATAGTTATCACCCAGCAAAGTGGAGATACTAAGGGTTGCATTCA
CTGCTCCTGCGATTCCATCGAGTGCACCTACACCCTGCTGAAGACCCTATGCGGCCTAAGAGACCTGCT
ACCAATGAATTAAAAAATGATTAATAAAAAATCACTTACTTGAAATCAGCAATAAGGTCTCTGTTGAAA
TTTTCTCCCAGCAGCACCTCACTTCCCTCTTCCCAACTCTGGTATTCTAAACCCCGTTCAGCGGCATAC
TTTCTCCATACTTTAAAGGGGATGTCAAATTTTAGCTCCTCTCCTGTACCCACAATCTTCATGTCTTTC
TTCCCAGATGACCAAGAGAGTCCGGCTCAGTGACTCCTTCAACCCTGTCTACCCCTATGAAGATGAAAG
CACCTCCCAACACCCCTTTATAAACCCAGGGTTTATTTCCCCAAATGGCTTCACACAAAGCCCAAACGG
AGTTCTTACTTTAAAATGTTTAACCCCACTAACAACCACAGGCGGATCTCTACAGCTAAAAGTGGGAGG
GGGACTTACAGTGGATGACACCAACGGTTTTTTGAAAGAAAACATAAGTGCCACCACACCACTCGTTAA
GACTGGTCACTCTATAGGTTTACCACTAGGAGCCGGATTGGGAACGAATGAAAATAAACTTTGTATCAA
ATTAGGACAAGGACTTACATTCAATTCAAACAACATTTGCATTGATGACAATATTAACACCTTATGGAC
AGGAGTCAACCCCACCGAAGCCAACTGTCAAATCATGAACTCCAGTGAATCTAATGATTGCAAATTAAT
TCTAACACTAGTTAAAACTGGAGCACTAGTCACTGCATTTGTTTATGTTATAGGAGTATCTAACAATTT
TAATATGCTAACTACACACAGAAATATAAATTTTACTGCAGAGCTGTTTTTCGATTCTACTGGTAATTT
ACTAACTAGACTCTCATCCCTCAAAACTCCACTTAATCATAAATCAGGACAAAACATGGCTACTGGTGC
CATTACTAATGCTAAAGGTTTCATGCCCAGCACGACTGCCTATCCTTTCAATGATAATTCTAGAGAAAA
AGAAAACTACATTTACGGAACTTGTTACTACACAGCTAGTGATCGCACTGCTTTTCCCATTGACATATC
TGTCATGCTTAACCGAAGAGCAATAAATGACGAGACATCATATTGTATTCGTATAACTTGGTCCTGGAA
CACAGGAGATGCCCCAGAGGTGCAAACCTCTGCTACAACCCTAGTCACCTCCCCATTTACCTTTTACTA
CATCAGAGAAGACGACTGACAAATAAAGTTTAACTTGTTTATTTGAAAATCAATTCACAAAATCCGAGT
AGTTATTTTGCCTCCCCCTTCCCATTTAACAGAATACACCAATCTCTCCCCACGCACAGCTTTAAACAT
TTGGATACCATTAGATATAGACATGGTTTTAGATTCCACATTCCAAACAGTTTCAGAGCGAGCCAATCT
GGGGTCAGTGATAGATAAAAATCCATCGGGATAGTCTTTTAAAGCGCTTTCACAGTCCAACTGCTGCGG
ATGCGACTCCGGAGTCTGGATCACGGTCATCTGGAAGAAGAACGATGGGAATCATAATCCGAAAACGGT
ATCGGACGATTGTGTCTCATCAAACCCACAAGCAGCCGCTGTCTGCGTCGCTCCGTGCGACTGCTGTTT
ATGGGATCAGGGTCCACAGTGTCCTGAAGCATGATTTTAATAGCCCTTAACATCAACTTTCTGGTGCGA
TGCGCGCAGCAACGCATTCTGATTTCACTCAAATCTTTGCAGTAGGTACAACACATTATTACAATATTG
TTTAATAAACCATAATTAAAAGCGCTCCAGCCAAAACTCATATCTGATATAATCGCCCCTGCATGACCA
TCATACCAAAGTTTAATATAAATTAAATGACGTTCCCTCAAAAACACACTACCCACATACATGATCTCT
TTTGGCATGTGCATATTAACAATCTGTCTGTACCATGGACAACGTTGGTTAATCATGCAACCCAATATA
ACCTTCCGGAACCACACTGCCAACACCGCTCCCCCAGCCATGCATTGAAGTGAACCCTGCTGATTACAA
TGACAATGAAGAACCCAATTCTCTCGACCGTGAATCACTTGAGAATGAAAAATATCTATAGTGGCACAA
CATAGACATAAATGCATGCATCTTCTCATAATTTTTAACTCCTCAGGATTTAGAAACATATCCCAGGGA
ATAGGAAGCTCTTGCAGAACAGTAAAGCTGGCAGAACAAGGAAGACCACGAACACAACTTACACTATGC
ATAGTCATAGTATCACAATCTGGCAACAGCGGGTGGTCTTCAGTCATAGAAGCTCGGGTTTCATTTTCC
TCACAACGTGGTAACTGGGCTCTGGTGTAAGGGTGATGTCTGGCGCATGATGTCGAGCGTGCGCGCAAC
CTTGTCATAATGGAGTTGCTTCCTGACATTCTCGTATTTTGTATAGCAAAACGCGGCCCTGGCAGAACA
CACTCTTCTTCGCCTTCTATCCTGCCGCTTAGCGTGTTCCGTGTGATAGTTCAAGTACAACCACACTCT
TAAGTTGGTCAAAAGAATGCTGGCTTCAGTTGTAATCAAAACTCCATCGCATCTAATCGTTCTGAGGAA
ATCATCCAAGCAATGCAACTGGATTGTGTTTCAAGCAGGAGAGGAGAGGGAAGAGACGGAAGAACCATG
TTAATTTTTATTCCAAACGATCTCGCAGTACTTCAAATTGTAGATCGCGCAGATGGCATCTCTCGCCCC
CACTGTGTTGGTGAAAAAGCACAGCTAGATCAAAAGAAATGCGATTTTCAAGGTGCTCAACGGTGGCTT
CCAGCAAAGCCTCCACGCGCACATCCAAGAACAAAAGAATACCAAAAGAAGGAGCATTTTCTAACTCCT
CAATCATCATATTACATTCCTGCACCATTCCCAGATAATTTTCAGCTTTCCAGCCTTGAATTATTCGTG
TCAGTTCTTGTGGTAAATCCAATCCACACATTACAAACAGGTCCCGGAGGGCGCCCTCCACCACCATTC
TTAAACACACCCTCATAATGACAAAATATCTTGCTCCTGTGTCACCTGTAGCGAATTGAGAATGGCAAC
ATCAATTGACATGCCCTTGGCTCTAAGTTCTTCTTTAAGTTCTAGTTGTAAAAACTCTCTCATATTATC
ACCAAACTGCTTAGCCAGAAGCCCCCCGGGAACAAGAGCAGGGGACGCTACAGTGCAGTACAAGCGCAG
ACCTCCCCAATTGGCTCCAGCAAAAACAAGATTGGAATAAGCATATTGGGAACCGCCAGTAATATCATC

GAAGTTGCTGGAAATATAATCAGGCAGAGTTTCTTGTAAAAATTGAATAAAAGAAAAATTTGCCAAAAA
AACATTCAAAACCTCTGGGATGCAAATGCAATAGGTTACCGCGCTGCGCTCCAACATTGTTAGTTTTGA
ATTAGTCTGCAAAAATAAAAAAAAAAACAAGCGTCATATCATAGTAGCCTGACGAACAGATGGATAAAT
CAGTCTTTCCATCACAAGACAAGCCACAGGGTCTCCAGCTCGACCCTCGTAAAACCTGTCATCATGATT
AAACAACAGCACCGAAAGTTCCTCGCGGTGACCAGCATGAATAATTCTTGATGAAGCATACAATCCAGA
CATGTTAGCATCAGTTAACGAGAAAAAACAGCCAACATAGCCTTTGGGTATAATTATGCTTAATCGTAA
GTATAGCAAAGCCACCCCTCGCGGATACAAAGTAAAAGGCACAGGAGAATAAAAAATATAATTATTTCT
CTGCTGCTGTTCAGGCAACGTCGCCCCCGGTCCCTCTAAATACACATACAAAGCCTCATCAGCCATGGC
TTACCAGACAAAGTACAGCGGGCACACAAAGCACAAGCTCTAAAGTGACTCTCCAACCTCTCCACAATA
TATATATACACAAGCCCTAAACTGACGTAATGGGAGTAAAGTGTAAAAAATCCCGCCAAACCCAACACA
CACCCCGAAACTGCGTCACCAGGGAAAAGTACAGTTTCACTTCCGCAATCCCAACAGGCGTAACTTCCT
CTTTCTCACGGTACGTGATATCCCACTAACTTGCAACGTCATTTTCCCACGGTCGCACCGCCCCTTTTA
GCCGTTAACCCCACAGCCAATCACCACACGATCCACACTTTTTAAAATCACCTCATTTACATATTGGCA
CCATTCCATCTATAAGGTATATTATATAGATAGA

Figure 48

SEQ ID NO: 87 DNA CORRESPONDING TO E2B REGION OF THE ENAD GENOME (BP 10355-5068)

CTATGGCATCTCGATCCAGCAGACCTCCTCGTTTCGCGGGTTTGGACGGCTCCTGGAATAGGGTATGAG
ACGATGGGCGTCCAGCGCTGCCAGGGTTCGGTCCTTCCAGGGTCTCAGTGTTCGAGTCAGGGTTGTTTC
CGTCACAGTGAAGGGGTGTGCGCCTGCTTGGGCGCTTGCCAGGGTGCGCTTCAGACTCATCCTGCTGGT
CGAAAACTTCTGTCGCTTGGCGCCCTGTATGTCGGCCAAGTAGCAGTTTACCATGAGTTCGTAGTTGAG
CGCCTCGGCTGCGTGGCCTTTGGCGCGGAGCTTACCTTTGGAAGTTTTCTTGCATACCGGGCAGTATAG
GCATTTCAGCGCATACAACTTGGGCGCAAGGAAAACGGATTCTGGGGAGTATGCATCTGCGCCGCAGGA
GGCGCAAACAGTTTCACATTCCACCAGCCAGGTTAAATCCGGTTCATTGGGGTCAAAAACAAGTTTTCC
GCCATATTTTTTGATGCGTTTCTTACCTTTGGTCTCCATGAGTTCGTGTCCTCGTTGAGTGACAAACAG
GCTGTCCGTGTCCCCGTAGACTGATTTTACAGGCCTCTTCTCCAGTGGAGTGCCTCGGTCTTCTTCGTA
CAGGAACTCTGACCACTCTGATACAAAGGCGCGCGTCCAGGCCAGCACAAAGGAGGCTATGTGGGAGGG
GTAGCGATCGTTGTCAACCAGGGGGTCCACCTTTTCCAAAGTATGCAAACACATGTCACCCTCTTCAAC
ATCCAGGAATGTGATTGGCTTGTAGGTGTATTTCACGTGACCTGGGGTCCCCGCTGGGGGGGTATAAAA
GGGGGCGGTTCTTTGCTCTTCCTCACTGTCTTCCGGATCGCTGTCCAGGAACGTCAGCTGTTGGGGTAG
GTATTCCCTCTCGAAGGCGGGCATGACCTCTGCACTCAGGTTGTCAGTTTCTAAGAACGAGGAGGATTT
GATATTGACAGTGCCGGTTGAGATGCCTTTCATGAGGTTTTCGTCCATCTGGTCAGAAAACACAATTTT
TTTATTGTCAAGTTTGGTGGCAAATGATCCATACAGGGCGTTGGATAAAAGTTTGGCAATGGATCGCAT
GGTTTGGTTCTTTTCCTTGTCCGCGCGCTCTTTGGCGGCGATGTTGAGTTGGACATACTCGCGTGCCAG
GCACTTCCATTCGGGGAAGATAGTTGTTAATTCATCTGGCACGATTCTCACTTGCCACCCTCGATTATG
CAAGGTAATTAAATCCACACTGGTGGCCACCTCGCCTCGAAGGGGTTCATTGGTCCAACAGAGCCTACC
TCCTTTCCTAGAACAGAAAGGGGGAAGTGGGTCTAGCATAAGTTCATCGGGAGGGTCTGCATCCATGGT
AAAGATTCCCGGAAGTAAATCCTTATCAAAATAGCTGATGGGAGTGGGGTCATCTAAGGCCATTTGCCA
TTCTCGAGCTGCCAGTGCGCGCTCATATGGGTTAAGGGGACTGCCCCATGGCATGGGATGGGTGAGTGC
AGAGGCATACATGCCACAGATGTCATAGACGTAGATGGGATCCTCAAAGATGCCTATGTAGGTTGGATA
GCATCGCCCCCCTCTGATACTTGCTCGCACATAGTCATATAGTTCATGTGATGGCGCTAGCAGCCCCGG
ACCCAAGTTGGTGCGATTGGGTTTTTCTGTTCTGTAGACGATCTGGCGAAAGATGGCGTGAGAATTGGA
AGAGATGGTGGGTCTTTGAAAAATGTTGAAATGGGCATGAGGTAGACCTACAGAGTCTCTGACAAAGTG
GGCATAAGATTCTTGAAGCTTGGTTACCAGTTCGGCGGTGACAAGTACGTCTAGGGCGCAGTAGTCAAG
TGTTTCTTGAATGATGTCATAACCTGGTTGGTTTTTCTTTTCCCACAGTTCGCGGTTGAGAAGGTATTC
TTCGCGATCCTTCCAGTACTCTTCTAGCGGAAACCCGTCTTTGTCTGCACGGTAAGATCCTAGCATGTA
GAACTGATTAACTGCCTTGTAAGGGCAGCAGCCCTTCTCTACGGGTAGAGAGTATGCTTGAGCAGCTTT
TCGTAGCGAAGCGTGAGTAAGGGCAAAGGTGTCTCTGACCATGACTTTGAGGAATTGGTATTTGAAGTC
GATGTCGTCACAGGCTCCCTGTTCCCAGAGTTGGAAGTCTACCCGTTTCTTGTAGGCGGGGTTGGGCAA
AGCGAAAGTAACATCATTGAAGAGAATCTTGCCGGCCCTGGGCATGAAATTGCGAGTGATGCGAAAAGG

Figure 48 (continued)

CTGTGGTACTTCCGCTCGGTTATTGATAACCTGGGCAGCTAGGACGATCTCGTCGAAACCGTTGATGTT
GTGTCCTACGATGTATAATTCTATGAAACGCGGCGTGCCTCTGACGTGAGGTAGCTTACTGAGCTCATC
AAAGGTTAGGTCTGTGGGGTCAGATAAGGCGTAGTGTTCGAGAGCCCATTCGTGCAGGTGAGGATTCGC
TTTAAGGAAGGAGGACCAGAGGTCCACTGCCAGTGCTGTTTGTAACTGGTCCCGGTACTGACGAAAATG
CCGTCCGACTGCCATTTTTTCTGGGGTGACGCAATAGAAGGTTTGGGGGTCCTGCCGCCAGCGATCCCA
CTTGAGTTTTATGGCGAGGTCATAGGCGATGTTGACGAGCCGCTGGTCTCCAGAGAGTTTCATGACCAG
CATGAAGGGGATTAGCTGCTTGCCAAAGGACCCCATCCAGGTGTAGGTTTCCACATCGTAGGTGAGAAA
GAGCCTTTCTGTGCGAGGATGAGAGCCAATCGGGAAGAACTGGATCTCCTGCCACCAGTTGGAGGAATG
GCTGTTGATGTGATGGAAGTAGAACTCCCTGCGACGCGCCGAGCATTCATGCTTGTGCTTGTACAGACG
GCCGCAGTAGTCGCAGCGTTGCACGGGTTGTATCTCGTGAATGAGTTGTACCTGGCTTCCCTTGACGAG
AAATTTCAGTGGGAAGCCGAGGCCTGGCGATTGTATCTCGTGCTTTACTATGTTGTCTGCATCGGCCTG
TTCATCTTCTGTCTCGATGGTGGTCATGCTGACGAGCCCTCGCGGGAGGCAAGTCCAGACCTCGGCGCG
GCAGGGGCGGAGCTCGAGGACGAGAGCGCGCAGGCTGGAGCTGTCCAGGGTCCTGAGACGCTGCGGACT
CAGGTTAGTAGGCAGTGTCAGGAGATTAACTTGCATGATCTTTTGGAGGGCGTGCGGGAGGTTCAGATA
GTACTTGATCTCAACGGGTCCGTTGGTGGAGATGTCGATGGCTTGCAGGGTTCCGTGTCCCTTGGGCGC
TACCACCGTGCCCTTGTTTTTCATTTTGGACGGCGGTGGCTCTGTTGCTTCTTGCATGTTTAGAAGCGG
TGTCGAGGGCGCGCACCGGGCGGCAGGGGCGGCTCGGGACCCGGCGGCATGGCTGGCAGTGGTACGTCG
GCGCCGCGCGCGGGTAGGTTCTGGTACTGCGCCCTGAGAAGACTCGCATGCGCGACGACGCGGCGGTTG
ACATCCTGGATCTGACGCCTCTGGGTGAAAGCTACCGGCCCCGTGAGCTTGAACCTGAAAGAGAGTTCA
ACAGAATCAATCTCGGTATCGTTGACGGCGGCTTGCCTAAGGATTTCTTGCACGTCACCAGAGTTGTCC
TGGTAGGCGATCTCCGCCATGAACTGCTCGATCTCTTCCTCTTGAAGATCTCCGCGGCCCGCTCTCTCG
ACGGTGGCCGCGAGGTCGTTGGAGATGCGCCCAATGAGTTGAGAGAATGCATTCATGCCCGCCTCGTTC
CAGACGCGGCTGTAGACCACGGCCCCCACGGGATCTCTCGCGCGCATGACCACCTGGGCGAGGTTGAGC
TCCACGTGGCGGGTGAAGACCGCATAGTTGCATAGGCGCTGGAAAAGGTAGTTGAGTGTGGTGGCGATG
TGCTCGGTGACGAAGAAATACATGATCCATCGTCTCAGCGGCATCTCGCTGACATCGCCCAGAGCTTCC
AAGCGCTCCATGGCCTCGTAGAAGTCCACGGCAAAATTAAAAAACTGGGAGTTTCGCGCGGACACGGTC
AACTCCTCTTCCAGAAGACGGATAAGTTCGGCGATGGTGGTGCGCACCTCGCGCTCGAAAGCCCCTGGG
ATTTCTTCCTCAATCTCTTCTTCTTCCACTAACATCTCTTCCTCTTCAGGTGGGGCTGCAGGAGGAGGG
GGAACGCGGCGACGCCGGCGGCGCACGGGCAGACGGTCGATGAATCTTTCAATGACCTCTCCGCGGCGG
CGGCGCATGGTTTCAGTGACGGCGCGGCCGTTCTCGCGCGGTCGCAGAGTAAAAACACCGCCCGCGCATC
TCCTTAAAGTGGTGACTGGGAGGTTCTCCGTTTGGGAGGGAGAGGGCGCTGATTATACATTTTATTAAT
TGGCCCGTAGGGACTGCACGCAGAGATCTGATCGTGTCAAGATCCACGGGATCTGAAAACCTTTCGACG
AAAGCGTCTAACCAGTCACAGTCACAAGGTAGGCTGAGTACGGCTTCTTGTGGGCGGGGGTGGTTATGT
GTTCGGTCTGGGTCTTCTGTTTCTTCTTCATCTCGGGAAGGTGAGACGATGCTGCTGGTGATGAAATTA
AAGTAGGCAGTTCTAAGACGGCGGATGGTGGCGAGGAGCACCAGGTCTTTGGGTCCGGCTTGCTGGATA
CGCAGGCGATTGGCCATTCCCCAAGCATTATCCTGACATCTAGCAAGATCTTTGTAGTAGTCTTGCATG
AGCCGTTCTACGGGCACTTCTTCCTCACCCGTTCTGCCATGCATACGTGTGAGTCCAAATCCGCGCATT
GGTTGTACCAGTGCCAAGTCAGCTACGACTCTTTCGGCGAGGATGGCTTGCTGTACTTGGGTAAGGGTG
GCTTGAAAGTCATCAAAATCCACAAAGCGGTGGTAAGCTCCTGTATTAATGGTGTAAGCACAGTTGGCC
ATGACTGACCAGTTAACTGTCTGGTGACCAGGGCGCACGAGCTCGGTGTATTTAAGGCGCGAATAGGCG
CGGGTGTCAAAGATGTAATCGTTGCAGGTGCGCACCAGATACTGGTACCCTATAAGAAAATGCGGCGGT
GGTTGGCGGTAGAGAGGCCATCGTTCTGTAGCTGGAGCGCCAGGGGCGAGGTCTTCCAACATAAGGCGG
TGATAGCCGTAGATGTACCTGGACATCCAGGTGATTCCTGCGGCGGTAGTAGAAGCCCGAGGAAACTCG
CGTACGCGGTTCCAAATGTTGCGTAGCGGCATGAAGTAGTTCAT

SEQ ID NO: 88 A NON-CODING SEQUENCE SUITABLE FOR INCLUSION INTO BX

Figure 48 (continued)

AAAATGATTAATAAAAAATCACTTACTTGAAATCAGCAATAAGGTCTCTGTTGAAATTTTCTCCCAGCA
GCACCTCACTTCCCTCTTCCCAACTCTGGTATTCTAAACCCCGTTCAGCGGCATACTTTCTCCATACTT
TAAAGGGGATGTCAAATTTTAGCTCCTCTCCTGTACCCACAATCTTCATGTCTTTCTTCCCAG

SEQ ID NO: 89 A NON-CODING SEQUENCE SUITABLE FOR INCLUSION INTO BY

CAAATAAAGTTTAACTTGTTTATTTGAAAATCAA

SEQ ID NO. 90 SPLICE ACCEPTOR SEQUENCE

TTTCTCTCTT CAGG

SEQ ID NO. 91 SPLICE ACCEPTOR SEQUENCE

TGCTAATCTT CCTTTCTCTC TTCAGG

Figure 49

SEQ ID NO: 93 Internal Ribosome Entry Sequence (IRES)

CGTTACTGGCCGAAGCCGCTTGGAATAAGGCCGGTGTGCGTTTGTCTATATGTTATTTTCCACCATATT
GCCGTCTTTTGGCAATGTGAGGGCCCGGAAACCTGGCCCTGTCTTCTTGACGAGCATTCCTAGGGGTCT
TTCCCCTCTCGCCAAAGGAATGCAAGGTCTGTTGAATGTCGTGAAGGAAGCAGTTCCTCTGGAAGCTTC
TTGAAGACAAACAACGTCTGTAGCGACCCTTTGCAGGCAGCGGAACCCCCCACCTGGCGACAGGTGCCT
CTGCGGCCAAAAGCCACGTGTATAAGATACACCTGCAAAGGCGGCACAACCCCAGTGCCACGTTGTGAG
TTGGATAGTTGTGGAAAGAGTCAAATGGCTCCCCTCAAGCGTATTCAACAAGGGGCTGAAGGATGCCCA
GAAGGTACCCCATTGTATGGGATCTGATCTGGGGCCTCGGTGCACATGCTTTTCATGTGTTTAGTCGAG
GTTAAAAAACGTCTAGGCCCCCCGAACCACGGGGACGTGGTTTTCCTTTGAAAAACACGATGATAATA

SEQ ID NO: 94 High efficiency self-cleavable P2A peptide sequence

GSGATNFSLLKQAGDVEENPGP

SEQ ID NO: 95 High efficiency self-cleavable F2A peptide sequence

GSGEGRGSLLTCGDVEENPGP

SEQ ID NO: 96 High efficiency self-cleavable E2A peptide sequence

GSGQCTNYALLKLAGDVESNPGP

SEQ ID NO: 97 High efficiency self-cleavable T2A peptide sequence

GSGVKQTLNFDLLKLAGDVESNPGP

SEQ ID NO: 98 Human CD80 amino acid sequence

MGHTRRQGTSPSKCPYLNFFQLLVLAGLSHFCSGVIHVTKEVKEVATLSCGHNVSVEELAQTRIYWQKE
KKMVLTMMSGDMNIWPEYKNRTIFDITNNLSIVILALRPSDEGTYECVVLKYEKDAFKREHLAEVTLSV
KADFPTPSISDFEIPTSNIRRIICSTSGGFPEPHLSWLENGEELNAINTTVSQDPETELYAVSSKLDFN
MTTNHSFMCLIKYGHLRVNQTFNWNTTKQEHFPDNLLPSWAITLISVNGIFVICCLTYCFAPRCRERRR
NERLRRESVRPV

SEQ ID NO. 99 poly adenylation sequence (SV40 late polyA sequence)

CAGACATGATAAGATACATTGATGAGTTTGGACAAACCACAACTAGAATGCAGTGAAAAAAATGCTTTA
TTTGTGAAATTTGTGATGCTATTGCTTTATTTGTAACCATTATAAGCTGCAATAAACAAGTTAACAACA
ACAATTGCATTCATTTTATGTTTCAGGTTCAGGGGGAGGTGTGGGAGGTTTTTT

SEQ ID NO. 100

Figure 50

NG-348 virus genome sequence comprising the EnAd genome with a transgene cassette that encodes a membrane-anchored chimeric form of the single chain Fv anti-human CD3e and the T lymphocyte activation antigen, CD80 inserted in the region Bγ. The transgene cassette contains a 5' SSA, membrane-anchored anti-CD3ε cDNA sequence, P2A peptide, human CD80 cDNA sequence and a 3' poly(A) sequence

Figure 50 (continued)

TCTATCTATATAATATACCTTATAGATGGAATGGTGCCAATATGTAAATGAGGTGATTTTAAAAAGTGT
GGATCGTGTGGTGATTGGCTGTGGGGTTAACGGCTAAAAGGGGCGGTGCGACCGTGGGAAAATGACGTT
TTGTGGGGGTGGAGTTTTTTTGCAAGTTGTCGCGGGAAATGTGACGCATAAAAAGGCTTTTTTCTCACG
GAACTACTTAGTTTTCCCACGGTATTTAACAGGAAATGAGGTAGTTTTGACCGGATGCAAGTGAAAATT
GTTGATTTTCGCGCGAAAACTGAATGAGGAAGTGTTTTTCTGAATAATGTGGTATTTATGGCAGGGTGG
AGTATTTGTTCAGGGCCAGGTAGACTTTGACCCATTACGTGGAGGTTTCGATTACCGTGTTTTTTACCT
GAATTTCCGCGTACCGTGTCAAAGTCTTCTGTTTTTACGTAGGTGTCAGCTGATCGCTAGGGTATTTAT
ACCTCAGGGTTTGTGTCAAGAGGCCACTCTTGAGTGCCAGCGAGAAGAGTTTTCTCCTCTGCGCCGGCA
GTTTAATAATAAAAAAATGAGAGATTTGCGATTTCTGCCTCAGGAAATAATCTCTGCTGAGACTGGAAA
TGAAATATTGGAGCTTGTGGTGCACGCCCTGATGGGAGACGATCCGGAGCCACCTGTGCAGCTTTTTGA
GCCTCCTACGCTTCAGGAACTGTATGATTTAGAGGTAGAGGGATCGGAGGATTCTAATGAGGAAGCTGT
AAATGGCTTTTTTACCGATTCTATGCTTTTAGCTGCTAATGAAGGGTTAGAATTAGATCCGCCTTTGGA
CACTTTTGATACTCCAGGGGTAATTGTGGAAAGCGGTACAGGTGTAAGAAAATTACCTGATTTGAGTTC
CGTGGACTGTGATTTGCACTGCTATGAAGACGGGTTTCCTCCGAGTGATGAGGAGGACCATGAAAAGGA
GCAGTCCATGCAGACTGCAGCGGGTGAGGGAGTGAAGGCTGCCAATGTTGGTTTTCAGTTGGATTGCCC
GGAGCTTCCTGGACATGGCTGTAAGTCTTGTGAATTTCACAGGAAAAATACTGGAGTAAAGGAACTGTT
ATGTTCGCTTTGTTATATGAGAACGCACTGCCACTTTATTTACAGTAAGTGTGTTTAAGTTAAAATTTA
AAGGAATATGCTGTTTTTCACATGTATATTGAGTGTGAGTTTTGTGCTTCTTATTATAGGTCCTGTGTC
TGATGCTGATGAATCACCATCTCCTGATTCTACTACCTCACCTCCTGAGATTCAAGCACCTGTTCCTGT
GGACGTGCGCAAGCCCATTCCTGTGAAGCTTAAGCCTGGGAAACGTCCAGCAGTGGAAAAACTTGAGGA
CTTGTTACAGGGTGGGGACGGACCTTTGGACTTGAGTACACGGAAACGTCCAAGACAATAAGTGTTCCA
TATCCGTGTTTACTTAAGGTGACGTCAATATTTGTGTGACAGTGCAATGTAATAAAAATATGTTAACTG
TTCACTGGTTTTTATTGCTTTTTGGGCGGGGACTCAGGTATATAAGTAGAAGCAGACCTGTGTGGTTAG
CTCATAGGAGCTGGCTTTCATCCATGGAGGTTTGGGCCATTTTGGAAGACCTTAGGAAGACTAGGCAAC
TGTTAGAGAACGCTTCGGACGGAGTCTCCGGTTTTTGGAGATTCTGGTTCGCTAGTGAATTAGCTAGGG
TAGTTTTTAGGATAAAACAGGACTATAAACAAGAATTTGAAAAGTTGTTGGTAGATTGCCCAGGACTTT
TTGAAGCTCTTAATTTGGGCCATCAGGTTCACTTTAAAGAAAAAGTTTTATCAGTTTTAGACTTTTCAA
CCCCAGGTAGAACTGCTGCTGCTGTGGCTTTTCTTACTTTTATATTAGATAAATGGATCCCGCAGACTC
ATTTCAGCAGGGGATACGTTTTGGATTTCATAGCCACAGCATTGTGGAGAACATGGAAGGTTCGCAAGA
TGAGGACAATCTTAGGTTACTGGCCAGTGCAGCCTTTGGGTGTAGCGGGAATCCTGAGGCATCCACCGG
TCATGCCAGCGGTTCTGGAGGAGGAACAGCAAGAGGACAACCCGAGAGCCGGCCTGGACCCTCCAGTGG
AGGAGGCGGAGTAGCTGACTTGTCTCCTGAACTGCAACGGGTGCTTACTGGATCTACGTCCACTGGACG
GGATAGGGGCGTTAAGAGGGAGAGGGCATCTAGTGGTACTGATGCTAGATCTGAGTTGGCTTTAAGTTT
AATGAGTCGCAGACGTCCTGAAACCATTTGGTGGCATGAGGTTCAGAAAGAGGGAAGGGATGAAGTTTC
TGTATTGCAGGAGAAATATTCACTGGAACAGGTGAAAACATGTTGGTTGGAGCCTGAGGATGATTGGGA
GGTGGCCATTAAAAATTATGCCAAGATAGCTTTGAGGCCTGATAAACAGTATAAGATTACTAGACGGAT
TAATATCCGGAATGCTTGTTACATATCTGGAAATGGGGCTGAGGTGGTAATAGATACTCAAGACAAGGC
AGTTATTAGATGCTGCATGATGGATATGTGGCCTGGGGTAGTCGGTATGGAAGCAGTAACTTTTGTAAA
TGTTAAGTTTAGGGGAGATGGTTATAATGGAATAGTGTTTATGGCCAATACCAAACTTATATTGCATGG
TTGTAGCTTTTTTGGTTTCAACAATACCTGTGTAGATGCCTGGGGACAGGTTAGTGTACGGGGATGTAG
TTTCTATGCGTGTTGGATTGCCACAGCTGGCAGAACCAAGAGTCAATTGTCTCTGAAGAAATGCATATT
TCAAAGATGTAACCTGGGCATTCTGAATGAAGGCGAAGCAAGGGTCCGCCACTGCGCTTCTACAGATAC
TGGATGTTTTATTTTGATTAAGGGAAATGCCAGCGTAAAGCATAACATGATTTGCGGTGCTTCCGATGA
GAGGCCTTATCAAATGCTCACTTGTGCTGGTGGGCATTGTAATATGCTGGCTACTGTGCATATTGTTTC
CCATCAACGCAAAAAATGGCCTGTTTTTGATCACAATGTGATGACGAAGTGTACCATGCATGCAGGTGG
GCGTAGAGGAATGTTTATGCCTTACCAGTGTAACATGAATCATGTGAAAGTGTTGTTGGAACCAGATGC
CTTTTCCAGAATGAGCCTAACAGGAATTTTTGACATGAACATGCAAATCTGGAAGATCCTGAGGTATGA
TGATACGAGATCGAGGGTACGCGCATGCGAATGCGGAGGCAAGCATGCCAGGTTCCAGCCGGTGTGTGT
AGATGTGACTGAAGATCTCAGACCGGATCATTTGGTTATTGCCCGCACTGGAGCAGAGTTCGGATCCAG
TGGAGAAGAAACTGACTAAGGTGAGTATTGGGAAAACTTTGGGGTGGGATTTTCAGATGGACAGATTGA
GTAAAAATTTGTTTTTTCTGTCTTGCAGCTGTCATGAGTGGAAACGCTTCTTTTAAGGGGGGAGTCTTC

Figure 50 (continued)

AGCCCTTATCTGACAGGGCGTCTCCCATCCTGGGCAGGAGTTCGTCAGAATGTTATGGGATCTACTGTG
GATGGAAGACCCGTCCAACCCGCCAATTCTTCAACGCTGACCTATGCTACTTTAAGTTCTTCACCTTTG
GACGCAGCTGCAGCTGCCGCCGCCGCTTCTGTTGCCGCTAACACTGTGCTTGGAATGGGTTACTATGGA
AGCATCATGGCTAATTCCACTTCCTCTAATAACCCTTCTACCCTGACTCAGGACAAGTTACTTGTCCTT
TTGGCCCAGCTGGAGGCTTTGACCCAACGTCTGGGTGAACTTTCTCAGCAGGTGGTCGAGTTGCGAGTA
CAAACTGAGTCTGCTGTCGGCACGGCAAAGTCTAAATAAAAAAATCCCAGAATCAATGAATAAATAAAC
AAGCTTGTTGTTGATTTAAAATCAAGTGTTTTTATTTCATTTTTCGCGCACGGTATGCCCTAGACCACC
GATCTCTATCATTGAGAACTCGGTGGATTTTTTCCAGGATCCTATAGAGGTGGGATTGAATGTTTAGAT
ACATGGGCATTAGGCCGTCTTTGGGGTGGAGATAGCTCCATTGAAGGGATTCATGCTCCGGGGTAGTGT
TGTAAATCACCCAGTCATAACAAGGTCGCAGTGCATGGTGTTGCACAATATCTTTTAGAAGTAGGCTGA
TTGCCACAGATAAGCCCTTGGTGTAGGTGTTTACAAACCGGTTGAGCTGGGATGGGTGCATTCGGGGTG
AAATTATGTGCATTTTGGATTGGATTTTTAAGTTGGCAATATTGCCGCCAAGATCCCGTCTTGGGTTCA
TGTTATGAAGGACCACCAAGACGGTGTATCCGGTACATTTAGGAAATTTATCGTGCAGCTTGGATGGAA
AAGCGTGGAAAAATTTGGAGACACCCTTGTGTCCTCCAAGATTTTCCATGCACTCATCCATGATAATAG
CAATGGGGCCGTGGGCAGCGGCGCGGGCAAACACGTTCCGTGGGTCTGACACATCATAGTTATGTTCCT
GAGTTAAATCATCATAAGCCATTTTAATGAATTTGGGGCGGAGAGTACCAGATTGGGGTATGAATGTTC
CTTCGGGCCCCGGAGCATAGTTCCCCTCACAGATTTGCATTTCCCAAGCTTTCAGTTCCGAGGGTGGAA
TCATGTCCACCTGGGGGGCTATGAAAAACACCGTTTCTGGGGCGGGGGTGATTAATTGTGATGATAGCA
AATTTCTGAGCAATTGAGATTTGCCACATCCGGTGGGGCCATAAATGATTCCGATTACGGGTTGCAGGT
GGTAGTTTAGGGAACGGCAACTGCCGTCTTCTCGAAGCAAGGGGGCCACCTCGTTCATCATTTCCCTTA
CATGCATATTTTCCCGCACCAAATCCATTAGGAGGCGCTCTCCTCCTAGTGATAGAAGTTCTTGTAGTG
AGGAAAAGTTTTTCAGCGGTTTCAGACCGTCAGCCATGGGCATTTTGGAGAGAGTTTGCTGCAAAAGTT
CTAGTCTGTTCCACAGTTCAGTGATGTGTTCTATGGCATCTCGATCCAGCAGACCTCCTCGTTTCGCGG
GTTTGGACGGCTCCTGGAATAGGGTATGAGACGATGGGCGTCCAGCGCTGCCAGGGTTCGGTCCTTCCA
GGGTCTCAGTGTTCGAGTCAGGGTTGTTTCCGTCACAGTGAAGGGGTGTGCGCCTGCTTGGGCGCTTGC
CAGGGTGCGCTTCAGACTCATCCTGCTGGTCGAAAACTTCTGTCGCTTGGCGCCCTGTATGTCGGCCAA
GTAGCAGTTTACCATGAGTTCGTAGTTGAGCGCCTCGGCTGCGTGGCCTTTGGCGCGGAGCTTACCTTT
GGAAGTTTTCTTGCATACCGGGCAGTATAGGCATTTCAGCGCATACAACTTGGGCGCAAGGAAAACGGA
TTCTGGGGAGTATGCATCTGCGCCGCAGGAGGCGCAAACAGTTTCACATTCCACCAGCCAGGTTAAATC
CGGTTCATTGGGGTCAAAAACAAGTTTTCCGCCATATTTTTTGATGCGTTTCTTACCTTTGGTCTCCAT
GAGTTCGTGTCCTCGTTGAGTGACAAACAGGCTGTCCGTGTCCCCGTAGACTGATTTACAGGCCTCTT
CTCCAGTGGAGTGCCTCGGTCTTCTTCGTACAGGAACTCTGACCACTCTGATACAAAGGCGCGCGTCCA
GGCCAGCACAAAGGAGGCTATGTGGGAGGGGTAGCGATCGTTGTCAACCAGGGGGTCCACCTTTTCCAA
AGTATGCAAACACATGTCACCCTCTTCAACATCCAGGAATGTGATTGGCTTGTAGGTGTATTTCACGTG
ACCTGGGGTCCCCGCTGGGGGGGTATAAAAGGGGGCGGTTCTTTGCTCTTCCTCACTGTCTTCCGGATC
GCTGTCCAGGAACGTCAGCTGTTGGGGTAGGTATTCCCTCTCGAAGGCGGGCATGACCTCTGCACTCAG
GTTGTCAGTTTCTAAGAACGAGGAGGATTTGATATTGACAGTGCCGGTTGAGATGCCTTTCATGAGGTT
TTCGTCCATCTGGTCAGAAAACACAATTTTTTTATTGTCAAGTTTGGTGGCAAATGATCCATACAGGGC
GTTGGATAAAAGTTTGGCAATGGATCGCATGGTTTGGTTCTTTTCCTTGTCCGCGCGCTCTTTGGCGGC
GATGTTGAGTTGGACATACTCGCGTGCCAGGCACTTCCATTCGGGGAAGATAGTTGTTAATTCATCTGG
CACGATTCTCACTTGCCACCCTCGATTATGCAAGGTAATTAAATCCACACTGGTGGCCACCTCGCCTCG
AAGGGGTTCATTGGTCCAACAGAGCCTACCTCCTTTCCTAGAACAGAAAGGGGGAAGTGGGTCTAGCAT
AAGTTCATCGGGAGGGTCTGCATCCATGGTAAAGATTCCCGGAAGTAAATCCTTATCAAAATAGCTGAT
GGGAGTGGGGTCATCTAAGGCCATTTGCCATTCTCGAGCTGCCAGTGCGCGCTCATATGGGTTAAGGGG
ACTGCCCCATGGCATGGGATGGGTGAGTGCAGAGGCATACATGCCACAGATGTCATAGACGTAGATGGG
ATCCTCAAAGATGCCTATGTAGGTTGGATAGCATCGCCCCCCTCTGATACTTGCTCGCACATAGTCATA
TAGTTCATGTGATGGCGCTAGCAGCCCCGGACCCAAGTTGGTGCGATTGGGTTTTTCTGTTCTGTAGAC
GATCTGGCGAAAGATGGCGTGAGAATTGGAAGAGATGGTGGGTCTTTGAAAAATGTTGAAATGGGCATG
AGGTAGACCTACAGAGTCTCTGACAAAGTGGGCATAAGATTCTTGAAGCTTGGTTACCAGTTCGGCGGT
GACAAGTACGTCTAGGGCGCAGTAGTCAAGTGTTTCTTGAATGATGTCATAACCTGGTTGGTTTTTCTT
TTCCCACAGTTCGCGGTTGAGAAGGTATTCTTCGCGATCCTTCCAGTACTCTTCTAGCGGAAACCCGTC

Figure 50 (continued)

TTTGTCTGCACGGTAAGATCCTAGCATGTAGAACTGATTAACTGCCTTGTAAGGGCAGCAGCCCTTCTC
TACGGGTAGAGAGTATGCTTGAGCAGCTTTTCGTAGCGAAGCGTGAGTAAGGGCAAAGGTGTCTCTGAC
CATGACTTTGAGGAATTGGTATTTGAAGTCGATGTCGTCACAGGCTCCCTGTTCCCAGAGTTGGAAGTC
TACCCGTTTCTTGTAGGCGGGGTTGGGCAAAGCGAAAGTAACATCATTGAAGAGAATCTTGCCGGCCCT
GGGCATGAAATTGCGAGTGATGCGAAAAGGCTGTGGTACTTCCGCTCGGTTATTGATAACCTGGGCAGC
TAGGACGATCTCGTCGAAACCGTTGATGTTGTGTCCTACGATGTATAATTCTATGAAACGCGGCGTGCC
TCTGACGTGAGGTAGCTTACTGAGCTCATCAAAGGTTAGGTCTGTGGGGTCAGATAAGGCGTAGTGTTC
GAGAGCCCATTCGTGCAGGTGAGGATTCGCTTTAAGGAAGGAGGACCAGAGGTCCACTGCCAGTGCTGT
TTGTAACTGGTCCCGGTACTGACGAAAATGCCGTCCGACTGCCATTTTTTCTGGGGTGACGCAATAGAA
GGTTTGGGGGTCCTGCCGCCAGCGATCCCACTTGAGTTTTATGGCGAGGTCATAGGCGATGTTGACGAG
CCGCTGGTCTCCAGAGAGTTTCATGACCAGCATGAAGGGGATTAGCTGCTTGCCAAAGGACCCCATCCA
GGTGTAGGTTTCCACATCGTAGGTGAGAAAGAGCCTTTCTGTGCGAGGATGAGAGCCAATCGGGAAGAA
CTGGATCTCCTGCCACCAGTTGGAGGAATGGCTGTTGATGTGATGGAAGTAGAACTCCCTGCGACGCGC
CGAGCATTCATGCTTGTGCTTGTACAGACGGCCGCAGTAGTCGCAGCGTTGCACGGGTTGTATCTCGTG
AATGAGTTGTACCTGGCTTCCCTTGACGAGAAATTTCAGTGGGAAGCCGAGGCCTGGCGATTGTATCTC
GTGCTTTACTATGTTGTCTGCATCGGCCTGTTCATCTTCTGTCTCGATGGTGGTCATGCTGACGAGCCC
TCGCGGGAGGCAAGTCCAGACCTCGGCGCGGCAGGGGCGGAGCTCGAGGACGAGAGCGCGCAGGCTGGA
GCTGTCCAGGGTCCTGAGACGCTGCGGACTCAGGTTAGTAGGCAGTGTCAGGAGATTAACTTGCATGAT
CTTTTGGAGGGCGTGCGGGAGGTTCAGATAGTACTTGATCTCAACGGGTCCGTTGGTGGAGATGTCGAT
GGCTTGCAGGGTTCCGTGTCCCTTGGGCGCTACCACCGTGCCCTTGTTTTTCATTTTGGACGGCGGTGG
CTCTGTTGCTTCTTGCATGTTTAGAAGCGGTGTCGAGGGCGCGCACCGGGCGGCAGGGGCGGCTCGGGA
CCCGGCGGCATGGCTGGCAGTGGTACGTCGGCGCCGCGCGCGGGTAGGTTCTGGTACTGCGCCCTGAGA
AGACTCGCATGCGCGACGACGCGGCGGTTGACATCCTGGATCTGACGCCTCTGGGTGAAAGCTACCGGC
CCCGTGAGCTTGAACCTGAAAGAGAGTTCAACAGAATCAATCTCGGTATCGTTGACGGCGGCTTGCCTA
AGGATTTCTTGCACGTCACCAGAGTTGTCCTGGTAGGCGATCTCCGCCATGAACTGCTCGATCTCTTCC
TCTTGAAGATCTCCGCGGCCCGCTCTCTCGACGGTGGCCGCGAGGTCGTTGGAGATGCGCCCAATGAGT
TGAGAGAATGCATTCATGCCCGCCTCGTTCCAGACGCGGCTGTAGACCACGGCCCCCACGGATCTCTC
GCGCGCATGACCACCTGGGCGAGGTTGAGCTCCACGTGGCGGGTGAAGACCGCATAGTTGCATAGGCGC
TGGAAAAGGTAGTTGAGTGTGGTGGCGATGTGCTCGGTGACGAAGAAATACATGATCCATCGTCTCAGC
GGCATCTCGCTGACATCGCCCAGAGCTTCCAAGCGCTCCATGGCCTCGTAGAAGTCCACGGCAAAATTA
AAAAACTGGGAGTTTCGCGCGGACACGGTCAACTCCTCTTCCAGAAGACGGATAAGTTCGGCGATGGTG
GTGCGCACCTCGCGCTCGAAAGCCCCTGGGATTTCTTCCTCAATCTCTTCTTCTTCCACTAACATCTCT
TCCTCTTCAGGTGGGGCTGCAGGAGGAGGGGGAACGCGGCGACGCCGGCGGCGCACGGGCAGACGGTCG
ATGAATCTTTCAATGACCTCTCCGCGGCGGCGGCGCATGGTTTCAGTGACGGCGCGGCCGTTCTCGCGC
GGTCGCAGAGTAAAAACACCGCCGCGCATCTCCTTAAAGTGGTGACTGGGAGGTTCTCCGTTTGGGAGG
GAGAGGGCGCTGATTATACATTTTATTAATTGGCCCGTAGGGACTGCACGCAGAGATCTGATCGTGTCA
AGATCCACGGGATCTGAAAACCTTTCGACGAAAGCGTCTAACCAGTCACAGTCACAAGGTAGGCTGAGT
ACGGCTTCTTGTGGGCGGGGGTGGTTATGTGTTCGGTCTGGGTCTTCTGTTTCTTCTTCATCTCGGGAA
GGTGAGACGATGCTGCTGGTGATGAAATTAAAGTAGGCAGTTCTAAGACGGCGGATGGTGGCGAGGAGC
ACCAGGTCTTTGGGTCCGGCTTGCTGGATACGCAGGCGATTGGCCATTCCCCAAGCATTATCCTGACAT
CTAGCAAGATCTTTGTAGTAGTCTTGCATGAGCCGTTCTACGGGCACTTCTTCCTCACCCGTTCTGCCA
TGCATACGTGTGAGTCCAAATCCGCGCATTGGTTGTACCAGTGCCAAGTCAGCTACGACTCTTTCGGCG
AGGATGGCTTGCTGTACTTGGGTAAGGGTGGCTTGAAAGTCATCAAAATCCACAAAGCGGTGGTAAGCT
CCTGTATTAATGGTGTAAGCACAGTTGGCCATGACTGACCAGTTAACTGTCTGGTGACCAGGGCGCACG
AGCTCGGTGTATTTAAGGCGCGAATAGGCGCGGGTGTCAAAGATGTAATCGTTGCAGGTGCGCACCAGA
TACTGGTACCCTATAAGAAAATGCGGCGGTGGTTGGCGGTAGAGAGGCCATCGTTCTGTAGCTGGAGCG
CCAGGGGCGAGGTCTTCCAACATAAGGCGGTGATAGCCGTAGATGTACCTGGACATCCAGGTGATTCCT
GCGGCGGTAGTAGAAGCCCGAGGAAACTCGCGTACGCGGTTCCAAATGTTGCGTAGCGGCATGAAGTAG
TTCATTGTAGGCACGGTTTGACCAGTGAGGCGCGCGCAGTCATTGATGCTCTATAGACACGGAGAAAAT
GAAAGCGTTCAGCGACTCGACTCCGTAGCCTGGAGGAACGTGAACGGGTTGGGTCGCGGTGTACCCCGG
TTCGAGACTTGTACTCGAGCCGGCCGGAGCCGCGGCTAACGTGGTATTGGCACTCCCGTCTCGACCCAG

Figure 50 (continued)

CCTACAAAAATCCAGGATACGGAATCGAGTCGTTTTGCTGGTTTCCGAATGGCAGGGAAGTGAGTCCTA
TTTTTTTTTTTTGCCGCTCAGATGCATCCCGTGCTGCGACAGATGCGCCCCCAACAACAGCCCCCCTCG
CAGCAGCAGCAGCAGCAATCACAAAAGGCTGTCCCTGCAACTACTGCAACTGCCGCCGTGAGCGGTGCG
GGACAGCCCGCCTATGATCTGGACTTGGAAGAGGGCGAAGGACTGGCACGTCTAGGTGCGCCTTCACCC
GAGCGGCATCCGCGAGTTCAACTGAAAAAAGATTCTCGCGAGGCGTATGTGCCCCAACAGAACCTATTT
AGAGACAGAAGCGGCGAGGAGCCGGAGGAGATGCGAGCTTCCCGCTTTAACGCGGGTCGTGAGCTGCGT
CACGGTTTGGACCGAAGACGAGTGTTGCGGGACGAGGATTTCGAAGTTGATGAAATGACAGGGATCAGT
CCTGCCAGGGCACACGTGGCTGCAGCCAACCTTGTATCGGCTTACGAGCAGACAGTAAAGGAAGAGCGT
AACTTCCAAAAGTCTTTTAATAATCATGTGCGAACCCTGATTGCCCGCGAAGAAGTTACCCTTGGTTTG
ATGCATTTGTGGGATTTGATGGAAGCTATCATTCAGAACCCTACTAGCAAACCTCTGACCGCCCAGCTG
TTTCTGGTGGTGCAACACAGCAGAGACAATGAGGCTTTCAGAGAGGCGCTGCTGAACATCACCGAACCC
GAGGGGAGATGGTTGTATGATCTTATCAACATTCTACAGAGTATCATAGTGCAGGAGCGGAGCCTGGGC
CTGGCCGAGAAGGTGGCTGCCATCAATTACTCGGTTTTGAGCTTGGGAAAATATTACGCTCGCAAAATC
TACAAGACTCCATACGTTCCCATAGACAAGGAGGTGAAGATAGATGGGTTCTACATGCGCATGACGCTC
AAGGTCTTGACCCTGAGCGATGATCTTGGGGTGTATCGCAATGACAGAATGCATCGCGCGGTTAGCGCC
AGCAGGAGGCGCGAGTTAAGCGACAGGGAACTGATGCACAGTTTGCAAAGAGCTCTGACTGGAGCTGGA
ACCGAGGGTGAGAATTACTTCGACATGGGAGCTGACTTGCAGTGGCAGCCTAGTCGCAGGGCTCTGAGC
GCCGCGACGGCAGGATGTGAGCTTCCTTACATAGAAGAGGCGGATGAAGGCGAGGAGGAAGAGGGCGAG
TACTTGGAAGACTGATGGCACAACCCGTGTTTTTTGCTAGATGGAACAGCAAGCACCGGATCCCGCAAT
GCGGGCGGCGCTGCAGAGCCAGCCGTCCGGCATTAACTCCTCGGACGATTGGACCCAGGCCATGCAACG
TATCATGGCGTTGACGACTCGCAACCCCGAAGCCTTTAGACAGCAACCCCAGGCCAACCGTCTATCGGC
CATCATGGAAGCTGTAGTGCCTTCCCGCTCTAATCCCACTCATGAGAAGGTCCTGGCCATCGTGAACGC
GTTGGTGGAGAACAAAGCTATTCGTCCAGATGAGGCCGGACTGGTATACAACGCTCTCTTAGAACGCGT
GGCTCGCTACAACAGTAGCAATGTGCAAACCAATTTGGACCGTATGATAACAGATGTACGCGAAGCCGT
GTCTCAGCGCGAAAGGTTCCAGCGTGATGCCAACCTGGGTTCGCTGGTGGCGTTAAATGCTTTCTTGAG
TACTCAGCCTGCTAATGTGCCGCGTGGTCAACAGGATTATACTAACTTTTTAAGTGCTTTGAGACTGAT
GGTATCAGAAGTACCTCAGAGCGAAGTGTATCAGTCCGGTCCTGATTACTTCTTTCAGACTAGCAGACA
GGGCTTGCAGACGGTAAATCTGAGCCAAGCTTTTAAAAACCTTAAAGGTTTGTGGGGAGTGCATGCCCC
GGTAGGAGAAAGAGCAACCGTGTCTAGCTTGTTAACTCCGAACTCCCGCCTATTATTACTGTTGGTAGC
TCCTTTCACCGACAGCGGTAGCATCGACCGTAATTCCTATTTGGGTTACCTACTAAACCTGTATCGCGA
AGCCATAGGGCAAAGTCAGGTGGACGAGCAGACCTATCAAGAAATTACCCAAGTCAGTCGCGCTTTGGG
ACAGGAAGACACTGGCAGTTTGGAAGCCACTCTGAACTTCTTGCTTACCAATCGGTCTCAAAAGATCCC
TCCTCAATATGCTCTTACTGCGGAGGAGGAGAGGATCCTTAGATATGTGCAGCAGAGCGTGGGATTGTT
TCTGATGCAAGAGGGGGCAACTCCGACTGCAGCACTGGACATGACAGCGCGAAATATGGAGCCCAGCAT
GTATGCCAGTAACCGACCTTTCATTAACAAACTGCTGGACTACTTGCACAGAGCTGCCGCTATGAACTC
TGATTATTTCACCAATGCCATCTTAAACCCGCACTGGCTGCCCCCACCTGGTTTCTACACGGGCGAATA
TGACATGCCCGACCCTAATGACGGATTTCTGTGGGACGACGTGGACAGCGATGTTTTTTCACCTCTTTC
TGATCATCGCACGTGGAAAAAGGAAGGCGGCGATAGAATGCATTCTTCTGCATCGCTGTCCGGGGTCAT
GGGTGCTACCGCGGCTGAGCCCGAGTCTGCAAGTCCTTTTCCTAGTCTACCCTTTTCTCTACACAGTGT
ACGTAGCAGCGAAGTGGGTAGAATAAGTCGCCCGAGTTTAATGGGCGAAGAGGAGTATCTAAACGATTC
CTTGCTCAGACCGGCAAGAGAAAAAAATTTCCCAAACAATGGAATAGAAAGTTTGGTGGATAAAATGAG
TAGATGGAAGACTTATGCTCAGGATCACAGAGACGAGCCTGGGATCATGGGGATTACAAGTAGAGCGAG
CCGTAGACGCCAGCGCCATGACAGACAGAGGGGTCTTGTGTGGGACGATGAGGATTCGGCCGATGATAG
CAGCGTGCTGGACTTGGGTGGGAGAGGAAGGGGCAACCCGTTTGCTCATTTGCGCCCTCGCTTGGGTGG
TATGTTGTAAAAAAAAATAAAAAAAAAACTCACCAAGGCCATGGCGACGAGCGTACGTTCGTTCTTCTT
TATTATCTGTGTCTAGTATAATGAGGCGAGTCGTGCTAGGCGGAGCGGTGGTGTATCCGGAGGGTCCTC
CTCCTTCGTACGAGAGCGTGATGCAGCAGCAGCAGGCGACGGCGGTGATGCAATCCCCACTGGAGGCTC
CCTTTGTGCCTCCGCGATACCTGGCACCTACGGAGGGCAGAAACAGCATTCGTTATTCGGAACTGGCAC
CTCAGTACGATACCACCAGGTTGTATCTGGTGGACAACAAGTCGGCGGACATTGCTTCTCTGAACTATC
AGAATGACCACAGCAACTTCTTGACCACGGTGGTGCAAAACAATGACTTTACCCCTACGGAAGCCAGCA
CCCAGACCATTAACTTTGATGAACGATCGCGGTGGGGCGGTCAGCTAAAGACCATCATGCATACTAACA

Figure 50 (continued)

TGCCAAACGTGAACGAGTATATGTTTAGTAACAAGTTCAAAGCGCGTGTGATGGTGTCCAGAAAACCTC
CCGACGGTGCTGCAGTTGGGGATACTTATGATCACAAGCAGGATATTTTGAAATATGAGTGGTTCGAGT
TTACTTTGCCAGAAGGCAACTTTTCAGTTACTATGACTATTGATTTGATGAACAATGCCATCATAGATA
ATTACTTGAAAGTGGGTAGACAGAATGGAGTGCTTGAAAGTGACATTGGTGTTAAGTTCGACACCAGGA
ACTTCAAGCTGGGATGGGATCCCGAAACCAAGTTGATCATGCCTGGAGTGTATACGTATGAAGCCTTCC
ATCCTGACATTGTCTTACTGCCTGGCTGCGGAGTGGATTTTACCGAGAGTCGTTTGAGCAACCTTCTTG
GTATCAGAAAAAAACAGCCATTTCAAGAGGGTTTTAAGATTTTGTATGAAGATTTAGAAGGTGGTAATA
TTCCGGCCCTCTTGGATGTAGATGCCTATGAGAACAGTAAGAAAGAACAAAAAGCCAAAATAGAAGCTG
CTACAGCTGCTGCAGAAGCTAAGGCAAACATAGTTGCCAGCGACTCTACAAGGGTTGCTAACGCTGGAG
AGGTCAGAGGAGACAATTTTGCGCCAACACCTGTTCCGACTGCAGAATCATTATTGGCCGATGTGTCTG
AAGGAACGGACGTGAAACTCACTATTCAACCTGTAGAAAAAGATAGTAAGAATAGAAGCTATAATGTGT
TGGAAGACAAAATCAACACAGCCTATCGCAGTTGGTATCTTTCGTACAATTATGGCGATCCCGAAAAAG
GAGTGCGTTCCTGGACATTGCTCACCACCTCAGATGTCACCTGCGGAGCAGAGCAGGTCTACTGGTCGC
TTCCAGACATGATGAAGGATCCTGTCACTTTCCGCTCCACTAGACAAGTCAGTAACTACCCTGTGGTGG
GTGCAGAGCTTATGCCCGTCTTCTCAAAGAGCTTCTACAACGAACAAGCTGTGTACTCCCAGCAGCTCC
GCCAGTCCACCTCGCTTACGCACGTCTTCAACCGCTTTCCTGAGAACCAGATTTTAATCCGTCCGCCGG
CGCCCACCATTACCACCGTCAGTGAAAACGTTCCTGCTCTCACAGATCACGGGACCCTGCCGTTGCGCA
GCAGTATCCGGGGAGTCCAACGTGTGACCGTTACTGACGCCAGACGCCGCACCTGTCCCTACGTGTACA
AGGCACTGGGCATAGTCGCACCGCGCGTCCTTTCAAGCCGCACTTTCTAAAAAAAAAAAAAAATGTCCAT
TCTTATCTCGCCCAGTAATAACACCGGTTGGGGTCTGCGCGCTCCAAGCAAGATGTACGGAGGCGCACG
CAAACGTTCTACCCAACATCCTGTCCGTGTTCGCGGACATTTTCGCGCTCCATGGGGCGCCCTCAAGGG
CCGCACTCGCGTTCGAACCACCGTCGATGATGTAATCGATCAGGTGGTTGCCGACGCCCGTAATTATAC
TCCTACTGCGCCTACATCTACTGTGGATGCAGTTATTGACAGTGTAGTGGCTGACGCTCGCAACTATGC
TCGACGTAAGAGCCGGCGAAGGCGCATTGCCAGACGCCACCGAGCTACCACTGCCATGCGAGCCGCAAG
AGCTCTGCTACGAAGAGCTAGACGCGTGGGGCGAAGAGCCATGCTTAGGGCGGCCAGACGTGCAGCTTC
GGGCGCCAGCGCCGGCAGGTCCCGCAGGCAAGCAGCCGCTGTCGCAGCGGCGACTATTGCCGACATGGC
CCAATCGCGAAGAGGCAATGTATACTGGGTGCGTGACGCTGCCACCGGTCAACGTGTACCCGTGCGCAC
CCGTCCCCCTCGCACTTAGAAGATACTGAGCAGTCTCCGATGTTGTGTCCCAGCGGCGAGGATGTCCAA
GCGCAAATACAAGGAAGAAATGCTGCAGGTTATCGCACCTGAAGTCTACGGCCAACCGTTGAAGGATGA
AAAAAAACCCCGCAAAATCAAGCGGGTTAAAAAGGACAAAAAAGAAGAGGAAGATGGCGATGATGGGCT
GGCGGAGTTTGTGCGCGAGTTTGCCCCACGGCGACGCGTGCAATGGCGTGGGCGCAAAGTTCGACATGT
GTTGAGACCTGGAACTTCGGTGGTCTTTACACCCGGCGAGCGTTCAAGCGCTACTTTTAAGCGTTCCTA
TGATGAGGTGTACGGGGATGATGATATTCTTGAGCAGGCGGCTGACCGATTAGGCGAGTTTGCTTATGG
CAAGCGTAGTAGAATAACTTCCAAGGATGAGACAGTGTCGATACCCTTGGATCATGGAAATCCCACCCC
TAGTCTTAAACCGGTCACTTTGCAGCAAGTGTTACCCGTAACTCCGCGAACAGGTGTTAAACGCGAAGG
TGAAGATTTGTATCCCACTATGCAACTGATGGTACCCAAACGCCAGAAGTTGGAGGACGTTTTGGAGAA
AGTAAAAGTGGATCCAGATATTCAACCTGAGGTTAAAGTGAGACCCATTAAGCAGGTAGCGCCTGGTCT
GGGGGTACAAACTGTAGACATTAAGATTCCCACTGAAAGTATGGAAGTGCAAACTGAACCCGCAAAGCC
TACTGCCACCTCCACTGAAGTGCAAACGGATCCATGGATGCCCATGCCTATTACAACTGACGCCGCCGG
TCCCACTCGAAGATCCCGACGAAAGTACGGTCCAGCAAGTCTGTTGATGCCCAATTATGTTGTACACCC
ATCTATTATTCCTACTCCTGGTTACCGAGGCACTCGCTACTATCGCAGCCGAAACAGTACCTCCCGCCG
TCGCCGCAAGACACCTGCAAATCGCAGTCGTCGCCGTAGACGCACAAGCAAACCGACTCCCGGCGCCCT
GGTGCGGCAAGTGTACCGCAATGGTAGTGCGGAACCTTTGACACTGCCGCGTGCGCGTTACCATCCGAG
TATCATCACTTAATCAATGTTGCCGCTGCCTCCTTGCAGATATGGCCCTCACTTGTCGCCTTCGCGTTC
CCATCACTGGTTACCGAGGAAGAAACTCGCGCCGTAGAAGAGGGATGTTGGGACGCGGAATGCGACGCT
ACAGGCGACGGCGTGCTATCCGCAAGCAATTGCGGGGTGGTTTTTACCAGCCTTAATTCCAATTATCG
CTGCTGCAATTGGCGCGATACCAGGCATAGCTTCCGTGGCGGTTCAGGCCTCGCAACGACATTGACATT
GGAAAAAAACGTATAAATAAAAAAAAAAAAAATACAATGGACTCTGACACTCCTGGTCCTGTGACTATGT
TTTCTTAGAGATGGAAGACATCAATTTTTCATCCTTGGCTCCGCGACACGGCACGAAGCCGTACATGGG
CACCTGGAGCGACATCGGCACGAGCCAACTGAACGGGGGCGCCTTCAATTGGAGCAGTATCTGGAGCGG
GCTTAAAAATTTTGGCTCAACCATAAAAACATACGGGAACAAAGCTTGGAACAGCAGTACAGGACAGGC

Figure 50 (continued)

GCTTAGAAATAAACTTAAAGACCAGAACTTCCAACAAAAAGTAGTCGATGGGATAGCTTCCGGCATCAA
TGGAGTGGTAGATTTGGCTAACCAGGCTGTGCAGAAAAAGATAAACAGTCGTTTGGACCCGCCGCCAGC
AACCCCAGGTGAAATGCAAGTGGAGGAAGAAATTCCTCCGCCAGAAAAACGAGGCGACAAGCGTCCGCG
TCCCGATTTGGAAGAGACGCTGGTGACGCGCGTAGATGAACCGCCTTCTTATGAGGAAGCAACGAAGCT
TGGAATGCCCACCACTAGACCGATAGCCCCAATGGCCACCGGGGTGATGAAACCTTCTCAGTTGCATCG
ACCCGTCACCTTGGATTTGCCCCCTCCCCCTGCTGCTACTGCTGTACCCGCTTCTAAGCCTGTCGCTGC
CCCGAAACCAGTCGCCGTAGCCAGGTCACGTCCCGGGGGCGCTCCTCGTCCAAATGCGCACTGGCAAAA
TACTCTGAACAGCATCGTGGGTCTAGGCGTGCAAAGTGTAAAACGCCGTCGCTGCTTTTAATTAAATAT
GGAGTAGCGCTTAACTTGCCTATCTGTGTATATGTGTCATTACACGCCGTCACAGCAGCAGAGGAAAAA
AGGAAGAGGTCGTGCGTCGACGCTGAGTTACTTTCAAGATGGCCACCCCATCGATGCTGCCCCAATGGG
CATACATGCACATCGCCGGACAGGATGCTTCGGAGTACCTGAGTCCGGGTCTGGTGCAGTTCGCCCGCG
CCACAGACACCTACTTCAATCTGGGAAATAAGTTTAGAAATCCCACCGTAGCGCCGACCCACGATGTGA
CCACCGACCGTAGCCAGCGGCTCATGTTGCGCTTCGTGCCCGTTGACCGGGAGGACAATACATACTCTT
ACAAAGTGCGGTACACCCTGGCCGTGGGCGACAACAGAGTGCTGGATATGGCCAGCACGTTCTTTGACA
TTAGGGGTGTGTTGGACAGAGGTCCCAGTTTCAAACCCTATTCTGGTACGGCTTACAACTCCCTGGCTC
CTAAAGGCGCTCCAAATACATCTCAGTGGATTGCAGAAGGTGTAAAAAATACAACTGGTGAGGAACACG
TAACAGAAGAGGAAACCAATACTACTACTTACACTTTTGGCAATGCTCCTGTAAAAGCTGAAGCTGAAA
TTACAAAAGAAGGACTCCCAGTAGGTTTGGAAGTTTCAGATGAAGAAAGTAAACCGATTTATGCTGATA
AAACATATCAGCCAGAACCTCAGCTGGGAGATGAAACTTGGACTGACCTTGATGGAAAAACCGAAAAGT
ATGGAGGCAGGGCTCTCAAACCCGATACTAAGATGAAACCATGCTACGGGTCCTTTGCCAAACCTACTA
ATGTGAAAGGCGGTCAGGCAAAACAAAAAACAACGGAGCAGCCAAATCAGAAAGTCGAATATGATATCG
ACATGGAGTTTTTTGATGCGGCATCGCAGAAAACAAACTTAAGTCCTAAAATTGTCATGTATGCAGAAA
ATGTAAATTTGGAAACTCCAGACACTCATGTAGTGTACAAACCTGGAACAGAAGACACAAGTTCCGAAG
CTAATTTGGGACAACAATCTATGCCCAACAGACCCAACTACATTGGCTTCAGAGATAACTTTATTGGAC
TTATGTACTATAACAGTACTGGTAACATGGGGGTGCTGGCTGGTCAAGCGTCTCAGTTAAATGCAGTGG
TTGACTTGCAGGACAGAAACACAGAACTTTCTTACCAACTCTTGCTTGACTCTCTGGGCGACAGAACCA
GATACTTTAGCATGTGGAATCAGGCTGTGGACAGTTATGATCCTGATGTACGTGTTATTGAAAATCATG
GTGTGGAAGATGAACTTCCCAACTACTGTTTTCCACTGGACGGCATAGGTGTTCCAACAACCAGTTACA
AATCAATAGTTCCAAATGGAGACAATGCGCCTAATTGGAAGGAACCTGAAGTAAATGGAACAAGTGAGA
TCGGACAGGGTAATTTGTTTGCCATGGAAATTAACCTTCAAGCCAATCTATGGCGAAGTTTCCTTTATT
CCAATGTGGCTCTATATCTCCCAGACTCGTACAAATACACCCCGTCCAATGTCACTCTTCCAGAAAACA
AAAACACCTACGACTACATGAACGGGCGGGTGGTGCCGCCATCTCTAGTAGACACCTATGTGAACATTG
GTGCCAGGTGGTCTCTGGATGCCATGGACAATGTCAACCCATTCAACCACCACCGTAACGCTGGCTTGC
GTTACCGATCCATGCTTCTGGGTAACGGACGTTATGTGCCTTTCCACATACAAGTGCCTCAAAAATTCT
TCGCTGTTAAAAACCTGCTGCTTCTCCCAGGCTCCTACACTTATGAGTGGAACTTTAGGAAGGATGTGA
ACATGGTTCTACAGAGTTCCCTCGGTAACGACCTGCGGGTAGATGGCGCCAGCATCAGTTTCACGAGCA
TCAACCTCTATGCTACTTTTTTCCCCATGGCTCACAACACCGCTTCCACCCTTGAAGCCATGCTGCGGA
ATGACACCAATGATCAGTCATTCAACGACTACCTATCTGCAGCTAACATGCTCTACCCCATTCCTGCCA
ATGCAACCAATATTCCCATTTCCATTCCTTCTCGCAACTGGGCGGCTTTCAGAGGCTGGTCATTTACCA
GACTGAAAACCAAAGAAACTCCCTCTTTGGGGTCTGGATTTGACCCCTACTTTGTCTATTCTGGTTCTA
TTCCCTACCTGGATGGTACCTTCTACCTGAACCACACTTTTAAGAAGGTTTCCATCATGTTTGACTCTT
CAGTGAGCTGGCCTGGAAATGACAGGTTACTATCTCCTAACGAATTTGAAATAAAGCGCACTGTGGATG
GCGAAGGCTACAACGTAGCCCAATGCAACATGACCAAAGACTGGTTCTTGGTACAGATGCTCGCCAACT
ACAACATCGGCTATCAGGGCTTCTACATTCCAGAAGGATACAAAGATCGCATGTATTCATTTTTCAGAA
ACTTCCAGCCCATGAGCAGGCAGGTGGTTGATGAGGTCAATTACAAAGACTTCAAGGCCGTCGCCATAC
CCTACCAACACAACAACTCTGGCTTTGTGGGTTACATGGCTCCGACCATGCGCCAAGGTCAACCCTATC
CCGCTAACTATCCCTATCCACTCATTGGAACAACTGCCGTAAATAGTGTTACGCAGAAAAAGTTCTTGT
GTGACAGAACCATGTGGCGCATACCGTTCTCGAGCAACTTCATGTCTATGGGGGCCCTTACAGACTTGG
GACAGAATATGCTCTATGCCAACTCAGCTCATGCTCTGGACATGACCTTTGAGGTGGATCCCATGGATG
AGCCCACCCTGCTTTATCTTCTCTTCGAAGTTTTCGACGTGGTCAGAGTGCATCAGCCACACCGCGGCA
TCATCGAGGCAGTCTACCTGCGTACACCGTTCTCGGCCGGTAACGCTACCACGTAAGAAGCTTCTTGCT

Figure 50 (continued)

TCTTGCAAATAGCAGCTGCAACCATGGCCTGCGGATCCCAAAACGGCTCCAGCGAGCAAGAGCTCAGAG
CCATTGTCCAAGACCTGGGTTGCGGACCCTATTTTTTGGGAACCTACGATAAGCGCTTCCCGGGGTTCA
TGGCCCCCGATAAGCTCGCCTGTGCCATTGTAAATACGGCCGGACGTGAGACGGGGGGAGAGCACTGGT
TGGCTTTCGGTTGGAACCCACGTTCTAACACCTGCTACCTTTTTGATCCTTTTGGATTCTCGGATGATC
GTCTCAAACAGATTTACCAGTTTGAATATGAGGGTCTCCTGCGCCGCAGCGCTCTTGCTACCAAGGACC
GCTGTATTACGCTGGAAAAATCTACCCAGACCGTGCAGGGTCCCCGTTCTGCCGCCTGCGGACTTTTCT
GCTGCATGTTCCTTCACGCCTTTGTGCACTGGCCTGACCGTCCCATGGACGGAAACCCCACCATGAAAT
TGCTAACTGGAGTGCCAAACAACATGCTTCATTCTCCTAAAGTCCAGCCCACCCTGTGTGACAATCAAA
AAGCACTCTACCATTTTCTTAATACCCATTCGCCTTATTTTCGCTCCCATCGTACACACATCGAAAGGG
CCACTGCGTTCGACCGTATGGATGTTCAATAATGACTCATGTAAACAACGTGTTCAATAAACATCACTT
TATTTTTTTACATGTATCAAGGCTCTGCATTACTTATTTATTTACAAGTCGAATGGGTTCTGACGAGAA
TCAGAATGACCCGCAGGCAGTGATACGTTGCGGAACTGATACTTGGGTTGCCACTTGAATTCGGGAATC
ACCAACTTGGGAACCGGTATATCGGGCAGGATGTCACTCCACAGCTTTCTGGTCAGCTGCAAAGCTCCA
AGCAGGTCAGGAGCCGAAATCTTGAAATCACAATTAGGACCAGTGCTTTGAGCGCGAGAGTTGCGGTAC
ACCGGATTGCAGCACTGAAACACCATCAGCGACGGATGTCTCACGCTTGCCAGCACGGTGGGATCTGCA
ATCATGCCCACATCCAGATCTTCAGCATTGGCAATGCTGAACGGGGTCATCTTGCAGGTCTGCCTACCC
ATGGCGGGCACCCAATTAGGCTTGTGGTTGCAATCGCAGTGCAGGGGGATCAGTATCATCTTGGCCTGA
TCCTGTCTGATTCCTGGATACACGGCTCTCATGAAAGCATCATATTGCTTGAAAGCCTGCTGGGCTTTA
CTACCCTCGGTATAAAACATCCCGCAGGACCTGCTCGAAAACTGGTTAGCTGCACAGCCGGCATCATTC
ACACAGCAGCGGGCGTCATTGTTAGCTATTTGCACCACACTTCTGCCCCAGCGGTTTTGGGTGATTTTG
GTTCGCTCGGGATTCTCCTTTAAGGCTCGTTGTCCGTTCTCGCTGGCCACATCCATCTCGATAATCTGC
TCCTTCTGAATCATAATATTGCCATGCAGGCACTTCAGCTTGCCCTCATAATCATTGCAGCCATGAGGC
CACAACGCACAGCCTGTACATTCCCAATTATGGTGGGCGATCTGAGAAAAAGAATGTATCATTCCCTGC
AGAAATCTTCCCATCATCGTGCTCAGTGTCTTGTGACTAGTGAAAGTTAACTGGATGCCTCGGTGCTCC
TCGTTTACGTACTGGTGACAGATGCGCTTGTATTGTTCGTGTTGCTCAGGCATTAGTTTAAAAGAGGTT
CTAAGTTCGTTATCCAGCCTGTACTTCTCCATCAGCAGACACATCACTTCCATGCCTTTCTCCCAAGCA
GACACCAGGGGCAAGCTAATCGGATTCTTAACAGTGCAGGCAGCAGCTCCTTTAGCCAGAGGGTCATCT
TTAGCGATCTTCTCAATGCTTCTTTTGCCATCCTTCTCAACGATGCGCACGGGCGGGTAGCTGAAACCC
ACTGCTACAAGTTGCGCCTCTTCTCTTTCTTCTTCGCTGTCTTGACTGATGTCTTGCATGGGGATATGT
TTGGTCTTCCTTGGCTTCTTTTTGGGGGGTATCGGAGGAGGAGGACTGTCGCTCCGTTCCGGAGACAGG
GAGGATTGTGACGTTTCGCTCACCATTACCAACTGACTGTCGGTAGAAGAACCTGACCCCACACGGCGA
CAGGTGTTTCTCTTCGGGGGCAGAGGTGGAGGCGATTGCGAAGGGCTGCGGTCCGACCTGGAAGGCGGA
TGACTGGCAGAACCCCTTCCGCGTTCGGGGGTGTGCTCCCTGTGGCGGTCGCTTAACTGATTTCCTTCG
CGGCTGGCCATTGTGTTCTCCTAGGCAGAGAAACAACAGACATGGAAACTCAGCCATTGCTGTCAACAT
CGCCACGAGTGCCATCACATCTCGTCCTCAGCGACGAGGAAAAGGAGCAGAGCTTAAGCATTCCACCGC
CCAGTCCTGCCACCACCTCTACCCTAGAAGATAAGGAGGTCGACGCATCTCATGACATGCAGAATAAAA
AAGCGAAAGAGTCTGAGACAGACATCGAGCAAGACCCGGGCTATGTGACACCGGTGGAACACGAGGAAG
AGTTGAAACGCTTTCTAGAGAGAGAGGATGAAAACTGCCCAAAACAACGAGCAGATAACTATCACCAAG
ATGCTGGAAATAGGGATCAGAACACCGACTACCTCATAGGGCTTGACGGGGAAGACGCGCTCCTTAAAC
ATCTAGCAAGACAGTCGCTCATAGTCAAGGATGCATTATTGGACAGAACTGAAGTGCCCATCAGTGTGG
AAGAGCTCAGCCGCGCCTACGAGCTTAACCTCTTTTCACCTCGTACTCCCCCCAAACGTCAGCCAAACG
GCACCTGCGAGCCAAATCCTCGCTTAAACTTTTATCCAGCTTTTGCTGTGCCAGAAGTACTGGCTACCT
ATCACATCTTTTTTAAAAATCAAAAAATTCCAGTCTCCTGCCGCGCTAATCGCACCCGCGCCGATGCCC
TACTCAATCTGGGACCTGGTTCACGCTTACCTGATATAGCTTCCTTGGAAGAGGTTCCAAAGATCTTCG
AGGGTCTGGGCAATAATGAGACTCGGGCCGCAAATGCTCTGCAAAAGGGAGAAAATGGCATGGATGAGC
ATCACAGCGTTCTGGTGGAATTGGAAGGCGATAATGCCAGACTCGCAGTACTCAAGCGAAGCATCGAGG
TCACACACTTCGCATATCCCGCTGTCAACCTGCCCCCTAAAGTCATGACGGCGGTCATGGACCAGTTAC
TCATTAAGCGCGCAAGTCCCCTTTCAGAAGACATGCATGACCCAGATGCCTGTGATGAGGGTAAACCAG
TGGTCAGTGATGAGCAGCTAACCCGATGGCTGGGCACCGACTCTCCCAGGGATTTGGAAGAGCGTCGCA
AGCTTATGATGGCCGTGGTGCTGGTTACCGTAGAACTAGAGTGTCTCCGACGTTTCTTTACCGATTCAG
AAACCTTGCGCAAACTCGAAGAGAATCTGCACTACACTTTTAGACACGGCTTTGTGCGGCAGGCATGCA

Figure 50 (continued)

AGATATCTAACGTGGAACTCACCAACCTGGTTTCCTACATGGGTATTCTGCATGAGAATCGCCTAGGAC
AAAGCGTGCTGCACAGCACCCTGAAGGGGGAAGCCCGCCGTGATTACATCCGCGATTGTGTCTATCTGT
ACCTGTGCCACACGTGGCAAACCGGCATGGGTGTATGGCAGCAATGTTTAGAAGAACAGAACTTGAAAG
AGCTTGACAAGCTCTTACAGAAATCTCTTAAGGTTCTGTGGACAGGGTTCGACGAGCGCACCGTCGCTT
CCGACCTGGCAGACCTCATCTTCCCAGAGCGTCTCAGGGTTACTTTGCGAAACGGATTGCCTGACTTTA
TGAGCCAGAGCATGCTTAACAATTTTCGCTCTTTCATCCTGGAACGCTCCGGTATCCTGCCCGCCACCT
GCTGCGCACTGCCCTCCGACTTTGTGCCTCTCACCTACCGCGAGTGCCCCCCGCCGCTATGGAGTCACT
GCTACCTGTTCCGTCTGGCCAACTATCTCTCCTACCACTCGGATGTGATCGAGGATGTGAGCGGAGACG
GCTTGCTGGAGTGTCACTGCCGCTGCAATCTGTGCACGCCCCACCGGTCCCTAGCTTGCAACCCCCAGT
TGATGAGCGAAACCCAGATAATAGGCACCTTTGAATTGCAAGGCCCCAGCAGCCAAGGCGATGGGTCTT
CTCCTGGGCAAAGTTTAAAACTGACCCCGGGACTGTGGACCTCCGCCTACTTGCGCAAGTTTGCTCCGG
AAGATTACCACCCCTATGAAATCAAGTTCTATGAGGACCAATCACAGCCTCCAAAGGCCGAACTTTCGG
CCTGCGTCATCACCCAGGGGGCAATTCTGGCCCAATTGCAAGCCATCCAAAAATCCCGCCAAGAATTTC
TACTGAAAAAGGGTAAGGGGGTCTACCTTGACCCCCAGACCGGCGAGGAACTCAACACAAGGTTCCCTC
AGGATGTCCCAACGACGAGAAAACAAGAAGTTGAAGGTGCAGCCGCCGCCCCCAGAAGATATGGAGGAA
GATTGGGACAGTCAGGCAGAGGAGGCGGAGGAGGACAGTCTGGAGGACAGTCTGGAGGAAGACAGTTTG
GAGGAGGAAAACGAGGAGGCAGAGGAGGTGGAAGAAGTAACCGCCGACAAACAGTTATCCTCGGCTGCG
GAGACAAGCAACAGCGCTACCATCTCCGCTCCGAGTCGAGGAACCCGGCGGCGTCCCAGCAGTAGATGG
GACGAGACCGGACGCTTCCCGAACCCAACCAGCGCTTCCAAGACCGGTAAGAAGGATCGGCAGGGATAC
AAGTCCTGGCGGGGGCATAAGAATGCCATCATCTCCTGCTTGCATGAGTGCGGGGGCAACATATCCTTC
ACGCGGCGCTACTTGCTATTCCACCATGGGGTGAACTTTCCGCGCAATGTTTTGCATTACTACCGTCAC
CTCCACAGCCCCTACTATAGCCAGCAAATCCCGGCAGTCTCGACAGATAAAGACAGCGGCGGCGACCTC
CAACAGAAAACCAGCAGCGGCAGTTAGAAAATACACAACAAGTGCAGCAACAGGAGGATTAAAGATTAC
AGCCAACGAGCCAGCGCAAACCCGAGAGTTAAGAAATCGGATCTTTCCAACCCTGTATGCCATCTTCCA
GCAGAGTCGGGGTCAAGAGCAGGAACTGAAAATAAAAAACCGATCTCTGCGTTCGCTCACCAGAAGTTG
TTTGTATCACAAGAGCGAAGATCAACTTCAGCGCACTCTCGAGGACGCCGAGGCTCTCTTCAACAAGTA
CTGCGCGCTGACTCTTAAAGAGTAGGCAGCGACCGCGCTTATTCAAAAAAGGCGGGAATTACATCATCC
TCGACATGAGTAAAGAAATTCCCACGCCTTACATGTGGAGTTATCAACCCCAAATGGGATTGGCGGCAG
GCGCCTCCCAGGACTACTCCACCCGCATGAATTGGCTCAGCGCCGGGCCTTCTATGATTTCTCGAGTTA
ATGATATACGCGCCTACCGAAACCAAATACTTTTGGAACAGTCAGCTCTTACCACCACGCCCCGCCAAC
ACCTTAATCCCAGAAATTGGCCCGCCGCCCTAGTGTACCAGGAAAGTCCCGCTCCCACCACTGTATTAC
TTCCTCGAGACGCCCAGGCCGAAGTCCAAATGACTAATGCAGGTGCGCAGTTAGCTGGCGGCTCCACCC
TATGTCGTCACAGGCCTCGGCATAATATAAAACGCCTGATGATCAGAGGCCGAGGTATCCAGCTCAACG
ACGAGTCGGTGAGCTCTCCGCTTGGTCTACGACCAGACGGAATCTTTCAGATTGCCGGCTGCGGGAGAT
CTTCCTTCACCCCTCGTCAGGCTGTTCTGACTTTGGAAAGTTCGTCTTCGCAACCCCGCTCGGGCGGAA
TCGGGACCGTTCAATTTGTGGAGGAGTTTACTCCCTCTGTCTACTTCAACCCCTTCTCCGGATCTCCTG
GGCATTACCCGGACGAGTTCATACCGAACTTCGACGCGATTAGCGAGTCAGTGGACGGCTACGATTGAT
GTCTGGTGACGCGGCTGAGCTATCTCGGCTGCGACATCTAGACCACTGCCGCCGCTTTCGCTGCTTTGC
CCGGGAACTCATTGAGTTCATCTACTTCGAACTCCCCAAGGATCACCCTCAAGGTCCGGCCCACGGAGT
GCGGATTTCTATCGAAGGCAAAATAGACTCTCGCCTGCAACGAATTTTCTCCCAGCGGCCCGTGCTGAT
CGAGCGAGACCAGGGAAACACCACGGTTTCCATCTACTGCATTTGTAATCACCCCGGATTGCATGAAAG
CCTTTGCTGTCTTATGTGTACTGAGTTTAATAAAAACTGAATTAAGACTCTCCTACGGACTGCCGCTTC
TTCAACCCGGATTTTACAACCAGAAGAACGAAACTTTTCCTGTCGTCCAGGACTCTGTTAACTTCACCT
TTCCTACTCACAAACTAGAAGCTCAACGACTACACCGCTTTTCCAGAAGCATTTTCCCTACTAATACTA
CTTTCAAAACCGGAGGTGAGCTCCAAGGTCTTCCTACAGAAAACCCTTGGGTGGAAGCGGGCCTTGTAG
TGCTAGGAATTCTTGCGGGTGGGCTTGTGATTATTCTTTGCTACCTATACACACCTTGCTTCACTTTCT
TAGTGGTGTTGTGGTATTGGTTTAAAAAATGGGGCCCATACTAGTCTTGCTTGTTTTACTTTCGCTTTT
GGAACCGGGTTCTGCCAATTACGATCCATGTCTAGACTTCGACCCAGAAAACTGCACACTTACTTTTGC
ACCCGACACAAGCCGCATCTGTGGAGTTCATCGCCTCTCTTACGAACTTGGCCCCCAACGACAAAAATT
TACCTGCATGGTGGGAATCAACCCCATAGTTATCACCCAGCAAAGTGGAGATACTAAGGGTTGCATTCA
CTGCTCCTGCGATTCCATCGAGTGCACCTACACCCTGCTGAAGACCCTATGCGGCCTAAGAGACCTGCT

Figure 50 (continued)

ACCAATGAATTAAAAAATGATTAATAAAAAATCACTTACTTGAAATCAGCAATAAGGTCTCTGTTGAAA
TTTTCTCCCAGCAGCACCTCACTTCCCTCTTCCCAACTCTGGTATTCTAAACCCCGTTCAGCGGCATAC
TTTCTCCATACTTTAAAGGGGATGTCAAATTTTAGCTCCTCTCCTGTACCCACAATCTTCATGTCTTTC
TTCCCAGATGACCAAGAGAGTCCGGCTCAGTGACTCCTTCAACCCTGTCTACCCCTATGAAGATGAAAG
CACCTCCCAACACCCCTTTATAAACCCAGGGTTTATTTCCCCAAATGGCTTCACACAAAGCCCAAACGG
AGTTCTTACTTTAAAATGTTTAACCCCACTAACAACCACAGGCGGATCTCTACAGCTAAAAGTGGGAGG
GGGACTTACAGTGGATGACACCAACGGTTTTTTGAAAGAAAACATAAGTGCCACCACACCACTCGTTAA
GACTGGTCACTCTATAGGTTTACCACTAGGAGCCGGATTGGGAACGAATGAAAATAAACTTTGTATCAA
ATTAGGACAAGGACTTACATTCAATTCAAACAACATTTGCATTGATGACAATATTAACACCTTATGGAC
AGGAGTCAACCCCACCGAAGCCAACTGTCAAATCATGAACTCCAGTGAATCTAATGATTGCAAATTAAT
TCTAACACTAGTTAAAACTGGAGCACTAGTCACTGCATTTGTTTATGTTATAGGAGTATCTAACAATTT
TAATATGCTAACTACACACAGAAATATAAATTTTACTGCAGAGCTGTTTTTCGATTCTACTGGTAATTT
ACTAACTAGACTCTCATCCCTCAAAACTCCACTTAATCATAAATCAGGACAAAACATGGCTACTGGTGC
CATTACTAATGCTAAAGGTTTCATGCCCAGCACGACTGCCTATCCTTTCAATGATAATTCTAGAGAAAA
AGAAAACTACATTTACGGAACTTGTTACTACACAGCTAGTGATCGCACTGCTTTTCCCATTGACATATC
TGTCATGCTTAACCGAAGAGCAATAAATGACGAGACATCATATTGTATTCGTATAACTTGGTCCTGGAA
CACAGGAGATGCCCCAGAGGTGCAAACCTCTGCTACAACCCTAGTCACCTCCCCATTTACCTTTTACTA
CATCAGAGAAGACGACTGACAAATAAAGTTTGCGATCGCCAGGCCCACCATGGGATGGAGCTGTATCAT
CCTCTTCTTGGTAGCAACAGCTACAGGTGTCCACTCCCAGGTGCAGCTGCAGCAGTCTGGGGCTGAACT
GGCAAGACCTGGGGCCTCAGTGAAGATGTCCTGCAAGGCTTCTGGCTACACCTTTACTAGGTACACGAT
GCACTGGGTAAAACAGAGGCCTGGACAGGGTCTGGAATGGATTGGATACATTAATCCTAGCCGTGGTTA
TACTAATTACAATCAGAAGTTCAAGGACAAGGCCACATTGACTACAGACAAATCCTCCAGCACAGCCTA
CATGCAACTGAGCAGCCTGACATCTGAGGACTCTGCAGTCTATTACTGTGCAAGATATTATGATGATCA
TTACTGCCTTGACTACTGGGGCCAAGGCACCACTCTCACAGTCTCCTCAGGTGGCGGTGGCTCGGGCGG
TGGTGGATCTGGTGGCGGCGGATCTGATATCGTGCTCACTCAGTCTCCAGCAATCATGTCTGCATCTCC
AGGGGAGAAGGTCACCATGACCTGCAGTGCCAGCTCAAGTGTAAGTTACATGAACTGGTACCAGCAGAA
GTCAGGCACCTCCCCCAAAAGATGGATTTATGACACATCCAAACTGGCTTCTGGAGTCCCTGCTCACTT
CAGGGGCAGTGGGTCTGGGACCTCTTACTCTCTCACAATCAGCGGCATGGAGGCTGAAGATGCTGCCAC
TTATTACTGCCAGCAGTGGAGTAGTAACCCATTCACGTTCGGCTCGGGGACAAAGTTGGAAATAAACCG
GGGATCCGAACAAAAACTCATCTCAGAAGAGGATCTGAATGCTGTGGGCCAGGACACGCAGGAGGTCAT
CGTGGTGCCACACTCCTTGCCCTTTAAGGTGGTGGTGATCTCAGCCATCCTGGCCCTGGTGGTGCTCAC
CATCATCTCCCTTATCATCCTCATCATGCTTTGGCAGAAGAAGCCACGTGGAAGCGGAGCTACTAACTT
CAGCCTGCTGAAGCAGGCTGGAGACGTGGAGGAGAACCCTGGACCTGGCCACACACGGAGGCAGGGAAC
ATCACCATCCAAGTGTCCATACCTCAATTTCTTTCAGCTCTTGGTGCTGGCTGGTCTTTCTCACTTCTG
TTCAGGTGTTATCCACGTGACCAAGGAAGTGAAAGAAGTGGCAACGCTGTCCTGTGGTCACAATGTTTC
TGTTGAAGAGCTGGCACAAACTCGCATCTACTGGCAAAAGGAGAAGAAAATGGTGCTGACTATGATGTC
TGGGGACATGAATATATGGCCCGAGTACAAGAACCGGACCATCTTTGATATCACTAATAACCTCTCCAT
TGTGATCCTGGCTCTGCGCCCATCTGACGAGGGCACATACGAGTGTGTTGTTCTGAAGTATGAAAAAGA
CGCTTTCAAGCGGGAACACCTGGCTGAAGTGACGTTATCAGTCAAAGCTGACTTCCCTACACCTAGTAT
ATCTGACTTTGAAATTCCAACTTCTAATATTAGAAGGATAATTTGCTCAACCTCTGGAGGTTTTCCAGA
GCCTCACCTCTCCTGGTTGGAAAATGGAGAAGAATTAAATGCCATCAACACAACAGTTTCCCAAGATCC
TGAAACTGAGCTCTATGCTGTTAGCAGCAAACTGGATTTCAATATGACAACCAACCACAGCTTCATGTG
TCTCATCAAGTATGGACATTTAAGAGTGAATCAGACCTTCAACTGGAATACAACCAAGCAAGAGCATTT
TCCTGATAACCTGCTCCCATCCTGGGCCATTACCTTAATCTCAGTAAATGGAATTTTTGTGATATGCTG
CCTGACCTACTGCTTTGCCCCAAGATGCAGAGAGAGAAGGAGGAATGAGAGATTGAGAAGGGAAAGTGT
ACGCCCTGTATAAGCTAGCTTGACTGACTGAGATACAGCGTACCTTCAGCTCACAGACATGATAAGATA
CATTGATGAGTTTGGACAAACCACAACTAGAATGCAGTGAAAAAAATGCTTTATTTGTGAAATTTGTGA
TGCTATTGCTTTATTTGTAACCATTATAAGCTGCAATAAACAAGTTAACAACAACAATTGCATTCATTT
TATGTTTCAGGTTCAGGGGGAGGTGTGGGAGGTTTTTTAAAGCAAGTAAAACCTCTACAAATGTGGTAG
TCGTCAGCTATCCTGCAGGAACTTGTTTATTTGAAAATCAATTCACAAAATCCGAGTAGTTATTTTGCC
TCCCCCTTCCCATTTAACAGAATACACCAATCTCTCCCCACGCACAGCTTTAAACATTTGGATACCATT

Figure 50 (continued)

AGATATAGACATGGTTTTAGATTCCACATTCCAAACAGTTTCAGAGCGAGCCAATCTGGGGTCAGTGAT
AGATAAAAATCCATCGGGATAGTCTTTTAAAGCGCTTTCACAGTCCAACTGCTGCGGATGCGACTCCGG
AGTCTGGATCACGGTCATCTGGAAGAAGAACGATGGGAATCATAATCCGAAAACGGTATCGGACGATTG
TGTCTCATCAAACCCACAAGCAGCCGCTGTCTGCGTCGCTCCGTGCGACTGCTGTTTATGGGATCAGGG
TCCACAGTGTCCTGAAGCATGATTTTAATAGCCCTTAACATCAACTTTCTGGTGCGATGCGCGCAGCAA
CGCATTCTGATTTCACTCAAATCTTTGCAGTAGGTACAACACATTATTACAATATTGTTTAATAAACCA
TAATTAAAAGCGCTCCAGCCAAAACTCATATCTGATATAATCGCCCCTGCATGACCATCATACCAAAGT
TTAATATAAATTAAATGACGTTCCCTCAAAAACACACTACCCACATACATGATCTCTTTTGGCATGTGC
ATATTAACAATCTGTCTGTACCATGGACAACGTTGGTTAATCATGCAACCCAATATAACCTTCCGGAAC
CACACTGCCAACACCGCTCCCCCAGCCATGCATTGAAGTGAACCCTGCTGATTACAATGACAATGAAGA
ACCCAATTCTCTCGACCGTGAATCACTTGAGAATGAAAAATATCTATAGTGGCACAACATAGACATAAA
TGCATGCATCTTCTCATAATTTTTAACTCCTCAGGATTTAGAAACATATCCCAGGGAATAGGAAGCTCT
TGCAGAACAGTAAAGCTGGCAGAACAAGGAAGACCACGAACACAACTTACACTATGCATAGTCATAGTA
TCACAATCTGGCAACAGCGGGTGGTCTTCAGTCATAGAAGCTCGGGTTTCATTTTCCTCACAACGTGGT
AACTGGGCTCTGGTGTAAGGGTGATGTCTGGCGCATGATGTCGAGCGTGCGCGCAACCTTGTCATAATG
GAGTTGCTTCCTGACATTCTCGTATTTTGTATAGCAAAACGCGGCCCTGGCAGAACACACTCTTCTTCG
CCTTCTATCCTGCCGCTTAGCGTGTTCCGTGTGATAGTTCAAGTACAACCACACTCTTAAGTTGGTCAA
AAGAATGCTGGCTTCAGTTGTAATCAAAACTCCATCGCATCTAATCGTTCTGAGGAAATCATCCAAGCA
ATGCAACTGGATTGTGTTTCAAGCAGGAGAGGAGAGGGAAGAGACGGAAGAACCATGTTAATTTTTATT
CCAAACGATCTCGCAGTACTTCAAATTGTAGATCGCGCAGATGGCATCTCTCGCCCCCACTGTGTTGGT
GAAAAAGCACAGCTAGATCAAAAGAAATGCGATTTTCAAGGTGCTCAACGGTGGCTTCCAGCAAAGCCT
CCACGCGCACATCCAAGAACAAAAGAATACCAAAAGAAGGAGCATTTTCTAACTCCTCAATCATCATAT
TACATTCCTGCACCATTCCCAGATAATTTTCAGCTTTCCAGCCTTGAATTATTCGTGTCAGTTCTTGTG
GTAAATCCAATCCACACATTACAAACAGGTCCCGGAGGGCGCCCTCCACCACCATTCTTAAACACACCC
TCATAATGACAAAATATCTTGCTCCTGTGTCACCTGTAGCGAATTGAGAATGGCAACATCAATTGACAT
GCCCTTGGCTCTAAGTTCTTCTTTAAGTTCTAGTTGTAAAAACTCTCTCATATTATCACCAAACTGCTT
AGCCAGAAGCCCCCCGGGAACAAGAGCAGGGGACGCTACAGTGCAGTACAAGCGCAGACCTCCCCAATT
GGCTCCAGCAAAAACAAGATTGGAATAAGCATATTGGGAACCGCCAGTAATATCATCGAAGTTGCTGGA
AATATAATCAGGCAGAGTTTCTTGTAAAAATTGAATAAAAGAAAAATTTGCCAAAAAAACATTCAAAAC
CTCTGGGATGCAAATGCAATAGGTTACCGCGCTGCGCTCCAACATTGTTAGTTTTGAATTAGTCTGCAA
AAATAAAAAAAAAAACAAGCGTCATATCATAGTAGCCTGACGAACAGATGGATAAATCAGTCTTTCCAT
CACAAGACAAGCCACAGGGTCTCCAGCTCGACCCTCGTAAAACCTGTCATCATGATTAAACAACAGCAC
CGAAAGTTCCTCGCGGTGACCAGCATGAATAATTCTTGATGAAGCATACAATCCAGACATGTTAGCATC
AGTTAACGAGAAAAAACAGCCAACATAGCCTTTGGGTATAATTATGCTTAATCGTAAGTATAGCAAAGC
CACCCCTCGCGGATACAAAGTAAAAGGCACAGGAGAATAAAAAATATAATTATTTCTCTGCTGCTGTTC
AGGCAACGTCGCCCCCGGTCCCTCTAAATACACATACAAAGCCTCATCAGCCATGGCTTACCAGACAAA
GTACAGCGGGCACACAAAGCACAAGCTCTAAAGTGACTCTCCAACCTCTCCACAATATATATATACACA
AGCCCTAAACTGACGTAATGGGAGTAAAGTGTAAAAAATCCCGCCAAACCCAACACACACCCCGAAACT
GCGTCACCAGGGAAAAGTACAGTTTCACTTCCGCAATCCCAACAGGCGTAACTTCCTCTTTCTCACGGT
ACGTGATATCCCACTAACTTGCAACGTCATTTTCCCACGGTCGCACCGCCCCTTTTAGCCGTTAACCCC
ACAGCCAATCACCACACGATCCACACTTTTTAAAATCACCTCATTTACATATTGGCACCATTCCATCTA
TAAGGTATATTATATAGATAGA

SEQ ID NO: 101 V5 TAG

IPNPLLGLD

Figure 51

SEQUENCE ID NO. 102 NG-348A virus genome sequence comprising the EnAd genome with a transgene cassette that encodes a membrane-anchored chimeric form of the single chain Fv anti-human CD3e with C-terminal V5 tag and the T lymphocyte activation antigen, CD80 inserted in the region Bγ. The transgene cassette contains a 5' SSA, membrane-anchored anti-CD3ε cDNA sequence, V5 tag, P2A peptide, human CD80 cDNA sequence and a 3' poly(A) sequence

TCTATCTATATAATATACCTTATAGATGGAATGGTGCCAATATGTAAATGAGGTGATTTTAAAAAGTGT
GGATCGTGTGGTGATTGGCTGTGGGGTTAACGGCTAAAAGGGGCGGTGCGACCGTGGGAAAATGACGTT
TTGTGGGGGTGGAGTTTTTTTGCAAGTTGTCGCGGGAAATGTGACGCATAAAAAGGCTTTTTTCTCACG
GAACTACTTAGTTTTCCCACGGTATTTAACAGGAAATGAGGTAGTTTTGACCGGATGCAAGTGAAAATT
GTTGATTTTCGCGCGAAAACTGAATGAGGAAGTGTTTTTCTGAATAATGTGGTATTTATGGCAGGGTGG
AGTATTTGTTCAGGGCCAGGTAGACTTTGACCCATTACGTGGAGGTTTCGATTACCGTGTTTTTTACCT
GAATTTCCGCGTACCGTGTCAAAGTCTTCTGTTTTTACGTAGGTGTCAGCTGATCGCTAGGGTATTTAT
ACCTCAGGGTTTGTGTCAAGAGGCCACTCTTGAGTGCCAGCGAGAAGAGTTTTCTCCTCTGCGCCGGCA
GTTTAATAATAAAAAAATGAGAGATTTGCGATTTCTGCCTCAGGAAATAATCTCTGCTGAGACTGGAAA
TGAAATATTGGAGCTTGTGGTGCACGCCCTGATGGGAGACGATCCGGAGCCACCTGTGCAGCTTTTTGA
GCCTCCTACGCTTCAGGAACTGTATGATTTAGAGGTAGAGGGATCGGAGGATTCTAATGAGGAAGCTGT
AAATGGCTTTTTTACCGATTCTATGCTTTTAGCTGCTAATGAAGGGTTAGAATTAGATCCGCCTTTGGA
CACTTTTGATACTCCAGGGGTAATTGTGGAAAGCGGTACAGGTGTAAGAAAATTACCTGATTTGAGTTC
CGTGGACTGTGATTTGCACTGCTATGAAGACGGGTTTCCTCCGAGTGATGAGGAGGACCATGAAAAGGA
GCAGTCCATGCAGACTGCAGCGGGTGAGGGAGTGAAGGCTGCCAATGTTGGTTTTCAGTTGGATTGCCC
GGAGCTTCCTGGACATGGCTGTAAGTCTTGTGAATTTCACAGGAAAAATACTGGAGTAAAGGAACTGTT
ATGTTCGCTTTGTTATATGAGAACGCACTGCCACTTTATTTACAGTAAGTGTGTTTAAGTTAAAATTTA
AAGGAATATGCTGTTTTTCACATGTATATTGAGTGTGAGTTTTGTGCTTCTTATTATAGGTCCTGTGTC
TGATGCTGATGAATCACCATCTCCTGATTCTACTACCTCACCTCCTGAGATTCAAGCACCTGTTCCTGT
GGACGTGCGCAAGCCCATTCCTGTGAAGCTTAAGCCTGGGAAACGTCCAGCAGTGGAAAAACTTGAGGA
CTTGTTACAGGGTGGGGACGGACCTTTGGACTTGAGTACACGGAAACGTCCAAGACAATAAGTGTTCCA
TATCCGTGTTTACTTAAGGTGACGTCAATATTTGTGTGACAGTGCAATGTAATAAAAATATGTTAACTG
TTCACTGGTTTTTATTGCTTTTTGGGCGGGGACTCAGGTATATAAGTAGAAGCAGACCTGTGTGGTTAG
CTCATAGGAGCTGGCTTTCATCCATGGAGGTTTGGGCCATTTTGGAAGACCTTAGGAAGACTAGGCAAC
TGTTAGAGAACGCTTCGGACGGAGTCTCCGGTTTTTGGAGATTCTGGTTCGCTAGTGAATTAGCTAGGG
TAGTTTTTAGGATAAAACAGGACTATAAACAAGAATTTGAAAAGTTGTTGGTAGATTGCCCAGGACTTT
TTGAAGCTCTTAATTTGGGCCATCAGGTTCACTTTAAAGAAAAAGTTTTATCAGTTTTAGACTTTTCAA
CCCCAGGTAGAACTGCTGCTGCTGTGGCTTTTCTTACTTTTATATTAGATAAATGGATCCCGCAGACTC
ATTTCAGCAGGGGATACGTTTTGGATTTCATAGCCACAGCATTGTGGAGAACATGGAAGGTTCGCAAGA
TGAGGACAATCTTAGGTTACTGGCCAGTGCAGCCTTTGGGTGTAGCGGGAATCCTGAGGCATCCACCGG
TCATGCCAGCGGTTCTGGAGGAGGAACAGCAAGAGGACAACCCGAGAGCCGGCCTGGACCCTCCAGTGG
AGGAGGCGGAGTAGCTGACTTGTCTCCTGAACTGCAACGGGTGCTTACTGGATCTACGTCCACTGGACG
GGATAGGGGCGTTAAGAGGGAGAGGGCATCTAGTGGTACTGATGCTAGATCTGAGTTGGCTTTAAGTTT
AATGAGTCGCAGACGTCCTGAAACCATTTGGTGGCATGAGGTTCAGAAAGAGGGAAGGGATGAAGTTTC
TGTATTGCAGGAGAAATATTCACTGGAACAGGTGAAAACATGTTGGTTGGAGCCTGAGGATGATTGGGA
GGTGGCCATTAAAAATTATGCCAAGATAGCTTTGAGGCCTGATAAACAGTATAAGATTACTAGACGGAT
TAATATCCGGAATGCTTGTTACATATCTGGAAATGGGGCTGAGGTGGTAATAGATACTCAAGACAAGGC
AGTTATTAGATGCTGCATGATGGATATGTGGCCTGGGGTAGTCGGTATGGAAGCAGTAACTTTTGTAAA
TGTTAAGTTTAGGGGAGATGGTTATAATGGAATAGTGTTTATGGCCAATACCAAACTTATATTGCATGG
TTGTAGCTTTTTTGGTTTCAACAATACCTGTGTAGATGCCTGGGGACAGGTTAGTGTACGGGGATGTAG
TTTCTATGCGTGTTGGATTGCCACAGCTGGCAGAACCAAGAGTCAATTGTCTCTGAAGAAATGCATATT
TCAAAGATGTAACCTGGGCATTCTGAATGAAGGCGAAGCAAGGGTCCGCCACTGCGCTTCTACAGATAC
TGGATGTTTTATTTTGATTAAGGGAAATGCCAGCGTAAAGCATAACATGATTTGCGGTGCTTCCGATGA
GAGGCCTTATCAAATGCTCACTTGTGCTGGTGGGCATTGTAATATGCTGGCTACTGTGCATATTGTTTC
CCATCAACGCAAAAAATGGCCTGTTTTTGATCACAATGTGATGACGAAGTGTACCATGCATGCAGGTGG

Figure 51 (continued)

GCGTAGAGGAATGTTTATGCCTTACCAGTGTAACATGAATCATGTGAAAGTGTTGTTGGAACCAGATGC
CTTTTCCAGAATGAGCCTAACAGGAATTTTTGACATGAACATGCAAATCTGGAAGATCCTGAGGTATGA
TGATACGAGATCGAGGGTACGCGCATGCGAATGCGGAGGCAAGCATGCCAGGTTCCAGCCGGTGTGTGT
AGATGTGACTGAAGATCTCAGACCGGATCATTTGGTTATTGCCCGCACTGGAGCAGAGTTCGGATCCAG
TGGAGAAGAAACTGACTAAGGTGAGTATTGGGAAAACTTTGGGGTGGGATTTTCAGATGGACAGATTGA
GTAAAAATTTGTTTTTTCTGTCTTGCAGCTGTCATGAGTGGAAACGCTTCTTTTAAGGGGGGAGTCTTC
AGCCCTTATCTGACAGGGCGTCTCCCATCCTGGGCAGGAGTTCGTCAGAATGTTATGGGATCTACTGTG
GATGGAAGACCCGTCCAACCCGCCAATTCTTCAACGCTGACCTATGCTACTTTAAGTTCTTCACCTTTG
GACGCAGCTGCAGCTGCCGCCGCCGCTTCTGTTGCCGCTAACACTGTGCTTGGAATGGGTTACTATGGA
AGCATCATGGCTAATTCCACTTCCTCTAATAACCCTTCTACCCTGACTCAGGACAAGTTACTTGTCCTT
TTGGCCCAGCTGGAGGCTTTGACCCAACGTCTGGGTGAACTTTCTCAGCAGGTGGTCGAGTTGCGAGTA
CAAACTGAGTCTGCTGTCGGCACGGCAAAGTCTAAATAAAAAAATCCCAGAATCAATGAATAAATAAAC
AAGCTTGTTGTTGATTTAAAATCAAGTGTTTTTATTTCATTTTTCGCGCACGGTATGCCCTAGACCACC
GATCTCTATCATTGAGAACTCGGTGGATTTTTTCCAGGATCCTATAGAGGTGGGATTGAATGTTTAGAT
ACATGGGCATTAGGCCGTCTTTGGGGTGGAGATAGCTCCATTGAAGGGATTCATGCTCCGGGGTAGTGT
TGTAAATCACCCAGTCATAACAAGGTCGCAGTGCATGGTGTTGCACAATATCTTTTAGAAGTAGGCTGA
TTGCCACAGATAAGCCCTTGGTGTAGGTGTTTACAAACCGGTTGAGCTGGGATGGGTGCATTCGGGGTG
AAATTATGTGCATTTTGGATTGGATTTTTAAGTTGGCAATATTGCCGCCAAGATCCCGTCTTGGGTTCA
TGTTATGAAGGACCACCAAGACGGTGTATCCGGTACATTTAGGAAATTTATCGTGCAGCTTGGATGGAA
AAGCGTGGAAAAATTTGGAGACACCCTTGTGTCCTCCAAGATTTTCCATGCACTCATCCATGATAATAG
CAATGGGGCCGTGGGCAGCGGCGCGGGCAAACACGTTCCGTGGGTCTGACACATCATAGTTATGTTCCT
GAGTTAAATCATCATAAGCCATTTTAATGAATTTGGGGCGGAGAGTACCAGATTGGGGTATGAATGTTC
CTTCGGGCCCCGGAGCATAGTTCCCCTCACAGATTTGCATTTCCCAAGCTTTCAGTTCCGAGGGTGGAA
TCATGTCCACCTGGGGGGCTATGAAAAACACCGTTTCTGGGGCGGGGGTGATTAATTGTGATGATAGCA
AATTTCTGAGCAATTGAGATTTGCCACATCCGGTGGGGCCATAAATGATTCCGATTACGGGTTGCAGGT
GGTAGTTTAGGGAACGGCAACTGCCGTCTTCTCGAAGCAAGGGGGCCACCTCGTTCATCATTTCCCTTA
CATGCATATTTTCCCGCACCAAATCCATTAGGAGGCGCTCTCCTCCTAGTGATAGAAGTTCTTGTAGTG
AGGAAAAGTTTTTCAGCGGTTTCAGACCGTCAGCCATGGGCATTTTGGAGAGAGTTTGCTGCAAAAGTT
CTAGTCTGTTCCACAGTTCAGTGATGTGTTCTATGGCATCTCGATCCAGCAGACCTCCTCGTTTCGCGG
GTTTGGACGGCTCCTGGAATAGGGTATGAGACGATGGGCGTCCAGCGCTGCCAGGGTTCGGTCCTTCCA
GGGTCTCAGTGTTCGAGTCAGGGTTGTTTCCGTCACAGTGAAGGGGTGTGCGCCTGCTTGGGCGCTTGC
CAGGGTGCGCTTCAGACTCATCCTGCTGGTCGAAAACTTCTGTCGCTTGGCGCCCTGTATGTCGGCCAA
GTAGCAGTTTACCATGAGTTCGTAGTTGAGCGCCTCGGCTGCGTGGCCTTTGGCGCGGAGCTTACCTTT
GGAAGTTTTCTTGCATACCGGGCAGTATAGGCATTTCAGCGCATACAACTTGGGCGCAAGGAAAACGGA
TTCTGGGGAGTATGCATCTGCGCCGCAGGAGGCGCAAACAGTTTCACATTCCACCAGCCAGGTTAAATC
CGGTTCATTGGGGTCAAAAACAAGTTTTCCGCCATATTTTTTGATGCGTTTCTTACCTTTGGTCTCCAT
GAGTTCGTGTCCTCGTTGAGTGACAAACAGGCTGTCCGTGTCCCCGTAGACTGATTTTACAGGCCTCTT
CTCCAGTGGAGTGCCTCGGTCTTCTTCGTACAGGAACTCTGACCACTCTGATACAAAGGCGCGCGTCCA
GGCCAGCACAAAGGAGGCTATGTGGGAGGGGTAGCGATCGTTGTCAACCAGGGGGTCCACCTTTTCCAA
AGTATGCAAACACATGTCACCCTCTTCAACATCCAGGAATGTGATTGGCTTGTAGGTGTATTTCACGTG
ACCTGGGGTCCCCGCTGGGGGGGTATAAAAGGGGGCGGTTCTTTGCTCTTCCTCACTGTCTTCCGGATC
GCTGTCCAGGAACGTCAGCTGTTGGGGTAGGTATTCCCTCTCGAAGGCGGCATGACCTCTGCACTCAG
GTTGTCAGTTTCTAAGAACGAGGAGGATTTGATATTGACAGTGCCGGTTGAGATGCCTTTCATGAGGTT
TTCGTCCATCTGGTCAGAAAACACAATTTTTTTATTGTCAAGTTTGGTGGCAAATGATCCATACAGGGC
GTTGGATAAAAGTTTGGCAATGGATCGCATGGTTTGGTTCTTTTCCTTGTCCGCGCGCTCTTTGGCGGC
GATGTTGAGTTGGACATACTCGCGTGCCAGGCACTTCCATTCGGGGAAGATAGTTGTTAATTCATCTGG
CACGATTCTCACTTGCCACCCTCGATTATGCAAGGTAATTAAATCCACACTGGTGGCCACCTCGCCTCG
AAGGGGTTCATTGGTCCAACAGAGCCTACCTCCTTTCCTAGAACAGAAAGGGGGAAGTGGGTCTAGCAT
AAGTTCATCGGGAGGGTCTGCATCCATGGTAAAGATTCCCGGAAGTAAATCCTTATCAAAATAGCTGAT
GGGAGTGGGGTCATCTAAGGCCATTTGCCATTCTCGAGCTGCCAGTGCGCGCTCATATGGGTTAAGGGG
ACTGCCCCATGGCATGGGATGGGTGAGTGCAGAGGCATACATGCCACAGATGTCATAGACGTAGATGGG

Figure 51 (continued)

ATCCTCAAAGATGCCTATGTAGGTTGGATAGCATCGCCCCCCTCTGATACTTGCTCGCACATAGTCATA
TAGTTCATGTGATGGCGCTAGCAGCCCCGGACCCAAGTTGGTGCGATTGGGTTTTTCTGTTCTGTAGAC
GATCTGGCGAAAGATGGCGTGAGAATTGGAAGAGATGGTGGGTCTTTGAAAAATGTTGAAATGGGCATG
AGGTAGACCTACAGAGTCTCTGACAAAGTGGGCATAAGATTCTTGAAGCTTGGTTACCAGTTCGGCGGT
GACAAGTACGTCTAGGGCGCAGTAGTCAAGTGTTTCTTGAATGATGTCATAACCTGGTTGGTTTTTCTT
TTCCCACAGTTCGCGGTTGAGAAGGTATTCTTCGCGATCCTTCCAGTACTCTTCTAGCGGAAACCCGTC
TTTGTCTGCACGGTAAGATCCTAGCATGTAGAACTGATTAACTGCCTTGTAAGGGCAGCAGCCCTTCTC
TACGGGTAGAGAGTATGCTTGAGCAGCTTTTCGTAGCGAAGCGTGAGTAAGGGCAAAGGTGTCTCTGAC
CATGACTTTGAGGAATTGGTATTTGAAGTCGATGTCGTCACAGGCTCCCTGTTCCCAGAGTTGGAAGTC
TACCCGTTTCTTGTAGGCGGGGTTGGGCAAAGCGAAAGTAACATCATTGAAGAGAATCTTGCCGGCCCT
GGGCATGAAATTGCGAGTGATGCGAAAAGGCTGTGGTACTTCCGCTCGGTTATTGATAACCTGGGCAGC
TAGGACGATCTCGTCGAAACCGTTGATGTTGTGTCCTACGATGTATAATTCTATGAAACGCGGCGTGCC
TCTGACGTGAGGTAGCTTACTGAGCTCATCAAAGGTTAGGTCTGTGGGGTCAGATAAGGCGTAGTGTTC
GAGAGCCCATTCGTGCAGGTGAGGATTCGCTTTAAGGAAGGAGGACCAGAGGTCCACTGCCAGTGCTGT
TTGTAACTGGTCCCGGTACTGACGAAAATGCCGTCCGACTGCCATTTTTTCTGGGGTGACGCAATAGAA
GGTTTGGGGGTCCTGCCGCCAGCGATCCCACTTGAGTTTTATGGCGAGGTCATAGGCGATGTTGACGAG
CCGCTGGTCTCCAGAGAGTTTCATGACCAGCATGAAGGGGATTAGCTGCTTGCCAAAGGACCCCATCCA
GGTGTAGGTTTCCACATCGTAGGTGAGAAAGAGCCTTTCTGTGCGAGGATGAGAGCCAATCGGAAGAA
CTGGATCTCCTGCCACCAGTTGGAGGAATGGCTGTTGATGTGATGGAAGTAGAACTCCCTGCGACGCGC
CGAGCATTCATGCTTGTGCTTGTACAGACGGCCGCAGTAGTCGCAGCGTTGCACGGGTTGTATCTCGTG
AATGAGTTGTACCTGGCTTCCCTTGACGAGAAATTTCAGTGGGAAGCCGAGGCCTGGCGATTGTATCTC
GTGCTTTACTATGTTGTCTGCATCGGCCTGTTCATCTTCTGTCTCGATGGTGGTCATGCTGACGAGCCC
TCGCGGGAGGCAAGTCCAGACCTCGGCGCGGCAGGGGCGGAGCTCGAGGACGAGAGCGCGCAGGCTGGA
GCTGTCCAGGGTCCTGAGACGCTGCGGACTCAGGTTAGTAGGCAGTGTCAGGAGATTAACTTGCATGAT
CTTTTGGAGGGCGTGCGGGAGGTTCAGATAGTACTTGATCTCAACGGGTCCGTTGGTGGAGATGTCGAT
GGCTTGCAGGGTTCCGTGTCCCTTGGGCGCTACCACCGTGCCCTTGTTTTTCATTTTGGACGGCGGTGG
CTCTGTTGCTTCTTGCATGTTTAGAAGCGGTGTCGAGGGCGCGCACCGGGCGGCAGGGGCGGCTCGGGA
CCCGGCGGCATGGCTGGCAGTGGTACGTCGGCGCCGCGCGCGGGTAGGTTCTGGTACTGCGCCCTGAGA
AGACTCGCATGCGCGACGACGCGGCGGTTGACATCCTGGATCTGACGCCTCTGGGTGAAAGCTACCGGC
CCCGTGAGCTTGAACCTGAAAGAGAGTTCAACAGAATCAATCTCGGTATCGTTGACGGCGGCTTGCCTA
AGGATTTCTTGCACGTCACCAGAGTTGTCCTGGTAGGCGATCTCCGCCATGAACTGCTCGATCTCTTCC
TCTTGAAGATCTCCGCGGCCCGCTCTCTCGACGGTGGCCGCGAGGTCGTTGGAGATGCGCCCAATGAGT
TGAGAGAATGCATTCATGCCCGCCTCGTTCCAGACGCGGCTGTAGACCACGGCCCCCACGGGATCTCTC
GCGCGCATGACCACCTGGGCGAGGTTGAGCTCCACGTGGCGGGTGAAGACCGCATAGTTGCATAGGCGC
TGGAAAAGGTAGTTGAGTGTGGTGGCGATGTGCTCGGTGACGAAGAAATACATGATCCATCGTCTCAGC
GGCATCTCGCTGACATCGCCCAGAGCTTCCAAGCGCTCCATGGCCTCGTAGAAGTCCACGGCAAAATTA
AAAAACTGGGAGTTTCGCGCGGACACGGTCAACTCCTCTTCCAGAAGACGGATAAGTTCGGCGATGGTG
GTGCGCACCTCGCGCTCGAAAGCCCCTGGGATTTCTTCCTCAATCTCTTCTTCTTCCACTAACATCTCT
TCCTCTTCAGGTGGGGCTGCAGGAGGAGGGGGAACGCGGCGACGCCGGCGGCGCACGGGCAGACGGTCG
ATGAATCTTTCAATGACCTCTCCGCGGCGGCGGCGCATGGTTTCAGTGACGGCGCGGCCGTTCTCGCGC
GGTCGCAGAGTAAAAACACCGCCGCGCATCTCCTTAAAGTGGTGACTGGGAGGTTCTCCGTTTGGGAGG
GAGAGGGCGCTGATTATACATTTTATTAATTGGCCCGTAGGGACTGCACGCAGAGATCTGATCGTGTCA
AGATCCACGGGATCTGAAAACCTTTCGACGAAAGCGTCTAACCAGTCACAGTCACAAGGTAGGCTGAGT
ACGGCTTCTTGTGGGCGGGGGTGGTTATGTGTTCGGTCTGGGTCTTCTGTTTCTTCTTCATCTCGGGAA
GGTGAGACGATGCTGCTGGTGATGAAATTAAAGTAGGCAGTTCTAAGACGGCGGATGGTGGCGAGGAGC
ACCAGGTCTTTGGGTCCGGCTTGCTGGATACGCAGGCGATTGGCCATTCCCCAAGCATTATCCTGACAT
CTAGCAAGATCTTTGTAGTAGTCTTGCATGAGCCGTTCTACGGGCACTTCTTCCTCACCCGTTCTGCCA
TGCATACGTGTGAGTCCAAATCCGCGCATTGGTTGTACCAGTGCCAAGTCAGCTACGACTCTTTCGGCG
AGGATGGCTTGCTGTACTTGGGTAAGGGTGGCTTGAAAGTCATCAAAATCCACAAAGCGGTGGTAAGCT
CCTGTATTAATGGTGTAAGCACAGTTGGCCATGACTGACCAGTTAACTGTCTGGTGACCAGGGCGCACG
AGCTCGGTGTATTTAAGGCGCGAATAGGCGCGGGTGTCAAAGATGTAATCGTTGCAGGTGCGCACCAGA

Figure 51 (continued)

TACTGGTACCCTATAAGAAAATGCGGCGGTGGTTGGCGGTAGAGAGGCCATCGTTCTGTAGCTGGAGCG
CCAGGGGCGAGGTCTTCCAACATAAGGCGGTGATAGCCGTAGATGTACCTGGACATCCAGGTGATTCCT
GCGGCGGTAGTAGAAGCCCGAGGAAACTCGCGTACGCGGTTCCAAATGTTGCGTAGCGGCATGAAGTAG
TTCATTGTAGGCACGGTTTGACCAGTGAGGCGCGCGCAGTCATTGATGCTCTATAGACACGGAGAAAAT
GAAAGCGTTCAGCGACTCGACTCCGTAGCCTGGAGGAACGTGAACGGGTTGGGTCGCGGTGTACCCCGG
TTCGAGACTTGTACTCGAGCCGGCCGGAGCCGCGGCTAACGTGGTATTGGCACTCCCGTCTCGACCCAG
CCTACAAAAATCCAGGATACGGAATCGAGTCGTTTTGCTGGTTTCCGAATGGCAGGGAAGTGAGTCCTA
TTTTTTTTTTTTGCCGCTCAGATGCATCCCGTGCTGCGACAGATGCGCCCCCAACAACAGCCCCCCTCG
CAGCAGCAGCAGCAGCAATCACAAAAGGCTGTCCCTGCAACTACTGCAACTGCCGCCGTGAGCGGTGCG
GGACAGCCCGCCTATGATCTGGACTTGGAAGAGGGCGAAGGACTGGCACGTCTAGGTGCGCCTTCACCC
GAGCGGCATCCGCGAGTTCAACTGAAAAAAGATTCTCGCGAGGCGTATGTGCCCCAACAGAACCTATTT
AGAGACAGAAGCGGCGAGGAGCCGGAGGAGATGCGAGCTTCCCGCTTTAACGCGGGTCGTGAGCTGCGT
CACGGTTTGGACCGAAGACGAGTGTTGCGGGACGAGGATTTCGAAGTTGATGAAATGACAGGGATCAGT
CCTGCCAGGGCACACGTGGCTGCAGCCAACCTTGTATCGGCTTACGAGCAGACAGTAAAGGAAGAGCGT
AACTTCCAAAAGTCTTTTAATAATCATGTGCGAACCCTGATTGCCCGCGAAGAAGTTACCCTTGGTTTG
ATGCATTTGTGGGATTTGATGGAAGCTATCATTCAGAACCCTACTAGCAAACCTCTGACCGCCCAGCTG
TTTCTGGTGGTGCAACACAGCAGAGACAATGAGGCTTTCAGAGAGGCGCTGCTGAACATCACCGAACCC
GAGGGGAGATGGTTGTATGATCTTATCAACATTCTACAGAGTATCATAGTGCAGGAGCGGAGCCTGGGC
CTGGCCGAGAAGGTGGCTGCCATCAATTACTCGGTTTTGAGCTTGGGAAAATATTACGCTCGCAAAATC
TACAAGACTCCATACGTTCCCATAGACAAGGAGGTGAAGATAGATGGGTTCTACATGCGCATGACGCTC
AAGGTCTTGACCCTGAGCGATGATCTTGGGGTGTATCGCAATGACAGAATGCATCGCGCGGTTAGCGCC
AGCAGGAGGCGCGAGTTAAGCGACAGGGAACTGATGCACAGTTTGCAAAGAGCTCTGACTGGAGCTGGA
ACCGAGGGTGAGAATTACTTCGACATGGGAGCTGACTTGCAGTGGCAGCCTAGTCGCAGGGCTCTGAGC
GCCGCGACGGCAGGATGTGAGCTTCCTTACATAGAAGAGGCGGATGAAGGCGAGGAGGAAGAGGGCGAG
TACTTGGAAGACTGATGGCACAACCCGTGTTTTTTGCTAGATGGAACAGCAAGCACCGGATCCCGCAAT
GCGGGCGGCGCTGCAGAGCCAGCCGTCCGGCATTAACTCCTCGGACGATTGGACCCAGGCCATGCAACG
TATCATGGCGTTGACGACTCGCAACCCCGAAGCCTTTAGACAGCAACCCCAGGCCAACCGTCTATCGGC
CATCATGGAAGCTGTAGTGCCTTCCCGCTCTAATCCCACTCATGAGAAGGTCCTGGCCATCGTGAACGC
GTTGGTGGAGAACAAAGCTATTCGTCCAGATGAGGCCGGACTGGTATACAACGCTCTCTTAGAACGCGT
GGCTCGCTACAACAGTAGCAATGTGCAAACCAATTTGGACCGTATGATAACAGATGTACGCGAAGCCGT
GTCTCAGCGCGAAAGGTTCCAGCGTGATGCCAACCTGGGTTCGCTGGTGGCGTTAAATGCTTTCTTGAG
TACTCAGCCTGCTAATGTGCCGCGTGGTCAACAGGATTATACTAACTTTTTAAGTGCTTTGAGACTGAT
GGTATCAGAAGTACCTCAGAGCGAAGTGTATCAGTCCGGTCCTGATTACTTCTTTCAGACTAGCAGACA
GGGCTTGCAGACGGTAAATCTGAGCCAAGCTTTTAAAAACCTTAAAGGTTTGTGGGGAGTGCATGCCCC
GGTAGGAGAAAGAGCAACCGTGTCTAGCTTGTTAACTCCGAACTCCCGCCTATTATTACTGTTGGTAGC
TCCTTTCACCGACAGCGGTAGCATCGACCGTAATTCCTATTTGGGTTACCTACTAAACCTGTATCGCGA
AGCCATAGGGCAAAGTCAGGTGGACGAGCAGACCTATCAAGAAATTACCCAAGTCAGTCGCGCTTTGGG
ACAGGAAGACACTGGCAGTTTGGAAGCCACTCTGAACTTCTTGCTTACCAATCGGTCTCAAAAGATCCC
TCCTCAATATGCTCTTACTGCGGAGGAGGAGAGGATCCTTAGATATGTGCAGCAGAGCGTGGGATTGTT
TCTGATGCAAGAGGGGGCAACTCCGACTGCAGCACTGGACATGACAGCGCGAAATATGGAGCCCAGCAT
GTATGCCAGTAACCGACCTTTCATTAACAAACTGCTGGACTACTTGCACAGAGCTGCCGCTATGAACTC
TGATTATTTCACCAATGCCATCTTAAACCCGCACTGGCTGCCCCCACCTGGTTTCTACACGGGCGAATA
TGACATGCCCGACCCTAATGACGGATTTCTGTGGGACGACGTGGACAGCGATGTTTTTTCACCTCTTTC
TGATCATCGCACGTGGAAAAAGGAAGGCGGCGATAGAATGCATTCTTCTGCATCGCTGTCCGGGGTCAT
GGGTGCTACCGCGGCTGAGCCCGAGTCTGCAAGTCCTTTTCCTAGTCTACCCTTTTCTCTACACAGTGT
ACGTAGCAGCGAAGTGGGTAGAATAAGTCGCCCGAGTTTAATGGGCGAAGAGGAGTATCTAAACGATTC
CTTGCTCAGACCGGCAAGAGAAAAAAATTTCCCAAACAATGGAATAGAAAGTTTGGTGGATAAAATGAG
TAGATGGAAGACTTATGCTCAGGATCACAGAGACGAGCCTGGGATCATGGGGATTACAAGTAGAGCGAG
CCGTAGACGCCAGCGCCATGACAGACAGAGGGGTCTTGTGTGGGACGATGAGGATTCGGCCGATGATAG
CAGCGTGCTGGACTTGGGTGGGAGAGGAAGGGGCAACCCGTTTGCTCATTTGCGCCCTCGCTTGGGTGG
TATGTTGTAAAAAAAAATAAAAAAAAAACTCACCAAGGCCATGGCGACGAGCGTACGTTCGTTCTTCT

Figure 51 (continued)

TATTATCTGTGTCTAGTATAATGAGGCGAGTCGTGCTAGGCGGAGCGGTGGTGTATCCGGAGGGTCCTC
CTCCTTCGTACGAGAGCGTGATGCAGCAGCAGCAGGCGACGGCGGTGATGCAATCCCCACTGGAGGCTC
CCTTTGTGCCTCCGCGATACCTGGCACCTACGGAGGGCAGAAACAGCATTCGTTATTCGGAACTGGCAC
CTCAGTACGATACCACCAGGTTGTATCTGGTGGACAACAAGTCGGCGGACATTGCTTCTCTGAACTATC
AGAATGACCACAGCAACTTCTTGACCACGGTGGTGCAAAACAATGACTTTACCCCTACGGAAGCCAGCA
CCCAGACCATTAACTTTGATGAACGATCGCGGTGGGGCGGTCAGCTAAAGACCATCATGCATACTAACA
TGCCAAACGTGAACGAGTATATGTTTAGTAACAAGTTCAAAGCGCGTGTGATGGTGTCCAGAAAACCTC
CCGACGGTGCTGCAGTTGGGGATACTTATGATCACAAGCAGGATATTTTGAAATATGAGTGGTTCGAGT
TTACTTTGCCAGAAGGCAACTTTTCAGTTACTATGACTATTGATTTGATGAACAATGCCATCATAGATA
ATTACTTGAAAGTGGGTAGACAGAATGGAGTGCTTGAAAGTGACATTGGTGTTAAGTTCGACACCAGGA
ACTTCAAGCTGGGATGGGATCCCGAAACCAAGTTGATCATGCCTGGAGTGTATACGTATGAAGCCTTCC
ATCCTGACATTGTCTTACTGCCTGGCTGCGGAGTGGATTTTACCGAGAGTCGTTTGAGCAACCTTCTTG
GTATCAGAAAAAAACAGCCATTTCAAGAGGGTTTTAAGATTTTGTATGAAGATTTAGAAGGTGGTAATA
TTCCGGCCCTCTTGGATGTAGATGCCTATGAGAACAGTAAGAAAGAACAAAAAGCCAAAATAGAAGCTG
CTACAGCTGCTGCAGAAGCTAAGGCAAACATAGTTGCCAGCGACTCTACAAGGGTTGCTAACGCTGGAG
AGGTCAGAGGAGACAATTTTGCGCCAACACCTGTTCCGACTGCAGAATCATTATTGGCCGATGTGTCTG
AAGGAACGGACGTGAAACTCACTATTCAACCTGTAGAAAAAGATAGTAAGAATAGAAGCTATAATGTGT
TGGAAGACAAAATCAACACAGCCTATCGCAGTTGGTATCTTTCGTACAATTATGGCGATCCCGAAAAAG
GAGTGCGTTCCTGGACATTGCTCACCACCTCAGATGTCACCTGCGGAGCAGAGCAGGTCTACTGGTCGC
TTCCAGACATGATGAAGGATCCTGTCACTTTCCGCTCCACTAGACAAGTCAGTAACTACCCTGTGGTGG
GTGCAGAGCTTATGCCCGTCTTCTCAAAGAGCTTCTACAACGAACAAGCTGTGTACTCCCAGCAGCTCC
GCCAGTCCACCTCGCTTACGCACGTCTTCAACCGCTTTCCTGAGAACCAGATTTTAATCCGTCCGCCGG
CGCCCACCATTACCACCGTCAGTGAAAACGTTCCTGCTCTCACAGATCACGGGACCCTGCCGTTGCGCA
GCAGTATCCGGGGAGTCCAACGTGTGACCGTTACTGACGCCAGACGCCGCACCTGTCCCTACGTGTACA
AGGCACTGGGCATAGTCGCACCGCGCGTCCTTTCAAGCCGCACTTTCTAAAAAAAAAAAAAAATGTCCAT
TCTTATCTCGCCCAGTAATAACACCGGTTGGGGTCTGCGCGCTCCAAGCAAGATGTACGGAGGCGCACG
CAAACGTTCTACCCAACATCCTGTCCGTGTTCGCGGACATTTTCGCGCTCCATGGGGCGCCCTCAAGGG
CCGCACTCGCGTTCGAACCACCGTCGATGATGTAATCGATCAGGTGGTTGCCGACGCCCGTAATTATAC
TCCTACTGCGCCTACATCTACTGTGGATGCAGTTATTGACAGTGTAGTGGCTGACGCTCGCAACTATGC
TCGACGTAAGAGCCGGCGAAGGCGCATTGCCAGACGCCACCGAGCTACCACTGCCATGCGAGCCGCAAG
AGCTCTGCTACGAAGAGCTAGACGCGTGGGGCGAAGAGCCATGCTTAGGGCGGCCAGACGTGCAGCTTC
GGGCGCCAGCGCCGGCAGGTCCCGCAGGCAAGCAGCCGCTGTCGCAGCGGCGACTATTGCCGACATGGC
CCAATCGCGAAGAGGCAATGTATACTGGGTGCGTGACGCTGCCACCGGTCAACGTGTACCCGTGCGCAC
CCGTCCCCCTCGCACTTAGAAGATACTGAGCAGTCTCCGATGTTGTGTCCCAGCGGCGAGGATGTCCAA
GCGCAAATACAAGGAAGAAATGCTGCAGGTTATCGCACCTGAAGTCTACGGCCAACCGTTGAAGGATGA
AAAAAAACCCCGCAAAATCAAGCGGGTTAAAAAGGACAAAAAAGAAGAGGAAGATGGCGATGATGGGCT
GGCGGAGTTTGTGCGCGAGTTTGCCCCACGGCGACGCGTGCAATGGCGTGGGCGCAAAGTTCGACATGT
GTTGAGACCTGGAACTTCGGTGGTCTTTACACCCGGCGAGCGTTCAAGCGCTACTTTTAAGCGTTCCTA
TGATGAGGTGTACGGGGATGATGATATTCTTGAGCAGGCGGCTGACCGATTAGGCGAGTTTGCTTATGG
CAAGCGTAGTAGAATAACTTCCAAGGATGAGACAGTGTCGATACCCTTGGATCATGGAAATCCCACCCC
TAGTCTTAAACCGGTCACTTTGCAGCAAGTGTTACCCGTAACTCCGCGAACAGGTGTTAAACGCGAAGG
TGAAGATTTGTATCCCACTATGCAACTGATGGTACCCAAACGCCAGAAGTTGGAGGACGTTTTGGAGAA
AGTAAAAGTGGATCCAGATATTCAACCTGAGGTTAAAGTGAGACCCATTAAGCAGGTAGCGCCTGGTCT
GGGGGTACAAACTGTAGACATTAAGATTCCCACTGAAAGTATGGAAGTGCAAACTGAACCCGCAAAGCC
TACTGCCACCTCCACTGAAGTGCAAACGGATCCATGGATGCCCATGCCTATTACAACTGACGCCGCCGG
TCCCACTCGAAGATCCCGACGAAAGTACGGTCCAGCAAGTCTGTTGATGCCCAATTATGTTGTACACCC
ATCTATTATTCCTACTCCTGGTTACCGAGGCACTCGCTACTATCGCAGCCGAAACAGTACCTCCCGCCG
TCGCCGCAAGACACCTGCAAATCGCAGTCGTCGCCCGTAGACGCACAAGCAAACCGACTCCCGGCGCCCT
GGTGCGGCAAGTGTACCGCAATGGTAGTGCGGAACCTTTGACACTGCCGCGTGCGCGTTACCATCCGAG
TATCATCACTTAATCAATGTTGCCGCTGCCTCCTTGCAGATATGGCCCTCACTTGTCGCCTTCGCGTTC
CCATCACTGGTTACCGAGGAAGAAACTCGCGCCGTAGAAGAGGGATGTTGGGACGCGGAATGCGACGCT

Figure 51 (continued)

ACAGGCGACGGCGTGCTATCCGCAAGCAATTGCGGGGTGGTTTTTTACCAGCCTTAATTCCAATTATCG
CTGCTGCAATTGGCGCGATACCAGGCATAGCTTCCGTGGCGGTTCAGGCCTCGCAACGACATTGACATT
GGAAAAAAACGTATAAATAAAAAAAAAAAAAATACAATGGACTCTGACACTCCTGGTCCTGTGACTATGT
TTTCTTAGAGATGGAAGACATCAATTTTTCATCCTTGGCTCCGCGACACGGCACGAAGCCGTACATGGG
CACCTGGAGCGACATCGGCACGAGCCAACTGAACGGGGGCGCCTTCAATTGGAGCAGTATCTGGAGCGG
GCTTAAAAATTTTGGCTCAACCATAAAAACATACGGGAACAAAGCTTGGAACAGCAGTACAGGACAGGC
GCTTAGAAATAAACTTAAAGACCAGAACTTCCAACAAAAAGTAGTCGATGGGATAGCTTCCGGCATCAA
TGGAGTGGTAGATTTGGCTAACCAGGCTGTGCAGAAAAAGATAAACAGTCGTTTGGACCCGCCGCCAGC
AACCCCAGGTGAAATGCAAGTGGAGGAAGAAATTCCTCCGCCAGAAAAACGAGGCGACAAGCGTCCGCG
TCCCGATTTGGAAGAGACGCTGGTGACGCGCGTAGATGAACCGCCTTCTTATGAGGAAGCAACGAAGCT
TGGAATGCCCACCACTAGACCGATAGCCCCAATGGCCACCGGGGTGATGAAACCTTCTCAGTTGCATCG
ACCCGTCACCTTGGATTTGCCCCCTCCCCCTGCTGCTACTGCTGTACCCGCTTCTAAGCCTGTCGCTGC
CCCGAAACCAGTCGCCGTAGCCAGGTCACGTCCCGGGGGCGCTCCTCGTCCAAATGCGCACTGGCAAAA
TACTCTGAACAGCATCGTGGGTCTAGGCGTGCAAAGTGTAAAACGCCGTCGCTGCTTTTAATTAAATAT
GGAGTAGCGCTTAACTTGCCTATCTGTGTATATGTGTCATTACACGCCGTCACAGCAGCAGAGGAAAAA
AGGAAGAGGTCGTGCGTCGACGCTGAGTTACTTTCAAGATGGCCACCCCATCGATGCTGCCCCAATGGG
CATACATGCACATCGCCGGACAGGATGCTTCGGAGTACCTGAGTCCGGGTCTGGTGCAGTTCGCCCGCG
CCACAGACACCTACTTCAATCTGGGAAATAAGTTTAGAAATCCCACCGTAGCGCCGACCCACGATGTGA
CCACCGACCGTAGCCAGCGGCTCATGTTGCGCTTCGTGCCCGTTGACCGGGAGGACAATACATACTCTT
ACAAAGTGCGGTACACCCTGGCCGTGGGCGACAACAGAGTGCTGGATATGGCCAGCACGTTCTTTGACA
TTAGGGGTGTGTTGGACAGAGGTCCCAGTTTCAAACCCTATTCTGGTACGGCTTACAACTCCCTGGCTC
CTAAAGGCGCTCCAAATACATCTCAGTGGATTGCAGAAGGTGTAAAAAATACAACTGGTGAGGAACACG
TAACAGAAGAGGAAACCAATACTACTACTTACACTTTTGGCAATGCTCCTGTAAAAGCTGAAGCTGAAA
TTACAAAAGAAGGACTCCCAGTAGGTTTGGAAGTTTCAGATGAAGAAAGTAAACCGATTTATGCTGATA
AAACATATCAGCCAGAACCTCAGCTGGGAGATGAAACTTGGACTGACCTTGATGGAAAAACCGAAAAGT
ATGGAGGCAGGGCTCTCAAACCCGATACTAAGATGAAACCATGCTACGGGTCCTTTGCCAAACCTACTA
ATGTGAAAGGCGGTCAGGCAAAACAAAAAACAACGGAGCAGCCAAATCAGAAAGTCGAATATGATATCG
ACATGGAGTTTTTTGATGCGGCATCGCAGAAAACAAACTTAAGTCCTAAAATTGTCATGTATGCAGAAA
ATGTAAATTTGGAAACTCCAGACACTCATGTAGTGTACAAACCTGGAACAGAAGACACAAGTTCCGAAG
CTAATTTGGGACAACAATCTATGCCCAACAGACCCAACTACATTGGCTTCAGAGATAACTTTATTGGAC
TTATGTACTATAACAGTACTGGTAACATGGGGGTGCTGGCTGGTCAAGCGTCTCAGTTAAATGCAGTGG
TTGACTTGCAGGACAGAAACACAGAACTTTCTTACCAACTCTTGCTTGACTCTCTGGGCGACAGAACCA
GATACTTTAGCATGTGGAATCAGGCTGTGGACAGTTATGATCCTGATGTACGTGTTATTGAAAATCATG
GTGTGGAAGATGAACTTCCCAACTACTGTTTTCCACTGGACGGCATAGGTGTTCCAACAACCAGTTACA
AATCAATAGTTCCAAATGGAGACAATGCGCCTAATTGGAAGGAACCTGAAGTAAATGGAACAAGTGAGA
TCGGACAGGGTAATTTGTTTGCCATGGAAATTAACCTTCAAGCCAATCTATGGCGAAGTTTCCTTTATT
CCAATGTGGCTCTATATCTCCCAGACTCGTACAAATACACCCCGTCCAATGTCACTCTTCCAGAAAACA
AAAACACCTACGACTACATGAACGGGCGGGTGGTGCCGCCATCTCTAGTAGACACCTATGTGAACATTG
GTGCCAGGTGGTCTCTGGATGCCATGGACAATGTCAACCCATTCAACCACCACCGTAACGCTGGCTTGC
GTTACCGATCCATGCTTCTGGGTAACGGACGTTATGTGCCTTTCCACATACAAGTGCCTCAAAAATTCT
TCGCTGTTAAAAACCTGCTGCTTCTCCCAGGCTCCTACACTTATGAGTGGAACTTTAGGAAGGATGTGA
ACATGGTTCTACAGAGTTCCCTCGGTAACGACCTGCGGGTAGATGGCGCCAGCATCAGTTTCACGAGCA
TCAACCTCTATGCTACTTTTTTCCCCATGGCTCACAACACCGCTTCCACCCTTGAAGCCATGCTGCGGA
ATGACACCAATGATCAGTCATTCAACGACTACCTATCTGCAGCTAACATGCTCTACCCCATTCCTGCCA
ATGCAACCAATATTCCCATTTCCATTCCTTCTCGCAACTGGGCGGCTTTCAGAGGCTGGTCATTTACCA
GACTGAAAACCAAAGAAACTCCCTCTTTGGGGTCTGGATTTGACCCCTACTTTGTCTATTCTGGTTCTA
TTCCCTACCTGGATGGTACCTTCTACCTGAACCACACTTTTAAGAAGGTTTCCATCATGTTTGACTCTT
CAGTGAGCTGGCCTGGAAATGACAGGTTACTATCTCCTAACGAATTTGAAATAAAGCGCACTGTGGATG
GCGAAGGCTACAACGTAGCCCAATGCAACATGACCAAAGACTGGTTCTTGGTACAGATGCTCGCCAACT
ACAACATCGGCTATCAGGGCTTCTACATTCCAGAAGGATACAAAGATCGCATGTATTCATTTTTCAGAA
ACTTCCAGCCCATGAGCAGGCAGGTGGTTGATGAGGTCAATTACAAAGACTTCAAGGCCGTCGCCATAC

Figure 51 (continued)

CCTACCAACACAACAACTCTGGCTTTGTGGGTTACATGGCTCCGACCATGCGCCAAGGTCAACCCTATC
CCGCTAACTATCCCTATCCACTCATTGGAACAACTGCCGTAAATAGTGTTACGCAGAAAAAGTTCTTGT
GTGACAGAACCATGTGGCGCATACCGTTCTCGAGCAACTTCATGTCTATGGGGGCCCTTACAGACTTGG
GACAGAATATGCTCTATGCCAACTCAGCTCATGCTCTGGACATGACCTTTGAGGTGGATCCCATGGATG
AGCCCACCCTGCTTTATCTTCTCTTCGAAGTTTTCGACGTGGTCAGAGTGCATCAGCCACACCGCGGCA
TCATCGAGGCAGTCTACCTGCGTACACCGTTCTCGGCCGGTAACGCTACCACGTAAGAAGCTTCTTGCT
TCTTGCAAATAGCAGCTGCAACCATGGCCTGCGGATCCCAAAACGGCTCCAGCGAGCAAGAGCTCAGAG
CCATTGTCCAAGACCTGGGTTGCGGACCCTATTTTTTGGGAACCTACGATAAGCGCTTCCCGGGGTTCA
TGGCCCCCGATAAGCTCGCCTGTGCCATTGTAAATACGGCCGGACGTGAGACGGGGGGAGAGCACTGGT
TGGCTTTCGGTTGGAACCCACGTTCTAACACCTGCTACCTTTTTGATCCTTTTGGATTCTCGGATGATC
GTCTCAAACAGATTTACCAGTTTGAATATGAGGGTCTCCTGCGCCGCAGCGCTCTTGCTACCAAGGACC
GCTGTATTACGCTGGAAAAATCTACCCAGACCGTGCAGGGTCCCCGTTCTGCCGCCTGCGGACTTTTCT
GCTGCATGTTCCTTCACGCCTTTGTGCACTGGCCTGACCGTCCCATGGACGGAAACCCCACCATGAAAT
TGCTAACTGGAGTGCCAAACAACATGCTTCATTCTCCTAAAGTCCAGCCCACCCTGTGTGACAATCAAA
AAGCACTCTACCATTTTCTTAATACCCATTCGCCTTATTTTCGCTCCCATCGTACACACATCGAAAGGG
CCACTGCGTTCGACCGTATGGATGTTCAATAATGACTCATGTAAACAACGTGTTCAATAAACATCACTT
TATTTTTTTACATGTATCAAGGCTCTGCATTACTTATTTATTTACAAGTCGAATGGGTTCTGACGAGAA
TCAGAATGACCCGCAGGCAGTGATACGTTGCGGAACTGATACTTGGGTTGCCACTTGAATTCGGGAATC
ACCAACTTGGGAACCGGTATATCGGGCAGGATGTCACTCCACAGCTTTCTGGTCAGCTGCAAAGCTCCA
AGCAGGTCAGGAGCCGAAATCTTGAAATCACAATTAGGACCAGTGCTTTGAGCGCGAGAGTTGCGGTAC
ACCGGATTGCAGCACTGAAACACCATCAGCGACGGATGTCTCACGCTTGCCAGCACGGTGGGATCTGCA
ATCATGCCCACATCCAGATCTTCAGCATTGGCAATGCTGAACGGGGTCATCTTGCAGGTCTGCCTACCC
ATGGCGGGCACCCAATTAGGCTTGTGGTTGCAATCGCAGTGCAGGGGGATCAGTATCATCTTGGCCTGA
TCCTGTCTGATTCCTGGATACACGGCTCTCATGAAAGCATCATATTGCTTGAAAGCCTGCTGGGCTTTA
CTACCCTCGGTATAAAACATCCCGCAGGACCTGCTCGAAAACTGGTTAGCTGCACAGCCGGCATCATTC
ACACAGCAGCGGGCGTCATTGTTAGCTATTTGCACCACACTTCTGCCCCAGCGGTTTTGGGTGATTTTG
GTTCGCTCGGGATTCTCCTTTAAGGCTCGTTGTCCGTTCTCGCTGGCCACATCCATCTCGATAATCTGC
TCCTTCTGAATCATAATATTGCCATGCAGGCACTTCAGCTTGCCCTCATAATCATTGCAGCCATGAGGC
CACAACGCACAGCCTGTACATTCCCAATTATGGTGGGCGATCTGAGAAAAAGAATGTATCATTCCCTGC
AGAAATCTTCCCATCATCGTGCTCAGTGTCTTGTGACTAGTGAAAGTTAACTGGATGCCTCGGTGCTCC
TCGTTTACGTACTGGTGACAGATGCGCTTGTATTGTTCGTGTTGCTCAGGCATTAGTTTAAAAGAGGTT
CTAAGTTCGTTATCCAGCCTGTACTTCTCCATCAGCAGACACATCACTTCCATGCCTTTCTCCCAAGCA
GACACCAGGGGCAAGCTAATCGGATTCTTAACAGTGCAGGCAGCAGCTCCTTTAGCCAGAGGGTCATCT
TTAGCGATCTTCTCAATGCTTCTTTTGCCATCCTTCTCAACGATGCGCACGGGCGGGTAGCTGAAACCC
ACTGCTACAAGTTGCGCCTCTTCTCTTTCTTCTTCGCTGTCTTGACTGATGTCTTGCATGGGGATATGT
TTGGTCTTCCTTGGCTTCTTTTTGGGGGGTATCGGAGGAGGAGGACTGTCGCTCCGTTCCGGAGACAGG
GAGGATTGTGACGTTTCGCTCACCATTACCAACTGACTGTCGGTAGAAGAACCTGACCCCACACGGCGA
CAGGTGTTTCTCTTCGGGGGCAGAGGTGGAGGCGATTGCGAAGGGCTGCGGTCCGACCTGGAAGGCGGA
TGACTGGCAGAACCCCTTCCGCGTTCGGGGGTGTGCTCCCTGTGGCGGTCGCTTAACTGATTTCCTTCG
CGGCTGGCCATTGTGTTCTCCTAGGCAGAGAAACAACAGACATGGAAACTCAGCCATTGCTGTCAACAT
CGCCACGAGTGCCATCACATCTCGTCCTCAGCGACGAGGAAAAGGAGCAGAGCTTAAGCATTCCACCGC
CCAGTCCTGCCACCACCTCTACCCTAGAAGATAAGGAGGTCGACGCATCTCATGACATGCAGAATAAAA
AAGCGAAAGAGTCTGAGACAGACATCGAGCAAGACCCGGGCTATGTGACACCGGTGGAACACGAGGAAG
AGTTGAAACGCTTTCTAGAGAGAGAGGATGAAAACTGCCCAAAACAACGAGCAGATAACTATCACCAAG
ATGCTGGAAATAGGGATCAGAACACCGACTACCTCATAGGGCTTGACGGGGAAGACGCGCTCCTTAAAC
ATCTAGCAAGACAGTCGCTCATAGTCAAGGATGCATTATTGGACAGAACTGAAGTGCCCATCAGTGTGG
AAGAGCTCAGCCGCGCCTACGAGCTTAACCTCTTTTCACCTCGTACTCCCCCCAAACGTCAGCCAAACG
GCACCTGCGAGCCAAATCCTCGCTTAAACTTTTATCCAGCTTTTGCTGTGCCAGAAGTACTGGCTACCT
ATCACATCTTTTTTAAAAATCAAAAAATTCCAGTCTCCTGCCGCGCTAATCGCACCCGCGCCGATGCCC
TACTCAATCTGGGACCTGGTTCACGCTTACCTGATATAGCTTCCTTGGAAGAGGTTCCAAAGATCTTCG
AGGGTCTGGGCAATAATGAGACTCGGGCCGCAAATGCTCTGCAAAAGGGAGAAAATGGCATGGATGAGC

Figure 51 (continued)

ATCACAGCGTTCTGGTGGAATTGGAAGGCGATAATGCCAGACTCGCAGTACTCAAGCGAAGCATCGAGG
TCACACACTTCGCATATCCCGCTGTCAACCTGCCCCCTAAAGTCATGACGGCGGTCATGGACCAGTTAC
TCATTAAGCGCGCAAGTCCCCTTTCAGAAGACATGCATGACCCAGATGCCTGTGATGAGGGTAAACCAG
TGGTCAGTGATGAGCAGCTAACCCGATGGCTGGGCACCGACTCTCCCAGGGATTTGGAAGAGCGTCGCA
AGCTTATGATGGCCGTGGTGCTGGTTACCGTAGAACTAGAGTGTCTCCGACGTTTCTTTACCGATTCAG
AAACCTTGCGCAAACTCGAAGAGAATCTGCACTACACTTTTAGACACGGCTTTGTGCGGCAGGCATGCA
AGATATCTAACGTGGAACTCACCAACCTGGTTTCCTACATGGGTATTCTGCATGAGAATCGCCTAGGAC
AAAGCGTGCTGCACAGCACCCTGAAGGGGGAAGCCCGCCGTGATTACATCCGCGATTGTGTCTATCTGT
ACCTGTGCCACACGTGGCAAACCGGCATGGGTGTATGGCAGCAATGTTTAGAAGAACAGAACTTGAAAG
AGCTTGACAAGCTCTTACAGAAATCTCTTAAGGTTCTGTGGACAGGGTTCGACGAGCGCACCGTCGCTT
CCGACCTGGCAGACCTCATCTTCCCAGAGCGTCTCAGGGTTACTTTGCGAAACGGATTGCCTGACTTTA
TGAGCCAGAGCATGCTTAACAATTTTCGCTCTTTCATCCTGGAACGCTCCGGTATCCTGCCCGCCACCT
GCTGCGCACTGCCCTCCGACTTTGTGCCTCTCACCTACCGCGAGTGCCCCCCGCCGCTATGGAGTCACT
GCTACCTGTTCCGTCTGGCCAACTATCTCTCCTACCACTCGGATGTGATCGAGGATGTGAGCGGAGACG
GCTTGCTGGAGTGTCACTGCCGCTGCAATCTGTGCACGCCCCACCGGTCCCTAGCTTGCAACCCCCAGT
TGATGAGCGAAACCCAGATAATAGGCACCTTTGAATTGCAAGGCCCCAGCAGCCAAGGCGATGGGTCTT
CTCCTGGGCAAAGTTTAAAACTGACCCCGGGACTGTGGACCTCCGCCTACTTGCGCAAGTTTGCTCCGG
AAGATTACCACCCCTATGAAATCAAGTTCTATGAGGACCAATCACAGCCTCCAAAGGCCGAACTTTCGG
CCTGCGTCATCACCCAGGGGGCAATTCTGGCCCAATTGCAAGCCATCCAAAAATCCCGCCAAGAATTTC
TACTGAAAAAGGGTAAGGGGGTCTACCTTGACCCCCAGACCGGCGAGGAACTCAACACAAGGTTCCCTC
AGGATGTCCCAACGACGAGAAAACAAGAAGTTGAAGGTGCAGCCGCCGCCCCCAGAAGATATGGAGGAA
GATTGGGACAGTCAGGCAGAGGAGGCGGAGGAGGACAGTCTGGAGGACAGTCTGGAGGAAGACAGTTTG
GAGGAGGAAAACGAGGAGGCAGAGGAGGTGGAAGAAGTAACCGCCGACAAACAGTTATCCTCGGCTGCG
GAGACAAGCAACAGCGCTACCATCTCCGCTCCGAGTCGAGGAACCCGGCGGCGTCCCAGCAGTAGATGG
GACGAGACCGGACGCTTCCCGAACCCAACCAGCGCTTCCAAGACCGGTAAGAAGGATCGGCAGGGATAC
AAGTCCTGGCGGGGGCATAAGAATGCCATCATCTCCTGCTTGCATGAGTGCGGGGGCAACATATCCTTC
ACGCGGCGCTACTTGCTATTCCACCATGGGGTGAACTTTCCGCGCAATGTTTTGCATTACTACCGTCAC
CTCCACAGCCCCTACTATAGCCAGCAAATCCCGGCAGTCTCGACAGATAAAGACAGCGGCGGCGACCTC
CAACAGAAAACCAGCAGCGGCAGTTAGAAAATACACAACAAGTGCAGCAACAGGAGGATTAAAGATTAC
AGCCAACGAGCCAGCGCAAACCCGAGAGTTAAGAAATCGGATCTTTCCAACCCTGTATGCCATCTTCCA
GCAGAGTCGGGGTCAAGAGCAGGAACTGAAAATAAAAAACCGATCTCTGCGTTCGCTCACCAGAAGTTG
TTTGTATCACAAGAGCGAAGATCAACTTCAGCGCACTCTCGAGGACGCCGAGGCTCTCTTCAACAAGTA
CTGCGCGCTGACTCTTAAAGAGTAGGCAGCGACCGCGCTTATTCAAAAAAGGCGGGAATTACATCATCC
TCGACATGAGTAAAGAAATTCCCACGCCTTACATGTGGAGTTATCAACCCCAAATGGGATTGGCGGCAG
GCGCCTCCCAGGACTACTCCACCCGCATGAATTGGCTCAGCGCCGGGCCTTCTATGATTTCTCGAGTTA
ATGATATACGCGCCTACCGAAACCAAATACTTTTGGAACAGTCAGCTCTTACCACCACGCCCCGCCAAC
ACCTTAATCCCAGAAATTGGCCCGCCGCCCTAGTGTACCAGGAAAGTCCCGCTCCCACCACTGTATTAC
TTCCTCGAGACGCCCAGGCCGAAGTCCAAATGACTAATGCAGGTGCGCAGTTAGCTGGCGGCTCCACCC
TATGTCGTCACAGGCCTCGGCATAATATAAAACGCCTGATGATCAGAGGCCGAGGTATCCAGCTCAACG
ACGAGTCGGTGAGCTCTCCGCTTGGTCTACGACCAGACGGAATCTTTCAGATTGCCGGCTGCGGGAGAT
CTTCCTTCACCCCTCGTCAGGCTGTTCTGACTTTGGAAAGTTCGTCTTCGCAACCCCGCTCGGGCGGAA
TCGGGACCGTTCAATTTGTGGAGGAGTTTACTCCCTCTGTCTACTTCAACCCCTTCTCCGGATCTCCTG
GGCATTACCCGGACGAGTTCATACCGAACTTCGACGCGATTAGCGAGTCAGTGGACGGCTACGATTGAT
GTCTGGTGACGCGGCTGAGCTATCTCGGCTGCGACATCTAGACCACTGCCGCCGCTTTCGCTGCTTTGC
CCGGGAACTCATTGAGTTCATCTACTTCGAACTCCCCAAGGATCACCCTCAAGGTCCGGCCCACGGAGT
GCGGATTTCTATCGAAGGCAAAATAGACTCTCGCCTGCAACGAATTTTCTCCCAGCGGCCCGTGCTGAT
CGAGCGAGACCAGGGAAACACCACGGTTTCCATCTACTGCATTTGTAATCACCCCGGATTGCATGAAAG
CCTTTGCTGTCTTATGTGTACTGAGTTTAATAAAAACTGAATTAAGACTCTCCTACGGACTGCCGCTTC
TTCAACCCGGATTTTACAACCAGAAGAACGAAACTTTTCCTGTCGTCCAGGACTCTGTTAACTTCACCT
TTCCTACTCACAAACTAGAAGCTCAACGACTACACCGCTTTTCCAGAAGCATTTTCCCTACTAATACTA
CTTTCAAAACCGGAGGTGAGCTCCAAGGTCTTCCTACAGAAAACCCTTGGGTGGAAGCGGGCCTTGTAG

Figure 51 (continued)

TGCTAGGAATTCTTGCGGGTGGGCTTGTGATTATTCTTTGCTACCTATACACACCTTGCTTCACTTTCT
TAGTGGTGTTGTGGTATTGGTTTAAAAAATGGGGCCCATACTAGTCTTGCTTGTTTTACTTTCGCTTTT
GGAACCGGGTTCTGCCAATTACGATCCATGTCTAGACTTCGACCCAGAAAACTGCACACTTACTTTTGC
ACCCGACACAAGCCGCATCTGTGGAGTTCATCGCCTCTCTTACGAACTTGGCCCCCAACGACAAAAATT
TACCTGCATGGTGGGAATCAACCCCATAGTTATCACCCAGCAAAGTGGAGATACTAAGGGTTGCATTCA
CTGCTCCTGCGATTCCATCGAGTGCACCTACACCCTGCTGAAGACCCTATGCGGCCTAAGAGACCTGCT
ACCAATGAATTAAAAAATGATTAATAAAAAATCACTTACTTGAAATCAGCAATAAGGTCTCTGTTGAAA
TTTTCTCCCAGCAGCACCTCACTTCCCTCTTCCCAACTCTGGTATTCTAAACCCCGTTCAGCGGCATAC
TTTCTCCATACTTTAAAGGGGATGTCAAATTTTAGCTCCTCTCCTGTACCCACAATCTTCATGTCTTTC
TTCCCAGATGACCAAGAGAGTCCGGCTCAGTGACTCCTTCAACCCTGTCTACCCCTATGAAGATGAAAG
CACCTCCCAACACCCCTTTATAAACCCAGGGTTTATTTCCCCAAATGGCTTCACACAAAGCCCAAACGG
AGTTCTTACTTTAAAATGTTTAACCCCACTAACAACCACAGGCGGATCTCTACAGCTAAAAGTGGGAGG
GGGACTTACAGTGGATGACACCAACGGTTTTTTGAAAGAAAACATAAGTGCCACCACACCACTCGTTAA
GACTGGTCACTCTATAGGTTTACCACTAGGAGCCGGATTGGGAACGAATGAAAATAAACTTTGTATCAA
ATTAGGACAAGGACTTACATTCAATTCAAACAACATTTGCATTGATGACAATATTAACACCTTATGGAC
AGGAGTCAACCCCACCGAAGCCAACTGTCAAATCATGAACTCCAGTGAATCTAATGATTGCAAATTAAT
TCTAACACTAGTTAAAACTGGAGCACTAGTCACTGCATTTGTTTATGTTATAGGAGTATCTAACAATTT
TAATATGCTAACTACACACAGAAATATAAATTTTACTGCAGAGCTGTTTTTCGATTCTACTGGTAATTT
ACTAACTAGACTCTCATCCCTCAAAACTCCACTTAATCATAAATCAGGACAAAACATGGCTACTGGTGC
CATTACTAATGCTAAAGGTTTCATGCCCAGCACGACTGCCTATCCTTTCAATGATAATTCTAGAGAAAA
AGAAAACTACATTTACGGAACTTGTTACTACACAGCTAGTGATCGCACTGCTTTTCCCATTGACATATC
TGTCATGCTTAACCGAAGAGCAATAAATGACGAGACATCATATTGTATTCGTATAACTTGGTCCTGGAA
CACAGGAGATGCCCCAGAGGTGCAAACCTCTGCTACAACCCTAGTCACCTCCCCATTTACCTTTTACTA
CATCAGAGAAGACGACTGACAAATAAAGTTTGCGATCGCCAGGCCCACCATGGGATGGAGCTGTATCAT
CCTCTTCTTGGTAGCAACAGCTACAGGTGTCCACTCCCAGGTGCAGCTGCAGCAGTCTGGGGCTGAACT
GGCAAGACCTGGGGCCTCAGTGAAGATGTCCTGCAAGGCTTCTGGCTACACCTTTACTAGGTACACGAT
GCACTGGGTAAAACAGAGGCCTGGACAGGGTCTGGAATGGATTGGATACATTAATCCTAGCCGTGGTTA
TACTAATTACAATCAGAAGTTCAAGGACAAGGCCACATTGACTACAGACAAATCCTCCAGCACAGCCTA
CATGCAACTGAGCAGCCTGACATCTGAGGACTCTGCAGTCTATTACTGTGCAAGATATTATGATGATCA
TTACTGCCTTGACTACTGGGGCCAAGGCACCACTCTCACAGTCTCCTCAGGTGGCGGTGGCTCGGGCGG
TGGTGGATCTGGTGGCGGCGGATCTGATATCGTGCTCACTCAGTCTCCAGCAATCATGTCTGCATCTCC
AGGGGAGAAGGTCACCATGACCTGCAGTGCCAGCTCAAGTGTAAGTTACATGAACTGGTACCAGCAGAA
GTCAGGCACCTCCCCCAAAAGATGGATTTATGACACATCCAAACTGGCTTCTGGAGTCCCTGCTCACTT
CAGGGGCAGTGGGTCTGGGACCTCTTACTCTCTCACAATCAGCGGCATGGAGGCTGAAGATGCTGCCAC
TTATTACTGCCAGCAGTGGAGTAGTAACCCATTCACGTTCGGCTCGGGGACAAAGTTGGAAATAAACCG
GGGATCCGAACAAAAACTCATCTCAGAAGAGGATCTGAATGCTGTGGGCCAGGACACGCAGGAGGTCAT
CGTGGTGCCACACTCCTTGCCCTTTAAGGTGGTGGTGATCTCAGCCATCCTGGCCCTGGTGGTGCTCAC
CATCATCTCCCTTATCATCCTCATCATGCTTTGGCAGAAGAAGCCACGTGGTTCAATCCCTAACCCTCT
CCTCGGTCTCGATGGAAGCGGAGCTACTAACTTCAGCCTGCTGAAGCAGGCTGGAGACGTGGAGGAGAA
CCCTGGACCTGGCCACACACGGAGGCAGGGAACATCACCATCCAAGTGTCCATACCTCAATTTCTTTCA
GCTCTTGGTGCTGGCTGGTCTTTCTCACTTCTGTTCAGGTGTTATCCACGTGACCAAGGAAGTGAAAGA
AGTGGCAACGCTGTCCTGTGGTCACAATGTTTCTGTTGAAGAGCTGGCACAAACTCGCATCTACTGGCA
AAAGGAGAAGAAAATGGTGCTGACTATGATGTCTGGGGACATGAATATATGGCCCGAGTACAAGAACCG
GACCATCTTTGATATCACTAATAACCTCTCCATTGTGATCCTGGCTCTGCGCCCATCTGACGAGGGCAC
ATACGAGTGTGTTGTTCTGAAGTATGAAAAAGACGCTTTCAAGCGGGAACACCTGGCTGAAGTGACGTT
ATCAGTCAAAGCTGACTTCCCTACACCTAGTATATCTGACTTTGAAATTCCAACTTCTAATATTAGAAG
GATAATTTGCTCAACCTCTGGAGGTTTTCCAGAGCCTCACCTCTCCTGGTTGGAAAATGGAGAAGAATT
AAATGCCATCAACACAACAGTTTCCCAAGATCCTGAAACTGAGCTCTATGCTGTTAGCAGCAAACTGGA
TTTCAATATGACAACCAACCACAGCTTCATGTGTCTCATCAAGTATGGACATTTAAGAGTGAATCAGAC
CTTCAACTGGAATACAACCAAGCAAGAGCATTTTCCTGATAACCTGCTCCCATCCTGGGCCATTACCTT
AATCTCAGTAAATGGAATTTTTGTGATATGCTGCCTGACCTACTGCTTTGCCCCAAGATGCAGAGAGAG

Figure 51 (continued)

AAGGAGGAATGAGAGATTGAGAAGGGAAAGTGTACGCCCTGTATAAGCTAGCTTGACTGACTGAGATAC
AGCGTACCTTCAGCTCACAGACATGATAAGATACATTGATGAGTTTGGACAAACCACAACTAGAATGCA
GTGAAAAAAATGCTTTATTTGTGAAATTTGTGATGCTATTGCTTTATTTGTAACCATTATAAGCTGCAA
TAAACAAGTTAACAACAACAATTGCATTCATTTTATGTTTCAGGTTCAGGGGGAGGTGTGGGAGGTTTT
TTAAAGCAAGTAAAACCTCTACAAATGTGGTAGTCGTCAGCTATCCTGCAGGAACTTGTTTATTTGAAA
ATCAATTCACAAAATCCGAGTAGTTATTTTGCCTCCCCCTTCCCATTTAACAGAATACACCAATCTCTC
CCCACGCACAGCTTTAAACATTTGGATACCATTAGATATAGACATGGTTTTAGATTCCACATTCCAAAC
AGTTTCAGAGCGAGCCAATCTGGGGTCAGTGATAGATAAAAATCCATCGGGATAGTCTTTTAAAGCGCT
TTCACAGTCCAACTGCTGCGGATGCGACTCCGGAGTCTGGATCACGGTCATCTGGAAGAAGAACGATGG
GAATCATAATCCGAAAACGGTATCGGACGATTGTGTCTCATCAAACCCACAAGCAGCCGCTGTCTGCGT
CGCTCCGTGCGACTGCTGTTTATGGGATCAGGGTCCACAGTGTCCTGAAGCATGATTTTAATAGCCCTT
AACATCAACTTTCTGGTGCGATGCGCGCAGCAACGCATTCTGATTTCACTCAAATCTTTGCAGTAGGTA
CAACACATTATTACAATATTGTTTAATAAACCATAATTAAAAGCGCTCCAGCCAAAACTCATATCTGAT
ATAATCGCCCCTGCATGACCATCATACCAAAGTTTAATATAAATTAAATGACGTTCCCTCAAAAACACA
CTACCCACATACATGATCTCTTTTGGCATGTGCATATTAACAATCTGTCTGTACCATGGACAACGTTGG
TTAATCATGCAACCCAATATAACCTTCCGGAACCACACTGCCAACACCGCTCCCCCAGCCATGCATTGA
AGTGAACCCTGCTGATTACAATGACAATGAAGAACCCAATTCTCTCGACCGTGAATCACTTGAGAATGA
AAAATATCTATAGTGGCACAACATAGACATAAATGCATGCATCTTCTCATAATTTTTAACTCCTCAGGA
TTTAGAAACATATCCCAGGGAATAGGAAGCTCTTGCAGAACAGTAAAGCTGGCAGAACAAGGAAGACCA
CGAACACAACTTACACTATGCATAGTCATAGTATCACAATCTGGCAACAGCGGGTGGTCTTCAGTCATA
GAAGCTCGGGTTTCATTTTCCTCACAACGTGGTAACTGGGCTCTGGTGTAAGGGTGATGTCTGGCGCAT
GATGTCGAGCGTGCGCGCAACCTTGTCATAATGGAGTTGCTTCCTGACATTCTCGTATTTTGTATAGCA
AAACGCGGCCCTGGCAGAACACACTCTTCTTCGCCTTCTATCCTGCCGCTTAGCGTGTTCCGTGTGATA
GTTCAAGTACAACCACACTCTTAAGTTGGTCAAAAGAATGCTGGCTTCAGTTGTAATCAAAACTCCATC
GCATCTAATCGTTCTGAGGAAATCATCCAAGCAATGCAACTGGATTGTGTTTCAAGCAGGAGAGGAGAG
GGAAGAGACGGAAGAACCATGTTAATTTTTATTCCAAACGATCTCGCAGTACTTCAAATTGTAGATCGC
GCAGATGGCATCTCTCGCCCCCACTGTGTTGGTGAAAAAGCACAGCTAGATCAAAAGAAATGCGATTTT
CAAGGTGCTCAACGGTGGCTTCCAGCAAAGCCTCCACGCGCACATCCAAGAACAAAAGAATACCAAAAG
AAGGAGCATTTTCTAACTCCTCAATCATCATATTACATTCCTGCACCATTCCCAGATAATTTTCAGCTT
TCCAGCCTTGAATTATTCGTGTCAGTTCTTGTGGTAAATCCAATCCACACATTACAAACAGGTCCCGGA
GGGCGCCCTCCACCACCATTCTTAAACACACCCTCATAATGACAAAATATCTTGCTCCTGTGTCACCTG
TAGCGAATTGAGAATGGCAACATCAATTGACATGCCCTTGGCTCTAAGTTCTTCTTTAAGTTCTAGTTG
TAAAAACTCTCTCATATTATCACCAAACTGCTTAGCCAGAAGCCCCCCGGGAACAAGAGCAGGGGACGC
TACAGTGCAGTACAAGCGCAGACCTCCCCAATTGGCTCCAGCAAAAACAAGATTGGAATAAGCATATTG
GGAACCGCCAGTAATATCATCGAAGTTGCTGGAAATATAATCAGGCAGAGTTTCTTGTAAAAATTGAAT
AAAAGAAAAATTTGCCAAAAAAACATTCAAAACCTCTGGGATGCAAATGCAATAGGTTACCGCGCTGCG
CTCCAACATTGTTAGTTTTGAATTAGTCTGCAAAAATAAAAAAAAAAACAAGCGTCATATCATAGTAGC
CTGACGAACAGATGGATAAATCAGTCTTTCCATCACAAGACAAGCCACAGGGTCTCCAGCTCGACCCTC
GTAAAACCTGTCATCATGATTAAACAACAGCACCGAAAGTTCCTCGCGGTGACCAGCATGAATAATTCT
TGATGAAGCATACAATCCAGACATGTTAGCATCAGTTAACGAGAAAAAACAGCCAACATAGCCTTTGGG
TATAATTATGCTTAATCGTAAGTATAGCAAAGCCACCCCTCGCGGATACAAAGTAAAAGGCACAGGAGA
ATAAAAAATATAATTATTTCTCTGCTGCTGTTCAGGCAACGTCGCCCCCGGTCCCTCTAAATACACATA
CAAAGCCTCATCAGCCATGGCTTACCAGACAAAGTACAGCGGGCACACAAAGCACAAGCTCTAAAGTGA
CTCTCCAACCTCTCCACAATATATATATACACAAGCCCTAAACTGACGTAATGGGAGTAAAGTGTAAAA
AATCCCGCCAAACCCAACACACACCCCGAAACTGCGTCACCAGGGAAAAGTACAGTTTCACTTCCGCAA
TCCCAACAGGCGTAACTTCCTCTTTCTCACGGTACGTGATATCCCACTAACTTGCAACGTCATTTTCCC
ACGGTCGCACCGCCCCTTTTAGCCGTTAACCCCACAGCCAATCACCACACGATCCACACTTTTTAAAAT
CACCTCATTTACATATTGGCACCATTCCATCTATAAGGTATATTATATAGATAGA

Figure 52

SEQ ID NO. 103 NG-420 virus genome sequence comprising the EnAd genome with a transgene cassette that encodes a membrane-anchored chimeric form of the single chain Fv anti-human CD3e inserted in the region Bγ. The transgene cassette contains a 5' SSA, membrane-anchored anti-CD3ε cDNA sequence and a 3' poly(A) sequence

TCTATCTATATAATATACCTTATAGATGGAATGGTGCCAATATGTAAATGAGGTGATTTTAAAAAGTGT
GGATCGTGTGGTGATTGGCTGTGGGGTTAACGGCTAAAAGGGGCGGTGCGACCGTGGGAAAATGACGTT
TTGTGGGGGTGGAGTTTTTTTGCAAGTTGTCGCGGGAAATGTGACGCATAAAAAGGCTTTTTTCTCACG
GAACTACTTAGTTTTCCCACGGTATTTAACAGGAAATGAGGTAGTTTTGACCGGATGCAAGTGAAAATT
GTTGATTTTCGCGCGAAAACTGAATGAGGAAGTGTTTTTCTGAATAATGTGGTATTTATGGCAGGGTGG
AGTATTTGTTCAGGGCCAGGTAGACTTTGACCCATTACGTGGAGGTTTCGATTACCGTGTTTTTTACCT
GAATTTCCGCGTACCGTGTCAAAGTCTTCTGTTTTTACGTAGGTGTCAGCTGATCGCTAGGGTATTTAT
ACCTCAGGGTTTGTGTCAAGAGGCCACTCTTGAGTGCCAGCGAGAAGAGTTTTCTCCTCTGCGCCGGCA
GTTTAATAATAAAAAAATGAGAGATTTGCGATTTCTGCCTCAGGAAATAATCTCTGCTGAGACTGGAAA
TGAAATATTGGAGCTTGTGGTGCACGCCCTGATGGGAGACGATCCGGAGCCACCTGTGCAGCTTTTTGA
GCCTCCTACGCTTCAGGAACTGTATGATTTAGAGGTAGAGGGATCGGAGGATTCTAATGAGGAAGCTGT
AAATGGCTTTTTTACCGATTCTATGCTTTTAGCTGCTAATGAAGGGTTAGAATTAGATCCGCCTTTGGA
CACTTTTGATACTCCAGGGGTAATTGTGGAAAGCGGTACAGGTGTAAGAAAATTACCTGATTTGAGTTC
CGTGGACTGTGATTTGCACTGCTATGAAGACGGGTTTCCTCCGAGTGATGAGGAGGACCATGAAAAGGA
GCAGTCCATGCAGACTGCAGCGGGTGAGGGAGTGAAGGCTGCCAATGTTGGTTTTCAGTTGGATTGCCC
GGAGCTTCCTGGACATGGCTGTAAGTCTTGTGAATTTCACAGGAAAAATACTGGAGTAAAGGAACTGTT
ATGTTCGCTTTGTTATATGAGAACGCACTGCCACTTTATTTACAGTAAGTGTGTTTAAGTTAAAATTTA
AAGGAATATGCTGTTTTTCACATGTATATTGAGTGTGAGTTTTGTGCTTCTTATTATAGGTCCTGTGTC
TGATGCTGATGAATCACCATCTCCTGATTCTACTACCTCACCTCCTGAGATTCAAGCACCTGTTCCTGT
GGACGTGCGCAAGCCCATTCCTGTGAAGCTTAAGCCTGGGAAACGTCCAGCAGTGGAAAAACTTGAGGA
CTTGTTACAGGGTGGGGACGGACCTTTGGACTTGAGTACACGGAAACGTCCAAGACAATAAGTGTTCCA
TATCCGTGTTTACTTAAGGTGACGTCAATATTTGTGTGACAGTGCAATGTAATAAAAATATGTTAACTG
TTCACTGGTTTTTATTGCTTTTTGGGCGGGGACTCAGGTATATAAGTAGAAGCAGACCTGTGTGGTTAG
CTCATAGGAGCTGGCTTTCATCCATGGAGGTTTGGGCCATTTTGGAAGACCTTAGGAAGACTAGGCAAC
TGTTAGAGAACGCTTCGGACGGAGTCTCCGGTTTTTGGAGATTCTGGTTCGCTAGTGAATTAGCTAGGG
TAGTTTTTAGGATAAAACAGGACTATAAACAAGAATTTGAAAAGTTGTTGGTAGATTGCCCAGGACTTT
TTGAAGCTCTTAATTTGGGCCATCAGGTTCACTTTAAAGAAAAAGTTTTATCAGTTTTAGACTTTTCAA
CCCCAGGTAGAACTGCTGCTGCTGTGGCTTTTCTTACTTTTATATTAGATAAATGGATCCCGCAGACTC
ATTTCAGCAGGGGATACGTTTTGGATTTCATAGCCACAGCATTGTGGAGAACATGGAAGGTTCGCAAGA
TGAGGACAATCTTAGGTTACTGGCCAGTGCAGCCTTTGGGTGTAGCGGGAATCCTGAGGCATCCACCGG
TCATGCCAGCGGTTCTGGAGGAGGAACAGCAAGAGGACAACCCGAGAGCCGGCCTGGACCCTCCAGTGG
AGGAGGCGGAGTAGCTGACTTGTCTCCTGAACTGCAACGGGTGCTTACTGGATCTACGTCCACTGGACG
GGATAGGGGCGTTAAGAGGGAGAGGGCATCTAGTGGTACTGATGCTAGATCTGAGTTGGCTTTAAGTTT
AATGAGTCGCAGACGTCCTGAAACCATTTGGTGGCATGAGGTTCAGAAAGAGGGAAGGGATGAAGTTTC
TGTATTGCAGGAGAAATATTCACTGGAACAGGTGAAAACATGTTGGTTGGAGCCTGAGGATGATTGGGA
GGTGGCCATTAAAAATTATGCCAAGATAGCTTTGAGGCCTGATAAACAGTATAAGATTACTAGACGGAT
TAATATCCGGAATGCTTGTTACATATCTGGAAATGGGGCTGAGGTGGTAATAGATACTCAAGACAAGGC
AGTTATTAGATGCTGCATGATGGATATGTGGCCTGGGGTAGTCGGTATGGAAGCAGTAACTTTTGTAAA
TGTTAAGTTTAGGGGAGATGGTTATAATGGAATAGTGTTTATGGCCAATACCAAACTTATATTGCATGG
TTGTAGCTTTTTTGGTTTCAACAATACCTGTGTAGATGCCTGGGGACAGGTTAGTGTACGGGGATGTAG
TTTCTATGCGTGTTGGATTGCCACAGCTGGCAGAACCAAGAGTCAATTGTCTCTGAAGAAATGCATATT
TCAAAGATGTAACCTGGGCATTCTGAATGAAGGCGAAGCAAGGGTCCGCCACTGCGCTTCTACAGATAC
TGGATGTTTTATTTTGATTAAGGGAAATGCCAGCGTAAAGCATAACATGATTTGCGGTGCTTCCGATGA

Figure 52 (continued)

GAGGCCTTATCAAATGCTCACTTGTGCTGGTGGGCATTGTAATATGCTGGCTACTGTGCATATTGTTTC
CCATCAACGCAAAAAATGGCCTGTTTTTGATCACAATGTGATGACGAAGTGTACCATGCATGCAGGTGG
GCGTAGAGGAATGTTTATGCCTTACCAGTGTAACATGAATCATGTGAAAGTGTTGTTGGAACCAGATGC
CTTTTCCAGAATGAGCCTAACAGGAATTTTTGACATGAACATGCAAATCTGGAAGATCCTGAGGTATGA
TGATACGAGATCGAGGGTACGCGCATGCGAATGCGGAGGCAAGCATGCCAGGTTCCAGCCGGTGTGTGT
AGATGTGACTGAAGATCTCAGACCGGATCATTTGGTTATTGCCCGCACTGGAGCAGAGTTCGGATCCAG
TGGAGAAGAAACTGACTAAGGTGAGTATTGGGAAAACTTTGGGGTGGGATTTTCAGATGGACAGATTGA
GTAAAAATTTGTTTTTTCTGTCTTGCAGCTGTCATGAGTGGAAACGCTTCTTTTAAGGGGGGAGTCTTC
AGCCCTTATCTGACAGGGCGTCTCCCATCCTGGGCAGGAGTTCGTCAGAATGTTATGGGATCTACTGTG
GATGGAAGACCCGTCCAACCCGCCAATTCTTCAACGCTGACCTATGCTACTTTAAGTTCTTCACCTTTG
GACGCAGCTGCAGCTGCCGCCGCCGCTTCTGTTGCCGCTAACACTGTGCTTGGAATGGGTTACTATGGA
AGCATCATGGCTAATTCCACTTCCTCTAATAACCCTTCTACCCTGACTCAGGACAAGTTACTTGTCCTT
TTGGCCCAGCTGGAGGCTTTGACCCAACGTCTGGGTGAACTTTCTCAGCAGGTGGTCGAGTTGCGAGTA
CAAACTGAGTCTGCTGTCGGCACGGCAAAGTCTAAATAAAAAAATCCCAGAATCAATGAATAAATAAAC
AAGCTTGTTGTTGATTTAAAATCAAGTGTTTTTATTTCATTTTTCGCGCACGGTATGCCCTAGACCACC
GATCTCTATCATTGAGAACTCGGTGGATTTTTTCCAGGATCCTATAGAGGTGGGATTGAATGTTTAGAT
ACATGGGCATTAGGCCGTCTTTGGGGTGGAGATAGCTCCATTGAAGGGATTCATGCTCCGGGGTAGTGT
TGTAAATCACCCAGTCATAACAAGGTCGCAGTGCATGGTGTTGCACAATATCTTTTAGAAGTAGGCTGA
TTGCCACAGATAAGCCCTTGGTGTAGGTGTTTACAAACCGGTTGAGCTGGGATGGGTGCATTCGGGGTG
AAATTATGTGCATTTTGGATTGGATTTTTAAGTTGGCAATATTGCCGCCAAGATCCCGTCTTGGGTTCA
TGTTATGAAGGACCACCAAGACGGTGTATCCGGTACATTTAGGAAATTTATCGTGCAGCTTGGATGGAA
AAGCGTGGAAAAATTTGGAGACACCCTTGTGTCCTCCAAGATTTTCCATGCACTCATCCATGATAATAG
CAATGGGGCCGTGGGCAGCGGCGCGGGCAAACACGTTCCGTGGGTCTGACACATCATAGTTATGTTCCT
GAGTTAAATCATCATAAGCCATTTTAATGAATTTGGGGCGGAGAGTACCAGATTGGGGTATGAATGTTC
CTTCGGGCCCCGGAGCATAGTTCCCCTCACAGATTTGCATTTCCCAAGCTTTCAGTTCCGAGGGTGGAA
TCATGTCCACCTGGGGGGCTATGAAAAACACCGTTTCTGGGGCGGGGGTGATTAATTGTGATGATAGCA
AATTTCTGAGCAATTGAGATTTGCCACATCCGGTGGGGCCATAAATGATTCCGATTACGGGTTGCAGGT
GGTAGTTTAGGGAACGGCAACTGCCGTCTTCTCGAAGCAAGGGGGCCACCTCGTTCATCATTTCCCTTA
CATGCATATTTTCCCGCACCAAATCCATTAGGAGGCGCTCTCCTCCTAGTGATAGAAGTTCTTGTAGTG
AGGAAAAGTTTTTCAGCGGTTTCAGACCGTCAGCCATGGGCATTTTGGAGAGAGTTTGCTGCAAAAGTT
CTAGTCTGTTCCACAGTTCAGTGATGTGTTCTATGGCATCTCGATCCAGCAGACCTCCTCGTTTCGCGG
GTTTGGACGGCTCCTGGAATAGGGTATGAGACGATGGGCGTCCAGCGCTGCCAGGGTTCGGTCCTTCCA
GGGTCTCAGTGTTCGAGTCAGGGTTGTTTCCGTCACAGTGAAGGGGTGTGCGCCTGCTTGGGCGCTTGC
CAGGGTGCGCTTCAGACTCATCCTGCTGGTCGAAAACTTCTGTCGCTTGGCGCCCTGTATGTCGGCCAA
GTAGCAGTTTACCATGAGTTCGTAGTTGAGCGCCTCGGCTGCGTGGCCTTTGGCGCGGAGCTTACCTTT
GGAAGTTTTCTTGCATACCGGGCAGTATAGGCATTTCAGCGCATACAACTTGGGCGCAAGGAAAACGGA
TTCTGGGGAGTATGCATCTGCGCCGCAGGAGGCGCAAACAGTTTCACATTCCACCAGCCAGGTTAAATC
CGGTTCATTGGGGTCAAAAACAAGTTTTCCGCCATATTTTTTGATGCGTTTCTTACCTTTGGTCTCCAT
GAGTTCGTGTCCTCGTTGAGTGACAAACAGGCTGTCCGTGTCCCCGTAGACTGATTTACAGGCCTCTT
CTCCAGTGGAGTGCCTCGGTCTTCTTCGTACAGGAACTCTGACCACTCTGATACAAAGGCGCGCGTCCA
GGCCAGCACAAAGGAGGCTATGTGGGAGGGGTAGCGATCGTTGTCAACCAGGGGGTCCACCTTTTCCAA
AGTATGCAAACACATGTCACCCTCTTCAACATCCAGGAATGTGATTGGCTTGTAGGTGTATTTCACGTG
ACCTGGGGTCCCCGCTGGGGGGGTATAAAAGGGGGCGGTTCTTTGCTCTTCCTCACTGTCTTCCGGATC
GCTGTCCAGGAACGTCAGCTGTTGGGGTAGGTATTCCCTCTCGAAGGCGGGCATGACCTCTGCACTCAG
GTTGTCAGTTTCTAAGAACGAGGAGGATTTGATATTGACAGTGCCGGTTGAGATGCCTTTCATGAGGTT
TTCGTCCATCTGGTCAGAAAACACAATTTTTTTATTGTCAAGTTTGGTGGCAAATGATCCATACAGGGC
GTTGGATAAAAGTTTGGCAATGGATCGCATGGTTTGGTTCTTTTCCTTGTCCGCGCGCTCTTTGGCGGC
GATGTTGAGTTGGACATACTCGCGTGCCAGGCACTTCCATTCGGGGAAGATAGTTGTTAATTCATCTGG

Figure 52 (continued)

CACGATTCTCACTTGCCACCCTCGATTATGCAAGGTAATTAAATCCACACTGGTGGCCACCTCGCCTCG
AAGGGGTTCATTGGTCCAACAGAGCCTACCTCCTTTCCTAGAACAGAAAGGGGGAAGTGGGTCTAGCAT
AAGTTCATCGGGAGGGTCTGCATCCATGGTAAAGATTCCCGGAAGTAAATCCTTATCAAAATAGCTGAT
GGGAGTGGGGTCATCTAAGGCCATTTGCCATTCTCGAGCTGCCAGTGCGCGCTCATATGGGTTAAGGGG
ACTGCCCCATGGCATGGGATGGGTGAGTGCAGAGGCATACATGCCACAGATGTCATAGACGTAGATGGG
ATCCTCAAAGATGCCTATGTAGGTTGGATAGCATCGCCCCCCTCTGATACTTGCTCGCACATAGTCATA
TAGTTCATGTGATGGCGCTAGCAGCCCCGGACCCAAGTTGGTGCGATTGGGTTTTTCTGTTCTGTAGAC
GATCTGGCGAAAGATGGCGTGAGAATTGGAAGAGATGGTGGGTCTTTGAAAAATGTTGAAATGGGCATG
AGGTAGACCTACAGAGTCTCTGACAAAGTGGGCATAAGATTCTTGAAGCTTGGTTACCAGTTCGGCGGT
GACAAGTACGTCTAGGGCGCAGTAGTCAAGTGTTTCTTGAATGATGTCATAACCTGGTTGGTTTTTCTT
TTCCCACAGTTCGCGGTTGAGAAGGTATTCTTCGCGATCCTTCCAGTACTCTTCTAGCGGAAACCCGTC
TTTGTCTGCACGGTAAGATCCTAGCATGTAGAACTGATTAACTGCCTTGTAAGGGCAGCAGCCCTTCTC
TACGGGTAGAGAGTATGCTTGAGCAGCTTTTCGTAGCGAAGCGTGAGTAAGGGCAAAGGTGTCTCTGAC
CATGACTTTGAGGAATTGGTATTTGAAGTCGATGTCGTCACAGGCTCCCTGTTCCCAGAGTTGGAAGTC
TACCCGTTTCTTGTAGGCGGGGTTGGGCAAAGCGAAAGTAACATCATTGAAGAGAATCTTGCCGGCCCT
GGGCATGAAATTGCGAGTGATGCGAAAAGGCTGTGGTACTTCCGCTCGGTTATTGATAACCTGGGCAGC
TAGGACGATCTCGTCGAAACCGTTGATGTTGTGTCCTACGATGTATAATTCTATGAAACGCGGCGTGCC
TCTGACGTGAGGTAGCTTACTGAGCTCATCAAAGGTTAGGTCTGTGGGGTCAGATAAGGCGTAGTGTTC
GAGAGCCCATTCGTGCAGGTGAGGATTCGCTTTAAGGAAGGAGGACCAGAGGTCCACTGCCAGTGCTGT
TTGTAACTGGTCCCGGTACTGACGAAAATGCCGTCCGACTGCCATTTTTTCTGGGGTGACGCAATAGAA
GGTTTGGGGGTCCTGCCGCCAGCGATCCCACTTGAGTTTTATGGCGAGGTCATAGGCGATGTTGACGAG
CCGCTGGTCTCCAGAGAGTTTCATGACCAGCATGAAGGGGATTAGCTGCTTGCCAAAGGACCCCATCCA
GGTGTAGGTTTCCACATCGTAGGTGAGAAAGAGCCTTTCTGTGCGAGGATGAGAGCCAATCGGGAAGAA
CTGGATCTCCTGCCACCAGTTGGAGGAATGGCTGTTGATGTGATGGAAGTAGAACTCCCTGCGACGCGC
CGAGCATTCATGCTTGTGCTTGTACAGACGGCCGCAGTAGTCGCAGCGTTGCACGGGTTGTATCTCGTG
AATGAGTTGTACCTGGCTTCCCTTGACGAGAAATTTCAGTGGGAAGCCGAGGCCTGGCGATTGTATCTC
GTGCTTTACTATGTTGTCTGCATCGGCCTGTTCATCTTCTGTCTCGATGGTGGTCATGCTGACGAGCCC
TCGCGGGAGGCAAGTCCAGACCTCGGCGCGGCAGGGGCGGAGCTCGAGGACGAGAGCGCGCAGGCTGGA
GCTGTCCAGGGTCCTGAGACGCTGCGGACTCAGGTTAGTAGGCAGTGTCAGGAGATTAACTTGCATGAT
CTTTTGGAGGGCGTGCGGGAGGTTCAGATAGTACTTGATCTCAACGGGTCCGTTGGTGGAGATGTCGAT
GGCTTGCAGGGTTCCGTGTCCCTTGGGCGCTACCACCGTGCCCTTGTTTTTCATTTTGGACGGCGGTGG
CTCTGTTGCTTCTTGCATGTTTAGAAGCGGTGTCGAGGGCGCGCACCGGGCGGCAGGGGCGGCTCGGGA
CCCGGCGGCATGGCTGGCAGTGGTACGTCGGCGCCGCGCGCGGGTAGGTTCTGGTACTGCGCCCTGAGA
AGACTCGCATGCGCGACGACGCGGCGGTTGACATCCTGGATCTGACGCCTCTGGGTGAAAGCTACCGGC
CCCGTGAGCTTGAACCTGAAAGAGAGTTCAACAGAATCAATCTCGGTATCGTTGACGGCGGCTTGCCTA
AGGATTTCTTGCACGTCACCAGAGTTGTCCTGGTAGGCGATCTCCGCCATGAACTGCTCGATCTCTTCC
TCTTGAAGATCTCCGCGGCCCGCTCTCTCGACGGTGGCCGCGAGGTCGTTGGAGATGCGCCCAATGAGT
TGAGAGAATGCATTCATGCCCGCCTCGTTCCAGACGCGGCTGTAGACCACGGCCCCCACGGGATCTCTC
GCGCGCATGACCACCTGGGCGAGGTTGAGCTCCACGTGGCGGGTGAAGACCGCATAGTTGCATAGGCGC
TGGAAAAGGTAGTTGAGTGTGGTGGCGATGTGCTCGGTGACGAAGAAATACATGATCCATCGTCTCAGC
GGCATCTCGCTGACATCGCCCAGAGCTTCCAAGCGCTCCATGGCCTCGTAGAAGTCCACGGCAAAATTA
AAAAACTGGGAGTTTCGCGCGGACACGGTCAACTCCTCTTCCAGAAGACGGATAAGTTCGGCGATGGTG
GTGCGCACCTCGCGCTCGAAAGCCCCTGGGATTTCTTCCTCAATCTCTTCTTCTTCCACTAACATCTCT
TCCTCTTCAGGTGGGGCTGCAGGAGGAGGGGGAACGCGGCGACGCCGGCGGCGCACGGGCAGACGGTCG
ATGAATCTTTCAATGACCTCTCCGCGGCGGCGGCGCATGGTTTCAGTGACGGCGCGGCCGTTCTCGCGC
GGTCGCAGAGTAAAAACACCGCCGCGCATCTCCTTAAAGTGGTGACTGGGAGGTTCTCCGTTTGGGAGG
GAGAGGGCGCTGATTATACATTTTATTAATTGGCCCGTAGGGACTGCACGCAGAGATCTGATCGTGTCA
AGATCCACGGGATCTGAAAACCTTTCGACGAAAGCGTCTAACCAGTCACAGTCACAAGGTAGGCTGAGT

Figure 52 (continued)

ACGGCTTCTTGTGGCGGGGGTGGTTATGTGTTCGGTCTGGGTCTTCTGTTTCTTCTTCATCTCGGGAA
GGTGAGACGATGCTGCTGGTGATGAAATTAAAGTAGGCAGTTCTAAGACGGCGGATGGTGGCGAGGAGC
ACCAGGTCTTTGGGTCCGGCTTGCTGGATACGCAGGCGATTGGCCATTCCCCAAGCATTATCCTGACAT
CTAGCAAGATCTTTGTAGTAGTCTTGCATGAGCCGTTCTACGGGCACTTCTTCCTCACCCGTTCTGCCA
TGCATACGTGTGAGTCCAAATCCGCGCATTGGTTGTACCAGTGCCAAGTCAGCTACGACTCTTTCGGCG
AGGATGGCTTGCTGTACTTGGGTAAGGGTGGCTTGAAAGTCATCAAAATCCACAAAGCGGTGGTAAGCT
CCTGTATTAATGGTGTAAGCACAGTTGGCCATGACTGACCAGTTAACTGTCTGGTGACCAGGGCGCACG
AGCTCGGTGTATTTAAGGCGCGAATAGGCGCGGGTGTCAAAGATGTAATCGTTGCAGGTGCGCACCAGA
TACTGGTACCCTATAAGAAAATGCGGCGGTGGTTGGCGGTAGAGAGGCCATCGTTCTGTAGCTGGAGCG
CCAGGGGCGAGGTCTTCCAACATAAGGCGGTGATAGCCGTAGATGTACCTGGACATCCAGGTGATTCCT
GCGGCGGTAGTAGAAGCCCGAGGAAACTCGCGTACGCGGTTCCAAATGTTGCGTAGCGGCATGAAGTAG
TTCATTGTAGGCACGGTTTGACCAGTGAGGCGCGCGCAGTCATTGATGCTCTATAGACACGGAGAAAAT
GAAAGCGTTCAGCGACTCGACTCCGTAGCCTGGAGGAACGTGAACGGGTTGGGTCGCGGTGTACCCCGG
TTCGAGACTTGTACTCGAGCCGGCCGGAGCCGCGGCTAACGTGGTATTGGCACTCCCGTCTCGACCCAG
CCTACAAAAATCCAGGATACGGAATCGAGTCGTTTTGCTGGTTTCCGAATGGCAGGGAAGTGAGTCCTA
TTTTTTTTTTTTGCCGCTCAGATGCATCCCGTGCTGCGACAGATGCGCCCCCAACAACAGCCCCCCTCG
CAGCAGCAGCAGCAGCAATCACAAAAGGCTGTCCCTGCAACTACTGCAACTGCCGCCGTGAGCGGTGCG
GGACAGCCCGCCTATGATCTGGACTTGGAAGAGGGCGAAGGACTGGCACGTCTAGGTGCGCCTTCACCC
GAGCGGCATCCGCGAGTTCAACTGAAAAAAGATTCTCGCGAGGCGTATGTGCCCCAACAGAACCTATTT
AGAGACAGAAGCGGCGAGGAGCCGGAGGAGATGCGAGCTTCCCGCTTTAACGCGGGTCGTGAGCTGCGT
CACGGTTTGGACCGAAGACGAGTGTTGCGGGACGAGGATTTCGAAGTTGATGAAATGACAGGGATCAGT
CCTGCCAGGGCACACGTGGCTGCAGCCAACCTTGTATCGGCTTACGAGCAGACAGTAAAGGAAGAGCGT
AACTTCCAAAAGTCTTTTAATAATCATGTGCGAACCCTGATTGCCCGCGAAGAAGTTACCCTTGGTTTG
ATGCATTTGTGGGATTTGATGGAAGCTATCATTCAGAACCCTACTAGCAAACCTCTGACCGCCCAGCTG
TTTCTGGTGGTGCAACACAGCAGAGACAATGAGGCTTTCAGAGAGGCGCTGCTGAACATCACCGAACCC
GAGGGGAGATGGTTGTATGATCTTATCAACATTCTACAGAGTATCATAGTGCAGGAGCGGAGCCTGGGC
CTGGCCGAGAAGGTGGCTGCCATCAATTACTCGGTTTTGAGCTTGGGAAAATATTACGCTCGCAAAATC
TACAAGACTCCATACGTTCCCATAGACAAGGAGGTGAAGATAGATGGGTTCTACATGCGCATGACGCTC
AAGGTCTTGACCCTGAGCGATGATCTTGGGGTGTATCGCAATGACAGAATGCATCGCGCGGTTAGCGCC
AGCAGGAGGCGCGAGTTAAGCGACAGGGAACTGATGCACAGTTTGCAAAGAGCTCTGACTGGAGCTGGA
ACCGAGGGTGAGAATTACTTCGACATGGGAGCTGACTTGCAGTGGCAGCCTAGTCGCAGGGCTCTGAGC
GCCGCGACGGCAGGATGTGAGCTTCCTTACATAGAAGAGGCGGATGAAGGCGAGGAGGAAGAGGGCGAG
TACTTGGAAGACTGATGGCACAACCCGTGTTTTTTGCTAGATGGAACAGCAAGCACCGGATCCCGCAAT
GCGGGCGGCGCTGCAGAGCCAGCCGTCCGGCATTAACTCCTCGGACGATTGGACCCAGGCCATGCAACG
TATCATGGCGTTGACGACTCGCAACCCCGAAGCCTTTAGACAGCAACCCCAGGCCAACCGTCTATCGGC
CATCATGGAAGCTGTAGTGCCTTCCCGCTCTAATCCCACTCATGAGAAGGTCCTGGCCATCGTGAACGC
GTTGGTGGAGAACAAAGCTATTCGTCCAGATGAGGCCGGACTGGTATACAACGCTCTCTTAGAACGCGT
GGCTCGCTACAACAGTAGCAATGTGCAAACCAATTTGGACCGTATGATAACAGATGTACGCGAAGCCGT
GTCTCAGCGCGAAAGGTTCCAGCGTGATGCCAACCTGGGTTCGCTGGTGGCGTTAAATGCTTTCTTGAG
TACTCAGCCTGCTAATGTGCCGCGTGGTCAACAGGATTATACTAACTTTTTAAGTGCTTTGAGACTGAT
GGTATCAGAAGTACCTCAGAGCGAAGTGTATCAGTCCGGTCCTGATTACTTCTTTCAGACTAGCAGACA
GGGCTTGCAGACGGTAAATCTGAGCCAAGCTTTTAAAAACCTTAAAGGTTTGTGGGGAGTGCATGCCCC
GGTAGGAGAAAGAGCAACCGTGTCTAGCTTGTTAACTCCGAACTCCCGCCTATTATTACTGTTGGTAGC
TCCTTTCACCGACAGCGGTAGCATCGACCGTAATTCCTATTTGGGTTACCTACTAAACCTGTATCGCGA
AGCCATAGGGCAAAGTCAGGTGGACGAGCAGACCTATCAAGAAATTACCCAAGTCAGTCGCGCTTTGGG
ACAGGAAGACACTGGCAGTTTGGAAGCCACTCTGAACTTCTTGCTTACCAATCGGTCTCAAAAGATCCC
TCCTCAATATGCTCTTACTGCGGAGGAGGAGAGGATCCTTAGATATGTGCAGCAGAGCGTGGGATTGTT
TCTGATGCAAGAGGGGGCAACTCCGACTGCAGCACTGGACATGACAGCGCGAAATATGGAGCCCAGCAT

Figure 52 (continued)

GTATGCCAGTAACCGACCTTTCATTAACAAACTGCTGGACTACTTGCACAGAGCTGCCGCTATGAACTC
TGATTATTTCACCAATGCCATCTTAAACCCGCACTGGCTGCCCCCACCTGGTTTCTACACGGGCGAATA
TGACATGCCCGACCCTAATGACGGATTTCTGTGGGACGACGTGGACAGCGATGTTTTTTCACCTCTTTC
TGATCATCGCACGTGGAAAAAGGAAGGCGGCGATAGAATGCATTCTTCTGCATCGCTGTCCGGGGTCAT
GGGTGCTACCGCGGCTGAGCCCGAGTCTGCAAGTCCTTTTCCTAGTCTACCCTTTTCTCTACACAGTGT
ACGTAGCAGCGAAGTGGGTAGAATAAGTCGCCCGAGTTTAATGGGCGAAGAGGAGTATCTAAACGATTC
CTTGCTCAGACCGGCAAGAGAAAAAAATTTCCCAAACAATGGAATAGAAAGTTTGGTGGATAAAATGAG
TAGATGGAAGACTTATGCTCAGGATCACAGAGACGAGCCTGGGATCATGGGGATTACAAGTAGAGCGAG
CCGTAGACGCCAGCGCCATGACAGACAGAGGGGTCTTGTGTGGGACGATGAGGATTCGGCCGATGATAG
CAGCGTGCTGGACTTGGGTGGGAGAGGAAGGGGCAACCCGTTTGCTCATTTGCGCCCTCGCTTGGGTGG
TATGTTGTAAAAAAAAATAAAAAAAAAACTCACCAAGGCCATGGCGACGAGCGTACGTTCGTTCTTCTT
TATTATCTGTGTCTAGTATAATGAGGCGAGTCGTGCTAGGCGGAGCGGTGGTGTATCCGGAGGGTCCTC
CTCCTTCGTACGAGAGCGTGATGCAGCAGCAGCAGGCGACGGCGGTGATGCAATCCCCACTGGAGGCTC
CCTTTGTGCCTCCGCGATACCTGGCACCTACGGAGGGCAGAAACAGCATTCGTTATTCGGAACTGGCAC
CTCAGTACGATACCACCAGGTTGTATCTGGTGGACAACAAGTCGGCGGACATTGCTTCTCTGAACTATC
AGAATGACCACAGCAACTTCTTGACCACGGTGGTGCAAAACAATGACTTTACCCCTACGGAAGCCAGCA
CCCAGACCATTAACTTTGATGAACGATCGCGGTGGGGCGGTCAGCTAAAGACCATCATGCATACTAACA
TGCCAAACGTGAACGAGTATATGTTTAGTAACAAGTTCAAAGCGCGTGTGATGGTGTCCAGAAAACCTC
CCGACGGTGCTGCAGTTGGGGATACTTATGATCACAAGCAGGATATTTTGAAATATGAGTGGTTCGAGT
TTACTTTGCCAGAAGGCAACTTTTCAGTTACTATGACTATTGATTTGATGAACAATGCCATCATAGATA
ATTACTTGAAAGTGGGTAGACAGAATGGAGTGCTTGAAAGTGACATTGGTGTTAAGTTCGACACCAGGA
ACTTCAAGCTGGGATGGGATCCCGAAACCAAGTTGATCATGCCTGGAGTGTATACGTATGAAGCCTTCC
ATCCTGACATTGTCTTACTGCCTGGCTGCGGAGTGGATTTTACCGAGAGTCGTTTGAGCAACCTTCTTG
GTATCAGAAAAAAACAGCCATTTCAAGAGGGTTTTAAGATTTTGTATGAAGATTTAGAAGGTGGTAATA
TTCCGGCCCTCTTGGATGTAGATGCCTATGAGAACAGTAAGAAAGAACAAAAAGCCAAAATAGAAGCTG
CTACAGCTGCTGCAGAAGCTAAGGCAAACATAGTTGCCAGCGACTCTACAAGGGTTGCTAACGCTGGAG
AGGTCAGAGGAGACAATTTTGCGCCAACACCTGTTCCGACTGCAGAATCATTATTGGCCGATGTGTCTG
AAGGAACGGACGTGAAACTCACTATTCAACCTGTAGAAAAAGATAGTAAGAATAGAAGCTATAATGTGT
TGGAAGACAAAATCAACACAGCCTATCGCAGTTGGTATCTTTCGTACAATTATGGCGATCCCGAAAAAG
GAGTGCGTTCCTGGACATTGCTCACCACCTCAGATGTCACCTGCGGAGCAGAGCAGGTCTACTGGTCGC
TTCCAGACATGATGAAGGATCCTGTCACTTTCCGCTCCACTAGACAAGTCAGTAACTACCCTGTGGTGG
GTGCAGAGCTTATGCCCGTCTTCTCAAAGAGCTTCTACAACGAACAAGCTGTGTACTCCCAGCAGCTCC
GCCAGTCCACCTCGCTTACGCACGTCTTCAACCGCTTTCCTGAGAACCAGATTTTAATCCGTCCGCCGG
CGCCCACCATTACCACCGTCAGTGAAAACGTTCCTGCTCTCACAGATCACGGGACCCTGCCGTTGCGCA
GCAGTATCCGGGGAGTCCAACGTGTGACCGTTACTGACGCCAGACGCCGCACCTGTCCCTACGTGTACA
AGGCACTGGGCATAGTCGCACCGCGCGTCCTTTCAAGCCGCACTTTCTAAAAAAAAAAAAAAATGTCCAT
TCTTATCTCGCCCAGTAATAACACCGGTTGGGGTCTGCGCGCTCCAAGCAAGATGTACGGAGGCGCACG
CAAACGTTCTACCCAACATCCTGTCCGTGTTCGCGGACATTTTCGCGCTCCATGGGGCGCCCTCAAGGG
CCGCACTCGCGTTCGAACCACCGTCGATGATGTAATCGATCAGGTGGTTGCCGACGCCCGTAATTATAC
TCCTACTGCGCCTACATCTACTGTGGATGCAGTTATTGACAGTGTAGTGGCTGACGCTCGCAACTATGC
TCGACGTAAGAGCCGGCGAAGGCGCATTGCCAGACGCCACCGAGCTACCACTGCCATGCGAGCCGCAAG
AGCTCTGCTACGAAGAGCTAGACGCGTGGGGCGAAGAGCCATGCTTAGGGCGGCCAGACGTGCAGCTTC
GGGCGCCAGCGCCGGCAGGTCCCGCAGGCAAGCAGCCGCTGTCGCAGCGGCGACTATTGCCGACATGGC
CCAATCGCGAAGAGGCAATGTATACTGGGTGCGTGACGCTGCCACCGGTCAACGTGTACCCGTGCGCAC
CCGTCCCCCTCGCACTTAGAAGATACTGAGCAGTCTCCGATGTTGTGTCCCAGCGGCGAGGATGTCCAA
GCGCAAATACAAGGAAGAAATGCTGCAGGTTATCGCACCTGAAGTCTACGGCCAACCGTTGAAGGATGA
AAAAAAACCCCGCAAAATCAAGCGGGTTAAAAAGGACAAAAAAGAAGAGGAAGATGGCGATGATGGGCT
GGCGGAGTTTGTGCGCGAGTTTGCCCCACGGCGACGCGTGCAATGGCGTGGGCGCAAAGTTCGACATGT

Figure 52 (continued)

GTTGAGACCTGGAACTTCGGTGGTCTTTACACCCGGCGAGCGTTCAAGCGCTACTTTTAAGCGTTCCTA
TGATGAGGTGTACGGGGATGATGATATTCTTGAGCAGGCGGCTGACCGATTAGGCGAGTTTGCTTATGG
CAAGCGTAGTAGAATAACTTCCAAGGATGAGACAGTGTCGATACCCTTGGATCATGGAAATCCCACCCC
TAGTCTTAAACCGGTCACTTTGCAGCAAGTGTTACCCGTAACTCCGCGAACAGGTGTTAAACGCGAAGG
TGAAGATTTGTATCCCACTATGCAACTGATGGTACCCAAACGCCAGAAGTTGGAGGACGTTTTGGAGAA
AGTAAAAGTGGATCCAGATATTCAACCTGAGGTTAAAGTGAGACCCATTAAGCAGGTAGCGCCTGGTCT
GGGGGTACAAACTGTAGACATTAAGATTCCCACTGAAAGTATGGAAGTGCAAACTGAACCCGCAAAGCC
TACTGCCACCTCCACTGAAGTGCAAACGGATCCATGGATGCCCATGCCTATTACAACTGACGCCGCCGG
TCCCACTCGAAGATCCCGACGAAAGTACGGTCCAGCAAGTCTGTTGATGCCCAATTATGTTGTACACCC
ATCTATTATTCCTACTCCTGGTTACCGAGGCACTCGCTACTATCGCAGCCGAAACAGTACCTCCCGCCG
TCGCCGCAAGACACCTGCAAATCGCAGTCGTCGCCGTAGACGCACAAGCAAACCGACTCCCGGCGCCCT
GGTGCGGCAAGTGTACCGCAATGGTAGTGCGGAACCTTTGACACTGCCGCGTGCGCGTTACCATCCGAG
TATCATCACTTAATCAATGTTGCCGCTGCCTCCTTGCAGATATGGCCCTCACTTGTCGCCTTCGCGTTC
CCATCACTGGTTACCGAGGAAGAAACTCGCGCCGTAGAAGAGGGATGTTGGGACGCGGAATGCGACGCT
ACAGGCGACGGCGTGCTATCCGCAAGCAATTGCGGGGTGGTTTTTTACCAGCCTTAATTCCAATTATCG
CTGCTGCAATTGGCGCGATACCAGGCATAGCTTCCGTGGCGGTTCAGGCCTCGCAACGACATTGACATT
GGAAAAAAACGTATAAATAAAAAAAAAAAAAATACAATGGACTCTGACACTCCTGGTCCTGTGACTATGT
TTTCTTAGAGATGGAAGACATCAATTTTTCATCCTTGGCTCCGCGACACGGCACGAAGCCGTACATGGG
CACCTGGAGCGACATCGGCACGAGCCAACTGAACGGGGGCGCCTTCAATTGGAGCAGTATCTGGAGCGG
GCTTAAAAATTTTGGCTCAACCATAAAAACATACGGGAACAAAGCTTGGAACAGCAGTACAGGACAGGC
GCTTAGAAATAAACTTAAAGACCAGAACTTCCAACAAAAAGTAGTCGATGGGATAGCTTCCGGCATCAA
TGGAGTGGTAGATTTGGCTAACCAGGCTGTGCAGAAAAAGATAAACAGTCGTTTGGACCCGCCGCCAGC
AACCCCAGGTGAAATGCAAGTGGAGGAAGAAATTCCTCCGCCAGAAAAACGAGGCGACAAGCGTCCGCG
TCCCGATTTGGAAGAGACGCTGGTGACGCGCGTAGATGAACCGCCTTCTTATGAGGAAGCAACGAAGCT
TGGAATGCCCACCACTAGACCGATAGCCCCAATGGCCACCGGGGTGATGAAACCTTCTCAGTTGCATCG
ACCCGTCACCTTGGATTTGCCCCCTCCCCCTGCTGCTACTGCTGTACCCGCTTCTAAGCCTGTCGCTGC
CCCGAAACCAGTCGCCGTAGCCAGGTCACGTCCCGGGGGCGCTCCTCGTCCAAATGCGCACTGGCAAAA
TACTCTGAACAGCATCGTGGGTCTAGGCGTGCAAAGTGTAAAACGCCGTCGCTGCTTTTAATTAAATAT
GGAGTAGCGCTTAACTTGCCTATCTGTGTATATGTGTCATTACACGCCGTCACAGCAGCAGAGGAAAAA
AGGAAGAGGTCGTGCGTCGACGCTGAGTTACTTTCAAGATGGCCACCCCATCGATGCTGCCCCAATGGG
CATACATGCACATCGCCGGACAGGATGCTTCGGAGTACCTGAGTCCGGGTCTGGTGCAGTTCGCCCGCG
CCACAGACACCTACTTCAATCTGGGAAATAAGTTTAGAAATCCCACCGTAGCGCCGACCCACGATGTGA
CCACCGACCGTAGCCAGCGGCTCATGTTGCGCTTCGTGCCCGTTGACCGGGAGGACAATACATACTCTT
ACAAAGTGCGGTACACCCTGGCCGTGGGCGACAACAGAGTGCTGGATATGGCCAGCACGTTCTTTGACA
TTAGGGGTGTGTTGGACAGAGGTCCCAGTTTCAAACCCTATTCTGGTACGGCTTACAACTCCCTGGCTC
CTAAAGGCGCTCCAAATACATCTCAGTGGATTGCAGAAGGTGTAAAAAATACAACTGGTGAGGAACACG
TAACAGAAGAGGAAACCAATACTACTACTTACACTTTTGGCAATGCTCCTGTAAAAGCTGAAGCTGAAA
TTACAAAAGAAGGACTCCCAGTAGGTTTGGAAGTTTCAGATGAAGAAAGTAAACCGATTTATGCTGATA
AAACATATCAGCCAGAACCTCAGCTGGGAGATGAAACTTGGACTGACCTTGATGGAAAAACCGAAAAGT
ATGGAGGCAGGGCTCTCAAACCCGATACTAAGATGAAACCATGCTACGGGTCCTTTGCCAAACCTACTA
ATGTGAAAGGCGGTCAGGCAAAACAAAAAACAACGGAGCAGCCAAATCAGAAAGTCGAATATGATATCG
ACATGGAGTTTTTTGATGCGGCATCGCAGAAAACAAACTTAAGTCCTAAAATTGTCATGTATGCAGAAA
ATGTAAATTTGGAAACTCCAGACACTCATGTAGTGTACAAACCTGGAACAGAAGACACAAGTTCCGAAG
CTAATTTGGGACAACAATCTATGCCCAACAGACCCAACTACATTGGCTTCAGAGATAACTTTATTGGAC
TTATGTACTATAACAGTACTGGTAACATGGGGGTGCTGGCTGGTCAAGCGTCTCAGTTAAATGCAGTGG
TTGACTTGCAGGACAGAAACACAGAACTTTCTTACCAACTCTTGCTTGACTCTCTGGGCGACAGAACCA
GATACTTTAGCATGTGGAATCAGGCTGTGGACAGTTATGATCCTGATGTACGTGTTATTGAAAATCATG
GTGTGGAAGATGAACTTCCCAACTACTGTTTTCCACTGGACGGCATAGGTGTTCCAACAACCAGTTACA

Figure 52 (continued)

AATCAATAGTTCCAAATGGAGACAATGCGCCTAATTGGAAGGAACCTGAAGTAAATGGAACAAGTGAGA
TCGGACAGGGTAATTTGTTTGCCATGGAAATTAACCTTCAAGCCAATCTATGGCGAAGTTTCCTTTATT
CCAATGTGGCTCTATATCTCCCAGACTCGTACAAATACACCCCGTCCAATGTCACTCTTCCAGAAAACA
AAAACACCTACGACTACATGAACGGGCGGGTGGTGCCGCCATCTCTAGTAGACACCTATGTGAACATTG
GTGCCAGGTGGTCTCTGGATGCCATGGACAATGTCAACCCATTCAACCACCACCGTAACGCTGGCTTGC
GTTACCGATCCATGCTTCTGGGTAACGGACGTTATGTGCCTTTCCACATACAAGTGCCTCAAAAATTCT
TCGCTGTTAAAAACCTGCTGCTTCTCCCAGGCTCCTACACTTATGAGTGGAACTTTAGGAAGGATGTGA
ACATGGTTCTACAGAGTTCCCTCGGTAACGACCTGCGGGTAGATGGCGCCAGCATCAGTTTCACGAGCA
TCAACCTCTATGCTACTTTTTTCCCCATGGCTCACAACACCGCTTCCACCCTTGAAGCCATGCTGCGGA
ATGACACCAATGATCAGTCATTCAACGACTACCTATCTGCAGCTAACATGCTCTACCCCATTCCTGCCA
ATGCAACCAATATTCCCATTTCCATTCCTTCTCGCAACTGGGCGGCTTTCAGAGGCTGGTCATTTACCA
GACTGAAAACCAAAGAAACTCCCTCTTTGGGGTCTGGATTTGACCCCTACTTTGTCTATTCTGGTTCTA
TTCCCTACCTGGATGGTACCTTCTACCTGAACCACACTTTTAAGAAGGTTTCCATCATGTTTGACTCTT
CAGTGAGCTGGCCTGGAAATGACAGGTTACTATCTCCTAACGAATTTGAAATAAAGCGCACTGTGGATG
GCGAAGGCTACAACGTAGCCCAATGCAACATGACCAAAGACTGGTTCTTGGTACAGATGCTCGCCAACT
ACAACATCGGCTATCAGGGCTTCTACATTCCAGAAGGATACAAAGATCGCATGTATTCATTTTTCAGAA
ACTTCCAGCCCATGAGCAGGCAGGTGGTTGATGAGGTCAATTACAAAGACTTCAAGGCCGTCGCCATAC
CCTACCAACACAACAACTCTGGCTTTGTGGGTTACATGGCTCCGACCATGCGCCAAGGTCAACCCTATC
CCGCTAACTATCCCTATCCACTCATTGGAACAACTGCCGTAAATAGTGTTACGCAGAAAAAGTTCTTGT
GTGACAGAACCATGTGGCGCATACCGTTCTCGAGCAACTTCATGTCTATGGGGGCCCTTACAGACTTGG
GACAGAATATGCTCTATGCCAACTCAGCTCATGCTCTGGACATGACCTTTGAGGTGGATCCCATGGATG
AGCCCACCCTGCTTTATCTTCTCTTCGAAGTTTTCGACGTGGTCAGAGTGCATCAGCCACACCGCGGCA
TCATCGAGGCAGTCTACCTGCGTACACCGTTCTCGGCCGGTAACGCTACCACGTAAGAAGCTTCTTGCT
TCTTGCAAATAGCAGCTGCAACCATGGCCTGCGGATCCCAAAACGGCTCCAGCGAGCAAGAGCTCAGAG
CCATTGTCCAAGACCTGGGTTGCGGACCCTATTTTTTGGGAACCTACGATAAGCGCTTCCCGGGGTTCA
TGGCCCCCGATAAGCTCGCCTGTGCCATTGTAAATACGGCCGGACGTGAGACGGGGGGAGAGCACTGGT
TGGCTTTCGGTTGGAACCCACGTTCTAACACCTGCTACCTTTTTGATCCTTTTGGATTCTCGGATGATC
GTCTCAAACAGATTTACCAGTTTGAATATGAGGGTCTCCTGCGCCGCAGCGCTCTTGCTACCAAGGACC
GCTGTATTACGCTGGAAAAATCTACCCAGACCGTGCAGGGTCCCCGTTCTGCCGCCTGCGGACTTTTCT
GCTGCATGTTCCTTCACGCCTTTGTGCACTGGCCTGACCGTCCCATGGACGGAAACCCCACCATGAAAT
TGCTAACTGGAGTGCCAAACAACATGCTTCATTCTCCTAAAGTCCAGCCCACCCTGTGTGACAATCAAA
AAGCACTCTACCATTTTCTTAATACCCATTCGCCTTATTTTCGCTCCCATCGTACACACATCGAAAGGG
CCACTGCGTTCGACCGTATGGATGTTCAATAATGACTCATGTAAACAACGTGTTCAATAAACATCACTT
TATTTTTTTACATGTATCAAGGCTCTGCATTACTTATTTATTTACAAGTCGAATGGGTTCTGACGAGAA
TCAGAATGACCCGCAGGCAGTGATACGTTGCGGAACTGATACTTGGGTTGCCACTTGAATTCGGGAATC
ACCAACTTGGGAACCGGTATATCGGGCAGGATGTCACTCCACAGCTTTCTGGTCAGCTGCAAAGCTCCA
AGCAGGTCAGGAGCCGAAATCTTGAAATCACAATTAGGACCAGTGCTTTGAGCGCGAGAGTTGCGGTAC
ACCGGATTGCAGCACTGAAACACCATCAGCGACGGATGTCTCACGCTTGCCAGCACGGTGGGATCTGCA
ATCATGCCCACATCCAGATCTTCAGCATTGGCAATGCTGAACGGGGTCATCTTGCAGGTCTGCCTACCC
ATGGCGGGCACCCAATTAGGCTTGTGGTTGCAATCGCAGTGCAGGGGGATCAGTATCATCTTGGCCTGA
TCCTGTCTGATTCCTGGATACACGGCTCTCATGAAAGCATCATATTGCTTGAAAGCCTGCTGGGCTTTA
CTACCCTCGGTATAAAACATCCCGCAGGACCTGCTCGAAAACTGGTTAGCTGCACAGCCGGCATCATTC
ACACAGCAGCGGGCGTCATTGTTAGCTATTTGCACCACACTTCTGCCCCAGCGGTTTTGGGTGATTTTG
GTTCGCTCGGGATTCTCCTTTAAGGCTCGTTGTCCGTTCTCGCTGGCCACATCCATCTCGATAATCTGC
TCCTTCTGAATCATAATATTGCCATGCAGGCACTTCAGCTTGCCCTCATAATCATTGCAGCCATGAGGC
CACAACGCACAGCCTGTACATTCCCAATTATGGTGGGCGATCTGAGAAAAAGAATGTATCATTCCCTGC
AGAAATCTTCCCATCATCGTGCTCAGTGTCTTGTGACTAGTGAAAGTTAACTGGATGCCTCGGTGCTCC
TCGTTTACGTACTGGTGACAGATGCGCTTGTATTGTTCGTGTTGCTCAGGCATTAGTTTAAAAGAGGTT

Figure 52 (continued)

CTAAGTTCGTTATCCAGCCTGTACTTCTCCATCAGCAGACACATCACTTCCATGCCTTTCTCCCAAGCA
GACACCAGGGGCAAGCTAATCGGATTCTTAACAGTGCAGGCAGCAGCTCCTTTAGCCAGAGGGTCATCT
TTAGCGATCTTCTCAATGCTTCTTTTGCCATCCTTCTCAACGATGCGCACGGGCGGGTAGCTGAAACCC
ACTGCTACAAGTTGCGCCTCTTCTCTTTCTTCTTCGCTGTCTTGACTGATGTCTTGCATGGGGATATGT
TTGGTCTTCCTTGGCTTCTTTTTGGGGGGTATCGGAGGAGGAGGACTGTCGCTCCGTTCCGGAGACAGG
GAGGATTGTGACGTTTCGCTCACCATTACCAACTGACTGTCGGTAGAAGAACCTGACCCCACACGGCGA
CAGGTGTTTCTCTTCGGGGGCAGAGGTGGAGGCGATTGCGAAGGGCTGCGGTCCGACCTGGAAGGCGGA
TGACTGGCAGAACCCCTTCCGCGTTCGGGGGTGTGCTCCCTGTGGCGGTCGCTTAACTGATTTCCTTCG
CGGCTGGCCATTGTGTTCTCCTAGGCAGAGAAACAACAGACATGGAAACTCAGCCATTGCTGTCAACAT
CGCCACGAGTGCCATCACATCTCGTCCTCAGCGACGAGGAAAAGGAGCAGAGCTTAAGCATTCCACCGC
CCAGTCCTGCCACCACCTCTACCCTAGAAGATAAGGAGGTCGACGCATCTCATGACATGCAGAATAAAA
AAGCGAAAGAGTCTGAGACAGACATCGAGCAAGACCCGGGCTATGTGACACCGGTGGAACACGAGGAAG
AGTTGAAACGCTTTCTAGAGAGAGAGGATGAAAACTGCCCAAAACAACGAGCAGATAACTATCACCAAG
ATGCTGGAAATAGGGATCAGAACACCGACTACCTCATAGGGCTTGACGGGGAAGACGCGCTCCTTAAAC
ATCTAGCAAGACAGTCGCTCATAGTCAAGGATGCATTATTGGACAGAACTGAAGTGCCCATCAGTGTGG
AAGAGCTCAGCCGCGCCTACGAGCTTAACCTCTTTTCACCTCGTACTCCCCCCAAACGTCAGCCAAACG
GCACCTGCGAGCCAAATCCTCGCTTAAACTTTTATCCAGCTTTTGCTGTGCCAGAAGTACTGGCTACCT
ATCACATCTTTTTTAAAAATCAAAAAATTCCAGTCTCCTGCCGCGCTAATCGCACCCGCGCCGATGCCC
TACTCAATCTGGGACCTGGTTCACGCTTACCTGATATAGCTTCCTTGGAAGAGGTTCCAAAGATCTTCG
AGGGTCTGGGCAATAATGAGACTCGGGCCGCAAATGCTCTGCAAAAGGGAGAAAATGGCATGGATGAGC
ATCACAGCGTTCTGGTGGAATTGGAAGGCGATAATGCCAGACTCGCAGTACTCAAGCGAAGCATCGAGG
TCACACACTTCGCATATCCCGCTGTCAACCTGCCCCCTAAAGTCATGACGGCGGTCATGGACCAGTTAC
TCATTAAGCGCGCAAGTCCCCTTTCAGAAGACATGCATGACCCAGATGCCTGTGATGAGGGTAAACCAG
TGGTCAGTGATGAGCAGCTAACCCGATGGCTGGGCACCGACTCTCCCAGGGATTTGGAAGAGCGTCGCA
AGCTTATGATGGCCGTGGTGCTGGTTACCGTAGAACTAGAGTGTCTCCGACGTTTCTTTACCGATTCAG
AAACCTTGCGCAAACTCGAAGAGAATCTGCACTACACTTTTAGACACGGCTTTGTGCGGCAGGCATGCA
AGATATCTAACGTGGAACTCACCAACCTGGTTTCCTACATGGGTATTCTGCATGAGAATCGCCTAGGAC
AAAGCGTGCTGCACAGCACCCTGAAGGGGGAAGCCCGCCGTGATTACATCCGCGATTGTGTCTATCTGT
ACCTGTGCCACACGTGGCAAACCGGCATGGGTGTATGGCAGCAATGTTTAGAAGAACAGAACTTGAAAG
AGCTTGACAAGCTCTTACAGAAATCTCTTAAGGTTCTGTGGACAGGGTTCGACGAGCGCACCGTCGCTT
CCGACCTGGCAGACCTCATCTTCCCAGAGCGTCTCAGGGTTACTTTGCGAAACGGATTGCCTGACTTTA
TGAGCCAGAGCATGCTTAACAATTTTCGCTCTTTCATCCTGGAACGCTCCGGTATCCTGCCCGCCACCT
GCTGCGCACTGCCCTCCGACTTTGTGCCTCTCACCTACCGCGAGTGCCCCCCGCCGCTATGGAGTCACT
GCTACCTGTTCCGTCTGGCCAACTATCTCTCCTACCACTCGGATGTGATCGAGGATGTGAGCGGAGACG
GCTTGCTGGAGTGTCACTGCCGCTGCAATCTGTGCACGCCCCACCGGTCCCTAGCTTGCAACCCCCAGT
TGATGAGCGAAACCCAGATAATAGGCACCTTTGAATTGCAAGGCCCCAGCAGCCAAGGCGATGGGTCTT
CTCCTGGGCAAAGTTTAAAACTGACCCCGGGACTGTGGACCTCCGCCTACTTGCGCAAGTTTGCTCCGG
AAGATTACCACCCCTATGAAATCAAGTTCTATGAGGACCAATCACAGCCTCCAAAGGCCGAACTTTCGG
CCTGCGTCATCACCCAGGGGGCAATTCTGGCCCAATTGCAAGCCATCCAAAAATCCCGCCAAGAATTTC
TACTGAAAAAGGGTAAGGGGGTCTACCTTGACCCCCAGACCGGCGAGGAACTCAACACAAGGTTCCCTC
AGGATGTCCCAACGACGAGAAAACAAGAAGTTGAAGGTGCAGCCGCCGCCCCCAGAAGATATGGAGGAA
GATTGGGACAGTCAGGCAGAGGAGGCGGAGGAGGACAGTCTGGAGGACAGTCTGGAGGAAGACAGTTTG
GAGGAGGAAAACGAGGAGGCAGAGGAGGTGGAAGAAGTAACCGCCGACAAACAGTTATCCTCGGCTGCG
GAGACAAGCAACAGCGCTACCATCTCCGCTCCGAGTCGAGGAACCCGGCGGCGTCCCAGCAGTAGATGG
GACGAGACCGGACGCTTCCCGAACCCAACCAGCGCTTCCAAGACCGGTAAGAAGGATCGGCAGGGATAC
AAGTCCTGGCGGGGGCATAAGAATGCCATCATCTCCTGCTTGCATGAGTGCGGGGGCAACATATCCTTC
ACGCGGCGCTACTTGCTATTCCACCATGGGGTGAACTTTCCGCGCAATGTTTTGCATTACTACCGTCAC
CTCCACAGCCCCTACTATAGCCAGCAAATCCCGGCAGTCTCGACAGATAAAGACAGCGGCGGCGACCTC

Figure 52 (continued)

CAACAGAAAACCAGCAGCGGCAGTTAGAAAATACACAACAAGTGCAGCAACAGGAGGATTAAAGATTAC
AGCCAACGAGCCAGCGCAAACCCGAGAGTTAAGAAATCGGATCTTTCCAACCCTGTATGCCATCTTCCA
GCAGAGTCGGGGTCAAGAGCAGGAACTGAAAATAAAAAACCGATCTCTGCGTTCGCTCACCAGAAGTTG
TTTGTATCACAAGAGCGAAGATCAACTTCAGCGCACTCTCGAGGACGCCGAGGCTCTCTTCAACAAGTA
CTGCGCGCTGACTCTTAAAGAGTAGGCAGCGACCGCGCTTATTCAAAAAGGCGGGAATTACATCATCC
TCGACATGAGTAAAGAAATTCCCACGCCTTACATGTGGAGTTATCAACCCCAAATGGGATTGGCGGCAG
GCGCCTCCCAGGACTACTCCACCCGCATGAATTGGCTCAGCGCCGGGCCTTCTATGATTTCTCGAGTTA
ATGATATACGCGCCTACCGAAACCAAATACTTTTGGAACAGTCAGCTCTTACCACCACGCCCCGCCAAC
ACCTTAATCCCAGAAATTGGCCCGCCGCCCTAGTGTACCAGGAAAGTCCCGCTCCCACCACTGTATTAC
TTCCTCGAGACGCCCAGGCCGAAGTCCAAATGACTAATGCAGGTGCGCAGTTAGCTGGCGGCTCCACCC
TATGTCGTCACAGGCCTCGGCATAATATAAAACGCCTGATGATCAGAGGCCGAGGTATCCAGCTCAACG
ACGAGTCGGTGAGCTCTCCGCTTGGTCTACGACCAGACGGAATCTTTCAGATTGCCGGCTGCGGGAGAT
CTTCCTTCACCCCTCGTCAGGCTGTTCTGACTTTGGAAAGTTCGTCTTCGCAACCCCGCTCGGGCGGAA
TCGGGACCGTTCAATTTGTGGAGGAGTTTACTCCCTCTGTCTACTTCAACCCCTTCTCCGGATCTCCTG
GGCATTACCCGGACGAGTTCATACCGAACTTCGACGCGATTAGCGAGTCAGTGGACGGCTACGATTGAT
GTCTGGTGACGCGGCTGAGCTATCTCGGCTGCGACATCTAGACCACTGCCGCCGCTTTCGCTGCTTTGC
CCGGGAACTCATTGAGTTCATCTACTTCGAACTCCCCAAGGATCACCCTCAAGGTCCGGCCCACGGAGT
GCGGATTTCTATCGAAGGCAAAATAGACTCTCGCCTGCAACGAATTTTCTCCCAGCGGCCCGTGCTGAT
CGAGCGAGACCAGGGAAACACCACGGTTTCCATCTACTGCATTTGTAATCACCCCGGATTGCATGAAAG
CCTTTGCTGTCTTATGTGTACTGAGTTTAATAAAAACTGAATTAAGACTCTCCTACGGACTGCCGCTTC
TTCAACCCGGATTTTACAACCAGAAGAACGAAACTTTTCCTGTCGTCCAGGACTCTGTTAACTTCACCT
TTCCTACTCACAAACTAGAAGCTCAACGACTACACCGCTTTTCCAGAAGCATTTTCCCTACTAATACTA
CTTTCAAAACCGGAGGTGAGCTCCAAGGTCTTCCTACAGAAAACCCTTGGGTGGAAGCGGGCCTTGTAG
TGCTAGGAATTCTTGCGGGTGGGCTTGTGATTATTCTTTGCTACCTATACACACCTTGCTTCACTTTCT
TAGTGGTGTTGTGGTATTGGTTTAAAAAATGGGGCCCATACTAGTCTTGCTTGTTTTACTTTCGCTTTT
GGAACCGGGTTCTGCCAATTACGATCCATGTCTAGACTTCGACCCAGAAAACTGCACACTTACTTTTGC
ACCCGACACAAGCCGCATCTGTGGAGTTCATCGCCTCTCTTACGAACTTGGCCCCCAACGACAAAAATT
TACCTGCATGGTGGGAATCAACCCCATAGTTATCACCCAGCAAAGTGGAGATACTAAGGGTTGCATTCA
CTGCTCCTGCGATTCCATCGAGTGCACCTACACCCTGCTGAAGACCCTATGCGGCCTAAGAGACCTGCT
ACCAATGAATTAAAAAATGATTAATAAAAAATCACTTACTTGAAATCAGCAATAAGGTCTCTGTTGAAA
TTTTCTCCCAGCAGCACCTCACTTCCCTCTTCCCAACTCTGGTATTCTAAACCCCGTTCAGCGGCATAC
TTTCTCCATACTTTAAAGGGGATGTCAAATTTTAGCTCCTCTCCTGTACCCACAATCTTCATGTCTTTC
TTCCCAGATGACCAAGAGAGTCCGGCTCAGTGACTCCTTCAACCCTGTCTACCCCTATGAAGATGAAAG
CACCTCCCAACACCCCTTTATAAACCCAGGGTTTATTTCCCCAAATGGCTTCACACAAAGCCCAAACGG
AGTTCTTACTTTAAAATGTTTAACCCCACTAACAACCACAGGCGGATCTCTACAGCTAAAAGTGGGAGG
GGGACTTACAGTGGATGACACCAACGGTTTTTTGAAAGAAAACATAAGTGCCACCACACCACTCGTTAA
GACTGGTCACTCTATAGGTTTACCACTAGGAGCCGGATTGGGAACGAATGAAAATAAACTTTGTATCAA
ATTAGGACAAGGACTTACATTCAATTCAAACAACATTTGCATTGATGACAATATTAACACCTTATGGAC
AGGAGTCAACCCCACCGAAGCCAACTGTCAAATCATGAACTCCAGTGAATCTAATGATTGCAAATTAAT
TCTAACACTAGTTAAAACTGGAGCACTAGTCACTGCATTTGTTTATGTTATAGGAGTATCTAACAATTT
TAATATGCTAACTACACACAGAAATATAAATTTTACTGCAGAGCTGTTTTTCGATTCTACTGGTAATTT
ACTAACTAGACTCTCATCCCTCAAAACTCCACTTAATCATAAATCAGGACAAAACATGGCTACTGGTGC
CATTACTAATGCTAAAGGTTTCATGCCCAGCACGACTGCCTATCCTTTCAATGATAATTCTAGAGAAAA
AGAAAACTACATTTACGGAACTTGTTACTACACAGCTAGTGATCGCACTGCTTTTCCCATTGACATATC
TGTCATGCTTAACCGAAGAGCAATAAATGACGAGACATCATATTGTATTCGTATAACTTGGTCCTGGAA
CACAGGAGATGCCCCAGAGGTGCAAACCTCTGCTACAACCCTAGTCACCTCCCCATTTACCTTTTACTA
CATCAGAGAAGACGACTGACAAATAAAGTTTGCGATCGCCAGGCCCACCATGGGATGGAGCTGTATCAT
CCTCTTCTTGGTAGCAACAGCTACAGGTGTCCACTCCCAGGTGCAGCTGCAGCAGTCTGGGGCTGAACT

Figure 52 (continued)

GGCAAGACCTGGGGCCTCAGTGAAGATGTCCTGCAAGGCTTCTGGCTACACCTTTACTAGGTACACGAT
GCACTGGGTAAAACAGAGGCCTGGACAGGGTCTGGAATGGATTGGATACATTAATCCTAGCCGTGGTTA
TACTAATTACAATCAGAAGTTCAAGGACAAGGCCACATTGACTACAGACAAATCCTCCAGCACAGCCTA
CATGCAACTGAGCAGCCTGACATCTGAGGACTCTGCAGTCTATTACTGTGCAAGATATTATGATGATCA
TTACTGCCTTGACTACTGGGGCCAAGGCACCACTCTCACAGTCTCCTCAGGTGGCGGTGGCTCGGGCGG
TGGTGGATCTGGTGGCGGCGGATCTGATATCGTGCTCACTCAGTCTCCAGCAATCATGTCTGCATCTCC
AGGGGAGAAGGTCACCATGACCTGCAGTGCCAGCTCAAGTGTAAGTTACATGAACTGGTACCAGCAGAA
GTCAGGCACCTCCCCCAAAAGATGGATTTATGACACATCCAAACTGGCTTCTGGAGTCCCTGCTCACTT
CAGGGGCAGTGGGTCTGGGACCTCTTACTCTCTCACAATCAGCGGCATGGAGGCTGAAGATGCTGCCAC
TTATTACTGCCAGCAGTGGAGTAGTAACCCATTCACGTTCGGCTCGGGGACAAAGTTGGAAATAAACCG
GGGATCCGAACAAAAACTCATCTCAGAAGAGGATCTGAATGCTGTGGGCCAGGACACGCAGGAGGTCAT
CGTGGTGCCACACTCCTTGCCCTTTAAGGTGGTGGTGATCTCAGCCATCCTGGCCCTGGTGGTGCTCAC
CATCATCTCCCTTATCATCCTCATCATGCTTTGGCAGAAGAAGCCACGTTAAGCTAGCTTGACTGACTG
AGATACAGCGTACCTTCAGCTCACAGACATGATAAGATACATTGATGAGTTTGGACAAACCACAACTAG
AATGCAGTGAAAAAAATGCTTTATTTGTGAAATTTGTGATGCTATTGCTTTATTTGTAACCATTATAAG
CTGCAATAAACAAGTTAACAACAACAATTGCATTCATTTTATGTTTCAGGTTCAGGGGGAGGTGTGGGA
GGTTTTTTAAAGCAAGTAAAACCTCTACAAATGTGGTAGTCGTCAGCTATCCTGCAGGAACTTGTTTAT
TTGAAAATCAATTCACAAAATCCGAGTAGTTATTTTGCCTCCCCCTTCCCATTTAACAGAATACACCAA
TCTCTCCCCACGCACAGCTTTAAACATTTGGATACCATTAGATATAGACATGGTTTTAGATTCCACATT
CCAAACAGTTTCAGAGCGAGCCAATCTGGGGTCAGTGATAGATAAAAATCCATCGGGATAGTCTTTTAA
AGCGCTTTCACAGTCCAACTGCTGCGGATGCGACTCCGGAGTCTGGATCACGGTCATCTGGAAGAAGAA
CGATGGGAATCATAATCCGAAAACGGTATCGGACGATTGTGTCTCATCAAACCCACAAGCAGCCGCTGT
CTGCGTCGCTCCGTGCGACTGCTGTTTATGGGATCAGGGTCCACAGTGTCCTGAAGCATGATTTTAATA
GCCCTTAACATCAACTTTCTGGTGCGATGCGCGCAGCAACGCATTCTGATTTCACTCAAATCTTTGCAG
TAGGTACAACACATTATTACAATATTGTTTAATAAACCATAATTAAAAGCGCTCCAGCCAAAACTCATA
TCTGATATAATCGCCCCTGCATGACCATCATACCAAAGTTTAATATAAATTAAATGACGTTCCCTCAAA
AACACACTACCCACATACATGATCTCTTTTGGCATGTGCATATTAACAATCTGTCTGTACCATGGACAA
CGTTGGTTAATCATGCAACCCAATATAACCTTCCGGAACCACACTGCCAACACCGCTCCCCCAGCCATG
CATTGAAGTGAACCCTGCTGATTACAATGACAATGAAGAACCCAATTCTCTCGACCGTGAATCACTTGA
GAATGAAAAATATCTATAGTGGCACAACATAGACATAAATGCATGCATCTTCTCATAATTTTTAACTCC
TCAGGATTTAGAAACATATCCCAGGGAATAGGAAGCTCTTGCAGAACAGTAAAGCTGGCAGAACAAGGA
AGACCACGAACACAACTTACACTATGCATAGTCATAGTATCACAATCTGGCAACAGCGGGTGGTCTTCA
GTCATAGAAGCTCGGGTTTCATTTTCCTCACAACGTGGTAACTGGGCTCTGGTGTAAGGGTGATGTCTG
GCGCATGATGTCGAGCGTGCGCGCAACCTTGTCATAATGGAGTTGCTTCCTGACATTCTCGTATTTTGT
ATAGCAAAACGCGGCCCTGGCAGAACACACTCTTCTTCGCCTTCTATCCTGCCGCTTAGCGTGTTCCGT
GTGATAGTTCAAGTACAACCACACTCTTAAGTTGGTCAAAAGAATGCTGGCTTCAGTTGTAATCAAAAC
TCCATCGCATCTAATCGTTCTGAGGAAATCATCCAAGCAATGCAACTGGATTGTGTTTCAAGCAGGAGA
GGAGAGGGAAGAGACGGAAGAACCATGTTAATTTTTATTCCAAACGATCTCGCAGTACTTCAAATTGTA
GATCGCGCAGATGGCATCTCTCGCCCCCACTGTGTTGGTGAAAAAGCACAGCTAGATCAAAAGAAATGC
GATTTTCAAGGTGCTCAACGGTGGCTTCCAGCAAAGCCTCCACGCGCACATCCAAGAACAAAAGAATAC
CAAAAGAAGGAGCATTTTCTAACTCCTCAATCATCATATTACATTCCTGCACCATTCCCAGATAATTTT
CAGCTTTCCAGCCTTGAATTATTCGTGTCAGTTCTTGTGGTAAATCCAATCCACACATTACAAACAGGT
CCCGGAGGGCGCCCTCCACCACCATTCTTAAACACACCCTCATAATGACAAAATATCTTGCTCCTGTGT
CACCTGTAGCGAATTGAGAATGGCAACATCAATTGACATGCCCTTGGCTCTAAGTTCTTCTTTAAGTTC
TAGTTGTAAAAACTCTCTCATATTATCACCAAACTGCTTAGCCAGAAGCCCCCCGGGAACAAGAGCAGG
GGACGCTACAGTGCAGTACAAGCGCAGACCTCCCCAATTGGCTCCAGCAAAAACAAGATTGGAATAAGC
ATATTGGGAACCGCCAGTAATATCATCGAAGTTGCTGGAAATATAATCAGGCAGAGTTTCTTGTAAAAA
TTGAATAAAAGAAAAATTTGCCAAAAAAACATTCAAAACCTCTGGGATGCAAATGCAATAGGTTACCGC

Figure 52 (continued)

GCTGCGCTCCAACATTGTTAGTTTTGAATTAGTCTGCAAAAATAAAAAAAAAAACAAGCGTCATATCAT
AGTAGCCTGACGAACAGATGGATAAATCAGTCTTTCCATCACAAGACAAGCCACAGGGTCTCCAGCTCG
ACCCTCGTAAAACCTGTCATCATGATTAAACAACAGCACCGAAAGTTCCTCGCGGTGACCAGCATGAAT
AATTCTTGATGAAGCATACAATCCAGACATGTTAGCATCAGTTAACGAGAAAAAACAGCCAACATAGCC
TTTGGGTATAATTATGCTTAATCGTAAGTATAGCAAAGCCACCCCTCGCGGATACAAAGTAAAAGGCAC
AGGAGAATAAAAAATATAATTATTTCTCTGCTGCTGTTCAGGCAACGTCGCCCCCGGTCCCTCTAAATA
CACATACAAAGCCTCATCAGCCATGGCTTACCAGACAAAGTACAGCGGGCACACAAAGCACAAGCTCTA
AAGTGACTCTCCAACCTCTCCACAATATATATATACACAAGCCCTAAACTGACGTAATGGGAGTAAAGT
GTAAAAAATCCCGCCAAACCCAACACACACCCCGAAACTGCGTCACCAGGGAAAAGTACAGTTTCACTT
CCGCAATCCCAACAGGCGTAACTTCCTCTTTCTCACGGTACGTGATATCCCACTAACTTGCAACGTCAT
TTTCCCACGGTCGCACCGCCCCTTTTAGCCGTTAACCCCACAGCCAATCACCACACGATCCACACTTTT
TAAAATCACCTCATTTACATATTGGCACCATTCCATCTATAAGGTATATTATATAGATAGA

Figure 53

SEQ ID NO. 104 NG-420A virus genome sequence comprising the EnAd genome with a transgene cassette that encodes a membrane-anchored chimeric form of the single chain Fv anti-human CD3e and a C-terminal V5 tag, inserted in the region Bγ. The transgene cassette contains a 5' SSA, membrane-anchored anti-CD3Ɛ cDNA sequence, V5 tag sequence and a 3' poly(A) sequence.

TCTATCTATATAATATACCTTATAGATGGAATGGTGCCAATATGTAAATGAGGTGATTTTAAAAAGTGT
GGATCGTGTGGTGATTGGCTGTGGGGTTAACGGCTAAAAGGGGCGGTGCGACCGTGGGAAAATGACGTT
TTGTGGGGGTGGAGTTTTTTTGCAAGTTGTCGCGGGAAATGTGACGCATAAAAAGGCTTTTTTCTCACG
GAACTACTTAGTTTTCCCACGGTATTTAACAGGAAATGAGGTAGTTTTGACCGGATGCAAGTGAAAATT
GTTGATTTTCGCGCGAAAACTGAATGAGGAAGTGTTTTTCTGAATAATGTGGTATTTATGGCAGGGTGG
AGTATTTGTTCAGGGCCAGGTAGACTTTGACCCATTACGTGGAGGTTTCGATTACCGTGTTTTTTACCT
GAATTTCCGCGTACCGTGTCAAAGTCTTCTGTTTTTACGTAGGTGTCAGCTGATCGCTAGGGTATTTAT
ACCTCAGGGTTTGTGTCAAGAGGCCACTCTTGAGTGCCAGCGAGAAGAGTTTTCTCCTCTGCGCCGGCA
GTTTAATAATAAAAAAATGAGAGATTTGCGATTTCTGCCTCAGGAAATAATCTCTGCTGAGACTGGAAA
TGAAATATTGGAGCTTGTGGTGCACGCCCTGATGGGAGACGATCCGGAGCCACCTGTGCAGCTTTTTGA
GCCTCCTACGCTTCAGGAACTGTATGATTTAGAGGTAGAGGGATCGGAGGATTCTAATGAGGAAGCTGT
AAATGGCTTTTTTACCGATTCTATGCTTTTAGCTGCTAATGAAGGGTTAGAATTAGATCCGCCTTTGGA
CACTTTTGATACTCCAGGGGTAATTGTGGAAAGCGGTACAGGTGTAAGAAAATTACCTGATTTGAGTTC
CGTGGACTGTGATTTGCACTGCTATGAAGACGGGTTTCCTCCGAGTGATGAGGAGGACCATGAAAAGGA
GCAGTCCATGCAGACTGCAGCGGGTGAGGGAGTGAAGGCTGCCAATGTTGGTTTTCAGTTGGATTGCCC
GGAGCTTCCTGGACATGGCTGTAAGTCTTGTGAATTTCACAGGAAAAATACTGGAGTAAAGGAACTGTT
ATGTTCGCTTTGTTATATGAGAACGCACTGCCACTTTATTTACAGTAAGTGTGTTTAAGTTAAAATTTA
AAGGAATATGCTGTTTTTCACATGTATATTGAGTGTGAGTTTTGTGCTTCTTATTATAGGTCCTGTGTC
TGATGCTGATGAATCACCATCTCCTGATTCTACTACCTCACCTCCTGAGATTCAAGCACCTGTTCCTGT
GGACGTGCGCAAGCCCATTCCTGTGAAGCTTAAGCCTGGGAAACGTCCAGCAGTGGAAAAACTTGAGGA
CTTGTTACAGGGTGGGGACGGACCTTTGGACTTGAGTACACGGAAACGTCCAAGACAATAAGTGTTCCA
TATCCGTGTTTACTTAAGGTGACGTCAATATTTGTGTGACAGTGCAATGTAATAAAAATATGTTAACTG
TTCACTGGTTTTTATTGCTTTTTGGGCGGGGACTCAGGTATATAAGTAGAAGCAGACCTGTGTGGTTAG
CTCATAGGAGCTGGCTTTCATCCATGGAGGTTTGGGCCATTTTGGAAGACCTTAGGAAGACTAGGCAAC
TGTTAGAGAACGCTTCGGACGGAGTCTCCGGTTTTTGGAGATTCTGGTTCGCTAGTGAATTAGCTAGGG
TAGTTTTTAGGATAAAACAGGACTATAAACAAGAATTTGAAAAGTTGTTGGTAGATTGCCCAGGACTTT
TTGAAGCTCTTAATTTGGGCCATCAGGTTCACTTTAAAGAAAAAGTTTTATCAGTTTTAGACTTTTCAA
CCCCAGGTAGAACTGCTGCTGCTGTGGCTTTTCTTACTTTTATATTAGATAAATGGATCCCGCAGACTC
ATTTCAGCAGGGGATACGTTTTGGATTTCATAGCCACAGCATTGTGGAGAACATGGAAGGTTCGCAAGA

Figure 53 (continued)

TGAGGACAATCTTAGGTTACTGGCCAGTGCAGCCTTTGGGTGTAGCGGGAATCCTGAGGCATCCACCGG
TCATGCCAGCGGTTCTGGAGGAGGAACAGCAAGAGGACAACCCGAGAGCCGGCCTGGACCCTCCAGTGG
AGGAGGCGGAGTAGCTGACTTGTCTCCTGAACTGCAACGGGTGCTTACTGGATCTACGTCCACTGGACG
GGATAGGGGCGTTAAGAGGGAGAGGGCATCTAGTGGTACTGATGCTAGATCTGAGTTGGCTTTAAGTTT
AATGAGTCGCAGACGTCCTGAAACCATTTGGTGGCATGAGGTTCAGAAAGAGGGAAGGGATGAAGTTTC
TGTATTGCAGGAGAAATATTCACTGGAACAGGTGAAAACATGTTGGTTGGAGCCTGAGGATGATTGGGA
GGTGGCCATTAAAAATTATGCCAAGATAGCTTTGAGGCCTGATAAACAGTATAAGATTACTAGACGGAT
TAATATCCGGAATGCTTGTTACATATCTGGAAATGGGGCTGAGGTGGTAATAGATACTCAAGACAAGGC
AGTTATTAGATGCTGCATGATGGATATGTGGCCTGGGGTAGTCGGTATGGAAGCAGTAACTTTTGTAAA
TGTTAAGTTTAGGGGAGATGGTTATAATGGAATAGTGTTTATGGCCAATACCAAACTTATATTGCATGG
TTGTAGCTTTTTTGGTTTCAACAATACCTGTGTAGATGCCTGGGGACAGGTTAGTGTACGGGGATGTAG
TTTCTATGCGTGTTGGATTGCCACAGCTGGCAGAACCAAGAGTCAATTGTCTCTGAAGAAATGCATATT
TCAAAGATGTAACCTGGGCATTCTGAATGAAGGCGAAGCAAGGGTCCGCCACTGCGCTTCTACAGATAC
TGGATGTTTTATTTTGATTAAGGGAAATGCCAGCGTAAAGCATAACATGATTTGCGGTGCTTCCGATGA
GAGGCCTTATCAAATGCTCACTTGTGCTGGTGGGCATTGTAATATGCTGGCTACTGTGCATATTGTTTC
CCATCAACGCAAAAAATGGCCTGTTTTTGATCACAATGTGATGACGAAGTGTACCATGCATGCAGGTGG
GCGTAGAGGAATGTTTATGCCTTACCAGTGTAACATGAATCATGTGAAAGTGTTGTTGGAACCAGATGC
CTTTTCCAGAATGAGCCTAACAGGAATTTTTGACATGAACATGCAAATCTGGAAGATCCTGAGGTATGA
TGATACGAGATCGAGGGTACGCGCATGCGAATGCGGAGGCAAGCATGCCAGGTTCCAGCCGGTGTGTGT
AGATGTGACTGAAGATCTCAGACCGGATCATTTGGTTATTGCCCGCACTGGAGCAGAGTTCGGATCCAG
TGGAGAAGAAACTGACTAAGGTGAGTATTGGGAAAACTTTGGGGTGGGATTTTCAGATGGACAGATTGA
GTAAAAATTTGTTTTTTCTGTCTTGCAGCTGTCATGAGTGGAAACGCTTCTTTTAAGGGGGGAGTCTTC
AGCCCTTATCTGACAGGGCGTCTCCCATCCTGGGCAGGAGTTCGTCAGAATGTTATGGGATCTACTGTG
GATGGAAGACCCGTCCAACCCGCCAATTCTTCAACGCTGACCTATGCTACTTTAAGTTCTTCACCTTTG
GACGCAGCTGCAGCTGCCGCCGCCGCTTCTGTTGCCGCTAACACTGTGCTTGGAATGGGTTACTATGGA
AGCATCATGGCTAATTCCACTTCCTCTAATAACCCTTCTACCCTGACTCAGGACAAGTTACTTGTCCTT
TTGGCCCAGCTGGAGGCTTTGACCCAACGTCTGGGTGAACTTTCTCAGCAGGTGGTCGAGTTGCGAGTA
CAAACTGAGTCTGCTGTCGGCACGGCAAAGTCTAAATAAAAAAATCCCAGAATCAATGAATAAATAAAC
AAGCTTGTTGTTGATTTAAAATCAAGTGTTTTTATTTCATTTTTCGCGCACGGTATGCCCTAGACCACC
GATCTCTATCATTGAGAACTCGGTGGATTTTTTCCAGGATCCTATAGAGGTGGGATTGAATGTTTAGAT
ACATGGGCATTAGGCCGTCTTTGGGGTGGAGATAGCTCCATTGAAGGGATTCATGCTCCGGGGTAGTGT
TGTAAATCACCCAGTCATAACAAGGTCGCAGTGCATGGTGTTGCACAATATCTTTTAGAAGTAGGCTGA
TTGCCACAGATAAGCCCTTGGTGTAGGTGTTTACAAACCGGTTGAGCTGGGATGGGTGCATTCGGGGTG
AAATTATGTGCATTTTGGATTGGATTTTTAAGTTGGCAATATTGCCGCCAAGATCCCGTCTTGGGTTCA
TGTTATGAAGGACCACCAAGACGGTGTATCCGGTACATTTAGGAAATTTATCGTGCAGCTTGGATGGAA
AAGCGTGGAAAAATTTGGAGACACCCTTGTGTCCTCCAAGATTTTCCATGCACTCATCCATGATAATAG
CAATGGGGCCGTGGGCAGCGGCGCGGGCAAACACGTTCCGTGGGTCTGACACATCATAGTTATGTTCCT
GAGTTAAATCATCATAAGCCATTTTAATGAATTTGGGGCGGAGAGTACCAGATTGGGGTATGAATGTTC
CTTCGGGCCCCGGAGCATAGTTCCCCTCACAGATTTGCATTTCCCAAGCTTTCAGTTCCGAGGGTGGAA
TCATGTCCACCTGGGGGGCTATGAAAAACACCGTTTCTGGGGCGGGGGTGATTAATTGTGATGATAGCA
AATTTCTGAGCAATTGAGATTTGCCACATCCGGTGGGGCCATAAATGATTCCGATTACGGGTTGCAGGT
GGTAGTTTAGGGAACGGCAACTGCCGTCTTCTCGAAGCAAGGGGGCCACCTCGTTCATCATTTCCCTTA
CATGCATATTTTCCCGCACCAAATCCATTAGGAGGCGCTCTCCTCCTAGTGATAGAAGTTCTTGTAGTG
AGGAAAAGTTTTTCAGCGGTTTCAGACCGTCAGCCATGGGCATTTTGGAGAGAGTTTGCTGCAAAAGTT
CTAGTCTGTTCCACAGTTCAGTGATGTGTTCTATGGCATCTCGATCCAGCAGACCTCCTCGTTTCGCGG
GTTTGGACGGCTCCTGGAATAGGGTATGAGACGATGGGCGTCCAGCGCTGCCAGGGTTCGGTCCTTCCA
GGGTCTCAGTGTTCGAGTCAGGGTTGTTTCCGTCACAGTGAAGGGGTGTGCGCCTGCTTGGGCGCTTGC
CAGGGTGCGCTTCAGACTCATCCTGCTGGTCGAAAACTTCTGTCGCTTGGCGCCCTGTATGTCGGCCAA

Figure 53 (continued)

GTAGCAGTTTACCATGAGTTCGTAGTTGAGCGCCTCGGCTGCGTGGCCTTTGGCGCGGAGCTTACCTTT
GGAAGTTTTCTTGCATACCGGGCAGTATAGGCATTTCAGCGCATACAACTTGGGCGCAAGGAAAACGGA
TTCTGGGGAGTATGCATCTGCGCCGCAGGAGGCGCAAACAGTTTCACATTCCACCAGCCAGGTTAAATC
CGGTTCATTGGGGTCAAAAACAAGTTTTCCGCCATATTTTTTGATGCGTTTCTTACCTTTGGTCTCCAT
GAGTTCGTGTCCTCGTTGAGTGACAAACAGGCTGTCCGTGTCCCCGTAGACTGATTTTACAGGCCTCTT
CTCCAGTGGAGTGCCTCGGTCTTCTTCGTACAGGAACTCTGACCACTCTGATACAAAGGCGCGCGTCCA
GGCCAGCACAAAGGAGGCTATGTGGGAGGGGTAGCGATCGTTGTCAACCAGGGGGTCCACCTTTTCCAA
AGTATGCAAACACATGTCACCCTCTTCAACATCCAGGAATGTGATTGGCTTGTAGGTGTATTTCACGTG
ACCTGGGGTCCCCGCTGGGGGGGTATAAAAGGGGGCGGTTCTTTGCTCTTCCTCACTGTCTTCCGGATC
GCTGTCCAGGAACGTCAGCTGTTGGGGTAGGTATTCCCTCTCGAAGGCGGGCATGACCTCTGCACTCAG
GTTGTCAGTTTCTAAGAACGAGGAGGATTTGATATTGACAGTGCCGGTTGAGATGCCTTTCATGAGGTT
TTCGTCCATCTGGTCAGAAAACACAATTTTTTTATTGTCAAGTTTGGTGGCAAATGATCCATACAGGGC
GTTGGATAAAAGTTTGGCAATGGATCGCATGGTTTGGTTCTTTTCCTTGTCCGCGCGCTCTTTGGCGGC
GATGTTGAGTTGGACATACTCGCGTGCCAGGCACTTCCATTCGGGGAAGATAGTTGTTAATTCATCTGG
CACGATTCTCACTTGCCACCCTCGATTATGCAAGGTAATTAAATCCACACTGGTGGCCACCTCGCCTCG
AAGGGGTTCATTGGTCCAACAGAGCCTACCTCCTTTCCTAGAACAGAAAGGGGGAAGTGGGTCTAGCAT
AAGTTCATCGGGAGGGTCTGCATCCATGGTAAAGATTCCCGGAAGTAAATCCTTATCAAAATAGCTGAT
GGGAGTGGGGTCATCTAAGGCCATTTGCCATTCTCGAGCTGCCAGTGCGCGCTCATATGGGTTAAGGGG
ACTGCCCCATGGCATGGGATGGGTGAGTGCAGAGGCATACATGCCACAGATGTCATAGACGTAGATGGG
ATCCTCAAAGATGCCTATGTAGGTTGGATAGCATCGCCCCCCTCTGATACTTGCTCGCACATAGTCATA
TAGTTCATGTGATGGCGCTAGCAGCCCCGGACCCAAGTTGGTGCGATTGGGTTTTTCTGTTCTGTAGAC
GATCTGGCGAAAGATGGCGTGAGAATTGGAAGAGATGGTGGGTCTTTGAAAAATGTTGAAATGGGCATG
AGGTAGACCTACAGAGTCTCTGACAAAGTGGGCATAAGATTCTTGAAGCTTGGTTACCAGTTCGGCGGT
GACAAGTACGTCTAGGGCGCAGTAGTCAAGTGTTTCTTGAATGATGTCATAACCTGGTTGGTTTTTCTT
TTCCCACAGTTCGCGGTTGAGAAGGTATTCTTCGCGATCCTTCCAGTACTCTTCTAGCGGAAACCCGTC
TTTGTCTGCACGGTAAGATCCTAGCATGTAGAACTGATTAACTGCCTTGTAAGGGCAGCAGCCCTTCTC
TACGGGTAGAGAGTATGCTTGAGCAGCTTTTCGTAGCGAAGCGTGAGTAAGGGCAAAGGTGTCTCTGAC
CATGACTTTGAGGAATTGGTATTTGAAGTCGATGTCGTCACAGGCTCCCTGTTCCCAGAGTTGGAAGTC
TACCCGTTTCTTGTAGGCGGGGTTGGGCAAAGCGAAAGTAACATCATTGAAGAGAATCTTGCCGGCCCT
GGGCATGAAATTGCGAGTGATGCGAAAAGGCTGTGGTACTTCCGCTCGGTTATTGATAACCTGGGCAGC
TAGGACGATCTCGTCGAAACCGTTGATGTTGTGTCCTACGATGTATAATTCTATGAAACGCGGCGTGCC
TCTGACGTGAGGTAGCTTACTGAGCTCATCAAAGGTTAGGTCTGTGGGGTCAGATAAGGCGTAGTGTTC
GAGAGCCCATTCGTGCAGGTGAGGATTCGCTTTAAGGAAGGAGGACCAGAGGTCCACTGCCAGTGCTGT
TTGTAACTGGTCCCGGTACTGACGAAAATGCCGTCCGACTGCCATTTTTTCTGGGGTGACGCAATAGAA
GGTTTGGGGGTCCTGCCGCCAGCGATCCCACTTGAGTTTTATGGCGAGGTCATAGGCGATGTTGACGAG
CCGCTGGTCTCCAGAGAGTTTCATGACCAGCATGAAGGGGATTAGCTGCTTGCCAAAGGACCCCATCCA
GGTGTAGGTTTCCACATCGTAGGTGAGAAAGAGCCTTTCTGTGCGAGGATGAGAGCCAATCGGGAAGAA
CTGGATCTCCTGCCACCAGTTGGAGGAATGGCTGTTGATGTGATGGAAGTAGAACTCCCTGCGACGCGC
CGAGCATTCATGCTTGTGCTTGTACAGACGGCCGCAGTAGTCGCAGCGTTGCACGGGTTGTATCTCGTG
AATGAGTTGTACCTGGCTTCCCTTGACGAGAAATTTCAGTGGGAAGCCGAGGCCTGGCGATTGTATCTC
GTGCTTTACTATGTTGTCTGCATCGGCCTGTTCATCTTCTGTCTCGATGGTGGTCATGCTGACGAGCCC
TCGCGGGAGGCAAGTCCAGACCTCGGCGCGGCAGGGGCGGAGCTCGAGGACGAGAGCGCGCAGGCTGGA
GCTGTCCAGGGTCCTGAGACGCTGCGGACTCAGGTTAGTAGGCAGTGTCAGGAGATTAACTTGCATGAT
CTTTTGGAGGGCGTGCGGGAGGTTCAGATAGTACTTGATCTCAACGGGTCCGTTGGTGGAGATGTCGAT
GGCTTGCAGGGTTCCGTGTCCCTTGGGCGCTACCACCGTGCCCTTGTTTTTCATTTTGGACGGCGGTGG
CTCTGTTGCTTCTTGCATGTTTAGAAGCGGTGTCGAGGGCGCGCACCGGGCGGCAGGGGCGGCTCGGGA
CCCGGCGGCATGGCTGGCAGTGGTACGTCGGCGCCGCGCGCGGGTAGGTTCTGGTACTGCGCCCTGAGA
AGACTCGCATGCGCGACGACGCGGCGGTTGACATCCTGGATCTGACGCCTCTGGGTGAAAGCTACCGGC

Figure 53 (continued)

CCCGTGAGCTTGAACCTGAAAGAGAGTTCAACAGAATCAATCTCGGTATCGTTGACGGCGGCTTGCCTA
AGGATTTCTTGCACGTCACCAGAGTTGTCCTGGTAGGCGATCTCCGCCATGAACTGCTCGATCTCTTCC
TCTTGAAGATCTCCGCGGCCCGCTCTCTCGACGGTGGCCGCGAGGTCGTTGGAGATGCGCCCAATGAGT
TGAGAGAATGCATTCATGCCCGCCTCGTTCCAGACGCGGCTGTAGACCACGGCCCCCACGGGATCTCTC
GCGCGCATGACCACCTGGGCGAGGTTGAGCTCCACGTGGCGGGTGAAGACCGCATAGTTGCATAGGCGC
TGGAAAAGGTAGTTGAGTGTGGTGGCGATGTGCTCGGTGACGAAGAAATACATGATCCATCGTCTCAGC
GGCATCTCGCTGACATCGCCCAGAGCTTCCAAGCGCTCCATGGCCTCGTAGAAGTCCACGGCAAAATTA
AAAAACTGGGAGTTTCGCGCGGACACGGTCAACTCCTCTTCCAGAAGACGGATAAGTTCGGCGATGGTG
GTGCGCACCTCGCGCTCGAAAGCCCCTGGGATTTCTTCCTCAATCTCTTCTTCTTCCACTAACATCTCT
TCCTCTTCAGGTGGGGCTGCAGGAGGAGGGGGAACGCGGCGACGCCGGCGGCGCACGGGCAGACGGTCG
ATGAATCTTTCAATGACCTCTCCGCGGCGGCGGCGCATGGTTTCAGTGACGGCGCGGCCGTTCTCGCGC
GGTCGCAGAGTAAAAACACCGCCGCGCATCTCCTTAAAGTGGTGACTGGGAGGTTCTCCGTTTGGGAGG
GAGAGGGCGCTGATTATACATTTTATTAATTGGCCCGTAGGGACTGCACGCAGAGATCTGATCGTGTCA
AGATCCACGGGATCTGAAAACCTTTCGACGAAAGCGTCTAACCAGTCACAGTCACAAGGTAGGCTGAGT
ACGGCTTCTTGTGGGCGGGGGTGGTTATGTGTTCGGTCTGGGTCTTCTGTTTCTTCTTCATCTCGGGAA
GGTGAGACGATGCTGCTGGTGATGAAATTAAAGTAGGCAGTTCTAAGACGGCGGATGGTGGCGAGGAGC
ACCAGGTCTTTGGGTCCGGCTTGCTGGATACGCAGGCGATTGGCCATTCCCCAAGCATTATCCTGACAT
CTAGCAAGATCTTTGTAGTAGTCTTGCATGAGCCGTTCTACGGGCACTTCTTCCTCACCCGTTCTGCCA
TGCATACGTGTGAGTCCAAATCCGCGCATTGGTTGTACCAGTGCCAAGTCAGCTACGACTCTTTCGGCG
AGGATGGCTTGCTGTACTTGGGTAAGGGTGGCTTGAAAGTCATCAAAATCCACAAAGCGGTGGTAAGCT
CCTGTATTAATGGTGTAAGCACAGTTGGCCATGACTGACCAGTTAACTGTCTGGTGACCAGGGCGCACG
AGCTCGGTGTATTTAAGGCGCGAATAGGCGCGGGTGTCAAAGATGTAATCGTTGCAGGTGCGCACCAGA
TACTGGTACCCTATAAGAAAATGCGGCGGTGGTTGGCGGTAGAGAGGCCATCGTTCTGTAGCTGGAGCG
CCAGGGGCGAGGTCTTCCAACATAAGGCGGTGATAGCCGTAGATGTACCTGGACATCCAGGTGATTCCT
GCGGCGGTAGTAGAAGCCCGAGGAAACTCGCGTACGCGGTTCCAAATGTTGCGTAGCGGCATGAAGTAG
TTCATTGTAGGCACGGTTTGACCAGTGAGGCGCGCGCAGTCATTGATGCTCTATAGACACGGAGAAAAT
GAAAGCGTTCAGCGACTCGACTCCGTAGCCTGGAGGAACGTGAACGGGTTGGGTCGCGGTGTACCCCGG
TTCGAGACTTGTACTCGAGCCGGCCGGAGCCGCGGCTAACGTGGTATTGGCACTCCCGTCTCGACCCAG
CCTACAAAAATCCAGGATACGGAATCGAGTCGTTTTGCTGGTTTCCGAATGGCAGGGAAGTGAGTCCTA
TTTTTTTTTTTTGCCGCTCAGATGCATCCCGTGCTGCGACAGATGCGCCCCCAACAACAGCCCCCCTCG
CAGCAGCAGCAGCAGCAATCACAAAAGGCTGTCCCTGCAACTACTGCAACTGCCGCCGTGAGCGGTGCG
GGACAGCCCGCCTATGATCTGGACTTGGAAGAGGGCGAAGGACTGGCACGTCTAGGTGCGCCTTCACCC
GAGCGGCATCCGCGAGTTCAACTGAAAAAAGATTCTCGCGAGGCGTATGTGCCCCAACAGAACCTATTT
AGAGACAGAAGCGGCGAGGAGCCGGAGGAGATGCGAGCTTCCCGCTTTAACGCGGGTCGTGAGCTGCGT
CACGGTTTGGACCGAAGACGAGTGTTGCGGGACGAGGATTTCGAAGTTGATGAAATGACAGGGATCAGT
CCTGCCAGGGCACACGTGGCTGCAGCCAACCTTGTATCGGCTTACGAGCAGACAGTAAAGGAAGAGCGT
AACTTCCAAAAGTCTTTTAATAATCATGTGCGAACCCTGATTGCCCGCGAAGAAGTTACCCTTGGTTTG
ATGCATTTGTGGGATTTGATGGAAGCTATCATTCAGAACCCTACTAGCAAACCTCTGACCGCCCAGCTG
TTTCTGGTGGTGCAACACAGCAGAGACAATGAGGCTTTCAGAGAGGCGCTGCTGAACATCACCGAACCC
GAGGGGAGATGGTTGTATGATCTTATCAACATTCTACAGAGTATCATAGTGCAGGAGCGGAGCCTGGGC
CTGGCCGAGAAGGTGGCTGCCATCAATTACTCGGTTTTGAGCTTGGGAAAATATTACGCTCGCAAAATC
TACAAGACTCCATACGTTCCCATAGACAAGGAGGTGAAGATAGATGGGTTCTACATGCGCATGACGCTC
AAGGTCTTGACCCTGAGCGATGATCTTGGGGTGTATCGCAATGACAGAATGCATCGCGCGGTTAGCGCC
AGCAGGAGGCGCGAGTTAAGCGACAGGGAACTGATGCACAGTTTGCAAAGAGCTCTGACTGGAGCTGGA
ACCGAGGGTGAGAATTACTTCGACATGGGAGCTGACTTGCAGTGGCAGCCTAGTCGCAGGGCTCTGAGC
GCCGCGACGGCAGGATGTGAGCTTCCTTACATAGAAGAGGCGGATGAAGGCGAGGAGGAAGAGGGCGAG
TACTTGGAAGACTGATGGCACAACCCGTGTTTTTGCTAGATGGAACAGCAAGCACCGGATCCCGCAAT
GCGGGCGGCGCTGCAGAGCCAGCCGTCCGGCATTAACTCCTCGGACGATTGGACCCAGGCCATGCAACG

Figure 53 (continued)

TATCATGGCGTTGACGACTCGCAACCCCGAAGCCTTTAGACAGCAACCCCAGGCCAACCGTCTATCGGC
CATCATGGAAGCTGTAGTGCCTTCCCGCTCTAATCCCACTCATGAGAAGGTCCTGGCCATCGTGAACGC
GTTGGTGGAGAACAAAGCTATTCGTCCAGATGAGGCCGGACTGGTATACAACGCTCTCTTAGAACGCGT
GGCTCGCTACAACAGTAGCAATGTGCAAACCAATTTGGACCGTATGATAACAGATGTACGCGAAGCCGT
GTCTCAGCGCGAAAGGTTCCAGCGTGATGCCAACCTGGGTTCGCTGGTGGCGTTAAATGCTTTCTTGAG
TACTCAGCCTGCTAATGTGCCGCGTGGTCAACAGGATTATACTAACTTTTTAAGTGCTTTGAGACTGAT
GGTATCAGAAGTACCTCAGAGCGAAGTGTATCAGTCCGGTCCTGATTACTTCTTTCAGACTAGCAGACA
GGGCTTGCAGACGGTAAATCTGAGCCAAGCTTTTAAAAACCTTAAAGGTTTGTGGGGAGTGCATGCCCC
GGTAGGAGAAAGAGCAACCGTGTCTAGCTTGTTAACTCCGAACTCCCGCCTATTATTACTGTTGGTAGC
TCCTTTCACCGACAGCGGTAGCATCGACCGTAATTCCTATTTGGGTTACCTACTAAACCTGTATCGCGA
AGCCATAGGGCAAAGTCAGGTGGACGAGCAGACCTATCAAGAAATTACCCAAGTCAGTCGCGCTTTGGG
ACAGGAAGACACTGGCAGTTTGGAAGCCACTCTGAACTTCTTGCTTACCAATCGGTCTCAAAAGATCCC
TCCTCAATATGCTCTTACTGCGGAGGAGGAGAGGATCCTTAGATATGTGCAGCAGAGCGTGGGATTGTT
TCTGATGCAAGAGGGGGCAACTCCGACTGCAGCACTGGACATGACAGCGCGAAATATGGAGCCCAGCAT
GTATGCCAGTAACCGACCTTTCATTAACAAACTGCTGGACTACTTGCACAGAGCTGCCGCTATGAACTC
TGATTATTTCACCAATGCCATCTTAAACCCGCACTGGCTGCCCCCACCTGGTTTCTACACGGGCGAATA
TGACATGCCCGACCCTAATGACGGATTTCTGTGGGACGACGTGGACAGCGATGTTTTTTCACCTCTTTC
TGATCATCGCACGTGGAAAAAGGAAGGCGGCGATAGAATGCATTCTTCTGCATCGCTGTCCGGGGTCAT
GGGTGCTACCGCGGCTGAGCCCGAGTCTGCAAGTCCTTTTCCTAGTCTACCCTTTTCTCTACACAGTGT
ACGTAGCAGCGAAGTGGGTAGAATAAGTCGCCCGAGTTTAATGGGCGAAGAGGAGTATCTAAACGATTC
CTTGCTCAGACCGGCAAGAGAAAAAAATTTCCCAAACAATGGAATAGAAAGTTTGGTGGATAAAATGAG
TAGATGGAAGACTTATGCTCAGGATCACAGAGACGAGCCTGGGATCATGGGGATTACAAGTAGAGCGAG
CCGTAGACGCCAGCGCCATGACAGACAGAGGGGTCTTGTGTGGGACGATGAGGATTCGGCCGATGATAG
CAGCGTGCTGGACTTGGGTGGGAGAGGAAGGGGCAACCCGTTTGCTCATTTGCGCCCTCGCTTGGGTGG
TATGTTGTAAAAAAAAATAAAAAAAAAACTCACCAAGGCCATGGCGACGAGCGTACGTTCGTTCTTCTT
TATTATCTGTGTCTAGTATAATGAGGCGAGTCGTGCTAGGCGGAGCGGTGGTGTATCCGGAGGGTCCTC
CTCCTTCGTACGAGAGCGTGATGCAGCAGCAGCAGGCGACGGCGGTGATGCAATCCCCACTGGAGGCTC
CCTTTGTGCCTCCGCGATACCTGGCACCTACGGAGGGCAGAAACAGCATTCGTTATTCGGAACTGGCAC
CTCAGTACGATACCACCAGGTTGTATCTGGTGGACAACAAGTCGGCGGACATTGCTTCTCTGAACTATC
AGAATGACCACAGCAACTTCTTGACCACGGTGGTGCAAAACAATGACTTTACCCCTACGGAAGCCAGCA
CCCAGACCATTAACTTTGATGAACGATCGCGGTGGGGCGGTCAGCTAAAGACCATCATGCATACTAACA
TGCCAAACGTGAACGAGTATATGTTTAGTAACAAGTTCAAAGCGCGTGTGATGGTGTCCAGAAAACCTC
CCGACGGTGCTGCAGTTGGGGATACTTATGATCACAAGCAGGATATTTTGAAATATGAGTGGTTCGAGT
TTACTTTGCCAGAAGGCAACTTTTCAGTTACTATGACTATTGATTTGATGAACAATGCCATCATAGATA
ATTACTTGAAAGTGGGTAGACAGAATGGAGTGCTTGAAAGTGACATTGGTGTTAAGTTCGACACCAGGA
ACTTCAAGCTGGGATGGGATCCCGAAACCAAGTTGATCATGCCTGGAGTGTATACGTATGAAGCCTTCC
ATCCTGACATTGTCTTACTGCCTGGCTGCGGAGTGGATTTTACCGAGAGTCGTTTGAGCAACCTTCTTG
GTATCAGAAAAAAACAGCCATTTCAAGAGGGTTTTAAGATTTTGTATGAAGATTTAGAAGGTGGTAATA
TTCCGGCCCTCTTGGATGTAGATGCCTATGAGAACAGTAAGAAAGAACAAAAAGCCAAAATAGAAGCTG
CTACAGCTGCTGCAGAAGCTAAGGCAAACATAGTTGCCAGCGACTCTACAAGGGTTGCTAACGCTGGAG
AGGTCAGAGGAGACAATTTTGCGCCAACACCTGTTCCGACTGCAGAATCATTATTGGCCGATGTGTCTG
AAGGAACGGACGTGAAACTCACTATTCAACCTGTAGAAAAAGATAGTAAGAATAGAAGCTATAATGTGT
TGGAAGACAAAATCAACACAGCCTATCGCAGTTGGTATCTTTCGTACAATTATGGCGATCCCGAAAAAG
GAGTGCGTTCCTGGACATTGCTCACCACCTCAGATGTCACCTGCGGAGCAGAGCAGGTCTACTGGTCGC
TTCCAGACATGATGAAGGATCCTGTCACTTTCCGCTCCACTAGACAAGTCAGTAACTACCCTGTGGTGG
GTGCAGAGCTTATGCCCGTCTTCTCAAAGAGCTTCTACAACGAACAAGCTGTGTACTCCCAGCAGCTCC
GCCAGTCCACCTCGCTTACGCACGTCTTCAACCGCTTTCCTGAGAACCAGATTTTAATCCGTCCGCCGG
CGCCCACCATTACCACCGTCAGTGAAAACGTTCCTGCTCTCACAGATCACGGGACCCTGCCGTTGCGCA

Figure 53 (continued)

GCAGTATCCGGGGAGTCCAACGTGTGACCGTTACTGACGCCAGACGCCGCACCTGTCCCTACGTGTACA
AGGCACTGGGCATAGTCGCACCGCGCGTCCTTTCAAGCCGCACTTTCTAAAAAAAAAAAAAATGTCCAT
TCTTATCTCGCCCAGTAATAACACCGGTTGGGGTCTGCGCGCTCCAAGCAAGATGTACGGAGGCGCACG
CAAACGTTCTACCCAACATCCTGTCCGTGTTCGCGGACATTTTCGCGCTCCATGGGGCGCCCTCAAGGG
CCGCACTCGCGTTCGAACCACCGTCGATGATGTAATCGATCAGGTGGTTGCCGACGCCCGTAATTATAC
TCCTACTGCGCCTACATCTACTGTGGATGCAGTTATTGACAGTGTAGTGGCTGACGCTCGCAACTATGC
TCGACGTAAGAGCCGGCGAAGGCGCATTGCCAGACGCCACCGAGCTACCACTGCCATGCGAGCCGCAAG
AGCTCTGCTACGAAGAGCTAGACGCGTGGGGCGAAGAGCCATGCTTAGGGCGGCCAGACGTGCAGCTTC
GGGCGCCAGCGCCGGCAGGTCCCGCAGGCAAGCAGCCGCTGTCGCAGCGGCGACTATTGCCGACATGGC
CCAATCGCGAAGAGGCAATGTATACTGGGTGCGTGACGCTGCCACCGGTCAACGTGTACCCGTGCGCAC
CCGTCCCCCTCGCACTTAGAAGATACTGAGCAGTCTCCGATGTTGTGTCCCAGCGGCGAGGATGTCCAA
GCGCAAATACAAGGAAGAAATGCTGCAGGTTATCGCACCTGAAGTCTACGGCCAACCGTTGAAGGATGA
AAAAAAACCCCGCAAAATCAAGCGGGTTAAAAAGGACAAAAAAGAAGAGGAAGATGGCGATGATGGGCT
GGCGGAGTTTGTGCGCGAGTTTGCCCCACGGCGACGCGTGCAATGGCGTGGGCGCAAAGTTCGACATGT
GTTGAGACCTGGAACTTCGGTGGTCTTTACACCCGGCGAGCGTTCAAGCGCTACTTTTAAGCGTTCCTA
TGATGAGGTGTACGGGGATGATGATATTCTTGAGCAGGCGGCTGACCGATTAGGCGAGTTTGCTTATGG
CAAGCGTAGTAGAATAACTTCCAAGGATGAGACAGTGTCGATACCCTTGGATCATGGAAATCCCACCCC
TAGTCTTAAACCGGTCACTTTGCAGCAAGTGTTACCCGTAACTCCGCGAACAGGTGTTAAACGCGAAGG
TGAAGATTTGTATCCCACTATGCAACTGATGGTACCCAAACGCCAGAAGTTGGAGGACGTTTTGGAGAA
AGTAAAAGTGGATCCAGATATTCAACCTGAGGTTAAAGTGAGACCCATTAAGCAGGTAGCGCCTGGTCT
GGGGGTACAAACTGTAGACATTAAGATTCCCACTGAAAGTATGGAAGTGCAAACTGAACCCGCAAAGCC
TACTGCCACCTCCACTGAAGTGCAAACGGATCCATGGATGCCCATGCCTATTACAACTGACGCCGCCGG
TCCCACTCGAAGATCCCGACGAAAGTACGGTCCAGCAAGTCTGTTGATGCCCAATTATGTTGTACACCC
ATCTATTATTCCTACTCCTGGTTACCGAGGCACTCGCTACTATCGCAGCCGAAACAGTACCTCCCGCCG
TCGCCGCAAGACACCTGCAAATCGCAGTCGTCGCCGTAGACGCACAAGCAAACCGACTCCCGGCGCCCT
GGTGCGGCAAGTGTACCGCAATGGTAGTGCGGAACCTTTGACACTGCCGCGTGCGCGTTACCATCCGAG
TATCATCACTTAATCAATGTTGCCGCTGCCTCCTTGCAGATATGGCCCTCACTTGTCGCCTTCGCGTTC
CCATCACTGGTTACCGAGGAAGAAACTCGCGCCGTAGAAGAGGGATGTTGGGACGCGGAATGCGACGCT
ACAGGCGACGGCGTGCTATCCGCAAGCAATTGCGGGGTGGTTTTTTACCAGCCTTAATTCCAATTATCG
CTGCTGCAATTGGCGCGATACCAGGCATAGCTTCCGTGGCGGTTCAGGCCTCGCAACGACATTGACATT
GGAAAAAAACGTATAAATAAAAAAAAAAAAAATACAATGGACTCTGACACTCCTGGTCCTGTGACTATGT
TTTCTTAGAGATGGAAGACATCAATTTTTCATCCTTGGCTCCGCGACACGGCACGAAGCCGTACATGGG
CACCTGGAGCGACATCGGCACGAGCCAACTGAACGGGGGCGCCTTCAATTGGAGCAGTATCTGGAGCGG
GCTTAAAAATTTTGGCTCAACCATAAAAACATACGGGAACAAAGCTTGGAACAGCAGTACAGGACAGGC
GCTTAGAAATAAACTTAAAGACCAGAACTTCCAACAAAAAGTAGTCGATGGGATAGCTTCCGGCATCAA
TGGAGTGGTAGATTTGGCTAACCAGGCTGTGCAGAAAAAGATAAACAGTCGTTTGGACCCGCCGCCAGC
AACCCCAGGTGAAATGCAAGTGGAGGAAGAAATTCCTCCGCCAGAAAAACGAGGCGACAAGCGTCCGCG
TCCCGATTTGGAAGAGACGCTGGTGACGCGCGTAGATGAACCGCCTTCTTATGAGGAAGCAACGAAGCT
TGGAATGCCCACCACTAGACCGATAGCCCCAATGGCCACCGGGGTGATGAAACCTTCTCAGTTGCATCG
ACCCGTCACCTTGGATTTGCCCCCTCCCCCTGCTGCTACTGCTGTACCCGCTTCTAAGCCTGTCGCTGC
CCCGAAACCAGTCGCCGTAGCCAGGTCACGTCCCGGGGGCGCTCCTCGTCCAAATGCGCACTGGCAAAA
TACTCTGAACAGCATCGTGGGTCTAGGCGTGCAAAGTGTAAAACGCCGTCGCTGCTTTTAATTAAATAT
GGAGTAGCGCTTAACTTGCCTATCTGTGTATATGTGTCATTACACGCCGTCACAGCAGCAGAGGAAAAA
AGGAAGAGGTCGTGCGTCGACGCTGAGTTACTTTCAAGATGGCCACCCCATCGATGCTGCCCCAATGGG
CATACATGCACATCGCCGGACAGGATGCTTCGGAGTACCTGAGTCCGGGTCTGGTGCAGTTCGCCCGCG
CCACAGACACCTACTTCAATCTGGGAAATAAGTTTAGAAATCCCACCGTAGCGCCGACCCACGATGTGA
CCACCGACCGTAGCCAGCGGCTCATGTTGCGCTTCGTGCCCGTTGACCGGGAGGACAATACATACTCTT
ACAAAGTGCGGTACACCCTGGCCGTGGGCGACAACAGAGTGCTGGATATGGCCAGCACGTTCTTTGACA

Figure 53 (continued)

TTAGGGGTGTGTTGGACAGAGGTCCCAGTTTCAAACCCTATTCTGGTACGGCTTACAACTCCCTGGCTC
CTAAAGGCGCTCCAAATACATCTCAGTGGATTGCAGAAGGTGTAAAAAATACAACTGGTGAGGAACACG
TAACAGAAGAGGAAACCAATACTACTACTTACACTTTTGGCAATGCTCCTGTAAAAGCTGAAGCTGAAA
TTACAAAAGAAGGACTCCCAGTAGGTTTGGAAGTTTCAGATGAAGAAAGTAAACCGATTTATGCTGATA
AAACATATCAGCCAGAACCTCAGCTGGGAGATGAAACTTGGACTGACCTTGATGGAAAAACCGAAAAGT
ATGGAGGCAGGGCTCTCAAACCCGATACTAAGATGAAACCATGCTACGGGTCCTTTGCCAAACCTACTA
ATGTGAAAGGCGGTCAGGCAAAACAAAAAACAACGGAGCAGCCAAATCAGAAAGTCGAATATGATATCG
ACATGGAGTTTTTTGATGCGGCATCGCAGAAAACAAACTTAAGTCCTAAAATTGTCATGTATGCAGAAA
ATGTAAATTTGGAAACTCCAGACACTCATGTAGTGTACAAACCTGGAACAGAAGACACAAGTTCCGAAG
CTAATTTGGGACAACAATCTATGCCCAACAGACCCAACTACATTGGCTTCAGAGATAACTTTATTGGAC
TTATGTACTATAACAGTACTGGTAACATGGGGGTGCTGGCTGGTCAAGCGTCTCAGTTAAATGCAGTGG
TTGACTTGCAGGACAGAAACACAGAACTTTCTTACCAACTCTTGCTTGACTCTCTGGGCGACAGAACCA
GATACTTTAGCATGTGGAATCAGGCTGTGGACAGTTATGATCCTGATGTACGTGTTATTGAAAATCATG
GTGTGGAAGATGAACTTCCCAACTACTGTTTTCCACTGGACGGCATAGGTGTTCCAACAACCAGTTACA
AATCAATAGTTCCAAATGGAGACAATGCGCCTAATTGGAAGGAACCTGAAGTAAATGGAACAAGTGAGA
TCGGACAGGGTAATTTGTTTGCCATGGAAATTAACCTTCAAGCCAATCTATGGCGAAGTTTCCTTTATT
CCAATGTGGCTCTATATCTCCCAGACTCGTACAAATACACCCCGTCCAATGTCACTCTTCCAGAAAACA
AAAACACCTACGACTACATGAACGGGCGGGTGGTGCCGCCATCTCTAGTAGACACCTATGTGAACATTG
GTGCCAGGTGGTCTCTGGATGCCATGGACAATGTCAACCCATTCAACCACCACCGTAACGCTGGCTTGC
GTTACCGATCCATGCTTCTGGGTAACGGACGTTATGTGCCTTTCCACATACAAGTGCCTCAAAAATTCT
TCGCTGTTAAAAACCTGCTGCTTCTCCCAGGCTCCTACACTTATGAGTGGAACTTTAGGAAGGATGTGA
ACATGGTTCTACAGAGTTCCCTCGGTAACGACCTGCGGGTAGATGGCGCCAGCATCAGTTTCACGAGCA
TCAACCTCTATGCTACTTTTTTCCCCATGGCTCACAACACCGCTTCCACCCTTGAAGCCATGCTGCGGA
ATGACACCAATGATCAGTCATTCAACGACTACCTATCTGCAGCTAACATGCTCTACCCCATTCCTGCCA
ATGCAACCAATATTCCCATTTCCATTCCTTCTCGCAACTGGGCGGCTTTCAGAGGCTGGTCATTTACCA
GACTGAAAACCAAAGAAACTCCCTCTTTGGGGTCTGGATTTGACCCCTACTTTGTCTATTCTGGTTCTA
TTCCCTACCTGGATGGTACCTTCTACCTGAACCACACTTTTAAGAAGGTTTCCATCATGTTTGACTCTT
CAGTGAGCTGGCCTGGAAATGACAGGTTACTATCTCCTAACGAATTTGAAATAAAGCGCACTGTGGATG
GCGAAGGCTACAACGTAGCCCAATGCAACATGACCAAAGACTGGTTCTTGGTACAGATGCTCGCCAACT
ACAACATCGGCTATCAGGGCTTCTACATTCCAGAAGGATACAAAGATCGCATGTATTCATTTTTCAGAA
ACTTCCAGCCCATGAGCAGGCAGGTGGTTGATGAGGTCAATTACAAAGACTTCAAGGCCGTCGCCATAC
CCTACCAACACAACAACTCTGGCTTTGTGGGTTACATGGCTCCGACCATGCGCCAAGGTCAACCCTATC
CCGCTAACTATCCCTATCCACTCATTGGAACAACTGCCGTAAATAGTGTTACGCAGAAAAAGTTCTTGT
GTGACAGAACCATGTGGCGCATACCGTTCTCGAGCAACTTCATGTCTATGGGGGCCCTTACAGACTTGG
GACAGAATATGCTCTATGCCAACTCAGCTCATGCTCTGGACATGACCTTTGAGGTGGATCCCATGGATG
AGCCCACCCTGCTTTATCTTCTCTTCGAAGTTTTCGACGTGGTCAGAGTGCATCAGCCACACCGCGGCA
TCATCGAGGCAGTCTACCTGCGTACACCGTTCTCGGCCGGTAACGCTACCACGTAAGAAGCTTCTTGCT
TCTTGCAAATAGCAGCTGCAACCATGGCCTGCGGATCCCAAAACGGCTCCAGCGAGCAAGAGCTCAGAG
CCATTGTCCAAGACCTGGGTTGCGGACCCTATTTTTTGGGAACCTACGATAAGCGCTTCCCGGGGTTCA
TGGCCCCCGATAAGCTCGCCTGTGCCATTGTAAATACGGCCGGACGTGAGACGGGGGGAGAGCACTGGT
TGGCTTTCGGTTGGAACCCACGTTCTAACACCTGCTACCTTTTTGATCCTTTTGGATTCTCGGATGATC
GTCTCAAACAGATTTACCAGTTTGAATATGAGGGTCTCCTGCGCCGCAGCGCTCTTGCTACCAAGGACC
GCTGTATTACGCTGGAAAAATCTACCCAGACCGTGCAGGGTCCCCGTTCTGCCGCCTGCGGACTTTTCT
GCTGCATGTTCCTTCACGCCTTTGTGCACTGGCCTGACCGTCCCATGGACGGAAACCCCACCATGAAAT
TGCTAACTGGAGTGCCAAACAACATGCTTCATTCTCCTAAAGTCCAGCCCACCCTGTGTGACAATCAAA
AAGCACTCTACCATTTTCTTAATACCCATTCGCCTTATTTTCGCTCCCATCGTACACACATCGAAAGGG
CCACTGCGTTCGACCGTATGGATGTTCAATAATGACTCATGTAAACAACGTGTTCAATAAACATCACTT
TATTTTTTTACATGTATCAAGGCTCTGCATTACTTATTTATTTACAAGTCGAATGGGTTCTGACGAGAA

Figure 53 (continued)

TCAGAATGACCCGCAGGCAGTGATACGTTGCGGAACTGATACTTGGGTTGCCACTTGAATTCGGGAATC
ACCAACTTGGGAACCGGTATATCGGGCAGGATGTCACTCCACAGCTTTCTGGTCAGCTGCAAAGCTCCA
AGCAGGTCAGGAGCCGAAATCTTGAAATCACAATTAGGACCAGTGCTTTGAGCGCGAGAGTTGCGGTAC
ACCGGATTGCAGCACTGAAACACCATCAGCGACGGATGTCTCACGCTTGCCAGCACGGTGGGATCTGCA
ATCATGCCCACATCCAGATCTTCAGCATTGGCAATGCTGAACGGGGTCATCTTGCAGGTCTGCCTACCC
ATGGCGGGCACCCAATTAGGCTTGTGGTTGCAATCGCAGTGCAGGGGGATCAGTATCATCTTGGCCTGA
TCCTGTCTGATTCCTGGATACACGGCTCTCATGAAAGCATCATATTGCTTGAAAGCCTGCTGGGCTTTA
CTACCCTCGGTATAAAACATCCCGCAGGACCTGCTCGAAAACTGGTTAGCTGCACAGCCGGCATCATTC
ACACAGCAGCGGGCGTCATTGTTAGCTATTTGCACCACACTTCTGCCCCAGCGGTTTTGGGTGATTTTG
GTTCGCTCGGGATTCTCCTTTAAGGCTCGTTGTCCGTTCTCGCTGGCCACATCCATCTCGATAATCTGC
TCCTTCTGAATCATAATATTGCCATGCAGGCACTTCAGCTTGCCCTCATAATCATTGCAGCCATGAGGC
CACAACGCACAGCCTGTACATTCCCAATTATGGTGGGCGATCTGAGAAAAAGAATGTATCATTCCCTGC
AGAAATCTTCCCATCATCGTGCTCAGTGTCTTGTGACTAGTGAAAGTTAACTGGATGCCTCGGTGCTCC
TCGTTTACGTACTGGTGACAGATGCGCTTGTATTGTTCGTGTTGCTCAGGCATTAGTTTAAAAGAGGTT
CTAAGTTCGTTATCCAGCCTGTACTTCTCCATCAGCAGACACATCACTTCCATGCCTTTCTCCCAAGCA
GACACCAGGGGCAAGCTAATCGGATTCTTAACAGTGCAGGCAGCAGCTCCTTTAGCCAGAGGGTCATCT
TTAGCGATCTTCTCAATGCTTCTTTTGCCATCCTTCTCAACGATGCGCACGGGCGGGTAGCTGAAACCC
ACTGCTACAAGTTGCGCCTCTTCTCTTTCTTCTTCGCTGTCTTGACTGATGTCTTGCATGGGGATATGT
TTGGTCTTCCTTGGCTTCTTTTTGGGGGGTATCGGAGGAGGAGGACTGTCGCTCCGTTCCGGAGACAGG
GAGGATTGTGACGTTTCGCTCACCATTACCAACTGACTGTCGGTAGAAGAACCTGACCCCACACGGCGA
CAGGTGTTTCTCTTCGGGGGCAGAGGTGGAGGCGATTGCGAAGGGCTGCGGTCCGACCTGGAAGGCGGA
TGACTGGCAGAACCCCTTCCGCGTTCGGGGGTGTGCTCCCTGTGGCGGTCGCTTAACTGATTTCCTTCG
CGGCTGGCCATTGTGTTCTCCTAGGCAGAGAAACAACAGACATGGAAACTCAGCCATTGCTGTCAACAT
CGCCACGAGTGCCATCACATCTCGTCCTCAGCGACGAGGAAAAGGAGCAGAGCTTAAGCATTCCACCGC
CCAGTCCTGCCACCACCTCTACCCTAGAAGATAAGGAGGTCGACGCATCTCATGACATGCAGAATAAAA
AAGCGAAAGAGTCTGAGACAGACATCGAGCAAGACCCGGGCTATGTGACACCGGTGGAACACGAGGAAG
AGTTGAAACGCTTTCTAGAGAGAGAGGATGAAAACTGCCCAAAACAACGAGCAGATAACTATCACCAAG
ATGCTGGAAATAGGGATCAGAACACCGACTACCTCATAGGGCTTGACGGGGAAGACGCGCTCCTTAAAC
ATCTAGCAAGACAGTCGCTCATAGTCAAGGATGCATTATTGGACAGAACTGAAGTGCCCATCAGTGTGG
AAGAGCTCAGCCGCGCCTACGAGCTTAACCTCTTTTCACCTCGTACTCCCCCCAAACGTCAGCCAAACG
GCACCTGCGAGCCAAATCCTCGCTTAAACTTTTATCCAGCTTTTGCTGTGCCAGAAGTACTGGCTACCT
ATCACATCTTTTTTAAAAATCAAAAAATTCCAGTCTCCTGCCGCGCTAATCGCACCCGCGCCGATGCCC
TACTCAATCTGGGACCTGGTTCACGCTTACCTGATATAGCTTCCTTGGAAGAGGTTCCAAAGATCTTCG
AGGGTCTGGGCAATAATGAGACTCGGGCCGCAAATGCTCTGCAAAAGGGAGAAAATGGCATGGATGAGC
ATCACAGCGTTCTGGTGGAATTGGAAGGCGATAATGCCAGACTCGCAGTACTCAAGCGAAGCATCGAGG
TCACACACTTCGCATATCCCGCTGTCAACCTGCCCCCTAAAGTCATGACGGCGGTCATGGACCAGTTAC
TCATTAAGCGCGCAAGTCCCCTTTCAGAAGACATGCATGACCCAGATGCCTGTGATGAGGGTAAACCAG
TGGTCAGTGATGAGCAGCTAACCCGATGGCTGGGCACCGACTCTCCCAGGGATTTGGAAGAGCGTCGCA
AGCTTATGATGGCCGTGGTGCTGGTTACCGTAGAACTAGAGTGTCTCCGACGTTTCTTTACCGATTCAG
AAACCTTGCGCAAACTCGAAGAGAATCTGCACTACACTTTTAGACACGGCTTTGTGCGGCAGGCATGCA
AGATATCTAACGTGGAACTCACCAACCTGGTTTCCTACATGGGTATTCTGCATGAGAATCGCCTAGGAC
AAAGCGTGCTGCACAGCACCCTGAAGGGGGAAGCCCGCCGTGATTACATCCGCGATTGTGTCTATCTGT
ACCTGTGCCACACGTGGCAAACCGGCATGGGTGTATGGCAGCAATGTTTAGAAGAACAGAACTTGAAAG
AGCTTGACAAGCTCTTACAGAAATCTCTTAAGGTTCTGTGGACAGGGTTCGACGAGCGCACCGTCGCTT
CCGACCTGGCAGACCTCATCTTCCCAGAGCGTCTCAGGGTTACTTTGCGAAACGGATTGCCTGACTTTA
TGAGCCAGAGCATGCTTAACAATTTTCGCTCTTTCATCCTGGAACGCTCCGGTATCCTGCCCGCCACCT
GCTGCGCACTGCCCTCCGACTTTGTGCCTCTCACCTACCGCGAGTGCCCCCCGCCGCTATGGAGTCACT
GCTACCTGTTCCGTCTGGCCAACTATCTCTCCTACCACTCGGATGTGATCGAGGATGTGAGCGGAGACG

Figure 53 (continued)

GCTTGCTGGAGTGTCACTGCCGCTGCAATCTGTGCACGCCCCACCGGTCCCTAGCTTGCAACCCCCAGT
TGATGAGCGAAACCCAGATAATAGGCACCTTTGAATTGCAAGGCCCCAGCAGCCAAGGCGATGGGTCTT
CTCCTGGGCAAAGTTTAAAACTGACCCCGGGACTGTGGACCTCCGCCTACTTGCGCAAGTTTGCTCCGG
AAGATTACCACCCCTATGAAATCAAGTTCTATGAGGACCAATCACAGCCTCCAAAGGCCGAACTTTCGG
CCTGCGTCATCACCCAGGGGGCAATTCTGGCCCAATTGCAAGCCATCCAAAAATCCCGCCAAGAATTTC
TACTGAAAAAGGGTAAGGGGGTCTACCTTGACCCCCAGACCGGCGAGGAACTCAACACAAGGTTCCCTC
AGGATGTCCCAACGACGAGAAAACAAGAAGTTGAAGGTGCAGCCGCCGCCCCCAGAAGATATGGAGGAA
GATTGGGACAGTCAGGCAGAGGAGGCGGAGGAGGACAGTCTGGAGGACAGTCTGGAGGAAGACAGTTTG
GAGGAGGAAAACGAGGAGGCAGAGGAGGTGGAAGAAGTAACCGCCGACAAACAGTTATCCTCGGCTGCG
GAGACAAGCAACAGCGCTACCATCTCCGCTCCGAGTCGAGGAACCCGGCGGCGTCCCAGCAGTAGATGG
GACGAGACCGGACGCTTCCCGAACCCAACCAGCGCTTCCAAGACCGGTAAGAAGGATCGGCAGGGATAC
AAGTCCTGGCGGGGGCATAAGAATGCCATCATCTCCTGCTTGCATGAGTGCGGGGGCAACATATCCTTC
ACGCGGCGCTACTTGCTATTCCACCATGGGGTGAACTTTCCGCGCAATGTTTTGCATTACTACCGTCAC
CTCCACAGCCCCTACTATAGCCAGCAAATCCCGGCAGTCTCGACAGATAAAGACAGCGGCGGCGACCTC
CAACAGAAAACCAGCAGCGGCAGTTAGAAAATACACAACAAGTGCAGCAACAGGAGGATTAAAGATTAC
AGCCAACGAGCCAGCGCAAACCCGAGAGTTAAGAAATCGGATCTTTCCAACCCTGTATGCCATCTTCCA
GCAGAGTCGGGGTCAAGAGCAGGAACTGAAAATAAAAAACCGATCTCTGCGTTCGCTCACCAGAAGTTG
TTTGTATCACAAGAGCGAAGATCAACTTCAGCGCACTCTCGAGGACGCCGAGGCTCTCTTCAACAAGTA
CTGCGCGCTGACTCTTAAAGAGTAGGCAGCGACCGCGCTTATTCAAAAAAGGCGGGAATTACATCATCC
TCGACATGAGTAAAGAAATTCCCACGCCTTACATGTGGAGTTATCAACCCCAAATGGGATTGGCGGCAG
GCGCCTCCCAGGACTACTCCACCCGCATGAATTGGCTCAGCGCCGGGCCTTCTATGATTTCTCGAGTTA
ATGATATACGCGCCTACCGAAACCAAATACTTTTGGAACAGTCAGCTCTTACCACCACGCCCCGCCAAC
ACCTTAATCCCAGAAATTGGCCCGCCGCCCTAGTGTACCAGGAAAGTCCCGCTCCCACCACTGTATTAC
TTCCTCGAGACGCCCAGGCCGAAGTCCAAATGACTAATGCAGGTGCGCAGTTAGCTGGCGGCTCCACCC
TATGTCGTCACAGGCCTCGGCATAATATAAAACGCCTGATGATCAGAGGCCGAGGTATCCAGCTCAACG
ACGAGTCGGTGAGCTCTCCGCTTGGTCTACGACCAGACGGAATCTTTCAGATTGCCGGCTGCGGGAGAT
CTTCCTTCACCCCTCGTCAGGCTGTTCTGACTTTGGAAAGTTCGTCTTCGCAACCCCGCTCGGGCGGAA
TCGGGACCGTTCAATTTGTGGAGGAGTTTACTCCCTCTGTCTACTTCAACCCCTTCTCCGGATCTCCTG
GGCATTACCCGGACGAGTTCATACCGAACTTCGACGCGATTAGCGAGTCAGTGGACGGCTACGATTGAT
GTCTGGTGACGCGGCTGAGCTATCTCGGCTGCGACATCTAGACCACTGCCGCCGCTTTCGCTGCTTTGC
CCGGGAACTCATTGAGTTCATCTACTTCGAACTCCCCAAGGATCACCCTCAAGGTCCGGCCCACGGAGT
GCGGATTTCTATCGAAGGCAAAATAGACTCTCGCCTGCAACGAATTTTCTCCCAGCGGCCCGTGCTGAT
CGAGCGAGACCAGGGAAACACCACGGTTTCCATCTACTGCATTTGTAATCACCCCGGATTGCATGAAAG
CCTTTGCTGTCTTATGTGTACTGAGTTTAATAAAAACTGAATTAAGACTCTCCTACGGACTGCCGCTTC
TTCAACCCGGATTTTACAACCAGAAGAACGAAACTTTTCCTGTCGTCCAGGACTCTGTTAACTTCACCT
TTCCTACTCACAAACTAGAAGCTCAACGACTACACCGCTTTTCCAGAAGCATTTTCCCTACTAATACTA
CTTTCAAAACCGGAGGTGAGCTCCAAGGTCTTCCTACAGAAAACCCTTGGGTGGAAGCGGGCCTTGTAG
TGCTAGGAATTCTTGCGGGTGGGCTTGTGATTATTCTTTGCTACCTATACACACCTTGCTTCACTTTCT
TAGTGGTGTTGTGGTATTGGTTTAAAAAATGGGGCCCATACTAGTCTTGCTTGTTTTACTTTCGCTTTT
GGAACCGGGTTCTGCCAATTACGATCCATGTCTAGACTTCGACCCAGAAAACTGCACACTTACTTTTGC
ACCCGACACAAGCCGCATCTGTGGAGTTCATCGCCTCTCTTACGAACTTGGCCCCCAACGACAAAAATT
TACCTGCATGGTGGGAATCAACCCCATAGTTATCACCCAGCAAAGTGGAGATACTAAGGGTTGCATTCA
CTGCTCCTGCGATTCCATCGAGTGCACCTACACCCTGCTGAAGACCCTATGCGGCCTAAGAGACCTGCT
ACCAATGAATTAAAAAATGATTAATAAAAAATCACTTACTTGAAATCAGCAATAAGGTCTCTGTTGAAA
TTTTCTCCCAGCAGCACCTCACTTCCCTCTTCCCAACTCTGGTATTCTAAACCCCGTTCAGCGGCATAC
TTTCTCCATACTTTAAAGGGGATGTCAAATTTTAGCTCCTCTCCTGTACCCACAATCTTCATGTCTTTC
TTCCCAGATGACCAAGAGAGTCCGGCTCAGTGACTCCTTCAACCCTGTCTACCCCTATGAAGATGAAAG
CACCTCCCAACACCCCTTTATAAACCCAGGGTTTATTTCCCCAAATGGCTTCACACAAAGCCCAAACGG

Figure 53 (continued)

AGTTCTTACTTTAAAATGTTTAACCCCACTAACAACCACAGGCGGATCTCTACAGCTAAAAGTGGGAGG
GGGACTTACAGTGGATGACACCAACGGTTTTTGAAAGAAAACATAAGTGCCACCACACCACTCGTTAA
GACTGGTCACTCTATAGGTTTACCACTAGGAGCCGGATTGGGAACGAATGAAAATAAACTTTGTATCAA
ATTAGGACAAGGACTTACATTCAATTCAAACAACATTTGCATTGATGACAATATTAACACCTTATGGAC
AGGAGTCAACCCCACCGAAGCCAACTGTCAAATCATGAACTCCAGTGAATCTAATGATTGCAAATTAAT
TCTAACACTAGTTAAAACTGGAGCACTAGTCACTGCATTTGTTTATGTTATAGGAGTATCTAACAATTT
TAATATGCTAACTACACACAGAAATATAAATTTTACTGCAGAGCTGTTTTTCGATTCTACTGGTAATTT
ACTAACTAGACTCTCATCCCTCAAAACTCCACTTAATCATAAATCAGGACAAAACATGGCTACTGGTGC
CATTACTAATGCTAAAGGTTTCATGCCCAGCACGACTGCCTATCCTTTCAATGATAATTCTAGAGAAAA
AGAAAACTACATTTACGGAACTTGTTACTACACAGCTAGTGATCGCACTGCTTTTCCCATTGACATATC
TGTCATGCTTAACCGAAGAGCAATAAATGACGAGACATCATATTGTATTCGTATAACTTGGTCCTGGAA
CACAGGAGATGCCCCAGAGGTGCAAACCTCTGCTACAACCCTAGTCACCTCCCCATTTACCTTTTACTA
CATCAGAGAAGACGACTGACAAATAAAGTTTGCGATCGCCAGGCCCACCATGGGATGGAGCTGTATCAT
CCTCTTCTTGGTAGCAACAGCTACAGGTGTCCACTCCCAGGTGCAGCTGCAGCAGTCTGGGGCTGAACT
GGCAAGACCTGGGGCCTCAGTGAAGATGTCCTGCAAGGCTTCTGGCTACACCTTTACTAGGTACACGAT
GCACTGGGTAAAACAGAGGCCTGGACAGGGTCTGGAATGGATTGGATACATTAATCCTAGCCGTGGTTA
TACTAATTACAATCAGAAGTTCAAGGACAAGGCCACATTGACTACAGACAAATCCTCCAGCACAGCCTA
CATGCAACTGAGCAGCCTGACATCTGAGGACTCTGCAGTCTATTACTGTGCAAGATATTATGATGATCA
TTACTGCCTTGACTACTGGGGCCAAGGCACCACTCTCACAGTCTCCTCAGGTGGCGGTGGCTCGGGCGG
TGGTGGATCTGGTGGCGGCGGATCTGATATCGTGCTCACTCAGTCTCCAGCAATCATGTCTGCATCTCC
AGGGGAGAAGGTCACCATGACCTGCAGTGCCAGCTCAAGTGTAAGTTACATGAACTGGTACCAGCAGAA
GTCAGGCACCTCCCCCAAAAGATGGATTTATGACACATCCAAACTGGCTTCTGGAGTCCCTGCTCACTT
CAGGGGCAGTGGGTCTGGGACCTCTTACTCTCTCACAATCAGCGGCATGGAGGCTGAAGATGCTGCCAC
TTATTACTGCCAGCAGTGGAGTAGTAACCCATTCACGTTCGGCTCGGGGACAAAGTTGGAAATAAACCG
GGGATCCGAACAAAAACTCATCTCAGAAGAGGATCTGAATGCTGTGGGCCAGGACACGCAGGAGGTCAT
CGTGGTGCCACACTCCTTGCCCTTTAAGGTGGTGGTGATCTCAGCCATCCTGGCCCTGGTGGTGCTCAC
CATCATCTCCCTTATCATCCTCATCATGCTTTGGCAGAAGAAGCCACGTGGTTCAATCCCTAACCCTCT
CCTCGGTCTCGATTAAGCTAGCTTGACTGACTGAGATACAGCGTACCTTCAGCTCACAGACATGATAAG
ATACATTGATGAGTTTGGACAAACCACAACTAGAATGCAGTGAAAAAAATGCTTTATTTGTGAAATTTG
TGATGCTATTGCTTTATTTGTAACCATTATAAGCTGCAATAAACAAGTTAACAACAACAATTGCATTCA
TTTTATGTTTCAGGTTCAGGGGGAGGTGTGGGAGGTTTTTTAAAGCAAGTAAAACCTCTACAAATGTGG
TAGTCGTCAGCTATCCTGCAGGAACTTGTTTATTTGAAAATCAATTCACAAAATCCGAGTAGTTATTTT
GCCTCCCCCTTCCCATTTAACAGAATACACCAATCTCTCCCCACGCACAGCTTTAAACATTTGGATACC
ATTAGATATAGACATGGTTTTAGATTCCACATTCCAAACAGTTTCAGAGCGAGCCAATCTGGGGTCAGT
GATAGATAAAAATCCATCGGGATAGTCTTTTAAAGCGCTTTCACAGTCCAACTGCTGCGGATGCGACTC
CGGAGTCTGGATCACGGTCATCTGGAAGAAGAACGATGGGAATCATAATCCGAAAACGGTATCGGACGA
TTGTGTCTCATCAAACCCACAAGCAGCCGCTGTCTGCGTCGCTCCGTGCGACTGCTGTTTATGGGATCA
GGGTCCACAGTGTCCTGAAGCATGATTTTAATAGCCCTTAACATCAACTTTCTGGTGCGATGCGCGCAG
CAACGCATTCTGATTTCACTCAAATCTTTGCAGTAGGTACAACACATTATTACAATATTGTTTAATAAA
CCATAATTAAAAGCGCTCCAGCCAAAACTCATATCTGATATAATCGCCCCTGCATGACCATCATACCAA
AGTTTAATATAAATTAAATGACGTTCCCTCAAAAACACACTACCCACATACATGATCTCTTTTGGCATG
TGCATATTAACAATCTGTCTGTACCATGGACAACGTTGGTTAATCATGCAACCCAATATAACCTTCCGG
AACCACACTGCCAACACCGCTCCCCCAGCCATGCATTGAAGTGAACCCTGCTGATTACAATGACAATGA
AGAACCCAATTCTCTCGACCGTGAATCACTTGAGAATGAAAAATATCTATAGTGGCACAACATAGACAT
AAATGCATGCATCTTCTCATAATTTTTAACTCCTCAGGATTTAGAAACATATCCCAGGGAATAGGAAGC
TCTTGCAGAACAGTAAAGCTGGCAGAACAAGGAAGACCACGAACACAACTTACACTATGCATAGTCATA
GTATCACAATCTGGCAACAGCGGGTGGTCTTCAGTCATAGAAGCTCGGGTTTCATTTTCCTCACAACGT
GGTAACTGGGCTCTGGTGTAAGGGTGATGTCTGGCGCATGATGTCGAGCGTGCGCGCAACCTTGTCATA

Figure 53 (continued)

ATGGAGTTGCTTCCTGACATTCTCGTATTTTGTATAGCAAAACGCGGCCCTGGCAGAACACACTCTTCT
TCGCCTTCTATCCTGCCGCTTAGCGTGTTCCGTGTGATAGTTCAAGTACAACCACACTCTTAAGTTGGT
CAAAAGAATGCTGGCTTCAGTTGTAATCAAAACTCCATCGCATCTAATCGTTCTGAGGAAATCATCCAA
GCAATGCAACTGGATTGTGTTTCAAGCAGGAGAGGAGAGGGAAGAGACGGAAGAACCATGTTAATTTTT
ATTCCAAACGATCTCGCAGTACTTCAAATTGTAGATCGCGCAGATGGCATCTCTCGCCCCCACTGTGTT
GGTGAAAAAGCACAGCTAGATCAAAAGAAATGCGATTTTCAAGGTGCTCAACGGTGGCTTCCAGCAAAG
CCTCCACGCGCACATCCAAGAACAAAAGAATACCAAAAGAAGGAGCATTTTCTAACTCCTCAATCATCA
TATTACATTCCTGCACCATTCCCAGATAATTTTCAGCTTTCCAGCCTTGAATTATTCGTGTCAGTTCTT
GTGGTAAATCCAATCCACACATTACAAACAGGTCCCGGAGGGCGCCCTCCACCACCATTCTTAAACACA
CCCTCATAATGACAAAATATCTTGCTCCTGTGTCACCTGTAGCGAATTGAGAATGGCAACATCAATTGA
CATGCCCTTGGCTCTAAGTTCTTCTTTAAGTTCTAGTTGTAAAAACTCTCTCATATTATCACCAAACTG
CTTAGCCAGAAGCCCCCCGGGAACAAGAGCAGGGGACGCTACAGTGCAGTACAAGCGCAGACCTCCCCA
ATTGGCTCCAGCAAAAACAAGATTGGAATAAGCATATTGGGAACCGCCAGTAATATCATCGAAGTTGCT
GGAAATATAATCAGGCAGAGTTTCTTGTAAAAATTGAATAAAAGAAAAATTTGCCAAAAAAACATTCAA
AACCTCTGGGATGCAAATGCAATAGGTTACCGCGCTGCGCTCCAACATTGTTAGTTTTGAATTAGTCTG
CAAAAATAAAAAAAAAAACAAGCGTCATATCATAGTAGCCTGACGAACAGATGGATAAATCAGTCTTTC
CATCACAAGACAAGCCACAGGGTCTCCAGCTCGACCCTCGTAAAACCTGTCATCATGATTAAACAACAG
CACCGAAAGTTCCTCGCGGTGACCAGCATGAATAATTCTTGATGAAGCATACAATCCAGACATGTTAGC
ATCAGTTAACGAGAAAAAACAGCCAACATAGCCTTTGGGTATAATTATGCTTAATCGTAAGTATAGCAA
AGCCACCCCTCGCGGATACAAAGTAAAAGGCACAGGAGAATAAAAAATATAATTATTTCTCTGCTGCTG
TTCAGGCAACGTCGCCCCCGGTCCCTCTAAATACACATACAAAGCCTCATCAGCCATGGCTTACCAGAC
AAAGTACAGCGGGCACACAAAGCACAAGCTCTAAAGTGACTCTCCAACCTCTCCACAATATATATATAC
ACAAGCCCTAAACTGACGTAATGGGAGTAAAGTGTAAAAAATCCCGCCAAACCCAACACACACCCCGAA
ACTGCGTCACCAGGGAAAAGTACAGTTTCACTTCCGCAATCCCAACAGGCGTAACTTCCTCTTTCTCAC
GGTACGTGATATCCCACTAACTTGCAACGTCATTTTCCCACGGTCGCACCGCCCCTTTTAGCCGTTAAC
CCCACAGCCAATCACCACACGATCCACACTTTTTAAAATCACCTCATTTACATATTGGCACCATTCCAT
CTATAAGGTATATTATATAGATAGA

SEQUENCE LISTING

```
<160> NUMBER OF SEQ ID NOS: 119

<210> SEQ ID NO 1
<211> LENGTH: 119
<212> TYPE: PRT
<213> ORGANISM: Artificial Sequence
<220> FEATURE:
<223> OTHER INFORMATION: Muromonab-CD3 (OKT3) VH

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115


<210> SEQ ID NO 2
<211> LENGTH: 107
<212> TYPE: PRT
<213> ORGANISM: Artificial Sequence
<220> FEATURE:
<223> OTHER INFORMATION: Muromonab-CD3 (OKT3) VL

<400> SEQUENCE: 2

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30
```

-continued

```
Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105


<210> SEQ ID NO 3
<211> LENGTH: 241
<212> TYPE: PRT
<213> ORGANISM: Artificial Sequence
<220> FEATURE:
<223> OTHER INFORMATION: Muromonab -CD3 (OKT3) single chain Fv

<400> SEQUENCE: 3

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Asp Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Asn
225                 230                 235                 240

Arg


<210> SEQ ID NO 4
<211> LENGTH: 322
<212> TYPE: PRT
<213> ORGANISM: Artificial Sequence
<220> FEATURE:
```

-continued

<223> OTHER INFORMATION: Membrane anchored form of the anti-human CD3
      single chain Fv

<400> SEQUENCE: 4

```
Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Gly Ser Asp Ile Val Leu Thr Gln Ser
145                 150                 155                 160

Pro Ala Ile Met Ser Ala Ser Pro Gly Glu Lys Val Thr Met Thr Cys
                165                 170                 175

Ser Ala Ser Ser Ser Val Ser Tyr Met Asn Trp Tyr Gln Gln Lys Ser
            180                 185                 190

Gly Thr Ser Pro Lys Arg Trp Ile Tyr Asp Thr Ser Lys Leu Ala Ser
        195                 200                 205

Gly Val Pro Ala His Phe Arg Gly Ser Gly Ser Gly Thr Ser Tyr Ser
    210                 215                 220

Leu Thr Ile Ser Gly Met Glu Ala Glu Asp Ala Ala Thr Tyr Tyr Cys
225                 230                 235                 240

Gln Gln Trp Ser Ser Asn Pro Phe Thr Phe Gly Ser Gly Thr Lys Leu
                245                 250                 255

Glu Ile Asn Arg Gly Ser Glu Gln Lys Leu Ile Ser Glu Glu Asp Leu
            260                 265                 270

Asn Ala Val Gly Gln Asp Thr Gln Glu Val Ile Val Val Pro His Ser
        275                 280                 285

Leu Pro Phe Lys Val Val Val Ile Ser Ala Ile Leu Ala Leu Val Val
    290                 295                 300

Leu Thr Ile Ile Ser Leu Ile Ile Leu Ile Met Leu Trp Gln Lys Lys
305                 310                 315                 320

Pro Arg
```

<210> SEQ ID NO 5
<211> LENGTH: 333
<212> TYPE: PRT
<213> ORGANISM: Artificial Sequence
<220> FEATURE:
<223> OTHER INFORMATION: Membrane anchored form of anti-human CD3 single
      chain Fv with C-terminal V5 tag

<400> SEQUENCE: 5

```
Met Gly Trp Ser Cys Ile Ile Leu Phe Leu Val Ala Thr Ala Thr Gly
1               5                   10                  15
```

```
Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Gly Ser Asp Ile Val Leu Thr Gln Ser
145                 150                 155                 160

Pro Ala Ile Met Ser Ala Ser Pro Gly Glu Lys Val Thr Met Thr Cys
                165                 170                 175

Ser Ala Ser Ser Ser Val Ser Tyr Met Asn Trp Tyr Gln Gln Lys Ser
            180                 185                 190

Gly Thr Ser Pro Lys Arg Trp Ile Tyr Asp Thr Ser Lys Leu Ala Ser
        195                 200                 205

Gly Val Pro Ala His Phe Arg Gly Ser Gly Ser Gly Thr Ser Tyr Ser
    210                 215                 220

Leu Thr Ile Ser Gly Met Glu Ala Glu Asp Ala Ala Thr Tyr Tyr Cys
225                 230                 235                 240

Gln Gln Trp Ser Ser Asn Pro Phe Thr Phe Gly Ser Gly Thr Lys Leu
                245                 250                 255

Glu Ile Asn Arg Gly Ser Glu Gln Lys Leu Ile Ser Glu Glu Asp Leu
            260                 265                 270

Asn Ala Val Gly Gln Asp Thr Gln Glu Val Ile Val Val Pro His Ser
        275                 280                 285

Leu Pro Phe Lys Val Val Val Ile Ser Ala Ile Leu Ala Leu Val Val
    290                 295                 300

Leu Thr Ile Ile Ser Leu Ile Ile Leu Ile Met Leu Trp Gln Lys Lys
305                 310                 315                 320

Pro Arg Gly Ser Ile Pro Asn Pro Leu Leu Gly Leu Asp
                325                 330
```

<210> SEQ ID NO 6
<211> LENGTH: 119
<212> TYPE: PRT
<213> ORGANISM: Artificial Sequence
<220> FEATURE:
<223> OTHER INFORMATION: Teplizumab VH sequence

<400> SEQUENCE: 6

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45
```

-continued

```
Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115


<210> SEQ ID NO 7
<211> LENGTH: 107
<212> TYPE: PRT
<213> ORGANISM: Artificial Sequence
<220> FEATURE:
<223> OTHER INFORMATION: Teplizumab VL sequence

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105


<210> SEQ ID NO 8
<211> LENGTH: 449
<212> TYPE: PRT
<213> ORGANISM: Artificial Sequence
<220> FEATURE:
<223> OTHER INFORMATION: Teplizumab Heavy chain sequence

<400> SEQUENCE: 8

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110
```

```
Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 9
<211> LENGTH: 213
<212> TYPE: PRT
<213> ORGANISM: Artificial Sequence
<220> FEATURE:
<223> OTHER INFORMATION: Teplizumab Light Chain Sequence

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30
```

-continued

```
Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 10
<211> LENGTH: 20
<212> TYPE: PRT
<213> ORGANISM: Artificial Sequence
<220> FEATURE:
<223> OTHER INFORMATION: PDGFR Receptor A

<400> SEQUENCE: 10

Ala Val Leu Val Leu Leu Val Ile Val Ile Ile Ser Leu Ile Val Leu
1               5                   10                  15

Val Val Ile Trp
            20


<210> SEQ ID NO 11
<211> LENGTH: 21
<212> TYPE: PRT
<213> ORGANISM: Artificial Sequence
<220> FEATURE:
<223> OTHER INFORMATION: PDGFR Receptor B

<400> SEQUENCE: 11

Val Val Ile Ser Ala Ile Leu Ala Leu Val Val Leu Thr Ile Ile Ser
1               5                   10                  15

Leu Ile Ile Leu Ile
            20


<210> SEQ ID NO 12
<211> LENGTH: 24
<212> TYPE: PRT
<213> ORGANISM: Artificial Sequence
<220> FEATURE:
<223> OTHER INFORMATION: Insulin-Like growth factor 1

<400> SEQUENCE: 12
```

Ile Ile Ile Gly Pro Pro Leu Ile Phe Val Phe Leu Phe Ser Val Val
1 5 10 15

Ile Gly Ser Ile Tyr Leu Phe Leu
20

<210> SEQ ID NO 13
<211> LENGTH: 28
<212> TYPE: PRT
<213> ORGANISM: Artificial Sequence
<220> FEATURE:
<223> OTHER INFORMATION: IL6-R

<400> SEQUENCE: 13

Ser Ser Ser Val Pro Leu Pro Thr Phe Leu Val Ala Gly Gly Ser Leu
1 5 10 15

Ala Phe Gly Thr Leu Leu Cys Ile Ala Ile Val Leu
20 25

<210> SEQ ID NO 14
<211> LENGTH: 27
<212> TYPE: PRT
<213> ORGANISM: Artificial Sequence
<220> FEATURE:
<223> OTHER INFORMATION: CD28

<400> SEQUENCE: 14

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 15
<211> LENGTH: 49
<212> TYPE: PRT
<213> ORGANISM: Artificial Sequence
<220> FEATURE:
<223> OTHER INFORMATION: PDGFR TM Domain

<400> SEQUENCE: 15

Ala Val Gly Gln Asp Thr Gln Glu Val Ile Val Val Pro His Ser Leu
1 5 10 15

Pro Phe Lys Val Val Val Ile Ser Ala Ile Leu Ala Leu Val Val Leu
20 25 30

Thr Ile Ile Ser Leu Ile Ile Leu Ile Met Leu Trp Gln Lys Lys Pro
35 40 45

Arg

<210> SEQ ID NO 16
<211> LENGTH: 10
<212> TYPE: PRT
<213> ORGANISM: Artificial Sequence
<220> FEATURE:
<223> OTHER INFORMATION: c-myc tag

<400> SEQUENCE: 16

Glu Gln Lys Leu Ile Ser Glu Glu Asp Leu
1 5 10

<210> SEQ ID NO 17
<211> LENGTH: 13
<212> TYPE: PRT
<213> ORGANISM: Artificial Sequence
<220> FEATURE:
<223> OTHER INFORMATION: c-myc tag with spacers

<400> SEQUENCE: 17

Gly Ser Glu Gln Lys Leu Ile Ser Glu Glu Asp Leu Asn
1 5 10

<210> SEQ ID NO 18
<211> LENGTH: 62
<212> TYPE: PRT
<213> ORGANISM: Artificial Sequence
<220> FEATURE:
<223> OTHER INFORMATION: PDGFR TM Domain with N-terminal c-myc tag

<400> SEQUENCE: 18

Gly Ser Glu Gln Lys Leu Ile Ser Glu Glu Asp Leu Asn Ala Val Gly
1 5 10 15

Gln Asp Thr Gln Glu Val Ile Val Val Pro His Ser Leu Pro Phe Lys
20 25 30

Val Val Val Ile Ser Ala Ile Leu Ala Leu Val Val Leu Thr Ile Ile
35 40 45

Ser Leu Ile Ile Leu Ile Met Leu Trp Gln Lys Lys Pro Arg
50 55 60

<210> SEQ ID NO 19
<211> LENGTH: 19
<212> TYPE: PRT
<213> ORGANISM: Artificial Sequence
<220> FEATURE:
<223> OTHER INFORMATION: HuVH human VH leader sequence

<400> SEQUENCE: 19

Met Gly Trp Ser Cys Ile Ile Leu Phe Leu Val Ala Thr Ala Thr Gly
1 5 10 15

Val His Ser

<210> SEQ ID NO 20
<211> LENGTH: 15
<212> TYPE: PRT
<213> ORGANISM: Artificial Sequence
<220> FEATURE:
<223> OTHER INFORMATION: Linker

<400> SEQUENCE: 20

Gly Gly Gly Gly Ser Gly Gly Gly Gly Ser Gly Gly Gly Gly Ser
1 5 10 15

<210> SEQ ID NO 21
<211> LENGTH: 32326
<212> TYPE: DNA
<213> ORGANISM: Artificial Sequence
<220> FEATURE:
<223> OTHER INFORMATION: EnAd Genome

<400> SEQUENCE: 21
tctatctata taatatacct tatagatgga atggtgccaa tatgtaaatg aggtgatttt 60
aaaaagtgtg gatcgtgtgg tgattggctg tggggttaac ggctaaaagg ggcggtgcga 120
ccgtgggaaa atgacgtttt gtgggggtgg agttttttg caagttgtcg cgggaaatgt 180
gacgcataaa aaggcttttt tctcacggaa ctacttagtt ttcccacggt atttaacagg 240
aaatgaggta gttttgaccg gatgcaagtg aaaattgttg attttcgcgc gaaaactgaa 300
tgaggaagtg tttttctgaa taatgtggta tttatggcag ggtggagtat ttgttcaggg 360
ccaggtagac tttgacccat tacgtggagg tttcgattac cgtgtttttt acctgaattt 420

-continued

```
ccgcgtaccg tgtcaaagtc ttctgttttt acgtaggtgt cagctgatcg ctagggtatt    480
tatacctcag ggtttgtgtc aagaggccac tcttgagtgc cagcgagaag agttttctcc    540
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agctttttga gcctcctacg cttcaggaac tgtatgattt    720
agaggtagag ggatcggagg attctaatga ggaagctgta aatggctttt ttaccgattc    780
tatgctttta gctgctaatg aagggttaga attagatccg cctttggaca cttttgatac    840
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
```

-continued tttctatgcg tgttggattg ccacagctgg cagaaccaag agtcaattgt ctctgaagaa 2820
atgcatattt caaagatgta acctgggcat tctgaatgaa ggcgaagcaa gggtccgcca 2880
ctgcgcttct acagatactg gatgttttat tttgattaag ggaaatgcca gcgtaaagca 2940
taacatgatt tgcggtgctt ccgatgagag gccttatcaa atgctcactt gtgctggtgg 3000
gcattgtaat atgctggcta ctgtgcatat tgtttcccat caacgcaaaa aatggcctgt 3060
ttttgatcac aatgtgatga cgaagtgtac catgcatgca ggtgggcgta gaggaatgtt 3120
tatgccttac cagtgtaaca tgaatcatgt gaaagtgttg ttggaaccag atgccttttc 3180
cagaatgagc ctaacaggaa tttttgacat gaacatgcaa atctggaaga tcctgaggta 3240
tgatgatacg agatcgaggg tacgcgcatg cgaatgcgga ggcaagcatg ccaggttcca 3300
gccggtgtgt gtagatgtga ctgaagatct cagaccggat catttggtta ttgcccgcac 3360
tggagcagag ttcggatcca gtggagaaga aactgactaa ggtgagtatt gggaaaactt 3420
tggggtggga ttttcagatg gacagattga gtaaaaattt gtttttctg tcttgcagct 3480 gtcatgagtg gaaacgcttc ttttaagggg ggagtcttca gcccttatct gacagggcgt 3540
ctcccatcct gggcaggagt tcgtcagaat gttatgggat ctactgtgga tggaagaccc 3600
gtccaacccg ccaattcttc aacgctgacc tatgctactt taagttcttc acctttggac 3660
gcagctgcag ctgccgccgc cgcttctgtt gccgctaaca ctgtgcttgg aatgggttac 3720
tatggaagca tcatggctaa ttccacttcc tctaataacc cttctaccct gactcaggac 3780
aagttacttg tccttttggc ccagctggag gctttgaccc aacgtctggg tgaacttttct 3840 cagcaggtgg tcgagttgcg agtacaaact gagtctgctg tcggcacggc aaagtctaaa 3900
taaaaaaatc ccagaatcaa tgaataaata aacaagcttg ttgttgattt aaaatcaagt 3960
gtttttattt catttttcgc gcacggtatg ccctagacca ccgatctcta tcattgagaa 4020
ctcggtggat tttttccagg atcctataga ggtgggattg aatgtttaga tacatgggca 4080
ttaggccgtc tttggggtgg agatagctcc attgaaggga ttcatgctcc ggggtagtgt 4140
tgtaaatcac ccagtcataa caaggtcgca gtgcatggtg ttgcacaata tcttttagaa 4200
gtaggctgat tgccacagat aagcccttgg tgtaggtgtt tacaaaccgg ttgagctggg 4260
atgggtgcat tcggggtgaa attatgtgca ttttggattg gatttttaag ttggcaatat 4320
tgccgccaag atcccgtctt gggttcatgt tatgaaggac caccaagacg gtgtatccgg 4380
tacatttagg aaatttatcg tgcagcttgg atggaaaagc gtggaaaaat ttggagacac 4440
ccttgtgtcc tccaagattt tccatgcact catccatgat aatagcaatg gggccgtggg 4500
cagcggcgcg ggcaaacacg ttccgtgggt ctgacacatc atagttatgt tcctgagtta 4560
aatcatcata agccatttta atgaatttgg ggcggagagt accagattgg ggtatgaatg 4620
ttccttcggg ccccggagca tagttcccct cacagatttg catttcccaa gctttcagtt 4680
ccgagggtgg aatcatgtcc acctgggggg ctatgaaaaa caccgtttct ggggcggggg 4740
tgattaattg tgatgatagc aaatttctga gcaattgaga tttgccacat ccggtggggc 4800
cataaatgat tccgattacg ggttgcaggt ggtagtttag ggaacggcaa ctgccgtctt 4860
ctcgaagcaa gggggccacc tcgttcatca tttcccttac atgcatattt tcccgcacca 4920
aatccattag gaggcgctct cctcctagtg atagaagttc ttgtagtgag gaaaagtttt 4980
tcagcggttt cagaccgtca gccatgggca ttttggagag agtttgctgc aaaagttcta 5040
gtctgttcca cagttcagtg atgtgttcta tggcatctcg atccagcaga cctcctcgtt 5100
tcgcgggttt ggacggctcc tggaataggg tatgagacga tgggcgtcca gcgctgccag 5160
ggttcggtcc ttccagggtc tcagtgttcg agtcagggtt gtttccgtca cagtgaaggg 5220
gtgtgcgcct gcttgggcgc ttgccagggt gcgcttcaga ctcatcctgc tggtcgaaaa 5280
cttctgtcgc ttggcgccct gtatgtcggc caagtagcag tttaccatga gttcgtagtt 5340
gagcgcctcg gctgcgtggc ctttggcgcg gagcttacct ttggaagttt tcttgcatac 5400
cgggcagtat aggcatttca gcgcatacaa cttgggcgca aggaaaacgg attctgggga 5460
gtatgcatct gcgccgcagg aggcgcaaac agtttcacat tccaccagcc aggttaaatc 5520
cggttcattg gggtcaaaaa caagttttcc gccatatttt ttgatgcgtt tcttaccttt 5580
ggtctccatg agttcgtgtc ctcgttgagt gacaaacagg ctgtccgtgt ccccgtagac 5640
tgattttaca ggcctcttct ccagtggagt gcctcggtct tcttcgtaca ggaactctga 5700
ccactctgat acaaaggcgc gcgtccaggc cagcacaaag gaggctatgt gggaggggta 5760
gcgatcgttg tcaaccaggg ggtccacctt ttccaaagta tgcaaacaca tgtcaccctc 5820
ttcaacatcc aggaatgtga ttggcttgta ggtgtatttc acgtgacctg gggtccccgc 5880
tggggggggta taaaaggggg cggttctttg ctcttcctca ctgtcttccg gatcgctgtc 5940
caggaacgtc agctgttggg gtaggtattc cctctcgaag gcgggcatga cctctgcact 6000
caggttgtca gtttctaaga acgaggagga tttgatattg acagtgccgg ttgagatgcc 6060
tttcatgagg ttttcgtcca tctggtcaga aaacacaatt tttttattgt caagtttggt 6120
ggcaaatgat ccatacaggg cgttggataa aagtttggca atggatcgca tggtttggtt 6180
cttttccttg tccgcgcgct ctttggcggc gatgttgagt tggacatact cgcgtgccag 6240
gcacttccat tcggggaaga tagttgttaa ttcatctggc acgattctca cttgccaccc 6300
tcgattatgc aaggtaatta aatccacact ggtggccacc tcgcctcgaa ggggttcatt 6360
ggtccaacag agcctacctc ctttcctaga acagaaaggg ggaagtgggt ctagcataag 6420
ttcatcggga gggtctgcat ccatggtaaa gattcccgga agtaaatcct tatcaaaata 6480
gctgatggga gtggggtcat ctaaggccat ttgccattct cgagctgcca gtgcgcgctc 6540
atatgggtta aggggactgc cccatggcat gggatgggtg agtgcagagg catacatgcc 6600
acagatgtca tagacgtaga tgggatcctc aaagatgcct atgtaggttg gatagcatcg 6660
ccccccctctg atacttgctc gcacatagtc atatagttca tgtgatggcg ctagcagccc 6720
cggacccaag ttggtgcgat tgggtttttc tgttctgtag acgatctggc gaaagatggc 6780
gtgagaattg gaagagatgg tgggtctttg aaaaatgttg aaatgggcat gaggtagacc 6840
tacagagtct ctgacaaagt gggcataaga ttcttgaagc ttggttacca gttcggcggt 6900
gacaagtacg tctagggcgc agtagtcaag tgtttcttga atgatgtcat aacctggttg 6960
gtttttcttt tcccacagtt cgcggttgag aaggtattct tcgcgatcct tccagtactc 7020
ttctagcgga aacccgtctt tgtctgcacg gtaagatcct agcatgtaga actgattaac 7080
tgccttgtaa gggcagcagc ccttctctac gggtagagag tatgcttgag cagcttttcg 7140
tagcgaagcg tgagtaaggg caaaggtgtc tctgaccatg actttgagga attggtattt 7200
gaagtcgatg tcgtcacagg ctccctgttc ccagagttgg aagtctaccc gtttcttgta 7260
ggcggggttg ggcaaagcga aagtaacatc attgaagaga atcttgccgg ccctgggcat 7320
gaaattgcga gtgatgcgaa aaggctgtgg tacttccgct cggttattga taacctgggc 7380
agctaggacg atctcgtcga aaccgttgat gttgtgtcct acgatgtata attctatgaa 7440
acgcggcgtg cctctgacgt gaggtagctt actgagctca tcaaaggtta ggtctgtggg 7500

-continued

```
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
```

```
tgtaccagtg ccaagtcagc tacgactctt tcggcgagga tggcttgctg tacttgggta    9960
agggtggctt gaaagtcatc aaaatccaca aagcggtggt aagctcctgt attaatggtg   10020
taagcacagt tggccatgac tgaccagtta actgtctggt gaccagggcg cacgagctcg   10080
gtgtatttaa ggcgcgaata ggcgcgggtg tcaaagatgt aatcgttgca ggtgcgcacc   10140
agatactggt accctataag aaaatgcggc ggtggttggc ggtagagagg ccatcgttct   10200
gtagctggag cgccaggggc gaggtcttcc aacataaggc ggtgatagcc gtagatgtac   10260
ctggacatcc aggtgattcc tgcggcggta gtagaagccc gaggaaactc gcgtacgcgg   10320
ttccaaatgt tgcgtagcgg catgaagtag ttcattgtag gcacggtttg accagtgagg   10380
cgcgcgcagt cattgatgct ctatagacac ggagaaaatg aaagcgttca gcgactcgac   10440
tccgtagcct ggaggaacgt gaacgggttg ggtcgcggtg taccccggtt cgagacttgt   10500
actcgagccg gccggagccg cggctaacgt ggtattggca ctcccgtctc gacccagcct   10560
acaaaaatcc aggatacgga atcgagtcgt tttgctggtt tccgaatggc agggaagtga   10620
gtcctatttt tttttttgc cgctcagatg catcccgtgc tgcgacagat gcgcccccaa   10680
caacagcccc cctcgcagca gcagcagcag caatcacaaa aggctgtccc tgcaactact   10740
gcaactgccg ccgtgagcgg tgcgggacag cccgcctatg atctggactt ggaagagggc   10800
gaaggactgg cacgtctagg tgcgccttca cccgagcggc atccgcgagt tcaactgaaa   10860
aaagattctc gcgaggcgta tgtgccccaa cagaacctat ttagagacag aagcggcgag   10920
gagccggagg agatgcgagc ttcccgcttt aacgcgggtc gtgagctgcg tcacggtttg   10980
gaccgaagac gagtgttgcg ggacgaggat ttcgaagttg atgaaatgac agggatcagt   11040
cctgccaggg cacacgtggc tgcagccaac cttgtatcgg cttacgagca gacagtaaag   11100
gaagagcgta acttccaaaa gtcttttaat aatcatgtgc gaaccctgat tgcccgcgaa   11160
gaagttaccc ttggtttgat gcatttgtgg gatttgatgg aagctatcat tcagaaccct   11220
actagcaaac ctctgaccgc ccagctgttt ctggtggtgc aacacagcag agacaatgag   11280
gctttcagag aggcgctgct gaacatcacc gaacccgagg ggagatggtt gtatgatctt   11340
atcaacattc tacagagtat catagtgcag gagcggagcc tgggcctggc cgagaaggtg   11400
gctgccatca attactcggt tttgagcttg ggaaaatatt acgctcgcaa aatctacaag   11460
actccatacg ttcccataga caaggaggtg aagatagatg ggttctacat gcgcatgacg   11520
ctcaaggtct tgaccctgag cgatgatctt ggggtgtatc gcaatgacag aatgcatcgc   11580
gcggttagcg ccagcaggag gcgcgagtta agcgacaggg aactgatgca cagtttgcaa   11640
agagctctga ctggagctgg aaccgagggt gagaattact tcgacatggg agctgacttg   11700
cagtggcagc ctagtcgcag ggctctgagc gccgcgacgg caggatgtga gcttccttac   11760
atagaagagg cggatgaagg cgaggaggaa gagggcgagt acttggaaga ctgatggcac   11820
aacccgtgtt ttttgctaga tggaacagca agcaccggat cccgcaatgc gggcggcgct   11880
gcagagccag ccgtccggca ttaactcctc ggacgattgg acccaggcca tgcaacgtat   11940
catggcgttg acgactcgca accccgaagc ctttagacag caaccccagg ccaaccgtct   12000
atcggccatc atggaagctg tagtgccttc ccgctctaat cccactcatg agaaggtcct   12060
ggccatcgtg aacgcgttgg tggagaacaa agctattcgt ccagatgagg ccggactggt   12120
atacaacgct ctcttagaac gcgtggctcg ctacaacagt agcaatgtgc aaaccaattt   12180
ggaccgtatg ataacagatg tacgcgaagc cgtgtctcag cgcgaaaggt tccagcgtga   12240
```

-continued

```
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgccccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
```

cagaagctaa ggcaaacata gttgccagcg actctacaag ggttgctaac gctggagagg 14700
tcagaggaga caattttgcg ccaacacctg ttccgactgc agaatcatta ttggccgatg 14760
tgtctgaagg aacggacgtg aaactcacta ttcaacctgt agaaaaagat agtaagaata 14820
gaagctataa tgtgttggaa gacaaaatca acacagccta tcgcagttgg tatctttcgt 14880
acaattatgg cgatcccgaa aaaggagtgc gttcctggac attgctcacc acctcagatg 14940
tcacctgcgg agcagagcag gtctactggt cgcttccaga catgatgaag gatcctgtca 15000
ctttccgctc cactagacaa gtcagtaact accctgtggt gggtgcagag cttatgcccg 15060
tcttctcaaa gagcttctac aacgaacaag ctgtgtactc ccagcagctc cgccagtcca 15120
cctcgcttac gcacgtcttc aaccgctttc ctgagaacca gattttaatc cgtccgccgg 15180
cgcccaccat taccaccgtc agtgaaaacg ttcctgctct cacagatcac gggaccctgc 15240
cgttgcgcag cagtatccgg ggagtccaac gtgtgaccgt tactgacgcc agacgccgca 15300
cctgtcccta cgtgtacaag gcactgggca tagtcgcacc gcgcgtcctt tcaagccgca 15360
ctttctaaaa aaaaaaaaaa tgtccattct tatctcgccc agtaataaca ccggttgggg 15420
tctgcgcgct ccaagcaaga tgtacggagg cgcacgcaaa cgttctaccc aacatcctgt 15480
ccgtgttcgc ggacattttc gcgctccatg gggcgccctc aagggccgca ctcgcgttcg 15540
aaccaccgtc gatgatgtaa tcgatcaggt ggttgccgac gcccgtaatt atactcctac 15600
tgcgcctaca tctactgtgg atgcagttat tgacagtgta gtggctgacg ctcgcaacta 15660
tgctcgacgt aagagccggc gaaggcgcat tgccagacgc caccgagcta ccactgccat 15720
gcgagccgca agagctctgc tacgaagagc tagacgcgtg ggcgcgaagag ccatgcttag 15780 ggcggccaga cgtgcagctt cgggcgccag cgccggcagg tcccgcaggc aagcagccgc 15840
tgtcgcagcg gcgactattg ccgacatggc ccaatcgcga agaggcaatg tatactgggt 15900
gcgtgacgct gccaccggtc aacgtgtacc cgtgcgcacc cgtccccctc gcacttagaa 15960
gatactgagc agtctccgat gttgtgtccc agcggcgagg atgtccaagc gcaaatacaa 16020
ggaagaaatg ctgcaggtta tcgcacctga agtctacggc caaccgttga aggatgaaaa 16080
aaaaccccgc aaaatcaagc gggttaaaaa ggacaaaaaa gaagaggaag atggcgatga 16140
tgggctggcg gagtttgtgc gcgagtttgc cccacggcga cgcgtgcaat ggcgtgggcg 16200
caaagttcga catgtgttga gacctggaac ttcggtggtc tttacacccg gcgagcgttc 16260
aagcgctact tttaagcgtt cctatgatga ggtgtacggg gatgatgata ttcttgagca 16320
ggcggctgac cgattaggcg agtttgctta tggcaagcgt agtagaataa cttccaagga 16380
tgagacagtg tcgataccct tggatcatgg aaatcccacc cctagtctta aaccggtcac 16440
tttgcagcaa gtgttacccg taactccgcg aacaggtgtt aaacgcgaag gtgaagattt 16500
gtatcccact atgcaactga tggtacccaa acgccagaag ttggaggacg ttttggagaa 16560
agtaaaagtg gatccagata ttcaacctga ggttaaagtg agacccatta agcaggtagc 16620
gcctggtctg ggggtacaaa ctgtagacat taagattccc actgaaagta tggaagtgca 16680
aactgaaccc gcaaagccta ctgccacctc cactgaagtg caaacggatc catggatgcc 16740
catgcctatt acaactgacg ccgccggtcc cactcgaaga tcccgacgaa agtacggtcc 16800
agcaagtctg ttgatgccca attatgttgt acacccatct attattccta ctcctggtta 16860
ccgaggcact cgctactatc gcagccgaaa cagtacctcc cgccgtcgcc gcaagacacc 16920
tgcaaatcgc agtcgtcgcc gtagacgcac aagcaaaccg actcccggcg ccctggtgcg 16980
gcaagtgtac cgcaatggta gtgcggaacc tttgacactg ccgcgtgcgc gttaccatcc 17040
gagtatcatc acttaatcaa tgttgccgct gcctccttgc agatatggcc ctcacttgtc 17100
gccttcgcgt tcccatcact ggttaccgag gaagaaactc gcgccgtaga agagggatgt 17160
tgggacgcgg aatgcgacgc tacaggcgac ggcgtgctat ccgcaagcaa ttgcggggtg 17220
gtttttttacc agccttaatt ccaattatcg ctgctgcaat tggcgcgata ccaggcatag 17280
cttccgtggc ggttcaggcc tcgcaacgac attgacattg gaaaaaaacg tataaataaa 17340
aaaaaaaaaa tacaatggac tctgacactc ctggtcctgt gactatgttt tcttagagat 17400
ggaagacatc aatttttcat ccttggctcc gcgacacggc acgaagccgt acatgggcac 17460
ctggagcgac atcggcacga gccaactgaa cgggggcgcc ttcaattgga gcagtatctg 17520
gagcgggctt aaaaattttg gctcaaccat aaaaacatac gggaacaaag cttggaacag 17580
cagtacagga caggcgctta gaaataaact taaagaccag aacttccaac aaaaagtagt 17640
cgatgggata gcttccggca tcaatggagt ggtagatttg gctaaccagg ctgtgcagaa 17700
aaagataaac agtcgtttgg acccgccgcc agcaacccca ggtgaaatgc aagtggagga 17760
agaaattcct ccgccagaaa aacgaggcga caagcgtccg cgtcccgatt tggaagagac 17820
gctggtgacg cgcgtagatg aaccgccttc ttatgaggaa gcaacgaagc ttggaatgcc 17880
caccactaga ccgatagccc caatggccac cggggtgatg aaaccttctc agttgcatcg 17940
acccgtcacc ttggatttgc cccctccccc tgctgctact gctgtacccg cttctaagcc 18000
tgtcgctgcc ccgaaaccag tcgccgtagc caggtcacgt cccgggggcg ctcctcgtcc 18060
aaatgcgcac tggcaaaata ctctgaacag catcgtgggt ctaggcgtgc aaagtgtaaa 18120
acgccgtcgc tgcttttaat taaatatgga gtagcgctta acttgcctat ctgtgtatat 18180
gtgtcattac acgccgtcac agcagcagag gaaaaaagga agaggtcgtg cgtcgacgct 18240
gagttacttt caagatggcc accccatcga tgctgcccca atgggcatac atgcacatcg 18300
ccggacagga tgcttcggag tacctgagtc cgggtctggt gcagttcgcc cgcgccacag 18360
acacctactt caatctggga aataagttta gaaatcccac cgtagcgccg acccacgatg 18420
tgaccaccga ccgtagccag cggctcatgt tgcgcttcgt gcccgttgac cgggaggaca 18480
atacatactc ttacaaagtg cggtacaccc tggccgtggg cgacaacaga gtgctggata 18540
tggccagcac gttctttgac attaggggtg tgttggacag aggtcccagt ttcaaaccct 18600
attctggtac ggcttacaac tccctggctc ctaaaggcgc tccaaataca tctcagtgga 18660
ttgcagaagg tgtaaaaaat acaactggtg aggaacacgt aacagaagag gaaaccaata 18720
ctactactta cacttttggc aatgctcctg taaaagctga agctgaaatt acaaaagaag 18780
gactcccagt aggtttggaa gtttcagatg aagaaagtaa accgatttat gctgataaaa 18840
catatcagcc agaacctcag ctgggagatg aaacttggac tgaccttgat ggaaaaaccg 18900
aaaagtatgg aggcagggct ctcaaacccg atactaagat gaaaccatgc tacgggtcct 18960
ttgccaaacc tactaatgtg aaaggcggtc aggcaaaaca aaaaacaacg gagcagccaa 19020
atcagaaagt cgaatatgat atcgacatgg agttttttga tgcggcatcg cagaaaacaa 19080
acttaagtcc taaaattgtc atgtatgcag aaaatgtaaa tttggaaact ccagacactc 19140
atgtagtgta caaacctgga acagaagaca caagttccga agctaatttg ggacaacaat 19200
ctatgcccaa cagacccaac tacattggct tcagagataa ctttattgga cttatgtact 19260
ataacagtac tggtaacatg gggtgctgg ctggtcaagc gtctcagtta aatgcagtgg 19320
ttgacttgca ggacagaaac acagaacttt cttaccaact cttgcttgac tctctgggcg 19380

-continued acagaaccag atactttagc atgtggaatc aggctgtgga cagttatgat cctgatgtac 19440
gtgttattga aaatcatggt gtggaagatg aacttcccaa ctactgtttt ccactggacg 19500
gcataggtgt tccaacaacc agttacaaat caatagttcc aaatggagac aatgcgccta 19560
attggaagga acctgaagta aatggaacaa gtgagatcgg acagggtaat ttgtttgcca 19620
tggaaattaa ccttcaagcc aatctatggc gaagtttcct ttattccaat gtggctctat 19680
atctcccaga ctcgtacaaa tacaccccgt ccaatgtcac tcttccagaa aacaaaaaca 19740
cctacgacta catgaacggg cgggtggtgc cgccatctct agtagacacc tatgtgaaca 19800
ttggtgccag gtggtctctg gatgccatgg acaatgtcaa cccattcaac caccaccgta 19860
acgctggctt gcgttaccga tccatgcttc tgggtaacgg acgttatgtg cctttccaca 19920
tacaagtgcc tcaaaaattc ttcgctgtta aaaacctgct gcttctccca ggctcctaca 19980
cttatgagtg gaactttagg aaggatgtga acatggttct acagagttcc ctcggtaacg 20040
acctgcgggt agatggcgcc agcatcagtt tcacgagcat caacctctat gctacttttt 20100
tccccatggc tcacaacacc gcttccaccc ttgaagccat gctgcggaat gacaccaatg 20160
atcagtcatt caacgactac ctatctgcag ctaacatgct ctaccccatt cctgccaatg 20220
caaccaatat tcccatttcc attccttctc gcaactgggc ggctttcaga ggctggtcat 20280
ttaccagact gaaaaccaaa gaaactccct ctttggggtc tggatttgac ccctactttg 20340
tctattctgg ttctattccc tacctggatg gtaccttcta cctgaaccac acttttaaga 20400
aggtttccat catgtttgac tcttcagtga gctggcctgg aaatgacagg ttactatctc 20460
ctaacgaatt tgaaataaag cgcactgtgg atggcgaagg ctacaacgta gcccaatgca 20520
acatgaccaa agactggttc ttggtacaga tgctcgccaa ctacaacatc ggctatcagg 20580
gcttctacat tccagaagga tacaaagatc gcatgtattc atttttcaga aacttccagc 20640
ccatgagcag gcaggtggtt gatgaggtca attacaaaga cttcaaggcc gtcgccatac 20700
cctaccaaca caacaactct ggctttgtgg gttacatggc tccgaccatg cgccaaggtc 20760
aaccctatcc cgctaactat ccctatccac tcattggaac aactgccgta aatagtgtta 20820
cgcagaaaaa gttcttgtgt gacagaacca tgtggcgcat accgttctcg agcaacttca 20880
tgtctatggg ggcccttaca gacttgggac agaatatgct ctatgccaac tcagctcatg 20940
ctctggacat gacctttgag gtggatccca tggatgagcc caccctgctt tatcttctct 21000
tcgaagtttt cgacgtggtc agagtgcatc agccacaccg cggcatcatc gaggcagtct 21060
acctgcgtac accgttctcg gccggtaacg ctaccacgta agaagcttct tgcttcttgc 21120
aaatagcagc tgcaaccatg gcctgcggat cccaaaacgg ctccagcgag caagagctca 21180
gagccattgt ccaagacctg ggttgcggac cctatttttt gggaacctac gataagcgct 21240
tcccggggtt catggccccc gataagctcg cctgtgccat tgtaaatacg gccggacgtg 21300
agacgggggg agagcactgg ttggctttcg gttggaaccc acgttctaac acctgctacc 21360
tttttgatcc ttttggattc tcggatgatc gtctcaaaca gatttaccag tttgaatatg 21420
agggtctcct gcgccgcagc gctcttgcta ccaaggaccg ctgtattacg ctggaaaaat 21480
ctacccagac cgtgcagggt ccccgttctg ccgcctgcgg acttttctgc tgcatgttcc 21540
ttcacgcctt tgtgcactgg cctgaccgtc ccatggacgg aaaccccacc atgaaattgc 21600
taactggagt gccaaacaac atgcttcatt ctcctaaagt ccagcccacc ctgtgtgaca 21660
atcaaaaagc actctaccat tttcttaata cccattcgcc ttattttcgc tcccatcgta 21720
cacacatcga aagggccact gcgttcgacc gtatggatgt tcaataatga ctcatgtaaa 21780
caacgtgttc aataaacatc actttatttt tttacatgta tcaaggctct gcattactta 21840
tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120

-continued cttccttgga agaggttcca aagatcttcg agggtctggg caataatgag actcgggccg 24180
caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg ccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac caccccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460

-continued

```
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
ccccttata aacccagggt ttatttcccc aaatggcttc acacaaagcc caaacggagt  28500
tcttacttta aaatgtttaa ccccactaac aaccacaggc ggatctctac agctaaaagt  28560
gggagggga cttacagtgg atgacaccaa cggtttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
```

-continued

```
tggagcacta gtcactgcat ttgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttaact tgtttatttg aaaatcaatt cacaaaatcc gagtagttat  29400
tttgcctccc ccttcccatt taacagaata caccaatctc tccccacgca cagctttaaa  29460
catttggata ccattagata tagacatggt tttagattcc acattccaaa cagtttcaga  29520
gcgagccaat ctggggtcag tgatagataa aaatccatcg ggatagtctt ttaaagcgct  29580
ttcacagtcc aactgctgcg gatgcgactc cggagtctgg atcacggtca tctggaagaa  29640
gaacgatggg aatcataatc cgaaaacggt atcggacgat tgtgtctcat caaacccaca  29700
agcagccgct gtctgcgtcg ctccgtgcga ctgctgttta tgggatcagg gtccacagtg  29760
tcctgaagca tgattttaat agcccttaac atcaactttc tggtgcgatg cgcgcagcaa  29820
cgcattctga tttcactcaa atctttgcag taggtacaac acattattac aatattgttt  29880
aataaaccat aattaaaagc gctccagcca aaactcatat ctgatataat cgcccctgca  29940
tgaccatcat accaaagttt aatataaatt aaatgacgtt ccctcaaaaa cacactaccc  30000
acatacatga tctcttttgg catgtgcata ttaacaatct gtctgtacca tggacaacgt  30060
tggttaatca tgcaacccaa tataaccttc cggaaccaca ctgccaacac cgctccccca  30120
gccatgcatt gaagtgaacc ctgctgatta caatgacaat gaagaaccca attctctcga  30180
ccgtgaatca cttgagaatg aaaaatatct atagtggcac aacatagaca taaatgcatg  30240
catcttctca taatttttaa ctcctcagga tttagaaaca tatcccaggg aataggaagc  30300
tcttgcagaa cagtaaagct ggcagaacaa ggaagaccac gaacacaact tacactatgc  30360
atagtcatag tatcacaatc tggcaacagc gggtggtctt cagtcataga agctcgggtt  30420
tcattttcct cacaacgtgg taactgggct ctggtgtaag ggtgatgtct ggcgcatgat  30480
gtcgagcgtg cgcgcaacct tgtcataatg gagttgcttc ctgacattct cgtattttgt  30540
atagcaaaac gcggccctgg cagaacacac tcttcttcgc cttctatcct gccgcttagc  30600
gtgttccgtg tgatagttca agtacaacca cactcttaag ttggtcaaaa gaatgctggc  30660
ttcagttgta atcaaaactc catcgcatct aatcgttctg aggaaatcat ccaagcaatg  30720
caactggatt gtgtttcaag caggagagga gagggaagag acggaagaac catgttaatt  30780
tttattccaa acgatctcgc agtacttcaa attgtagatc gcgcagatgg catctctcgc  30840
ccccactgtg ttggtgaaaa agcacagcta gatcaaaaga aatgcgattt tcaaggtgct  30900
caacggtggc ttccagcaaa gcctccacgc gcacatccaa gaacaaaaga ataccaaaag  30960
aaggagcatt ttctaactcc tcaatcatca tattacattc ctgcaccatt cccagataat  31020
tttcagcttt ccagccttga attattcgtg tcagttcttg tggtaaatcc aatccacaca  31080
ttacaaacag gtcccggagg gcgccctcca ccaccattct taaacacacc ctcataatga  31140
caaaatatct tgctcctgtg tcacctgtag cgaattgaga atggcaacat caattgacat  31200
```

-continued

```
gcccttggct ctaagttctt ctttaagttc tagttgtaaa aactctctca tattatcacc  31260
aaactgctta gccagaagcc ccccgggaac aagagcaggg gacgctacag tgcagtacaa  31320
gcgcagacct ccccaattgg ctccagcaaa aacaagattg gaataagcat attgggaacc  31380
gccagtaata tcatcgaagt tgctggaaat ataatcaggc agagtttctt gtaaaaattg  31440
aataaaagaa aaatttgcca aaaaaacatt caaaacctct gggatgcaaa tgcaataggt  31500
taccgcgctg cgctccaaca ttgttagttt tgaattagtc tgcaaaaata aaaaaaaaaa  31560
caagcgtcat atcatagtag cctgacgaac agatggataa atcagtcttt ccatcacaag  31620
acaagccaca gggtctccag ctcgaccctc gtaaaacctg tcatcatgat taaacaacag  31680
caccgaaagt tcctcgcggt gaccagcatg aataattctt gatgaagcat acaatccaga  31740
catgttagca tcagttaacg agaaaaaaca gccaacatag cctttgggta taattatgct  31800
taatcgtaag tatagcaaag ccacccctcg cggatacaaa gtaaaaggca caggagaata  31860
aaaaatataa ttatttctct gctgctgttc aggcaacgtc gcccccggtc cctctaaata  31920
cacatacaaa gcctcatcag ccatggctta ccagacaaag tacagcgggc acacaaagca  31980
caagctctaa agtgactctc caacctctcc acaatatata tatacacaag ccctaaactg  32040
acgtaatggg agtaaagtgt aaaaaatccc gccaaaccca acacacaccc cgaaactgcg  32100
tcaccaggga aaagtacagt ttcacttccg caatcccaac aggcgtaact tcctctttct  32160
cacggtacgt gatatcccac taacttgcaa cgtcattttc ccacggtcgc accgcccctt  32220
ttagccgtta accccacagc caatcaccac acgatccaca ctttttaaaa tcacctcatt  32280
tacatattgg caccattcca tctataaggt atattatata gataga                 32326
```

```
<210> SEQ ID NO 22
<211> LENGTH: 8
<212> TYPE: PRT
<213> ORGANISM: Artificial Sequence
<220> FEATURE:
<223> OTHER INFORMATION: hinge linker sequence

<400> SEQUENCE: 22

Asp Lys Thr His Thr Cys Ala Ala
1               5


<210> SEQ ID NO 23
<211> LENGTH: 11
<212> TYPE: PRT
<213> ORGANISM: Artificial Sequence
<220> FEATURE:
<223> OTHER INFORMATION: hinge linker sequence

<400> SEQUENCE: 23

Asp Lys Thr His Thr Cys Pro Pro Cys Pro Ala
1               5                   10


<210> SEQ ID NO 24
<211> LENGTH: 18
<212> TYPE: PRT
<213> ORGANISM: Artificial Sequence
<220> FEATURE:
<223> OTHER INFORMATION: hinge linker sequence

<400> SEQUENCE: 24

Asp Lys Thr His Thr Cys Pro Pro Cys Pro Ala Thr Cys Pro Pro Cys
1               5                   10                  15

Pro Ala
```

<210> SEQ ID NO 25
<211> LENGTH: 25
<212> TYPE: PRT
<213> ORGANISM: Artificial Sequence
<220> FEATURE:
<223> OTHER INFORMATION: hinge linker sequence

<400> SEQUENCE: 25

```
Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25
```

<210> SEQ ID NO 26
<211> LENGTH: 30
<212> TYPE: PRT
<213> ORGANISM: Artificial Sequence
<220> FEATURE:
<223> OTHER INFORMATION: hinge linker sequence

<400> SEQUENCE: 26

```
Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30
```

<210> SEQ ID NO 27
<211> LENGTH: 31
<212> TYPE: PRT
<213> ORGANISM: Artificial Sequence
<220> FEATURE:
<223> OTHER INFORMATION: hinge linker sequence

<400> SEQUENCE: 27

```
Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30
```

<210> SEQ ID NO 28
<211> LENGTH: 15
<212> TYPE: PRT
<213> ORGANISM: Artificial Sequence
<220> FEATURE:
<223> OTHER INFORMATION: hinge linker sequence

<400> SEQUENCE: 28

```
Asp Lys Thr His Thr Cys Cys Val Glu Cys Pro Pro Cys Pro Ala
1               5                   10                  15
```

<210> SEQ ID NO 29
<211> LENGTH: 26
<212> TYPE: PRT
<213> ORGANISM: Artificial Sequence
<220> FEATURE:
<223> OTHER INFORMATION: hinge linker sequence

<400> SEQUENCE: 29

```
Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25
```

<210> SEQ ID NO 30

<211> LENGTH: 11
<212> TYPE: PRT
<213> ORGANISM: Artificial Sequence
<220> FEATURE:
<223> OTHER INFORMATION: hinge linker sequence

<400> SEQUENCE: 30

Asp Lys Thr His Thr Cys Pro Ser Cys Pro Ala
1 5 10

<210> SEQ ID NO 31
<211> LENGTH: 7
<212> TYPE: PRT
<213> ORGANISM: Artificial Sequence
<220> FEATURE:
<223> OTHER INFORMATION: flexible linker sequence

<400> SEQUENCE: 31

Ser Gly Gly Gly Gly Ser Glu
1 5

<210> SEQ ID NO 32
<211> LENGTH: 6
<212> TYPE: PRT
<213> ORGANISM: Artificial Sequence
<220> FEATURE:
<223> OTHER INFORMATION: flexible linker sequence

<400> SEQUENCE: 32

Asp Lys Thr His Thr Ser
1 5

<210> SEQ ID NO 33
<211> LENGTH: 6
<212> TYPE: PRT
<213> ORGANISM: Artificial Sequence
<220> FEATURE:
<223> OTHER INFORMATION: flexible linker sequence
<220> FEATURE:
<221> NAME/KEY: misc_feature
<222> LOCATION: (1)..(1)
<223> OTHER INFORMATION: Xaa is absent or S

<400> SEQUENCE: 33

Xaa Gly Gly Gly Gly Ser
1 5

<210> SEQ ID NO 34
<211> LENGTH: 11
<212> TYPE: PRT
<213> ORGANISM: Artificial Sequence
<220> FEATURE:
<223> OTHER INFORMATION: flexible linker sequence
<220> FEATURE:
<221> NAME/KEY: misc_feature
<222> LOCATION: (1)..(1)
<223> OTHER INFORMATION: Xaa is absent or S

<400> SEQUENCE: 34

Xaa Gly Gly Gly Gly Ser Gly Gly Gly Gly Ser
1 5 10

<210> SEQ ID NO 35
<211> LENGTH: 16
<212> TYPE: PRT
<213> ORGANISM: Artificial Sequence
<220> FEATURE:
<223> OTHER INFORMATION: flexible linker sequence
<220> FEATURE:

<221> NAME/KEY: misc_feature
<222> LOCATION: (1)..(1)
<223> OTHER INFORMATION: Xaa is absent or S

<400> SEQUENCE: 35

```
Xaa Gly Gly Gly Gly Ser Gly Gly Gly Gly Ser Gly Gly Gly Gly Ser
1               5                   10                  15
```

<210> SEQ ID NO 36
<211> LENGTH: 21
<212> TYPE: PRT
<213> ORGANISM: Artificial Sequence
<220> FEATURE:
<223> OTHER INFORMATION: flexible linker sequence
<220> FEATURE:
<221> NAME/KEY: misc_feature
<222> LOCATION: (1)..(1)
<223> OTHER INFORMATION: Xaa is absent or S

<400> SEQUENCE: 36

```
Xaa Gly Gly Gly Gly Ser Gly Gly Gly Gly Ser Gly Gly Gly Gly Ser
1               5                   10                  15

Gly Gly Gly Gly Ser
            20
```

<210> SEQ ID NO 37
<211> LENGTH: 26
<212> TYPE: PRT
<213> ORGANISM: Artificial Sequence
<220> FEATURE:
<223> OTHER INFORMATION: flexible linker sequence
<220> FEATURE:
<221> NAME/KEY: misc_feature
<222> LOCATION: (1)..(1)
<223> OTHER INFORMATION: Xaa is absent or S

<400> SEQUENCE: 37

```
Xaa Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25
```

<210> SEQ ID NO 38
<211> LENGTH: 11
<212> TYPE: PRT
<213> ORGANISM: Artificial Sequence
<220> FEATURE:
<223> OTHER INFORMATION: flexible linker sequence

<400> SEQUENCE: 38

```
Ala Ala Ala Gly Ser Gly Gly Ala Ser Ala Ser
1               5                   10
```

<210> SEQ ID NO 39
<211> LENGTH: 16
<212> TYPE: PRT
<213> ORGANISM: Artificial Sequence
<220> FEATURE:
<223> OTHER INFORMATION: flexible linker sequence
<220> FEATURE:
<221> NAME/KEY: misc_feature
<222> LOCATION: (7)..(7)
<223> OTHER INFORMATION: X represents an amino acid

<400> SEQUENCE: 39

```
Ala Ala Ala Gly Ser Gly Xaa Gly Gly Gly Ser Gly Ala Ser Ala Ser
1               5                   10                  15
```

<210> SEQ ID NO 40
<211> LENGTH: 21
<212> TYPE: PRT
<213> ORGANISM: Artificial Sequence
<220> FEATURE:
<223> OTHER INFORMATION: flexible linker sequence
<220> FEATURE:
<221> NAME/KEY: misc_feature
<222> LOCATION: (7)..(7)
<223> OTHER INFORMATION: X represents an amino acid
<220> FEATURE:
<221> NAME/KEY: misc_feature
<222> LOCATION: (12)..(12)
<223> OTHER INFORMATION: X represents an amino acid

<400> SEQUENCE: 40

```
Ala Ala Ala Gly Ser Gly Xaa Gly Gly Gly Ser Xaa Gly Gly Gly Ser
1               5                   10                  15

Gly Ala Ser Ala Ser
            20
```

<210> SEQ ID NO 41
<211> LENGTH: 26
<212> TYPE: PRT
<213> ORGANISM: Artificial Sequence
<220> FEATURE:
<223> OTHER INFORMATION: flexible linker sequence
<220> FEATURE:
<221> NAME/KEY: misc_feature
<222> LOCATION: (7)..(7)
<223> OTHER INFORMATION: X represents an amino acid
<220> FEATURE:
<221> NAME/KEY: misc_feature
<222> LOCATION: (12)..(12)
<223> OTHER INFORMATION: X represents an amino acid
<220> FEATURE:
<221> NAME/KEY: misc_feature
<222> LOCATION: (17)..(17)
<223> OTHER INFORMATION: X represents an amino acid

<400> SEQUENCE: 41

```
Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25
```

<210> SEQ ID NO 42
<211> LENGTH: 31
<212> TYPE: PRT
<213> ORGANISM: Artificial Sequence
<220> FEATURE:
<223> OTHER INFORMATION: flexible linker sequence
<220> FEATURE:
<221> NAME/KEY: misc_feature
<222> LOCATION: (7)..(7)
<223> OTHER INFORMATION: X represents an amino acid
<220> FEATURE:
<221> NAME/KEY: misc_feature
<222> LOCATION: (12)..(12)
<223> OTHER INFORMATION: X represents an amino acid
<220> FEATURE:
<221> NAME/KEY: misc_feature
<222> LOCATION: (17)..(17)
<223> OTHER INFORMATION: X represents an amino acid
<220> FEATURE:
<221> NAME/KEY: misc_feature
<222> LOCATION: (22)..(22)
<223> OTHER INFORMATION: X represents an amino acid

<400> SEQUENCE: 42

```
Ala Ala Ala Gly Ser Gly Xaa Gly Gly Gly Ser Xaa Gly Gly Gly Ser
```

1 5 10 15

Xaa Gly Gly Gly Ser Xaa Gly Gly Gly Ser Gly Ala Ser Ala Ser
20 25 30

<210> SEQ ID NO 43
<211> LENGTH: 13
<212> TYPE: PRT
<213> ORGANISM: Artificial Sequence
<220> FEATURE:
<223> OTHER INFORMATION: flexible linker sequence
<220> FEATURE:
<221> NAME/KEY: misc_feature
<222> LOCATION: (7)..(7)
<223> OTHER INFORMATION: X represents an amino acid

<400> SEQUENCE: 43

Ala Ala Ala Gly Ser Gly Xaa Ser Gly Ala Ser Ala Ser
1 5 10

<210> SEQ ID NO 44
<211> LENGTH: 28
<212> TYPE: PRT
<213> ORGANISM: Artificial Sequence
<220> FEATURE:
<223> OTHER INFORMATION: flexible linker sequence

<400> SEQUENCE: 44

Pro Gly Gly Asn Arg Gly Thr Thr Thr Thr Arg Arg Pro Ala Thr Thr
1 5 10 15

Thr Gly Ser Ser Pro Gly Pro Thr Gln Ser His Tyr
20 25

<210> SEQ ID NO 45
<211> LENGTH: 11
<212> TYPE: PRT
<213> ORGANISM: Artificial Sequence
<220> FEATURE:
<223> OTHER INFORMATION: flexible linker sequence

<400> SEQUENCE: 45

Ala Thr Thr Thr Gly Ser Ser Pro Gly Pro Thr
1 5 10

<210> SEQ ID NO 46
<211> LENGTH: 6
<212> TYPE: PRT
<213> ORGANISM: Artificial Sequence
<220> FEATURE:
<223> OTHER INFORMATION: flexible linker sequence

<400> SEQUENCE: 46

Ala Thr Thr Thr Gly Ser
1 5

<210> SEQ ID NO 47
<211> LENGTH: 21
<212> TYPE: PRT
<213> ORGANISM: Artificial Sequence
<220> FEATURE:
<223> OTHER INFORMATION: Flexible linker sequence

<400> SEQUENCE: 47

Glu Pro Ser Gly Pro Ile Ser Thr Ile Asn Ser Pro Pro Ser Lys Glu
1 5 10 15

Ser His Lys Ser Pro
20

<210> SEQ ID NO 48
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 48

Gly Thr Val Ala Ala Pro Ser Val Phe Ile Phe Pro Pro Ser Asp
1 5 10 15

<210> SEQ ID NO 49
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 49

Gly Gly Gly Gly Ile Ala Pro Ser Met Val Gly Gly Gly Gly Ser
1 5 10 15

<210> SEQ ID NO 50
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 50

Gly Gly Gly Gly Lys Val Glu Gly Ala Gly Gly Gly Gly Gly Ser
1 5 10 15

<210> SEQ ID NO 51
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 51

Gly Gly Gly Gly Ser Met Lys Ser His Asp Gly Gly Gly Gly Ser
1 5 10 15

<210> SEQ ID NO 52
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 52

Gly Gly Gly Gly Asn Leu Ile Thr Ile Val Gly Gly Gly Gly Ser
1 5 10 15

<210> SEQ ID NO 53
<211> LENGTH: 15
<212> TYPE: PRT
<213> ORGANISM: Artificial Sequence
<220> FEATURE:
<223> OTHER INFORMATION: Flexible linker sequence

<400> SEQUENCE: 53

Gly Gly Gly Gly Val Val Pro Ser Leu Pro Gly Gly Gly Gly Ser
1 5 10 15

<210> SEQ ID NO 54
<211> LENGTH: 12
<212> TYPE: PRT
<213> ORGANISM: Artificial Sequence
<220> FEATURE:
<223> OTHER INFORMATION: Flexible linker sequence

<400> SEQUENCE: 54

Gly Gly Glu Lys Ser Ile Pro Gly Gly Gly Gly Ser
1 5 10

<210> SEQ ID NO 55
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 55

Arg Pro Leu Ser Tyr Arg Pro Pro Phe Pro Phe Gly Phe Pro Ser Val
1 5 10 15

Arg Pro

<210> SEQ ID NO 56
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 56

Tyr Pro Arg Ser Ile Tyr Ile Arg Arg Arg His Pro Ser Pro Ser Leu
1 5 10 15

Thr Thr

<210> SEQ ID NO 57
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 57

Thr Pro Ser His Leu Ser His Ile Leu Pro Ser Phe Gly Leu Pro Thr
1 5 10 15

Phe Asn

<210> SEQ ID NO 58
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 58

Arg Pro Val Ser Pro Phe Thr Phe Pro Arg Leu Ser Asn Ser Trp Leu
1 5 10 15

Pro Ala

<210> SEQ ID NO 59
<211> LENGTH: 18
<212> TYPE: PRT
<213> ORGANISM: Artificial Sequence
<220> FEATURE:

<223> OTHER INFORMATION: Flexible linker sequence

<400> SEQUENCE: 59

Ser Pro Ala Ala His Phe Pro Arg Ser Ile Pro Arg Pro Gly Pro Ile
1 5 10 15

Arg Thr

<210> SEQ ID NO 60
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 60

Ala Pro Gly Pro Ser Ala Pro Ser His Arg Ser Leu Pro Ser Arg Ala
1 5 10 15

Phe Gly

<210> SEQ ID NO 61
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 61

Pro Arg Asn Ser Ile His Phe Leu His Pro Leu Leu Val Ala Pro Leu
1 5 10 15

Gly Ala

<210> SEQ ID NO 62
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 62

Met Pro Ser Leu Ser Gly Val Leu Gln Val Arg Tyr Leu Ser Pro Pro
1 5 10 15

Asp Leu

<210> SEQ ID NO 63
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 63

Ser Pro Gln Tyr Pro Ser Pro Leu Thr Leu Thr Leu Pro Pro His Pro
1 5 10 15

Ser Leu

<210> SEQ ID NO 64
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 64

Asn Pro Ser Leu Asn Pro Pro Ser Tyr Leu His Arg Ala Pro Ser Arg
1 5 10 15

Ile Ser

<210> SEQ ID NO 65
<211> LENGTH: 17
<212> TYPE: PRT
<213> ORGANISM: Artificial Sequence
<220> FEATURE:
<223> OTHER INFORMATION: Flexible linker sequence

<400> SEQUENCE: 65

Leu Pro Trp Arg Thr Ser Leu Leu Pro Ser Leu Pro Leu Arg Arg Arg
1 5 10 15

Pro

<210> SEQ ID NO 66
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 66

Pro Pro Leu Phe Ala Lys Gly Pro Val Gly Leu Leu Ser Arg Ser Phe
1 5 10 15

Pro Pro

<210> SEQ ID NO 67
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 67

Val Pro Pro Ala Pro Val Val Ser Leu Arg Ser Ala His Ala Arg Pro
1 5 10 15

Pro Tyr

<210> SEQ ID NO 68
<211> LENGTH: 17
<212> TYPE: PRT
<213> ORGANISM: Artificial Sequence
<220> FEATURE:
<223> OTHER INFORMATION: Flexible linker sequence

<400> SEQUENCE: 68

Leu Arg Pro Thr Pro Pro Arg Val Arg Ser Tyr Thr Cys Cys Pro Thr
1 5 10 15

Pro

<210> SEQ ID NO 69
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 69

Pro Asn Val Ala His Val Leu Pro Leu Leu Thr Val Pro Trp Asp Asn
1 5 10 15

Leu Arg

<210> SEQ ID NO 70
<211> LENGTH: 18
<212> TYPE: PRT
<213> ORGANISM: Artificial Sequence
<220> FEATURE:
<223> OTHER INFORMATION: Flexible linker sequence

<400> SEQUENCE: 70

Cys Asn Pro Leu Leu Pro Leu Cys Ala Arg Ser Pro Ala Val Arg Thr
1               5                   10                  15

Phe Pro

<210> SEQ ID NO 71
<211> LENGTH: 11
<212> TYPE: PRT
<213> ORGANISM: Artificial Sequence
<220> FEATURE:
<223> OTHER INFORMATION: linker sequence

<400> SEQUENCE: 71

Gly Ala Pro Ala Pro Ala Ala Pro Ala Pro Ala
1               5                   10

<210> SEQ ID NO 72
<211> LENGTH: 4
<212> TYPE: PRT
<213> ORGANISM: Artificial Sequence
<220> FEATURE:
<223> OTHER INFORMATION: linker sequence

<400> SEQUENCE: 72

Pro Pro Pro Pro
1

<210> SEQ ID NO 73
<211> LENGTH: 11
<212> TYPE: PRT
<213> ORGANISM: Artificial Sequence
<220> FEATURE:
<223> OTHER INFORMATION: Linker sequence

<400> SEQUENCE: 73

Asp Leu Cys Leu Arg Asp Trp Gly Cys Leu Trp
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Linker sequence

<400> SEQUENCE: 74

Asp Ile Cys Leu Pro Arg Trp Gly Cys Leu Trp
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Linker sequence

<400> SEQUENCE: 75

Met Glu Asp Ile Cys Leu Pro Arg Trp Gly Cys Leu Trp Gly Asp

-continued 1 5 10 15

<210> SEQ ID NO 76
<211> LENGTH: 20
<212> TYPE: PRT
<213> ORGANISM: Artificial Sequence
<220> FEATURE:
<223> OTHER INFORMATION: Linker sequence

<400> SEQUENCE: 76

Gln Arg Leu Met Glu Asp Ile Cys Leu Pro Arg Trp Gly Cys Leu Trp
1 5 10 15

Glu Asp Asp Glu
20

<210> SEQ ID NO 77
<211> LENGTH: 20
<212> TYPE: PRT
<213> ORGANISM: Artificial Sequence
<220> FEATURE:
<223> OTHER INFORMATION: Linker sequence

<400> SEQUENCE: 77

Gln Gly Leu Ile Gly Asp Ile Cys Leu Pro Arg Trp Gly Cys Leu Trp
1 5 10 15

Gly Arg Ser Val
20

<210> SEQ ID NO 78
<211> LENGTH: 21
<212> TYPE: PRT
<213> ORGANISM: Artificial Sequence
<220> FEATURE:
<223> OTHER INFORMATION: Linker sequence

<400> SEQUENCE: 78

Gln Gly Leu Ile Gly Asp Ile Cys Leu Pro Arg Trp Gly Cys Leu Trp
1 5 10 15

Gly Arg Ser Val Lys
20

<210> SEQ ID NO 79
<211> LENGTH: 15
<212> TYPE: PRT
<213> ORGANISM: Artificial Sequence
<220> FEATURE:
<223> OTHER INFORMATION: Linker sequence

<400> SEQUENCE: 79

Glu Asp Ile Cys Leu Pro Arg Trp Gly Cys Leu Trp Glu Asp Asp
1 5 10 15

<210> SEQ ID NO 80
<211> LENGTH: 18
<212> TYPE: PRT
<213> ORGANISM: Artificial Sequence
<220> FEATURE:
<223> OTHER INFORMATION: Linker sequence

<400> SEQUENCE: 80

Arg Leu Met Glu Asp Ile Cys Leu Pro Arg Trp Gly Cys Leu Trp Glu
1 5 10 15

Asp Asp

<210> SEQ ID NO 81
<211> LENGTH: 16
<212> TYPE: PRT
<213> ORGANISM: Artificial Sequence
<220> FEATURE:
<223> OTHER INFORMATION: Linker sequence

<400> SEQUENCE: 81

Met Glu Asp Ile Cys Leu Pro Arg Trp Gly Cys Leu Trp Glu Asp Asp
1 5 10 15

<210> SEQ ID NO 82
<211> LENGTH: 15
<212> TYPE: PRT
<213> ORGANISM: Artificial Sequence
<220> FEATURE:
<223> OTHER INFORMATION: Linker sequence

<400> SEQUENCE: 82

Met Glu Asp Ile Cys Leu Pro Arg Trp Gly Cys Leu Trp Glu Asp
1 5 10 15

<210> SEQ ID NO 83
<211> LENGTH: 18
<212> TYPE: PRT
<213> ORGANISM: Artificial Sequence
<220> FEATURE:
<223> OTHER INFORMATION: Linker sequence

<400> SEQUENCE: 83

Arg Leu Met Glu Asp Ile Cys Leu Ala Arg Trp Gly Cys Leu Trp Glu
1 5 10 15

Asp Asp

<210> SEQ ID NO 84
<211> LENGTH: 20
<212> TYPE: PRT
<213> ORGANISM: Artificial Sequence
<220> FEATURE:
<223> OTHER INFORMATION: Linker sequence

<400> SEQUENCE: 84

Glu Val Arg Ser Phe Cys Thr Arg Trp Pro Ala Glu Lys Ser Cys Lys
1 5 10 15

Pro Leu Arg Gly
20

<210> SEQ ID NO 85
<211> LENGTH: 20
<212> TYPE: PRT
<213> ORGANISM: Artificial Sequence
<220> FEATURE:
<223> OTHER INFORMATION: Linker sequence

<400> SEQUENCE: 85

Arg Ala Pro Glu Ser Phe Val Cys Tyr Trp Glu Thr Ile Cys Phe Glu
1 5 10 15

Arg Ser Glu Gln
20

<210> SEQ ID NO 86
<211> LENGTH: 11
<212> TYPE: PRT
<213> ORGANISM: Artificial Sequence
<220> FEATURE:
<223> OTHER INFORMATION: Linker sequence

<400> SEQUENCE: 86

Glu Met Cys Tyr Phe Pro Gly Ile Cys Trp Met
1 5 10

<210> SEQ ID NO 87
<211> LENGTH: 5288
<212> TYPE: DNA
<213> ORGANISM: Artificial Sequence
<220> FEATURE:
<223> OTHER INFORMATION: E2B region of the ENAD GENOME (BP 10355-5068)

<400> SEQUENCE: 87
ctatggcatc tcgatccagc agacctcctc gtttcgcggg tttggacggc tcctggaata 60
gggtatgaga cgatgggcgt ccagcgctgc cagggttcgg tccttccagg gtctcagtgt 120
tcgagtcagg gttgtttccg tcacagtgaa ggggtgtgcg cctgcttggg cgcttgccag 180
ggtgcgcttc agactcatcc tgctggtcga aaacttctgt cgcttggcgc cctgtatgtc 240
ggccaagtag cagtttacca tgagttcgta gttgagcgcc tcggctgcgt ggcctttggc 300
gcggagctta cctttggaag ttttcttgca taccgggcag tataggcatt tcagcgcata 360
caacttgggc gcaaggaaaa cggattctgg ggagtatgca tctgcgccgc aggaggcgca 420
aacagtttca cattccacca gccaggttaa atccggttca ttggggtcaa aaacaagttt 480
tccgccatat tttttgatgc gtttcttacc tttggtctcc atgagttcgt gtcctcgttg 540
agtgacaaac aggctgtccg tgtccccgta gactgatttt acaggcctct tctccagtgg 600
agtgcctcgg tcttcttcgt acaggaactc tgaccactct gatacaaagg cgcgcgtcca 660
ggccagcaca aaggaggcta tgtgggaggg gtagcgatcg ttgtcaacca gggggtccac 720
cttttccaaa gtatgcaaac acatgtcacc ctcttcaaca tccaggaatg tgattggctt 780
gtaggtgtat ttcacgtgac ctggggtccc cgctgggggg gtataaaagg gggcggttct 840
ttgctcttcc tcactgtctt ccggatcgct gtccaggaac gtcagctgtt ggggtaggta 900
ttccctctcg aaggcgggca tgacctctgc actcaggttg tcagtttcta agaacgagga 960
ggatttgata ttgacagtgc cggttgagat gcctttcatg aggttttcgt ccatctggtc 1020
agaaaacaca attttttat tgtcaagttt ggtggcaaat gatccataca gggcgttgga 1080
taaaagtttg gcaatggatc gcatggtttg gttcttttcc ttgtccgcgc gctctttggc 1140
ggcgatgttg agttggacat actcgcgtgc caggcacttc cattcgggga agatagttgt 1200
taattcatct ggcacgattc tcacttgcca ccctcgatta tgcaaggtaa ttaaatccac 1260
actggtggcc acctcgcctc gaaggggttc attggtccaa cagagcctac ctcctttcct 1320
agaacagaaa gggggaagtg ggtctagcat aagttcatcg ggagggtctg catccatggt 1380
aaagattccc ggaagtaaat ccttatcaaa atagctgatg ggagtggggt catctaaggc 1440
catttgccat tctcgagctg ccagtgcgcg ctcatatggg ttaaggggac tgccccatgg 1500
catgggatgg gtgagtgcag aggcatacat gccacagatg tcatagacgt agatgggatc 1560
ctcaaagatg cctatgtagg ttggatagca tcgccccccct ctgatacttg ctcgcacata 1620
gtcatatagt tcatgtgatg gcgctagcag ccccggaccc aagttggtgc gattgggttt 1680
ttctgttctg tagacgatct ggcgaaagat ggcgtgagaa ttggaagaga tggtgggtct 1740
ttgaaaaatg ttgaaatggg catgaggtag acctacagag tctctgacaa agtgggcata 1800
agattcttga agcttggtta ccagttcggc ggtgacaagt acgtctaggg cgcagtagtc 1860
aagtgtttct tgaatgatgt cataacctgg ttggtttttc ttttcccaca gttcgcggtt 1920
gagaaggtat tcttcgcgat ccttccagta ctcttctagc ggaaacccgt ctttgtctgc 1980
acggtaagat cctagcatgt agaactgatt aactgccttg taagggcagc agcccttctc 2040
tacgggtaga gagtatgctt gagcagcttt tcgtagcgaa gcgtgagtaa gggcaaaggt 2100
gtctctgacc atgactttga ggaattggta tttgaagtcg atgtcgtcac aggctccctg 2160
ttcccagagt tggaagtcta cccgtttctt gtaggcgggg ttgggcaaag cgaaagtaac 2220
atcattgaag agaatcttgc cggccctggg catgaaattg cgagtgatgc gaaaaggctg 2280
tggtacttcc gctcggttat tgataacctg ggcagctagg acgatctcgt cgaaaccgtt 2340
gatgttgtgt cctacgatgt ataattctat gaaacgcggc gtgcctctga cgtgaggtag 2400
cttactgagc tcatcaaagg ttaggtctgt ggggtcagat aaggcgtagt gttcgagagc 2460
ccattcgtgc aggtgaggat tcgctttaag gaaggaggac cagaggtcca ctgccagtgc 2520
tgtttgtaac tggtcccggt actgacgaaa atgccgtccg actgccattt tttctggggt 2580
gacgcaatag aaggtttggg ggtcctgccg ccagcgatcc cacttgagtt ttatggcgag 2640
gtcataggcg atgttgacga gccgctggtc tccagagagt ttcatgacca gcatgaaggg 2700
gattagctgc ttgccaaagg accccatcca ggtgtaggtt tccacatcgt aggtgagaaa 2760
gagcctttct gtgcgaggat gagagccaat cgggaagaac tggatctcct gccaccagtt 2820
ggaggaatgg ctgttgatgt gatggaagta gaactccctg cgacgcgccg agcattcatg 2880
cttgtgcttg tacagacggc cgcagtagtc gcagcgttgc acgggttgta tctcgtgaat 2940
gagttgtacc tggcttccct tgacgagaaa tttcagtggg aagccgaggc ctggcgattg 3000
tatctcgtgc tttactatgt tgtctgcatc ggcctgttca tcttctgtct cgatggtggt 3060
catgctgacg agccctcgcg ggaggcaagt ccagacctcg gcgcggcagg ggcggagctc 3120
gaggacgaga gcgcgcaggc tggagctgtc cagggtcctg agacgctgcg gactcaggtt 3180
agtaggcagt gtcaggagat taacttgcat gatcttttgg agggcgtgcg ggaggttcag 3240
atagtacttg atctcaacgg gtccgttggt ggagatgtcg atggcttgca gggttccgtg 3300
tcccttgggc gctaccaccg tgcccttgtt tttcattttg gacggcggtg gctctgttgc 3360
ttcttgcatg tttagaagcg gtgtcgaggg cgcgcaccgg gcggcagggg cggctcggga 3420
cccggcggca tggctggcag tggtacgtcg gcgccgcgcg cgggtaggtt ctggtactgc 3480
gccctgagaa gactcgcatg cgcgacgacg cggcggttga catcctggat ctgacgcctc 3540
tgggtgaaag ctaccggccc cgtgagcttg aacctgaaag agagttcaac agaatcaatc 3600
tcggtatcgt tgacggcggc ttgcctaagg atttcttgca cgtcaccaga gttgtcctgg 3660
taggcgatct ccgccatgaa ctgctcgatc tcttcctctt gaagatctcc gcggcccgct 3720
ctctcgacgg tggccgcgag gtcgttggag atgcgcccaa tgagttgaga gaatgcattc 3780
atgcccgcct cgttccagac gcggctgtag accacggccc ccacgggatc tctcgcgcgc 3840
atgaccacct gggcgaggtt gagctccacg tggcgggtga agaccgcata gttgcatagg 3900
cgctggaaaa ggtagttgag tgtggtggcg atgtgctcgg tgacgaagaa atacatgatc 3960
catcgtctca gcggcatctc gctgacatcg cccagagctt ccaagcgctc catggcctcg 4020
tagaagtcca cggcaaaatt aaaaaactgg gagtttcgcg cggacacggt caactcctct 4080
tccagaagac ggataagttc ggcgatggtg gtgcgcacct cgcgctcgaa agcccctggg 4140
atttcttcct caatctcttc ttcttccact aacatctctt cctcttcagg tggggctgca 4200
ggaggagggg gaacgcggcg acgccggcgg cgcacgggca gacggtcgat gaatctttca 4260

```
atgacctctc cgcggcggcg gcgcatggtt tcagtgacgg cgcggccgtt ctcgcgcggt   4320

cgcagagtaa aaacaccgcc gcgcatctcc ttaaagtggt gactgggagg ttctccgttt   4380

gggagggaga gggcgctgat tatacatttt attaattggc ccgtagggac tgcacgcaga   4440

gatctgatcg tgtcaagatc cacgggatct gaaaaccttt cgacgaaagc gtctaaccag   4500

tcacagtcac aaggtaggct gagtacggct tcttgtgggc gggggtggtt atgtgttcgg   4560

tctgggtctt ctgtttcttc ttcatctcgg gaaggtgaga cgatgctgct ggtgatgaaa   4620

ttaaagtagg cagttctaag acggcggatg gtggcgagga gcaccaggtc tttgggtccg   4680

gcttgctgga tacgcaggcg attggccatt ccccaagcat tatcctgaca tctagcaaga   4740

tctttgtagt agtcttgcat gagccgttct acgggcactt cttcctcacc cgttctgcca   4800

tgcatacgtg tgagtccaaa tccgcgcatt ggttgtacca gtgccaagtc agctacgact   4860

ctttcggcga ggatggcttg ctgtacttgg gtaagggtgg cttgaaagtc atcaaaatcc   4920

acaaagcggt ggtaagctcc tgtattaatg gtgtaagcac agttggccat gactgaccag   4980

ttaactgtct ggtgaccagg gcgcacgagc tcggtgtatt taaggcgcga ataggcgcgg   5040

gtgtcaaaga tgtaatcgtt gcaggtgcgc accagatact ggtaccctat aagaaaatgc   5100

ggcggtggtt ggcggtagag aggccatcgt tctgtagctg gagcgccagg ggcgaggtct   5160

tccaacataa ggcggtgata gccgtagatg tacctggaca tccaggtgat tcctgcggcg   5220

gtagtagaag cccgaggaaa ctcgcgtacg cggttccaaa tgttgcgtag cggcatgaag   5280

tagttcat                                                            5288
```

<210> SEQ ID NO 88
<211> LENGTH: 201
<212> TYPE: DNA
<213> ORGANISM: Artificial Sequence
<220> FEATURE:
<223> OTHER INFORMATION: A non-coding sequence suitable for inclusion into BX

<400> SEQUENCE: 88

```
aaaatgatta ataaaaaatc acttacttga aatcagcaat aaggtctctg ttgaaatttt     60

ctcccagcag cacctcactt ccctcttccc aactctggta ttctaaaccc cgttcagcgg    120

catactttct ccatacttta aaggggatgt caaattttag ctcctctcct gtacccacaa    180

tcttcatgtc tttcttccca g                                              201
```

<210> SEQ ID NO 89
<211> LENGTH: 34
<212> TYPE: DNA
<213> ORGANISM: Artificial Sequence
<220> FEATURE:
<223> OTHER INFORMATION: A non-coding sequence suitable for inclusion into BY

<400> SEQUENCE: 89

```
caaataaagt ttaacttgtt tatttgaaaa tcaa                                 34
```

<210> SEQ ID NO 90
<211> LENGTH: 14
<212> TYPE: DNA
<213> ORGANISM: Artificial Sequence
<220> FEATURE:
<223> OTHER INFORMATION: Splice acceptor sequence

<400> SEQUENCE: 90

```
tttctctctt cagg                                                       14
```

<210> SEQ ID NO 91
<211> LENGTH: 26
<212> TYPE: DNA
<213> ORGANISM: Artificial Sequence
<220> FEATURE:
<223> OTHER INFORMATION: Splice acceptor sequence

<400> SEQUENCE: 91
tgctaatctt cctttctctc ttcagg 26

<210> SEQ ID NO 92
<211> LENGTH: 13
<212> TYPE: RNA
<213> ORGANISM: Artificial Sequence
<220> FEATURE:
<223> OTHER INFORMATION: sequence comprising a start codon

<400> SEQUENCE: 92
gccgccrcca ugg 13

<210> SEQ ID NO 93
<211> LENGTH: 550
<212> TYPE: DNA
<213> ORGANISM: Artificial Sequence
<220> FEATURE:
<223> OTHER INFORMATION: Internal Ribosome Entry Sequence (IRES)

<400> SEQUENCE: 93
gttactggcc gaagccgctt ggaataaggc cggtgtgcgt ttgtctatat gttattttcc 60
accatattgc cgtcttttgg caatgtgagg gcccggaaac ctggccctgt cttcttgacg 120
agcattccta ggggtctttc ccctctcgcc aaaggaatgc aaggtctgtt gaatgtcgtg 180
aaggaagcag ttcctctgga agcttcttga agacaaacaa cgtctgtagc gaccctttgc 240
aggcagcgga acccccacc tggcgacagg tgcctctgcg gccaaaagcc acgtgtataa 300
gatacacctg caaaggcggc acaaccccag tgccacgttg tgagttggat agttgtggaa 360
agagtcaaat ggctcccctc aagcgtattc aacaaggggc tgaaggatgc ccagaaggta 420
ccccattgta tgggatctga tctggggcct cggtgcacat gcttttcatg tgtttagtcg 480
aggttaaaaa acgtctaggc cccccgaacc acggggacgt ggttttcctt tgaaaaacac 540
gatgataata 550

<210> SEQ ID NO 94
<211> LENGTH: 22
<212> TYPE: PRT
<213> ORGANISM: Artificial Sequence
<220> FEATURE:
<223> OTHER INFORMATION: High efficiency self-cleavable P2A peptide sequence

<400> SEQUENCE: 94

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 95
<211> LENGTH: 21
<212> TYPE: PRT
<213> ORGANISM: Artificial Sequence
<220> FEATURE:
<223> OTHER INFORMATION: High efficiency self-cleavable F2A peptide sequence

<400> SEQUENCE: 95

Gly Ser Gly Glu Gly Arg Gly Ser Leu Leu Thr Cys Gly Asp Val Glu
1 5 10 15

Glu Asn Pro Gly Pro
20

<210> SEQ ID NO 96
<211> LENGTH: 23
<212> TYPE: PRT
<213> ORGANISM: Artificial Sequence
<220> FEATURE:
<223> OTHER INFORMATION: High efficiency self-cleavable E2A peptide sequence

<400> SEQUENCE: 96

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 97
<211> LENGTH: 25
<212> TYPE: PRT
<213> ORGANISM: Artificial Sequence
<220> FEATURE:
<223> OTHER INFORMATION: High efficiency self-cleavable T2A peptide sequence

<400> SEQUENCE: 97

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 98
<211> LENGTH: 288
<212> TYPE: PRT
<213> ORGANISM: Artificial Sequence
<220> FEATURE:
<223> OTHER INFORMATION: Human CD80 amino acid sequence

<400> SEQUENCE: 98

Met Gly His Thr Arg Arg Gln Gly Thr Ser Pro Ser Lys Cys Pro Tyr
1 5 10 15

Leu Asn Phe Phe Gln Leu Leu Val Leu Ala Gly Leu Ser His Phe Cys
20 25 30

Ser Gly Val Ile His Val Thr Lys Glu Val Lys Glu Val Ala Thr Leu
35 40 45

Ser Cys Gly His Asn Val Ser Val Glu Glu Leu Ala Gln Thr Arg Ile
50 55 60

Tyr Trp Gln Lys Glu Lys Lys Met Val Leu Thr Met Met Ser Gly Asp
65 70 75 80

Met Asn Ile Trp Pro Glu Tyr Lys Asn Arg Thr Ile Phe Asp Ile Thr
85 90 95

Asn Asn Leu Ser Ile Val Ile Leu Ala Leu Arg Pro Ser Asp Glu Gly
100 105 110

Thr Tyr Glu Cys Val Val Leu Lys Tyr Glu Lys Asp Ala Phe Lys Arg
115 120 125

Glu His Leu Ala Glu Val Thr Leu Ser Val Lys Ala Asp Phe Pro Thr

-continued

```
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285


<210> SEQ ID NO 99
<211> LENGTH: 192
<212> TYPE: DNA
<213> ORGANISM: Artificial Sequence
<220> FEATURE:
<223> OTHER INFORMATION: poly adenylation sequence (SV40 late polyA
      sequence)

<400> SEQUENCE: 99

cagacatgat aagatacatt gatgagtttg gacaaaccac aactagaatg cagtgaaaaa     60

aatgctttat ttgtgaaatt tgtgatgcta ttgctttatt tgtaaccatt ataagctgca    120

ataaacaagt taacaacaac aattgcattc attttatgtt tcaggttcag ggggaggtgt    180

gggaggtttt tt                                                        192


<210> SEQ ID NO 100
<211> LENGTH: 34522
<212> TYPE: DNA
<213> ORGANISM: Artificial Sequence
<220> FEATURE:
<223> OTHER INFORMATION: NG-348 virus genome sequence comprising the
      EnAd genome with a transgene cassette that encodes a membrane-
      anchored chimeric form of the single chain Fv anti-human CD3e and
      the T lymphocyte activation antigen, CD80 inserted in the region
      BY.

<400> SEQUENCE: 100

tctatctata taatatacct tatagatgga atggtgccaa tatgtaaatg aggtgatttt     60

aaaaagtgtg gatcgtgtgg tgattggctg tggggttaac ggctaaaagg ggcggtgcga    120

ccgtgggaaa atgacgtttt gtgggggtgg agtttttttg caagttgtcg cgggaaatgt    180

gacgcataaa aaggcttttt tctcacggaa ctacttagtt ttcccacggt atttaacagg    240

aaatgaggta gttttgaccg gatgcaagtg aaaattgttg attttcgcgc gaaaactgaa    300

tgaggaagtg tttttctgaa taatgtggta tttatggcag ggtggagtat ttgttcaggg    360

ccaggtagac tttgacccat tacgtggagg tttcgattac cgtgtttttt acctgaattt    420

ccgcgtaccg tgtcaaagtc ttctgttttt acgtaggtgt cagctgatcg ctagggtatt    480

tatacctcag ggtttgtgtc aagaggccac tcttgagtgc cagcgagaag agttttctcc    540
```

```
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agctttttga gcctcctacg cttcaggaac tgtatgattt    720
agaggtagag ggatcggagg attctaatga ggaagctgta aatggctttt ttaccgattc    780
tatgctttta gctgctaatg aagggttaga attagatccg cctttggaca cttttgatac    840
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
```

```
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct   3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaactttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
```

cttctgtcgc ttggcgccct gtatgtcggc caagtagcag tttaccatga gttcgtagtt 5340
gagcgcctcg gctgcgtggc ctttggcgcg gagcttacct ttggaagttt tcttgcatac 5400
cgggcagtat aggcatttca gcgcatacaa cttgggcgca aggaaaacgg attctgggga 5460
gtatgcatct gcgccgcagg aggcgcaaac agtttcacat tccaccagcc aggttaaatc 5520
cggttcattg gggtcaaaaa caagttttcc gccatatttt ttgatgcgtt tcttaccttt 5580
ggtctccatg agttcgtgtc ctcgttgagt gacaaacagg ctgtccgtgt ccccgtagac 5640
tgattttaca ggcctcttct ccagtggagt gcctcggtct tcttcgtaca ggaactctga 5700
ccactctgat acaaaggcgc gcgtccaggc cagcacaaag gaggctatgt gggaggggta 5760
gcgatcgttg tcaaccaggg ggtccacctt ttccaaagta tgcaaacaca tgtcaccctc 5820
ttcaacatcc aggaatgtga ttggcttgta ggtgtatttc acgtgacctg gggtccccgc 5880
tgggggggta taaaaggggg cggttctttg ctcttcctca ctgtcttccg gatcgctgtc 5940
caggaacgtc agctgttggg gtaggtattc cctctcgaag gcgggcatga cctctgcact 6000
caggttgtca gtttctaaga acgaggagga tttgatattg acagtgccgg ttgagatgcc 6060
tttcatgagg ttttcgtcca tctggtcaga aaacacaatt tttttattgt caagtttggt 6120
ggcaaatgat ccatacaggg cgttggataa aagtttggca atggatcgca tggtttggtt 6180
cttttccttg tccgcgcgct ctttggcggc gatgttgagt tggacatact cgcgtgccag 6240
gcacttccat tcggggaaga tagttgttaa ttcatctggc acgattctca cttgccaccc 6300
tcgattatgc aaggtaatta aatccacact ggtggccacc tcgcctcgaa ggggttcatt 6360
ggtccaacag agcctacctc ctttcctaga acagaaaggg ggaagtgggt ctagcataag 6420
ttcatcggga gggtctgcat ccatggtaaa gattcccgga agtaaatcct tatcaaaata 6480
gctgatggga gtggggtcat ctaaggccat ttgccattct cgagctgcca gtgcgcgctc 6540
atatgggtta aggggactgc cccatggcat gggatgggtg agtgcagagg catacatgcc 6600
acagatgtca tagacgtaga tgggatcctc aaagatgcct atgtaggttg gatagcatcg 6660
ccccccctctg atacttgctc gcacatagtc atatagttca tgtgatggcg ctagcagccc 6720
cggacccaag ttggtgcgat tgggtttttc tgttctgtag acgatctggc gaaagatggc 6780
gtgagaattg gaagagatgg tgggtctttg aaaaatgttg aaatgggcat gaggtagacc 6840
tacagagtct ctgacaaagt gggcataaga ttcttgaagc ttggttacca gttcggcggt 6900
gacaagtacg tctagggcgc agtagtcaag tgtttcttga atgatgtcat aacctggttg 6960
gtttttcttt tcccacagtt cgcggttgag aaggtattct tcgcgatcct tccagtactc 7020
ttctagcgga aacccgtctt tgtctgcacg gtaagatcct agcatgtaga actgattaac 7080
tgccttgtaa gggcagcagc ccttctctac gggtagagag tatgcttgag cagcttttcg 7140
tagcgaagcg tgagtaaggg caaaggtgtc tctgaccatg actttgagga attggtattt 7200
gaagtcgatg tcgtcacagg ctccctgttc ccagagttgg aagtctaccc gtttcttgta 7260
ggcggggttg ggcaaagcga aagtaacatc attgaagaga atcttgccgg ccctgggcat 7320
gaaattgcga gtgatgcgaa aaggctgtgg tacttccgct cggttattga taacctgggc 7380
agctaggacg atctcgtcga aaccgttgat gttgtgtcct acgatgtata attctatgaa 7440
acgcggcgtg cctctgacgt gaggtagctt actgagctca tcaaaggtta ggtctgtggg 7500
gtcagataag gcgtagtgtt cgagagccca ttcgtgcagg tgaggattcg ctttaaggaa 7560
ggaggaccag aggtccactg ccagtgctgt ttgtaactgg tcccggtact gacgaaaatg 7620

-continued

```
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
```

taagcacagt tggccatgac tgaccagtta actgtctggt gaccagggcg cacgagctcg 10080
gtgtatttaa ggcgcgaata ggcgcgggtg tcaaagatgt aatcgttgca ggtgcgcacc 10140
agatactggt accctataag aaaatgcggc ggtggttggc ggtagagagg ccatcgttct 10200
gtagctggag cgccaggggc gaggtcttcc aacataaggc ggtgatagcc gtagatgtac 10260
ctggacatcc aggtgattcc tgcggcggta gtagaagccc gaggaaactc gcgtacgcgg 10320
ttccaaatgt tgcgtagcgg catgaagtag ttcattgtag gcacggtttg accagtgagg 10380
cgcgcgcagt cattgatgct ctatagacac ggagaaaatg aaagcgttca gcgactcgac 10440
tccgtagcct ggaggaacgt gaacgggttg ggtcgcggtg taccccggtt cgagacttgt 10500
actcgagccg gccggagccg cggctaacgt ggtattggca ctcccgtctc gacccagcct 10560
acaaaaatcc aggatacgga atcgagtcgt tttgctggtt tccgaatggc agggaagtga 10620
gtcctatttt tttttttgc cgctcagatg catcccgtgc tgcgacagat gcgcccccaa 10680
caacagcccc cctcgcagca gcagcagcag caatcacaaa aggctgtccc tgcaactact 10740
gcaactgccg ccgtgagcgg tgcgggacag cccgcctatg atctggactt ggaagagggc 10800
gaaggactgg cacgtctagg tgcgccttca cccgagcggc atccgcgagt tcaactgaaa 10860
aaagattctc gcgaggcgta tgtgccccaa cagaacctat ttagagacag aagcggcgag 10920
gagccggagg agatgcgagc ttcccgcttt aacgcgggtc gtgagctgcg tcacggtttg 10980
gaccgaagac gagtgttgcg ggacgaggat ttcgaagttg atgaaatgac agggatcagt 11040
cctgccaggg cacacgtggc tgcagccaac cttgtatcgg cttacgagca gacagtaaag 11100
gaagagcgta acttccaaaa gtcttttaat aatcatgtgc gaaccctgat tgcccgcgaa 11160
gaagttaccc ttggtttgat gcatttgtgg gatttgatgg aagctatcat tcagaaccct 11220
actagcaaac ctctgaccgc ccagctgttt ctggtggtgc aacacagcag agacaatgag 11280
gctttcagag aggcgctgct gaacatcacc gaacccgagg ggagatggtt gtatgatctt 11340
atcaacattc tacagagtat catagtgcag gagcggagcc tgggcctggc cgagaaggtg 11400
gctgccatca attactcggt tttgagcttg ggaaaatatt acgctcgcaa aatctacaag 11460
actccatacg ttcccataga caaggaggtg aagatagatg ggttctacat gcgcatgacg 11520
ctcaaggtct tgaccctgag cgatgatctt ggggtgtatc gcaatgacag aatgcatcgc 11580
gcggttagcg ccagcaggag gcgcgagtta agcgacaggg aactgatgca cagtttgcaa 11640
agagctctga ctggagctgg aaccgagggt gagaattact tcgacatggg agctgacttg 11700
cagtggcagc ctagtcgcag ggctctgagc gccgcgacgg caggatgtga gcttccttac 11760
atagaagagg cggatgaagg cgaggaggaa gagggcgagt acttggaaga ctgatggcac 11820
aacccgtgtt ttttgctaga tggaacagca agcaccggat cccgcaatgc gggcggcgct 11880
gcagagccag ccgtccggca ttaactcctc ggacgattgg acccaggcca tgcaacgtat 11940
catggcgttg acgactcgca accccgaagc ctttagacag caaccccagg ccaaccgtct 12000
atcggccatc atggaagctg tagtgccttc ccgctctaat cccactcatg agaaggtcct 12060
ggccatcgtg aacgcgttgg tggagaacaa agctattcgt ccagatgagg ccggactggt 12120
atacaacgct ctcttagaac gcgtggctcg ctacaacagt agcaatgtgc aaaccaattt 12180
ggaccgtatg ataacagatg tacgcgaagc cgtgtctcag cgcgaaaggt tccagcgtga 12240
tgccaacctg ggttcgctgg tggcgttaaa tgctttcttg agtactcagc ctgctaatgt 12300
gccgcgtggt caacaggatt atactaactt tttaagtgct ttgagactga tggtatcaga 12360
agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960
cgctatgaac tctgattatt tcaccaatgc catcttaaac ccgcactggc tgcccccacc 13020
tggtttctac acgggcgaat atgacatgcc cgaccctaat gacggatttc tgtgggacga 13080
cgtggacagc gatgtttttt cacctctttc tgatcatcgc acgtggaaaa aggaaggcgg 13140
cgatagaatg cattcttctg catcgctgtc cggggtcatg ggtgctaccg cggctgagcc 13200
cgagtctgca agtccttttc ctagtctacc cttttctcta cacagtgtac gtagcagcga 13260
agtgggtaga ataagtcgcc cgagtttaat gggcgaagag gagtatctaa acgattcctt 13320
gctcagaccg gcaagagaaa aaaatttccc aaacaatgga atagaaagtt tggtggataa 13380
aatgagtaga tggaagactt atgctcagga tcacagagac gagcctggga tcatggggat 13440
tacaagtaga gcgagccgta gacgccagcg ccatgacaga cagaggggtc ttgtgtggga 13500
cgatgaggat tcggccgatg atagcagcgt gctggacttg ggtgggagag gaaggggcaa 13560
cccgtttgct catttgcgcc ctcgcttggg tggtatgttg taaaaaaaaa taaaaaaaaa 13620
actcaccaag gccatggcga cgagcgtacg ttcgttcttc tttattatct gtgtctagta 13680
taatgaggcg agtcgtgcta ggcggagcgg tggtgtatcc ggagggtcct cctccttcgt 13740
acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040
ggggcggtca gctaaagacc atcatgcata ctaacatgcc aaacgtgaac gagtatatgt 14100
ttagtaacaa gttcaaagcg cgtgtgatgg tgtccagaaa acctcccgac ggtgctgcag 14160
ttggggatac ttatgatcac aagcaggata ttttgaaata tgagtggttc gagtttactt 14220
tgccagaagg caacttttca gttactatga ctattgattt gatgaacaat gccatcatag 14280
ataattactt gaaagtgggt agacagaatg gagtgcttga aagtgacatt ggtgttaagt 14340
tcgacaccag gaacttcaag ctgggatggg atcccgaaac caagttgatc atgcctggag 14400
tgtatacgta tgaagccttc catcctgaca ttgtcttact gcctggctgc ggagtggatt 14460
ttaccgagag tcgtttgagc aaccttcttg gtatcagaaa aaaacagcca tttcaagagg 14520
gttttaagat tttgtatgaa gatttagaag gtggtaatat tccggccctc ttggatgtag 14580
atgcctatga gaacagtaag aaagaacaaa aagccaaaat agaagctgct acagctgctg 14640
cagaagctaa ggcaaacata gttgccagcg actctacaag ggttgctaac gctggagagg 14700
tcagaggaga caattttgcg ccaacacctg ttccgactgc agaatcatta ttggccgatg 14760

-continued

```
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg ggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
```

-continued

```
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
```

gcataggtgt tccaacaacc agttacaaat caatagttcc aaatggagac aatgcgccta 19560
attggaagga acctgaagta aatggaacaa gtgagatcgg acagggtaat ttgtttgcca 19620
tggaaattaa ccttcaagcc aatctatggc gaagtttcct ttattccaat gtggctctat 19680
atctcccaga ctcgtacaaa tacaccccgt ccaatgtcac tcttccagaa aacaaaaaca 19740
cctacgacta catgaacggg cgggtggtgc cgccatctct agtagacacc tatgtgaaca 19800
ttggtgccag gtggtctctg gatgccatgg acaatgtcaa cccattcaac caccaccgta 19860
acgctggctt gcgttaccga tccatgcttc tgggtaacgg acgttatgtg cctttccaca 19920
tacaagtgcc tcaaaaattc ttcgctgtta aaaacctgct gcttctccca ggctcctaca 19980
cttatgagtg gaactttagg aaggatgtga acatggttct acagagttcc ctcggtaacg 20040
acctgcgggt agatggcgcc agcatcagtt tcacgagcat caacctctat gctacttttt 20100
tccccatggc tcacaacacc gcttccaccc ttgaagccat gctgcggaat gacaccaatg 20160
atcagtcatt caacgactac ctatctgcag ctaacatgct ctaccccatt cctgccaatg 20220
caaccaatat tcccatttcc attccttctc gcaactgggc ggctttcaga ggctggtcat 20280
ttaccagact gaaaaccaaa gaaactccct ctttggggtc tggatttgac ccctactttg 20340
tctattctgg ttctattccc tacctggatg gtaccttcta cctgaaccac acttttaaga 20400
aggtttccat catgtttgac tcttcagtga gctggcctgg aaatgacagg ttactatctc 20460
ctaacgaatt tgaaataaag cgcactgtgg atggcgaagg ctacaacgta gcccaatgca 20520
acatgaccaa agactggttc ttggtacaga tgctcgccaa ctacaacatc ggctatcagg 20580
gcttctacat tccagaagga tacaaagatc gcatgtattc atttttcaga aacttccagc 20640
ccatgagcag gcaggtggtt gatgaggtca attacaaaga cttcaaggcc gtcgccatac 20700
cctaccaaca caacaactct ggctttgtgg gttacatggc tccgaccatg cgccaaggtc 20760
aaccctatcc cgctaactat ccctatccac tcattggaac aactgccgta aatagtgtta 20820
cgcagaaaaa gttcttgtgt gacagaacca tgtggcgcat accgttctcg agcaacttca 20880
tgtctatggg ggcccttaca gacttgggac agaatatgct ctatgccaac tcagctcatg 20940
ctctggacat gacctttgag gtggatccca tggatgagcc caccctgctt tatcttctct 21000
tcgaagtttt cgacgtggtc agagtgcatc agccacaccg cggcatcatc gaggcagtct 21060
acctgcgtac accgttctcg gccggtaacg ctaccacgta agaagcttct tgcttcttgc 21120
aaatagcagc tgcaaccatg gcctgcggat cccaaaacgg ctccagcgag caagagctca 21180
gagccattgt ccaagacctg ggttgcggac cctatttttt gggaacctac gataagcgct 21240
tcccggggtt catggccccc gataagctcg cctgtgccat tgtaaatacg gccggacgtg 21300
agacgggggg agagcactgg ttggctttcg gttggaaccc acgttctaac acctgctacc 21360
tttttgatcc ttttggattc tcggatgatc gtctcaaaca gatttaccag tttgaatatg 21420
agggtctcct gcgccgcagc gctcttgcta ccaaggaccg ctgtattacg ctggaaaaat 21480
ctacccagac cgtgcagggt ccccgttctg ccgcctgcgg acttttctgc tgcatgttcc 21540
ttcacgcctt tgtgcactgg cctgaccgtc ccatggacgg aaaccccacc atgaaattgc 21600
taactggagt gccaaacaac atgcttcatt ctcctaaagt ccagcccacc ctgtgtgaca 21660
atcaaaaagc actctaccat tttcttaata cccattcgcc ttattttcgc tcccatcgta 21720
cacacatcga aagggccact gcgttcgacc gtatggatgt tcaataatga ctcatgtaaa 21780
caacgtgttc aataaacatc actttatttt tttacatgta tcaaggctct gcattactta 21840

```
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
```

```
tggaaggcga taatgccaga ctcgcagtac tcaagcgaag catcgaggtc acacacttcg  24300
catatcccgc tgtcaacctg cccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
```

```
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
ccccttttata aacccagggt ttatttcccc aaatggcttc acacaaagcc caaacggagt  28500
tcttacttta aaatgtttaa ccccactaac aaccacaggc ggatctctac agctaaaagt  28560
gggaggggga cttacagtgg atgacaccaa cggtttttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
aactacacac agaaatataa attttactgc agagctgttt ttcgattcta ctggtaattt  28980
```

-continued

```
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttgcga tcgccaggcc caccatggga tggagctgta tcatcctctt  29400
cttggtagca acagctacag gtgtccactc ccaggtgcag ctgcagcagt ctggggctga  29460
actggcaaga cctggggcct cagtgaagat gtcctgcaag gcttctggct acacctttac  29520
taggtacacg atgcactggg taaaacagag gcctggacag ggtctggaat ggattggata  29580
cattaatcct agccgtggtt atactaatta caatcagaag ttcaaggaca aggccacatt  29640
gactacagac aaatcctcca gcacagccta catgcaactg agcagcctga catctgagga  29700
ctctgcagtc tattactgtg caagatatta tgatgatcat tactgccttg actactgggg  29760
ccaaggcacc actctcacag tctcctcagg tggcggtggc tcgggcggtg gtggatctgg  29820
tggcggcgga tctgatatcg tgctcactca gtctccagca atcatgtctg catctccagg  29880
ggagaaggtc accatgacct gcagtgccag ctcaagtgta agttacatga actggtacca  29940
gcagaagtca ggcacctccc ccaaaagatg gatttatgac acatccaaac tggcttctgg  30000
agtccctgct cacttcaggg gcagtgggtc tgggacctct tactctctca caatcagcgg  30060
catggaggct gaagatgctg ccacttatta ctgccagcag tggagtagta acccattcac  30120
gttcggctcg gggacaaagt tggaaataaa ccggggatcc gaacaaaaac tcatctcaga  30180
agaggatctg aatgctgtgg gccaggacac gcaggaggtc atcgtggtgc cacactcctt  30240
gccctttaag gtggtggtga tctcagccat cctggccctg gtggtgctca ccatcatctc  30300
ccttatcatc ctcatcatgc tttggcagaa gaagccacgt ggaagcggag ctactaactt  30360
cagcctgctg aagcaggctg gagacgtgga ggagaaccct ggacctggcc acacacggag  30420
gcagggaaca tcaccatcca agtgtccata cctcaatttc tttcagctct tggtgctggc  30480
tggtctttct cacttctgtt caggtgttat ccacgtgacc aaggaagtga aagaagtggc  30540
aacgctgtcc tgtggtcaca atgtttctgt tgaagagctg gcacaaactc gcatctactg  30600
gcaaaaggag aagaaaatgg tgctgactat gatgtctggg gacatgaata tatggcccga  30660
gtacaagaac cggaccatct ttgatatcac taataacctc tccattgtga tcctggctct  30720
gcgcccatct gacgagggca catacgagtg tgttgttctg aagtatgaaa aagacgcttt  30780
caagcgggaa cacctggctg aagtgacgtt atcagtcaaa gctgacttcc ctacacctag  30840
tatatctgac tttgaaattc caacttctaa tattagaagg ataatttgct caacctctgg  30900
aggttttcca gagcctcacc tctcctggtt ggaaaatgga gaagaattaa atgccatcaa  30960
cacaacagtt tcccaagatc ctgaaactga gctctatgct gttagcagca aactggattt  31020
caatatgaca accaaccaca gcttcatgtg tctcatcaag tatggacatt taagagtgaa  31080
tcagaccttc aactggaata caaccaagca agagcatttt cctgataacc tgctcccatc  31140
ctgggccatt accttaatct cagtaaatgg aatttttgtg atatgctgcc tgacctactg  31200
ctttgcccca agatgcagag agagaaggag gaatgagaga ttgagaaggg aaagtgtacg  31260
ccctgtataa gctagcttga ctgactgaga tacagcgtac cttcagctca cagacatgat  31320
```

-continued

```
aagatacatt gatgagtttg gacaaaccac aactagaatg cagtgaaaaa aatgctttat  31380
ttgtgaaatt tgtgatgcta ttgctttatt tgtaaccatt ataagctgca ataaacaagt  31440
taacaacaac aattgcattc attttatgtt tcaggttcag ggggaggtgt gggaggtttt  31500
ttaaagcaag taaaacctct acaaatgtgg tagtcgtcag ctatcctgca ggaacttgtt  31560
tatttgaaaa tcaattcaca aaatccgagt agttattttg cctcccctt cccatttaac  31620
agaatacacc aatctctccc cacgcacagc tttaaacatt tggataccat tagatataga  31680
catggtttta gattccacat tccaaacagt ttcagagcga gccaatctgg ggtcagtgat  31740
agataaaaat ccatcgggat agtcttttaa agcgctttca cagtccaact gctgcggatg  31800
cgactccgga gtctggatca cggtcatctg gaagaagaac gatgggaatc ataatccgaa  31860
aacggtatcg gacgattgtg tctcatcaaa cccacaagca gccgctgtct gcgtcgctcc  31920
gtgcgactgc tgtttatggg atcagggtcc acagtgtcct gaagcatgat tttaatagcc  31980
cttaacatca actttctggt gcgatgcgcg cagcaacgca ttctgatttc actcaaatct  32040
ttgcagtagg tacaacacat tattacaata ttgtttaata aaccataatt aaaagcgctc  32100
cagccaaaac tcatatctga tataatcgcc cctgcatgac catcatacca aagtttaata  32160
taaattaaat gacgttccct caaaaacaca ctacccacat acatgatctc ttttggcatg  32220
tgcatattaa caatctgtct gtaccatgga caacgttggt taatcatgca acccaatata  32280
accttccgga accacactgc caacaccgct cccccagcca tgcattgaag tgaaccctgc  32340
tgattacaat gacaatgaag aacccaattc tctcgaccgt gaatcacttg agaatgaaaa  32400
atatctatag tggcacaaca tagacataaa tgcatgcatc ttctcataat ttttaactcc  32460
tcaggattta gaaacatatc ccagggaata ggaagctctt gcagaacagt aaagctggca  32520
gaacaaggaa gaccacgaac acaacttaca ctatgcatag tcatagtatc acaatctggc  32580
aacagcgggt ggtcttcagt catagaagct cgggtttcat tttcctcaca acgtggtaac  32640
tgggctctgg tgtaagggtg atgtctggcg catgatgtcg agcgtgcgcg caaccttgtc  32700
ataatggagt tgcttcctga cattctcgta ttttgtatag caaaacgcgg ccctggcaga  32760
acacactctt cttcgccttc tatcctgccg cttagcgtgt tccgtgtgat agttcaagta  32820
caaccacact cttaagttgg tcaaaagaat gctggcttca gttgtaatca aaactccatc  32880
gcatctaatc gttctgagga aatcatccaa gcaatgcaac tggattgtgt ttcaagcagg  32940
agaggagagg gaagagacgg aagaaccatg ttaattttta ttccaaacga tctcgcagta  33000
cttcaaattg tagatcgcgc agatggcatc tctcgccccc actgtgttgg tgaaaaagca  33060
cagctagatc aaaagaaatg cgattttcaa ggtgctcaac ggtggcttcc agcaaagcct  33120
ccacgcgcac atccaagaac aaaagaatac caaaagaagg agcattttct aactcctcaa  33180
tcatcatatt acattcctgc accattccca gataattttc agctttccag ccttgaatta  33240
ttcgtgtcag ttcttgtggt aaatccaatc cacacattac aaacaggtcc cggagggcgc  33300
cctccaccac cattcttaaa cacaccctca taatgacaaa atatcttgct cctgtgtcac  33360
ctgtagcgaa ttgagaatgg caacatcaat tgacatgccc ttggctctaa gttcttcttt  33420
aagttctagt tgtaaaaact ctctcatatt atcaccaaac tgcttagcca gaagcccccc  33480
gggaacaaga gcaggggacg ctacagtgca gtacaagcgc agacctcccc aattggctcc  33540
agcaaaaaca agattggaat aagcatattg ggaaccgcca gtaatatcat cgaagttgct  33600
ggaaatataa tcaggcagag tttcttgtaa aaattgaata aaagaaaaat ttgccaaaaa  33660
aacattcaaa acctctggga tgcaaatgca ataggttacc gcgctgcgct ccaacattgt  33720
```

tagttttgaa ttagtctgca aaaataaaaa aaaaaacaag cgtcatatca tagtagcctg 33780
acgaacagat ggataaatca gtctttccat cacaagacaa gccacagggt ctccagctcg 33840
accctcgtaa aacctgtcat catgattaaa caacagcacc gaaagttcct cgcggtgacc 33900
agcatgaata attcttgatg aagcatacaa tccagacatg ttagcatcag ttaacgagaa 33960
aaaacagcca acatagcctt tgggtataat tatgcttaat cgtaagtata gcaaagccac 34020
ccctcgcgga tacaaagtaa aaggcacagg agaataaaaa atataattat ttctctgctg 34080
ctgttcaggc aacgtcgccc ccggtccctc taaatacaca tacaaagcct catcagccat 34140
ggcttaccag acaaagtaca gcgggcacac aaagcacaag ctctaaagtg actctccaac 34200
ctctccacaa tatatatata cacaagccct aaactgacgt aatgggagta aagtgtaaaa 34260
aatcccgcca aacccaacac acaccccgaa actgcgtcac cagggaaaag tacagtttca 34320
cttccgcaat cccaacaggc gtaacttcct ctttctcacg gtacgtgata tcccactaac 34380
ttgcaacgtc attttcccac ggtcgcaccg ccccttttag ccgttaaccc cacagccaat 34440
caccacacga tccacacttt ttaaaatcac ctcatttaca tattggcacc attccatcta 34500
taaggtatat tatatagata ga 34522

<210> SEQ ID NO 101
<211> LENGTH: 9
<212> TYPE: PRT
<213> ORGANISM: Artificial Sequence
<220> FEATURE:
<223> OTHER INFORMATION: V5 TAG

<400> SEQUENCE: 101

Ile Pro Asn Pro Leu Leu Gly Leu Asp
1 5

<210> SEQ ID NO 102
<211> LENGTH: 34555
<212> TYPE: DNA
<213> ORGANISM: Artificial Sequence
<220> FEATURE:
<223> OTHER INFORMATION: NG-348A virus genome sequence comprising the EnAd genome with a transgene cassette that encodes a membrane-anchored chimeric form of the single chain Fv anti-human CD3e with C-terminal V5 tag and the T lymphocyte activation antigen, CD80 inserted in region BY

<400> SEQUENCE: 102
tctatctata taatatacct tatagatgga atggtgccaa tatgtaaatg aggtgatttt 60
aaaaagtgtg gatcgtgtgg tgattggctg tggggttaac ggctaaaagg ggcggtgcga 120
ccgtgggaaa atgacgtttt gtgggggtgg agtttttttg caagttgtcg cgggaaatgt 180
gacgcataaa aaggcttttt tctcacggaa ctacttagtt ttcccacggt atttaacagg 240
aaatgaggta gttttgaccg gatgcaagtg aaaattgttg attttcgcgc gaaaactgaa 300
tgaggaagtg tttttctgaa taatgtggta tttatggcag ggtggagtat ttgttcaggg 360
ccaggtagac tttgacccat tacgtggagg tttcgattac cgtgtttttt acctgaattt 420
ccgcgtaccg tgtcaaagtc ttctgttttt acgtaggtgt cagctgatcg ctagggtatt 480
tatacctcag ggtttgtgtc aagaggccac tcttgagtgc cagcgagaag agttttctcc 540
tctgcgccgg cagtttaata ataaaaaaat gagagatttg cgatttctgc ctcaggaaat 600
aatctctgct gagactggaa atgaaatatt ggagcttgtg gtgcacgccc tgatgggaga 660
cgatccggag ccacctgtgc agctttttga gcctcctacg cttcaggaac tgtatgattt 720

-continued

```
agaggtagag ggatcggagg attctaatga ggaagctgta aatggctttt ttaccgattc    780
tatgctttta gctgctaatg aagggttaga attagatccg cctttggaca cttttgatac    840
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
```

-continued

```
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct   3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaacttttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
```

-continued

```
gtatgcatct gcgccgcagg aggcgcaaac agtttcacat tccaccagcc aggttaaatc   5520
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg gggtccccgc   5880
tggggggggta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
```

-continued

```
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
```

```
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt ttttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
```

```
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgcccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
```

tcacctgcgg agcagagcag gtctactggt cgcttccaga catgatgaag gatcctgtca 15000
ctttccgctc cactagacaa gtcagtaact accctgtggt gggtgcagag cttatgcccg 15060
tcttctcaaa gagcttctac aacgaacaag ctgtgtactc ccagcagctc cgccagtcca 15120
cctcgcttac gcacgtcttc aaccgctttc ctgagaacca gattttaatc cgtccgccgg 15180
cgcccaccat taccaccgtc agtgaaaacg ttcctgctct cacagatcac gggaccctgc 15240
cgttgcgcag cagtatccgg ggagtccaac gtgtgaccgt tactgacgcc agacgccgca 15300
cctgtcccta cgtgtacaag gcactgggca tagtcgcacc gcgcgtcctt tcaagccgca 15360
ctttctaaaa aaaaaaaaaa tgtccattct tatctcgccc agtaataaca ccggttgggg 15420
tctgcgcgct ccaagcaaga tgtacggagg cgcacgcaaa cgttctaccc aacatcctgt 15480
ccgtgttcgc ggacattttc gcgctccatg ggcgccctc aagggccgca ctcgcgttcg 15540
aaccaccgtc gatgatgtaa tcgatcaggt ggttgccgac gcccgtaatt atactcctac 15600
tgcgcctaca tctactgtgg atgcagttat tgacagtgta gtggctgacg ctcgcaacta 15660
tgctcgacgt aagagccggc gaaggcgcat tgccagacgc caccgagcta ccactgccat 15720
gcgagccgca agagctctgc tacgaagagc tagacgcgtg gggcgaagag ccatgcttag 15780
ggcggccaga cgtgcagctt cgggcgccag cgccggcagg tcccgcaggc aagcagccgc 15840
tgtcgcagcg gcgactattg ccgacatggc ccaatcgcga agaggcaatg tatactgggt 15900
gcgtgacgct gccaccggtc aacgtgtacc cgtgcgcacc cgtcccctc gcacttagaa 15960
gatactgagc agtctccgat gttgtgtccc agcggcgagg atgtccaagc gcaaatacaa 16020
ggaagaaatg ctgcaggtta tcgcacctga agtctacggc caaccgttga aggatgaaaa 16080
aaaaccccgc aaaatcaagc gggttaaaaa ggacaaaaaa gaagaggaag atggcgatga 16140
tgggctggcg gagtttgtgc gcgagtttgc cccacggcga cgcgtgcaat ggcgtgggcg 16200
caaagttcga catgtgttga gacctggaac ttcggtggtc tttacacccg gcgagcgttc 16260
aagcgctact tttaagcgtt cctatgatga ggtgtacggg gatgatgata ttcttgagca 16320
ggcggctgac cgattaggcg agtttgctta tggcaagcgt agtagaataa cttccaagga 16380
tgagacagtg tcgataccct tggatcatgg aaatcccacc cctagtctta aaccggtcac 16440
tttgcagcaa gtgttacccg taactccgcg aacaggtgtt aaacgcgaag gtgaagattt 16500
gtatcccact atgcaactga tggtacccaa acgccagaag ttggaggacg ttttggagaa 16560
agtaaaagtg gatccagata ttcaacctga ggttaaagtg agacccatta agcaggtagc 16620
gcctggtctg gggtacaaa ctgtagacat taagattccc actgaaagta tggaagtgca 16680
aactgaaccc gcaaagccta ctgccacctc cactgaagtg caaacggatc catggatgcc 16740
catgcctatt acaactgacg ccgccggtcc cactcgaaga tcccgacgaa agtacggtcc 16800
agcaagtctg ttgatgccca attatgttgt acacccatct attattccta ctcctggtta 16860
ccgaggcact cgctactatc gcagccgaaa cagtacctcc cgccgtcgcc gcaagacacc 16920
tgcaaatcgc agtcgtcgcc gtagacgcac aagcaaaccg actcccggcg ccctggtgcg 16980
gcaagtgtac cgcaatggta gtgcggaacc tttgacactg ccgcgtgcgc gttaccatcc 17040
gagtatcatc acttaatcaa tgttgccgct gcctccttgc agatatggcc ctcacttgtc 17100
gccttcgcgt tcccatcact ggttaccgag gaagaaactc gcgccgtaga agagggatgt 17160
tgggacgcgg aatgcgacgc tacaggcgac ggcgtgctat ccgcaagcaa ttgcggggtg 17220
gttttttacc agccttaatt ccaattatcg ctgctgcaat tggcgcgata ccaggcatag 17280

-continued

```
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
```

atctcccaga ctcgtacaaa tacaccccgt ccaatgtcac tcttccagaa aacaaaaaca 19740
cctacgacta catgaacggg cgggtggtgc cgccatctct agtagacacc tatgtgaaca 19800
ttggtgccag gtggtctctg gatgccatgg acaatgtcaa cccattcaac caccaccgta 19860
acgctggctt gcgttaccga tccatgcttc tgggtaacgg acgttatgtg cctttccaca 19920
tacaagtgcc tcaaaaattc ttcgctgtta aaaacctgct gcttctccca ggctcctaca 19980
cttatgagtg gaactttagg aaggatgtga acatggttct acagagttcc ctcggtaacg 20040
acctgcgggt agatggcgcc agcatcagtt tcacgagcat caacctctat gctacttttt 20100
tccccatggc tcacaacacc gcttccaccc ttgaagccat gctgcggaat gacaccaatg 20160
atcagtcatt caacgactac ctatctgcag ctaacatgct ctaccccatt cctgccaatg 20220
caaccaatat tcccatttcc attccttctc gcaactgggc ggctttcaga ggctggtcat 20280
ttaccagact gaaaaccaaa gaaactccct ctttggggtc tggatttgac ccctactttg 20340
tctattctgg ttctattccc tacctggatg gtaccttcta cctgaaccac acttttaaga 20400
aggtttccat catgtttgac tcttcagtga gctggcctgg aaatgacagg ttactatctc 20460
ctaacgaatt tgaaataaag cgcactgtgg atggcgaagg ctacaacgta gcccaatgca 20520
acatgaccaa agactggttc ttggtacaga tgctcgccaa ctacaacatc ggctatcagg 20580
gcttctacat tccagaagga tacaaagatc gcatgtattc atttttcaga aacttccagc 20640
ccatgagcag gcaggtggtt gatgaggtca attacaaaga cttcaaggcc gtcgccatac 20700
cctaccaaca caacaactct ggctttgtgg gttacatggc tccgaccatg cgccaaggtc 20760
aaccctatcc cgctaactat ccctatccac tcattggaac aactgccgta aatagtgtta 20820
cgcagaaaaa gttcttgtgt gacagaacca tgtggcgcat accgttctcg agcaacttca 20880
tgtctatggg ggcccttaca gacttgggac agaatatgct ctatgccaac tcagctcatg 20940
ctctggacat gacctttgag gtggatccca tggatgagcc caccctgctt tatcttctct 21000
tcgaagtttt cgacgtggtc agagtgcatc agccacaccg cggcatcatc gaggcagtct 21060
acctgcgtac accgttctcg gccggtaacg ctaccacgta agaagcttct tgcttcttgc 21120
aaatagcagc tgcaaccatg gcctgcggat cccaaaacgg ctccagcgag caagagctca 21180
gagccattgt ccaagacctg ggttgcggac cctatttttt gggaacctac gataagcgct 21240
tcccggggtt catggccccc gataagctcg cctgtgccat tgtaaatacg gccggacgtg 21300
agacgggggg agagcactgg ttggctttcg gttggaaccc acgttctaac acctgctacc 21360
tttttgatcc ttttggattc tcggatgatc gtctcaaaca gatttaccag tttgaatatg 21420
agggtctcct gcgccgcagc gctcttgcta ccaaggaccg ctgtattacg ctggaaaaat 21480
ctacccagac cgtgcagggt ccccgttctg ccgcctgcgg acttttctgc tgcatgttcc 21540
ttcacgcctt tgtgcactgg cctgaccgtc ccatggacgg aaaccccacc atgaaattgc 21600
taactggagt gccaaacaac atgcttcatt ctcctaaagt ccagcccacc ctgtgtgaca 21660
atcaaaaagc actctaccat tttcttaata cccattcgcc ttattttcgc tcccatcgta 21720
cacacatcga aagggccact gcgttcgacc gtatggatgt tcaataatga ctcatgtaaa 21780
caacgtgttc aataaacatc actttatttt tttacatgta tcaaggctct gcattactta 21840
tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020

-continued

```
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
```

aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac caccccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460
cgcgcttatt caaaaaaggc gggaattaca tcatcctcga catgagtaaa gaaattccca 26520
cgccttacat gtggagttat caaccccaaa tgggattggc ggcaggcgcc tcccaggact 26580
actccacccg catgaattgg ctcagcgccg ggccttctat gatttctcga gttaatgata 26640
tacgcgccta ccgaaaccaa atacttttgg aacagtcagc tcttaccacc acgccccgcc 26700
aacaccttaa tcccagaaat tggcccgccg ccctagtgta ccaggaaagt cccgctccca 26760
ccactgtatt acttcctcga gacgcccagg ccgaagtcca aatgactaat gcaggtgcgc 26820
agttagctgg cggctccacc ctatgtcgtc acaggcctcg gcataatata aaacgcctga 26880
tgatcagagg ccgaggtatc cagctcaacg acgagtcggt gagctctccg cttggtctac 26940
gaccagacgg aatctttcag attgccggct gcgggagatc ttccttcacc cctcgtcagg 27000
ctgttctgac tttggaaagt tcgtcttcgc aaccccgctc gggcggaatc gggaccgttc 27060
aatttgtgga ggagtttact ccctctgtct acttcaaccc cttctccgga tctcctgggc 27120
attacccgga cgagttcata ccgaacttcg acgcgattag cgagtcagtg gacggctacg 27180
attgatgtct ggtgacgcgg ctgagctatc tcggctgcga catctagacc actgccgccg 27240
ctttcgctgc tttgcccggg aactcattga gttcatctac ttcgaactcc ccaaggatca 27300
ccctcaaggt ccggcccacg gagtgcggat ttctatcgaa ggcaaaatag actctcgcct 27360
gcaacgaatt ttctcccagc ggcccgtgct gatcgagcga gaccagggaa acaccacggt 27420
ttccatctac tgcatttgta atcaccccgg attgcatgaa agcctttgct gtcttatgtg 27480
tactgagttt aataaaaact gaattaagac tctcctacgg actgccgctt cttcaacccg 27540
gattttacaa ccagaagaac gaaacttttc ctgtcgtcca ggactctgtt aacttcacct 27600
ttcctactca caaactagaa gctcaacgac tacaccgctt ttccagaagc attttcccta 27660
ctaatactac tttcaaaacc ggaggtgagc tccaaggtct tcctacagaa aacccttggg 27720
tggaagcggg ccttgtagtg ctaggaattc ttgcgggtgg gcttgtgatt attctttgct 27780
acctatacac accttgcttc actttcttag tggtgttgtg gtattggttt aaaaaatggg 27840
gcccatacta gtcttgcttg ttttactttc gcttttggaa ccgggttctg ccaattacga 27900
tccatgtcta gacttcgacc cagaaaactg cacacttact tttgcacccg acacaagccg 27960
catctgtgga gttcatcgcc tctcttacga acttggcccc caacgacaaa aatttacctg 28020
catggtggga atcaacccca tagttatcac ccagcaaagt ggagatacta agggttgcat 28080
tcactgctcc tgcgattcca tcgagtgcac ctacaccctg ctgaagaccc tatgcggcct 28140
aagagacctg ctaccaatga attaaaaaat gattaataaa aatcactta cttgaaatca 28200
gcaataaggt ctctgttgaa attttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta cccctatgaa gatgaaagca cctcccaaca 28440
ccccttata aacccagggt ttatttcccc aaatggcttc acacaaagcc caaacggagt 28500
tcttacttta aaatgtttaa ccccactaac aaccacaggc ggatctctac agctaaaagt 28560
gggaggggga cttacagtgg atgacaccaa cggtttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920
aactacacac agaaatataa attttactgc agagctgttt ttcgattcta ctggtaattt 28980
actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct tttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttgcga tcgccaggcc caccatggga tggagctgta tcatcctctt 29400
cttggtagca acagctacag gtgtccactc ccaggtgcag ctgcagcagt ctggggctga 29460
actggcaaga cctggggcct cagtgaagat gtcctgcaag gcttctggct acacctttac 29520
taggtacacg atgcactggg taaaacagag gcctggacag ggtctggaat ggattggata 29580
cattaatcct agccgtggtt atactaatta caatcagaag ttcaaggaca aggccacatt 29640
gactacagac aaatcctcca gcacagccta catgcaactg agcagcctga catctgagga 29700
ctctgcagtc tattactgtg caagatatta tgatgatcat tactgccttg actactgggg 29760
ccaaggcacc actctcacag tctcctcagg tggcggtggc tcgggcggtg gtggatctgg 29820
tggcggcgga tctgatatcg tgctcactca gtctccagca atcatgtctg catctccagg 29880
ggagaaggtc accatgacct gcagtgccag ctcaagtgta agttacatga actggtacca 29940
gcagaagtca ggcacctccc ccaaaagatg gatttatgac acatccaaac tggcttctgg 30000
agtccctgct cacttcaggg gcagtgggtc tgggacctct tactctctca caatcagcgg 30060
catggaggct gaagatgctg ccacttatta ctgccagcag tggagtagta acccattcac 30120
gttcggctcg gggacaaagt tggaaataaa ccggggatcc gaacaaaaac tcatctcaga 30180
agaggatctg aatgctgtgg gccaggacac gcaggaggtc atcgtggtgc cacactcctt 30240
gccctttaag gtggtggtga tctcagccat cctggccctg gtggtgctca ccatcatctc 30300
ccttatcatc ctcatcatgc tttggcagaa gaagccacgt ggttcaatcc ctaaccctct 30360
cctcggtctc gatggaagcg gagctactaa cttcagcctg ctgaagcagg ctggagacgt 30420
ggaggagaac cctggacctg gccacacacg gaggcaggga acatcaccat ccaagtgtcc 30480
atacctcaat ttctttcagc tcttggtgct ggctggtctt tctcacttct gttcaggtgt 30540
tatccacgtg accaaggaag tgaaagaagt ggcaacgctg tcctgtggtc acaatgtttc 30600
tgttgaagag ctggcacaaa ctcgcatcta ctggcaaaag gagaagaaaa tggtgctgac 30660
tatgatgtct ggggacatga atatatggcc cgagtacaag aaccggacca tctttgatat 30720
cactaataac ctctccattg tgatcctggc tctgcgccca tctgacgagg gcacatacga 30780
gtgtgttgtt ctgaagtatg aaaaagacgc tttcaagcgg gaacacctgg ctgaagtgac 30840
gttatcagtc aaagctgact tccctacacc tagtatatct gactttgaaa ttccaacttc 30900
taatattaga aggataattt gctcaacctc tggaggtttt ccagagcctc acctctcctg 30960
gttggaaaat ggagaagaat taaatgccat caacacaaca gtttcccaag atcctgaaac 31020
tgagctctat gctgttagca gcaaactgga tttcaatatg acaaccaacc acagcttcat 31080
gtgtctcatc aagtatggac atttaagagt gaatcagacc ttcaactgga atacaaccaa 31140
gcaagagcat ttttcctgata acctgctccc atcctgggcc attaccttaa tctcagtaaa 31200
tggaattttt gtgatatgct gcctgaccta ctgctttgcc ccaagatgca gagagagaag 31260
gaggaatgag agattgagaa gggaaagtgt acgccctgta taagctagct tgactgactg 31320
agatacagcg taccttcagc tcacagacat gataagatac attgatgagt ttggacaaac 31380
cacaactaga atgcagtgaa aaaaatgctt tatttgtgaa atttgtgatg ctattgcttt 31440
atttgtaacc attataagct gcaataaaca agttaacaac aacaattgca ttcattttat 31500

-continued gtttcaggtt caggggggagg tgtgggaggt tttttaaagc aagtaaaacc tctacaaatg 31560
tggtagtcgt cagctatcct gcaggaactt gtttatttga aaatcaattc acaaaatccg 31620
agtagttatt ttgcctcccc cttcccattt aacagaatac accaatctct ccccacgcac 31680
agctttaaac atttggatac cattagatat agacatggtt ttagattcca cattccaaac 31740
agtttcagag cgagccaatc tggggtcagt gatagataaa aatccatcgg gatagtcttt 31800
taaagcgctt tcacagtcca actgctgcgg atgcgactcc ggagtctgga tcacggtcat 31860
ctggaagaag aacgatggga atcataatcc gaaaacggta tcggacgatt gtgtctcatc 31920
aaacccacaa gcagccgctg tctgcgtcgc tccgtgcgac tgctgtttat gggatcaggg 31980
tccacagtgt cctgaagcat gattttaata gcccttaaca tcaactttct ggtgcgatgc 32040
gcgcagcaac gcattctgat ttcactcaaa tctttgcagt aggtacaaca cattattaca 32100
atattgttta ataaaccata attaaaagcg ctccagccaa aactcatatc tgatataatc 32160
gcccctgcat gaccatcata ccaaagttta atataaatta aatgacgttc cctcaaaaac 32220
acactaccca catacatgat ctcttttggc atgtgcatat taacaatctg tctgtaccat 32280
ggacaacgtt ggttaatcat gcaacccaat ataaccttcc ggaaccacac tgccaacacc 32340
gctcccccag ccatgcattg aagtgaaccc tgctgattac aatgacaatg aagaacccaa 32400
ttctctcgac cgtgaatcac ttgagaatga aaaatatcta tagtggcaca acatagacat 32460
aaatgcatgc atcttctcat aatttttaac tcctcaggat ttagaaacat atcccaggga 32520
ataggaagct cttgcagaac agtaaagctg gcagaacaag gaagaccacg aacacaactt 32580
acactatgca tagtcatagt atcacaatct ggcaacagcg ggtggtcttc agtcatagaa 32640
gctcgggttt cattttcctc acaacgtggt aactgggctc tggtgtaagg gtgatgtctg 32700
gcgcatgatg tcgagcgtgc gcgcaacctt gtcataatgg agttgcttcc tgacattctc 32760
gtattttgta tagcaaaacg cggccctggc agaacacact cttcttcgcc ttctatcctg 32820
ccgcttagcg tgttccgtgt gatagttcaa gtacaaccac actcttaagt tggtcaaaag 32880
aatgctggct tcagttgtaa tcaaaactcc atcgcatcta atcgttctga ggaaatcatc 32940
caagcaatgc aactggattg tgtttcaagc aggagaggag agggaagaga cggaagaacc 33000
atgttaattt ttattccaaa cgatctcgca gtacttcaaa ttgtagatcg cgcagatggc 33060
atctctcgcc cccactgtgt tggtgaaaaa gcacagctag atcaaaagaa atgcgatttt 33120
caaggtgctc aacggtggct tccagcaaag cctccacgcg cacatccaag aacaaaagaa 33180
taccaaaaga aggagcattt tctaactcct caatcatcat attacattcc tgcaccattc 33240
ccagataatt ttcagctttc cagccttgaa ttattcgtgt cagttcttgt ggtaaatcca 33300
atccacacat tacaaacagg tcccggaggg cgccctccac caccattctt aaacacaccc 33360
tcataatgac aaaatatctt gctcctgtgt cacctgtagc gaattgagaa tggcaacatc 33420
aattgacatg cccttggctc taagttcttc tttaagttct agttgtaaaa actctctcat 33480
attatcacca aactgcttag ccagaagccc cccgggaaca agagcagggg acgctacagt 33540
gcagtacaag cgcagacctc cccaattggc tccagcaaaa acaagattgg aataagcata 33600
ttgggaaccg ccagtaatat catcgaagtt gctggaaata taatcaggca gagtttcttg 33660
taaaaattga ataaaagaaa aatttgccaa aaaaacattc aaaacctctg ggatgcaaat 33720
gcaataggtt accgcgctgc gctccaacat tgttagtttt gaattagtct gcaaaaataa 33780
aaaaaaaaac aagcgtcata tcatagtagc ctgacgaaca gatggataaa tcagtctttc 33840
catcacaaga caagccacag ggtctccagc tcgaccctcg taaaacctgt catcatgatt 33900
aaacaacagc accgaaagtt cctcgcggtg accagcatga ataattcttg atgaagcata 33960
caatccagac atgttagcat cagttaacga gaaaaaacag ccaacatagc ctttgggtat 34020
aattatgctt aatcgtaagt atagcaaagc cacccctcgc ggatacaaag taaaaggcac 34080
aggagaataa aaaatataat tatttctctg ctgctgttca ggcaacgtcg cccccggtcc 34140
ctctaaatac acatacaaag cctcatcagc catggcttac cagacaaagt acagcgggca 34200
cacaaagcac aagctctaaa gtgactctcc aacctctcca caatatatat atacacaagc 34260
cctaaactga cgtaatggga gtaaagtgta aaaaatcccg ccaaacccaa cacacacccc 34320
gaaactgcgt caccagggaa aagtacagtt tcacttccgc aatcccaaca ggcgtaactt 34380
cctctttctc acggtacgtg atatcccact aacttgcaac gtcattttcc cacggtcgca 34440
ccgccccttt tagccgttaa ccccacagcc aatcaccaca cgatccacac tttttaaaat 34500
cacctcattt acatattggc accattccat ctataaggta tattatatag ataga 34555

<210> SEQ ID NO 103
<211> LENGTH: 33595
<212> TYPE: DNA
<213> ORGANISM: Artificial Sequence
<220> FEATURE:
<223> OTHER INFORMATION: NG-420 virus genome sequence comprising the EnAd genome with a transgene cassette that encodes a membrane-anchored chimeric form of the single chain Fv anti-human CD3e inserted in the region BY.

<400> SEQUENCE: 103
tctatctata taatatacct tatagatgga atggtgccaa tatgtaaatg aggtgatttt 60
aaaaagtgtg gatcgtgtgg tgattggctg tggggttaac ggctaaaagg ggcggtgcga 120
ccgtgggaaa atgacgtttt gtgggggtgg agtttttttg caagttgtcg cgggaaatgt 180
gacgcataaa aaggcttttt tctcacggaa ctacttagtt ttcccacggt atttaacagg 240
aaatgaggta gttttgaccg gatgcaagtg aaaattgttg attttcgcgc gaaaactgaa 300
tgaggaagtg tttttctgaa taatgtggta tttatggcag ggtggagtat ttgttcaggg 360
ccaggtagac tttgacccat tacgtggagg tttcgattac cgtgtttttt acctgaattt 420
ccgcgtaccg tgtcaaagtc ttctgttttt acgtaggtgt cagctgatcg ctagggtatt 480
tatacctcag ggtttgtgtc aagaggccac tcttgagtgc cagcgagaag agttttctcc 540
tctgcgccgg cagtttaata ataaaaaaat gagagatttg cgatttctgc ctcaggaaat 600
aatctctgct gagactggaa atgaaatatt ggagcttgtg gtgcacgccc tgatgggaga 660
cgatccggag ccacctgtgc agctttttga gcctcctacg cttcaggaac tgtatgattt 720
agaggtagag ggatcggagg attctaatga ggaagctgta aatggctttt ttaccgattc 780
tatgctttta gctgctaatg aagggttaga attagatccg cctttggaca cttttgatac 840
tccaggggta attgtggaaa gcggtacagg tgtaagaaaa ttacctgatt tgagttccgt 900
ggactgtgat ttgcactgct atgaagacgg gtttcctccg agtgatgagg aggaccatga 960
aaaggagcag tccatgcaga ctgcagcggg tgagggagtg aaggctgcca atgttggttt 1020
tcagttggat tgcccggagc ttcctggaca tggctgtaag tcttgtgaat ttcacaggaa 1080
aaatactgga gtaaaggaac tgttatgttc gctttgttat atgagaacgc actgccactt 1140
tatttacagt aagtgtgttt aagttaaaat ttaaaggaat atgctgtttt tcacatgtat 1200
attgagtgtg agttttgtgc ttcttattat aggtcctgtg tctgatgctg atgaatcacc 1260
atctcctgat tctactacct cacctcctga gattcaagca cctgttcctg tggacgtgcg 1320

-continued caagcccatt cctgtgaagc ttaagcctgg gaaacgtcca gcagtggaaa aacttgagga 1380
cttgttacag ggtggggacg gacctttgga cttgagtaca cggaaacgtc caagacaata 1440
agtgttccat atccgtgttt acttaaggtg acgtcaatat ttgtgtgaca gtgcaatgta 1500
ataaaaatat gttaactgtt cactggtttt tattgctttt tgggcgggga ctcaggtata 1560
taagtagaag cagacctgtg tggttagctc ataggagctg gctttcatcc atggaggttt 1620
gggccatttt ggaagacctt aggaagacta ggcaactgtt agagaacgct tcggacggag 1680
tctccggttt ttggagattc tggttcgcta gtgaattagc tagggtagtt tttaggataa 1740
aacaggacta taaacaagaa tttgaaaagt tgttggtaga ttgcccagga ctttttgaag 1800
ctcttaattt gggccatcag gttcacttta aagaaaaagt tttatcagtt ttagactttt 1860
caaccccagg tagaactgct gctgctgtgg cttttcttac ttttatatta gataaatgga 1920
tcccgcagac tcatttcagc aggggatacg ttttggattt catagccaca gcattgtgga 1980
gaacatggaa ggttcgcaag atgaggacaa tcttaggtta ctggccagtg cagcctttgg 2040
gtgtagcggg aatcctgagg catccaccgg tcatgccagc ggttctggag gaggaacagc 2100
aagaggacaa cccgagagcc ggcctggacc ctccagtgga ggaggcggag tagctgactt 2160
gtctcctgaa ctgcaacggg tgcttactgg atctacgtcc actggacggg ataggggcgt 2220
taagagggag agggcatcta gtggtactga tgctagatct gagttggctt taagtttaat 2280
gagtcgcaga cgtcctgaaa ccatttggtg gcatgaggtt cagaaagagg gaagggatga 2340
agtttctgta ttgcaggaga aatattcact ggaacaggtg aaaacatgtt ggttggagcc 2400
tgaggatgat tgggaggtgg ccattaaaaa ttatgccaag atagctttga ggcctgataa 2460
acagtataag attactagac ggattaatat ccggaatgct tgttacatat ctggaaatgg 2520
ggctgaggtg gtaatagata ctcaagacaa ggcagttatt agatgctgca tgatggatat 2580
gtggcctggg gtagtcggta tggaagcagt aacttttgta aatgttaagt ttaggggaga 2640
tggttataat ggaatagtgt ttatggccaa taccaaactt atattgcatg gttgtagctt 2700
ttttggtttc aacaatacct gtgtagatgc ctggggacag gttagtgtac ggggatgtag 2760
tttctatgcg tgttggattg ccacagctgg cagaaccaag agtcaattgt ctctgaagaa 2820
atgcatattt caaagatgta acctgggcat tctgaatgaa ggcgaagcaa gggtccgcca 2880
ctgcgcttct acagatactg gatgttttat tttgattaag ggaaatgcca gcgtaaagca 2940
taacatgatt tgcggtgctt ccgatgagag gccttatcaa atgctcactt gtgctggtgg 3000
gcattgtaat atgctggcta ctgtgcatat tgtttcccat caacgcaaaa aatggcctgt 3060
ttttgatcac aatgtgatga cgaagtgtac catgcatgca ggtgggcgta gaggaatgtt 3120
tatgccttac cagtgtaaca tgaatcatgt gaaagtgttg ttggaaccag atgccttttc 3180
cagaatgagc ctaacaggaa tttttgacat gaacatgcaa atctggaaga tcctgaggta 3240
tgatgatacg agatcgaggg tacgcgcatg cgaatgcgga ggcaagcatg ccaggttcca 3300
gccggtgtgt gtagatgtga ctgaagatct cagaccggat catttggtta ttgcccgcac 3360
tggagcagag ttcggatcca gtggagaaga aactgactaa ggtgagtatt gggaaaactt 3420
tggggtggga ttttcagatg gacagattga gtaaaaattt gtttttctgt tcttgcagct 3480
gtcatgagtg gaaacgcttc ttttaagggg ggagtcttca gcccttatct gacagggcgt 3540
ctcccatcct gggcaggagt tcgtcagaat gttatgggat ctactgtgga tggaagaccc 3600
gtccaacccg ccaattcttc aacgctgacc tatgctactt taagttcttc acctttggac 3660

-continued gcagctgcag ctgccgccgc cgcttctgtt gccgctaaca ctgtgcttgg aatgggttac 3720
tatggaagca tcatggctaa ttccacttcc tctaataacc cttctaccct gactcaggac 3780
aagttacttg tccttttggc ccagctggag gctttgaccc aacgtctggg tgaacttttct 3840 cagcaggtgg tcgagttgcg agtacaaact gagtctgctg tcggcacggc aaagtctaaa 3900
taaaaaaatc ccagaatcaa tgaataaata aacaagcttg ttgttgattt aaaatcaagt 3960
gtttttattt catttttcgc gcacggtatg ccctagacca ccgatctcta tcattgagaa 4020
ctcggtggat tttttccagg atcctataga ggtgggattg aatgtttaga tacatgggca 4080
ttaggccgtc tttggggtgg agatagctcc attgaaggga ttcatgctcc ggggtagtgt 4140
tgtaaatcac ccagtcataa caaggtcgca gtgcatggtg ttgcacaata tcttttagaa 4200
gtaggctgat tgccacagat aagcccttgg tgtaggtgtt tacaaaccgg ttgagctggg 4260
atgggtgcat tcggggtgaa attatgtgca ttttggattg gatttttaag ttggcaatat 4320
tgccgccaag atcccgtctt gggttcatgt tatgaaggac caccaagacg gtgtatccgg 4380
tacatttagg aaatttatcg tgcagcttgg atggaaaagc gtggaaaaat ttggagacac 4440
ccttgtgtcc tccaagattt tccatgcact catccatgat aatagcaatg gggccgtggg 4500
cagcggcgcg ggcaaacacg ttccgtgggt ctgacacatc atagttatgt tcctgagtta 4560
aatcatcata agccatttta atgaatttgg ggcggagagt accagattgg ggtatgaatg 4620
ttccttcggg ccccggagca tagttcccct cacagatttg catttcccaa gctttcagtt 4680
ccgagggtgg aatcatgtcc acctgggggg ctatgaaaaa caccgtttct ggggcggggg 4740
tgattaattg tgatgatagc aaatttctga gcaattgaga tttgccacat ccggtggggc 4800
cataaatgat tccgattacg ggttgcaggt ggtagtttag ggaacggcaa ctgccgtctt 4860
ctcgaagcaa gggggccacc tcgttcatca tttcccttac atgcatattt tcccgcacca 4920
aatccattag gaggcgctct cctcctagtg atagaagttc ttgtagtgag gaaaagtttt 4980
tcagcggttt cagaccgtca gccatgggca ttttggagag agtttgctgc aaaagttcta 5040
gtctgttcca cagttcagtg atgtgttcta tggcatctcg atccagcaga cctcctcgtt 5100
tcgcgggttt ggacggctcc tggaataggg tatgagacga tgggcgtcca gcgctgccag 5160
ggttcggtcc ttccagggtc tcagtgttcg agtcagggtt gtttccgtca cagtgaaggg 5220
gtgtgcgcct gcttgggcgc ttgccagggt gcgcttcaga ctcatcctgc tggtcgaaaa 5280
cttctgtcgc ttggcgccct gtatgtcggc caagtagcag tttaccatga gttcgtagtt 5340
gagcgcctcg gctgcgtggc ctttggcgcg gagcttacct ttggaagttt tcttgcatac 5400
cgggcagtat aggcatttca gcgcatacaa cttgggcgca aggaaaacgg attctgggga 5460
gtatgcatct gcgccgcagg aggcgcaaac agtttcacat tccaccagcc aggttaaatc 5520
cggttcattg gggtcaaaaa caagttttcc gccatatttt ttgatgcgtt tcttaccttt 5580
ggtctccatg agttcgtgtc ctcgttgagt gacaaacagg ctgtccgtgt ccccgtagac 5640
tgattttaca ggcctcttct ccagtggagt gcctcggtct tcttcgtaca ggaactctga 5700
ccactctgat acaaaggcgc gcgtccaggc cagcacaaag gaggctatgt gggaggggta 5760
gcgatcgttg tcaaccaggg ggtccacctt ttccaaagta tgcaaacaca tgtcaccctc 5820
ttcaacatcc aggaatgtga ttggcttgta ggtgtatttc acgtgacctg gggtccccgc 5880 tggggggggta taaaaggggg cggttctttg ctcttcctca ctgtcttccg gatcgctgtc 5940
caggaacgtc agctgttggg gtaggtattc cctctcgaag gcgggcatga cctctgcact 6000
caggttgtca gtttctaaga acgaggagga tttgatattg acagtgccgg ttgagatgcc 6060

-continued

```
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
```

-continued

```
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
```

gaaggactgg cacgtctagg tgcgccttca cccgagcggc atccgcgagt tcaactgaaa 10860
aaagattctc gcgaggcgta tgtgccccaa cagaacctat ttagagacag aagcggcgag 10920
gagccggagg agatgcgagc ttcccgcttt aacgcgggtc gtgagctgcg tcacggtttg 10980
gaccgaagac gagtgttgcg ggacgaggat ttcgaagttg atgaaatgac agggatcagt 11040
cctgccaggg cacacgtggc tgcagccaac cttgtatcgg cttacgagca gacagtaaag 11100
gaagagcgta acttccaaaa gtcttttaat aatcatgtgc gaaccctgat tgcccgcgaa 11160
gaagttaccc ttggtttgat gcatttgtgg gatttgatgg aagctatcat tcagaaccct 11220
actagcaaac ctctgaccgc ccagctgttt ctggtggtgc aacacagcag agacaatgag 11280
gctttcagag aggcgctgct gaacatcacc gaacccgagg ggagatggtt gtatgatctt 11340
atcaacattc tacagagtat catagtgcag gagcggagcc tgggcctggc cgagaaggtg 11400
gctgccatca attactcggt tttgagcttg ggaaaatatt acgctcgcaa aatctacaag 11460
actccatacg ttcccataga caaggaggtg aagatagatg ggttctacat gcgcatgacg 11520
ctcaaggtct tgaccctgag cgatgatctt ggggtgtatc gcaatgacag aatgcatcgc 11580
gcggttagcg ccagcaggag gcgcgagtta agcgacaggg aactgatgca cagtttgcaa 11640
agagctctga ctggagctgg aaccgagggt gagaattact tcgacatggg agctgacttg 11700
cagtggcagc ctagtcgcag ggctctgagc gccgcgacgg caggatgtga gcttccttac 11760
atagaagagg cggatgaagg cgaggaggaa gagggcgagt acttggaaga ctgatggcac 11820
aacccgtgtt ttttgctaga tggaacagca agcaccggat cccgcaatgc gggcggcgct 11880
gcagagccag ccgtccggca ttaactcctc ggacgattgg acccaggcca tgcaacgtat 11940
catggcgttg acgactcgca accccgaagc ctttagacag caaccccagg ccaaccgtct 12000
atcggccatc atggaagctg tagtgccttc ccgctctaat cccactcatg agaaggtcct 12060
ggccatcgtg aacgcgttgg tggagaacaa agctattcgt ccagatgagg ccggactggt 12120
atacaacgct ctcttagaac gcgtggctcg ctacaacagt agcaatgtgc aaaccaattt 12180
ggaccgtatg ataacagatg tacgcgaagc cgtgtctcag cgcgaaaggt tccagcgtga 12240
tgccaacctg ggttcgctgg tggcgttaaa tgctttcttg agtactcagc ctgctaatgt 12300
gccgcgtggt caacaggatt atactaactt tttaagtgct ttgagactga tggtatcaga 12360
agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960
cgctatgaac tctgattatt tcaccaatgc catcttaaac ccgcactggc tgcccccacc 13020
tggtttctac acgggcgaat atgacatgcc cgaccctaat gacggatttc tgtgggacga 13080
cgtggacagc gatgtttttt cacctctttc tgatcatcgc acgtggaaaa aggaaggcgg 13140

-continued cgatagaatg cattcttctg catcgctgtc cggggtcatg ggtgctaccg cggctgagcc 13200
cgagtctgca agtccttttc ctagtctacc cttttctcta cacagtgtac gtagcagcga 13260
agtgggtaga ataagtcgcc cgagtttaat gggcgaagag gagtatctaa acgattcctt 13320
gctcagaccg gcaagagaaa aaaatttccc aaacaatgga atagaaagtt tggtggataa 13380
aatgagtaga tggaagactt atgctcagga tcacagagac gagcctggga tcatggggat 13440
tacaagtaga gcgagccgta gacgccagcg ccatgacaga cagaggggtc ttgtgtggga 13500
cgatgaggat tcggccgatg atagcagcgt gctggacttg ggtgggagag gaaggggcaa 13560
cccgtttgct catttgcgcc ctcgcttggg tggtatgttg taaaaaaaaa taaaaaaaaa 13620
actcaccaag gccatggcga cgagcgtacg ttcgttcttc tttattatct gtgtctagta 13680
taatgaggcg agtcgtgcta ggcggagcgg tggtgtatcc ggagggtcct cctccttcgt 13740
acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040
ggggcggtca gctaaagacc atcatgcata ctaacatgcc aaacgtgaac gagtatatgt 14100
ttagtaacaa gttcaaagcg cgtgtgatgg tgtccagaaa acctcccgac ggtgctgcag 14160
ttggggatac ttatgatcac aagcaggata ttttgaaata tgagtggttc gagtttactt 14220
tgccagaagg caacttttca gttactatga ctattgattt gatgaacaat gccatcatag 14280
ataattactt gaaagtgggt agacagaatg gagtgcttga aagtgacatt ggtgttaagt 14340
tcgacaccag gaacttcaag ctgggatggg atcccgaaac caagttgatc atgcctggag 14400
tgtatacgta tgaagccttc catcctgaca ttgtcttact gcctggctgc ggagtggatt 14460
ttaccgagag tcgtttgagc aaccttcttg gtatcagaaa aaaacagcca tttcaagagg 14520
gttttaagat tttgtatgaa gatttagaag gtggtaatat tccggccctc ttggatgtag 14580
atgcctatga gaacagtaag aaagaacaaa aagccaaaat agaagctgct acagctgctg 14640
cagaagctaa ggcaaacata gttgccagcg actctacaag ggttgctaac gctggagagg 14700
tcagaggaga caattttgcg ccaacacctg ttccgactgc agaatcatta ttggccgatg 14760
tgtctgaagg aacggacgtg aaactcacta ttcaacctgt agaaaaagat agtaagaata 14820
gaagctataa tgtgttggaa gacaaaatca acacagccta tcgcagttgg tatctttcgt 14880
acaattatgg cgatcccgaa aaaggagtgc gttcctggac attgctcacc acctcagatg 14940
tcacctgcgg agcagagcag gtctactggt cgcttccaga catgatgaag gatcctgtca 15000
ctttccgctc cactagacaa gtcagtaact accctgtggt gggtgcagag cttatgcccg 15060
tcttctcaaa gagcttctac aacgaacaag ctgtgtactc ccagcagctc cgccagtcca 15120
cctcgcttac gcacgtcttc aaccgctttc ctgagaacca gattttaatc cgtccgccgg 15180
cgcccaccat taccaccgtc agtgaaaacg ttcctgctct cacagatcac gggaccctgc 15240
cgttgcgcag cagtatccgg ggagtccaac gtgtgaccgt tactgacgcc agacgccgca 15300
cctgtcccta cgtgtacaag gcactgggca tagtcgcacc gcgcgtcctt tcaagccgca 15360
ctttctaaaa aaaaaaaaaa tgtccattct tatctcgccc agtaataaca ccggttgggg 15420
tctgcgcgct ccaagcaaga tgtacggagg cgcacgcaaa cgttctaccc aacatcctgt 15480
ccgtgttcgc ggacattttc gcgctccatg ggcgccctc aagggccgca ctcgcgttcg 15540
aaccaccgtc gatgatgtaa tcgatcaggt ggttgccgac gcccgtaatt atactcctac 15600
tgcgcctaca tctactgtgg atgcagttat tgacagtgta gtggctgacg ctcgcaacta 15660
tgctcgacgt aagagccggc gaaggcgcat tgccagacgc caccgagcta ccactgccat 15720
gcgagccgca agagctctgc tacgaagagc tagacgcgtg gggcgaagag ccatgcttag 15780
ggcggccaga cgtgcagctt cgggcgccag cgccggcagg tcccgcaggc aagcagccgc 15840
tgtcgcagcg gcgactattg ccgacatggc ccaatcgcga agaggcaatg tatactgggt 15900
gcgtgacgct gccaccggtc aacgtgtacc cgtgcgcacc cgtcccccctc gcacttagaa 15960
gatactgagc agtctccgat gttgtgtccc agcggcgagg atgtccaagc gcaaatacaa 16020
ggaagaaatg ctgcaggtta tcgcacctga agtctacggc caaccgttga aggatgaaaa 16080
aaaaccccgc aaaatcaagc gggttaaaaa ggacaaaaaa gaagaggaag atggcgatga 16140
tgggctggcg gagtttgtgc gcgagtttgc cccacggcga cgcgtgcaat ggcgtgggcg 16200
caaagttcga catgtgttga gacctggaac ttcggtggtc tttacacccg gcgagcgttc 16260
aagcgctact tttaagcgtt cctatgatga ggtgtacggg gatgatgata ttcttgagca 16320
ggcggctgac cgattaggcg agtttgctta tggcaagcgt agtagaataa cttccaagga 16380
tgagacagtg tcgataccct tggatcatgg aaatcccacc cctagtctta aaccggtcac 16440
tttgcagcaa gtgttacccg taactccgcg aacaggtgtt aaacgcgaag gtgaagattt 16500
gtatcccact atgcaactga tggtacccaa acgccagaag ttggaggacg ttttggagaa 16560
agtaaaagtg gatccagata ttcaacctga ggttaaagtg agacccatta agcaggtagc 16620
gcctggtctg gggtacaaa ctgtagacat taagattccc actgaaagta tggaagtgca 16680
aactgaaccc gcaaagccta ctgccacctc cactgaagtg caaacggatc catggatgcc 16740
catgcctatt acaactgacg ccgccggtcc cactcgaaga tcccgacgaa agtacggtcc 16800
agcaagtctg ttgatgccca attatgttgt acacccatct attattccta ctcctggtta 16860
ccgaggcact cgctactatc gcagccgaaa cagtacctcc cgccgtcgcc gcaagacacc 16920
tgcaaatcgc agtcgtcgcc gtagacgcac aagcaaaccg actcccggcg ccctggtgcg 16980
gcaagtgtac cgcaatggta gtgcggaacc tttgacactg ccgcgtgcgc gttaccatcc 17040
gagtatcatc acttaatcaa tgttgccgct gcctccttgc agatatggcc ctcacttgtc 17100
gccttcgcgt tcccatcact ggttaccgag gaagaaactc gcgccgtaga agagggatgt 17160
tgggacgcgg aatgcgacgc tacaggcgac ggcgtgctat ccgcaagcaa ttgcggggtg 17220
gtttttttacc agccttaatt ccaattatcg ctgctgcaat tggcgcgata ccaggcatag 17280
cttccgtggc ggttcaggcc tcgcaacgac attgacattg gaaaaaaacg tataaataaa 17340
aaaaaaaaaa tacaatggac tctgacactc ctggtcctgt gactatgttt tcttagagat 17400
ggaagacatc aatttttcat ccttggctcc gcgacacggc acgaagccgt acatgggcac 17460
ctggagcgac atcggcacga gccaactgaa cgggggcgcc ttcaattgga gcagtatctg 17520
gagcgggctt aaaaatttg gctcaaccat aaaaacatac gggaacaaag cttggaacag 17580
cagtacagga caggcgctta gaaataaact taaagaccag aacttccaac aaaaagtagt 17640
cgatgggata gcttccggca tcaatggagt ggtagatttg gctaaccagg ctgtgcagaa 17700
aaagataaac agtcgtttgg acccgccgcc agcaacccca ggtgaaatgc aagtggagga 17760
agaaattcct ccgccagaaa aacgaggcga caagcgtccg cgtcccgatt tggaagagac 17820
gctggtgacg cgcgtagatg aaccgccttc ttatgaggaa gcaacgaagc ttggaatgcc 17880

```
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
```

ttaccagact gaaaaccaaa gaaactccct ctttggggtc tggatttgac ccctactttg 20340
tctattctgg ttctattccc tacctggatg gtaccttcta cctgaaccac acttttaaga 20400
aggtttccat catgtttgac tcttcagtga gctggcctgg aaatgacagg ttactatctc 20460
ctaacgaatt tgaaataaag cgcactgtgg atggcgaagg ctacaacgta gcccaatgca 20520
acatgaccaa agactggttc ttggtacaga tgctcgccaa ctacaacatc ggctatcagg 20580
gcttctacat tccagaagga tacaaagatc gcatgtattc atttttcaga aacttccagc 20640
ccatgagcag gcaggtggtt gatgaggtca attacaaaga cttcaaggcc gtcgccatac 20700
cctaccaaca caacaactct ggctttgtgg gttacatggc tccgaccatg cgccaaggtc 20760
aaccctatcc cgctaactat ccctatccac tcattggaac aactgccgta aatagtgtta 20820
cgcagaaaaa gttcttgtgt gacagaacca tgtggcgcat accgttctcg agcaacttca 20880
tgtctatggg ggcccttaca gacttgggac agaatatgct ctatgccaac tcagctcatg 20940
ctctggacat gacctttgag gtggatccca tggatgagcc caccctgctt tatcttctct 21000
tcgaagtttt cgacgtggtc agagtgcatc agccacaccg cggcatcatc gaggcagtct 21060
acctgcgtac accgttctcg gccggtaacg ctaccacgta agaagcttct tgcttcttgc 21120
aaatagcagc tgcaaccatg gcctgcggat cccaaaacgg ctccagcgag caagagctca 21180
gagccattgt ccaagacctg ggttgcggac cctatttttt gggaacctac gataagcgct 21240
tcccggggtt catggccccc gataagctcg cctgtgccat tgtaaatacg gccggacgtg 21300
agacgggggg agagcactgg ttggctttcg gttggaaccc acgttctaac acctgctacc 21360
tttttgatcc ttttggattc tcggatgatc gtctcaaaca gatttaccag tttgaatatg 21420
agggtctcct gcgccgcagc gctcttgcta ccaaggaccg ctgtattacg ctggaaaaat 21480
ctacccagac cgtgcagggt ccccgttctg ccgcctgcgg acttttctgc tgcatgttcc 21540
ttcacgcctt tgtgcactgg cctgaccgtc ccatggacgg aaacccccacc atgaaattgc 21600
taactggagt gccaaacaac atgcttcatt ctcctaaagt ccagcccacc ctgtgtgaca 21660
atcaaaaagc actctaccat tttcttaata cccattcgcc ttattttcgc tcccatcgta 21720
cacacatcga aagggccact gcgttcgacc gtatggatgt tcaataatga ctcatgtaaa 21780
caacgtgttc aataaacatc actttatttt tttacatgta tcaaggctct gcattactta 21840
tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180
caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg cccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac caccccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460
cgcgcttatt caaaaaaggc gggaattaca tcatcctcga catgagtaaa gaaattccca 26520
cgccttacat gtggagttat caaccccaaa tgggattggc ggcaggcgcc tcccaggact 26580
actccacccg catgaattgg ctcagcgccg ggccttctat gatttctcga gttaatgata 26640
tacgcgccta ccgaaaccaa atacttttgg aacagtcagc tcttaccacc acgccccgcc 26700
aacaccttaa tcccagaaat tggcccgccg ccctagtgta ccaggaaagt cccgctccca 26760
ccactgtatt acttcctcga gacgcccagg ccgaagtcca aatgactaat gcaggtgcgc 26820
agttagctgg cggctccacc ctatgtcgtc acaggcctcg gcataatata aaacgcctga 26880
tgatcagagg ccgaggtatc cagctcaacg acgagtcggt gagctctccg cttggtctac 26940
gaccagacgg aatctttcag attgccggct gcgggagatc ttccttcacc cctcgtcagg 27000
ctgttctgac tttggaaagt tcgtcttcgc aaccccgctc gggcggaatc gggaccgttc 27060
aatttgtgga ggagtttact ccctctgtct acttcaaccc cttctccgga tctcctgggc 27120
attacccgga cgagttcata ccgaacttcg acgcgattag cgagtcagtg gacggctacg 27180
attgatgtct ggtgacgcgg ctgagctatc tcggctgcga catctagacc actgccgccg 27240
ctttcgctgc tttgcccggg aactcattga gttcatctac ttcgaactcc ccaaggatca 27300
ccctcaaggt ccggcccacg gagtgcggat ttctatcgaa ggcaaaatag actctcgcct 27360

-continued

```
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
cccctttata aacccagggt ttatttcccc aaatggcttc acacaaagcc caaacggagt  28500
tcttacttta aaatgtttaa ccccactaac aaccacaggc ggatctctac agctaaaagt  28560
gggagggggga cttacagtgg atgacaccaa cggtttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acacccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttgcga tcgccaggcc caccatggga tggagctgta tcatcctctt  29400
cttggtagca acagctacag gtgtccactc ccaggtgcag ctgcagcagt ctggggctga  29460
actggcaaga cctggggcct cagtgaagat gtcctgcaag gcttctggct acacctttac  29520
taggtacacg atgcactggg taaaacagag gcctggacag ggtctggaat ggattggata  29580
cattaatcct agccgtggtt atactaatta caatcagaag ttcaaggaca aggccacatt  29640
gactacagac aaatcctcca gcacagccta catgcaactg agcagcctga catctgagga  29700
ctctgcagtc tattactgtg caagatatta tgatgatcat tactgccttg actactgggg  29760
```

ccaaggcacc actctcacag tctcctcagg tggcggtggc tcgggcggtg gtggatctgg 29820
tggcggcgga tctgatatcg tgctcactca gtctccagca atcatgtctg catctccagg 29880
ggagaaggtc accatgacct gcagtgccag ctcaagtgta agttacatga actggtacca 29940
gcagaagtca ggcacctccc ccaaaagatg gatttatgac acatccaaac tggcttctgg 30000
agtccctgct cacttcaggg gcagtgggtc tgggacctct tactctctca caatcagcgg 30060
catggaggct gaagatgctg ccacttatta ctgccagcag tggagtagta acccattcac 30120
gttcggctcg gggacaaagt tggaaataaa ccggggatcc gaacaaaaac tcatctcaga 30180
agaggatctg aatgctgtgg gccaggacac gcaggaggtc atcgtggtgc cacactcctt 30240
gccctttaag gtggtggtga tctcagccat cctggccctg gtggtgctca ccatcatctc 30300
ccttatcatc ctcatcatgc tttggcagaa gaagccacgt taagctagct tgactgactg 30360
agatacagcg taccttcagc tcacagacat gataagatac attgatgagt ttggacaaac 30420
cacaactaga atgcagtgaa aaaaatgctt tatttgtgaa atttgtgatg ctattgcttt 30480
atttgtaacc attataagct gcaataaaca agttaacaac aacaattgca ttcattttat 30540
gtttcaggtt cagggggagg tgtgggaggt tttttaaagc aagtaaaacc tctacaaatg 30600
tggtagtcgt cagctatcct gcaggaactt gtttatttga aatcaattc acaaaatccg 30660
agtagttatt ttgcctcccc cttcccattt aacagaatac accaatctct ccccacgcac 30720
agctttaaac atttggatac cattagatat agacatggtt ttagattcca cattccaaac 30780
agtttcagag cgagccaatc tggggtcagt gatagataaa aatccatcgg gatagtcttt 30840
taaagcgctt tcacagtcca actgctgcgg atgcgactcc ggagtctgga tcacggtcat 30900
ctggaagaag aacgatggga atcataatcc gaaaacggta tcggacgatt gtgtctcatc 30960
aaacccacaa gcagccgctg tctgcgtcgc tccgtgcgac tgctgtttat gggatcaggg 31020
tccacagtgt cctgaagcat gattttaata gcccttaaca tcaactttct ggtgcgatgc 31080
gcgcagcaac gcattctgat ttcactcaaa tctttgcagt aggtacaaca cattattaca 31140
atattgttta ataaaccata attaaaagcg ctccagccaa aactcatatc tgatataatc 31200
gcccctgcat gaccatcata ccaaagttta atataaatta aatgacgttc cctcaaaaac 31260
acactaccca catacatgat ctcttttggc atgtgcatat taacaatctg tctgtaccat 31320
ggacaacgtt ggttaatcat gcaacccaat ataaccttcc ggaaccacac tgccaacacc 31380
gctcccccag ccatgcattg aagtgaaccc tgctgattac aatgacaatg aagaacccaa 31440
ttctctcgac cgtgaatcac ttgagaatga aaaatatcta tagtggcaca acatagacat 31500
aaatgcatgc atcttctcat aatttttaac tcctcaggat ttagaaacat atcccaggga 31560
ataggaagct cttgcagaac agtaaagctg gcagaacaag gaagaccacg aacacaactt 31620
acactatgca tagtcatagt atcacaatct ggcaacagcg ggtggtcttc agtcatagaa 31680
gctcgggttt cattttcctc acaacgtggt aactgggctc tggtgtaagg gtgatgtctg 31740
gcgcatgatg tcgagcgtgc gcgcaacctt gtcataatgg agttgcttcc tgacattctc 31800
gtattttgta tagcaaaacg cggccctggc agaacacact cttcttcgcc ttctatcctg 31860
ccgcttagcg tgttccgtgt gatagttcaa gtacaaccac actcttaagt tggtcaaaag 31920
aatgctggct tcagttgtaa tcaaaactcc atcgcatcta atcgttctga ggaaatcatc 31980
caagcaatgc aactggattg tgtttcaagc aggagaggag agggaagaga cggaagaacc 32040
atgttaattt ttattccaaa cgatctcgca gtacttcaaa ttgtagatcg cgcagatggc 32100

```
atctctcgcc cccactgtgt tggtgaaaaa gcacagctag atcaaaagaa atgcgatttt  32160

caaggtgctc aacggtggct tccagcaaag cctccacgcg cacatccaag aacaaaagaa  32220

taccaaaaga aggagcattt tctaactcct caatcatcat attacattcc tgcaccattc  32280

ccagataatt ttcagctttc cagccttgaa ttattcgtgt cagttcttgt ggtaaatcca  32340

atccacacat tacaaacagg tcccggaggg cgccctccac caccattctt aaacacaccc  32400

tcataatgac aaaatatctt gctcctgtgt cacctgtagc gaattgagaa tggcaacatc  32460

aattgacatg cccttggctc taagttcttc tttaagttct agttgtaaaa actctctcat  32520

attatcacca aactgcttag ccagaagccc cccgggaaca agagcagggg acgctacagt  32580

gcagtacaag cgcagacctc cccaattggc tccagcaaaa acaagattgg aataagcata  32640

ttgggaaccg ccagtaatat catcgaagtt gctggaaata taatcaggca gagtttcttg  32700

taaaaattga ataaaagaaa aatttgccaa aaaaacattc aaaacctctg ggatgcaaat  32760

gcaataggtt accgcgctgc gctccaacat tgttagtttt gaattagtct gcaaaaataa  32820

aaaaaaaaac aagcgtcata tcatagtagc ctgacgaaca gatggataaa tcagtctttc  32880

catcacaaga caagccacag ggtctccagc tcgaccctcg taaaacctgt catcatgatt  32940

aaacaacagc accgaaagtt cctcgcggtg accagcatga ataattcttg atgaagcata  33000

caatccagac atgttagcat cagttaacga gaaaaaacag ccaacatagc ctttgggtat  33060

aattatgctt aatcgtaagt atagcaaagc cacccctcgc ggatacaaag taaaaggcac  33120

aggagaataa aaaatataat tatttctctg ctgctgttca ggcaacgtcg cccccggtcc  33180

ctctaaatac acatacaaag cctcatcagc catggcttac cagacaaagt acagcgggca  33240

cacaaagcac aagctctaaa gtgactctcc aacctctcca caatatatat atacacaagc  33300

cctaaactga cgtaatggga gtaaagtgta aaaaatcccg ccaaacccaa cacacacccc  33360

gaaactgcgt caccagggaa aagtacagtt tcacttccgc aatcccaaca ggcgtaactt  33420

cctctttctc acggtacgtg atatcccact aacttgcaac gtcattttcc cacggtcgca  33480

ccgccccttt tagccgttaa ccccacagcc aatcaccaca cgatccacac tttttaaaat  33540

cacctcattt acatattggc accattccat ctataaggta tattatatag ataga       33595


<210> SEQ ID NO 104
<211> LENGTH: 33628
<212> TYPE: DNA
<213> ORGANISM: Artificial Sequence
<220> FEATURE:
<223> OTHER INFORMATION: NG-420A virus genome sequence comprising the
      EnAd genome with a transgene cassette that encodes a membrane-
      anchored chimeric form of the single chain Fv anti-human CD3e and
      a C-terminal V5 tag, inserted in the region BY

<400> SEQUENCE: 104

tctatctata taatatacct tatagatgga atggtgccaa tatgtaaatg aggtgatttt     60

aaaaagtgtg gatcgtgtgg tgattggctg tggggttaac ggctaaaagg ggcggtgcga    120

ccgtgggaaa atgacgtttt gtgggggtgg agtttttttg caagttgtcg cgggaaatgt    180

gacgcataaa aaggcttttt tctcacggaa ctacttagtt ttcccacggt atttaacagg    240

aaatgaggta gttttgaccg gatgcaagtg aaaattgttg attttcgcgc gaaaactgaa    300

tgaggaagtg tttttctgaa taatgtggta tttatggcag ggtggagtat ttgttcaggg    360

ccaggtagac tttgacccat tacgtggagg tttcgattac cgtgtttttt acctgaattt    420

ccgcgtaccg tgtcaaagtc ttctgttttt acgtaggtgt cagctgatcg ctagggtatt    480
```

-continued

```
tatacctcag ggtttgtgtc aagaggccac tcttgagtgc cagcgagaag agttttctcc    540
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agctttttga gcctcctacg cttcaggaac tgtatgattt    720
agaggtagag ggatcggagg attctaatga ggaagctgta aatggctttt ttaccgattc    780
tatgctttta gctgctaatg aagggttaga attagatccg cctttggaca cttttgatac    840
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
```

```
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct    3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaactttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
```

-continued

```
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg gggtccccgc   5880
tggggggta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
```

ccgtccgact gccatttttt ctggggtgac gcaatagaag gtttgggggt cctgccgcca 7680
gcgatcccac ttgagtttta tggcgaggtc ataggcgatg ttgacgagcc gctggtctcc 7740
agagagtttc atgaccagca tgaaggggat tagctgcttg ccaaaggacc ccatccaggt 7800
gtaggtttcc acatcgtagg tgagaaagag cctttctgtg cgaggatgag agccaatcgg 7860
gaagaactgg atctcctgcc accagttgga ggaatggctg ttgatgtgat ggaagtagaa 7920
ctccctgcga cgcgccgagc attcatgctt gtgcttgtac agacggccgc agtagtcgca 7980
gcgttgcacg ggttgtatct cgtgaatgag ttgtacctgg cttcccttga cgagaaattt 8040
cagtgggaag ccgaggcctg gcgattgtat ctcgtgcttt actatgttgt ctgcatcggc 8100
ctgttcatct tctgtctcga tggtggtcat gctgacgagc cctcgcggga ggcaagtcca 8160
gacctcggcg cggcaggggc ggagctcgag gacgagagcg cgcaggctgg agctgtccag 8220
ggtcctgaga cgctgcggac tcaggttagt aggcagtgtc aggagattaa cttgcatgat 8280
cttttggagg gcgtgcggga ggttcagata gtacttgatc tcaacgggtc cgttggtgga 8340
gatgtcgatg gcttgcaggg ttccgtgtcc cttgggcgct accaccgtgc ccttgttttt 8400
cattttggac ggcggtggct ctgttgcttc ttgcatgttt agaagcggtg tcgagggcgc 8460
gcaccgggcg gcaggggcgg ctcgggaccc ggcggcatgg ctggcagtgg tacgtcggcg 8520
ccgcgcgcgg gtaggttctg gtactgcgcc ctgagaagac tcgcatgcgc gacgacgcgg 8580
cggttgacat cctggatctg acgcctctgg gtgaaagcta ccggccccgt gagcttgaac 8640
ctgaaagaga gttcaacaga atcaatctcg gtatcgttga cggcggcttg cctaaggatt 8700
tcttgcacgt caccagagtt gtcctggtag gcgatctccg ccatgaactg ctcgatctct 8760
tcctcttgaa gatctccgcg gcccgctctc tcgacggtgg ccgcgaggtc gttggagatg 8820
cgcccaatga gttgagagaa tgcattcatg cccgcctcgt tccagacgcg gctgtagacc 8880
acggccccca cgggatctct cgcgcgcatg accacctggg cgaggttgag ctccacgtgg 8940
cgggtgaaga ccgcatagtt gcataggcgc tggaaaaggt agttgagtgt ggtggcgatg 9000
tgctcggtga cgaagaaata catgatccat cgtctcagcg gcatctcgct gacatcgccc 9060
agagcttcca agcgctccat ggcctcgtag aagtccacgg caaaattaaa aaactgggag 9120
tttcgcgcgg acacggtcaa ctcctcttcc agaagacgga taagttcggc gatggtggtg 9180
cgcacctcgc gctcgaaagc ccctgggatt tcttcctcaa tctcttcttc ttccactaac 9240
atctcttcct cttcaggtgg ggctgcagga ggagggggaa cgcggcgacg ccggcggcgc 9300
acgggcagac ggtcgatgaa tctttcaatg acctctccgc ggcggcggcg catggtttca 9360
gtgacggcgc ggccgttctc gcgcggtcgc agagtaaaaa caccgccgcg catctcctta 9420
aagtggtgac tgggaggttc tccgtttggg agggagaggg cgctgattat acattttatt 9480
aattggcccg tagggactgc acgcagagat ctgatcgtgt caagatccac gggatctgaa 9540
aacctttcga cgaaagcgtc taaccagtca cagtcacaag gtaggctgag tacggcttct 9600
tgtgggcggg ggtggttatg tgttcggtct gggtcttctg tttcttcttc atctcgggaa 9660
ggtgagacga tgctgctggt gatgaaatta aagtaggcag ttctaagacg gcggatggtg 9720
gcgaggagca ccaggtcttt gggtccggct tgctggatac gcaggcgatt ggccattccc 9780
caagcattat cctgacatct agcaagatct ttgtagtagt cttgcatgag ccgttctacg 9840
ggcacttctt cctcacccgt tctgccatgc atacgtgtga gtccaaatcc gcgcattggt 9900
tgtaccagtg ccaagtcagc tacgactctt tcggcgagga tggcttgctg tacttgggta 9960

```
agggtggctt gaaagtcatc aaaatccaca aagcggtggt aagctcctgt attaatggtg    10020

taagcacagt tggccatgac tgaccagtta actgtctggt gaccagggcg cacgagctcg    10080

gtgtatttaa ggcgcgaata ggcgcgggtg tcaaagatgt aatcgttgca ggtgcgcacc    10140

agatactggt accctataag aaaatgcggc ggtggttggc ggtagagagg ccatcgttct    10200

gtagctggag cgccaggggc gaggtcttcc aacataaggc ggtgatagcc gtagatgtac    10260

ctggacatcc aggtgattcc tgcggcggta gtagaagccc gaggaaactc gcgtacgcgg    10320

ttccaaatgt tgcgtagcgg catgaagtag ttcattgtag gcacggtttg accagtgagg    10380

cgcgcgcagt cattgatgct ctatagacac ggagaaaatg aaagcgttca gcgactcgac    10440

tccgtagcct ggaggaacgt gaacgggttg ggtcgcggtg taccccggtt cgagacttgt    10500

actcgagccg gccggagccg cggctaacgt ggtattggca ctcccgtctc gacccagcct    10560

acaaaaatcc aggatacgga atcgagtcgt tttgctggtt tccgaatggc agggaagtga    10620

gtcctatttt tttttttgc cgctcagatg catcccgtgc tgcgacagat gcgcccccaa    10680

caacagcccc cctcgcagca gcagcagcag caatcacaaa aggctgtccc tgcaactact    10740

gcaactgccg ccgtgagcgg tgcgggacag cccgcctatg atctggactt ggaagagggc    10800

gaaggactgg cacgtctagg tgcgccttca cccgagcggc atccgcgagt tcaactgaaa    10860

aaagattctc gcgaggcgta tgtgccccaa cagaacctat ttagagacag aagcggcgag    10920

gagccggagg agatgcgagc ttcccgcttt aacgcgggtc gtgagctgcg tcacggtttg    10980

gaccgaagac gagtgttgcg ggacgaggat ttcgaagttg atgaaatgac agggatcagt    11040

cctgccaggg cacacgtggc tgcagccaac cttgtatcgg cttacgagca gacagtaaag    11100

gaagagcgta acttccaaaa gtcttttaat aatcatgtgc gaaccctgat tgcccgcgaa    11160

gaagttaccc ttggtttgat gcatttgtgg gatttgatgg aagctatcat tcagaaccct    11220

actagcaaac ctctgaccgc ccagctgttt ctggtggtgc aacacagcag agacaatgag    11280

gctttcagag aggcgctgct gaacatcacc gaacccgagg ggagatggtt gtatgatctt    11340

atcaacattc tacagagtat catagtgcag gagcggagcc tgggcctggc cgagaaggtg    11400

gctgccatca attactcggt tttgagcttg ggaaaatatt acgctcgcaa aatctacaag    11460

actccatacg ttcccataga caaggaggtg aagatagatg ggttctacat gcgcatgacg    11520

ctcaaggtct tgaccctgag cgatgatctt ggggtgtatc gcaatgacag aatgcatcgc    11580

gcggttagcg ccagcaggag gcgcgagtta agcgacaggg aactgatgca cagtttgcaa    11640

agagctctga ctggagctgg aaccgagggt gagaattact tcgacatggg agctgacttg    11700

cagtggcagc ctagtcgcag ggctctgagc gccgcgacgg caggatgtga gcttccttac    11760

atagaagagg cggatgaagg cgaggaggaa gagggcgagt acttggaaga ctgatggcac    11820

aacccgtgtt ttttgctaga tggaacagca agcaccggat cccgcaatgc gggcggcgct    11880

gcagagccag ccgtccggca ttaactcctc ggacgattgg acccaggcca tgcaacgtat    11940

catggcgttg acgactcgca accccgaagc ctttagacag caaccccagg ccaaccgtct    12000

atcggccatc atggaagctg tagtgccttc ccgctctaat cccactcatg agaaggtcct    12060

ggccatcgtg aacgcgttgg tggagaacaa agctattcgt ccagatgagg ccggactggt    12120

atacaacgct ctcttagaac gcgtggctcg ctacaacagt agcaatgtgc aaaccaattt    12180

ggaccgtatg ataacagatg tacgcgaagc cgtgtctcag cgcgaaaggt tccagcgtga    12240

tgccaacctg ggttcgctgg tggcgttaaa tgctttcttg agtactcagc ctgctaatgt    12300

gccgcgtggt caacaggatt atactaactt tttaagtgct ttgagactga tggtatcaga    12360
```

agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960
cgctatgaac tctgattatt tcaccaatgc catcttaaac ccgcactggc tgcccccacc 13020
tggtttctac acgggcgaat atgacatgcc cgaccctaat gacggatttc tgtgggacga 13080
cgtggacagc gatgtttttt cacctctttc tgatcatcgc acgtggaaaa aggaaggcgg 13140
cgatagaatg cattcttctg catcgctgtc cggggtcatg ggtgctaccg cggctgagcc 13200
cgagtctgca agtccttttc ctagtctacc cttttctcta cacagtgtac gtagcagcga 13260
agtgggtaga ataagtcgcc cgagtttaat gggcgaagag gagtatctaa acgattcctt 13320
gctcagaccg gcaagagaaa aaaatttccc aaacaatgga atagaaagtt tggtggataa 13380
aatgagtaga tggaagactt atgctcagga tcacagagac gagcctggga tcatggggat 13440
tacaagtaga gcgagccgta gacgccagcg ccatgacaga cagaggggtc ttgtgtggga 13500
cgatgaggat tcggccgatg atagcagcgt gctggacttg ggtgggagag gaaggggcaa 13560
cccgtttgct catttgcgcc ctcgcttggg tggtatgttg taaaaaaaaa taaaaaaaaa 13620
actcaccaag gccatggcga cgagcgtacg ttcgttcttc tttattatct gtgtctagta 13680
taatgaggcg agtcgtgcta ggcggagcgg tggtgtatcc ggagggtcct cctccttcgt 13740
acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040
ggggcggtca gctaaagacc atcatgcata ctaacatgcc aaacgtgaac gagtatatgt 14100
ttagtaacaa gttcaaagcg cgtgtgatgg tgtccagaaa acctcccgac ggtgctgcag 14160
ttggggatac ttatgatcac aagcaggata ttttgaaata tgagtggttc gagtttactt 14220
tgccagaagg caacttttca gttactatga ctattgattt gatgaacaat gccatcatag 14280
ataattactt gaaagtgggt agacagaatg gagtgcttga aagtgacatt ggtgttaagt 14340
tcgacaccag gaacttcaag ctgggatggg atcccgaaac caagttgatc atgcctggag 14400
tgtatacgta tgaagccttc catcctgaca ttgtcttact gcctggctgc ggagtggatt 14460
ttaccgagag tcgtttgagc aaccttcttg gtatcagaaa aaaacagcca tttcaagagg 14520
gttttaagat tttgtatgaa gatttagaag gtggtaatat tccggccctc ttggatgtag 14580
atgcctatga gaacagtaag aaagaacaaa aagccaaaat agaagctgct acagctgctg 14640
cagaagctaa ggcaaacata gttgccagcg actctacaag ggttgctaac gctggagagg 14700
tcagaggaga caattttgcg ccaacacctg ttccgactgc agaatcatta ttggccgatg 14760
tgtctgaagg aacggacgtg aaactcacta ttcaacctgt agaaaaagat agtaagaata 14820
gaagctataa tgtgttggaa gacaaaatca acacagccta tcgcagttgg tatctttcgt 14880
acaattatgg cgatcccgaa aaaggagtgc gttcctggac attgctcacc acctcagatg 14940
tcacctgcgg agcagagcag gtctactggt cgcttccaga catgatgaag gatcctgtca 15000
ctttccgctc cactagacaa gtcagtaact accctgtggt gggtgcagag cttatgcccg 15060
tcttctcaaa gagcttctac aacgaacaag ctgtgtactc ccagcagctc cgccagtcca 15120
cctcgcttac gcacgtcttc aaccgctttc ctgagaacca gattttaatc cgtccgccgg 15180
cgcccaccat taccaccgtc agtgaaaacg ttcctgctct cacagatcac gggaccctgc 15240
cgttgcgcag cagtatccgg ggagtccaac gtgtgaccgt tactgacgcc agacgccgca 15300
cctgtcccta cgtgtacaag gcactgggca tagtcgcacc gcgcgtcctt tcaagccgca 15360
ctttctaaaa aaaaaaaaaa tgtccattct tatctcgccc agtaataaca ccggttgggg 15420
tctgcgcgct ccaagcaaga tgtacggagg cgcacgcaaa cgttctaccc aacatcctgt 15480
ccgtgttcgc ggacattttc gcgctccatg ggcgccctc aagggccgca ctcgcgttcg 15540
aaccaccgtc gatgatgtaa tcgatcaggt ggttgccgac gcccgtaatt atactcctac 15600
tgcgcctaca tctactgtgg atgcagttat tgacagtgta gtggctgacg ctcgcaacta 15660
tgctcgacgt aagagccggc gaaggcgcat tgccagacgc caccgagcta ccactgccat 15720
gcgagccgca agagctctgc tacgaagagc tagacgcgtg gggcgaagag ccatgcttag 15780
ggcggccaga cgtgcagctt cgggcgccag cgccggcagg tcccgcaggc aagcagccgc 15840
tgtcgcagcg gcgactattg ccgacatggc ccaatcgcga agaggcaatg tatactgggt 15900
gcgtgacgct gccaccggtc aacgtgtacc cgtgcgcacc cgtcccccctc gcacttagaa 15960 gatactgagc agtctccgat gttgtgtccc agcggcgagg atgtccaagc gcaaatacaa 16020
ggaagaaatg ctgcaggtta tcgcacctga agtctacggc caaccgttga aggatgaaaa 16080
aaaaccccgc aaaatcaagc gggttaaaaa ggacaaaaaa gaagaggaag atggcgatga 16140
tgggctggcg gagtttgtgc gcgagtttgc cccacggcga cgcgtgcaat ggcgtgggcg 16200
caaagttcga catgtgttga gacctggaac ttcggtggtc tttacacccg gcgagcgttc 16260
aagcgctact tttaagcgtt cctatgatga ggtgtacggg gatgatgata ttcttgagca 16320
ggcggctgac cgattaggcg agtttgctta tggcaagcgt agtagaataa cttccaagga 16380
tgagacagtg tcgataccct tggatcatgg aaatcccacc cctagtctta aaccggtcac 16440
tttgcagcaa gtgttacccg taactccgcg aacaggtgtt aaacgcgaag gtgaagattt 16500
gtatcccact atgcaactga tggtacccaa acgccagaag ttggaggacg ttttggagaa 16560
agtaaaagtg gatccagata ttcaacctga ggttaaagtg agacccatta agcaggtagc 16620
gcctggtctg gggtacaaa ctgtagacat taagattccc actgaaagta tggaagtgca 16680
aactgaaccc gcaaagccta ctgccacctc cactgaagtg caaacggatc catggatgcc 16740
catgcctatt acaactgacg ccgccggtcc cactcgaaga tcccgacgaa agtacggtcc 16800
agcaagtctg ttgatgccca attatgttgt acacccatct attattccta ctcctggtta 16860
ccgaggcact cgctactatc gcagccgaaa cagtacctcc cgccgtcgcc gcaagacacc 16920
tgcaaatcgc agtcgtcgcc gtagacgcac aagcaaaccg actcccggcg ccctggtgcg 16980
gcaagtgtac cgcaatggta gtgcggaacc tttgacactg ccgcgtgcgc gttaccatcc 17040
gagtatcatc acttaatcaa tgttgccgct gcctccttgc agatatggcc ctcacttgtc 17100

-continued

```
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
```

-continued

```
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
```

tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180

-continued

```
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg cccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataatagge acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac caccccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
```

actccacccg catgaattgg ctcagcgccg ggccttctat gatttctcga gttaatgata 26640
tacgcgccta ccgaaaccaa atacttttgg aacagtcagc tcttaccacc acgccccgcc 26700
aacaccttaa tcccagaaat tggcccgccg ccctagtgta ccaggaaagt cccgctccca 26760
ccactgtatt acttcctcga gacgcccagg ccgaagtcca aatgactaat gcaggtgcgc 26820
agttagctgg cggctccacc ctatgtcgtc acaggcctcg gcataatata aaacgcctga 26880
tgatcagagg ccgaggtatc cagctcaacg acgagtcggt gagctctccg cttggtctac 26940
gaccagacgg aatctttcag attgccggct gcgggagatc ttccttcacc cctcgtcagg 27000
ctgttctgac tttggaaagt tcgtcttcgc aaccccgctc gggcggaatc gggaccgttc 27060
aatttgtgga ggagtttact ccctctgtct acttcaaccc cttctccgga tctcctgggc 27120
attacccgga cgagttcata ccgaacttcg acgcgattag cgagtcagtg gacggctacg 27180
attgatgtct ggtgacgcgg ctgagctatc tcggctgcga catctagacc actgccgccg 27240
ctttcgctgc tttgcccggg aactcattga gttcatctac ttcgaactcc ccaaggatca 27300
ccctcaaggt ccggcccacg gagtgcggat ttctatcgaa ggcaaaatag actctcgcct 27360
gcaacgaatt ttctcccagc ggcccgtgct gatcgagcga gaccagggaa acaccacggt 27420
ttccatctac tgcatttgta atcaccccgg attgcatgaa agcctttgct gtcttatgtg 27480
tactgagttt aataaaaact gaattaagac tctcctacgg actgccgctt cttcaacccg 27540
gattttacaa ccagaagaac gaaacttttc ctgtcgtcca ggactctgtt aacttcacct 27600
ttcctactca caaactagaa gctcaacgac tacaccgctt ttccagaagc attttcccta 27660
ctaatactac tttcaaaacc ggaggtgagc tccaaggtct tcctacagaa aacccttggg 27720
tggaagcggg ccttgtagtg ctaggaattc ttgcgggtgg gcttgtgatt attctttgct 27780
acctatacac accttgcttc actttcttag tggtgttgtg gtattggttt aaaaaatggg 27840
gcccatacta gtcttgcttg ttttactttc gcttttggaa ccgggttctg ccaattacga 27900
tccatgtcta gacttcgacc cagaaaactg cacacttact tttgcacccg acacaagccg 27960
catctgtgga gttcatcgcc tctcttacga acttggcccc caacgacaaa aatttacctg 28020
catggtggga atcaacccca tagttatcac ccagcaaagt ggagatacta agggttgcat 28080
tcactgctcc tgcgattcca tcgagtgcac ctacaccctg ctgaagaccc tatgcggcct 28140
aagagacctg ctaccaatga attaaaaaat gattaataaa aaatcactta cttgaaatca 28200
gcaataaggt ctctgttgaa attttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta cccctatgaa gatgaaagca cctcccaaca 28440
cccctttata aacccagggt ttatttcccc aaatggcttc acacaaagcc caaacggagt 28500
tcttacttta aaatgtttaa ccccactaac aaccacaggc ggatctctac agctaaaagt 28560
gggaggggga cttacagtgg atgacaccaa cggtttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920

-continued

```
aactacacac agaaatataa attttactgc agagctgttt ttcgattcta ctggtaattt  28980
actaactaga ctctcatccc tcaaaactcc acttaatcat aaatcaggac aaaacatggc  29040
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttgcga tcgccaggcc caccatggga tggagctgta tcatcctctt  29400
cttggtagca acagctacag gtgtccactc ccaggtgcag ctgcagcagt ctggggctga  29460
actggcaaga cctggggcct cagtgaagat gtcctgcaag gcttctggct acacctttac  29520
taggtacacg atgcactggg taaaacagag gcctggacag ggtctggaat ggattggata  29580
cattaatcct agccgtggtt atactaatta caatcagaag ttcaaggaca aggccacatt  29640
gactacagac aaatcctcca gcacagccta catgcaactg agcagcctga catctgagga  29700
ctctgcagtc tattactgtg caagatatta tgatgatcat tactgccttg actactgggg  29760
ccaaggcacc actctcacag tctcctcagg tggcggtggc tcgggcggtg gtggatctgg  29820
tggcggcgga tctgatatcg tgctcactca gtctccagca atcatgtctg catctccagg  29880
ggagaaggtc accatgacct gcagtgccag ctcaagtgta agttacatga actggtacca  29940
gcagaagtca ggcacctccc ccaaaagatg gatttatgac acatccaaac tggcttctgg  30000
agtccctgct cacttcaggg gcagtgggtc tgggacctct tactctctca caatcagcgg  30060
catggaggct gaagatgctg ccacttatta ctgccagcag tggagtagta acccattcac  30120
gttcggctcg gggacaaagt tggaaataaa ccggggatcc gaacaaaaac tcatctcaga  30180
agaggatctg aatgctgtgg gccaggacac gcaggaggtc atcgtggtgc cacactcctt  30240
gccctttaag gtggtggtga tctcagccat cctggccctg gtggtgctca ccatcatctc  30300
ccttatcatc ctcatcatgc tttggcagaa gaagccacgt ggttcaatcc ctaaccctct  30360
cctcggtctc gattaagcta gcttgactga ctgagataca gcgtaccttc agctcacaga  30420
catgataaga tacattgatg agtttggaca aaccacaact agaatgcagt gaaaaaaatg  30480
ctttatttgt gaaatttgtg atgctattgc tttatttgta accattataa gctgcaataa  30540
acaagttaac aacaacaatt gcattcattt tatgtttcag gttcaggggg aggtgtggga  30600
ggttttttaa agcaagtaaa acctctacaa atgtggtagt cgtcagctat cctgcaggaa  30660
cttgtttatt tgaaaatcaa ttcacaaaat ccgagtagtt attttgcctc cccttccca  30720
tttaacagaa tacaccaatc tctccccacg cacagcttta aacatttgga taccattaga  30780
tatagacatg gttttagatt ccacattcca aacagtttca gagcgagcca atctggggtc  30840
agtgatagat aaaaatccat cgggatagtc ttttaaagcg ctttcacagt ccaactgctg  30900
cggatgcgac tccggagtct ggatcacggt catctggaag aagaacgatg ggaatcataa  30960
tccgaaaacg gtatcggacg attgtgtctc atcaaaccca caagcagccg ctgtctgcgt  31020
cgctccgtgc gactgctgtt tatgggatca gggtccacag tgtcctgaag catgatttta  31080
atagccctta acatcaactt tctggtgcga tgcgcgcagc aacgcattct gatttcactc  31140
aaatctttgc agtaggtaca acacattatt acaatattgt ttaataaacc ataattaaaa  31200
gcgctccagc caaaactcat atctgatata atcgcccctg catgaccatc ataccaaagt  31260
ttaatataaa ttaaatgacg ttccctcaaa aacacactac ccacatacat gatctctttt  31320
```

ggcatgtgca tattaacaat ctgtctgtac catggacaac gttggttaat catgcaaccc 31380
aatataacct tccggaacca cactgccaac accgctcccc cagccatgca ttgaagtgaa 31440
ccctgctgat tacaatgaca atgaagaacc caattctctc gaccgtgaat cacttgagaa 31500
tgaaaaatat ctatagtggc acaacataga cataaatgca tgcatcttct cataattttt 31560
aactcctcag gatttagaaa catatcccag ggaataggaa gctcttgcag aacagtaaag 31620
ctggcagaac aaggaagacc acgaacacaa cttacactat gcatagtcat agtatcacaa 31680
tctggcaaca gcgggtggtc ttcagtcata gaagctcggg tttcattttc ctcacaacgt 31740
ggtaactggg ctctggtgta agggtgatgt ctggcgcatg atgtcgagcg tgcgcgcaac 31800
cttgtcataa tggagttgct tcctgacatt ctcgtatttt gtatagcaaa acgcggccct 31860
ggcagaacac actcttcttc gccttctatc ctgccgctta gcgtgttccg tgtgatagtt 31920
caagtacaac cacactctta agttggtcaa aagaatgctg gcttcagttg taatcaaaac 31980
tccatcgcat ctaatcgttc tgaggaaatc atccaagcaa tgcaactgga ttgtgtttca 32040
agcaggagag gagagggaag agacggaaga accatgttaa tttttattcc aaacgatctc 32100
gcagtacttc aaattgtaga tcgcgcagat ggcatctctc gcccccactg tgttggtgaa 32160
aaagcacagc tagatcaaaa gaaatgcgat tttcaaggtg ctcaacggtg gcttccagca 32220
aagcctccac gcgcacatcc aagaacaaaa gaataccaaa agaaggagca ttttctaact 32280
cctcaatcat catattacat tcctgcacca ttcccagata attttcagct ttccagcctt 32340
gaattattcg tgtcagttct tgtggtaaat ccaatccaca cattacaaac aggtcccgga 32400
gggcgccctc caccaccatt cttaaacaca ccctcataat gacaaaatat cttgctcctg 32460
tgtcacctgt agcgaattga gaatggcaac atcaattgac atgcccttgg ctctaagttc 32520
ttctttaagt tctagttgta aaaactctct catattatca ccaaactgct tagccagaag 32580
ccccccggga acaagagcag gggacgctac agtgcagtac aagcgcagac ctccccaatt 32640
ggctccagca aaaacaagat tggaataagc atattgggaa ccgccagtaa tatcatcgaa 32700
gttgctggaa atataatcag gcagagtttc ttgtaaaaat tgaataaaag aaaaatttgc 32760
caaaaaaaca ttcaaaacct ctgggatgca aatgcaatag gttaccgcgc tgcgctccaa 32820
cattgttagt tttgaattag tctgcaaaaa taaaaaaaaa aacaagcgtc atatcatagt 32880
agcctgacga acagatggat aaatcagtct ttccatcaca agacaagcca cagggtctcc 32940
agctcgaccc tcgtaaaacc tgtcatcatg attaaacaac agcaccgaaa gttcctcgcg 33000
gtgaccagca tgaataattc ttgatgaagc atacaatcca gacatgttag catcagttaa 33060
cgagaaaaaa cagccaacat agcctttggg tataattatg cttaatcgta agtatagcaa 33120
agccacccct cgcggataca aagtaaaagg cacaggagaa taaaaaatat aattatttct 33180
ctgctgctgt tcaggcaacg tcgcccccgg tccctctaaa tacacataca aagcctcatc 33240
agccatggct taccagacaa agtacagcgg gcacacaaag cacaagctct aaagtgactc 33300
tccaacctct ccacaatata tatatacaca agccctaaac tgacgtaatg ggagtaaagt 33360
gtaaaaaatc ccgccaaacc caacacacac cccgaaactg cgtcaccagg gaaaagtaca 33420
gtttcacttc cgcaatccca acaggcgtaa cttcctcttt ctcacggtac gtgatatccc 33480
actaacttgc aacgtcattt tcccacggtc gcaccgcccc ttttagccgt taaccccaca 33540
gccaatcacc acacgatcca cactttttaa aatcacctca tttacatatt ggcaccattc 33600
catctataag gtatattata tagataga 33628

<210> SEQ ID NO 105
<211> LENGTH: 188
<212> TYPE: PRT
<213> ORGANISM: Artificial Sequence
<220> FEATURE:
<223> OTHER INFORMATION: Human Interferona amino acid sequence

<400> SEQUENCE: 105

```
Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185
```

<210> SEQ ID NO 106
<211> LENGTH: 179
<212> TYPE: PRT
<213> ORGANISM: Artificial Sequence
<220> FEATURE:
<223> OTHER INFORMATION: Human soluble Flt3 ligand amino acid sequence

<400> SEQUENCE: 106

```
Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125
```

```
Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro


<210> SEQ ID NO 107
<211> LENGTH: 93
<212> TYPE: PRT
<213> ORGANISM: Artificial Sequence
<220> FEATURE:
<223> OTHER INFORMATION: Human Macrophage Inflammatory protein 1a amino
      acid sequence (LD78b isoform)

<400> SEQUENCE: 107

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90


<210> SEQ ID NO 108
<211> LENGTH: 322
<212> TYPE: PRT
<213> ORGANISM: Artificial Sequence
<220> FEATURE:
<223> OTHER INFORMATION: Membrane anchored form of the anti-human CD3
      single chain Fv

<400> SEQUENCE: 108

Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140
```

```
Gly Gly Gly Ser Gly Gly Gly Gly Ser Asp Ile Val Leu Thr Gln Ser
145                 150                 155                 160

Pro Ala Ile Met Ser Ala Ser Pro Gly Glu Lys Val Thr Met Thr Cys
                165                 170                 175

Ser Ala Ser Ser Ser Val Ser Tyr Met Asn Trp Tyr Gln Gln Lys Ser
            180                 185                 190

Gly Thr Ser Pro Lys Arg Trp Ile Tyr Asp Thr Ser Lys Leu Ala Ser
        195                 200                 205

Gly Val Pro Ala His Phe Arg Gly Ser Gly Ser Gly Thr Ser Tyr Ser
    210                 215                 220

Leu Thr Ile Ser Gly Met Glu Ala Glu Asp Ala Ala Thr Tyr Tyr Cys
225                 230                 235                 240

Gln Gln Trp Ser Ser Asn Pro Phe Thr Phe Gly Ser Gly Thr Lys Leu
                245                 250                 255

Glu Ile Asn Arg Gly Ser Glu Gln Lys Leu Ile Ser Glu Glu Asp Leu
            260                 265                 270

Asn Ala Val Gly Gln Asp Thr Gln Glu Val Ile Val Val Pro His Ser
        275                 280                 285

Leu Pro Phe Lys Val Val Val Ile Ser Ala Ile Leu Ala Leu Val Val
    290                 295                 300

Leu Thr Ile Ile Ser Leu Ile Ile Leu Ile Met Leu Trp Gln Lys Lys
305                 310                 315                 320

Pro Arg
```

<210> SEQ ID NO 109
<211> LENGTH: 33493
<212> TYPE: DNA
<213> ORGANISM: Artificial Sequence
<220> FEATURE:
<223> OTHER INFORMATION: NG-330 virus genome sequence comprising the EnAd genome with a transgene cassette that encodes the T lymphocyte activation antigen, CD80, inserted in the region By. The transgene cassette contains a 5' SSA, human CD80 cDNA sequence and a 3' poly(A)

<400> SEQUENCE: 109

```
tctatctata taatatacct tatagatgga atggtgccaa tatgtaaatg aggtgatttt     60

aaaaagtgtg gatcgtgtgg tgattggctg tggggttaac ggctaaaagg ggcggtgcga    120

ccgtgggaaa atgacgtttt gtgggggtgg agtttttttg caagttgtcg cgggaaatgt    180

gacgcataaa aaggcttttt tctcacggaa ctacttagtt ttcccacggt atttaacagg    240

aaatgaggta gttttgaccg gatgcaagtg aaaattgttg attttcgcgc gaaaactgaa    300

tgaggaagtg tttttctgaa taatgtggta tttatggcag ggtggagtat ttgttcaggg    360

ccaggtagac tttgacccat tacgtggagg tttcgattac cgtgtttttt acctgaattt    420

ccgcgtaccg tgtcaaagtc ttctgttttt acgtaggtgt cagctgatcg ctagggtatt    480

tatacctcag ggtttgtgtc aagaggccac tcttgagtgc cagcgagaag agttttctcc    540

tctgcgccgg cagtttaata ataaaaaaat gagagatttg cgatttctgc ctcaggaaat    600

aatctctgct gagactggaa atgaaatatt ggagcttgtg gtgcacgccc tgatgggaga    660

cgatccggag ccacctgtgc agctttttga gcctcctacg cttcaggaac tgtatgattt    720

agaggtagag ggatcggagg attctaatga ggaagctgta aatggctttt ttaccgattc    780

tatgctttta gctgctaatg aagggttaga attagatccg cctttggaca cttttgatac    840

tccaggggta attgtggaaa gcggtacagg tgtaagaaaa ttacctgatt tgagttccgt    900
```

-continued

```
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
tttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
```

gccggtgtgt gtagatgtga ctgaagatct cagaccggat catttggtta ttgcccgcac 3360
tggagcagag ttcggatcca gtggagaaga aactgactaa ggtgagtatt gggaaaactt 3420
tggggtggga ttttcagatg gacagattga gtaaaaattt gtttttctg tcttgcagct 3480
gtcatgagtg gaaacgcttc ttttaagggg ggagtcttca gcccttatct gacagggcgt 3540
ctcccatcct gggcaggagt tcgtcagaat gttatgggat ctactgtgga tggaagaccc 3600
gtccaacccg ccaattcttc aacgctgacc tatgctactt taagttcttc acctttggac 3660
gcagctgcag ctgccgccgc cgcttctgtt gccgctaaca ctgtgcttgg aatgggttac 3720
tatggaagca tcatggctaa ttccacttcc tctaataacc cttctaccct gactcaggac 3780
aagttacttg tccttttggc ccagctggag gctttgaccc aacgtctggg tgaactttct 3840
cagcaggtgg tcgagttgcg agtacaaact gagtctgctg tcggcacggc aaagtctaaa 3900
taaaaaaatc ccagaatcaa tgaataaata aacaagcttg ttgttgattt aaaatcaagt 3960
gtttttattt catttttcgc gcacggtatg ccctagacca ccgatctcta tcattgagaa 4020
ctcggtggat tttttccagg atcctataga ggtgggattg aatgtttaga tacatgggca 4080
ttaggccgtc tttggggtgg agatagctcc attgaaggga ttcatgctcc ggggtagtgt 4140
tgtaaatcac ccagtcataa caaggtcgca gtgcatggtg ttgcacaata tcttttagaa 4200
gtaggctgat tgccacagat aagcccttgg tgtaggtgtt tacaaaccgg ttgagctggg 4260
atgggtgcat tcggggtgaa attatgtgca ttttggattg gatttttaag ttggcaatat 4320
tgccgccaag atcccgtctt gggttcatgt tatgaaggac caccaagacg gtgtatccgg 4380
tacatttagg aaatttatcg tgcagcttgg atggaaaagc gtggaaaaat ttggagacac 4440
ccttgtgtcc tccaagattt tccatgcact catccatgat aatagcaatg gggccgtggg 4500
cagcggcgcg ggcaaacacg ttccgtgggt ctgacacatc atagttatgt tcctgagtta 4560
aatcatcata agccatttta atgaatttgg ggcggagagt accagattgg ggtatgaatg 4620
ttccttcggg ccccggagca tagttcccct cacagatttg catttcccaa gctttcagtt 4680
ccgagggtgg aatcatgtcc acctgggggg ctatgaaaaa caccgtttct ggggcggggg 4740
tgattaattg tgatgatagc aaatttctga gcaattgaga tttgccacat ccggtggggc 4800
cataaatgat tccgattacg ggttgcaggt ggtagtttag ggaacggcaa ctgccgtctt 4860
ctcgaagcaa gggggccacc tcgttcatca tttcccttac atgcatattt tcccgcacca 4920
aatccattag gaggcgctct cctcctagtg atagaagttc ttgtagtgag gaaaagtttt 4980
tcagcggttt cagaccgtca gccatgggca ttttggagag agtttgctgc aaaagttcta 5040
gtctgttcca cagttcagtg atgtgttcta tggcatctcg atccagcaga cctcctcgtt 5100
tcgcgggttt ggacggctcc tggaataggg tatgagacga tgggcgtcca gcgctgccag 5160
ggttcggtcc ttccagggtc tcagtgttcg agtcagggtt gtttccgtca cagtgaaggg 5220
gtgtgcgcct gcttgggcgc ttgccagggt gcgcttcaga ctcatcctgc tggtcgaaaa 5280
cttctgtcgc ttggcgccct gtatgtcggc caagtagcag tttaccatga gttcgtagtt 5340
gagcgcctcg gctgcgtggc ctttggcgcg gagcttacct ttggaagttt tcttgcatac 5400
cgggcagtat aggcatttca gcgcatacaa cttgggcgca aggaaaacgg attctgggga 5460
gtatgcatct gcgccgcagg aggcgcaaac agtttcacat tccaccagcc aggttaaatc 5520
cggttcattg ggtcaaaaa caagttttcc gccatatttt ttgatgcgtt tcttaccttt 5580
ggtctccatg agttcgtgtc ctcgttgagt gacaaacagg ctgtccgtgt ccccgtagac 5640

-continued

```
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg ggtccccgc    5880
tggggggta taaaagggg cggttctttg ctcttcctca ctgtcttccg gatcgctgtc     5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccccctctg atacttgctc gcacatagtc atatagttca tgtgatggcg ctagcagccc  6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
```

cagtgggaag ccgaggcctg gcgattgtat ctcgtgcttt actatgttgt ctgcatcggc 8100
ctgttcatct tctgtctcga tggtggtcat gctgacgagc cctcgcggga ggcaagtcca 8160
gacctcggcg cggcaggggc ggagctcgag gacgagagcg cgcaggctgg agctgtccag 8220
ggtcctgaga cgctgcggac tcaggttagt aggcagtgtc aggagattaa cttgcatgat 8280
cttttggagg gcgtgcggga ggttcagata gtacttgatc tcaacgggtc cgttggtgga 8340
gatgtcgatg gcttgcaggg ttccgtgtcc cttgggcgct accaccgtgc ccttgttttt 8400
cattttggac ggcggtggct ctgttgcttc ttgcatgttt agaagcggtg tcgagggcgc 8460
gcaccgggcg gcaggggcgg ctcgggaccc ggcggcatgg ctggcagtgg tacgtcggcg 8520
ccgcgcgcgg gtaggttctg gtactgcgcc ctgagaagac tcgcatgcgc gacgacgcgg 8580
cggttgacat cctggatctg acgcctctgg gtgaaagcta ccggccccgt gagcttgaac 8640
ctgaaagaga gttcaacaga atcaatctcg gtatcgttga cggcggcttg cctaaggatt 8700
tcttgcacgt caccagagtt gtcctggtag gcgatctccg ccatgaactg ctcgatctct 8760
tcctcttgaa gatctccgcg gcccgctctc tcgacggtgg ccgcgaggtc gttggagatg 8820
cgcccaatga gttgagagaa tgcattcatg cccgcctcgt tccagacgcg gctgtagacc 8880
acggccccca cgggatctct cgcgcgcatg accacctggg cgaggttgag ctccacgtgg 8940
cgggtgaaga ccgcatagtt gcataggcgc tggaaaaggt agttgagtgt ggtggcgatg 9000
tgctcggtga cgaagaaata catgatccat cgtctcagcg gcatctcgct gacatcgccc 9060
agagcttcca agcgctccat ggcctcgtag aagtccacgg caaaattaaa aaactgggag 9120
tttcgcgcgg acacggtcaa ctcctcttcc agaagacgga taagttcggc gatggtggtg 9180
cgcacctcgc gctcgaaagc ccctgggatt tcttcctcaa tctcttcttc ttccactaac 9240
atctcttcct cttcaggtgg ggctgcagga ggagggggaa cgcggcgacg ccggcggcgc 9300
acgggcagac ggtcgatgaa tctttcaatg acctctccgc ggcggcggcg catggtttca 9360
gtgacggcgc ggccgttctc gcgcggtcgc agagtaaaaa caccgccgcg catctcctta 9420
aagtggtgac tgggaggttc tccgtttggg agggagaggg cgctgattat acattttatt 9480
aattggcccg tagggactgc acgcagagat ctgatcgtgt caagatccac gggatctgaa 9540
aacctttcga cgaaagcgtc taaccagtca cagtcacaag gtaggctgag tacggcttct 9600
tgtgggcggg ggtggttatg tgttcggtct gggtcttctg tttcttcttc atctcgggaa 9660
ggtgagacga tgctgctggt gatgaaatta aagtaggcag ttctaagacg gcggatggtg 9720
gcgaggagca ccaggtcttt gggtccggct tgctggatac gcaggcgatt ggccattccc 9780
caagcattat cctgacatct agcaagatct ttgtagtagt cttgcatgag ccgttctacg 9840
ggcacttctt cctcacccgt tctgccatgc atacgtgtga gtccaaatcc gcgcattggt 9900
tgtaccagtg ccaagtcagc tacgactctt tcggcgagga tggcttgctg tacttgggta 9960
agggtggctt gaaagtcatc aaaatccaca aagcggtggt aagctcctgt attaatggtg 10020
taagcacagt tggccatgac tgaccagtta actgtctggt gaccagggcg cacgagctcg 10080
gtgtatttaa ggcgcgaata ggcgcgggtg tcaaagatgt aatcgttgca ggtgcgcacc 10140
agatactggt accctataag aaaatgcggc ggtggttggc ggtagagagg ccatcgttct 10200
gtagctggag cgccaggggc gaggtcttcc aacataaggc ggtgatagcc gtagatgtac 10260
ctggacatcc aggtgattcc tgcggcggta gtagaagccc gaggaaactc gcgtacgcgg 10320
ttccaaatgt tgcgtagcgg catgaagtag ttcattgtag gcacggtttg accagtgagg 10380

-continued

```
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
```

tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960
cgctatgaac tctgattatt tcaccaatgc catcttaaac ccgcactggc tgcccccacc 13020
tggtttctac acgggcgaat atgacatgcc cgaccctaat gacggatttc tgtgggacga 13080
cgtggacagc gatgtttttt cacctctttc tgatcatcgc acgtggaaaa aggaaggcgg 13140
cgatagaatg cattcttctg catcgctgtc cggggtcatg ggtgctaccg cggctgagcc 13200
cgagtctgca agtccttttc ctagtctacc cttttctcta cacagtgtac gtagcagcga 13260
agtgggtaga ataagtcgcc cgagtttaat gggcgaagag gagtatctaa acgattcctt 13320
gctcagaccg gcaagagaaa aaaatttccc aaacaatgga atagaaagtt tggtggataa 13380
aatgagtaga tggaagactt atgctcagga tcacagagac gagcctggga tcatggggat 13440
tacaagtaga gcgagccgta gacgccagcg ccatgacaga cagaggggtc ttgtgtggga 13500
cgatgaggat tcggccgatg atagcagcgt gctggacttg ggtgggagag gaaggggcaa 13560
cccgtttgct catttgcgcc ctcgcttggg tggtatgttg taaaaaaaaa taaaaaaaaa 13620
actcaccaag gccatggcga cgagcgtacg ttcgttcttc tttattatct gtgtctagta 13680
taatgaggcg agtcgtgcta ggcggagcgg tggtgtatcc ggagggtcct cctccttcgt 13740
acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040
ggggcggtca gctaaagacc atcatgcata ctaacatgcc aaacgtgaac gagtatatgt 14100
ttagtaacaa gttcaaagcg cgtgtgatgg tgtccagaaa acctcccgac ggtgctgcag 14160
ttggggatac ttatgatcac aagcaggata ttttgaaata tgagtggttc gagtttactt 14220
tgccagaagg caacttttca gttactatga ctattgattt gatgaacaat gccatcatag 14280
ataattactt gaaagtgggt agacagaatg gagtgcttga aagtgacatt ggtgttaagt 14340
tcgacaccag gaacttcaag ctgggatggg atcccgaaac caagttgatc atgcctggag 14400
tgtatacgta tgaagccttc catcctgaca ttgtcttact gcctggctgc ggagtggatt 14460
ttaccgagag tcgtttgagc aaccttcttg gtatcagaaa aaaacagcca tttcaagagg 14520
gttttaagat tttgtatgaa gatttagaag gtggtaatat tccggccctc ttggatgtag 14580
atgcctatga gaacagtaag aaagaacaaa aagccaaaat agaagctgct acagctgctg 14640
cagaagctaa ggcaaacata gttgccagcg actctacaag ggttgctaac gctggagagg 14700
tcagaggaga caattttgcg ccaacacctg ttccgactgc agaatcatta ttggccgatg 14760
tgtctgaagg aacggacgtg aaactcacta ttcaacctgt agaaaaagat agtaagaata 14820
gaagctataa tgtgttggaa gacaaaatca acacagccta tcgcagttgg tatctttcgt 14880
acaattatgg cgatcccgaa aaaggagtgc gttcctggac attgctcacc acctcagatg 14940
tcacctgcgg agcagagcag gtctactggt cgcttccaga catgatgaag gatcctgtca 15000
ctttccgctc cactagacaa gtcagtaact accctgtggt gggtgcagag cttatgcccg 15060
tcttctcaaa gagcttctac aacgaacaag ctgtgtactc ccagcagctc cgccagtcca 15120

```
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg ggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtcccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
```

gagcgggctt aaaaatttg gctcaaccat aaaaacatac gggaacaaag cttggaacag 17580
cagtacagga caggcgctta gaaataaact taaagaccag aacttccaac aaaaagtagt 17640
cgatgggata gcttccggca tcaatggagt ggtagatttg gctaaccagg ctgtgcagaa 17700
aaagataaac agtcgtttgg acccgccgcc agcaacccca ggtgaaatgc aagtggagga 17760
agaaattcct ccgccagaaa aacgaggcga caagcgtccg cgtcccgatt tggaagagac 17820
gctggtgacg cgcgtagatg aaccgccttc ttatgaggaa gcaacgaagc ttggaatgcc 17880
caccactaga ccgatagccc caatggccac cggggtgatg aaaccttctc agttgcatcg 17940
acccgtcacc ttggatttgc cccctccccc tgctgctact gctgtacccg cttctaagcc 18000
tgtcgctgcc ccgaaaccag tcgccgtagc caggtcacgt cccgggggcg ctcctcgtcc 18060
aaatgcgcac tggcaaaata ctctgaacag catcgtgggt ctaggcgtgc aaagtgtaaa 18120
acgccgtcgc tgcttttaat taaatatgga gtagcgctta acttgcctat ctgtgtatat 18180
gtgtcattac acgccgtcac agcagcagag gaaaaaagga agaggtcgtg cgtcgacgct 18240
gagttacttt caagatggcc accccatcga tgctgcccca atgggcatac atgcacatcg 18300
ccggacagga tgcttcggag tacctgagtc cgggtctggt gcagttcgcc cgcgccacag 18360
acacctactt caatctggga aataagttta gaaatcccac cgtagcgccg acccacgatg 18420
tgaccaccga ccgtagccag cggctcatgt tgcgcttcgt gcccgttgac cgggaggaca 18480
atacatactc ttacaaagtg cggtacaccc tggccgtggg cgacaacaga gtgctggata 18540
tggccagcac gttctttgac attaggggtg tgttggacag aggtcccagt ttcaaaccct 18600
attctggtac ggcttacaac tccctggctc ctaaaggcgc tccaaataca tctcagtgga 18660
ttgcagaagg tgtaaaaaat acaactggtg aggaacacgt aacagaagag gaaaccaata 18720
ctactactta cacttttggc aatgctcctg taaaagctga agctgaaatt acaaaagaag 18780
gactcccagt aggtttggaa gtttcagatg aagaaagtaa accgatttat gctgataaaa 18840
catatcagcc agaacctcag ctgggagatg aaacttggac tgaccttgat ggaaaaaccg 18900
aaaagtatgg aggcagggct ctcaaacccg atactaagat gaaaccatgc tacgggtcct 18960
ttgccaaacc tactaatgtg aaaggcggtc aggcaaaaca aaaaacaacg gagcagccaa 19020
atcagaaagt cgaatatgat atcgacatgg agtttttttga tgcggcatcg cagaaaacaa 19080
acttaagtcc taaaattgtc atgtatgcag aaaatgtaaa tttggaaact ccagacactc 19140
atgtagtgta caaacctgga acagaagaca caagttccga agctaatttg ggacaacaat 19200
ctatgcccaa cagacccaac tacattggct tcagagataa ctttattgga cttatgtact 19260
ataacagtac tggtaacatg gggggtgctgg ctggtcaagc gtctcagtta aatgcagtgg 19320
ttgacttgca ggacagaaac acagaacttt cttaccaact cttgcttgac tctctgggcg 19380
acagaaccag atactttagc atgtggaatc aggctgtgga cagttatgat cctgatgtac 19440
gtgttattga aaatcatggt gtggaagatg aacttcccaa ctactgtttt ccactggacg 19500
gcataggtgt tccaacaacc agttacaaat caatagttcc aaatggagac aatgcgccta 19560
attggaagga acctgaagta aatggaacaa gtgagatcgg acagggtaat ttgtttgcca 19620
tggaaattaa ccttcaagcc aatctatggc gaagtttcct ttattccaat gtggctctat 19680
atctcccaga ctcgtacaaa tacaccccgt ccaatgtcac tcttccagaa aacaaaaaca 19740
cctacgacta catgaacggg cgggtggtgc cgccatctct agtagacacc tatgtgaaca 19800
ttggtgccag gtggtctctg gatgccatgg acaatgtcaa cccattcaac caccaccgta 19860
acgctggctt gcgttaccga tccatgcttc tgggtaacgg acgttatgtg cctttccaca 19920
tacaagtgcc tcaaaaattc ttcgctgtta aaaacctgct gcttctccca ggctcctaca 19980
cttatgagtg gaactttagg aaggatgtga acatggttct acagagttcc ctcggtaacg 20040
acctgcgggt agatggcgcc agcatcagtt tcacgagcat caacctctat gctacttttt 20100
tccccatggc tcacaacacc gcttccaccc ttgaagccat gctgcggaat gacaccaatg 20160
atcagtcatt caacgactac ctatctgcag ctaacatgct ctaccccatt cctgccaatg 20220
caaccaatat tcccatttcc attccttctc gcaactgggc ggctttcaga ggctggtcat 20280
ttaccagact gaaaaccaaa gaaactccct ctttggggtc tggatttgac ccctactttg 20340
tctattctgg ttctattccc tacctggatg gtaccttcta cctgaaccac acttttaaga 20400
aggtttccat catgtttgac tcttcagtga gctggcctgg aaatgacagg ttactatctc 20460
ctaacgaatt tgaaataaag cgcactgtgg atggcgaagg ctacaacgta gcccaatgca 20520
acatgaccaa agactggttc ttggtacaga tgctcgccaa ctacaacatc ggctatcagg 20580
gcttctacat tccagaagga tacaaagatc gcatgtattc atttttcaga aacttccagc 20640
ccatgagcag gcaggtggtt gatgaggtca attacaaaga cttcaaggcc gtcgccatac 20700
cctaccaaca caacaactct ggctttgtgg gttacatggc tccgaccatg cgccaaggtc 20760
aaccctatcc cgctaactat ccctatccac tcattggaac aactgccgta aatagtgtta 20820
cgcagaaaaa gttcttgtgt gacagaacca tgtggcgcat accgttctcg agcaacttca 20880
tgtctatggg ggcccttaca gacttgggac agaatatgct ctatgccaac tcagctcatg 20940
ctctggacat gacctttgag gtggatccca tggatgagcc caccctgctt tatcttctct 21000
tcgaagtttt cgacgtggtc agagtgcatc agccacaccg cggcatcatc gaggcagtct 21060
acctgcgtac accgttctcg gccggtaacg ctaccacgta agaagcttct tgcttcttgc 21120
aaatagcagc tgcaaccatg gcctgcggat cccaaaacgg ctccagcgag caagagctca 21180
gagccattgt ccaagacctg ggttgcggac cctatttttt gggaacctac gataagcgct 21240
tcccggggtt catggccccc gataagctcg cctgtgccat tgtaaatacg gccggacgtg 21300
agacgggggg agagcactgg ttggctttcg gttggaaccc acgttctaac acctgctacc 21360
tttttgatcc ttttggattc tcggatgatc gtctcaaaca gatttaccag tttgaatatg 21420
agggtctcct gcgccgcagc gctcttgcta ccaaggaccg ctgtattacg ctggaaaaat 21480
ctacccagac cgtgcagggt ccccgttctg ccgcctgcgg acttttctgc tgcatgttcc 21540
ttcacgcctt tgtgcactgg cctgaccgtc ccatggacgg aaaccccacc atgaaattgc 21600
taactggagt gccaaacaac atgcttcatt ctcctaaagt ccagcccacc ctgtgtgaca 21660
atcaaaaagc actctaccat tttcttaata cccattcgcc ttattttcgc tcccatcgta 21720
cacacatcga aagggccact gcgttcgacc gtatggatgt tcaataatga ctcatgtaaa 21780
caacgtgttc aataaacatc actttatttt tttacatgta tcaaggctct gcattactta 21840
tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260

```
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa actttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
```

-continued

```
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
```

ctgttctgac tttggaaagt tcgtcttcgc aaccccgctc gggcggaatc gggaccgttc 27060
aatttgtgga ggagtttact ccctctgtct acttcaaccc cttctccgga tctcctgggc 27120
attacccgga cgagttcata ccgaacttcg acgcgattag cgagtcagtg gacggctacg 27180
attgatgtct ggtgacgcgg ctgagctatc tcggctgcga catctagacc actgccgccg 27240
ctttcgctgc tttgcccggg aactcattga gttcatctac ttcgaactcc ccaaggatca 27300
ccctcaaggt ccggcccacg gagtgcggat ttctatcgaa ggcaaaatag actctcgcct 27360
gcaacgaatt ttctcccagc ggcccgtgct gatcgagcga gaccagggaa acaccacggt 27420
ttccatctac tgcatttgta atcaccccgg attgcatgaa agcctttgct gtcttatgtg 27480
tactgagttt aataaaaact gaattaagac tctcctacgg actgccgctt cttcaacccg 27540
gattttacaa ccagaagaac gaaacttttc ctgtcgtcca ggactctgtt aacttcacct 27600
ttcctactca caaactagaa gctcaacgac tacaccgctt ttccagaagc attttcccta 27660
ctaatactac tttcaaaacc ggaggtgagc tccaaggtct tcctacagaa aacccttggg 27720
tggaagcggg ccttgtagtg ctaggaattc ttgcgggtgg gcttgtgatt attctttgct 27780
acctatacac accttgcttc actttcttag tggtgttgtg gtattggttt aaaaaatggg 27840
gcccatacta gtcttgcttg ttttactttc gcttttggaa ccgggttctg ccaattacga 27900
tccatgtcta gacttcgacc cagaaaactg cacacttact tttgcacccg acacaagccg 27960
catctgtgga gttcatcgcc tctcttacga acttggcccc caacgacaaa aatttacctg 28020
catggtggga atcaacccca tagttatcac ccagcaaagt ggagatacta agggttgcat 28080
tcactgctcc tgcgattcca tcgagtgcac ctacaccctg ctgaagaccc tatgcggcct 28140
aagagacctg ctaccaatga attaaaaaat gattaataaa aaatcactta cttgaaatca 28200
gcaataaggt ctctgttgaa atttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta cccctatgaa gatgaaagca cctcccaaca 28440
ccccttata aacccagggt ttatttcccc aaatggcttc acacaaagcc caaacggagt 28500
tcttacttta aaatgtttaa ccccactaac aaccacaggc ggatctctac agctaaaagt 28560
gggaggggga cttacagtgg atgacaccaa cggtttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920
aactacacac agaaatataa attttactgc agagctgttt ttcgattcta ctggtaattt 28980
actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct tttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttgcga tcgccaggcc caccatgggc cacacacgga ggcagggaac 29400
atcaccatcc aagtgtccat acctcaattt ctttcagctc ttggtgctgg ctggtctttc 29460
tcacttctgt tcaggtgtta tccacgtgac caaggaagtg aaagaagtgg caacgctgtc 29520
ctgtggtcac aatgtttctg ttgaagagct ggcacaaact cgcatctact ggcaaaagga 29580
gaagaaaatg gtgctgacta tgatgtctgg ggacatgaat atatggcccg agtacaagaa 29640
ccggaccatc tttgatatca ctaataacct ctccattgtg atcctggctc tgcgcccatc 29700
tgacgagggc acatacgagt gtgttgttct gaagtatgaa aaagacgctt tcaagcggga 29760
acacctggct gaagtgacgt tatcagtcaa agctgacttc cctacaccta gtatatctga 29820
ctttgaaatt ccaacttcta atattagaag gataatttgc tcaacctctg gaggttttcc 29880
agagcctcac ctctcctggt tggaaaatgg agaagaatta aatgccatca acacaacagt 29940
ttcccaagat cctgaaactg agctctatgc tgttagcagc aaactggatt tcaatatgac 30000
aaccaaccac agcttcatgt gtctcatcaa gtatggacat ttaagagtga atcagacctt 30060
caactggaat acaaccaagc aagagcattt tcctgataac ctgctcccat cctgggccat 30120
taccttaatc tcagtaaatg gaatttttgt gatatgctgc ctgacctact gctttgcccc 30180
aagatgcaga gagagaagga ggaatgagag attgagaagg gaaagtgtac gccctgtata 30240
agctagcttg actgactgag atacagcgta ccttcagctc acagacatga taagatacat 30300
tgatgagttt ggacaaacca caactagaat gcagtgaaaa aaatgcttta tttgtgaaat 30360
ttgtgatgct attgctttat ttgtaaccat tataagctgc aataaacaag ttaacaacaa 30420
caattgcatt cattttatgt ttcaggttca gggggaggtg tgggaggttt tttaaagcaa 30480
gtaaaacctc tacaaatgtg gtagtcgtca gctatcctgc aggaacttgt ttatttgaaa 30540
atcaattcac aaaatccgag tagttatttt gcctccccct tcccatttaa cagaatacac 30600
caatctctcc ccacgcacag ctttaaacat ttggatacca ttagatatag acatggtttt 30660
agattccaca ttccaaacag tttcagagcg agccaatctg gggtcagtga tagataaaaa 30720
tccatcggga tagtctttta aagcgctttc acagtccaac tgctgcggat gcgactccgg 30780
agtctggatc acggtcatct ggaagaagaa cgatgggaat cataatccga aaacggtatc 30840
ggacgattgt gtctcatcaa acccacaagc agccgctgtc tgcgtcgctc cgtgcgactg 30900
ctgtttatgg gatcagggtc cacagtgtcc tgaagcatga ttttaatagc ccttaacatc 30960
aactttctgg tgcgatgcgc gcagcaacgc attctgattt cactcaaatc tttgcagtag 31020
gtacaacaca ttattacaat attgtttaat aaaccataat taaaagcgct ccagccaaaa 31080
ctcatatctg atataatcgc ccctgcatga ccatcatacc aaagtttaat ataaattaaa 31140
tgacgttccc tcaaaaacac actacccaca tacatgatct cttttggcat gtgcatatta 31200
acaatctgtc tgtaccatgg acaacgttgg ttaatcatgc aacccaatat aaccttccgg 31260
aaccacactg ccaacaccgc tcccccagcc atgcattgaa gtgaaccctg ctgattacaa 31320
tgacaatgaa gaacccaatt ctctcgaccg tgaatcactt gagaatgaaa aatatctata 31380
gtggcacaac atagacataa atgcatgcat cttctcataa tttttaactc ctcaggattt 31440
agaaacatat cccagggaat aggaagctct tgcagaacag taaagctggc agaacaagga 31500
agaccacgaa cacaacttac actatgcata gtcatagtat cacaatctgg caacagcggg 31560
tggtcttcag tcatagaagc tcgggtttca ttttcctcac aacgtggtaa ctgggctctg 31620
gtgtaagggt gatgtctggc gcatgatgtc gagcgtgcgc gcaaccttgt cataatggag 31680
ttgcttcctg acattctcgt attttgtata gcaaaacgcg gccctggcag aacacactct 31740

```
tcttcgcctt ctatcctgcc gcttagcgtg ttccgtgtga tagttcaagt acaaccacac  31800
tcttaagttg gtcaaaagaa tgctggcttc agttgtaatc aaaactccat cgcatctaat  31860
cgttctgagg aaatcatcca agcaatgcaa ctggattgtg tttcaagcag gagaggagag  31920
ggaagagacg gaagaaccat gttaattttt attccaaacg atctcgcagt acttcaaatt  31980
gtagatcgcg cagatggcat ctctcgcccc cactgtgttg gtgaaaaagc acagctagat  32040
caaaagaaat gcgattttca aggtgctcaa cggtggcttc cagcaaagcc tccacgcgca  32100
catccaagaa caaaagaata ccaaaagaag gagcattttc taactcctca atcatcatat  32160
tacattcctg caccattccc agataatttt cagctttcca gccttgaatt attcgtgtca  32220
gttcttgtgg taaatccaat ccacacatta caaacaggtc ccggagggcg ccctccacca  32280
ccattcttaa acacaccctc ataatgacaa aatatcttgc tcctgtgtca cctgtagcga  32340
attgagaatg gcaacatcaa ttgacatgcc cttggctcta agttcttctt taagttctag  32400
ttgtaaaaac tctctcatat tatcaccaaa ctgcttagcc agaagccccc cgggaacaag  32460
agcaggggac gctacagtgc agtacaagcg cagacctccc caattggctc cagcaaaaac  32520
aagattggaa taagcatatt gggaaccgcc agtaatatca tcgaagttgc tggaaatata  32580
atcaggcaga gtttcttgta aaaattgaat aaaagaaaaa tttgccaaaa aaacattcaa  32640
aacctctggg atgcaaatgc aataggttac cgcgctgcgc tccaacattg ttagttttga  32700
attagtctgc aaaaataaaa aaaaaaacaa gcgtcatatc atagtagcct gacgaacaga  32760
tggataaatc agtctttcca tcacaagaca agccacaggg tctccagctc gaccctcgta  32820
aaacctgtca tcatgattaa acaacagcac cgaaagttcc tcgcggtgac cagcatgaat  32880
aattcttgat gaagcataca atccagacat gttagcatca gttaacgaga aaaaacagcc  32940
aacatagcct ttgggtataa ttatgcttaa tcgtaagtat agcaaagcca cccctcgcgg  33000
atacaaagta aaaggcacag gagaataaaa aatataatta tttctctgct gctgttcagg  33060
caacgtcgcc cccggtccct ctaaatacac atacaaagcc tcatcagcca tggcttacca  33120
gacaaagtac agcgggcaca caaagcacaa gctctaaagt gactctccaa cctctccaca  33180
atatatatat acacaagccc taaactgacg taatgggagt aaagtgtaaa aaatcccgcc  33240
aaacccaaca cacaccccga aactgcgtca ccagggaaaa gtacagtttc acttccgcaa  33300
tcccaacagg cgtaacttcc tctttctcac ggtacgtgat atcccactaa cttgcaacgt  33360
cattttccca cggtcgcacc gccccttta gccgttaacc ccacagccaa tcaccacacg  33420
atccacactt tttaaaatca cctcatttac atattggcac cattccatct ataaggtata  33480
ttatatagat aga                                                     33493
```

<210> SEQ ID NO 110
<211> LENGTH: 34119
<212> TYPE: DNA
<213> ORGANISM: Artificial Sequence
<220> FEATURE:
<223> OTHER INFORMATION: NG-343 virus genome sequence comprising the EnAd genome with a transgene cassette that encodes IFNa, and CD80, inserted in the region By. The transgene cassette contains a 5' SSA, IFNa cDNA sequence, P2A peptide, CD80 cDNA sequence and a 3' poly(A)

<400> SEQUENCE: 110

```
tctatctata taatatacct tatagatgga atggtgccaa tatgtaaatg aggtgatttt     60
aaaaagtgtg gatcgtgtgg tgattggctg tggggttaac ggctaaaagg ggcggtgcga    120
```

```
ccgtgggaaa atgacgtttt gtgggggtgg agttttttttg caagttgtcg cgggaaatgt    180
gacgcataaa aaggcttttt tctcacggaa ctacttagtt ttcccacggt atttaacagg    240
aaatgaggta gttttgaccg gatgcaagtg aaaattgttg attttcgcgc gaaaactgaa    300
tgaggaagtg tttttctgaa taatgtggta tttatggcag ggtggagtat ttgttcaggg    360
ccaggtagac tttgacccat tacgtggagg tttcgattac cgtgtttttt acctgaattt    420
ccgcgtaccg tgtcaaagtc ttctgttttt acgtaggtgt cagctgatcg ctagggtatt    480
tatacctcag ggtttgtgtc aagaggccac tcttgagtgc cagcgagaag agttttctcc    540
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agctttttga gcctcctacg cttcaggaac tgtatgattt    720
agaggtagag ggatcggagg attctaatga ggaagctgta aatggctttt ttaccgattc    780
tatgctttta gctgctaatg aagggttaga attagatccg cctttggaca cttttgatac    840
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
```

ggctgaggtg gtaatagata ctcaagacaa ggcagttatt agatgctgca tgatggatat 2580
gtggcctggg gtagtcggta tggaagcagt aacttttgta aatgttaagt ttaggggaga 2640
tggttataat ggaatagtgt ttatggccaa taccaaactt atattgcatg gttgtagctt 2700
ttttggtttc aacaatacct gtgtagatgc ctggggacag gttagtgtac ggggatgtag 2760
tttctatgcg tgttggattg ccacagctgg cagaaccaag agtcaattgt ctctgaagaa 2820
atgcatattt caaagatgta acctgggcat tctgaatgaa ggcgaagcaa gggtccgcca 2880
ctgcgcttct acagatactg gatgttttat tttgattaag ggaaatgcca gcgtaaagca 2940
taacatgatt tgcggtgctt ccgatgagag gccttatcaa atgctcactt gtgctggtgg 3000
gcattgtaat atgctggcta ctgtgcatat tgtttcccat caacgcaaaa aatggcctgt 3060
ttttgatcac aatgtgatga cgaagtgtac catgcatgca ggtgggcgta gaggaatgtt 3120
tatgccttac cagtgtaaca tgaatcatgt gaaagtgttg ttggaaccag atgccttttc 3180
cagaatgagc ctaacaggaa tttttgacat gaacatgcaa atctggaaga tcctgaggta 3240
tgatgatacg agatcgaggg tacgcgcatg cgaatgcgga ggcaagcatg ccaggttcca 3300
gccggtgtgt gtagatgtga ctgaagatct cagaccggat catttggtta ttgcccgcac 3360
tggagcagag ttcggatcca gtggagaaga aactgactaa ggtgagtatt gggaaaactt 3420
tggggtggga ttttcagatg gacagattga gtaaaaattt gtttttctg tcttgcagct 3480
gtcatgagtg gaaacgcttc ttttaagggg ggagtcttca gcccttatct gacagggcgt 3540
ctcccatcct gggcaggagt tcgtcagaat gttatgggat ctactgtgga tggaagaccc 3600
gtccaacccg ccaattcttc aacgctgacc tatgctactt taagttcttc acctttggac 3660
gcagctgcag ctgccgccgc cgcttctgtt gccgctaaca ctgtgcttgg aatgggttac 3720
tatggaagca tcatggctaa ttccacttcc tctaataacc cttctaccct gactcaggac 3780
aagttacttg tccttttggc ccagctggag gctttgaccc aacgtctggg tgaactttct 3840
cagcaggtgg tcgagttgcg agtacaaact gagtctgctg tcggcacggc aaagtctaaa 3900
taaaaaaatc ccagaatcaa tgaataaata aacaagcttg ttgttgattt aaaatcaagt 3960
gtttttattt catttttcgc gcacggtatg ccctagacca ccgatctcta tcattgagaa 4020
ctcggtggat tttttccagg atcctataga ggtgggattg aatgtttaga tacatgggca 4080
ttaggccgtc tttggggtgg agatagctcc attgaaggga ttcatgctcc ggggtagtgt 4140
tgtaaatcac ccagtcataa caaggtcgca gtgcatggtg ttgcacaata tcttttagaa 4200
gtaggctgat tgccacagat aagcccttgg tgtaggtgtt tacaaaccgg ttgagctggg 4260
atgggtgcat tcggggtgaa attatgtgca ttttggattg gatttttaag ttggcaatat 4320
tgccgccaag atcccgtctt gggttcatgt tatgaaggac caccaagacg gtgtatccgg 4380
tacatttagg aaatttatcg tgcagcttgg atggaaaagc gtggaaaaat ttggagacac 4440
ccttgtgtcc tccaagattt tccatgcact catccatgat aatagcaatg gggccgtggg 4500
cagcggcgcg ggcaaacacg ttccgtgggt ctgacacatc atagttatgt tcctgagtta 4560
aatcatcata agccatttta atgaatttgg ggcggagagt accagattgg ggtatgaatg 4620
ttccttcggg ccccggagca tagttcccct cacagatttg catttcccaa gctttcagtt 4680
ccgagggtgg aatcatgtcc acctgggggg ctatgaaaaa caccgtttct ggggcggggg 4740
tgattaattg tgatgatagc aaatttctga gcaattgaga tttgccacat ccggtggggc 4800
cataaatgat tccgattacg ggttgcaggt ggtagtttag ggaacggcaa ctgccgtctt 4860

```
ctcgaagcaa gggggccacc tcgttcatca tttcccttac atgcatattt tcccgcacca    4920
aatccattag gaggcgctct cctcctagtg atagaagttc ttgtagtgag gaaaagtttt    4980
tcagcggttt cagaccgtca gccatgggca ttttggagag agtttgctgc aaaagttcta    5040
gtctgttcca cagttcagtg atgtgttcta tggcatctcg atccagcaga cctcctcgtt    5100
tcgcgggttt ggacggctcc tggaataggg tatgagacga tgggcgtcca gcgctgccag    5160
ggttcggtcc ttccagggtc tcagtgttcg agtcagggtt gtttccgtca cagtgaaggg    5220
gtgtgcgcct gcttgggcgc ttgccagggt gcgcttcaga ctcatcctgc tggtcgaaaa    5280
cttctgtcgc ttggcgccct gtatgtcggc caagtagcag tttaccatga gttcgtagtt    5340
gagcgcctcg gctgcgtggc ctttggcgcg gagcttacct ttggaagttt tcttgcatac    5400
cgggcagtat aggcatttca gcgcatacaa cttgggcgca aggaaaacgg attctgggga    5460
gtatgcatct gcgccgcagg aggcgcaaac agtttcacat tccaccagcc aggttaaatc    5520
cggttcattg gggtcaaaaa caagttttcc gccatatttt ttgatgcgtt tcttaccttt    5580
ggtctccatg agttcgtgtc ctcgttgagt gacaaacagg ctgtccgtgt ccccgtagac    5640
tgattttaca ggcctcttct ccagtggagt gcctcggtct tcttcgtaca ggaactctga    5700
ccactctgat acaaaggcgc gcgtccaggc cagcacaaag gaggctatgt gggaggggta    5760
gcgatcgttg tcaaccaggg ggtccacctt ttccaaagta tgcaaacaca tgtcaccctc    5820
ttcaacatcc aggaatgtga ttggcttgta ggtgtatttc acgtgacctg gggtccccgc    5880
tggggggggta taaaaggggg cggttctttg ctcttcctca ctgtcttccg gatcgctgtc    5940
caggaacgtc agctgttggg gtaggtattc cctctcgaag gcgggcatga cctctgcact    6000
caggttgtca gtttctaaga acgaggagga tttgatattg acagtgccgg ttgagatgcc    6060
tttcatgagg ttttcgtcca tctggtcaga aaacacaatt tttttattgt caagtttggt    6120
ggcaaatgat ccatacaggg cgttggataa aagtttggca atggatcgca tggtttggtt    6180
cttttccttg tccgcgcgct ctttggcggc gatgttgagt tggacatact cgcgtgccag    6240
gcacttccat tcggggaaga tagttgttaa ttcatctggc acgattctca cttgccaccc    6300
tcgattatgc aaggtaatta aatccacact ggtggccacc tcgcctcgaa ggggttcatt    6360
ggtccaacag agcctacctc ctttcctaga acagaaaggg ggaagtgggt ctagcataag    6420
ttcatcggga gggtctgcat ccatggtaaa gattcccgga agtaaatcct tatcaaaata    6480
gctgatggga gtggggtcat ctaaggccat ttgccattct cgagctgcca gtgcgcgctc    6540
atatgggtta aggggactgc ccccatggcat gggatgggtg agtgcagagg catacatgcc    6600
acagatgtca tagacgtaga tgggatcctc aaagatgcct atgtaggttg gatagcatcg    6660
ccccccctctg atacttgctc gcacatagtc atatagttca tgtgatggcg ctagcagccc    6720
cggacccaag ttggtgcgat tgggtttttc tgttctgtag acgatctggc gaaagatggc    6780
gtgagaattg gaagagatgg tgggtctttg aaaaatgttg aaatgggcat gaggtagacc    6840
tacagagtct ctgacaaagt gggcataaga ttcttgaagc ttggttacca gttcggcggt    6900
gacaagtacg tctagggcgc agtagtcaag tgtttcttga atgatgtcat aacctggttg    6960
gtttttcttt tcccacagtt cgcggttgag aaggtattct tcgcgatcct tccagtactc    7020
ttctagcgga aacccgtctt tgtctgcacg gtaagatcct agcatgtaga actgattaac    7080
tgccttgtaa gggcagcagc ccttctctac gggtagagag tatgcttgag cagcttttcg    7140
tagcgaagcg tgagtaaggg caaaggtgtc tctgaccatg actttgagga attggtattt    7200
gaagtcgatg tcgtcacagg ctccctgttc ccagagttgg aagtctaccc gtttcttgta    7260
```

ggcggggttg ggcaaagcga aagtaacatc attgaagaga atcttgccgg ccctgggcat 7320
gaaattgcga gtgatgcgaa aaggctgtgg tacttccgct cggttattga taacctgggc 7380
agctaggacg atctcgtcga aaccgttgat gttgtgtcct acgatgtata attctatgaa 7440
acgcggcgtg cctctgacgt gaggtagctt actgagctca tcaaaggtta ggtctgtggg 7500
gtcagataag gcgtagtgtt cgagagccca ttcgtgcagg tgaggattcg ctttaaggaa 7560
ggaggaccag aggtccactg ccagtgctgt ttgtaactgg tcccggtact gacgaaaatg 7620
ccgtccgact gccatttttt ctggggtgac gcaatagaag gtttgggggt cctgccgcca 7680
gcgatcccac ttgagtttta tggcgaggtc ataggcgatg ttgacgagcc gctggtctcc 7740
agagagtttc atgaccagca tgaaggggat tagctgcttg ccaaaggacc ccatccaggt 7800
gtaggtttcc acatcgtagg tgagaaagag cctttctgtg cgaggatgag agccaatcgg 7860
gaagaactgg atctcctgcc accagttgga ggaatggctg ttgatgtgat ggaagtagaa 7920
ctccctgcga cgcgccgagc attcatgctt gtgcttgtac agacggccgc agtagtcgca 7980
gcgttgcacg ggttgtatct cgtgaatgag ttgtacctgg cttcccttga cgagaaattt 8040
cagtgggaag ccgaggcctg gcgattgtat ctcgtgcttt actatgttgt ctgcatcggc 8100
ctgttcatct tctgtctcga tggtggtcat gctgacgagc cctcgcggga ggcaagtcca 8160
gacctcggcg cggcaggggc ggagctcgag gacgagagcg cgcaggctgg agctgtccag 8220
ggtcctgaga cgctgcggac tcaggttagt aggcagtgtc aggagattaa cttgcatgat 8280
cttttggagg gcgtgcggga ggttcagata gtacttgatc tcaacgggtc cgttggtgga 8340
gatgtcgatg gcttgcaggg ttccgtgtcc cttgggcgct accaccgtgc ccttgttttt 8400
cattttggac ggcggtggct ctgttgcttc ttgcatgttt agaagcggtg tcgagggcgc 8460
gcaccgggcg gcaggggcgg ctcgggaccc ggcggcatgg ctggcagtgg tacgtcggcg 8520
ccgcgcgcgg gtaggttctg gtactgcgcc ctgagaagac tcgcatgcgc gacgacgcgg 8580
cggttgacat cctggatctg acgcctctgg gtgaaagcta ccggccccgt gagcttgaac 8640
ctgaaagaga gttcaacaga atcaatctcg gtatcgttga cggcggcttg cctaaggatt 8700
tcttgcacgt caccagagtt gtcctggtag gcgatctccg ccatgaactg ctcgatctct 8760
tcctcttgaa gatctccgcg gcccgctctc tcgacggtgg ccgcgaggtc gttggagatg 8820
cgcccaatga gttgagagaa tgcattcatg cccgcctcgt tccagacgcg gctgtagacc 8880
acggccccca cgggatctct cgcgcgcatg accacctggg cgaggttgag ctccacgtgg 8940
cgggtgaaga ccgcatagtt gcataggcgc tggaaaaggt agttgagtgt ggtggcgatg 9000
tgctcggtga cgaagaaata catgatccat cgtctcagcg gcatctcgct gacatcgccc 9060
agagcttcca agcgctccat ggcctcgtag aagtccacgg caaaattaaa aaactgggag 9120
tttcgcgcgg acacggtcaa ctcctcttcc agaagacgga taagttcggc gatggtggtg 9180
cgcacctcgc gctcgaaagc ccctgggatt tcttcctcaa tctcttcttc ttccactaac 9240
atctcttcct cttcaggtgg ggctgcagga ggagggggaa cgcggcgacg ccggcggcgc 9300
acgggcagac ggtcgatgaa tctttcaatg acctctccgc ggcggcggcg catggtttca 9360
gtgacggcgc ggccgttctc gcgcggtcgc agagtaaaaa caccgccgcg catctcctta 9420
aagtggtgac tgggaggttc tccgtttggg agggagaggg cgctgattat acattttatt 9480
aattggcccg tagggactgc acgcagagat ctgatcgtgt caagatccac gggatctgaa 9540
aacctttcga cgaaagcgtc taaccagtca cagtcacaag gtaggctgag tacggcttct 9600

-continued

```
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
```

atcggccatc atggaagctg tagtgccttc ccgctctaat cccactcatg agaaggtcct 12060
ggccatcgtg aacgcgttgg tggagaacaa agctattcgt ccagatgagg ccggactggt 12120
atacaacgct ctcttagaac gcgtggctcg ctacaacagt agcaatgtgc aaaccaattt 12180
ggaccgtatg ataacagatg tacgcgaagc cgtgtctcag cgcgaaaggt tccagcgtga 12240
tgccaacctg ggttcgctgg tggcgttaaa tgctttcttg agtactcagc ctgctaatgt 12300
gccgcgtggt caacaggatt atactaactt tttaagtgct ttgagactga tggtatcaga 12360
agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960
cgctatgaac tctgattatt tcaccaatgc catcttaaac ccgcactggc tgcccccacc 13020
tggtttctac acgggcgaat atgacatgcc cgaccctaat gacggatttc tgtgggacga 13080
cgtggacagc gatgtttttt cacctctttc tgatcatcgc acgtggaaaa aggaaggcgg 13140
cgatagaatg cattcttctg catcgctgtc cggggtcatg ggtgctaccg cggctgagcc 13200
cgagtctgca agtccttttc ctagtctacc cttttctcta cacagtgtac gtagcagcga 13260
agtgggtaga ataagtcgcc cgagtttaat gggcgaagag gagtatctaa acgattcctt 13320
gctcagaccg gcaagagaaa aaaatttccc aaacaatgga atagaaagtt tggtggataa 13380
aatgagtaga tggaagactt atgctcagga tcacagagac gagcctggga tcatggggat 13440
tacaagtaga gcgagccgta gacgccagcg ccatgacaga cagaggggtc ttgtgtggga 13500
cgatgaggat tcggccgatg atagcagcgt gctggacttg ggtgggagag gaaggggcaa 13560
cccgtttgct catttgcgcc ctcgcttggg tggtatgttg taaaaaaaaa taaaaaaaaa 13620
actcaccaag gccatggcga cgagcgtacg ttcgttcttc tttattatct gtgtctagta 13680
taatgaggcg agtcgtgcta ggcggagcgg tggtgtatcc ggagggtcct cctccttcgt 13740
acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040
ggggcggtca gctaaagacc atcatgcata ctaacatgcc aaacgtgaac gagtatatgt 14100
ttagtaacaa gttcaaagcg cgtgtgatgg tgtccagaaa acctcccgac ggtgctgcag 14160
ttggggatac ttatgatcac aagcaggata ttttgaaata tgagtggttc gagtttactt 14220
tgccagaagg caacttttca gttactatga ctattgattt gatgaacaat gccatcatag 14280
ataattactt gaaagtgggt agacagaatg gagtgcttga aagtgacatt ggtgttaagt 14340

-continued

```
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg ggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg ggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtcccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
```

catgcctatt acaactgacg ccgccggtcc cactcgaaga tcccgacgaa agtacggtcc 16800
agcaagtctg ttgatgccca attatgttgt acacccatct attattccta ctcctggtta 16860
ccgaggcact cgctactatc gcagccgaaa cagtacctcc cgccgtcgcc gcaagacacc 16920
tgcaaatcgc agtcgtcgcc gtagacgcac aagcaaaccg actcccggcg ccctggtgcg 16980
gcaagtgtac cgcaatggta gtgcggaacc tttgacactg ccgcgtgcgc gttaccatcc 17040
gagtatcatc acttaatcaa tgttgccgct gcctccttgc agatatggcc ctcacttgtc 17100
gccttcgcgt tcccatcact ggttaccgag gaagaaactc gcgccgtaga agagggatgt 17160
tgggacgcgg aatgcgacgc tacaggcgac ggcgtgctat ccgcaagcaa ttgcggggtg 17220
gtttttttacc agccttaatt ccaattatcg ctgctgcaat tggcgcgata ccaggcatag 17280
cttccgtggc ggttcaggcc tcgcaacgac attgacattg gaaaaaaacg tataaataaa 17340
aaaaaaaaaa tacaatggac tctgacactc ctggtcctgt gactatgttt tcttagagat 17400
ggaagacatc aatttttcat ccttggctcc gcgacacggc acgaagccgt acatgggcac 17460
ctggagcgac atcggcacga gccaactgaa cgggggcgcc ttcaattgga gcagtatctg 17520
gagcgggctt aaaaatttg gctcaaccat aaaaacatac gggaacaaag cttggaacag 17580
cagtacagga caggcgctta gaaataaact taaagaccag aacttccaac aaaaagtagt 17640
cgatgggata gcttccggca tcaatggagt ggtagatttg gctaaccagg ctgtgcagaa 17700
aaagataaac agtcgtttgg acccgccgcc agcaacccca ggtgaaatgc aagtggagga 17760
agaaattcct ccgccagaaa aacgaggcga caagcgtccg cgtcccgatt tggaagagac 17820
gctggtgacg cgcgtagatg aaccgccttc ttatgaggaa gcaacgaagc ttggaatgcc 17880
caccactaga ccgatagccc caatggccac cggggtgatg aaaccttctc agttgcatcg 17940
acccgtcacc ttggatttgc cccctccccc tgctgctact gctgtacccg cttctaagcc 18000
tgtcgctgcc ccgaaaccag tcgccgtagc caggtcacgt cccgggggcg ctcctcgtcc 18060
aaatgcgcac tggcaaaata ctctgaacag catcgtgggt ctaggcgtgc aaagtgtaaa 18120
acgccgtcgc tgcttttaat taaatatgga gtagcgctta acttgcctat ctgtgtatat 18180
gtgtcattac acgccgtcac agcagcagag gaaaaaagga agaggtcgtg cgtcgacgct 18240
gagttacttt caagatggcc accccatcga tgctgcccca atgggcatac atgcacatcg 18300
ccggacagga tgcttcggag tacctgagtc cgggtctggt gcagttcgcc cgcgccacag 18360
acacctactt caatctggga aataagttta gaaatcccac cgtagcgccg acccacgatg 18420
tgaccaccga ccgtagccag cggctcatgt tgcgcttcgt gcccgttgac cgggaggaca 18480
atacatactc ttacaaagtg cggtacaccc tggccgtggg cgacaacaga gtgctggata 18540
tggccagcac gttctttgac attaggggtg tgttggacag aggtcccagt ttcaaaccct 18600
attctggtac ggcttacaac tccctggctc ctaaaggcgc tccaaataca tctcagtgga 18660
ttgcagaagg tgtaaaaaat acaactggtg aggaacacgt aacagaagag gaaaccaata 18720
ctactactta cacttttggc aatgctcctg taaaagctga agctgaaatt acaaaagaag 18780
gactcccagt aggtttggaa gtttcagatg aagaaagtaa accgatttat gctgataaaa 18840
catatcagcc agaacctcag ctgggagatg aaacttggac tgaccttgat ggaaaaaccg 18900
aaaagtatgg aggcagggct ctcaaacccg atactaagat gaaaccatgc tacgggtcct 18960
ttgccaaacc tactaatgtg aaaggcggtc aggcaaaaca aaaaacaacg gagcagccaa 19020
atcagaaagt cgaatatgat atcgacatgg agtttttttga tgcggcatcg cagaaaacaa 19080

-continued

```
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
```

ctacccagac cgtgcagggt ccccgttctg ccgcctgcgg acttttctgc tgcatgttcc 21540
ttcacgcctt tgtgcactgg cctgaccgtc ccatggacgg aaaccccacc atgaaattgc 21600
taactggagt gccaaacaac atgcttcatt ctcctaaagt ccagcccacc ctgtgtgaca 21660
atcaaaaagc actctaccat tttcttaata cccattcgcc ttattttcgc tcccatcgta 21720
cacacatcga aagggccact gcgttcgacc gtatggatgt tcaataatga ctcatgtaaa 21780
caacgtgttc aataaacatc actttatttt tttacatgta tcaaggctct gcattactta 21840
tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820

-continued

```
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
```

```
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
cccctttata aacccagggt ttatttcccc aaatggcttc acacaaagcc caaacggagt  28500
tcttacttta aaatgtttaa ccccactaac aaccacaggc ggatctctac agctaaaagt  28560
```

gggaggggga cttacagtgg atgacaccaa cggtttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920
aactacacac agaaatataa attttactgc agagctgttt ttcgattcta ctggtaattt 28980
actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct tttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttgcga tcgccaggcc accatggcct tgacctttgc tttactggtg 29400
gccctcctgg tgctcagctg caagtcaagc tgctctgtgg gctgtgatct gcctcaaacc 29460
cacagcctgg gtagcaggag gaccttgatg ctcctggcac agatgaggag aatctctctt 29520
ttctcctgct tgaaggacag acatgacttt ggatttcccc aggaggagtt tggcaaccag 29580
ttccaaaagg ctgaaaccat ccctgtcctc catgagatga tccagcagat cttcaatctc 29640
ttcagcacaa aggactcatc tgctgcttgg gatgagaccc tcctagacaa attctacact 29700
gaactctacc agcagctgaa tgacctggaa gcctgtgtga tacagggggt gggggtgaca 29760
gagactcccc tgatgaagga ggactccatt ctggctgtga ggaaatactt ccaaagaatc 29820
actctctatc tgaaagagaa gaaatacagc ccttgtgcct gggaggttgt cagagcagaa 29880
atcatgagat ctttttcttt gtcaacaaac ttgcaagaaa gtttaagaag taaggaagga 29940
agcggagcta ctaacttcag cctgctgaag caggctggag acgtggagga gaaccctgga 30000
cctggccaca cacggaggca gggaacatca ccatccaagt gtccatacct caatttcttt 30060
cagctcttgg tgctggctgg tctttctcac ttctgttcag gtgttatcca cgtgaccaag 30120
gaagtgaaag aagtggcaac gctgtcctgt ggtcacaatg tttctgttga agagctggca 30180
caaactcgca tctactggca aaaggagaag aaaatggtgc tgactatgat gtctggggac 30240
atgaatatat ggcccgagta caagaaccgg accatctttg atatcactaa taacctctcc 30300
attgtgatcc tggctctgcg cccatctgac gagggcacat acgagtgtgt tgttctgaag 30360
tatgaaaaag acgctttcaa gcgggaacac ctggctgaag tgacgttatc agtcaaagct 30420
gacttcccta cacctagtat atctgacttt gaaattccaa cttctaatat tagaaggata 30480
atttgctcaa cctctggagg ttttccagag cctcacctct cctggttgga aaatggagaa 30540
gaattaaatg ccatcaacac aacagtttcc caagatcctg aaactgagct ctatgctgtt 30600
agcagcaaac tggatttcaa tatgacaacc aaccacagct tcatgtgtct catcaagtat 30660
ggacatttaa gagtgaatca gaccttcaac tggaatacaa ccaagcaaga gcattttcct 30720
gataacctgc tcccatcctg ggccattacc ttaatctcag taaatggaat ttttgtgata 30780
tgctgcctga cctactgctt tgccccaaga tgcagagaga gaaggaggaa tgagagattg 30840
agaagggaaa gtgtacgccc tgtataagct agcttgactg actgagatac agcgtacctt 30900
cagctcacag acatgataag atacattgat gagtttggac aaaccacaac tagaatgcag 30960
tgaaaaaaat gctttatttg tgaaatttgt gatgctattg ctttatttgt aaccattata 31020
agctgcaata aacaagttaa caacaacaat tgcattcatt ttatgtttca ggttcagggg 31080
gaggtgtggg aggtttttta aagcaagtaa aacctctaca aatgtggtag tcgtcagcta 31140
tcctgcagga acttgtttat ttgaaaatca attcacaaaa tccgagtagt tattttgcct 31200
ccccccttccc atttaacaga atacaccaat ctctccccac gcacagcttt aaacatttgg 31260
ataccattag atatagacat ggttttagat tccacattcc aaacagtttc agagcgagcc 31320
aatctggggt cagtgataga taaaaatcca tcgggatagt cttttaaagc gctttcacag 31380
tccaactgct gcggatgcga ctccggagtc tggatcacgg tcatctggaa gaagaacgat 31440
gggaatcata atccgaaaac ggtatcggac gattgtgtct catcaaaccc acaagcagcc 31500
gctgtctgcg tcgctccgtg cgactgctgt ttatgggatc agggtccaca gtgtcctgaa 31560
gcatgatttt aatagccctt aacatcaact ttctggtgcg atgcgcgcag caacgcattc 31620
tgatttcact caaatctttg cagtaggtac aacacattat tacaatattg tttaataaac 31680
cataattaaa agcgctccag ccaaaactca tatctgatat aatcgcccct gcatgaccat 31740
cataccaaag tttaatataa attaaatgac gttccctcaa aaacacacta cccacataca 31800
tgatctcttt tggcatgtgc atattaacaa tctgtctgta ccatggacaa cgttggttaa 31860
tcatgcaacc caatataacc ttccggaacc acactgccaa caccgctccc ccagccatgc 31920
attgaagtga accctgctga ttacaatgac aatgaagaac ccaattctct cgaccgtgaa 31980
tcacttgaga atgaaaaata tctatagtgg cacaacatag acataaatgc atgcatcttc 32040
tcataatttt taactcctca ggatttagaa acatatccca gggaatagga agctcttgca 32100
gaacagtaaa gctggcagaa caaggaagac cacgaacaca acttacacta tgcatagtca 32160
tagtatcaca atctggcaac agcgggtggt cttcagtcat agaagctcgg gtttcatttt 32220
cctcacaacg tggtaactgg gctctggtgt aagggtgatg tctggcgcat gatgtcgagc 32280
gtgcgcgcaa ccttgtcata atggagttgc ttcctgacat tctcgtattt tgtatagcaa 32340
aacgcggccc tggcagaaca cactcttctt cgccttctat cctgccgctt agcgtgttcc 32400
gtgtgatagt tcaagtacaa ccacactctt aagttggtca aaagaatgct ggcttcagtt 32460
gtaatcaaaa ctccatcgca tctaatcgtt ctgaggaaat catccaagca atgcaactgg 32520
attgtgtttc aagcaggaga ggagagggaa gagacggaag aaccatgtta atttttattc 32580
caaacgatct cgcagtactt caaattgtag atcgcgcaga tggcatctct cgcccccact 32640
gtgttggtga aaaagcacag ctagatcaaa agaaatgcga ttttcaaggt gctcaacggt 32700
ggcttccagc aaagcctcca cgcgcacatc caagaacaaa agaataccaa aagaaggagc 32760
attttctaac tcctcaatca tcatattaca ttcctgcacc attcccagat aattttcagc 32820
tttccagcct tgaattattc gtgtcagttc ttgtggtaaa tccaatccac acattacaaa 32880
caggtcccgg agggcgccct ccaccaccat tcttaaacac accctcataa tgacaaaata 32940
tcttgctcct gtgtcacctg tagcgaattg agaatggcaa catcaattga catgcccttg 33000
gctctaagtt cttctttaag ttctagttgt aaaaactctc tcatattatc accaaactgc 33060
ttagccagaa gccccccggg aacaagagca ggggacgcta cagtgcagta caagcgcaga 33120
cctccccaat tggctccagc aaaaacaaga ttggaataag catattggga accgccagta 33180
atatcatcga agttgctgga aatataatca ggcagagttt cttgtaaaaa ttgaataaaa 33240
gaaaaatttg ccaaaaaaac attcaaaacc tctgggatgc aaatgcaata ggttaccgcg 33300

```
ctgcgctcca acattgttag ttttgaatta gtctgcaaaa ataaaaaaaa aaacaagcgt  33360

catatcatag tagcctgacg aacagatgga taaatcagtc tttccatcac aagacaagcc  33420

acagggtctc cagctcgacc ctcgtaaaac ctgtcatcat gattaaacaa cagcaccgaa  33480

agttcctcgc ggtgaccagc atgaataatt cttgatgaag catacaatcc agacatgtta  33540

gcatcagtta acgagaaaaa acagccaaca tagcctttgg gtataattat gcttaatcgt  33600

aagtatagca aagccacccc tcgcggatac aaagtaaaag gcacaggaga ataaaaaata  33660

taattatttc tctgctgctg ttcaggcaac gtcgcccccg gtccctctaa atacacatac  33720

aaagcctcat cagccatggc ttaccagaca aagtacagcg ggcacacaaa gcacaagctc  33780

taaagtgact ctccaacctc tccacaatat atatatacac aagccctaaa ctgacgtaat  33840

gggagtaaag tgtaaaaaat cccgccaaac ccaacacaca ccccgaaact gcgtcaccag  33900

ggaaaagtac agtttcactt ccgcaatccc aacaggcgta acttcctctt tctcacggta  33960

cgtgatatcc cactaacttg caacgtcatt ttcccacggt cgcaccgccc cttttagccg  34020

ttaaccccac agccaatcac cacacgatcc acacttttta aaatcacctc atttacatat  34080

tggcaccatt ccatctataa ggtatattat atagataga                         34119
```

<210> SEQ ID NO 111
<211> LENGTH: 34131
<212> TYPE: DNA
<213> ORGANISM: Artificial Sequence
<220> FEATURE:
<223> OTHER INFORMATION: NG-345 virus genome sequence comprising the EnAd genome with a transgene cassette that encodes Flt3 Ligand, MIP1a and IFNa, inserted in the region BY. The transgene cassette contains a 5' SSA, Flt3 Ligand cDNA , P2A peptide sequence, MIP1a cDNA sequence

<400> SEQUENCE: 111

```
tctatctata taatatacct tatagatgga atggtgccaa tatgtaaatg aggtgatttt     60

aaaaagtgtg gatcgtgtgg tgattggctg tggggttaac ggctaaaagg ggcggtgcga    120

ccgtgggaaa atgacgtttt gtgggggtgg agtttttttg caagttgtcg cgggaaatgt    180

gacgcataaa aaggcttttt tctcacggaa ctacttagtt ttcccacggt atttaacagg    240

aaatgaggta gttttgaccg gatgcaagtg aaaattgttg attttcgcgc gaaaactgaa    300

tgaggaagtg tttttctgaa taatgtggta tttatggcag ggtggagtat ttgttcaggg    360

ccaggtagac tttgacccat tacgtggagg tttcgattac cgtgtttttt acctgaattt    420

ccgcgtaccg tgtcaaagtc ttctgttttt acgtaggtgt cagctgatcg ctagggtatt    480

tatacctcag ggtttgtgtc aagaggccac tcttgagtgc cagcgagaag agttttctcc    540

tctgcgccgg cagtttaata ataaaaaaat gagagatttg cgatttctgc ctcaggaaat    600

aatctctgct gagactggaa atgaaatatt ggagcttgtg gtgcacgccc tgatgggaga    660

cgatccggag ccacctgtgc agctttttga gcctcctacg cttcaggaac tgtatgattt    720

agaggtagag ggatcggagg attctaatga ggaagctgta aatggctttt ttaccgattc    780

tatgctttta gctgctaatg aagggttaga attagatccg cctttggaca cttttgatac    840

tccaggggta attgtggaaa gcggtacagg tgtaagaaaa ttacctgatt tgagttccgt    900

ggactgtgat ttgcactgct atgaagacgg gtttcctccg agtgatgagg aggaccatga    960

aaaggagcag tccatgcaga ctgcagcggg tgagggagtg aaggctgcca atgttggttt   1020

tcagttggat tgcccggagc ttcctggaca tggctgtaag tcttgtgaat ttcacaggaa   1080

aaatactgga gtaaaggaac tgttatgttc gctttgttat atgagaacgc actgccactt   1140
```

```
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct    3480
```

gtcatgagtg gaaacgcttc ttttaagggg ggagtcttca gcccttatct gacagggcgt 3540
ctcccatcct gggcaggagt tcgtcagaat gttatgggat ctactgtgga tggaagaccc 3600
gtccaacccg ccaattcttc aacgctgacc tatgctactt taagttcttc acctttggac 3660
gcagctgcag ctgccgccgc cgcttctgtt gccgctaaca ctgtgcttgg aatgggttac 3720
tatggaagca tcatggctaa ttccacttcc tctaataacc cttctaccct gactcaggac 3780
aagttacttg tccttttggc ccagctggag gctttgaccc aacgtctggg tgaactttct 3840
cagcaggtgg tcgagttgcg agtacaaact gagtctgctg tcggcacggc aaagtctaaa 3900
taaaaaaatc ccagaatcaa tgaataaata aacaagcttg ttgttgattt aaaatcaagt 3960
gtttttattt catttttcgc gcacggtatg ccctagacca ccgatctcta tcattgagaa 4020
ctcggtggat tttttccagg atcctataga ggtgggattg aatgtttaga tacatgggca 4080
ttaggccgtc tttggggtgg agatagctcc attgaaggga ttcatgctcc ggggtagtgt 4140
tgtaaatcac ccagtcataa caaggtcgca gtgcatggtg ttgcacaata tcttttagaa 4200
gtaggctgat tgccacagat aagcccttgg tgtaggtgtt tacaaaccgg ttgagctggg 4260
atgggtgcat tcggggtgaa attatgtgca ttttggattg gatttttaag ttggcaatat 4320
tgccgccaag atcccgtctt gggttcatgt tatgaaggac caccaagacg gtgtatccgg 4380
tacatttagg aaatttatcg tgcagcttgg atggaaaagc gtggaaaaat ttggagacac 4440
ccttgtgtcc tccaagattt tccatgcact catccatgat aatagcaatg gggccgtggg 4500
cagcggcgcg ggcaaacacg ttccgtgggt ctgacacatc atagttatgt tcctgagtta 4560
aatcatcata agccatttta atgaatttgg ggcggagagt accagattgg ggtatgaatg 4620
ttccttcggg ccccggagca tagttcccct cacagatttg catttcccaa gctttcagtt 4680
ccgagggtgg aatcatgtcc acctgggggg ctatgaaaaa caccgtttct ggggcggggg 4740
tgattaattg tgatgatagc aaatttctga gcaattgaga tttgccacat ccggtggggc 4800
cataaatgat tccgattacg ggttgcaggt ggtagtttag ggaacggcaa ctgccgtctt 4860
ctcgaagcaa gggggccacc tcgttcatca tttcccttac atgcatattt tcccgcacca 4920
aatccattag gaggcgctct cctcctagtg atagaagttc ttgtagtgag gaaaagtttt 4980
tcagcggttt cagaccgtca gccatgggca ttttggagag agtttgctgc aaaagttcta 5040
gtctgttcca cagttcagtg atgtgttcta tggcatctcg atccagcaga cctcctcgtt 5100
tcgcgggttt ggacggctcc tggaataggg tatgagacga tgggcgtcca gcgctgccag 5160
ggttcggtcc ttccagggtc tcagtgttcg agtcagggtt gtttccgtca cagtgaaggg 5220
gtgtgcgcct gcttgggcgc ttgccagggt gcgcttcaga ctcatcctgc tggtcgaaaa 5280
cttctgtcgc ttggcgccct gtatgtcggc caagtagcag tttaccatga gttcgtagtt 5340
gagcgcctcg gctgcgtggc ctttggcgcg gagcttacct ttggaagttt tcttgcatac 5400
cgggcagtat aggcatttca gcgcatacaa cttgggcgca aggaaaacgg attctgggga 5460
gtatgcatct gcgccgcagg aggcgcaaac agtttcacat tccaccagcc aggttaaatc 5520
cggttcattg gggtcaaaaa caagttttcc gccatatttt ttgatgcgtt tcttaccttt 5580
ggtctccatg agttcgtgtc ctcgttgagt gacaaacagg ctgtccgtgt ccccgtagac 5640
tgattttaca ggcctcttct ccagtggagt gcctcggtct tcttcgtaca ggaactctga 5700
ccactctgat acaaaggcgc gcgtccaggc cagcacaaag gaggctatgt gggaggggta 5760
gcgatcgttg tcaaccaggg ggtccacctt ttccaaagta tgcaaacaca tgtcaccctc 5820
ttcaacatcc aggaatgtga ttggcttgta ggtgtatttc acgtgacctg ggtccccgc 5880

```
tgggggggta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
```

-continued

```
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
```

gtcctatttt ttttttttgc cgctcagatg catcccgtgc tgcgacagat gcgcccccaa 10680
caacagcccc cctcgcagca gcagcagcag caatcacaaa aggctgtccc tgcaactact 10740
gcaactgccg ccgtgagcgg tgcgggacag cccgcctatg atctggactt ggaagagggc 10800
gaaggactgg cacgtctagg tgcgccttca cccgagcggc atccgcgagt tcaactgaaa 10860
aaagattctc gcgaggcgta tgtgccccaa cagaacctat ttagagacag aagcggcgag 10920
gagccggagg agatgcgagc ttcccgcttt aacgcgggtc gtgagctgcg tcacggtttg 10980
gaccgaagac gagtgttgcg ggacgaggat ttcgaagttg atgaaatgac agggatcagt 11040
cctgccaggg cacacgtggc tgcagccaac cttgtatcgg cttacgagca gacagtaaag 11100
gaagagcgta acttccaaaa gtcttttaat aatcatgtgc gaaccctgat tgcccgcgaa 11160
gaagttaccc ttggtttgat gcatttgtgg gatttgatgg aagctatcat tcagaaccct 11220
actagcaaac ctctgaccgc ccagctgttt ctggtggtgc aacacagcag agacaatgag 11280
gctttcagag aggcgctgct gaacatcacc gaacccgagg ggagatggtt gtatgatctt 11340
atcaacattc tacagagtat catagtgcag gagcggagcc tgggcctggc cgagaaggtg 11400
gctgccatca attactcggt tttgagcttg ggaaaatatt acgctcgcaa aatctacaag 11460
actccatacg ttcccataga caaggaggtg aagatagatg ggttctacat gcgcatgacg 11520
ctcaaggtct tgaccctgag cgatgatctt ggggtgtatc gcaatgacag aatgcatcgc 11580
gcggttagcg ccagcaggag gcgcgagtta agcgacaggg aactgatgca cagtttgcaa 11640
agagctctga ctggagctgg aaccgagggt gagaattact tcgacatggg agctgacttg 11700
cagtggcagc ctagtcgcag ggctctgagc gccgcgacgg caggatgtga gcttccttac 11760
atagaagagg cggatgaagg cgaggaggaa gagggcgagt acttggaaga ctgatggcac 11820
aacccgtgtt ttttgctaga tggaacagca agcaccggat cccgcaatgc gggcggcgct 11880
gcagagccag ccgtccggca ttaactcctc ggacgattgg acccaggcca tgcaacgtat 11940
catggcgttg acgactcgca accccgaagc ctttagacag caaccccagg ccaaccgtct 12000
atcggccatc atggaagctg tagtgccttc ccgctctaat cccactcatg agaaggtcct 12060
ggccatcgtg aacgcgttgg tggagaacaa agctattcgt ccagatgagg ccggactggt 12120
atacaacgct ctcttagaac gcgtggctcg ctacaacagt agcaatgtgc aaaccaattt 12180
ggaccgtatg ataacagatg tacgcgaagc cgtgtctcag cgcgaaaggt tccagcgtga 12240
tgccaacctg ggttcgctgg tggcgttaaa tgctttcttg agtactcagc ctgctaatgt 12300
gccgcgtggt caacaggatt atactaactt tttaagtgct ttgagactga tggtatcaga 12360
agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960

```
cgctatgaac tctgattatt tcaccaatgc catcttaaac ccgcactggc tgcccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
```

```
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg ggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg ggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
```

```
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaaacaacg gagcagccaa  19020
atcagaaagt cgaatatgat atcgacatgg agtttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
```

```
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
```

-continued

```
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
```

agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac caccccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460
cgcgcttatt caaaaaaggc gggaattaca tcatcctcga catgagtaaa gaaattccca 26520
cgccttacat gtggagttat caaccccaaa tgggattggc ggcaggcgcc tcccaggact 26580
actccacccg catgaattgg ctcagcgccg ggccttctat gatttctcga gttaatgata 26640
tacgcgccta ccgaaaccaa atacttttgg aacagtcagc tcttaccacc acgccccgcc 26700
aacaccttaa tcccagaaat tggcccgccg ccctagtgta ccaggaaagt cccgctccca 26760
ccactgtatt acttcctcga gacgcccagg ccgaagtcca aatgactaat gcaggtgcgc 26820
agttagctgg cggctccacc ctatgtcgtc acaggcctcg gcataatata aaacgcctga 26880
tgatcagagg ccgaggtatc cagctcaacg acgagtcggt gagctctccg cttggtctac 26940
gaccagacgg aatctttcag attgccggct gcgggagatc ttccttcacc cctcgtcagg 27000
ctgttctgac tttggaaagt tcgtcttcgc aaccccgctc gggcggaatc gggaccgttc 27060
aatttgtgga ggagtttact ccctctgtct acttcaaccc cttctccgga tctcctgggc 27120
attacccgga cgagttcata ccgaacttcg acgcgattag cgagtcagtg gacggctacg 27180
attgatgtct ggtgacgcgg ctgagctatc tcggctgcga catctagacc actgccgccg 27240
ctttcgctgc tttgcccggg aactcattga gttcatctac ttcgaactcc ccaaggatca 27300
ccctcaaggt ccggcccacg gagtgcggat ttctatcgaa ggcaaaatag actctcgcct 27360
gcaacgaatt ttctcccagc ggcccgtgct gatcgagcga gaccagggaa acaccacggt 27420
ttccatctac tgcatttgta atcaccccgg attgcatgaa agcctttgct gtcttatgtg 27480
tactgagttt aataaaaact gaattaagac tctcctacgg actgccgctt cttcaacccg 27540
gattttacaa ccagaagaac gaaacttttc ctgtcgtcca ggactctgtt aacttcacct 27600
ttcctactca caaactagaa gctcaacgac tacaccgctt ttccagaagc attttcccta 27660
ctaatactac tttcaaaacc ggaggtgagc tccaaggtct tcctacagaa aacccttggg 27720
tggaagcggg ccttgtagtg ctaggaattc ttgcgggtgg gcttgtgatt attctttgct 27780
acctatacac accttgcttc actttcttag tggtgttgtg gtattggttt aaaaaatggg 27840
gcccatacta gtcttgcttg ttttactttc gcttttggaa ccgggttctg ccaattacga 27900
tccatgtcta gacttcgacc cagaaaactg cacacttact tttgcacccg acacaagccg 27960
catctgtgga gttcatcgcc tctcttacga acttggcccc caacgacaaa aatttacctg 28020
catggtggga atcaacccca tagttatcac ccagcaaagt ggagatacta agggttgcat 28080
tcactgctcc tgcgattcca tcgagtgcac ctacaccctg ctgaagaccc tatgcggcct 28140
aagagacctg ctaccaatga attaaaaaat gattaataaa aaatcactta cttgaaatca 28200
gcaataaggt ctctgttgaa attttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta cccctatgaa gatgaaagca cctcccaaca 28440
ccccctttata aacccagggt ttatttcccc aaatggcttc acacaaagcc caaacggagt 28500
tcttacttta aaatgtttaa ccccactaac aaccacaggc ggatctctac agctaaaagt 28560
gggagggggga cttacagtgg atgacaccaa cggtttttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920
aactacacac agaaatataa attttactgc agagctgttt ttcgattcta ctggtaattt 28980
actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct tttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttgcga tcgccaggcc accatgacag tgctggcgcc agcctggagc 29400
ccaacaacct atctcctcct gctgctgctg ctgagctcgg gactcagtgg gacccaggac 29460
tgctccttcc aacacagccc catctcctcc gacttcgctg tcaaaatccg tgagctgtct 29520
gactacctgc ttcaagatta cccagtcacc gtggcctcca acctccagga cgaggagctc 29580
tgcgggggcc tctggcggct ggtcctggca cagcgctgga tggagcggct caagactgtc 29640
gctgggtcca agatgcaagg cttgctggag cgcgtgaaca cggagataca ctttgtcacc 29700
aaatgtgcct ttcagccccc ccccagctgt cttcgcttcg tccagaccaa catctcccgc 29760
ctcctacagg agacctccga gcagctggtg gcgctgaagc cctggatcac tcgccagaac 29820
ttctcccggt gcctggagct gcagtgtcag cccgactcct caaccctgcc acccccatgg 29880
agtccccggc ccctggaggc cacagccccg ggaagcggag ctactaactt cagcctgctg 29940
aagcaggctg gagacgtgga ggagaaccct ggacctcagg tctccactgc tgcccttgcc 30000
gtcctcctct gcaccatggc tctctgcaac caggtcctct ctgcaccact tgctgctgac 30060
acgccgaccg cctgctgctt cagctacacc tcccgacaga ttccacagaa tttcatagct 30120
gactactttg agacgagcag ccagtgctcc aagcccagtg tcatcttcct aaccaagaga 30180
ggccggcagg tctgtgctga ccccagtgag gagtgggtcc agaaatacgt cagtgacctg 30240
gagctgagtg ccggaagcgg agagggcaga ggaagtctgc taacatgcgg tgacgtcgag 30300
gagaatcctg gacctgcctt gacctttgct ttactggtgg ccctcctggt gctcagctgc 30360
aagtcaagct gctctgtggg ctgtgatctg cctcaaaccc acagcctggg tagcaggagg 30420
accttgatgc tcctggcaca gatgaggaga atctctcttt tctcctgctt gaaggacaga 30480
catgactttg gatttcccca ggaggagttt ggcaaccagt tccaaaaggc tgaaaccatc 30540
cctgtcctcc atgagatgat ccagcagatc ttcaatctct tcagcacaaa ggactcatct 30600
gctgcttggg atgagaccct cctagacaaa ttctacactg aactctacca gcagctgaat 30660
gacctggaag cctgtgtgat acagggggtg ggggtgacag agactcccct gatgaaggag 30720
gactccattc tggctgtgag gaaatacttc caaagaatca ctctctatct gaaagagaag 30780
aaatacagcc cttgtgcctg ggaggttgtc agagcagaaa tcatgagatc tttttctttg 30840
tcaacaaact tgcaagaaag tttaagaagt aaggaataag ctagcttgac tgactgagat 30900
acagcgtacc ttcagctcac agacatgata agatacattg atgagtttgg acaaaccaca 30960
actagaatgc agtgaaaaaa atgctttatt tgtgaaattt gtgatgctat tgctttattt 31020
gtaaccatta taagctgcaa taaacaagtt aacaacaaca attgcattca ttttatgttt 31080
caggttcagg gggaggtgtg ggaggttttt taaagcaagt aaaacctcta caaatgtggt 31140
agtcgtcagc tatcctgcag gaacttgttt atttgaaaat caattcacaa aatccgagta 31200
gttattttgc ctcccccttc ccatttaaca gaatacacca atctctcccc acgcacagct 31260
ttaaacattt ggataccatt agatatagac atggttttag attccacatt ccaaacagtt 31320
tcagagcgag ccaatctggg gtcagtgata gataaaaatc catcgggata gtcttttaaa 31380
gcgctttcac agtccaactg ctgcggatgc gactccggag tctggatcac ggtcatctgg 31440
aagaagaacg atgggaatca taatccgaaa acggtatcgg acgattgtgt ctcatcaaac 31500
ccacaagcag ccgctgtctg cgtcgctccg tgcgactgct gtttatggga tcagggtcca 31560
cagtgtcctg aagcatgatt ttaatagccc ttaacatcaa ctttctggtg cgatgcgcgc 31620
agcaacgcat tctgatttca ctcaaatctt tgcagtaggt acaacacatt attacaatat 31680
tgtttaataa accataatta aaagcgctcc agccaaaact catatctgat ataatcgccc 31740
ctgcatgacc atcataccaa agtttaatat aaattaaatg acgttccctc aaaaacacac 31800
tacccacata catgatctct tttggcatgt gcatattaac aatctgtctg taccatggac 31860
aacgttggtt aatcatgcaa cccaatataa ccttccggaa ccacactgcc aacaccgctc 31920

| | |
|---|---|
| ccccagccat gcattgaagt gaaccctgct gattacaatg acaatgaaga acccaattct | 31980 |
| ctcgaccgtg aatcacttga gaatgaaaaa tatctatagt ggcacaacat agacataaat | 32040 |
| gcatgcatct tctcataatt tttaactcct caggatttag aaacatatcc cagggaatag | 32100 |
| gaagctcttg cagaacagta aagctggcag aacaaggaag accacgaaca caacttacac | 32160 |
| tatgcatagt catagtatca caatctggca acagcgggtg gtcttcagtc atagaagctc | 32220 |
| gggtttcatt ttcctcacaa cgtggtaact gggctctggt gtaagggtga tgtctggcgc | 32280 |
| atgatgtcga gcgtgcgcgc aaccttgtca taatggagtt gcttcctgac attctcgtat | 32340 |
| tttgtatagc aaaacgcggc cctggcagaa cacactcttc ttcgccttct atcctgccgc | 32400 |
| ttagcgtgtt ccgtgtgata gttcaagtac aaccacactc ttaagttggt caaaagaatg | 32460 |
| ctggcttcag ttgtaatcaa aactccatcg catctaatcg ttctgaggaa atcatccaag | 32520 |
| caatgcaact ggattgtgtt tcaagcagga gaggagaggg aagagacgga agaaccatgt | 32580 |
| taatttttat tccaaacgat ctcgcagtac ttcaaattgt agatcgcgca gatggcatct | 32640 |
| ctcgccccca ctgtgttggt gaaaaagcac agctagatca aaagaaatgc gattttcaag | 32700 |
| gtgctcaacg gtggcttcca gcaaagcctc cacgcgcaca tccaagaaca aaagaatacc | 32760 |
| aaaagaagga gcattttcta actcctcaat catcatatta cattcctgca ccattcccag | 32820 |
| ataattttca gctttccagc cttgaattat tcgtgtcagt tcttgtggta aatccaatcc | 32880 |
| acacattaca aacaggtccc ggagggcgcc ctccaccacc attcttaaac acccctcat | 32940 |
| aatgacaaaa tatcttgctc ctgtgtcacc tgtagcgaat tgagaatggc aacatcaatt | 33000 |
| gacatgccct tggctctaag ttcttcttta agttctagtt gtaaaaactc tctcatatta | 33060 |
| tcaccaaact gcttagccag aagccccccg ggaacaagag caggggacgc tacagtgcag | 33120 |
| tacaagcgca gacctcccca attggctcca gcaaaaacaa gattggaata agcatattgg | 33180 |
| gaaccgccag taatatcatc gaagttgctg gaaatataat caggcagagt ttcttgtaaa | 33240 |
| aattgaataa aagaaaaatt tgccaaaaaa acattcaaaa cctctgggat gcaaatgcaa | 33300 |
| taggttaccg cgctgcgctc caacattgtt agttttgaat tagtctgcaa aaataaaaaa | 33360 |
| aaaaacaagc gtcatatcat agtagcctga cgaacagatg gataaatcag tctttccatc | 33420 |
| acaagacaag ccacagggtc tccagctcga ccctcgtaaa acctgtcatc atgattaaac | 33480 |
| aacagcaccg aaagttcctc gcggtgacca gcatgaataa ttcttgatga agcatacaat | 33540 |
| ccagacatgt tagcatcagt taacgagaaa aaacagccaa catagccttt gggtataatt | 33600 |
| atgcttaatc gtaagtatag caaagccacc cctcgcggat acaaagtaaa aggcacagga | 33660 |
| gaataaaaaa tataattatt tctctgctgc tgttcaggca acgtcgcccc cggtccctct | 33720 |
| aaatacacat acaaagcctc atcagccatg gcttaccaga caaagtacag cgggcacaca | 33780 |
| aagcacaagc tctaaagtga ctctccaacc tctccacaat atatatatac acaagcccta | 33840 |
| aactgacgta atgggagtaa agtgtaaaaa atcccgccaa acccaacaca caccccgaaa | 33900 |
| ctgcgtcacc agggaaaagt acagtttcac ttccgcaatc ccaacaggcg taacttcctc | 33960 |
| tttctcacgg tacgtgatat cccactaact tgcaacgtca ttttcccacg gtcgcaccgc | 34020 |
| cccttttagc cgttaacccc acagccaatc accacacgat ccacactttt taaaatcacc | 34080 |
| tcatttacat attggcacca ttccatctat aaggtatatt atatagatag a | 34131 |

<210> SEQ ID NO 112
<211> LENGTH: 34432
<212> TYPE: DNA
<213> ORGANISM: Artificial Sequence
<220> FEATURE:
<223> OTHER INFORMATION: NG-346 virus genome sequence comprising a transgene cassette that encodes Flt3 Ligand, MIP1a and CD80, employing SSA and P2A sequence, inserted in the region BY

<400> SEQUENCE: 112

```
tctatctata taatatacct tatagatgga atggtgccaa tatgtaaatg aggtgatttt     60
aaaaagtgtg gatcgtgtgg tgattggctg tggggttaac ggctaaaagg ggcggtgcga    120
ccgtgggaaa atgacgtttt gtgggggtgg agtttttttg caagttgtcg cgggaaatgt    180
gacgcataaa aaggcttttt tctcacggaa ctacttagtt ttcccacggt atttaacagg    240
aaatgaggta gttttgaccg gatgcaagtg aaaattgttg attttcgcgc gaaaactgaa    300
tgaggaagtg tttttctgaa taatgtggta tttatggcag ggtggagtat ttgttcaggg    360
ccaggtagac tttgacccat tacgtggagg tttcgattac cgtgtttttt acctgaattt    420
ccgcgtaccg tgtcaaagtc ttctgttttt acgtaggtgt cagctgatcg ctagggtatt    480
tatacctcag ggtttgtgtc aagaggccac tcttgagtgc cagcgagaag agttttctcc    540
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agctttttga gcctcctacg cttcaggaac tgtatgattt    720
agaggtagag ggatcggagg attctaatga ggaagctgta aatggctttt ttaccgattc    780
tatgctttta gctgctaatg aagggttaga attagatccg cctttggaca cttttgatac    840
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
```

```
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gtttttctg tcttgcagct    3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaactttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
```

aatcatcata agccatttta atgaatttgg ggcggagagt accagattgg ggtatgaatg 4620
ttccttcggg ccccggagca tagttcccct cacagatttg catttcccaa gctttcagtt 4680
ccgagggtgg aatcatgtcc acctgggggg ctatgaaaaa caccgtttct ggggcggggg 4740
tgattaattg tgatgatagc aaatttctga gcaattgaga tttgccacat ccggtggggc 4800
cataaatgat tccgattacg ggttgcaggt ggtagtttag ggaacggcaa ctgccgtctt 4860
ctcgaagcaa gggggccacc tcgttcatca tttcccttac atgcatattt tcccgcacca 4920
aatccattag gaggcgctct cctcctagtg atagaagttc ttgtagtgag gaaaagtttt 4980
tcagcggttt cagaccgtca gccatgggca ttttggagag agtttgctgc aaaagttcta 5040
gtctgttcca cagttcagtg atgtgttcta tggcatctcg atccagcaga cctcctcgtt 5100
tcgcgggttt ggacggctcc tggaataggg tatgagacga tgggcgtcca gcgctgccag 5160
ggttcggtcc ttccagggtc tcagtgttcg agtcagggtt gtttccgtca cagtgaaggg 5220
gtgtgcgcct gcttgggcgc ttgccagggt gcgcttcaga ctcatcctgc tggtcgaaaa 5280
cttctgtcgc ttggcgccct gtatgtcggc caagtagcag tttaccatga gttcgtagtt 5340
gagcgcctcg gctgcgtggc ctttggcgcg gagcttacct ttggaagttt tcttgcatac 5400
cgggcagtat aggcatttca gcgcatacaa cttgggcgca aggaaaacgg attctgggga 5460
gtatgcatct gcgccgcagg aggcgcaaac agtttcacat tccaccagcc aggttaaatc 5520
cggttcattg gggtcaaaaa caagttttcc gccatatttt ttgatgcgtt tcttaccttt 5580
ggtctccatg agttcgtgtc ctcgttgagt gacaaacagg ctgtccgtgt ccccgtagac 5640
tgattttaca ggcctcttct ccagtggagt gcctcggtct tcttcgtaca ggaactctga 5700
ccactctgat acaaaggcgc gcgtccaggc cagcacaaag gaggctatgt gggaggggta 5760
gcgatcgttg tcaaccaggg ggtccacctt ttccaaagta tgcaaacaca tgtcaccctc 5820
ttcaacatcc aggaatgtga ttggcttgta ggtgtatttc acgtgacctg ggtccccgc 5880 tggggggta taaaaggggg cggttctttg ctcttcctca ctgtcttccg gatcgctgtc 5940
caggaacgtc agctgttggg gtaggtattc cctctcgaag gcgggcatga cctctgcact 6000
caggttgtca gtttctaaga acgaggagga tttgatattg acagtgccgg ttgagatgcc 6060
tttcatgagg ttttcgtcca tctggtcaga aaacacaatt tttttattgt caagtttggt 6120
ggcaaatgat ccatacaggg cgttggataa aagtttggca atggatcgca tggtttggtt 6180
cttttccttg tccgcgcgct ctttggcggc gatgttgagt tggacatact cgcgtgccag 6240
gcacttccat tcggggaaga tagttgttaa ttcatctggc acgattctca cttgccaccc 6300
tcgattatgc aaggtaatta aatccacact ggtggccacc tcgcctcgaa ggggttcatt 6360
ggtccaacag agcctacctc ctttcctaga acagaaaggg ggaagtgggt ctagcataag 6420
ttcatcggga gggtctgcat ccatggtaaa gattcccgga agtaaatcct tatcaaaata 6480
gctgatggga gtggggtcat ctaaggccat ttgccattct cgagctgcca gtgcgcgctc 6540
atatgggtta aggggactgc cccatggcat gggatgggtg agtgcagagg catacatgcc 6600
acagatgtca tagacgtaga tgggatcctc aaagatgcct atgtaggttg gatagcatcg 6660 ccccctctg atacttgctc gcacatagtc atatagttca tgtgatggcg ctagcagccc 6720
cggacccaag ttggtgcgat tgggtttttc tgttctgtag acgatctggc gaaagatggc 6780
gtgagaattg gaagagatgg tgggtctttg aaaaatgttg aaatgggcat gaggtagacc 6840
tacagagtct ctgacaaagt gggcataaga ttcttgaagc ttggttacca gttcggcggt 6900

```
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
```

acgggcagac ggtcgatgaa tctttcaatg acctctccgc ggcggcggcg catggtttca 9360
gtgacggcgc ggccgttctc gcgcggtcgc agagtaaaaa caccgccgcg catctcctta 9420
aagtggtgac tgggaggttc tccgtttggg agggagaggg cgctgattat acattttatt 9480
aattggcccg tagggactgc acgcagagat ctgatcgtgt caagatccac gggatctgaa 9540
aacctttcga cgaaagcgtc taaccagtca cagtcacaag gtaggctgag tacggcttct 9600
tgtgggcggg ggtggttatg tgttcggtct gggtcttctg tttcttcttc atctcgggaa 9660
ggtgagacga tgctgctggt gatgaaatta aagtaggcag ttctaagacg gcggatggtg 9720
gcgaggagca ccaggtcttt gggtccggct tgctggatac gcaggcgatt ggccattccc 9780
caagcattat cctgacatct agcaagatct ttgtagtagt cttgcatgag ccgttctacg 9840
ggcacttctt cctcacccgt tctgccatgc atacgtgtga gtccaaatcc gcgcattggt 9900
tgtaccagtg ccaagtcagc tacgactctt tcggcgagga tggcttgctg tacttgggta 9960
agggtggctt gaaagtcatc aaaatccaca aagcggtggt aagctcctgt attaatggtg 10020
taagcacagt tggccatgac tgaccagtta actgtctggt gaccagggcg cacgagctcg 10080
gtgtatttaa ggcgcgaata ggcgcgggtg tcaaagatgt aatcgttgca ggtgcgcacc 10140
agatactggt accctataag aaaatgcggc ggtggttggc ggtagagagg ccatcgttct 10200
gtagctggag cgccaggggc gaggtcttcc aacataaggc ggtgatagcc gtagatgtac 10260
ctggacatcc aggtgattcc tgcggcggta gtagaagccc gaggaaactc gcgtacgcgg 10320
ttccaaatgt tgcgtagcgg catgaagtag ttcattgtag gcacggtttg accagtgagg 10380
cgcgcgcagt cattgatgct ctatagacac ggagaaaatg aaagcgttca gcgactcgac 10440
tccgtagcct ggaggaacgt gaacgggttg ggtcgcggtg taccccggtt cgagacttgt 10500
actcgagccg gccggagccg cggctaacgt ggtattggca ctcccgtctc gacccagcct 10560
acaaaaatcc aggatacgga atcgagtcgt tttgctggtt tccgaatggc agggaagtga 10620
gtcctatttt tttttttgc cgctcagatg catcccgtgc tgcgacagat gcgcccccaa 10680
caacagcccc cctcgcagca gcagcagcag caatcacaaa aggctgtccc tgcaactact 10740
gcaactgccg ccgtgagcgg tgcgggacag cccgcctatg atctggactt ggaagagggc 10800
gaaggactgg cacgtctagg tgcgccttca cccgagcggc atccgcgagt tcaactgaaa 10860
aaagattctc gcgaggcgta tgtgccccaa cagaacctat ttagagacag aagcggcgag 10920
gagccggagg agatgcgagc ttcccgcttt aacgcgggtc gtgagctgcg tcacggtttg 10980
gaccgaagac gagtgttgcg ggacgaggat ttcgaagttg atgaaatgac agggatcagt 11040
cctgccaggg cacacgtggc tgcagccaac cttgtatcgg cttacgagca gacagtaaag 11100
gaagagcgta acttccaaaa gtcttttaat aatcatgtgc gaaccctgat tgcccgcgaa 11160
gaagttaccc ttggtttgat gcatttgtgg gatttgatgg aagctatcat tcagaaccct 11220
actagcaaac ctctgaccgc ccagctgttt ctggtggtgc aacacagcag agacaatgag 11280
gctttcagag aggcgctgct gaacatcacc gaacccgagg ggagatggtt gtatgatctt 11340
atcaacattc tacagagtat catagtgcag gagcggagcc tgggcctggc cgagaaggtg 11400
gctgccatca attactcggt tttgagcttg ggaaaatatt acgctcgcaa aatctacaag 11460
actccatacg ttcccataga caaggaggtg aagatagatg ggttctacat gcgcatgacg 11520
ctcaaggtct tgaccctgag cgatgatctt ggggtgtatc gcaatgacag aatgcatcgc 11580
gcggttagcg ccagcaggag gcgcgagtta agcgacaggg aactgatgca cagtttgcaa 11640
agagctctga ctggagctgg aaccgagggt gagaattact tcgacatggg agctgacttg 11700
cagtggcagc ctagtcgcag ggctctgagc gccgcgacgg caggatgtga gcttccttac 11760
atagaagagg cggatgaagg cgaggaggaa gagggcgagt acttggaaga ctgatggcac 11820
aacccgtgtt ttttgctaga tggaacagca agcaccggat cccgcaatgc gggcggcgct 11880
gcagagccag ccgtccggca ttaactcctc ggacgattgg acccaggcca tgcaacgtat 11940
catggcgttg acgactcgca accccgaagc ctttagacag caaccccagg ccaaccgtct 12000
atcggccatc atggaagctg tagtgccttc ccgctctaat cccactcatg agaaggtcct 12060
ggccatcgtg aacgcgttgg tggagaacaa agctattcgt ccagatgagg ccggactggt 12120
atacaacgct ctcttagaac gcgtggctcg ctacaacagt agcaatgtgc aaaccaattt 12180
ggaccgtatg ataacagatg tacgcgaagc cgtgtctcag cgcgaaaggt tccagcgtga 12240
tgccaacctg ggttcgctgg tggcgttaaa tgctttcttg agtactcagc ctgctaatgt 12300
gccgcgtggt caacaggatt atactaactt tttaagtgct ttgagactga tggtatcaga 12360
agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960
cgctatgaac tctgattatt tcaccaatgc catcttaaac ccgcactggc tgcccccacc 13020
tggtttctac acgggcgaat atgacatgcc cgaccctaat gacggatttc tgtgggacga 13080
cgtggacagc gatgtttttt cacctctttc tgatcatcgc acgtggaaaa aggaaggcgg 13140
cgatagaatg cattcttctg catcgctgtc cggggtcatg ggtgctaccg cggctgagcc 13200
cgagtctgca agtccttttc ctagtctacc cttttctcta cacagtgtac gtagcagcga 13260
agtgggtaga ataagtcgcc cgagtttaat gggcgaagag gagtatctaa acgattcctt 13320
gctcagaccg gcaagagaaa aaaatttccc aaacaatgga atagaaagtt tggtggataa 13380
aatgagtaga tggaagactt atgctcagga tcacagagac gagcctggga tcatggggat 13440
tacaagtaga gcgagccgta gacgccagcg ccatgacaga cagaggggtc ttgtgtggga 13500
cgatgaggat tcggccgatg atagcagcgt gctggacttg ggtgggagag gaaggggcaa 13560
cccgtttgct catttgcgcc ctcgcttggg tggtatgttg taaaaaaaaa taaaaaaaaa 13620
actcaccaag gccatggcga cgagcgtacg ttcgttcttc tttattatct gtgtctagta 13680
taatgaggcg agtcgtgcta ggcggagcgg tggtgtatcc ggagggtcct cctccttcgt 13740
acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040

```
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg ggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtcccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
```

-continued

```
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
```

```
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
```

-continued

```
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaacccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
```

ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc tttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180
caaatgctct gcaaaaggga gaaaatggca tggatgagca tcacagcgtt ctggtggaat 24240
tggaaggcga taatgccaga ctcgcagtac tcaagcgaag catcgaggtc acacacttcg 24300
catatcccgc tgtcaacctg cccccctaaag tcatgacggc ggtcatggac cagttactca 24360
ttaagcgcgc aagtcccctt tcagaagaca tgcatgaccc agatgcctgt gatgagggta 24420
aaccagtggt cagtgatgag cagctaaccc gatggctggg caccgactct cccagggatt 24480
tggaagagcg tcgcaagctt atgatggccg tggtgctggt taccgtagaa ctagagtgtc 24540
tccgacgttt ctttaccgat tcagaaacct tgcgcaaact cgaagagaat ctgcactaca 24600
cttttagaca cggctttgtg cggcaggcat gcaagatatc taacgtggaa ctcaccaacc 24660
tggtttccta catgggtatt ctgcatgaga atcgcctagg acaaagcgtg ctgcacagca 24720
ccctgaaggg ggaagcccgc cgtgattaca tccgcgattg tgtctatctg tacctgtgcc 24780
acacgtggca aaccggcatg ggtgtatggc agcaatgttt agaagaacag aacttgaaag 24840
agcttgacaa gctcttacag aaatctctta aggttctgtg gacagggttc gacgagcgca 24900
ccgtcgcttc cgacctggca gacctcatct tcccagagcg tctcagggtt actttgcgaa 24960
acggattgcc tgactttatg agccagagca tgcttaacaa ttttcgctct ttcatcctgg 25020
aacgctccgg tatcctgccc gccacctgct gcgcactgcc ctccgacttt gtgcctctca 25080
cctaccgcga gtgccccccg ccgctatgga gtcactgcta cctgttccgt ctggccaact 25140
atctctccta ccactcggat gtgatcgagg atgtgagcgg agacggcttg ctggagtgtc 25200
actgccgctg caatctgtgc acgccccacc ggtccctagc ttgcaacccc cagttgatga 25260
gcgaaaccca gataataggc acctttgaat tgcaaggccc cagcagccaa ggcgatgggt 25320
cttctcctgg gcaaagttta aaactgaccc cgggactgtg gacctccgcc tacttgcgca 25380
agtttgctcc ggaagattac cacccctatg aaatcaagtt ctatgaggac caatcacagc 25440
ctccaaaggc cgaactttcg gcctgcgtca tcacccaggg ggcaattctg gcccaattgc 25500
aagccatcca aaaatcccgc caagaatttc tactgaaaaa gggtaagggg gtctaccttg 25560
acccccagac cggcgaggaa ctcaacacaa ggttccctca ggatgtccca acgacgagaa 25620
aacaagaagt tgaaggtgca gccgccgccc ccagaagata tggaggaaga ttgggacagt 25680
caggcagagg aggcggagga ggacagtctg gaggacagtc tggaggaaga cagtttggag 25740
gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860

-continued cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460
cgcgcttatt caaaaaaggc gggaattaca tcatcctcga catgagtaaa gaaattccca 26520
cgccttacat gtggagttat caaccccaaa tgggattggc ggcaggcgcc tcccaggact 26580
actccacccg catgaattgg ctcagcgccg ggccttctat gatttctcga gttaatgata 26640
tacgcgccta ccgaaaccaa atacttttgg aacagtcagc tcttaccacc acgccccgcc 26700
aacaccttaa tcccagaaat tggcccgccg ccctagtgta ccaggaaagt cccgctccca 26760
ccactgtatt acttcctcga gacgcccagg ccgaagtcca aatgactaat gcaggtgcgc 26820
agttagctgg cggctccacc ctatgtcgtc acaggcctcg gcataatata aaacgcctga 26880
tgatcagagg ccgaggtatc cagctcaacg acgagtcggt gagctctccg cttggtctac 26940
gaccagacgg aatctttcag attgccggct gcgggagatc ttccttcacc cctcgtcagg 27000
ctgttctgac tttggaaagt tcgtcttcgc aaccccgctc gggcggaatc gggaccgttc 27060
aatttgtgga ggagtttact ccctctgtct acttcaaccc cttctccgga tctcctgggc 27120
attacccgga cgagttcata ccgaacttcg acgcgattag cgagtcagtg gacggctacg 27180
attgatgtct ggtgacgcgg ctgagctatc tcggctgcga catctagacc actgccgccg 27240
ctttcgctgc tttgcccggg aactcattga gttcatctac ttcgaactcc ccaaggatca 27300
ccctcaaggt ccggcccacg gagtgcggat ttctatcgaa ggcaaaatag actctcgcct 27360
gcaacgaatt ttctcccagc ggcccgtgct gatcgagcga gaccagggaa acaccacggt 27420
ttccatctac tgcatttgta atcaccccgg attgcatgaa agcctttgct gtcttatgtg 27480
tactgagttt aataaaaact gaattaagac tctcctacgg actgccgctt cttcaacccg 27540
gattttacaa ccagaagaac gaaacttttc ctgtcgtcca ggactctgtt aacttcacct 27600
ttcctactca caaactagaa gctcaacgac tacaccgctt ttccagaagc attttcccta 27660
ctaatactac tttcaaaacc ggaggtgagc tccaaggtct tcctacagaa aacccttggg 27720
tggaagcggg ccttgtagtg ctaggaattc ttgcgggtgg gcttgtgatt attctttgct 27780
acctatacac accttgcttc actttcttag tggtgttgtg gtattggttt aaaaaatggg 27840
gcccatacta gtcttgcttg ttttactttc gcttttggaa ccgggttctg ccaattacga 27900
tccatgtcta gacttcgacc cagaaaactg cacacttact tttgcacccg acacaagccg 27960
catctgtgga gttcatcgcc tctcttacga acttggcccc caacgacaaa aatttacctg 28020
catggtggga atcaacccca tagttatcac ccagcaaagt ggagatacta agggttgcat 28080
tcactgctcc tgcgattcca tcgagtgcac ctacaccctg ctgaagaccc tatgcggcct 28140
aagagacctg ctaccaatga attaaaaaat gattaataaa aaatcactta cttgaaatca 28200
gcaataaggt ctctgttgaa attttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta ccccatgaa gatgaaagca cctcccaaca 28440
cccctttata aacccagggt ttatttcccc aaatggcttc acacaaagcc caaacggagt 28500
tcttacttta aaatgtttaa ccccactaac aaccacaggc ggatctctac agctaaaagt 28560
gggaggggga cttacagtgg atgacaccaa cggtttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920
aactacacac agaaatataa attttactgc agagctgttt ttcgattcta ctggtaattt 28980
actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct tttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttgcga tcgccaggcc accatgacag tgctggcgcc agcctggagc 29400
ccaacaacct atctcctcct gctgctgctg ctgagctcgg gactcagtgg gacccaggac 29460
tgctccttcc aacacagccc catctcctcc gacttcgctg tcaaaatccg tgagctgtct 29520
gactacctgc ttcaagatta cccagtcacc gtggcctcca acctccagga cgaggagctc 29580
tgcgggggcc tctggcggct ggtcctggca cagcgctgga tggagcggct caagactgtc 29640
gctgggtcca agatgcaagg cttgctggag cgcgtgaaca cggagataca ctttgtcacc 29700
aaatgtgcct ttcagccccc cccagctgt cttcgcttcg tccagaccaa catctcccgc 29760
ctcctacagg agacctccga gcagctggtg gcgctgaagc cctggatcac tcgccagaac 29820
ttctcccggt gcctggagct gcagtgtcag cccgactcct caaccctgcc acccccatgg 29880
agtccccggc ccctggaggc cacagccccg ggaagcggag ctactaactt cagcctgctg 29940
aagcaggctg gagacgtgga ggagaaccct ggacctcagg tctccactgc tgcccttgcc 30000
gtcctcctct gcaccatggc tctctgcaac caggtcctct ctgcaccact tgctgctgac 30060
acgccgaccg cctgctgctt cagctacacc tcccgacaga ttccacagaa tttcatagct 30120
gactactttg agacgagcag ccagtgctcc aagcccagtg tcatcttcct aaccaagaga 30180
ggccggcagg tctgtgctga ccccagtgag gagtgggtcc agaaatacgt cagtgacctg 30240
gagctgagtg ccggaagcgg agagggcaga ggaagtctgc taacatgcgg tgacgtcgag 30300
gagaatcctg gacctggcca cacacggagg cagggaacat caccatccaa gtgtccatac 30360
ctcaatttct ttcagctctt ggtgctggct ggtctttctc acttctgttc aggtgttatc 30420
cacgtgacca aggaagtgaa agaagtggca acgctgtcct gtggtcacaa tgtttctgtt 30480
gaagagctgg cacaaactcg catctactgg caaaaggaga agaaaatggt gctgactatg 30540
atgtctgggg acatgaatat atggcccgag tacaagaacc ggaccatctt tgatatcact 30600
aataacctct ccattgtgat cctggctctg cgcccatctg acgagggcac atacgagtgt 30660
gttgttctga agtatgaaaa agacgctttc aagcgggaac acctggctga agtgacgtta 30720
tcagtcaaag ctgacttccc tacacctagt atatctgact ttgaaattcc aacttctaat 30780
attagaagga taatttgctc aacctctgga ggttttccag agcctcacct ctcctggttg 30840
gaaaatggag aagaattaaa tgccatcaac acaacagttt cccaagatcc tgaaactgag 30900
ctctatgctg ttagcagcaa actggatttc aatatgacaa ccaaccacag cttcatgtgt 30960
ctcatcaagt atggacattt aagagtgaat cagaccttca actggaatac aaccaagcaa 31020
gagcattttc ctgataacct gctcccatcc tgggccatta ccttaatctc agtaaatgga 31080
atttttgtga tatgctgcct gacctactgc tttgccccaa gatgcagaga gagaaggagg 31140
aatgagagat tgagaaggga aagtgtacgc cctgtataag ctagcttgac tgactgagat 31200
acagcgtacc ttcagctcac agacatgata agatacattg atgagtttgg acaaaccaca 31260
actagaatgc agtgaaaaaa atgctttatt tgtgaaattt gtgatgctat tgctttattt 31320
gtaaccatta taagctgcaa taaacaagtt aacaacaaca attgcattca ttttatgttt 31380
caggttcagg gggaggtgtg ggaggttttt taaagcaagt aaaacctcta caaatgtggt 31440
agtcgtcagc tatcctgcag gaacttgttt atttgaaaat caattcacaa aatccgagta 31500
gttattttgc ctcccccttc ccatttaaca gaatacacca atctctcccc acgcacagct 31560
ttaaacattt ggataccatt agatatagac atggttttag attccacatt ccaaacagtt 31620
tcagagcgag ccaatctggg gtcagtgata gataaaaatc catcgggata gtcttttaaa 31680
gcgctttcac agtccaactg ctgcggatgc gactccggag tctggatcac ggtcatctgg 31740
aagaagaacg atgggaatca taatccgaaa acggtatcgg acgattgtgt ctcatcaaac 31800
ccacaagcag ccgctgtctg cgtcgctccg tgcgactgct gtttatggga tcagggtcca 31860
cagtgtcctg aagcatgatt ttaatagccc ttaacatcaa ctttctggtg cgatgcgcgc 31920
agcaacgcat tctgatttca ctcaaatctt tgcagtaggt acaacacatt attacaatat 31980
tgtttaataa accataatta aaagcgctcc agccaaaact catatctgat ataatcgccc 32040
ctgcatgacc atcataccaa agtttaatat aaattaaatg acgttccctc aaaaacacac 32100
tacccacata catgatctct tttggcatgt gcatattaac aatctgtctg taccatggac 32160
aacgttggtt aatcatgcaa cccaatataa ccttccggaa ccacactgcc aacaccgctc 32220
ccccagccat gcattgaagt gaaccctgct gattacaatg acaatgaaga acccaattct 32280
ctcgaccgtg aatcacttga gaatgaaaaa tatctatagt ggcacaacat agacataaat 32340
gcatgcatct tctcataatt tttaactcct caggatttag aaacatatcc cagggaatag 32400
gaagctcttg cagaacagta aagctggcag aacaaggaag accacgaaca caacttacac 32460
tatgcatagt catagtatca caatctggca acagcgggtg gtcttcagtc atagaagctc 32520
gggtttcatt ttcctcacaa cgtggtaact gggctctggt gtaagggtga tgtctggcgc 32580
atgatgtcga gcgtgcgcgc aaccttgtca taatggagtt gcttcctgac attctcgtat 32640
tttgtatagc aaaacgcggc cctggcagaa cacactcttc ttcgccttct atcctgccgc 32700
ttagcgtgtt ccgtgtgata gttcaagtac aaccacactc ttaagttggt caaaagaatg 32760
ctggcttcag ttgtaatcaa aactccatcg catctaatcg ttctgaggaa atcatccaag 32820
caatgcaact ggattgtgtt tcaagcagga gaggagaggg aagagacgga agaaccatgt 32880
taatttttat tccaaacgat ctcgcagtac ttcaaattgt agatcgcgca gatggcatct 32940
ctcgcccccca ctgtgttggt gaaaaagcac agctagatca aaagaaatgc gattttcaag 33000
gtgctcaacg gtggcttcca gcaaagcctc cacgcgcaca tccaagaaca aaagaatacc 33060
aaaagaagga gcattttcta actcctcaat catcatatta cattcctgca ccattcccag 33120
ataattttca gctttccagc cttgaattat tcgtgtcagt tcttgtggta aatccaatcc 33180
acacattaca aacaggtccc ggagggcgcc ctccaccacc attcttaaac acaccctcat 33240
aatgacaaaa tatcttgctc ctgtgtcacc tgtagcgaat tgagaatggc aacatcaatt 33300
gacatgccct tggctctaag ttcttcttta agttctagtt gtaaaaactc tctcatatta 33360
tcaccaaact gcttagccag aagccccccg ggaacaagag caggggacgc tacagtgcag 33420
tacaagcgca gacctcccca attggctcca gcaaaaacaa gattggaata agcatattgg 33480
gaaccgccag taatatcatc gaagttgctg gaaatataat caggcagagt ttcttgtaaa 33540
aattgaataa aagaaaaatt tgccaaaaaa acattcaaaa cctctgggat gcaaatgcaa 33600
taggttaccg cgctgcgctc caacattgtt agttttgaat tagtctgcaa aaataaaaaa 33660
aaaaacaagc gtcatatcat agtagcctga cgaacagatg gataaatcag tctttccatc 33720
acaagacaag ccacagggtc tccagctcga ccctcgtaaa acctgtcatc atgattaaac 33780
aacagcaccg aaagttcctc gcggtgacca gcatgaataa ttcttgatga agcatacaat 33840
ccagacatgt tagcatcagt taacgagaaa aaacagccaa catagccttt gggtataatt 33900
atgcttaatc gtaagtatag caaagccacc cctcgcggat acaaagtaaa aggcacagga 33960
gaataaaaaa tataattatt tctctgctgc tgttcaggca acgtcgcccc cggtccctct 34020
aaatacacat acaaagcctc atcagccatg gcttaccaga caaagtacag cgggcacaca 34080
aagcacaagc tctaaagtga ctctccaacc tctccacaat atatatatac acaagcccta 34140
aactgacgta atgggagtaa agtgtaaaaa atcccgccaa acccaacaca caccccgaaa 34200
ctgcgtcacc agggaaaagt acagtttcac ttccgcaatc ccaacaggcg taacttcctc 34260
tttctcacgg tacgtgatat cccactaact tgcaacgtca ttttcccacg gtcgcaccgc 34320
cccttttagc cgttaacccc acagccaatc accacacgat ccacactttt taaaatcacc 34380
tcatttacat attggcacca ttccatctat aaggtatatt atatagatag ga 34432

<210> SEQ ID NO 113
<211> LENGTH: 34458
<212> TYPE: DNA
<213> ORGANISM: Artificial Sequence
<220> FEATURE:
<223> OTHER INFORMATION: NG-347 virus genome sequence comprising a transgene cassette encoding IFNa, MIP1a and CD80, employing SSA and a P2A sequence, inserted in the region BY

<400> SEQUENCE: 113
tctatctata taatatacct tatagatgga atggtgccaa tatgtaaatg aggtgatttt 60
aaaaagtgtg gatcgtgtgg tgattggctg tggggttaac ggctaaaagg ggcggtgcga 120
ccgtgggaaa atgacgtttt gtgggggtgg agtttttttg caagttgtcg cgggaaatgt 180
gacgcataaa aaggcttttt tctcacggaa ctacttagtt ttcccacggt atttaacagg 240
aaatgaggta gttttgaccg gatgcaagtg aaaattgttg attttcgcgc gaaaactgaa 300
tgaggaagtg tttttctgaa taatgtggta tttatggcag ggtggagtat ttgttcaggg 360
ccaggtagac tttgacccat tacgtggagg tttcgattac cgtgtttttt acctgaattt 420
ccgcgtaccg tgtcaaagtc ttctgttttt acgtaggtgt cagctgatcg ctagggtatt 480
tatacctcag ggtttgtgtc aagaggccac tcttgagtgc cagcgagaag agttttctcc 540

```
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agctttttga gcctcctacg cttcaggaac tgtatgattt    720
agaggtagag ggatcggagg attctaatga ggaagctgta aatggctttt ttaccgattc    780
tatgctttta gctgctaatg aagggttaga attagatccg cctttggaca cttttgatac    840
tccaggggta attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
```

taacatgatt tgcggtgctt ccgatgagag gccttatcaa atgctcactt gtgctggtgg 3000
gcattgtaat atgctggcta ctgtgcatat tgtttcccat caacgcaaaa aatggcctgt 3060
ttttgatcac aatgtgatga cgaagtgtac catgcatgca ggtgggcgta gaggaatgtt 3120
tatgccttac cagtgtaaca tgaatcatgt gaaagtgttg ttggaaccag atgccttttc 3180
cagaatgagc ctaacaggaa tttttgacat gaacatgcaa atctggaaga tcctgaggta 3240
tgatgatacg agatcgaggg tacgcgcatg cgaatgcgga ggcaagcatg ccaggttcca 3300
gccggtgtgt gtagatgtga ctgaagatct cagaccggat catttggtta ttgcccgcac 3360
tggagcagag ttcggatcca gtggagaaga aactgactaa ggtgagtatt gggaaaactt 3420
tggggtggga ttttcagatg gacagattga gtaaaaattt gtttttctg tcttgcagct 3480
gtcatgagtg gaaacgcttc ttttaagggg ggagtcttca gcccttatct gacagggcgt 3540
ctcccatcct gggcaggagt tcgtcagaat gttatgggat ctactgtgga tggaagaccc 3600
gtccaacccg ccaattcttc aacgctgacc tatgctactt taagttcttc acctttggac 3660
gcagctgcag ctgccgccgc cgcttctgtt gccgctaaca ctgtgcttgg aatgggttac 3720
tatggaagca tcatggctaa ttccacttcc tctaataacc cttctaccct gactcaggac 3780
aagttacttg tcctttggc ccagctggag gctttgaccc aacgtctggg tgaactttct 3840
cagcaggtgg tcgagttgcg agtacaaact gagtctgctg tcggcacggc aaagtctaaa 3900
taaaaaaatc ccagaatcaa tgaataaata aacaagcttg ttgttgattt aaaatcaagt 3960
gtttttattt catttttcgc gcacggtatg ccctagacca ccgatctcta tcattgagaa 4020
ctcggtggat tttttccagg atcctataga ggtgggattg aatgtttaga tacatgggca 4080
ttaggccgtc tttggggtgg agatagctcc attgaaggga ttcatgctcc ggggtagtgt 4140
tgtaaatcac ccagtcataa caaggtcgca gtgcatggtg ttgcacaata tcttttagaa 4200
gtaggctgat tgccacagat aagcccttgg tgtaggtgtt tacaaaccgg ttgagctggg 4260
atgggtgcat tcggggtgaa attatgtgca ttttggattg gatttttaag ttggcaatat 4320
tgccgccaag atcccgtctt gggttcatgt tatgaaggac caccaagacg gtgtatccgg 4380
tacatttagg aaatttatcg tgcagcttgg atggaaaagc gtggaaaaat ttggagacac 4440
ccttgtgtcc tccaagattt tccatgcact catccatgat aatagcaatg gggccgtggg 4500
cagcggcgcg ggcaaacacg ttccgtgggt ctgacacatc atagttatgt tcctgagtta 4560
aatcatcata agccatttta atgaatttgg ggcggagagt accagattgg ggtatgaatg 4620
ttccttcggg ccccggagca tagttcccct cacagatttg catttcccaa gctttcagtt 4680
ccgagggtgg aatcatgtcc acctgggggg ctatgaaaaa caccgtttct ggggcggggg 4740
tgattaattg tgatgatagc aaatttctga gcaattgaga tttgccacat ccggtggggc 4800
cataaatgat tccgattacg ggttgcaggt ggtagtttag ggaacggcaa ctgccgtctt 4860
ctcgaagcaa gggggccacc tcgttcatca tttcccttac atgcatattt tcccgcacca 4920
aatccattag gaggcgctct cctcctagtg atagaagttc ttgtagtgag gaaaagtttt 4980
tcagcggttt cagaccgtca gccatgggca ttttggagag agtttgctgc aaaagttcta 5040
gtctgttcca cagttcagtg atgtgttcta tggcatctcg atccagcaga cctcctcgtt 5100
tcgcgggttt ggacggctcc tggaataggg tatgagacga tgggcgtcca gcgctgccag 5160
ggttcggtcc ttccagggtc tcagtgttcg agtcagggtt gtttccgtca cagtgaaggg 5220
gtgtgcgcct gcttgggcgc ttgccagggt gcgcttcaga ctcatcctgc tggtcgaaaa 5280

-continued

```
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg gggtccccgc   5880
tggggggta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa aagtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
ccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
```

gcgatcccac ttgagtttta tggcgaggtc ataggcgatg ttgacgagcc gctggtctcc 7740
agagagtttc atgaccagca tgaaggggat tagctgcttg ccaaaggacc ccatccaggt 7800
gtaggtttcc acatcgtagg tgagaaagag cctttctgtg cgaggatgag agccaatcgg 7860
gaagaactgg atctcctgcc accagttgga ggaatggctg ttgatgtgat ggaagtagaa 7920
ctccctgcga cgcgccgagc attcatgctt gtgcttgtac agacggccgc agtagtcgca 7980
gcgttgcacg ggttgtatct cgtgaatgag ttgtacctgg cttcccttga cgagaaattt 8040
cagtgggaag ccgaggcctg gcgattgtat ctcgtgcttt actatgttgt ctgcatcggc 8100
ctgttcatct tctgtctcga tggtggtcat gctgacgagc cctcgcggga ggcaagtcca 8160
gacctcggcg cggcaggggc ggagctcgag gacgagagcg cgcaggctgg agctgtccag 8220
ggtcctgaga cgctgcggac tcaggttagt aggcagtgtc aggagattaa cttgcatgat 8280
cttttggagg gcgtgcggga ggttcagata gtacttgatc tcaacgggtc cgttggtgga 8340
gatgtcgatg gcttgcaggg ttccgtgtcc cttgggcgct accaccgtgc ccttgttttt 8400
cattttggac ggcggtggct ctgttgcttc ttgcatgttt agaagcggtg tcgagggcgc 8460
gcaccgggcg gcaggggcgg ctcgggaccc ggcggcatgg ctggcagtgg tacgtcggcg 8520
ccgcgcgcgg gtaggttctg gtactgcgcc ctgagaagac tcgcatgcgc gacgacgcgg 8580
cggttgacat cctggatctg acgcctctgg gtgaaagcta ccggccccgt gagcttgaac 8640
ctgaaagaga gttcaacaga atcaatctcg gtatcgttga cggcggcttg cctaaggatt 8700
tcttgcacgt caccagagtt gtcctggtag gcgatctccg ccatgaactg ctcgatctct 8760
tcctcttgaa gatctccgcg gcccgctctc tcgacggtgg ccgcgaggtc gttggagatg 8820
cgcccaatga gttgagagaa tgcattcatg cccgcctcgt tccagacgcg gctgtagacc 8880
acggccccca cgggatctct cgcgcgcatg accacctggg cgaggttgag ctccacgtgg 8940
cgggtgaaga ccgcatagtt gcataggcgc tggaaaaggt agttgagtgt ggtggcgatg 9000
tgctcggtga cgaagaaata catgatccat cgtctcagcg gcatctcgct gacatcgccc 9060
agagcttcca agcgctccat ggcctcgtag aagtccacgg caaaattaaa aaactgggag 9120
tttcgcgcgg acacggtcaa ctcctcttcc agaagacgga taagttcggc gatggtggtg 9180
cgcacctcgc gctcgaaagc ccctgggatt tcttcctcaa tctcttcttc ttccactaac 9240
atctcttcct cttcaggtgg ggctgcagga ggagggggaa cgcggcgacg ccggcggcgc 9300
acgggcagac ggtcgatgaa tctttcaatg acctctccgc ggcggcggcg catggtttca 9360
gtgacggcgc ggccgttctc gcgcggtcgc agagtaaaaa caccgccgcg catctcctta 9420
aagtggtgac tgggaggttc tccgtttggg agggagaggg cgctgattat acattttatt 9480
aattggcccg tagggactgc acgcagagat ctgatcgtgt caagatccac gggatctgaa 9540
aacctttcga cgaaagcgtc taaccagtca cagtcacaag gtaggctgag tacggcttct 9600
tgtgggcggg ggtggttatg tgttcggtct gggtcttctg tttcttcttc atctcgggaa 9660
ggtgagacga tgctgctggt gatgaaatta aagtaggcag ttctaagacg gcggatggtg 9720
gcgaggagca ccaggtcttt gggtccggct tgctggatac gcaggcgatt ggccattccc 9780
caagcattat cctgacatct agcaagatct ttgtagtagt cttgcatgag ccgttctacg 9840
ggcacttctt cctcacccgt tctgccatgc atacgtgtga gtccaaatcc gcgcattggt 9900
tgtaccagtg ccaagtcagc tacgactctt tcggcgagga tggcttgctg tacttgggta 9960
agggtggctt gaaagtcatc aaaatccaca aagcggtggt aagctcctgt attaatggtg 10020

```
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
```

gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900
catgtatgcc agtaaccgac ctttcattaa caaactgctg gactacttgc acagagctgc 12960
cgctatgaac tctgattatt tcaccaatgc catcttaaac ccgcactggc tgcccccacc 13020
tggtttctac acgggcgaat atgacatgcc cgaccctaat gacggatttc tgtgggacga 13080
cgtggacagc gatgtttttt cacctctttc tgatcatcgc acgtggaaaa aggaaggcgg 13140
cgatagaatg cattcttctg catcgctgtc cggggtcatg ggtgctaccg cggctgagcc 13200
cgagtctgca agtccttttc ctagtctacc cttttctcta cacagtgtac gtagcagcga 13260
agtgggtaga ataagtcgcc cgagtttaat gggcgaagag gagtatctaa acgattcctt 13320
gctcagaccg gcaagagaaa aaaatttccc aaacaatgga atagaaagtt tggtggataa 13380
aatgagtaga tggaagactt atgctcagga tcacagagac gagcctggga tcatggggat 13440
tacaagtaga gcgagccgta gacgccagcg ccatgacaga cagaggggtc ttgtgtggga 13500
cgatgaggat tcggccgatg atagcagcgt gctggacttg ggtgggagag gaaggggcaa 13560
cccgtttgct catttgcgcc ctcgcttggg tggtatgttg taaaaaaaaa taaaaaaaaa 13620
actcaccaag gccatggcga cgagcgtacg ttcgttcttc tttattatct gtgtctagta 13680
taatgaggcg agtcgtgcta ggcggagcgg tggtgtatcc ggagggtcct cctccttcgt 13740
acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040
ggggcggtca gctaaagacc atcatgcata ctaacatgcc aaacgtgaac gagtatatgt 14100
ttagtaacaa gttcaaagcg cgtgtgatgg tgtccagaaa acctcccgac ggtgctgcag 14160
ttggggatac ttatgatcac aagcaggata ttttgaaata tgagtggttc gagtttactt 14220
tgccagaagg caacttttca gttactatga ctattgattt gatgaacaat gccatcatag 14280
ataattactt gaaagtgggt agacagaatg gagtgcttga aagtgacatt ggtgttaagt 14340
tcgacaccag gaacttcaag ctgggatggg atcccgaaac caagttgatc atgcctggag 14400
tgtatacgta tgaagccttc catcctgaca ttgtcttact gcctggctgc ggagtggatt 14460
ttaccgagag tcgtttgagc aaccttcttg gtatcagaaa aaaacagcca tttcaagagg 14520
gttttaagat tttgtatgaa gatttagaag gtggtaatat tccggccctc ttggatgtag 14580
atgcctatga gaacagtaag aaagaacaaa aagccaaaat agaagctgct acagctgctg 14640
cagaagctaa ggcaaacata gttgccagcg actctacaag ggttgctaac gctggagagg 14700
tcagaggaga caattttgcg ccaacacctg ttccgactgc agaatcatta ttggccgatg 14760
tgtctgaagg aacggacgtg aaactcacta ttcaacctgt agaaaaagat agtaagaata 14820
gaagctataa tgtgttggaa gacaaaatca acacagccta tcgcagttgg tatctttcgt 14880
acaattatgg cgatcccgaa aaaggagtgc gttcctggac attgctcacc acctcagatg 14940
tcacctgcgg agcagagcag gtctactggt cgcttccaga catgatgaag gatcctgtca 15000
ctttccgctc cactagacaa gtcagtaact accctgtggt gggtgcagag cttatgcccg 15060
tcttctcaaa gagcttctac aacgaacaag ctgtgtactc ccagcagctc cgccagtcca 15120
cctcgcttac gcacgtcttc aaccgctttc ctgagaacca gattttaatc cgtccgccgg 15180
cgcccaccat taccaccgtc agtgaaaacg ttcctgctct cacagatcac gggaccctgc 15240
cgttgcgcag cagtatccgg ggagtccaac gtgtgaccgt tactgacgcc agacgccgca 15300
cctgtcccta cgtgtacaag gcactgggca tagtcgcacc gcgcgtcctt tcaagccgca 15360
ctttctaaaa aaaaaaaaaa tgtccattct tatctcgccc agtaataaca ccggttgggg 15420
tctgcgcgct ccaagcaaga tgtacggagg cgcacgcaaa cgttctaccc aacatcctgt 15480
ccgtgttcgc ggacattttc gcgctccatg ggcgccctc aagggccgca ctcgcgttcg 15540
aaccaccgtc gatgatgtaa tcgatcaggt ggttgccgac gcccgtaatt atactcctac 15600
tgcgcctaca tctactgtgg atgcagttat tgacagtgta gtggctgacg ctcgcaacta 15660
tgctcgacgt aagagccggc gaaggcgcat tgccagacgc caccgagcta ccactgccat 15720
gcgagccgca agagctctgc tacgaagagc tagacgcgtg gggcgaagag ccatgcttag 15780
ggcggccaga cgtgcagctt cgggcgccag cgccggcagg tcccgcaggc aagcagccgc 15840
tgtcgcagcg gcgactattg ccgacatggc ccaatcgcga agaggcaatg tatactgggt 15900
gcgtgacgct gccaccggtc aacgtgtacc cgtgcgcacc cgtcccccctc gcacttagaa 15960
gatactgagc agtctccgat gttgtgtccc agcggcgagg atgtccaagc gcaaatacaa 16020
ggaagaaatg ctgcaggtta tcgcacctga agtctacggc caaccgttga aggatgaaaa 16080
aaaaccccgc aaaatcaagc gggttaaaaa ggacaaaaaa gaagaggaag atggcgatga 16140
tgggctggcg gagtttgtgc gcgagtttgc cccacggcga cgcgtgcaat ggcgtgggcg 16200
caaagttcga catgtgttga gacctggaac ttcggtggtc tttacacccg gcgagcgttc 16260
aagcgctact tttaagcgtt cctatgatga ggtgtacggg gatgatgata ttcttgagca 16320
ggcggctgac cgattaggcg agtttgctta tggcaagcgt agtagaataa cttccaagga 16380
tgagacagtg tcgataccct tggatcatgg aaatcccacc cctagtctta aaccggtcac 16440
tttgcagcaa gtgttacccg taactccgcg aacaggtgtt aaacgcgaag gtgaagattt 16500
gtatcccact atgcaactga tggtacccaa acgccagaag ttggaggacg ttttggagaa 16560
agtaaaagtg gatccagata ttcaacctga ggttaaagtg agacccatta agcaggtagc 16620
gcctggtctg gggtacaaa ctgtagacat taagattccc actgaaagta tggaagtgca 16680
aactgaaccc gcaaagccta ctgccacctc cactgaagtg caaacggatc catggatgcc 16740
catgcctatt acaactgacg ccgccggtcc cactcgaaga tcccgacgaa agtacggtcc 16800
agcaagtctg ttgatgccca attatgttgt acacccatct attattccta ctcctggtta 16860
ccgaggcact cgctactatc gcagccgaaa cagtacctcc cgccgtcgcc gcaagacacc 16920
tgcaaatcgc agtcgtcgcc gtagacgcac aagcaaaccg actcccggcg ccctggtgcg 16980
gcaagtgtac cgcaatggta gtgcggaacc tttgacactg ccgcgtgcgc gttaccatcc 17040
gagtatcatc acttaatcaa tgttgccgct gcctccttgc agatatggcc ctcacttgtc 17100
gccttcgcgt tcccatcact ggttaccgag gaagaaactc gcgccgtaga agagggatgt 17160

-continued

```
tgggacgcgg aatgcgacgc tacaggcgac ggcgtgctat ccgcaagcaa ttgcggggtg  17220
gtttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
```

-continued

```
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
```

ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400
attgtgttct cctaggcaga gaaacaacag acatggaaac tcagccattg ctgtcaacat 23460
cgccacgagt gccatcacat ctcgtcctca gcgacgagga aaaggagcag agcttaagca 23520
ttccaccgcc cagtcctgcc accacctcta ccctagaaga taaggaggtc gacgcatctc 23580
atgacatgca gaataaaaaa gcgaaagagt ctgagacaga catcgagcaa gacccgggct 23640
atgtgacacc ggtggaacac gaggaagagt tgaaacgctt tctagagaga gaggatgaaa 23700
actgcccaaa acaacgagca gataactatc accaagatgc tggaaatagg gatcagaaca 23760
ccgactacct catagggctt gacggggaag acgcgctcct taaacatcta gcaagacagt 23820
cgctcatagt caaggatgca ttattggaca gaactgaagt gcccatcagt gtggaagagc 23880
tcagccgcgc ctacgagctt aacctctttt cacctcgtac tccccccaaa cgtcagccaa 23940
acggcacctg cgagccaaat cctcgcttaa acttttatcc agcttttgct gtgccagaag 24000
tactggctac ctatcacatc ttttttaaaa atcaaaaaat tccagtctcc tgccgcgcta 24060
atcgcacccg cgccgatgcc ctactcaatc tgggacctgg ttcacgctta cctgatatag 24120
cttccttgga agaggttcca aagatcttcg agggtctggg caataatgag actcgggccg 24180
caaatgctct gcaaaaggga gaaaatggca tggatgagca tcacagcgtt ctggtggaat 24240

-continued

```
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac caccccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
```

```
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aacccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
ccggctcagt gactccttca accctgtcta cccctatgaa gatgaaagca cctcccaaca  28440
ccccttata aacccagggt ttatttcccc aaatggcttc acacaaagcc caaacggagt  28500
tcttacttta aaatgtttaa ccccactaac aaccacaggc ggatctctac agctaaaagt  28560
gggaggggga cttacagtgg atgacaccaa cggtttttg aaagaaaaca taagtgccac  28620
cacaccactc gttaagactg gtcactctat aggtttacca ctaggagccg gattgggaac  28680
gaatgaaaat aaactttgta tcaaattagg acaaggactt acattcaatt caaacaacat  28740
ttgcattgat gacaatatta acaccttatg gacaggagtc aaccccaccg aagccaactg  28800
tcaaatcatg aactccagtg aatctaatga ttgcaaatta attctaacac tagttaaaac  28860
tggagcacta gtcactgcat ttgtttatgt tataggagta tctaacaatt ttaatatgct  28920
aactacacac agaaatataa attttactgc agagctgttt ttcgattcta ctggtaattt  28980
```

actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct tttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttgcga tcgccaggcc accatggcct tgacctttgc tttactggtg 29400
gccctcctgg tgctcagctg caagtcaagc tgctctgtgg gctgtgatct gcctcaaacc 29460
cacagcctgg gtagcaggag gaccttgatg ctcctggcac agatgaggag aatctctctt 29520
ttctcctgct tgaaggacag acatgacttt ggatttcccc aggaggagtt tggcaaccag 29580
ttccaaaagg ctgaaaccat ccctgtcctc catgagatga tccagcagat cttcaatctc 29640
ttcagcacaa aggactcatc tgctgcttgg gatgagaccc tcctagacaa attctacact 29700
gaactctacc agcagctgaa tgacctggaa gcctgtgtga tacagggggt gggggtgaca 29760
gagactcccc tgatgaagga ggactccatt ctggctgtga ggaaatactt ccaaagaatc 29820
actctctatc tgaaagagaa gaaatacagc ccttgtgcct gggaggttgt cagagcagaa 29880
atcatgagat ctttttcttt gtcaacaaac ttgcaagaaa gtttaagaag taaggaagga 29940
agcggagcta ctaacttcag cctgctgaag caggctggag acgtggagga gaaccctgga 30000
cctcaggtct ccactgctgc ccttgccgtc ctcctctgca ccatggctct ctgcaaccag 30060
gtcctctctg caccacttgc tgctgacacg ccgaccgcct gctgcttcag ctacacctcc 30120
cgacagattc cacagaattt catagctgac tactttgaga cgagcagcca gtgctccaag 30180
cccagtgtca tcttcctaac caagagaggc cggcaggtct gtgctgaccc cagtgaggag 30240
tgggtccaga aatacgtcag tgacctggag ctgagtgccg gaagcggaga gggcagagga 30300
agtctgctaa catgcggtga cgtcgaggag aatcctggac ctggccacac acggaggcag 30360
ggaacatcac catccaagtg tccatacctc aatttctttc agctcttggt gctggctggt 30420
ctttctcact tctgttcagg tgttatccac gtgaccaagg aagtgaaaga agtggcaacg 30480
ctgtcctgtg gtcacaatgt ttctgttgaa gagctggcac aaactcgcat ctactggcaa 30540
aaggagaaga aaatggtgct gactatgatg tctggggaca tgaatatatg gcccgagtac 30600
aagaaccgga ccatctttga tatcactaat aacctctcca ttgtgatcct ggctctgcgc 30660
ccatctgacg agggcacata cgagtgtgtt gttctgaagt atgaaaaaga cgctttcaag 30720
cgggaacacc tggctgaagt gacgttatca gtcaaagctg acttccctac acctagtata 30780
tctgactttg aaattccaac ttctaatatt agaaggataa tttgctcaac ctctggaggt 30840
tttccagagc ctcacctctc ctggttggaa aatggagaag aattaaatgc catcaacaca 30900
acagtttccc aagatcctga aactgagctc tatgctgtta gcagcaaact ggatttcaat 30960
atgacaacca accacagctt catgtgtctc atcaagtatg gacatttaag agtgaatcag 31020
accttcaact ggaatacaac caagcaagag cattttcctg ataacctgct cccatcctgg 31080
gccattacct taatctcagt aaatggaatt tttgtgatat gctgcctgac ctactgcttt 31140
gccccaagat gcagagagag aaggaggaat gagagattga gaagggaaag tgtacgccct 31200
gtataagcta gcttgactga ctgagataca gcgtaccttc agctcacaga catgataaga 31260
tacattgatg agtttggaca aaccacaact agaatgcagt gaaaaaaatg ctttatttgt 31320
gaaatttgtg atgctattgc tttatttgta accattataa gctgcaataa acaagttaac 31380
aacaacaatt gcattcattt tatgtttcag gttcaggggg aggtgtggga ggttttttaa 31440
agcaagtaaa acctctacaa atgtggtagt cgtcagctat cctgcaggaa cttgtttatt 31500
tgaaaatcaa ttcacaaaat ccgagtagtt attttgcctc ccccttccca tttaacagaa 31560
tacaccaatc tctccccacg cacagcttta aacatttgga taccattaga tatagacatg 31620
gttttagatt ccacattcca aacagtttca gagcgagcca atctggggtc agtgatagat 31680
aaaaatccat cgggatagtc ttttaaagcg ctttcacagt ccaactgctg cggatgcgac 31740
tccggagtct ggatcacggt catctggaag aagaacgatg ggaatcataa tccgaaaacg 31800
gtatcggacg attgtgtctc atcaaaccca caagcagccg ctgtctgcgt cgctccgtgc 31860
gactgctgtt tatgggatca gggtccacag tgtcctgaag catgatttta atagccctta 31920
acatcaactt tctggtgcga tgcgcgcagc aacgcattct gatttcactc aaatctttgc 31980
agtaggtaca acacattatt acaatattgt ttaataaacc ataattaaaa gcgctccagc 32040
caaaactcat atctgatata atcgcccctg catgaccatc ataccaaagt ttaatataaa 32100
ttaaatgacg ttccctcaaa aacacactac ccacatacat gatctctttt ggcatgtgca 32160
tattaacaat ctgtctgtac catggacaac gttggttaat catgcaaccc aatataacct 32220
tccggaacca cactgccaac accgctcccc cagccatgca ttgaagtgaa ccctgctgat 32280
tacaatgaca atgaagaacc caattctctc gaccgtgaat cacttgagaa tgaaaaatat 32340
ctatagtggc acaacataga cataaatgca tgcatcttct cataattttt aactcctcag 32400
gatttagaaa catatcccag ggaataggaa gctcttgcag aacagtaaag ctggcagaac 32460
aaggaagacc acgaacacaa cttacactat gcatagtcat agtatcacaa tctggcaaca 32520
gcgggtggtc ttcagtcata gaagctcggg tttcattttc ctcacaacgt ggtaactggg 32580
ctctggtgta agggtgatgt ctggcgcatg atgtcgagcg tgcgcgcaac cttgtcataa 32640
tggagttgct tcctgacatt ctcgtatttt gtatagcaaa acgcggccct ggcagaacac 32700
actcttcttc gccttctatc ctgccgctta gcgtgttccg tgtgatagtt caagtacaac 32760
cacactctta agttggtcaa aagaatgctg gcttcagttg taatcaaaac tccatcgcat 32820
ctaatcgttc tgaggaaatc atccaagcaa tgcaactgga ttgtgtttca agcaggagag 32880
gagagggaag agacggaaga accatgttaa tttttattcc aaacgatctc gcagtacttc 32940
aaattgtaga tcgcgcagat ggcatctctc gcccccactg tgttggtgaa aaagcacagc 33000
tagatcaaaa gaaatgcgat tttcaaggtg ctcaacggtg gcttccagca aagcctccac 33060
gcgcacatcc aagaacaaaa gaataccaaa agaaggagca ttttctaact cctcaatcat 33120
catattacat tcctgcacca ttcccagata attttcagct ttccagcctt gaattattcg 33180
tgtcagttct tgtggtaaat ccaatccaca cattacaaac aggtcccgga gggcgccctc 33240
caccaccatt cttaaacaca ccctcataat gacaaaatat cttgctcctg tgtcacctgt 33300
agcgaattga gaatggcaac atcaattgac atgcccttgg ctctaagttc ttctttaagt 33360
tctagttgta aaaactctct catattatca ccaaactgct tagccagaag ccccccggga 33420
acaagagcag gggacgctac agtgcagtac aagcgcagac ctccccaatt ggctccagca 33480
aaaacaagat tggaataagc atattgggaa ccgccagtaa tatcatcgaa gttgctggaa 33540
atataatcag gcagagtttc ttgtaaaaat tgaataaaag aaaaatttgc caaaaaaaca 33600
ttcaaaacct ctgggatgca aatgcaatag gttaccgcgc tgcgctccaa cattgttagt 33660
tttgaattag tctgcaaaaa taaaaaaaaa aacaagcgtc atatcatagt agcctgacga 33720
acagatggat aaatcagtct ttccatcaca agacaagcca cagggtctcc agctcgaccc 33780
tcgtaaaacc tgtcatcatg attaaacaac agcaccgaaa gttcctcgcg gtgaccagca 33840
tgaataattc ttgatgaagc atacaatcca gacatgttag catcagttaa cgagaaaaaa 33900
cagccaacat agcctttggg tataattatg cttaatcgta agtatagcaa agccacccct 33960
cgcggataca aagtaaaagg cacaggagaa taaaaaatat aattatttct ctgctgctgt 34020
tcaggcaacg tcgcccccgg tccctctaaa tacacataca aagcctcatc agccatggct 34080
taccagacaa agtacagcgg gcacacaaag cacaagctct aaagtgactc tccaacctct 34140
ccacaatata tatatacaca agccctaaac tgacgtaatg ggagtaaagt gtaaaaaatc 34200
ccgccaaacc caacacacac cccgaaactg cgtcaccagg gaaaagtaca gtttcacttc 34260
cgcaatccca acaggcgtaa cttcctcttt ctcacggtac gtgatatccc actaacttgc 34320
aacgtcattt tcccacggtc gcaccgcccc ttttagccgt taaccccaca gccaatcacc 34380
acacgatcca cactttttaa aatcacctca tttacatatt ggcaccattc catctataag 34440
gtatattata tagataga 34458

<210> SEQ ID NO 114
<211> LENGTH: 981
<212> TYPE: DNA
<213> ORGANISM: Artificial Sequence
<220> FEATURE:
<223> OTHER INFORMATION: E3 REGION FROM ENAD

<400> SEQUENCE: 114
atgtctggtg acgcggctga gctatctcgg ctgcgacatc tagaccactg ccgccgcttt 60
cgctgctttg cccgggaact cattgagttc atctacttcg aactccccaa ggatcaccct 120
caaggtccgg cccacggagt gcggatttct atcgaaggca aaatagactc tcgcctgcaa 180
cgaattttct cccagcggcc cgtgctgatc gagcgagacc agggaaacac cacggtttcc 240
atctactgca tttgtaatca ccccggattg catgaaagcc tttgctgtct tatgtgtact 300
gagtttaata aaaactgaat taagactctc ctacggactg ccgcttcttc aacccggatt 360
ttacaaccag aagaacgaaa cttttcctgt cgtccaggac tctgttaact tcacctttcc 420
tactcacaaa ctagaagctc aacgactaca ccgcttttcc agaagcattt tccctactaa 480
tactactttc aaaaccggag gtgagctcca aggtcttcct acagaaaacc cttgggtgga 540
agcgggcctt gtagtgctag gaattcttgc gggtgggctt gtgattattc tttgctacct 600
atacacacct tgcttcactt tcttagtggt gttgtggtat tggtttaaaa aatggggccc 660
atactagtct tgcttgtttt actttcgctt ttggaaccgg gttctgccaa ttacgatcca 720
tgtctagact tcgacccaga aaactgcaca cttacttttg cacccgacac aagccgcatc 780
tgtggagttc atcgcctctc ttacgaactt ggcccccaac gacaaaaatt tacctgcatg 840
gtgggaatca accccatagt tatcacccag caaagtggag atactaaggg ttgcattcac 900
tgctcctgcg attccatcga gtgcacctac accctgctga agaccctatg cggcctaaga 960
gacctgctac caatgaatta a 981

<210> SEQ ID NO 115
<211> LENGTH: 34
<212> TYPE: DNA
<213> ORGANISM: Artificial Sequence
<220> FEATURE:
<223> OTHER INFORMATION: A NON-CODING SEQUENCE SUITABLE FOR INCLUSION
INTO BY

<400> SEQUENCE: 115
caaataaagt ttaacttgtt tatttgaaaa tcaa 34

<210> SEQ ID NO 116
<211> LENGTH: 34522
<212> TYPE: DNA
<213> ORGANISM: Artificial Sequence
<220> FEATURE:
<223> OTHER INFORMATION: NG-348 virus genome sequence comprising a transgene cassette that encoding a membrane-anchored chimeric form an anti-human CD3e scFv, and CD80 inserted in the region BY

<400> SEQUENCE: 116
tctatctata taatatacct tatagatgga atggtgccaa tatgtaaatg aggtgatttt 60
aaaaagtgtg gatcgtgtgg tgattggctg tggggttaac ggctaaaagg ggcggtgcga 120
ccgtgggaaa atgacgtttt gtgggggtgg agtttttttg caagttgtcg cgggaaatgt 180
gacgcataaa aaggcttttt tctcacggaa ctacttagtt ttcccacggt atttaacagg 240
aaatgaggta gttttgaccg gatgcaagtg aaaattgttg attttcgcgc gaaaactgaa 300
tgaggaagtg tttttctgaa taatgtggta tttatggcag ggtggagtat ttgttcaggg 360
ccaggtagac tttgacccat tacgtggagg tttcgattac cgtgtttttt acctgaattt 420
ccgcgtaccg tgtcaaagtc ttctgttttt acgtaggtgt cagctgatcg ctagggtatt 480
tatacctcag ggtttgtgtc aagaggccac tcttgagtgc cagcgagaag agttttctcc 540
tctgcgccgg cagtttaata ataaaaaaat gagagatttg cgatttctgc ctcaggaaat 600
aatctctgct gagactggaa atgaaatatt ggagcttgtg gtgcacgccc tgatgggaga 660
cgatccggag ccacctgtgc agctttttga gcctcctacg cttcaggaac tgtatgattt 720
agaggtagag ggatcggagg attctaatga ggaagctgta aatggctttt ttaccgattc 780
tatgctttta gctgctaatg aagggttaga attagatccg cctttggaca cttttgatac 840
tccaggggta attgtggaaa gcggtacagg tgtaagaaaa ttacctgatt tgagttccgt 900
ggactgtgat ttgcactgct atgaagacgg gtttcctccg agtgatgagg aggaccatga 960
aaaggagcag tccatgcaga ctgcagcggg tgagggagtg aaggctgcca atgttggttt 1020
tcagttggat tgcccggagc ttcctggaca tggctgtaag tcttgtgaat ttcacaggaa 1080
aaatactgga gtaaaggaac tgttatgttc gctttgttat atgagaacgc actgccactt 1140
tatttacagt aagtgtgttt aagttaaaat ttaaaggaat atgctgtttt tcacatgtat 1200
attgagtgtg agttttgtgc ttcttattat aggtcctgtg tctgatgctg atgaatcacc 1260
atctcctgat tctactacct cacctcctga gattcaagca cctgttcctg tggacgtgcg 1320
caagcccatt cctgtgaagc ttaagcctgg gaaacgtcca gcagtggaaa aacttgagga 1380
cttgttacag ggtggggacg gacctttgga cttgagtaca cggaaacgtc caagacaata 1440
agtgttccat atccgtgttt acttaaggtg acgtcaatat ttgtgtgaca gtgcaatgta 1500
ataaaaatat gttaactgtt cactggtttt tattgctttt tgggcgggga ctcaggtata 1560
taagtagaag cagacctgtg tggttagctc ataggagctg gctttcatcc atggaggttt 1620
gggccatttt ggaagacctt aggaagacta ggcaactgtt agagaacgct tcggacggag 1680
tctccggttt ttggagattc tggttcgcta gtgaattagc tagggtagtt tttaggataa 1740
aacaggacta taaacaagaa tttgaaaagt tgttggtaga ttgcccagga ctttttgaag 1800
ctcttaattt gggccatcag gttcacttta aagaaaaagt tttatcagtt ttagactttt 1860
caaccccagg tagaactgct gctgctgtgg cttttcttac ttttatatta gataaatgga 1920
tcccgcagac tcatttcagc aggggatacg ttttggattt catagccaca gcattgtgga 1980
gaacatggaa ggttcgcaag atgaggacaa tcttaggtta ctggccagtg cagcctttgg 2040
gtgtagcggg aatcctgagg catccaccgg tcatgccagc ggttctggag gaggaacagc 2100
aagaggacaa cccgagagcc ggcctggacc ctccagtgga ggaggcggag tagctgactt 2160
gtctcctgaa ctgcaacggg tgcttactgg atctacgtcc actggacggg ataggggcgt 2220
taagagggag agggcatcta gtggtactga tgctagatct gagttggctt taagtttaat 2280
gagtcgcaga cgtcctgaaa ccatttggtg gcatgaggtt cagaaagagg gaagggatga 2340
agtttctgta ttgcaggaga aatattcact ggaacaggtg aaaacatgtt ggttggagcc 2400
tgaggatgat tgggaggtgg ccattaaaaa ttatgccaag atagctttga ggcctgataa 2460
acagtataag attactagac ggattaatat ccggaatgct tgttacatat ctggaaatgg 2520
ggctgaggtg gtaatagata ctcaagacaa ggcagttatt agatgctgca tgatggatat 2580
gtggcctggg gtagtcggta tggaagcagt aacttttgta aatgttaagt ttaggggaga 2640
tggttataat ggaatagtgt ttatggccaa taccaaactt atattgcatg gttgtagctt 2700
ttttggtttc aacaatacct gtgtagatgc ctggggacag gttagtgtac ggggatgtag 2760
tttctatgcg tgttggattg ccacagctgg cagaaccaag agtcaattgt ctctgaagaa 2820
atgcatattt caaagatgta acctgggcat tctgaatgaa ggcgaagcaa gggtccgcca 2880
ctgcgcttct acagatactg gatgttttat tttgattaag ggaaatgcca gcgtaaagca 2940
taacatgatt tgcggtgctt ccgatgagag gccttatcaa atgctcactt gtgctggtgg 3000
gcattgtaat atgctggcta ctgtgcatat tgtttcccat caacgcaaaa aatggcctgt 3060
ttttgatcac aatgtgatga cgaagtgtac catgcatgca ggtgggcgta gaggaatgtt 3120
tatgccttac cagtgtaaca tgaatcatgt gaaagtgttg ttggaaccag atgccttttc 3180
cagaatgagc ctaacaggaa tttttgacat gaacatgcaa atctggaaga tcctgaggta 3240
tgatgatacg agatcgaggg tacgcgcatg cgaatgcgga ggcaagcatg ccaggttcca 3300
gccggtgtgt gtagatgtga ctgaagatct cagaccggat catttggtta ttgcccgcac 3360
tggagcagag ttcggatcca gtggagaaga aactgactaa ggtgagtatt gggaaaactt 3420
tggggtggga ttttcagatg gacagattga gtaaaaattt gtttttctg tcttgcagct 3480
gtcatgagtg gaaacgcttc ttttaagggg ggagtcttca gcccttatct gacagggcgt 3540
ctcccatcct gggcaggagt tcgtcagaat gttatgggat ctactgtgga tggaagaccc 3600
gtccaacccg ccaattcttc aacgctgacc tatgctactt taagttcttc acctttggac 3660
gcagctgcag ctgccgccgc cgcttctgtt gccgctaaca ctgtgcttgg aatgggttac 3720
tatggaagca tcatggctaa ttccacttcc tctaataacc cttctaccct gactcaggac 3780
aagttacttg tccttttggc ccagctggag gctttgaccc aacgtctggg tgaacttttct 3840
cagcaggtgg tcgagttgcg agtacaaact gagtctgctg tcggcacggc aaagtctaaa 3900
taaaaaaatc ccagaatcaa tgaataaata aacaagcttg ttgttgattt aaaatcaagt 3960
gtttttattt catttttcgc gcacggtatg ccctagacca ccgatctcta tcattgagaa 4020
ctcggtggat tttttccagg atcctataga ggtgggattg aatgtttaga tacatgggca 4080
ttaggccgtc tttggggtgg agatagctcc attgaaggga ttcatgctcc ggggtagtgt 4140
tgtaaatcac ccagtcataa caaggtcgca gtgcatggtg ttgcacaata tcttttagaa 4200
gtaggctgat tgccacagat aagcccttgg tgtaggtgtt tacaaaccgg ttgagctggg 4260
atgggtgcat tcggggtgaa attatgtgca ttttggattg gatttttaag ttggcaatat 4320
tgccgccaag atcccgtctt gggttcatgt tatgaaggac caccaagacg gtgtatccgg 4380
tacatttagg aaatttatcg tgcagcttgg atggaaaagc gtggaaaaat ttggagacac 4440
ccttgtgtcc tccaagattt tccatgcact catccatgat aatagcaatg gggccgtggg 4500
cagcggcgcg ggcaaacacg ttccgtgggt ctgacacatc atagttatgt tcctgagtta 4560
aatcatcata agccatttta atgaatttgg ggcggagagt accagattgg ggtatgaatg 4620
ttccttcggg ccccggagca tagttcccct cacagatttg catttcccaa gctttcagtt 4680
ccgagggtgg aatcatgtcc acctgggggg ctatgaaaaa caccgtttct ggggcggggg 4740
tgattaattg tgatgatagc aaatttctga gcaattgaga tttgccacat ccggtggggc 4800
cataaatgat tccgattacg ggttgcaggt ggtagtttag ggaacggcaa ctgccgtctt 4860
ctcgaagcaa gggggccacc tcgttcatca tttcccttac atgcatattt tcccgcacca 4920
aatccattag gaggcgctct cctcctagtg atagaagttc ttgtagtgag gaaaagtttt 4980
tcagcggttt cagaccgtca gccatgggca ttttggagag agtttgctgc aaaagttcta 5040
gtctgttcca cagttcagtg atgtgttcta tggcatctcg atccagcaga cctcctcgtt 5100
tcgcgggttt ggacggctcc tggaataggg tatgagacga tgggcgtcca gcgctgccag 5160
ggttcggtcc ttccagggtc tcagtgttcg agtcagggtt gtttccgtca cagtgaaggg 5220
gtgtgcgcct gcttgggcgc ttgccagggt gcgcttcaga ctcatcctgc tggtcgaaaa 5280
cttctgtcgc ttggcgccct gtatgtcggc caagtagcag tttaccatga gttcgtagtt 5340
gagcgcctcg gctgcgtggc ctttggcgcg gagcttacct ttggaagttt tcttgcatac 5400
cgggcagtat aggcatttca gcgcatacaa cttgggcgca aggaaaacgg attctgggga 5460
gtatgcatct gcgccgcagg aggcgcaaac agtttcacat tccaccagcc aggttaaatc 5520
cggttcattg ggtcaaaaa caagttttcc gccatatttt ttgatgcgtt tcttaccttt 5580
ggtctccatg agttcgtgtc ctcgttgagt gacaaacagg ctgtccgtgt ccccgtagac 5640
tgattttaca ggcctcttct ccagtggagt gcctcggtct tcttcgtaca ggaactctga 5700
ccactctgat acaaaggcgc gcgtccaggc cagcacaaag gaggctatgt gggaggggta 5760
gcgatcgttg tcaaccaggg ggtccacctt ttccaaagta tgcaaacaca tgtcaccctc 5820
ttcaacatcc aggaatgtga ttggcttgta ggtgtatttc acgtgacctg gggtccccgc 5880 tggggggta taaaaggggg cggttctttg ctcttcctca ctgtcttccg gatcgctgtc 5940
caggaacgtc agctgttggg gtaggtattc cctctcgaag gcgggcatga cctctgcact 6000
caggttgtca gtttctaaga acgaggagga tttgatattg acagtgccgg ttgagatgcc 6060
tttcatgagg ttttcgtcca tctggtcaga aaacacaatt tttttattgt caagtttggt 6120
ggcaaatgat ccatacaggg cgttggataa aagtttggca atggatcgca tggtttggtt 6180
cttttccttg tccgcgcgct ctttggcggc gatgttgagt tggacatact cgcgtgccag 6240
gcacttccat tcggggaaga tagttgttaa ttcatctggc acgattctca cttgccaccc 6300
tcgattatgc aaggtaatta aatccacact ggtggccacc tcgcctcgaa ggggttcatt 6360
ggtccaacag agcctacctc ctttcctaga acagaaaggg ggaagtgggt ctagcataag 6420
ttcatcggga gggtctgcat ccatggtaaa gattcccgga agtaaatcct tatcaaaata 6480
gctgatggga gtggggtcat ctaaggccat ttgccattct cgagctgcca gtgcgcgctc 6540
atatgggtta aggggactgc cccatggcat gggatgggtg agtgcagagg catacatgcc 6600
acagatgtca tagacgtaga tgggatcctc aaagatgcct atgtaggttg gatagcatcg 6660

```
ccccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gtttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
```

-continued

```
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
actcgagccg gccggagccg cggctaacgt ggtattggca ctcccgtctc gacccagcct  10560
acaaaaatcc aggatacgga atcgagtcgt tttgctggtt tccgaatggc agggaagtga  10620
gtcctatttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
```

```
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgcccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
```

acgagagcgt gatgcagcag cagcaggcga cggcggtgat gcaatcccca ctggaggctc 13800
cctttgtgcc tccgcgatac ctggcaccta cggagggcag aaacagcatt cgttattcgg 13860
aactggcacc tcagtacgat accaccaggt tgtatctggt ggacaacaag tcggcggaca 13920
ttgcttctct gaactatcag aatgaccaca gcaacttctt gaccacggtg gtgcaaaaca 13980
atgactttac ccctacggaa gccagcaccc agaccattaa ctttgatgaa cgatcgcggt 14040
ggggcggtca gctaaagacc atcatgcata ctaacatgcc aaacgtgaac gagtatatgt 14100
ttagtaacaa gttcaaagcg cgtgtgatgg tgtccagaaa acctcccgac ggtgctgcag 14160
ttggggatac ttatgatcac aagcaggata ttttgaaata tgagtggttc gagtttactt 14220
tgccagaagg caacttttca gttactatga ctattgattt gatgaacaat gccatcatag 14280
ataattactt gaaagtgggt agacagaatg gagtgcttga aagtgacatt ggtgttaagt 14340
tcgacaccag gaacttcaag ctgggatggg atcccgaaac caagttgatc atgcctggag 14400
tgtatacgta tgaagccttc catcctgaca ttgtcttact gcctggctgc ggagtggatt 14460
ttaccgagag tcgtttgagc aaccttcttg gtatcagaaa aaaacagcca tttcaagagg 14520
gttttaagat tttgtatgaa gatttagaag gtggtaatat tccggccctc ttggatgtag 14580
atgcctatga gaacagtaag aaagaacaaa aagccaaaat agaagctgct acagctgctg 14640
cagaagctaa ggcaaacata gttgccagcg actctacaag ggttgctaac gctggagagg 14700
tcagaggaga caattttgcg ccaacacctg ttccgactgc agaatcatta ttggccgatg 14760
tgtctgaagg aacggacgtg aaactcacta ttcaacctgt agaaaaagat agtaagaata 14820
gaagctataa tgtgttggaa gacaaaatca acacagccta tcgcagttgg tatctttcgt 14880
acaattatgg cgatcccgaa aaaggagtgc gttcctggac attgctcacc acctcagatg 14940
tcacctgcgg agcagagcag gtctactggt cgcttccaga catgatgaag gatcctgtca 15000
ctttccgctc cactagacaa gtcagtaact accctgtggt gggtgcagag cttatgcccg 15060
tcttctcaaa gagcttctac aacgaacaag ctgtgtactc ccagcagctc cgccagtcca 15120
cctcgcttac gcacgtcttc aaccgctttc ctgagaacca gattttaatc cgtccgccgg 15180
cgcccaccat taccaccgtc agtgaaaacg ttcctgctct cacagatcac gggaccctgc 15240
cgttgcgcag cagtatccgg ggagtccaac gtgtgaccgt tactgacgcc agacgccgca 15300
cctgtcccta cgtgtacaag gcactgggca tagtcgcacc gcgcgtcctt tcaagccgca 15360
ctttctaaaa aaaaaaaaaa tgtccattct tatctcgccc agtaataaca ccggttgggg 15420
tctgcgcgct ccaagcaaga tgtacggagg cgcacgcaaa cgttctaccc aacatcctgt 15480
ccgtgttcgc ggacattttc gcgctccatg ggcgccctc aagggccgca ctcgcgttcg 15540
aaccaccgtc gatgatgtaa tcgatcaggt ggttgccgac gcccgtaatt atactcctac 15600
tgcgcctaca tctactgtgg atgcagttat tgacagtgta gtggctgacg ctcgcaacta 15660
tgctcgacgt aagagccggc gaaggcgcat tgccagacgc caccgagcta ccactgccat 15720
gcgagccgca agagctctgc tacgaagagc tagacgcgtg gggcgaagag ccatgcttag 15780
ggcggccaga cgtgcagctt cgggcgccag cgccggcagg tcccgcaggc aagcagccgc 15840
tgtcgcagcg gcgactattg ccgacatggc ccaatcgcga agaggcaatg tatactgggt 15900
gcgtgacgct gccaccggtc aacgtgtacc cgtgcgcacc cgtcccccctc gcacttagaa 15960
gatactgagc agtctccgat gttgtgtccc agcggcgagg atgtccaagc gcaaatacaa 16020
ggaagaaatg ctgcaggtta tcgcacctga agtctacggc caaccgttga aggatgaaaa 16080
aaaaccccgc aaaatcaagc gggttaaaaa ggacaaaaaa gaagaggaag atggcgatga 16140

-continued

```
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttgg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
```

```
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
```

```
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
```

-continued

```
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc tttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
```

-continued

```
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
```

catctgtgga gttcatcgcc tctcttacga acttggcccc caacgacaaa aatttacctg 28020
catggtggga atcaacccca tagttatcac ccagcaaagt ggagatacta agggttgcat 28080
tcactgctcc tgcgattcca tcgagtgcac ctacaccctg ctgaagaccc tatgcggcct 28140
aagagacctg ctaccaatga attaaaaaat gattaataaa aaatcactta cttgaaatca 28200
gcaataaggt ctctgttgaa atttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta ccccatgaa gatgaaagca cctcccaaca 28440
cccctttata aacccagggt ttatttcccc aaatggcttc acacaaagcc caaacggagt 28500
tcttacttta aaatgtttaa ccccactaac aaccacaggc ggatctctac agctaaaagt 28560
gggagggga cttacagtgg atgacaccaa cggtttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920
aactacacac agaaatataa attttactgc agagctgttt ttcgattcta ctggtaattt 28980
actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct tttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttgcga tcgccaggcc caccatggga tggagctgta tcatcctctt 29400
cttggtagca acagctacag gtgtccactc ccaggtgcag ctgcagcagt ctggggctga 29460
actggcaaga cctggggcct cagtgaagat gtcctgcaag gcttctggct acacctttac 29520
taggtacacg atgcactggg taaaacagag gcctggacag ggtctggaat ggattggata 29580
cattaatcct agccgtggtt atactaatta caatcagaag ttcaaggaca aggccacatt 29640
gactacagac aaatcctcca gcacagccta catgcaactg agcagcctga catctgagga 29700
ctctgcagtc tattactgtg caagatatta tgatgatcat tactgccttg actactgggg 29760
ccaaggcacc actctcacag tctcctcagg tggcggtggc tcgggcggtg gtggatctgg 29820
tggcggcgga tctgatatcg tgctcactca gtctccagca atcatgtctg catctccagg 29880
ggagaaggtc accatgacct gcagtgccag ctcaagtgta agttacatga actggtacca 29940
gcagaagtca ggcacctccc ccaaaagatg gatttatgac acatccaaac tggcttctgg 30000
agtccctgct cacttcaggg gcagtgggtc tgggacctct tactctctca caatcagcgg 30060
catggaggct gaagatgctg ccacttatta ctgccagcag tggagtagta acccattcac 30120
gttcggctcg gggacaaagt tggaaataaa ccggggatcc gaacaaaaac tcatctcaga 30180
agaggatctg aatgctgtgg gccaggacac gcaggaggtc atcgtggtgc cacactcctt 30240
gccctttaag gtggtggtga tctcagccat cctggccctg gtggtgctca ccatcatctc 30300
ccttatcatc ctcatcatgc tttggcagaa gaagccacgt ggaagcggag ctactaactt 30360
cagcctgctg aagcaggctg gagacgtgga ggagaaccct ggacctggcc acacacggag 30420
gcagggaaca tcaccatcca agtgtccata cctcaatttc tttcagctct tggtgctggc 30480
tggtctttct cacttctgtt caggtgttat ccacgtgacc aaggaagtga aagaagtggc 30540
aacgctgtcc tgtggtcaca atgtttctgt tgaagagctg gcacaaactc gcatctactg 30600
gcaaaaggag aagaaaatgg tgctgactat gatgtctggg gacatgaata tatggcccga 30660
gtacaagaac cggaccatct ttgatatcac taataacctc tccattgtga tcctggctct 30720
gcgcccatct gacgagggca catacgagtg tgttgttctg aagtatgaaa aagacgcttt 30780
caagcgggaa cacctggctg aagtgacgtt atcagtcaaa gctgacttcc ctacacctag 30840
tatatctgac tttgaaattc caacttctaa tattagaagg ataatttgct caacctctgg 30900
aggttttcca gagcctcacc tctcctggtt ggaaaatgga gaagaattaa atgccatcaa 30960
cacaacagtt tcccaagatc ctgaaactga gctctatgct gttagcagca aactggattt 31020
caatatgaca accaaccaca gcttcatgtg tctcatcaag tatggacatt taagagtgaa 31080
tcagaccttc aactggaata caaccaagca agagcatttt cctgataacc tgctcccatc 31140
ctgggccatt accttaatct cagtaaatgg aatttttgtg atatgctgcc tgacctactg 31200
ctttgcccca agatgcagag agagaaggag gaatgagaga ttgagaaggg aaagtgtacg 31260
ccctgtataa gctagcttga ctgactgaga tacagcgtac cttcagctca cagacatgat 31320
aagatacatt gatgagtttg gacaaaccac aactagaatg cagtgaaaaa aatgctttat 31380
ttgtgaaatt tgtgatgcta ttgctttatt tgtaaccatt ataagctgca ataaacaagt 31440
taacaacaac aattgcattc attttatgtt tcaggttcag ggggaggtgt gggaggtttt 31500
ttaaagcaag taaaacctct acaaatgtgg tagtcgtcag ctatcctgca ggaacttgtt 31560
tatttgaaaa tcaattcaca aaatccgagt agttattttg cctcccccctt cccatttaac 31620
agaatacacc aatctctccc cacgcacagc tttaaacatt tggataccat tagatataga 31680
catggtttta gattccacat tccaaacagt ttcagagcga gccaatctgg ggtcagtgat 31740
agataaaaat ccatcgggat agtcttttaa agcgctttca cagtccaact gctgcggatg 31800
cgactccgga gtctggatca cggtcatctg gaagaagaac gatgggaatc ataatccgaa 31860
aacggtatcg gacgattgtg tctcatcaaa cccacaagca gccgctgtct gcgtcgctcc 31920
gtgcgactgc tgtttatggg atcagggtcc acagtgtcct gaagcatgat tttaatagcc 31980
cttaacatca actttctggt gcgatgcgcg cagcaacgca ttctgatttc actcaaatct 32040
ttgcagtagg tacaacacat tattacaata ttgtttaata aaccataatt aaaagcgctc 32100
cagccaaaac tcatatctga tataatcgcc cctgcatgac catcatacca aagtttaata 32160
taaattaaat gacgttccct caaaaacaca ctacccacat acatgatctc ttttggcatg 32220
tgcatattaa caatctgtct gtaccatgga caacgttggt taatcatgca acccaatata 32280
accttccgga accacactgc caacaccgct cccccagcca tgcattgaag tgaaccctgc 32340
tgattacaat gacaatgaag aacccaattc tctcgaccgt gaatcacttg agaatgaaaa 32400
atatctatag tggcacaaca tagacataaa tgcatgcatc ttctcataat ttttaactcc 32460
tcaggattta gaaacatatc ccagggaata ggaagctctt gcagaacagt aaagctggca 32520
gaacaaggaa gaccacgaac acaacttaca ctatgcatag tcatagtatc acaatctggc 32580
aacagcgggt ggtcttcagt catagaagct cgggtttcat tttcctcaca acgtggtaac 32640
tgggctctgg tgtaagggtg atgtctggcg catgatgtcg agcgtgcgcg caaccttgtc 32700
ataatggagt tgcttcctga cattctcgta ttttgtatag caaaacgcgg ccctggcaga 32760
acacactctt cttcgccttc tatcctgccg cttagcgtgt tccgtgtgat agttcaagta 32820
caaccacact cttaagttgg tcaaaagaat gctggcttca gttgtaatca aaactccatc 32880
gcatctaatc gttctgagga aatcatccaa gcaatgcaac tggattgtgt ttcaagcagg 32940
agaggagagg gaagagacgg aagaaccatg ttaattttta ttccaaacga tctcgcagta 33000
cttcaaattg tagatcgcgc agatggcatc tctcgccccc actgtgttgg tgaaaaagca 33060
cagctagatc aaaagaaatg cgattttcaa ggtgctcaac ggtggcttcc agcaaagcct 33120
ccacgcgcac atccaagaac aaaagaatac caaaagaagg agcattttct aactcctcaa 33180
tcatcatatt acattcctgc accattccca gataattttc agctttccag ccttgaatta 33240
ttcgtgtcag ttcttgtggt aaatccaatc cacacattac aaacaggtcc cggagggcgc 33300
cctccaccac cattcttaaa cacaccctca taatgacaaa atatcttgct cctgtgtcac 33360
ctgtagcgaa ttgagaatgg caacatcaat tgacatgccc ttggctctaa gttcttcttt 33420
aagttctagt tgtaaaaact ctctcatatt atcaccaaac tgcttagcca gaagcccccc 33480
gggaacaaga gcaggggacg ctacagtgca gtacaagcgc agacctcccc aattggctcc 33540
agcaaaaaca agattggaat aagcatattg ggaaccgcca gtaatatcat cgaagttgct 33600
ggaaatataa tcaggcagag tttcttgtaa aaattgaata aaagaaaaat ttgccaaaaa 33660
aacattcaaa acctctggga tgcaaatgca ataggttacc gcgctgcgct ccaacattgt 33720
tagttttgaa ttagtctgca aaaataaaaa aaaaaacaag cgtcatatca tagtagcctg 33780
acgaacagat ggataaatca gtctttccat cacaagacaa gccacagggt ctccagctcg 33840
accctcgtaa aacctgtcat catgattaaa caacagcacc gaaagttcct cgcggtgacc 33900
agcatgaata attcttgatg aagcatacaa tccagacatg ttagcatcag ttaacgagaa 33960
aaaacagcca acatagcctt tgggtataat tatgcttaat cgtaagtata gcaaagccac 34020
ccctcgcgga tacaaagtaa aaggcacagg agaataaaaa atataattat ttctctgctg 34080
ctgttcaggc aacgtcgccc ccggtccctc taaatacaca tacaaagcct catcagccat 34140
ggcttaccag acaaagtaca gcgggcacac aaagcacaag ctctaaagtg actctccaac 34200
ctctccacaa tatatatata cacaagccct aaactgacgt aatgggagta aagtgtaaaa 34260
aatcccgcca aacccaacac acaccccgaa actgcgtcac cagggaaaag tacagtttca 34320
cttccgcaat cccaacaggc gtaacttcct ctttctcacg gtacgtgata tcccactaac 34380
ttgcaacgtc attttcccac ggtcgcaccg cccctttttag ccgttaaccc cacagccaat 34440
caccacacga tccacacttt ttaaaatcac ctcatttaca tattggcacc attccatcta 34500
taaggtatat tatatagata ga 34522

<210> SEQ ID NO 117
<211> LENGTH: 966
<212> TYPE: DNA
<213> ORGANISM: Artificial Sequence
<220> FEATURE:
<223> OTHER INFORMATION: MEMBRANE TETHERED OKT3-SCFV NUCLEIC ACID
SEQUENCE

<400> SEQUENCE: 117
atgggatgga gctgtatcat cctcttcttg gtagcaacag ctacaggtgt ccactcccag 60
gtgcagctgc agcagtctgg ggctgaactg gcaagacctg gggcctcagt gaagatgtcc 120
tgcaaggctt ctggctacac ctttactagg tacacgatgc actgggtaaa acagaggcct 180

```
ggacagggtc tggaatggat tggatacatt aatcctagcc gtggttatac taattacaat    240

cagaagttca aggacaaggc cacattgact acagacaaat cctccagcac agcctacatg    300

caactgagca gcctgacatc tgaggactct gcagtctatt actgtgcaag atattatgat    360

gatcattact gccttgacta ctggggccaa ggcaccactc tcacagtctc ctcaggtggc    420

ggtggctcgg gcggtggtgg atctggtggc ggcggatctg atatcgtgct cactcagtct    480

ccagcaatca tgtctgcatc tccaggggag aaggtcacca tgacctgcag tgccagctca    540

agtgtaagtt acatgaactg gtaccagcag aagtcaggca cctcccccaa aagatggatt    600

tatgacacat ccaaactggc ttctggagtc cctgctcact tcaggggcag tgggtctggg    660

acctcttact ctctcacaat cagcggcatg gaggctgaag atgctgccac ttattactgc    720

cagcagtgga gtagtaaccc attcacgttc ggctcgggga caaagttgga aataaaccgg    780

ggatccgaac aaaaactcat ctcagaagag gatctgaatg ctgtgggcca ggacacgcag    840

gaggtcatcg tggtgccaca ctccttgccc tttaaggtgg tggtgatctc agccatcctg    900

gccctggtgg tgctcaccat catctccctt atcatcctca tcatgctttg gcagaagaag    960

ccacgt                                                               966
```

```
<210> SEQ ID NO 118
<211> LENGTH: 2196
<212> TYPE: DNA
<213> ORGANISM: Artificial Sequence
<220> FEATURE:
<223> OTHER INFORMATION: Transgene Cassette sequence -  NG-348

<400> SEQUENCE: 118

gcgatcgcca ggcccaccat gggatggagc tgtatcatcc tcttcttggt agcaacagct     60

acaggtgtcc actcccaggt gcagctgcag cagtctgggg ctgaactggc aagacctggg    120

gcctcagtga agatgtcctg caaggcttct ggctacacct ttactaggta cacgatgcac    180

tgggtaaaac agaggcctgg acagggtctg gaatggattg gatacattaa tcctagccgt    240

ggttatacta attacaatca gaagttcaag gacaaggcca cattgactac agacaaatcc    300

tccagcacag cctacatgca actgagcagc ctgacatctg aggactctgc agtctattac    360

tgtgcaagat attatgatga tcattactgc cttgactact ggggccaagg caccactctc    420

acagtctcct caggtggcgg tggctcgggc ggtggtggat ctggtggcgg cggatctgat    480

atcgtgctca ctcagtctcc agcaatcatg tctgcatctc caggggagaa ggtcaccatg    540

acctgcagtg ccagctcaag tgtaagttac atgaactggt accagcagaa gtcaggcacc    600

tcccccaaaa gatggattta tgacacatcc aaactggctt ctggagtccc tgctcacttc    660

aggggcagtg ggtctgggac ctcttactct ctcacaatca gcggcatgga ggctgaagat    720

gctgccactt attactgcca gcagtggagt agtaacccat tcacgttcgg ctcggggaca    780

aagttggaaa taaaccgggg atccgaacaa aaactcatct cagaagagga tctgaatgct    840

gtgggccagg acacgcagga ggtcatcgtg gtgccacact ccttgccctt taaggtggtg    900

gtgatctcag ccatcctggc cctggtggtg ctcaccatca tctcccttat catcctcatc    960

atgctttggc agaagaagcc acgtggaagc ggagctacta acttcagcct gctgaagcag   1020

gctggagacg tggaggagaa ccctggacct ggccacacac ggaggcaggg aacatcacca   1080

tccaagtgtc catacctcaa tttctttcag ctcttggtgc tggctggtct ttctcacttc   1140

tgttcaggtg ttatccacgt gaccaaggaa gtgaaagaag tggcaacgct gtcctgtggt   1200

cacaatgttt ctgttgaaga gctggcacaa actcgcatct actggcaaaa ggagaagaaa   1260
```

atggtgctga ctatgatgtc tggggacatg aatatatggc ccgagtacaa gaaccggacc 1320
atctttgata tcactaataa cctctccatt gtgatcctgg ctctgcgccc atctgacgag 1380
ggcacatacg agtgtgttgt tctgaagtat gaaaaagacg ctttcaagcg ggaacacctg 1440
gctgaagtga cgttatcagt caaagctgac ttccctacac ctagtatatc tgactttgaa 1500
attccaactt ctaatattag aaggataatt tgctcaacct ctggaggttt tccagagcct 1560
cacctctcct ggttggaaaa tggagaagaa ttaaatgcca tcaacacaac agtttcccaa 1620
gatcctgaaa ctgagctcta tgctgttagc agcaaactgg atttcaatat gacaaccaac 1680
cacagcttca tgtgtctcat caagtatgga catttaagag tgaatcagac cttcaactgg 1740
aatacaacca agcaagagca ttttcctgat aacctgctcc catcctgggc cattacctta 1800
atctcagtaa atggaatttt tgtgatatgc tgcctgacct actgctttgc cccaagatgc 1860
agagagagaa ggaggaatga gagattgaga agggaaagtg tacgccctgt ataagctagc 1920
ttgactgact gagatacagc gtaccttcag ctcacagaca tgataagata cattgatgag 1980
tttggacaaa ccacaactag aatgcagtga aaaaaatgct ttatttgtga aatttgtgat 2040
gctattgctt tatttgtaac cattataagc tgcaataaac aagttaacaa caacaattgc 2100
attcatttta tgtttcaggt tcagggggag gtgtgggagg ttttttaaag caagtaaaac 2160
ctctacaaat gtggtagtcg tcagctatcc tgcagg 2196

<210> SEQ ID NO 119
<211> LENGTH: 32345
<212> TYPE: DNA
<213> ORGANISM: Artificial Sequence
<220> FEATURE:
<223> OTHER INFORMATION: Fully synthetic EnAd genome with incorporated
cloning site for transgene cassette insertion as in plasmid
pEnAd2.4

<400> SEQUENCE: 119
tctatctata taatatacct tatagatgga atggtgccaa tatgtaaatg aggtgatttt 60
aaaaagtgtg gatcgtgtgg tgattggctg tggggttaac ggctaaaagg ggcggtgcga 120
ccgtgggaaa atgacgtttt gtgggggtgg agtttttttg caagttgtcg cgggaaatgt 180
gacgcataaa aaggcttttt tctcacggaa ctacttagtt ttcccacggt atttaacagg 240
aaatgaggta gttttgaccg gatgcaagtg aaaattgttg attttcgcgc gaaaactgaa 300
tgaggaagtg tttttctgaa taatgtggta tttatggcag ggtggagtat ttgttcaggg 360
ccaggtagac tttgacccat tacgtggagg tttcgattac cgtgtttttt acctgaattt 420
ccgcgtaccg tgtcaaagtc ttctgttttt acgtaggtgt cagctgatcg ctagggtatt 480
tatacctcag ggtttgtgtc aagaggccac tcttgagtgc cagcgagaag agttttctcc 540
tctgcgccgg cagtttaata ataaaaaaat gagagatttg cgatttctgc ctcaggaaat 600
aatctctgct gagactggaa atgaaatatt ggagcttgtg gtgcacgccc tgatgggaga 660
cgatccggag ccacctgtgc agctttttga gcctcctacg cttcaggaac tgtatgattt 720
agaggtagag ggatcggagg attctaatga ggaagctgta aatggctttt ttaccgattc 780
tatgctttta gctgctaatg aagggttaga attagatccg cctttggaca cttttgatac 840
tccaggggta attgtggaaa gcggtacagg tgtaagaaaa ttacctgatt tgagttccgt 900
ggactgtgat ttgcactgct atgaagacgg gtttcctccg agtgatgagg aggaccatga 960
aaaggagcag tccatgcaga ctgcagcggg tgagggagtg aaggctgcca atgttggttt 1020
tcagttggat tgcccggagc ttcctggaca tggctgtaag tcttgtgaat ttcacaggaa 1080
aaatactgga gtaaaggaac tgttatgttc gctttgttat atgagaacgc actgccactt 1140
tatttacagt aagtgtgttt aagttaaaat ttaaaggaat atgctgtttt tcacatgtat 1200
attgagtgtg agttttgtgc ttcttattat aggtcctgtg tctgatgctg atgaatcacc 1260
atctcctgat tctactacct cacctcctga gattcaagca cctgttcctg tggacgtgcg 1320
caagcccatt cctgtgaagc ttaagcctgg gaaacgtcca gcagtggaaa aacttgagga 1380
cttgttacag ggtggggacg gacctttgga cttgagtaca cggaaacgtc caagacaata 1440
agtgttccat atccgtgttt acttaaggtg acgtcaatat ttgtgtgaca gtgcaatgta 1500
ataaaaatat gttaactgtt cactggtttt tattgctttt tgggcgggga ctcaggtata 1560
taagtagaag cagacctgtg tggttagctc ataggagctg gctttcatcc atggaggttt 1620
gggccatttt ggaagacctt aggaagacta ggcaactgtt agagaacgct tcggacggag 1680
tctccggttt ttggagattc tggttcgcta gtgaattagc tagggtagtt tttaggataa 1740
aacaggacta taaacaagaa tttgaaaagt tgttggtaga ttgcccagga ctttttgaag 1800
ctcttaattt gggccatcag gttcacttta aagaaaaagt tttatcagtt ttagactttt 1860
caaccccagg tagaactgct gctgctgtgg cttttcttac ttttatatta gataaatgga 1920
tcccgcagac tcatttcagc aggggatacg ttttggattt catagccaca gcattgtgga 1980
gaacatggaa ggttcgcaag atgaggacaa tcttaggtta ctggccagtg cagcctttgg 2040
gtgtagcggg aatcctgagg catccaccgg tcatgccagc ggttctggag gaggaacagc 2100
aagaggacaa cccgagagcc ggcctggacc ctccagtgga ggaggcggag tagctgactt 2160
gtctcctgaa ctgcaacggg tgcttactgg atctacgtcc actggacggg ataggggcgt 2220
taagagggag agggcatcta gtggtactga tgctagatct gagttggctt taagtttaat 2280
gagtcgcaga cgtcctgaaa ccatttggtg gcatgaggtt cagaaagagg gaagggatga 2340
agtttctgta ttgcaggaga aatattcact ggaacaggtg aaaacatgtt ggttggagcc 2400
tgaggatgat tgggaggtgg ccattaaaaa ttatgccaag atagctttga ggcctgataa 2460
acagtataag attactagac ggattaatat ccggaatgct tgttacatat ctggaaatgg 2520
ggctgaggtg gtaatagata ctcaagacaa ggcagttatt agatgctgca tgatggatat 2580
gtggcctggg gtagtcggta tggaagcagt aacttttgta aatgttaagt ttaggggaga 2640
tggttataat ggaatagtgt ttatggccaa taccaaactt atattgcatg gttgtagctt 2700
ttttggtttc aacaatacct gtgtagatgc ctggggacag gttagtgtac ggggatgtag 2760
tttctatgcg tgttggattg ccacagctgg cagaaccaag agtcaattgt ctctgaagaa 2820
atgcatattt caaagatgta acctgggcat tctgaatgaa ggcgaagcaa gggtccgcca 2880
ctgcgcttct acagatactg gatgttttat tttgattaag ggaaatgcca gcgtaaagca 2940
taacatgatt tgcggtgctt ccgatgagag gccttatcaa atgctcactt gtgctggtgg 3000
gcattgtaat atgctggcta ctgtgcatat tgtttcccat caacgcaaaa aatggcctgt 3060
ttttgatcac aatgtgatga cgaagtgtac catgcatgca ggtgggcgta gaggaatgtt 3120
tatgccttac cagtgtaaca tgaatcatgt gaaagtgttg ttggaaccag atgccttttc 3180
cagaatgagc ctaacaggaa tttttgacat gaacatgcaa atctggaaga tcctgaggta 3240
tgatgatacg agatcgaggg tacgcgcatg cgaatgcgga ggcaagcatg ccaggttcca 3300
gccggtgtgt gtagatgtga ctgaagatct cagaccggat catttggtta ttgcccgcac 3360
tggagcagag ttcggatcca gtggagaaga aactgactaa ggtgagtatt gggaaaactt 3420

-continued

```
tggggtggga ttttcagatg gacagattga gtaaaaattt gtttttctg tcttgcagct   3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720
tatggaagca tcatggctaa ttccacttcc tctaataacc cttctaccct gactcaggac   3780
aagttacttg tccttttggc ccagctggag gctttgaccc aacgtctggg tgaactttct   3840
cagcaggtgg tcgagttgcg agtacaaact gagtctgctg tcggcacggc aaagtctaaa   3900
taaaaaaatc ccagaatcaa tgaataaata aacaagcttg ttgttgattt aaaatcaagt   3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gatttttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
```

gcgatcgttg tcaaccaggg ggtccacctt ttccaaagta tgcaaacaca tgtcaccctc 5820
ttcaacatcc aggaatgtga ttggcttgta ggtgtatttc acgtgacctg gggtccccgc 5880 tggggggta taaaaggggg cggttctttg ctcttcctca ctgtcttccg gatcgctgtc 5940
caggaacgtc agctgttggg gtaggtattc cctctcgaag gcgggcatga cctctgcact 6000
caggttgtca gtttctaaga acgaggagga tttgatattg acagtgccgg ttgagatgcc 6060
tttcatgagg ttttcgtcca tctggtcaga aaacacaatt tttttattgt caagtttggt 6120
ggcaaatgat ccatacaggg cgttggataa aagtttggca atggatcgca tggtttggtt 6180
cttttccttg tccgcgcgct ctttggcggc gatgttgagt tggacatact cgcgtgccag 6240
gcacttccat tcggggaaga tagttgttaa ttcatctggc acgattctca cttgccaccc 6300
tcgattatgc aaggtaatta aatccacact ggtggccacc tcgcctcgaa ggggttcatt 6360
ggtccaacag agcctacctc ctttcctaga acagaaaggg ggaagtgggt ctagcataag 6420
ttcatcggga gggtctgcat ccatggtaaa gattcccgga agtaaatcct tatcaaaata 6480
gctgatggga gtggggtcat ctaaggccat ttgccattct cgagctgcca gtgcgcgctc 6540
atatgggtta aggggactgc cccatggcat gggatgggtg agtgcagagg catacatgcc 6600
acagatgtca tagacgtaga tgggatcctc aaagatgcct atgtaggttg gatagcatcg 6660 ccccctctg atacttgctc gcacatagtc atatagttca tgtgatggcg ctagcagccc 6720
cggacccaag ttggtgcgat tgggtttttc tgttctgtag acgatctggc gaaagatggc 6780
gtgagaattg gaagagatgg tgggtctttg aaaaatgttg aaatgggcat gaggtagacc 6840
tacagagtct ctgacaaagt gggcataaga ttcttgaagc ttggttacca gttcggcggt 6900
gacaagtacg tctagggcgc agtagtcaag tgtttcttga atgatgtcat aacctggttg 6960
gtttttcttt tcccacagtt cgcggttgag aaggtattct tcgcgatcct tccagtactc 7020
ttctagcgga aacccgtctt tgtctgcacg gtaagatcct agcatgtaga actgattaac 7080
tgccttgtaa gggcagcagc ccttctctac gggtagagag tatgcttgag cagcttttcg 7140
tagcgaagcg tgagtaaggg caaaggtgtc tctgaccatg actttgagga attggtattt 7200
gaagtcgatg tcgtcacagg ctccctgttc ccagagttgg aagtctaccc gtttcttgta 7260
ggcggggttg ggcaaagcga aagtaacatc attgaagaga atcttgccgg ccctgggcat 7320
gaaattgcga gtgatgcgaa aaggctgtgg tacttccgct cggttattga taacctgggc 7380
agctaggacg atctcgtcga aaccgttgat gttgtgtcct acgatgtata attctatgaa 7440
acgcggcgtg cctctgacgt gaggtagctt actgagctca tcaaaggtta ggtctgtggg 7500
gtcagataag gcgtagtgtt cgagagccca ttcgtgcagg tgaggattcg ctttaaggaa 7560
ggaggaccag aggtccactg ccagtgctgt ttgtaactgg tcccggtact gacgaaaatg 7620
ccgtccgact gccatttttt ctggggtgac gcaatagaag gtttgggggt cctgccgcca 7680
gcgatcccac ttgagtttta tggcgaggtc ataggcgatg ttgacgagcc gctggtctcc 7740
agagagtttc atgaccagca tgaaggggat tagctgcttg ccaaaggacc ccatccaggt 7800
gtaggtttcc acatcgtagg tgagaaagag cctttctgtg cgaggatgag agccaatcgg 7860
gaagaactgg atctcctgcc accagttgga ggaatggctg ttgatgtgat ggaagtagaa 7920
ctccctgcga cgcgccgagc attcatgctt gtgcttgtac agacggccgc agtagtcgca 7980
gcgttgcacg ggttgtatct cgtgaatgag ttgtacctgg cttcccttga cgagaaattt 8040
cagtgggaag ccgaggcctg gcgattgtat ctcgtgcttt actatgttgt ctgcatcggc 8100
ctgttcatct tctgtctcga tggtggtcat gctgacgagc cctcgcggga ggcaagtcca 8160

-continued

```
gacctcggcg cggcaggggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggccccgt gagcttgaac   8640
ctgaaagaga gttcaacaga atcaatctcg gtatcgttga cggcggcttg cctaaggatt   8700
tcttgcacgt caccagagtt gtcctggtag gcgatctccg ccatgaactg ctcgatctct   8760
tcctcttgaa gatctccgcg gcccgctctc tcgacggtgg ccgcgaggtc gttggagatg   8820
cgcccaatga gttgagagaa tgcattcatg cccgcctcgt tccagacgcg gctgtagacc   8880
acggccccca cgggatctct cgcgcgcatg accacctggg cgaggttgag ctccacgtgg   8940
cgggtgaaga ccgcatagtt gcataggcgc tggaaaaggt agttgagtgt ggtggcgatg   9000
tgctcggtga cgaagaaata catgatccat cgtctcagcg gcatctcgct gacatcgccc   9060
agagcttcca agcgctccat ggcctcgtag aagtccacgg caaaattaaa aaactgggag   9120
tttcgcgcgg acacggtcaa ctcctcttcc agaagacgga taagttcggc gatggtggtg   9180
cgcacctcgc gctcgaaagc ccctgggatt tcttcctcaa tctcttcttc ttccactaac   9240
atctcttcct cttcaggtgg ggctgcagga ggagggggaa cgcggcgacg ccggcggcgc   9300
acgggcagac ggtcgatgaa tctttcaatg acctctccgc ggcggcggcg catggtttca   9360
gtgacggcgc ggccgttctc gcgcggtcgc agagtaaaaa caccgccgcg catctcctta   9420
aagtggtgac tgggaggttc tccgtttggg agggagaggg cgctgattat acattttatt   9480
aattggcccg tagggactgc acgcagagat ctgatcgtgt caagatccac gggatctgaa   9540
aacctttcga cgaaagcgtc taaccagtca cagtcacaag gtaggctgag tacggcttct   9600
tgtgggcggg ggtggttatg tgttcggtct gggtcttctg tttcttcttc atctcgggaa   9660
ggtgagacga tgctgctggt gatgaaatta aagtaggcag ttctaagacg gcggatggtg   9720
gcgaggagca ccaggtcttt gggtccggct tgctggatac gcaggcgatt ggccattccc   9780
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca aagcggtggt aagctcctgt attaatggtg  10020
taagcacagt tggccatgac tgaccagtta actgtctggt gaccagggcg cacgagctcg  10080
gtgtatttaa ggcgcgaata ggcgcgggtg tcaaagatgt aatcgttgca ggtgcgcacc  10140
agatactggt accctataag aaaatgcggc ggtggttggc ggtagagagg ccatcgttct  10200
gtagctggag cgccaggggc gaggtcttcc aacataaggc ggtgatagcc gtagatgtac  10260
ctggacatcc aggtgattcc tgcggcggta gtagaagccc gaggaaactc gcgtacgcgg  10320
ttccaaatgt tgcgtagcgg catgaagtag ttcattgtag gcacggtttg accagtgagg  10380
cgcgcgcagt cattgatgct ctatagacac ggagaaaatg aaagcgttca gcgactcgac  10440
tccgtagcct ggaggaacgt gaacgggttg ggtcgcggtg taccccggtt cgagacttgt  10500
```

actcgagccg gccggagccg cggctaacgt ggtattggca ctcccgtctc gacccagcct 10560
acaaaaatcc aggatacgga atcgagtcgt tttgctggtt tccgaatggc agggaagtga 10620
gtcctatttt tttttttgc cgctcagatg catcccgtgc tgcgacagat gcgccccaa 10680
caacagcccc cctcgcagca gcagcagcag caatcacaaa aggctgtccc tgcaactact 10740
gcaactgccg ccgtgagcgg tgcgggacag cccgcctatg atctggactt ggaagagggc 10800
gaaggactgg cacgtctagg tgcgccttca cccgagcggc atccgcgagt tcaactgaaa 10860
aaagattctc gcgaggcgta tgtgccccaa cagaacctat ttagagacag aagcggcgag 10920
gagccggagg agatgcgagc ttcccgcttt aacgcgggtc gtgagctgcg tcacggtttg 10980
gaccgaagac gagtgttgcg ggacgaggat ttcgaagttg atgaaatgac agggatcagt 11040
cctgccaggg cacacgtggc tgcagccaac cttgtatcgg cttacgagca gacagtaaag 11100
gaagagcgta acttccaaaa gtcttttaat aatcatgtgc gaaccctgat tgcccgcgaa 11160
gaagttaccc ttggtttgat gcatttgtgg gatttgatgg aagctatcat tcagaaccct 11220
actagcaaac ctctgaccgc ccagctgttt ctggtggtgc aacacagcag agacaatgag 11280
gctttcagag aggcgctgct gaacatcacc gaacccgagg ggagatggtt gtatgatctt 11340
atcaacattc tacagagtat catagtgcag gagcggagcc tgggcctggc cgagaaggtg 11400
gctgccatca attactcggt tttgagcttg ggaaaatatt acgctcgcaa aatctacaag 11460
actccatacg ttcccataga caaggaggtg aagatagatg ggttctacat gcgcatgacg 11520
ctcaaggtct tgaccctgag cgatgatctt ggggtgtatc gcaatgacag aatgcatcgc 11580
gcggttagcg ccagcaggag gcgcgagtta agcgacaggg aactgatgca cagtttgcaa 11640
agagctctga ctggagctgg aaccgagggt gagaattact tcgacatggg agctgacttg 11700
cagtggcagc ctagtcgcag ggctctgagc gccgcgacgg caggatgtga gcttccttac 11760
atagaagagg cggatgaagg cgaggaggaa gagggcgagt acttggaaga ctgatggcac 11820
aacccgtgtt ttttgctaga tggaacagca agcaccggat cccgcaatgc gggcggcgct 11880
gcagagccag ccgtccggca ttaactcctc ggacgattgg acccaggcca tgcaacgtat 11940
catggcgttg acgactcgca accccgaagc ctttagacag caaccccagg ccaaccgtct 12000
atcggccatc atggaagctg tagtgccttc ccgctctaat cccactcatg agaaggtcct 12060
ggccatcgtg aacgcgttgg tggagaacaa agctattcgt ccagatgagg ccggactggt 12120
atacaacgct ctcttagaac gcgtggctcg ctacaacagt agcaatgtgc aaaccaattt 12180
ggaccgtatg ataacagatg tacgcgaagc cgtgtctcag cgcgaaaggt tccagcgtga 12240
tgccaacctg ggttcgctgg tggcgttaaa tgctttcttg agtactcagc ctgctaatgt 12300
gccgcgtggt caacaggatt atactaactt tttaagtgct ttgagactga tggtatcaga 12360
agtacctcag agcgaagtgt atcagtccgg tcctgattac ttctttcaga ctagcagaca 12420
gggcttgcag acggtaaatc tgagccaagc ttttaaaaac cttaaaggtt tgtggggagt 12480
gcatgccccg gtaggagaaa gagcaaccgt gtctagcttg ttaactccga actcccgcct 12540
attattactg ttggtagctc ctttcaccga cagcggtagc atcgaccgta attcctattt 12600
gggttaccta ctaaacctgt atcgcgaagc catagggcaa agtcaggtgg acgagcagac 12660
ctatcaagaa attacccaag tcagtcgcgc tttgggacag gaagacactg gcagtttgga 12720
agccactctg aacttcttgc ttaccaatcg gtctcaaaag atccctcctc aatatgctct 12780
tactgcggag gaggagagga tccttagata tgtgcagcag agcgtgggat tgtttctgat 12840
gcaagagggg gcaactccga ctgcagcact ggacatgaca gcgcgaaata tggagcccag 12900

-continued

```
catgtatgcc agtaaccgac ctttcattaa caaactgctg gactacttgc acagagctgc  12960
cgctatgaac tctgattatt tcaccaatgc catcttaaac ccgcactggc tgccccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
```

```
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg gggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtcccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg ggggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaattttg gctcaaccat aaaaacatac gggaacaaag cttggaacag  17580
cagtacagga caggcgctta gaaataaact taaagaccag aacttccaac aaaaagtagt  17640
```

```
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
```

```
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
```

-continued

```
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg cccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
```

```
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
```

attacccgga cgagttcata ccgaacttcg acgcgattag cgagtcagtg gacggctacg 27180
attgatgtct ggtgacgcgg ctgagctatc tcggctgcga catctagacc actgccgccg 27240
ctttcgctgc tttgcccggg aactcattga gttcatctac ttcgaactcc ccaaggatca 27300
ccctcaaggt ccggcccacg gagtgcggat ttctatcgaa ggcaaaatag actctcgcct 27360
gcaacgaatt ttctcccagc ggcccgtgct gatcgagcga gaccagggaa acaccacggt 27420
ttccatctac tgcatttgta atcaccccgg attgcatgaa agcctttgct gtcttatgtg 27480
tactgagttt aataaaaact gaattaagac tctcctacgg actgccgctt cttcaacccg 27540
gattttacaa ccagaagaac gaaacttttc ctgtcgtcca ggactctgtt aacttcacct 27600
ttcctactca caaactagaa gctcaacgac tacaccgctt ttccagaagc attttcccta 27660
ctaatactac tttcaaaacc ggaggtgagc tccaaggtct tcctacagaa aacccttggg 27720
tggaagcggg ccttgtagtg ctaggaattc ttgcgggtgg gcttgtgatt attctttgct 27780
acctatacac accttgcttc actttcttag tggtgttgtg gtattggttt aaaaaatggg 27840
gcccatacta gtcttgcttg ttttactttc gcttttggaa ccgggttctg ccaattacga 27900
tccatgtcta gacttcgacc cagaaaactg cacacttact tttgcacccg acacaagccg 27960
catctgtgga gttcatcgcc tctcttacga acttggcccc caacgacaaa aatttacctg 28020
catggtggga atcaacccca tagttatcac ccagcaaagt ggagatacta agggttgcat 28080
tcactgctcc tgcgattcca tcgagtgcac ctacaccctg ctgaagaccc tatgcggcct 28140
aagagacctg ctaccaatga attaaaaaat gattaataaa aaatcactta cttgaaatca 28200
gcaataaggt ctctgttgaa attttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta cccctatgaa gatgaaagca cctcccaaca 28440
ccccttata aacccagggt ttatttcccc aaatggcttc acacaaagcc caaacggagt 28500
tcttacttta aaatgtttaa ccccactaac aaccacaggc ggatctctac agctaaaagt 28560
gggagggga cttacagtgg atgacaccaa cggttttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920
aactacacac agaaatataa attttactgc agagctgttt ttcgattcta ctggtaattt 28980
actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct ttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttgcga tcgctaccct gcaggaactt gtttatttga aaatcaattc 29400
acaaaatccg agtagttatt ttgcctcccc cttcccattt aacagaatac accaatctct 29460

-continued

```
ccccacgcac agctttaaac atttggatac cattagatat agacatggtt ttagattcca  29520
cattccaaac agtttcagag cgagccaatc tggggtcagt gatagataaa aatccatcgg  29580
gatagtcttt taaagcgctt tcacagtcca actgctgcgg atgcgactcc ggagtctgga  29640
tcacggtcat ctggaagaag aacgatggga atcataatcc gaaaacggta tcggacgatt  29700
gtgtctcatc aaacccacaa gcagccgctg tctgcgtcgc tccgtgcgac tgctgtttat  29760
gggatcaggg tccacagtgt cctgaagcat gattttaata gcccttaaca tcaactttct  29820
ggtgcgatgc gcgcagcaac gcattctgat ttcactcaaa tctttgcagt aggtacaaca  29880
cattattaca atattgttta ataaaccata attaaaagcg ctccagccaa aactcatatc  29940
tgatataatc gcccctgcat gaccatcata ccaaagttta atataaatta aatgacgttc  30000
cctcaaaaac acactaccca catacatgat ctcttttggc atgtgcatat taacaatctg  30060
tctgtaccat ggacaacgtt ggttaatcat gcaacccaat ataaccttcc ggaaccacac  30120
tgccaacacc gctcccccag ccatgcattg aagtgaaccc tgctgattac aatgacaatg  30180
aagaacccaa ttctctcgac cgtgaatcac ttgagaatga aaaatatcta tagtggcaca  30240
acatagacat aaatgcatgc atcttctcat aatttttaac tcctcaggat ttagaaacat  30300
atcccaggga ataggaagct cttgcagaac agtaaagctg gcagaacaag gaagaccacg  30360
aacacaactt acactatgca tagtcatagt atcacaatct ggcaacagcg ggtggtcttc  30420
agtcatagaa gctcgggttt cattttcctc acaacgtggt aactgggctc tggtgtaagg  30480
gtgatgtctg gcgcatgatg tcgagcgtgc gcgcaacctt gtcataatgg agttgcttcc  30540
tgacattctc gtattttgta tagcaaaacg cggccctggc agaacacact cttcttcgcc  30600
ttctatcctg ccgcttagcg tgttccgtgt gatagttcaa gtacaaccac actcttaagt  30660
tggtcaaaag aatgctggct tcagttgtaa tcaaaactcc atcgcatcta atcgttctga  30720
ggaaatcatc caagcaatgc aactggattg tgtttcaagc aggagaggag agggaagaga  30780
cggaagaacc atgttaattt ttattccaaa cgatctcgca gtacttcaaa ttgtagatcg  30840
cgcagatggc atctctcgcc cccactgtgt tggtgaaaaa gcacagctag atcaaaagaa  30900
atgcgatttt caaggtgctc aacggtggct tccagcaaag cctccacgcg cacatccaag  30960
aacaaaagaa taccaaaaga aggagcattt tctaactcct caatcatcat attacattcc  31020
tgcaccattc ccagataatt ttcagctttc cagccttgaa ttattcgtgt cagttcttgt  31080
ggtaaatcca atccacacat tacaaacagg tcccggaggg cgccctccac caccattctt  31140
aaacacaccc tcataatgac aaaatatctt gctcctgtgt cacctgtagc gaattgagaa  31200
tggcaacatc aattgacatg cccttggctc taagttcttc tttaagttct agttgtaaaa  31260
actctctcat attatcacca aactgcttag ccagaagccc cccgggaaca agagcagggg  31320
acgctacagt gcagtacaag cgcagacctc cccaattggc tccagcaaaa acaagattgg  31380
aataagcata ttgggaaccg ccagtaatat catcgaagtt gctggaaata taatcaggca  31440
gagtttcttg taaaaattga ataaaagaaa aatttgccaa aaaaacattc aaaacctctg  31500
ggatgcaaat gcaataggtt accgcgctgc gctccaacat tgttagtttt gaattagtct  31560
gcaaaaataa aaaaaaaaac aagcgtcata tcatagtagc ctgacgaaca gatggataaa  31620
tcagtctttc catcacaaga caagccacag ggtctccagc tcgaccctcg taaaacctgt  31680
catcatgatt aaacaacagc accgaaagtt cctcgcggtg accagcatga ataattcttg  31740
atgaagcata caatccagac atgttagcat cagttaacga gaaaaaacag ccaacatagc  31800
ctttgggtat aattatgctt aatcgtaagt atagcaaagc cacccctcgc ggatacaaag  31860
```

-continued

```
taaaaggcac aggagaataa aaaatataat tatttctctg ctgctgttca ggcaacgtcg  31920

cccccggtcc ctctaaatac acatacaaag cctcatcagc catggcttac cagacaaagt  31980

acagcgggca cacaaagcac aagctctaaa gtgactctcc aacctctcca caatatatat  32040

atacacaagc cctaaactga cgtaatggga gtaaagtgta aaaaatcccg ccaaacccaa  32100

cacacacccc gaaactgcgt caccagggaa aagtacagtt tcacttccgc aatcccaaca  32160

ggcgtaactt cctctttctc acggtacgtg atatcccact aacttgcaac gtcattttcc  32220

cacggtcgca ccgcccettt tagccgttaa ccccacagcc aatcaccaca cgatccacac  32280

tttttaaaat cacctcattt acatattggc accattccat ctataaggta tattatatag  32340

ataga                                                              32345
```

GROUP B ADENOVIRUS ENCODING AN ANTI-TCR-COMPLEX ANTIBODY OR FRAGMENT

The present disclosure relates to an oncolytic virus derived from EnAd or Ad11 comprising a transgene encoding at least an agonistic antibody or binding fragment thereof specific to CD3 in the T-cell receptor complex (TCR), in particular for expression on the surface of a cancer cell, compositions comprising the same and use of said virus and composition for the treatment of cancer.

The present application is a 35 U.S.C. § 371 national phase application from, and claims priority to, International Application No. PCT/EP2016/081817, filed Dec. 19, 2016, and published under PCT Article 21(2) in English, which designated the U.S., and claims the benefit of priority from United Kingdom Patent Application Nos. GB1522334.0 filed on Dec. 17, 2015, GB1607463.5 filed on Apr. 29, 2016, GB1617207.4 filed on Oct. 10, 2016 and GB1617206.6 filed on Oct. 10, 2016, each of which are incorporated by reference herein into this application in their entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Oct. 12, 2018, is named 370908-3017US1_NewSequenceListing.txt and is 600,340 bytes in size.

BACKGROUND

Cancer is still a huge social burden to society in terms of the hardship and suffering of patients and their loved ones, and also in terms of the high financial cost of treating, caring for and supporting patients. It is now thought that the immune systems of healthy individuals clear cancerous cells routinely. However, in those patients with cancer one or more of the defense mechanisms involved in this clearance is/are down regulated or turned off completely.

It is now known that tumors change their microenvironment to make it more permissive to their growth. This occurs by the tumor releasing extracellular signals that, for example, promote tumor angiogenesis and/or induce local immune suppression or immune tolerance.

The T-cell receptor complex (TCR) on T-cells recognizes a particular antigen specifically when the antigen is in the form of peptide presented on a major histocompatibility (MHC) molecule on a cell surface. The T-cell receptor complex (TCR) comprises an antigen-binding heterodimer of alpha and beta or gamma and delta chains, together with the immunoglobulin family proteins CD3 epsilon, delta, gamma and zeta chains. The surface CD3 epsilon, delta and gamma chains play important roles in assembly of the TCR complex and stable surface expression. The zeta chain homodimer is almost completely intracellular and functions as the key signaling molecule of the complex when the TCR complex is cross-linked physiologically by antigen-MHC complexes on cell surfaces or by pharmacological modalities, for example antibodies to the TCR complex such as an anti-CD3 antibody (including a binding fragment thereof).

It is clear from many different preclinical and clinical studies that the microenvironment within tumours can suppress the development and activity of anti-tumour immune responses, with a wide variety of mechanisms being shown to potentially play a role. In particular immunosuppressive mechanisms ultimately prevent T-cell responses from mediating the killing of tumour cells. Suppressive mechanisms may include the exclusion of T-cells from entering tumour tissues, inhibiting activation or activity of T-cells that do enter the tumour and the modulation of tumour cell proteins which reduces the ability of T-cells to recognize or respond to them. The importance of such immunosuppressive pathways in supporting tumour progression has been particularly highlighted by the clinical efficacy shown by antibodies to receptors in two such suppressive pathways, CTLA4 and PD-1/PDL1, which has led to their marketing approval for the treatment of melanoma and other cancers.

Whilst adoptive transfer of T cells stimulated in vitro has been proposed to provide activated cytolytic T cells, for example for the treatment of cancers such as a nasopharyngeal cancer, this can be a difficult, expensive and inconvenient therapy. Furthermore, sometimes these therapies are only effective in specific patient sub-groups.

Some clinical trials have been performed with cancer antigens, for example MAGE, in the form a vaccine containing a cancer antigen and adjuvant, such as monophosphoryl A and CpG. However, these approaches have failed to deliver the high clinical successes that were anticipated. Thus true in vivo stimulation or activation of T cells focused on cancer cells for the treatment of cancer is not a practical reality and the present time.

The present inventors have generated data showing that cancer cells that are made to express at least an agonistic anti-TCR antibody or binding fragment on their surface are dealt with more effectively by the immune system than unmodified cancer cells which don't express the protein on their surface.

Whilst not wishing to be bound by theory the present inventors believe that making the cancer cell express at least an agonistic anti-TCR antibody is a way of focusing or kickstarting a patient's immune system to fight the cancer, for example the anti-TCR antibody or binding fragment thereof may engage and/or activate T cells. Such activation of T-cells that physiologically would recognize cancer-specific antigens, including patient-specific neoantigens, can also lead to generation of effector and memory T-cell progeny that can migrate to regions of the same tumour or other tumour sites (e.g. metastases) not expressing an agonistic anti-TCR antibody or fragment thereof. Thus this therapy has the potential to generate an extended immune response in the form of activated T cells to cancer cells expressing their physiological cancer-specific antigen to fight the cancer systemically in the patient.

Clearly a cancer treatment that engages the body's own immune responses to fight the cancer would be extremely advantageous. Furthermore, the therapy is very focused on cancer cells and thus the off-targets effects and toxicities are likely to be much less than traditional therapies, such as chemotherapy.

The cancer cell can be made to express an anti-TCR antibody or binding fragment thereof by infecting the cancer cell with a replication competent oncolytic virus or a replication deficient oncolytic viral vector encoding an anti-TCR antibody or a binding fragment thereof.

SUMMARY OF THE INVENTION

The present disclosure provides:

1. A replication deficient oncolytic viral vector or replication capable group B oncolytic adenovirus selected from the group consisting of Ad11 and enadenotucirev, wherein the virus encodes an antibody or a binding fragment thereof for expression on the surface of a cancer cell, wherein said antibody or binding fragment is specific to a CD3 protein of a T-cell receptor complex (TCR), wherein the virus does not encode a B7 protein or an active fragment thereof.

2. A replication deficient oncolytic viral vector or replication capable group B oncolytic adenovirus according to paragraph 1 wherein the virus is Ad11.
3. A replication deficient oncolytic viral vector or replication capable oncolytic virus according to paragraph 1 or paragraph 2, wherein the virus is replication competent.
4. A replication deficient oncolytic viral vector or replication capable oncolytic virus according to paragraph 1 or paragraph 2, wherein the virus is replication deficient.
5. A replication deficient oncolytic viral vector or replication competent oncolytic virus according to any one of paragraphs 1 to 4 wherein the encoded antibody further comprises a transmembrane domain or a GPI anchor.
6. A replication deficient oncolytic viral vector or replication competent oncolytic virus according to paragraph 5, wherein the transmembrane domain is selected from a sequence shown in SEQ ID NO: 10 to 14.
7. A replication deficient oncolytic viral vector or replication competent oncolytic virus according to any one of claims 1 to 6, wherein the oncolytic adenovirus is EnAd.
8. A replication deficient oncolytic viral vector or replication competent oncolytic virus according to any one of paragraph 1 to 7, wherein the antibody or binding fragment is selected from the group comprising a full length antibody, a Fab, modified Fab, Fab', modified Fab', F(ab')2, Fv, single domain antibodies, scFv, bi, tri or tetra-valent antibodies, Bis-scFv, diabodies, triabodies, tetrabodies, humabodies, disulfide stabilised forms of any one of the same and epitope-binding fragments thereof.
9. A replication deficient oncolytic viral vector or replication competent oncolytic virus according to paragraph 1 to 8, wherein the antibody binding fragment is a single chain Fv.
10. A replication deficient oncolytic viral vector or replication competent oncolytic virus according to any one of paragraph 1 to 9, wherein the oncolytic virus encodes at least one further transgene.
11. A replication deficient oncolytic viral vector or replication competent oncolytic virus according to paragraph 10, wherein the oncolytic virus encodes at least two further transgenes.
12. A replication deficient oncolytic viral vector or replication competent oncolytic virus according to paragraph 10 or 11, wherein the further transgene(s) encode(s) a protein independently selected from the group comprising a cytokine, a chemokine, an antagonistic antibody molecule or binding fragment thereof, an agonistic antibody molecule or binding fragment thereof, an immunomodulator and combinations thereof.
13. A replication deficient oncolytic viral vector or replication competent oncolytic virus according to paragraph 12, wherein at least one further transgene encodes an antibody molecule or a binding fragment thereof (for example which may be in a surface expressed form and/or secreted form).
14. A replication deficient oncolytic viral vector or replication competent oncolytic virus according to paragraph 13, wherein the antibody molecule or binding fragment is an inhibitor.
15. A replication deficient oncolytic viral vector or a replication competent oncolytic virus according to paragraph 14, wherein the inhibitor is an inhibitor of an angiogenesis factor or an inhibitor of a T cell deactivating factor.
16. A replication deficient oncolytic viral vector or a replication competent oncolytic virus according to any one of paragraphs 13 to 15, wherein antibody molecule or binding fragment is an agonist.
17. A replication deficient oncolytic viral vector or a replication competent oncolytic virus according to paragraph 16, wherein the agonist is independently selected from the group comprising antibodies to CD40, CD40 ligand (also known as CD154), GITR, OX40, CD27, 4-1BB and a combination thereof, such as CD40, GITR, OX40, CD27 and 4-1BB.
18. A replication deficient oncolytic viral vector or a replication competent oncolytic virus according to paragraph 17, wherein the antibody molecule or binding fragment thereof comprises a binding domain specific to CD40L.
19. A replication deficient oncolytic viral vector or a replication competent oncolytic virus according to paragraph 17 or 18, wherein the antibody molecule or binding fragment thereof comprises a binding domain specific to CD40.
20. A replication deficient oncolytic viral vector or a replication competent oncolytic virus according to any one of paragraphs 17 to 19 wherein the antibody molecule or binding fragment thereof comprises a binding domain specific to GITR.
21. A replication deficient oncolytic viral vector or a replication competent oncolytic virus according to any one of paragraphs 17 to 20, wherein the antibody molecule or binding fragment thereof comprises a binding domain specific to OX40.
22. A replication deficient oncolytic viral vector or a replication competent oncolytic virus according to any one of paragraphs 17 to 21, wherein the antibody molecule or binding fragment thereof comprises a binding domain specific to CD27.
23. A replication deficient oncolytic viral vector or a replication competent oncolytic virus according to any one of paragraphs 17 to 22 wherein the antibody molecule or binding fragment thereof comprises a binding domain specific to 4-1BB.
24. A replication deficient oncolytic viral vector or a replication competent oncolytic virus according to any one of paragraphs 12 to 23, where the immunomodulator is a membrane-associated protein ligand for immune cell surface receptors independently selected from the group comprising CTLA-4, PD-1, PD-L1, PD-L2, VISTA, B7-H3, B7-H4, HVEM, ILT-2, ILT-3, ILT-4, TIM-3, LAG-3, BTLA, LIGHT or CD160, for example CTLA-4, PD-1, PD-L1, PD-L2, CD16, CD25, CD33, CD332, CD127, CD31, CD43, CD44, CD162, CD301a, CD301b and Galectin-3, FLT-3, FLT-3 ligand, TLRs, TLR ligands, CCR7, CD1a, CD1c, CD11b, CD11c, CD80, CD83, CD86, CD123, CD172a, CD205, CD207, CD209, CD273, CD281, CD283, CD286, CD289, CD287, CXCR4, GITR Ligand, IFN-α2, IL-12, IL-23, ILT1, ILT2, ILT3, ILT4, ILT5, ILT7, TSLP Receptor, CD141, CD303, CADM1, CLEC9a, XCR1 and CD304, OX40, OX40 ligand, CD27, CD28, CD30, CD40, CD40 ligand, CD70, CD137, GITR, 4-1BB, ICOS, ICOS ligand and combinations thereof.
25. A replication deficient oncolytic viral vector or a replication competent oncolytic virus according to paragraph 24, wherein membrane-associated protein ligand for an immune cell surface receptor is or binds to CTLA-4.

26. A replication deficient oncolytic viral vector or a replication competent oncolytic virus according to paragraph 24 or 25, wherein the membrane-associated protein ligand for an immune cell surface receptor is or binds to PD-1.
27. A replication deficient oncolytic viral vector or a replication competent oncolytic virus according to any one of paragraphs 24 to 26, wherein the membrane-associated protein ligand for an immune cell surface receptor is or binds to PD-L1.
28. A replication deficient oncolytic viral vector or a replication competent oncolytic virus according to any one of paragraphs 24 to 27, wherein the membrane-associated protein ligand for an immune cell surface receptor is or binds to PD-L2.
29. A replication deficient oncolytic viral vector or a replication competent oncolytic virus according to any one of paragraphs 24 to 28, wherein the membrane-associated protein ligand for an immune cell surface receptor is or binds to VISTA.
30. A replication deficient oncolytic viral vector or a replication competent oncolytic virus according to any one of paragraphs 24 to 29, wherein the membrane-associated protein ligand for an immune cell surface receptor is or binds to B7-H3.
31. A replication deficient oncolytic viral vector or a replication competent oncolytic virus according to any one of paragraphs 24 to 30, wherein the membrane-associated protein ligand for an immune cell surface receptor is or binds to B7-H4.
32. A replication deficient oncolytic viral vector or a replication competent oncolytic virus according to any one of paragraphs 24 to 31, wherein the membrane-associated protein ligand for an immune cell surface receptor is or binds to HVEM.
33. A replication deficient oncolytic viral vector or a replication competent oncolytic virus according to any one of paragraphs 24 to 32, wherein the membrane-associated protein ligand for an immune cell surface receptor is or binds to ILT-2.
34. A replication deficient oncolytic viral vector or a replication competent oncolytic virus according to any one of paragraphs 24 to 33, wherein the membrane-associated protein ligand for an immune cell surface receptor is or binds to ILT-3.
35. A replication deficient oncolytic viral vector or a replication competent oncolytic virus according to any one of paragraphs 24 to 34, wherein the membrane-associated protein ligand for an immune cell surface receptor is or binds to ILT-4.
36. A replication deficient oncolytic viral vector or a replication competent oncolytic virus according to any one of paragraphs 24 to 35, wherein the membrane-associated protein ligand for an immune cell surface receptor is or binds to TIM-3.
37. A replication deficient oncolytic viral vector or a replication competent oncolytic virus according to any one of paragraphs 24 to 36, wherein the membrane-associated protein ligand for an immune cell surface receptor is or binds to LAG-3.
38. A replication deficient oncolytic viral vector or a replication competent oncolytic virus according to any one of paragraphs 24 to 37, wherein the membrane-associated protein ligand for an immune cell surface receptor is or binds to BTLA.
39. A replication deficient oncolytic viral vector or a replication competent oncolytic virus according to any one of paragraphs 24 to 38, wherein the membrane-associated protein ligand for an immune cell surface receptor is or binds to LIGHT.
40. A replication deficient oncolytic viral vector or a replication competent oncolytic virus according to any one of paragraphs 24 to 39, wherein the membrane-associated protein ligand for an immune cell surface receptor is or binds to CD160.
41. A replication deficient oncolytic viral vector or a replication competent oncolytic virus according to any one of paragraphs 24 to 40, wherein the membrane-associated protein ligand for an immune cell surface receptor is or binds to CD16.
42. A replication deficient oncolytic viral vector or a replication competent oncolytic virus according to any one of paragraphs 24 to 41, wherein the membrane-associated protein ligand for an immune cell surface receptor is or binds to CD25.
43. A replication deficient oncolytic viral vector or a replication competent oncolytic virus according to any one of paragraphs 24 to 42, wherein the membrane-associated protein ligand for an immune cell surface receptor is or binds to CD33.
44. A replication deficient oncolytic viral vector or a replication competent oncolytic virus according to any one of paragraphs 24 to 43, wherein the membrane-associated protein ligand for an immune cell surface receptor is or binds to CD332.
45. A replication deficient oncolytic viral vector or a replication competent oncolytic virus according to any one of paragraphs 24 to 44, wherein the membrane-associated protein ligand for an immune cell surface receptor is or binds to CD127.
46. A replication deficient oncolytic viral vector or a replication competent oncolytic virus according to any one of paragraphs 24 to 45, wherein the membrane-associated protein ligand for an immune cell surface receptor is or binds to CD31.
47. A replication deficient oncolytic viral vector or a replication competent oncolytic virus according to any one of paragraphs 24 to 46, wherein the membrane-associated protein ligand for an immune cell surface receptor is or binds to CD43.
48. A replication deficient oncolytic viral vector or a replication competent oncolytic virus according to any one of paragraphs 24 to 47, wherein the membrane-associated protein ligand for an immune cell surface receptor is or binds to CD44.
49. A replication deficient oncolytic viral vector or a replication competent oncolytic virus according to any one of paragraphs 24 to 48, wherein the membrane-associated protein ligand for an immune cell surface receptors is or binds to CD162.
50. A replication deficient oncolytic viral vector or a replication competent oncolytic virus according to any one of paragraphs 24 to 49, wherein the membrane-associated protein ligand for an immune cell surface receptor is or binds to CD301a.
51. A replication deficient oncolytic viral vector or a replication competent oncolytic virus according to any one of paragraphs 24 to 50, wherein the membrane-associated protein ligand for an immune cell surface receptor is or binds to CD301b.
52. A replication deficient oncolytic viral vector or a replication competent oncolytic virus according to any one of paragraphs 24 to 51, wherein the membrane-associated protein ligand for an immune cell surface receptor is or binds to Galectin-3.

53. A replication deficient oncolytic viral vector or a replication competent oncolytic virus according to any one of paragraphs 24 to 52, wherein the membrane-associated protein ligand for an immune cell surface receptor is or binds to FLT-3.

54. A replication deficient oncolytic viral vector or a replication competent oncolytic virus according to any one of paragraphs 24 to 53, wherein the membrane-associated protein ligand for an immune cell surface receptor is FLT-3 ligand.

55. A replication deficient oncolytic viral vector or a replication competent oncolytic virus according to any one of paragraphs 24 to 54, wherein the membrane-associated protein ligand for an immune cell surface receptor is a TLR.

56. A replication deficient oncolytic viral vector or a replication competent oncolytic virus according to any one of paragraphs 24 to 55, wherein the membrane-associated protein ligand for an immune cell surface receptor is a TLR-ligand.

57. A replication deficient oncolytic viral vector or a replication competent oncolytic virus according to any one of paragraphs 24 to 56, wherein the membrane-associated protein ligand for an immune cell surface receptor is or binds to CCR7.

58. A replication deficient oncolytic viral vector or a replication competent oncolytic virus according to any one of paragraphs 24 to 57, wherein the membrane-associated protein ligand for an immune cell surface receptor is or binds to CD1a.

59. A replication deficient oncolytic viral vector or a replication competent oncolytic virus according to any one of paragraphs 24 to 58, wherein the membrane-associated protein ligand for an immune cell surface receptor is or binds to CD1c.

60. A replication deficient oncolytic viral vector or a replication competent oncolytic virus according to any one of paragraphs 24 to 59, wherein the membrane-associated protein ligand for an immune cell surface receptor is or binds to CD11b.

61. A replication deficient oncolytic viral vector or a replication competent oncolytic virus according to any one of paragraphs 24 to 60, wherein the membrane-associated protein ligand for an immune cell surface receptor is or binds to CD11c.

62. A replication deficient oncolytic viral vector or a replication competent oncolytic virus according to any one of paragraphs 24 to 61, wherein the membrane-associated protein ligand for an immune cell surface receptor is CD80.

63. A replication deficient oncolytic viral vector or a replication competent oncolytic virus according to any one of paragraphs 24 to 62, wherein the membrane-associated protein ligand for an immune cell surface receptor is or binds to CD83.

64. A replication deficient oncolytic viral vector or a replication competent oncolytic virus according to any one of paragraphs 24 to 63, wherein the membrane-associated protein ligand for an immune cell surface receptor is CD86.

65. A replication deficient oncolytic viral vector or a replication competent oncolytic virus according to any one of paragraphs 24 to 64, wherein the membrane-associated protein ligand for an immune cell surface receptor is or binds to CD123.

66. A replication deficient oncolytic viral vector or a replication competent oncolytic virus according to any one of paragraphs 24 to 65, wherein the membrane-associated protein ligand for an immune cell surface receptor is or binds to CD172a.

67. A replication deficient oncolytic viral vector or a replication competent oncolytic virus according to any one of paragraphs 24 to 66, wherein the membrane-associated protein ligand for an immune cell surface receptor is or binds to CD205.

68. A replication deficient oncolytic viral vector or a replication competent oncolytic virus according to any one of paragraphs 24 to 67, wherein the membrane-associated protein ligand for an immune cell surface receptor is or binds to CD207.

69. A replication deficient oncolytic viral vector or a replication competent oncolytic virus according to any one of paragraphs 24 to 68, wherein the membrane-associated protein ligand for an immune cell surface receptor is or binds to CD209.

70. A replication deficient oncolytic viral vector or a replication competent oncolytic virus according to any one of paragraphs 24 to 69, wherein the membrane-associated protein ligand for an immune cell surface receptor is or binds to CD273.

71. A replication deficient oncolytic viral vector or a replication competent oncolytic virus according to any one of paragraphs 24 to 70, wherein the membrane-associated protein ligand for an immune cell surface receptor is or binds to CD281.

72. A replication deficient oncolytic viral vector or a replication competent oncolytic virus according to any one of paragraphs 24 to 71, wherein the membrane-associated protein ligand for an immune cell surface receptor is or binds to CD283.

73. A replication deficient oncolytic viral vector or a replication competent oncolytic virus according to any one of paragraphs 24 to 72, wherein the membrane-associated protein ligand for an immune cell surface receptor is or binds to CD286.

74. A replication deficient oncolytic viral vector or a replication competent oncolytic virus according to any one of paragraphs 24 to 73, wherein the membrane-associated protein ligand for an immune cell surface receptor is or binds to CD289.

75. A replication deficient oncolytic viral vector or a replication competent oncolytic virus according to any one of paragraphs 24 to 74, wherein the membrane-associated protein ligand for an immune cell surface receptor is or binds to CD287.

76. A replication deficient oncolytic viral vector or a replication competent oncolytic virus according to any one of paragraphs 24 to 75, wherein the membrane-associated protein ligand for an immune cell surface receptor is or binds to CXCR4.

77. A replication deficient oncolytic viral vector or a replication competent oncolytic virus according to any one of paragraphs 24 to 76, wherein the membrane-associated protein ligand for an immune cell surface receptor is or binds to GITR ligand.

78. A replication deficient oncolytic viral vector or a replication competent oncolytic virus according to any one of paragraphs 24 to 77, wherein the membrane-associated protein ligand for an immune cell surface receptor binds to IFN-α2.

79. A replication deficient oncolytic viral vector or a replication competent oncolytic virus according to any one of paragraphs 24 to 78, wherein the membrane-associated protein ligand for an immune cell surface receptor is IL-12.

80. A replication deficient oncolytic viral vector or a replication competent oncolytic virus according to any one of paragraphs 24 to 79, wherein the membrane-associated protein ligand for an immune cell surface receptor is IL-23.

81. A replication deficient oncolytic viral vector or a replication competent oncolytic virus according to any one of paragraphs 24 to 80, wherein the membrane-associated protein ligand for an immune cell surface receptor binds to ILT1.

82. A replication deficient oncolytic viral vector or a replication competent oncolytic virus according to any one of paragraphs 24 to 81, wherein the membrane-associated protein ligand for an immune cell surface receptor binds to ILT5.

83. A replication deficient oncolytic viral vector or a replication competent oncolytic virus according to any one of paragraphs 24 to 82, wherein the membrane-associated protein ligand for an immune cell surface receptor binds to ILT7.

84. A replication deficient oncolytic viral vector or a replication competent oncolytic virus according to any one of paragraphs 24 to 83, wherein the membrane-associated protein ligand for an immune cell surface receptor binds to TSLP Receptor.

85. A replication deficient oncolytic viral vector or a replication competent oncolytic virus according to any one of paragraphs 24 to 84, wherein the membrane-associated protein ligand for an immune cell surface receptor is or binds to CD141.

86. A replication deficient oncolytic viral vector or a replication competent oncolytic virus according to any one of paragraphs 24 to 85, wherein the membrane-associated protein ligand for an immune cell surface receptor is or binds to CD303.

87. A replication deficient oncolytic viral vector or a replication competent oncolytic virus according to any one of paragraphs 24 to 86, wherein the membrane-associated protein ligand for an immune cell surface receptor is or binds to CADM1.

88. A replication deficient oncolytic viral vector or a replication competent oncolytic virus according to any one of paragraphs 24 to 87, wherein the membrane-associated protein ligand for an immune cell surface receptor is or binds to CLEC9a.

89. A replication deficient oncolytic viral vector or a replication competent oncolytic virus according to any one of paragraphs 24 to 88, wherein the membrane-associated protein ligand for an immune cell surface receptor is or binds to XCR1.

90. A replication deficient oncolytic viral vector or a replication competent oncolytic virus according to any one of paragraphs 24 to 89, wherein the membrane-associated protein ligand for an immune cell surface receptor is or binds to CD304.

91. A replication deficient oncolytic viral vector or a replication competent oncolytic virus according to any one of paragraphs 24 to 90, wherein the membrane-associated protein ligand for an immune cell surface receptor is or binds to OX40.

92. A replication deficient oncolytic viral vector or a replication competent oncolytic virus according to any one of paragraphs 24 to 91, wherein the membrane-associated protein ligand for an immune cell surface receptor is or binds to OX40 ligand.

93. A replication deficient oncolytic viral vector or a replication competent oncolytic virus according to any one of paragraphs 24 to 92, wherein the membrane-associated protein ligand for an immune cell surface receptor is or binds to CD27.

94. A replication deficient oncolytic viral vector or a replication competent oncolytic virus according to any one of paragraphs 24 to 93, wherein the membrane-associated protein ligand for an immune cell surface receptor is or binds to CD28.

95. A replication deficient oncolytic viral vector or a replication competent oncolytic virus according to any one of paragraphs 24 to 94, wherein the membrane-associated protein ligand for an immune cell surface receptor is or binds to CD30.

96. A replication deficient oncolytic viral vector or a replication competent oncolytic virus according to any one of paragraphs 24 to 95, wherein the membrane-associated protein ligand for an immune cell surface receptor is or binds to CD40.

97. A replication deficient oncolytic viral vector or a replication competent oncolytic virus according to any one of paragraphs 24 to 96, wherein the membrane-associated protein ligand for an immune cell surface receptor is or binds to CD40 ligand.

98. A replication deficient oncolytic viral vector or a replication competent oncolytic virus according to any one of paragraphs 24 to 97, wherein the membrane-associated protein ligand for an immune cell surface receptor is or binds to CD70.

99. A replication deficient oncolytic viral vector or a replication competent oncolytic virus according to any one of paragraphs 24 to 98, wherein the membrane-associated protein ligand for an immune cell surface receptor is or binds to CD137.

100. A replication deficient oncolytic viral vector or a replication competent oncolytic virus according to any one of paragraphs 24 to 99, wherein the membrane-associated protein ligand for an immune cell surface receptor is or binds to GITR.

101. A replication deficient oncolytic viral vector or a replication competent oncolytic virus according to any one of paragraphs 24 to 100, wherein the membrane-associated protein ligand for an immune cell surface receptor is or binds to 4-1BB.

102. A replication deficient oncolytic viral vector or a replication competent oncolytic virus according to any one of paragraphs 24 to 101, wherein the membrane-associated protein ligand for an immune cell surface receptor is or binds to ICOS.

103. A replication deficient oncolytic viral vector or a replication competent oncolytic virus according to any one of paragraphs 24 to 102, wherein the membrane-associated protein ligand for an immune cell surface receptors is or binds to ICOS ligand.

104. A replication deficient oncolytic viral vector or replication competent oncolytic virus according to any one of claims 10 to 103, wherein at least one further transgene encodes a cytokine (including secreted or cell membrane associated molecules).

105. A replication deficient oncolytic viral vector or replication competent oncolytic virus according to any one of claims 11 to 104, wherein a second further transgene encodes a cytokine (including secreted or cell membrane associated molecules).

106. A replication deficient oncolytic viral vector or replication competent oncolytic virus according to any one claim 104 or 105, wherein the encoded cytokine is independently selected from TNF alpha super family (TNFSF includes TNF-alpha, TNF-C, OX40L, CD154, FasL, LIGHT, TL1A, CD70, Siva, CD153, 4-1BB ligand, TRAIL, RANKL, TWEAK, APRIL, BAFF, CAMLG, NGF, BDNF, NT-3, NT-4, GITR ligand, EDA-A, EDA-A2), TGF-beta superfamily, IL-1 family (i.e. IL-1 and IL-18), IL-2 family, IL-10 family, IL-17 family, interferon family.

107. A replication deficient oncolytic viral vector or replication competent oncolytic virus according to paragraph 106, wherein the cytokine is TNF-alpha.

108. A replication deficient oncolytic viral vector or replication competent oncolytic virus according to paragraph 106 or 107, wherein the cytokine is TNF-C.

109. A replication deficient oncolytic viral vector or replication competent oncolytic virus according to any one of paragraphs 106 to 108, wherein the cytokine is OX40L.

110. A replication deficient oncolytic viral vector or replication competent oncolytic virus according to any one of paragraphs 106 to 109, wherein the cytokine is CD154.

111. A replication deficient oncolytic viral vector or replication competent oncolytic virus according to any one of paragraphs 106 to 110, wherein the cytokine is FasL.

112. A replication deficient oncolytic viral vector or replication competent oncolytic virus according to any one of paragraphs 106 to 111, wherein the cytokine is LIGHT.

113. A replication deficient oncolytic viral vector or replication competent oncolytic virus according to any one of paragraphs 106 to 112, wherein the cytokine is TL1A.

114. A replication deficient oncolytic viral vector or replication competent oncolytic virus according to any one of paragraphs 106 to 113, wherein the cytokine is CD70.

115. A replication deficient oncolytic viral vector or replication competent oncolytic virus according to any one of paragraphs 106 to 114, wherein the cytokine is Siva.

116. A replication deficient oncolytic viral vector or replication competent oncolytic virus according to any one of paragraphs 106 to 115, wherein the cytokine is CD153.

117. A replication deficient oncolytic viral vector or replication competent oncolytic virus according to any one of paragraphs 106 to 116, wherein the cytokine is 4-1BB ligand.

118. A replication deficient oncolytic viral vector or replication competent oncolytic virus according to any one of paragraphs 106 to 117, wherein the cytokine is TRAIL.

119. A replication deficient oncolytic viral vector or replication competent oncolytic virus according to any one of paragraphs 106 to 118, wherein the cytokine is RANKL.

120. A replication deficient oncolytic viral vector or replication competent oncolytic virus according to any one of paragraphs 106 to 119, wherein the cytokine is TWEAK.

121. A replication deficient oncolytic viral vector or replication competent oncolytic virus according to any one of paragraphs 106 to 120, wherein the cytokine is APRIL.

122. A replication deficient oncolytic viral vector or replication competent oncolytic virus according to any one of paragraphs 106 to 121, wherein the cytokine is BAFF.

123. A replication deficient oncolytic viral vector or replication competent oncolytic virus according to any one of paragraphs 106 to 122, wherein the cytokine is CAMLG.

124. A replication deficient oncolytic viral vector or replication competent oncolytic virus according to any one of paragraphs 106 to 123, wherein the cytokine is NGF.

125. A replication deficient oncolytic viral vector or replication competent oncolytic virus according to any one of paragraphs 106 to 124, wherein the cytokine is BDNF.

126. A replication deficient oncolytic viral vector or replication competent oncolytic virus according to any one of paragraphs 106 to 125, wherein the cytokine is NT-3.

127. A replication deficient oncolytic viral vector or replication competent oncolytic virus according to any one of paragraphs 106 to 126, wherein the cytokine is GITR ligand.

128. A replication deficient oncolytic viral vector or replication competent oncolytic virus according to any one of paragraphs 106 to 127, wherein the cytokine is EDA-A.

129. A replication deficient oncolytic viral vector or replication competent oncolytic virus according to any one of paragraphs 106 to 128, wherein the cytokine is EDA-A2.

130. A replication deficient oncolytic viral vector or replication competent oncolytic virus according to any one of paragraphs 106 to 129, wherein the cytokine is from the TGF-beta superfamily.

131. A replication deficient oncolytic viral vector or replication competent oncolytic virus according to any one of paragraphs 106 to 130, wherein the cytokine is IL-1.

132. A replication deficient oncolytic viral vector or replication competent oncolytic virus according to any one of paragraphs 106 to 131, wherein the cytokine is IL-8.

133. A replication deficient oncolytic viral vector or replication competent oncolytic virus according to any one of paragraphs 106 to 132, wherein the cytokine is IL-2.

134. A replication deficient oncolytic viral vector or replication competent oncolytic virus according to any one of paragraphs 106 to 133, wherein the cytokine is IL-10.

135. A replication deficient oncolytic viral vector or replication competent oncolytic virus according to any one of paragraphs 106 to 134, wherein the cytokine is IL-17.

136. A replication deficient oncolytic viral vector or replication competent oncolytic virus according to any one of paragraphs 106 to 135, wherein the cytokine is from the interferon family.

137. A replication deficient oncolytic viral vector or replication competent oncolytic virus according to claim 106, wherein the encoded cytokine is independently selected from TNF-alpha, IL-1, IL-8, IL-10, IL-17, interferon, LIGHT, TL1A, Siva, TRAIL, RANKL, TWEAK, APRIL, NGF, BDNF, NT-3, and EDA-A2.

138. A replication deficient oncolytic viral vector or replication competent oncolytic virus according to claim 106 or 137, wherein the encoded cytokine is independently selected from TNF-C, OX40I, CD154, FasL, CD70, CD153, 4-1BB ligand, and EDA-A.

139. A replication deficient oncolytic viral vector or replication competent oncolytic virus according to any one of claim 106, 137 or 138, wherein the cytokine is independently selected from the group comprising IL-2, IFN-alpha, IFN-beta, IFN-gamma, Flt3 ligand, GM-CSF, IL-15, and IL-12.

140. A replication deficient oncolytic viral vector or replication competent oncolytic virus according to paragraph 139, wherein the cytokine is IL-2.
141. A replication deficient oncolytic viral vector or replication competent oncolytic virus according to paragraph 139 or 140, wherein the cytokine is IFN-alpha.
142. A replication deficient oncolytic viral vector or replication competent oncolytic virus according to any one of paragraphs 139 to 141, wherein the cytokine is IFN-beta.
143. A replication deficient oncolytic viral vector or replication competent oncolytic virus according to any one of paragraphs 139 to 142, wherein the cytokine is IFN-gamma.
144. A replication deficient oncolytic viral vector or replication competent oncolytic virus according to any one of paragraphs 139 to 143, wherein the cytokine is Flt3 ligand.
145. A replication deficient oncolytic viral vector or replication competent oncolytic virus according to any one of paragraphs 139 to 144, wherein the cytokine is GM-CSF.
146. A replication deficient oncolytic viral vector or replication competent oncolytic virus according to any one of paragraphs 139 to 145, wherein the cytokine is IL-15.
147. A replication deficient oncolytic viral vector or replication competent oncolytic virus according to any one of paragraphs 139 to 146, wherein the cytokine is IL-12.
148. A replication deficient oncolytic viral vector or replication competent oncolytic virus according to any one of paragraphs 10 to 147, wherein at least one further transgene encodes a chemokine.
149. A replication deficient oncolytic viral vector or replication competent oncolytic virus according to claim 148, wherein the chemokine is independently selected from the group comprising MIP-1 alpha, RANTES, IL-8, CCL5, CCL17, CCL20, CCL22, CXCL9, CXCL10, CXCL11, CXCL13, CXCL12, CCL2, CCL19 and CCL21.
150. A replication deficient oncolytic viral vector or replication competent oncolytic virus according to claim 149, wherein the chemokine encoded is MIP-1 alpha.
151. A replication deficient oncolytic viral vector or replication competent oncolytic virus according to paragraph 149 or 150, wherein the chemokine encoded is RANTES.
152. A replication deficient oncolytic viral vector or replication competent oncolytic virus according to any one of paragraphs 149 to 151, wherein the chemokine encoded is IL-8.
153. A replication deficient oncolytic viral vector or replication competent oncolytic virus according to any one of paragraphs 149 to 152, wherein the chemokine encoded is CCL5.
154. A replication deficient oncolytic viral vector or replication competent oncolytic virus according to any one of paragraphs 149 to 153, wherein the chemokine encoded is CCL17.
155. A replication deficient oncolytic viral vector or replication competent oncolytic virus according to any one of paragraphs 149 to 154, wherein the chemokine encoded is CCL20.
156. A replication deficient oncolytic viral vector or replication competent oncolytic virus according to any one of paragraphs 149 to 155, wherein the chemokine encoded is CCL22.
157. A replication deficient oncolytic viral vector or replication competent oncolytic virus according to any one of paragraphs 149 to 156, wherein the chemokine encoded is CXCL9.
158. A replication deficient oncolytic viral vector or replication competent oncolytic virus according to any one of paragraphs 149 to 157, wherein the chemokine encoded is CXCL10.
159. A replication deficient oncolytic viral vector or replication competent oncolytic virus according to any one of paragraphs 149 to 158, wherein the chemokine encoded is CXCL11.
160. A replication deficient oncolytic viral vector or replication competent oncolytic virus according to any one of paragraphs 149 to 159, wherein the chemokine encoded is CXCL12.
161. A replication deficient oncolytic viral vector or replication competent oncolytic virus according to any one of paragraphs 149 to 160, wherein the chemokine encoded is CXCL13.
162. A replication deficient oncolytic viral vector or replication competent oncolytic virus according to any one of paragraphs 149 to 161, wherein the chemokine encoded is CCL2.
163. A replication deficient oncolytic viral vector or replication competent oncolytic virus according to any one of paragraphs 149 to 162, wherein the chemokine encoded is CCL19.
164. A replication deficient oncolytic viral vector or replication competent oncolytic virus according to any one of paragraphs 149 to 163, wherein the chemokine encoded is CCL21.
165. A replication deficient oncolytic viral vector or replication competent oncolytic virus according to claim 149 or 150, wherein the virus comprises transgenes encoding a cytokine and chemokine combination selected from i) MIP-1$\alpha$ and Flt3, and ii) MIP-1$\alpha$ and IFN$\alpha$.
166. A replication deficient oncolytic viral vector or replication competent oncolytic virus according to any one of claims 1 to 166, wherein the anti-CD3 antibody or binding fragment has at least the binding domain comprising a VH and a VL regions from muromonab-CD3 (OKT3), otelixizumab, teplizumab or visilizumab.
167. A method of treating a cancer patient (for example by in vivo stimulation of T cells, for example T cells in the cancer cell environment, to focus on cancerous cells) comprising the step of:
administering a therapeutically effective amount of a replication deficient oncolytic viral vector or replication capable group B oncolytic adenovirus selected from the group consisting of Ad11 and enadenotucirev, wherein the virus encodes an antibody or a binding fragment thereof for expression on the surface of a cancer cell, wherein said antibody or binding fragment is specific to a CD3 protein of a T-cell receptor complex (TCR), wherein the virus does not encode a B7 protein or an active fragment thereof,
wherein the virus or viral vector selectively infects said cancerous cells and expresses on the surface of the cell the said encoded anti-CD3 antibody or binding fragment, as defined in any one of claims 1 to 166.
168. A replication deficient oncolytic viral vector or replication capable group B oncolytic adenovirus selected from the group consisting of Ad11 and enadenotucirev, wherein the virus encodes an antibody or a binding fragment thereof for expression on the surface of a cancer cell, wherein said antibody or binding fragment is specific to a CD3 protein of a T-cell receptor complex (TCR), wherein the virus does not encode a B7 protein or an active fragment thereof, as defined in any one of claims 1 to 166, for use in treatment.

169. A replication deficient oncolytic viral vector or replication capable group B oncolytic adenovirus according to claim 168, for use in the treatment of cancer.
170. A replication deficient oncolytic viral vector or replication capable group B oncolytic adenovirus according to claim 169, wherein the treatment is by in vivo stimulation of T cells, for example T cells in the cancer cell environment, to focus on cancerous cell.
171. A replication deficient oncolytic viral vector or replication capable group B oncolytic adenovirus selected from the group consisting of Ad11 and enadenotucirev, wherein the virus encodes an antibody or a binding fragment thereof for expression on the surface of a cancer cell, wherein said antibody or binding fragment is specific to a CD3 protein of a T-cell receptor complex (TCR), wherein the virus does not encode a B7 protein or an active fragment thereof, as defined in any one of claims 1 to 116, for use in in the manufacture of a medicament.

In one embodiment one or more transgene encoded by the virus of the present disclosure are under the control of an endogenous promoter, in particular the major late promoter.

In one embodiment one or more transgene encoded by the virus of the present disclosure are under the control of an exogenous promoter such as a CMV promoter.

In one embodiment there is provided a virus (replication deficient or replication competent virus comprising a transgene cassette disclosed here, including disclosed as part of complete virus sequence).

In one embodiment a protein or peptide encoded by a virus of the present disclosure for surface expression on a cancer cell is an immunogenic protein, for example a non-human protein.

In a one aspect the present disclosure provides a method of treating a cancer patient by stimulating in vivo T cells to focus on cancerous cells by administering a therapeutically effective amount of a replication deficient oncolytic viral vector or replication competent oncolytic virus encoding an anti-TCR antibody or a binding fragment thereof (such as an anti-CD3 antibody or binding fragment thereof), for expression on the surface of said cancerous cells.

Thus there is provided a method of treating a cancer patient by in vivo stimulation of T cells, for example T cells in the cancer cell environment, to focus on cancerous cells by:

administering a therapeutically effective amount of a replication deficient oncolytic viral vector or oncolytic replication competent virus encoding an anti-TCR antibody or a binding fragment thereof (such as an anti-CD3 antibody or binding fragment thereof), wherein the virus or viral vector selectively infects said cancerous cells and expresses on the surface of the cell the said encoded anti-TCR antibody or binding fragment.

Also provided is a replication deficient oncolytic viral vector or a replication competent oncolytic virus encoding an anti-TCR antibody or a binding fragment thereof (such as an anti-CD3 antibody or binding fragment thereof), for expression on the surface of cancerous cells, for use in treatment of a cancer patient by in vivo stimulation of T cells, in particular T cells in the cancer cell environment, to focus on said cancerous cells. As described herein the virus or viral vector selectively infects said cancerous cells and expresses on the surface of the cell the said encoded anti-TCR antibody or binding fragment (such as an anti-CD3 antibody or binding fragment thereof).

In one embodiment there is provided a replication deficient oncolytic viral vector or a replication competent oncolytic virus encoding a an anti-TCR antibody or a binding fragment thereof, encoding a an anti-TCR antibody or a binding fragment thereof (such as an anti-CD3 antibody or binding fragment thereof), for expression on the surface of cancerous cells for use in the manufacture of a medicament for the treatment cancer by in vivo stimulation of T cells, in particular T cells in the cancer cell environment, to focus on said cancerous cells.

In a second independent embodiment there is provided a method of treating a cancer patient comprising administering a therapeutically effective amount of a replication deficient oncolytic viral vector or oncolytic replication competent virus encoding an anti-TCR antibody or a binding fragment thereof (such as an anti-CD3 antibody or binding fragment thereof), for expression on the surface of a cancer cell, for example with the proviso that when the virus is a replication competent oncolytic adenovirus then: a transgene or transgenes therein are under the control of an exogenous promoter, and/or the virus does not encode a B7 protein or an active fragment thereof.

Thus there is provide a replication deficient oncolytic viral vector or oncolytic replication competent virus encoding an anti-TCR antibody or a binding fragment thereof (such as an anti-CD3 antibody or binding fragment thereof), for expression on the surface of a cancer cell, for use in the treatment of cancer, for example with the proviso that when the virus is a replication competent oncolytic adenovirus then: a transgene or transgenes therein is/are under the control of an exogenous promoter, and/or the virus does not encode a B7 protein or an active fragment thereof. In one embodiment a replication deficient oncolytic viral vector or oncolytic replication competent virus encoding an anti-TCR antibody or a binding fragment thereof (such as an anti-CD3 antibody or binding fragment thereof), for expression on the surface of a cancer cell, for the manufacture of a medicament for the treatment of cancer, for example with the proviso that when the virus is a replication competent oncolytic adenovirus then: a transgene or transgenes therein are under the control of an exogenous promoter, and/or the virus does not encode a B7 protein or an active fragment thereof.

In an independent aspect there is provided a replication deficient oncolytic viral vector or replication competent oncolytic virus encoding an anti TCR antibody or binding fragment thereof (such as an anti-CD3 antibody or binding fragment thereof) for expression on the surface of a cancer cell.

Thus in a third aspect there is provided a replication deficient oncolytic viral vector or replication competent oncolytic virus encoding an anti-TCR antibody or binding fragment thereof (such as an anti-CD3 antibody or binding fragment thereof) for expression on the surface of a cancer cell, for example with the proviso that when the virus is a replication competent oncolytic adenovirus then: a transgene or transgenes therein are under the control of an exogenous promoter, and/or the virus does not encode a B7 protein or an active fragment thereof.

In one embodiment of the present disclosure the virus is replication competent. In one embodiment the present disclosure is not a replication competent oncolytic adenovirus.

In one embodiment of the present disclosure the viral vector, which is replication deficient, is for example deleted in part or all of a gene essential for viral replication, such as the E1 region in adenoviruses.

In one embodiment of the disclosure the virus or viral vector is attenuated.

In one embodiment of the disclosure the oncolytic virus or viral vector is selected from an adenovirus (such as Ad5, Ad3, Ad11, Ad11/Ad3 and Ad5/3), herpes simplex virus (such as HSV-1), reovirus, vaccina virus, Seneca valley virus, coxsackie virus, Maraba virus, measles virus, vesicular stomatitis virus and New Castle disease virus, including mutated versions, variants or derivatives thereof comprising a transgene.

In one embodiment the virus or viral vector is selected from the group comprising Oncorine (H101), Talimogene, Reolysin, Pexastimogene devacirepvec (JX-594), Cavatak, Seprehvir, CGTG-102, MV-NIS, PV701, CL-ONC1, CG0070, and Enadenotucirev (EnAd), including mutated versions, variants or derivatives thereof comprising a transgene.

In one embodiment of the disclosure the oncolytic virus is an adenovirus, for example a group B virus, such as Ad11, more specifically EnAd.

In one embodiment of the disclosure the oncolytic virus is not an adenovirus, for example is not a group B adenovirus, such as is not Ad11, more specifically is not EnAd.

In one embodiment the anti-TCR antibody or binding fragment thereof is specific to the TCR alpha, beta, gamma or delta proteins that are directly involved in antigen binding or a combination thereof, for example an anti-TCR beta chain antibody.

In one embodiment the anti-TCR antibody or binding fragment is specific to CD3 delta, epsilon, gamma or a combination thereof, in particular is specific to CD3 epsilon. In one embodiment the binding domain comprises a VH and a VL from an antibody muromonab-CD3 (also known as OKT3), otelixizumab (also known as TRX4), teplizumab (also known as hOKT3γ1 (Ala-Ala)), or visilizumab.

In one embodiment of the disclosure when the replication competent virus is an adenovirus the binding domain of the agonistic anti-TCR antibody or binding fragment thereof does not comprise a VH and a VL from an antibody muromonab-CD3 (also known as OKT3), otelixizumab (also known as TRX4), teplizumab (also known as hOKT3γ1 (Ala-Ala)), or visilizumab.

In one embodiment of the disclosure the oncolytic virus or viral vector encodes a further transgene, for example a further transgene encoding a protein selected from the group comprising a cytokine, a chemokine, an antagonistic antibody molecule or fragment thereof, an agonistic antibody molecule or fragment thereof, an enzyme, an immunomodulator and combinations thereof.

In one embodiment the further transgene encodes an antibody or binding fragment thereof.

An antibody binding fragment which may be encoded by an oncolytic virus or viral vector of the disclosure in one embodiment is independently selected from a Fab, modified Fab, Fab', modified Fab', F(ab')2, Fv, single domain antibodies, scFv, bi, tri or tetra-valent antibodies, Bis-scFv, diabodies, triabodies, tetrabodies, disulfide stabilised forms of any one of the same and epitope-binding fragments thereof, in particular a scFv.

In one embodiment the antibody encoded is a full length antibody.

In one embodiment of the disclosure the further transgene encodes an antibody or binding fragment which activates T cells, for example is an agonist which stimulates T cell signalling, such an antibody or binding fragment specific to CD28, in particular an agonist specific to CD28. In one embodiment according to the present disclosure the cytokine encoded is selected from the group comprising IL-2, IFN-alpha, IFN-beta, IFN-gamma, Flt3 ligand, GM-CSF, IL-15, IL-12 and combinations thereof.

In one embodiment of the disclosure, the further transgene encodes a secreted or membrane associated cytokine.

Cytokine as employed herein means low-molecular-weight proteins that can regulate the nature, intensity and duration of immune response by binding to specific receptors on target cells and exerting a variety of effects on lymphocytes and/or other cells. As used herein, the term cytokine includes secreted versions of cell surface ligands or receptors, including fusion proteins (for example molecules fused to an immunoglobulin Fc domain).

In one embodiment according to the present disclosure the encoded cytokine is selected from the TNF alpha super family (TNFRSF includes TNF-alpha, TNF-C, OX40L, CD154, FasL, LIGHT, TL1A, CD70, Siva, CD153, 4-1BB ligand, TRAIL, RANKL, TWEAK, APRIL, BAFF, CAMLG, NGF, BDNF, NT-3, NT-4, GITR ligand, EDA-A, EDA-A2), TGF-beta superfamily, IL-1 family (i.e. IL-1 and IL-8), IL-2 family, IL-10 family, IL-17 family, interferon family.

In one embodiment according to the present disclosure the chemokine is selected from the group comprising MIP-1 alpha, IL-8, CCL5, CCL17, CCL20, CCL22, CXCL9, CXCL10, CXCL11, CXCL13, CXCL12, CCL2, CCL19, CCL21 and combinations thereof.

In one embodiment the further transgenes encode a first antibody or binding fragment thereof and a second antibody or binding fragment thereof, referred to herein an antibody/antibody combination.

In one embodiment the further transgene or transgenes encode an antibody or binding fragment and a cytokine, referred to herein as an antibody/cytokine combination.

In one embodiment the further transgene or transgenes encodes a first cytokine and a second cytokine, referred to herein as a cytokine/cytokine combination.

In one embodiment the further transgene or transgenes encode a first chemokine and a second chemokine, referred to herein as a chemokine/chemokine combination.

In one embodiment the further transgene or transgenes encode a chemokine and cytokine, referred to herein as cytokine/chemokine combination.

Where there are multiple transgenes one will generally encode one entity such as the cytokine or antibody etc. and a different gene will encode the entity, for example the chemokine or antibody etc.

In one embodiment according to the present disclosure the oncolytic virus or viral vector encodes a cytokine, chemokine combination, for example MIP-1α and Flt3 or MIP-1α and IFNα.

In one embodiment the anti-TCR antibody or binding fragment has at least the binding domain comprising a VH and a VL regions from muromonab-CD3 (OKT3) the variable regions for which are shown in SEQ ID NO: 1 and 2 and a single chain Fv version of which is shown in SEQ ID NO: 3, otelixizumab, teplizumab (the variable regions for which are shown in SEQ ID NO: 6 and 7) or visilizumab.

In one embodiment a transgene encoded by the virus, for example the anti-TCR antibody or binding fragment thereof (such as an anti-CD3 antibody or binding fragment thereof) comprises a transmembrane domain or a GPI anchor.

In one embodiment the anti-CD3 antibody or binding fragment is only surface expressed, that it is not expressed as a secreted protein.

In one embodiment a combination of a transmembrane domain and a secretory signal sequence is employed to express a protein encoded by the virus (for example as described herein) on the surface of an infected cancer cell. The present inventors have shown that the proteins encoded are expressed only on cells which are permissive to infection by the virus, i.e. cancer cells.

In one embodiment the fragment employed to express the protein on the surface of the infected cancer cell (such as the transmembrane fragment) is selected from the group comprising TM Domain Sequences (Minimal portions) given in SEQ ID NO: 10, 11, 12, 13 or 14:

| SEQ ID NO: | Name | SEQUENCE |
|---|---|---|
| 10 | PDGFR Receptor A | AVLVLLVIVIISLIVLVVIW |
| 11 | PDGFR Receptor B | VVISAILALVVLTIISLIILI |
| 12 | INSULIN-LIKE GROWTH FACTOR 1 | IIIGPPLIFVFLFSVVIGSIYLFL |
| 13 | IL6-R | SSSVPLPTFLVAGGSLAFGTLLCIAIVL |
| 14 | CD28 | FWVLVVVGGVLACYSLLVTVAFIIFWV |

In one embodiment the transmembrane domain is from a B7 protein.

In one embodiment the oncolytic virus or viral vector according to the present disclosure, in particular a replication competent adenovirus, such as Ad11 or EnAd does not encode a B7 protein nor an active fragment thereof.

SUMMARY OF THE FIGURES

FIGS. 2A-2G show schematics of transgene cassettes for viruses expressing human CD80 (FIG. 2A), co-expressing human IFNα and human CD80 (FIG. 2B), co-expressing OKT3 scFv and human CD80 (FIG. 2C), co-expressing human Flt3L, human MIP1α and human IFNα (FIG. 2D), co-expressing human Flt3L, human MIP1α and human CD80 (FIG. 2E), co-expressing human IFNα, human MIP1α and human CD80 (FIG. 2F), and a schematic of the open reading frame (ORF) or the OKT3 scFv (FIG. 2G)

FIG. 45-53 shows various amino acid and polynucleotide sequences.

SUMMARY OF THE SEQUENCE LISTING

Figure 1:
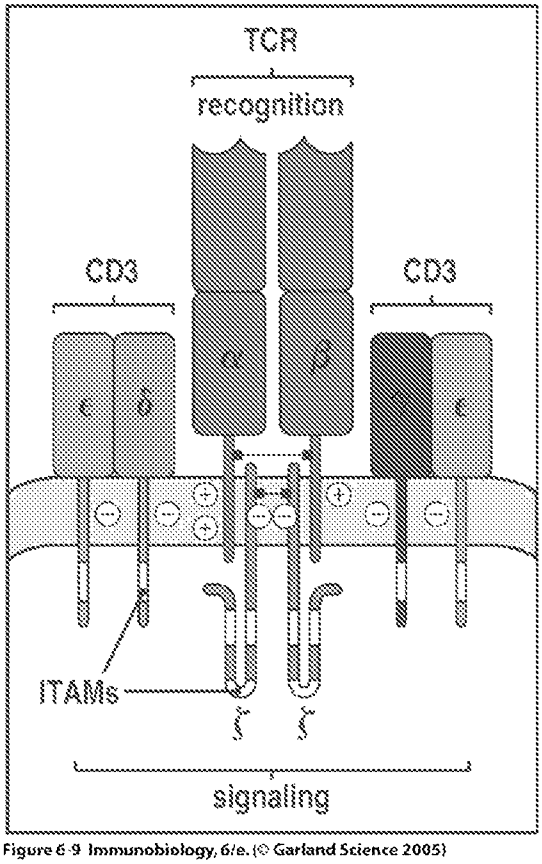
FIG. 1 shows a representation of a T cell receptor (example with alpha-beta antigen recognition chains)

The present application contains 119 sequences in the associated sequence listing.

SEQ ID NO: 1 Amino acid sequence of the VH region of the antibody OKT3.

SEQ ID NO: 2 Amino acid sequence of the VH region of the antibody OKT3.

SEQ ID NO: 3 Amino acid sequence of the scFv construct contain OKT3 VH and VL.

SEQ ID NO: 4 Amino acid sequence of membrane anchored version of the scFv of SEQ ID NO: 3

SEQ ID NO: 5 Amino acid sequence of SEQ ID NO: 4, with V5 tag.

SEQ ID NO: 6 Amino acid sequence of teplizumab VH.

SEQ ID NO: 7 Amino acid sequence of teplizumab VL.

SEQ ID NO: 8 Amino acid sequence of teplizumab heavy chain.

SEQ ID NO: 9 Amino acid sequence of teplizumab light chain.

SEQ ID NO: 10 Amino acid sequence of PDGFR Receptor A.

SEQ ID NO: 11 Amino acid sequence of PDGFR Receptor B.

SEQ ID NO: 12 Amino acid sequence of Insulin-Like growth factor 1.

SEQ ID NO: 13 Amino acid sequence of IL-6R.

SEQ ID NO: 14 Amino acid sequence of CD28.

SEQ ID NO: 15 Amino acid sequence of PDGFR TM Domain.

SEQ ID NO: 16 Amino acid sequence of c-myc tag.

SEQ ID NO: 17 Amino acid sequence of c-myc tag with spacers.

SEQ ID NO: 18 Amino acid sequence of PDGFR TM Domain with N-terminal c-myc tag.

SEQ ID NO: 19 Amino acid sequence of HuVH human VH leader sequence

SEQ ID NO: 20 Amino acid sequence of a linker.

SEQ ID NO: 21 Polynucleotide sequence of EnAd Genome

SEQ ID NO: 22 to 30 Amino acid sequence of hinge linker sequence.

SEQ ID NO: 31 to 70 Amino acid sequence of a flexible linker sequence.

SEQ ID NO: 71 to 86 Amino acid sequence of a linker sequence.

SEQ ID NO: 87 Polynucleotide sequence of E2B region of the EnAd GENOME (BP 10355-5068).

SEQ ID NO: 88 Polynucleotide sequence of a non-coding sequence suitable for inclusion into BX.

SEQ ID NO: 89 Polynucleotide sequence of a non-coding sequence suitable for inclusion into BY.

SEQ ID NO: 90 & 91 Polynucleotide sequence of a splice acceptor sequence.

SEQ ID NO: 92 Polynucleotide sequence comprising a start codon.

SEQ ID NO: 93 Polynucleotide sequence of IRES.

SEQ ID NO: 94 Amino acid sequence of high efficiency self-cleavable P2A peptide sequence.

SEQ ID NO: 95 Amino acid sequence of high efficiency self-cleavable F2A peptide sequence.

SEQ ID NO: 96 Amino acid sequence of high efficiency self-cleavable E2A peptide sequence.

SEQ ID NO: 97 Amino acid sequence of high efficiency self-cleavable T2A peptide sequence.

SEQ ID NO: 98 Amino acid sequence of human CD80 amino acid sequence.

SEQ ID NO: 99 Polynucleotide sequence of a polyadenylation sequence (5V40 late polyA sequence).

SEQ ID NO: 100 Polynucleotide of NG-348 virus genome sequence.

SEQ ID NO: 101 Amino acid of V5 TAG

SEQ ID NO: 102 Polynucleotide of NG-348A virus genome sequence.

SEQ ID NO: 103 Polynucleotide of NG-420 virus genome sequence.

SEQ ID NO: 104 Polynucleotide of NG-420A virus genome sequence.

SEQ ID NO: 105 Amino acid sequence human interferon-a amino acid sequence.

SEQ ID NO: 106 Amino acid sequence human soluble Flt3 ligand amino acid sequence.

SEQ ID NO: 107 Amino acid sequence human macrophage inflammatory protein 1a amino acid sequence (LD78b isoform).

SEQ ID NO: 108 Amino acid sequence membrane anchored form of the anti-human CD3 single chain Fv.

SEQ ID NO: 109 Polynucleotide sequence of NG-330 virus genome.

SEQ ID NO: 110 Polynucleotide sequence of NG-343 virus genome.

SEQ ID NO: 111 Polynucleotide sequence of NG-345 virus genome.

SEQ ID NO: 112 Polynucleotide sequence of NG-346 virus genome.

SEQ ID NO: 113 Polynucleotide sequence of NG-347 virus genome.

SEQ ID NO: 114 Polynucleotide of E3 region from EnAd.

SEQ ID NO: 115 Polynucleotide of a non-coding sequence suitable for inclusion into BY.

SEQ ID NO: 116 Polynucleotide sequence of NG-348 virus genome.

SEQ ID NO: 117 Polynucleotide sequence of membrane tethered OKT3-scFv.

SEQ ID NO: 118 Polynucleotide sequence of transgene cassette from NG-348.

SEQ ID NO: 119 Polynucleotide sequence of fully synthetic EnAd genome with incorporated
cloning site for transgene cassette insertion as in plasmid pEnAd2.4

DETAILED DISCLOSURE

T cells in the cancer environment include T cells inside a tumor and T cells in the vicinity of the tumor, for example T cells outside the tumor but able to engage the tumor or cancerous cell, in particular physically engage the tumor or cancerous cell.

There is evidence to suggest that the T cell infiltrate into tumors and once inside they are deactivated. Advantageously the method of the present disclosure is capable of activating T cells inside the tumor. In one embodiment the T cells inside the tumor are activated by oncolytic virus or viral vector according to the present disclosure.

In one embodiment a transmembrane tether or anchor sequence employed in the present disclosure comprises a PDGFR TM domain (e.g. ala513-arg561), such as shown in the sequence of SEQ ID NO: 15.

In one embodiment a tether or anchor sequence employed in the present disclosure comprises a tag attached to a PDGF receptor or fragment thereof, such as PDGFR TM domain.

Suitable tags include His-tags, Flag-tags, c-myc tag and the like. More specifically the tether or anchor may comprise a c-myc tag for example of SEQ ID NO: 16 EQKLISEEDL followed by a PDGFR TM domain is employed, for ala513-arg561), such as shown in the sequence of SEQ ID NO: 15

In one embodiment the c-myc tag comprises a spacer or spacer amino acids at the 3' and/or 5' end, for example as shown in the sequence of SEQ ID NO: 17 gsEQKLISEEDLn.

In one embodiment the tether or anchor sequence employed is shown in the sequence of SEQ ID NO: 18.

Generally the protein/polypeptide to which the tether or anchor is attached does not comprise a stop codon.

In one embodiment the leader sequence for the protein to be expressed on the cancer cell surface is human, for example the human VH leader sequence (HuVH)(SEQ ID NO. 19).

In one embodiment the structure of the ORF cassette is as follows:

```
LS-POLY-TAG-TM_D
```

wherein

LS is a leader sequence, for example a human leader sequence;

POLY is a polynucleotide encoding polypeptide or proteins of interest, in particular one disclosed herein;

TAG is a tag for example one disclosed herein, such as c-myc, in particular as described herein;

TM_D is a TM domain for example a PDGFR TM domain, also described herein.

When the polypeptide is a scFv then the ORF may be as follows:

$$LS\text{-}VAR_1\text{-}LINK\text{-}VAR_2\text{-}TAG\text{-}TM\_D$$

wherein

LS is a leader sequence, for example a human leader sequence;

$VAR_1$ is a polynucleotide encoding a variable region such as VH region;

LINK is a linker, for example as disclosed herein, such as a linker based on the units of $G_4S$, in particular the sequence of SEQ ID NO: 20 GGGGSGGGGSGGGGS;

$VAR_2$ is a polynucleotide encoding a variable region, such as a VL region;

TAG is a tag, for example one disclosed herein, such as c-myc, in particular a sequence described herein;

TM_D is a TM domain for example a PDGFR TM domain, for example a sequence described herein.

The disclosure also extends to embodiments, in particular those described specifically herein, which comprise a tag at the N- or C-termini of the polypeptide chains, such that it resides inside or on the outside of the membrane. Thus a C-termini tag located inside the membrane is advantageous because it is not likely to interfere with the binding or function of the polypeptide.

Alternative methods to employing transmembrane domains for expressing proteins on the surface of the infected cancer cell include approaches employing glycophospholipid anchor (also referred to as a GPI anchor) attached to the C-terminal amino acid of the extracellular protein or fragment (Low et al 1986, Cross 1987, Low and Saltiel 1988, Ferguson and William 1988). Known glycophospholipid anchors include those from Thy-1, N-CAM and DAF.

In one embodiment a combination of a transmembrane domain and a secretory signal sequence is employed to express a protein encoded by the virus (for example as described herein) on the surface of an infected cancer cell. The present inventors have shown that the proteins encoded are expressed only on cells which are permissive to infection by the oncolytic virus, i.e. cancer cells.

In one embodiment the fragment employed to express the protein on the surface of the infected cancer cell (such as the transmembrane fragment) is selected from the group comprising TM Domain Sequences (Minimal portions) given in SEQ ID NO: 10 to 15 (or 10 to 14).

In one embodiment a transmembrane domain from CD80 or CD86 is employed to express the protein on the surface the cancer cell.

In one embodiment the fragment employed to express the protein on the surface of the infected cancer cell (such as the transmembrane fragment) is selected from about 20 to 25 hydrophobic amino acids which form a transmembrane alpha helix, for example from the proteins including PDGF receptor, insulin-like growth factor receptor, IL-6 receptor, CD28, glycophorin, LDL receptor, influenza HA protein, insulin receptor, Asialoglycoprotein receptor, Transferrin receptor.

In one embodiment the transmembrane domain employed is derived from a G protein-coupled receptor or S antigen from hepatitis B.

In one embodiment a fusion protein comprising a full length extracellular domain of a B7 protein or fragment and also a transmembrane domain derived from a protein other than B7 is arranged such that the B7 protein is located at the terminal end of the fusion protein distal from the cancer cell surface, that is on the outside of the cancer cell facing the extracellular space.

Having the DNA sequence encoding B7 or an active fragment under the control of an endogenous promoter is also advantageous because the protein is expressed in accordance with the virus life cycle as opposed to being constitutively expressed. In the present situation continuous expression under an exogenous promoter, for example a strong promoter like the CMV promoter, may produce more B7 protein than is necessary for a therapeutic effect and result in off-target effects.

In one embodiment oncolytic virus according to present disclosure is an adenovirus, for example a group B adenovirus. In one embodiment the virus according to the present disclosure is a chimeric virus, for example EnAd. In one embodiment the adenovirus is replication competent.

In one embodiment the oncolytic virus is replication capable, for example replication competent.

Replication capable as employed herein is a virus that can replicate in a host cell. In one embodiment replication capable encompasses replication competent and replication selective viruses.

Replication competent as employed herein is intended to mean an oncolytic virus that is capable of replicating in a human cell, such as a cancer cell, without any additional complementation to that required by wild-type viruses, for example without relying on defective cellular machinery.

Replication selective or selective replication as employed herein is intended to mean an oncolytic virus that is able to replicate in cancer cells employing an element which is specific to said cancer cells or upregulated therein, for example defective cellular machinery, such as a p53 mutation, thereby allowing a degree of selectivity over healthy/normal cells.

A "replication capable oncolytic virus" is a replication capable virus which preferentially infects cancer cells. That is, they are tumour selective by infecting tumour cells in preference to non-tumour cells. EnAd is an example of a replication competent virus.

In one embodiment the virus is replication deficient and provided as a viral vector. Viral vectors require a packaging cell or helper to provide a complementary gene to allow replication.

Replication deficient oncolytic viral vector as employed herein refers a replication deficient virus which preferentially infects cancer cells. That is, they are tumour selective by infecting tumour cells in preference to non-tumour cells, for example the viral vector is derived from a replication competent oncolytic virus by deleting a gene essential for replication.

In one embodiment replication deficient oncolytic viral vectors according to the present disclosure In one embodiment the gene encoding the anti-TCR antibody or binding fragment thereof (such as an anti-CD3 antibody or binding fragment thereof) is located between the stop codon and polyA recognition site of the adenoviral gene L5 and the stop codon and polyA recognition site of the gene E4.

In one embodiment gene encoding the anti-TCR antibody or binding fragment thereof (such as an anti-CD3 antibody or binding fragment thereof) is located between about bp 29356 and about 29357 of the EnAd genome, for example as shown in SEQ ID NO: 21, or a position equivalent thereto. The skilled person will understand that the absolute numerical value of the location can change based on how the numbering is allocated.

The CD3 antibody component facilitates in vivo stimulation of T cells, for example T cells in the cancer cell environment, to focus on cancerous cells.

Immunomodulator as employed herein means a modulator of immune response. Immunomodulators function in adjustment of the immune response to a desired level, as in immunopotentiation, immunosuppression, or induction of immunologic tolerance.

In one embodiment the immunomodulator is an antibody or binding fragment (in particular an inhibitor antibody or binding fragment) specific to a target selected from the group comprising CTLA-4, PD-1, PD-L1, PD-L2, VISTA, B7-H3, B7-H4, HVEM, ILT-2, ILT-3, ILT-4, TIM-3, LAG-3, BTLA, LIGHT or CD160, for example CTLA-4, PD-1, PD-L1 and PD-L2.

In one embodiment the immunomodulator is an antibody or binding fragment (in particular an inhibitor antibody or binding fragment) specific to a target selected from the group comprising CD16, CD25, CD33, CD332, CD127, CD31, CD43, CD44, CD162, CD301a, CD301b and Galectin-3.

In one embodiment the immunomodulator is an antibody or binding fragment specific to a target selected from the group comprising: FLT-3, FLT-3 ligand, TLRs, TLR ligands, CCR7, CD1a, CD1c, CD11b, CD11c, CD80, CD83, CD86, CD123, CD172a, CD205, CD207, CD209, CD273, CD281, CD283, CD286, CD289, CD287, CXCR4, GITR Ligand, IFN-$\alpha$2, IL-12, IL-23, ILT1, ILT2, ILT3, ILT4, ILT7, TSLP Receptor, CD141, CD303, CADM1, CLEC9a, XCR1 and CD304.

In one embodiment the immunomodulator is an antibody or binding fragment specific to a target selected from the group comprising OX40, OX40 ligand, CD27, CD28, CD30, CD40, CD40 ligand, CD70, CD137, GITR, 4-1BB, ICOS and ICOS ligand, for example CD40 and CD40 ligand.

In one embodiment the immunomodulator is a membrane-associated protein ligand for immune cell surface receptors selected from the group comprising CTLA-4, PD-1, PD-L1, PD-L2, VISTA, B7-H3, B7-H4, HVEM, ILT-2, ILT-3, ILT-4, TIM-3, LAG-3, BTLA, LIGHT or CD160, for example CTLA-4, PD-1, PD-L1 and PD-L2.

In one embodiment the immunomodulator is a membrane-associated protein ligand for immune cell surface receptors selected from the group comprising CD16, CD25, CD33, CD332, CD127, CD31, CD43, CD44, CD162, CD301a, CD301b and Galectin-3.

In one embodiment the immunomodulator is a membrane-associated protein ligand for immune cell surface receptors selected from the group comprising: FLT-3, FLT-3 ligand, TLRs, TLR ligands, CCR7, CD1a, CD1c, CD11b, CD11c, CD80, CD83, CD86, CD123, CD172a, CD205, CD207, CD209, CD273, CD281, CD283, CD286, CD289, CD287, CXCR4, GITR Ligand, IFN-α2, IL-12, IL-23, ILT1, ILT2, ILT3, ILT4, ILT5, ILT7, TSLP Receptor, CD141, CD303, CADM1, CLEC9a, XCR1 and CD304.

In one embodiment the immunomodulator is a membrane-associated protein ligand for immune cell surface selected from the group comprising OX40, OX40 ligand, CD27, CD28, CD30, CD40, CD40 ligand, CD70, CD137, GITR, 4-1BB, ICOS and ICOS ligand, for example CD40 and CD40 ligand.

In one embodiment the immunomodulator is an antibody or binding fragment specific to a target selected from the group comprising IL-1α, IL-1β, IL-6, IL-9, IL-12, IL-13, IL-17, IL-18, IL-22, IL-23, IL-24, IL-25, IL-26, IL-27, IL-33, IL-35, interleukin-2 (IL-2), IL-4, IL-5, IL-7, IL-10, IL-15, IL-21, IL-25, IL-1RA, IFNα, IFNβ, IFNγ, TNFα, TGFβ, lymphotoxin α (LTA) and GM-CSF.

In one embodiment the oncolytic adenovirus according to the present disclosure has a formula (I):

$$5TTR\text{-}B_1\text{-}B_A\text{-}B_2\text{-}B_X\text{-}B_B\text{-}B_Y\text{-}B_3\text{-}3TTR \quad (I)$$

wherein:

$B_1$ is a bond or comprises: E1A, E1B or E1A-E1B;

$B_A$ is E2B-L1-L2-L3-E2A-L4;

$B_2$ is a bond or comprises E3 or a transgene, for example under an endogenous or exogenous promoter;

$B_X$ is a bond or a DNA sequence comprising: a restriction site, one or more transgenes or both;

$B_B$ comprises L5;

$B_Y$ comprises a transgene encoding a B7 protein or an active fragment thereof; and $B_3$ is a bond or comprises E4.

In one embodiment the oncolytic virus has a formula (Ia):

$$5TTR\text{-}B_1\text{-}B_A\text{-}B_2\text{-}B_B\text{-}B_Y\text{-}B_3\text{-}3TTR \quad (Ia)$$

wherein:

$B_1$ is a bond or comprises: E1A, E1B or E1A-E1B;

$B_A$ is E2B-L1-L2-L3-E2A-L4;

$B_2$ is a bond or comprises E3;

$B_B$ comprises L5;

$B_Y$ comprises a transgene encoding a B7 protein or an active fragment thereof; and $B_3$ is a bond or comprises E4.

In one embodiment the virus genome in constructs of formula (I) and/or (Ia) is from Ad11 or EnAd, in particular EnAd.

In one embodiment the transgene encoding the anti-TCR antibody or binding fragment thereof (such as an anti-CD3 antibody or binding fragment thereof), is under the control of an endogenous promoter, for example the major late promoter.

In one embodiment $B_Y$ comprises a transgene cassette, said cassette comprising a transgene encoding a B7 protein or fragment thereof and a regulatory element, such as combination of regulatory elements.

In one embodiment the regulatory element is splice acceptor sequence.

In one embodiment the regulatory element is a Kozak sequence.

In one embodiment, for example where the transgene encodes a polycistronic RNA molecule, the regulatory element is an IRES sequence.

In one embodiment the regulatory sequence is a high efficiency self-cleavable peptide sequence such as P2A, T2A, F2A, E2A.

In one embodiment the regulatory sequence is a polyA tail.

In one embodiment there are at least two regulatory sequences, for example a splice acceptor and a Kozak sequence or a splice acceptor and a polyA tail, or a splice acceptor and an IRES sequence, or a splice acceptor and a P2A sequence.

In one embodiment there are at least three regulator sequences, for example a splice acceptor sequence, a Kozak sequence and polyA tail, or a splice acceptor sequence an IRES or 2A sequence and a polyA tail; or a splice acceptor sequence, Kozak sequence and an IRES or 2A sequence.

In one embodiment there are at least four regulatory sequences, for example a splice acceptor sequence, a Kozak sequence, an IRES or 2A sequence and a polyA tail, in particular from L5 to E4 in the order splice acceptor sequence, Kozak sequence, IRES or 2A sequence and a polyA tail.

In on embodiment the transgene encodes a polycistronic RNA molecule comprising both an IRES and a 2A regulatory sequence In one embodiment a non-adenovirus encodes a B7 protein is independently selected from B7-1, B7-2, B7-DC, B7-H1, B7-H2, B7-H3, B7-H4, B7-H5, B7-H6, B7-H7, active fragments of the same, and combinations thereof. In one embodiment the B7 protein is B7-1 (CD80), B7-2 (CD86) or an active fragment of any of the same and combinations thereof, in particular B7-1 or an active fragment thereof.

In one embodiment the B7 fragment comprises or consists of a transmembrane domain from a B7 protein in particular one described herein, such as B7-1. This domain is thought to contribute expression on the cell surface.

In one embodiment the cytoplasmic domain of the B7 protein is present. In one embodiment the cytoplasmic domain is absent. The absence of the cytoplasmic domain may reduce or eliminate intracellular signaling to the cancer cell, which is relevant to one or more embodiments discussed below.

The elements in a fragment or full length B7 protein may be from the same or different B7 proteins. Thus in one embodiment the B7 fragment or protein is chimeric.

In one embodiment the virus of the present disclosure encodes multiple proteins for expression on the surface of the infected cancer cell, for example a non-adenovirus encodes at least one is a B7 protein or an active fragment thereof, for example two, three, four or more different proteins are encoded, in particular two or three proteins are encoded by the virus for expression on the cancer cell surface or secretion into the extracellular space.

In one embodiment a B7 protein or active fragment is encoded by the non-adenovirus of the present disclosure for expression on the surface of the cancer cell and a soluble form, which is released or secreted from the cell, of the same B7 protein or a different B7 protein (including active fragments) is also encoded by the virus.

In one embodiment at least two different B7 proteins or active fragments are encoded by a non-adenovirus of the present disclosure.

In one embodiment the multiple proteins may be encoded to be expressed as separate proteins which are independently processed and expressed in the cancer cell membrane. The independence of the proteins on the surface of the cancer cell may make a positive contribution to the immune activation. Whilst not wishing to be bound by theory, lipid packing can influence the fluidity (i.e. the viscosity) of the lipid bilayer in the membrane of the cancer cell. Viscosity of the membrane can affect the rotation and orientation of proteins and other bio-molecules within the membrane, thereby affecting the functions of these molecules. Thus when the proteins encoded by the virus are located as individual and separate proteins within the membrane of the infected cancer cell, the fluidity of the lipid bilayer allows independent movement of the molecules which may be a particularly suitable format similar to a natural format that is conducive to biological function.

In one embodiment the independently processed and expressed proteins are located (anchored) in different locations, such as physically separate locations, in the cancer cell membrane.

In one embodiment one or more proteins (for example all the proteins) encoded by the virus and expressed on the surface of the infected cancer cell are not fusion proteins. Thus in one embodiment the virus according to the present disclosure comprises DNA sequences encoding said multiple proteins for expression, for example on the surface or the infected cancer cell.

Thus in one embodiment the virus according to the present disclosure comprises two or more transgenes, in the same or different locations in the virus genome. When located at the same position in the virus genome the multiple proteins will still be expressed independently at the surface of the cancer cell.

In one embodiment the multiple proteins (including fusion proteins) are encoded in different locations in the virus genome, for example in E3, $B_X$ and/or $B_Y$ and are expressed separately on the surface of the infected cancer cell.

In one embodiment the multiple proteins (including fusion proteins) are encoded in the same location in the virus genome and expressed together on the infected cancer cell surface, for example where the proteins encoded are provided as a fusion protein wherein the fusion protein comprises a B7 protein or an active fragment thereof.

In one embodiment the B7 protein in the fusion protein is a full length protein, in particular a protein described herein, such as B7-1 and/or B7-2, fused or linked to another protein of interest or an active fragment thereof. In one embodiment, the fusion protein comprises a transmembrane from a B7 protein. In one embodiment the B7 is an active fragment excluding the transmembrane domain. In the latter embodiment a transmembrane other than one derived from a B7 protein may be employed to ensure the fusion protein is presented on the surface of the infected cancer cell.

In one embodiment the multiple proteins are encoded in the same location in the virus and are expressed as fusion proteins together on the surface of the infected cancer cell.

When the location in the virus is the same then the genes may, for example be linked by an IRES sequence or a 2A peptide.

In one embodiment the virus according to the present disclosure comprises a "second" transgene and optionally a third transgene (i.e. one or more of said multiple proteins, for example encoding a polypeptide selected from the group comprising a cytokine, a chemokine, a ligand, an antagonistic antibody molecule, and an agonistic antibody molecule.

In one embodiment the additional protein or proteins is/are independently selected from the group comprising an antibody, antibody fragment or protein ligand that binds CD3, CD28, CD80, CD86, 4-1BB, GITR, OX40, CD27, CD40 and combinations in forms suitable for expression on the surface of a cancer cell.

In one embodiment where the first transgene is specific to the alpha and/or beta chain of the TCR the additional protein is an anti-CD3 antibody or binding fragment thereof, for example independently selected from a Muromonab-CD3 (also known as OKT3), otelixizumab (also known as TRX4), teplizumab (also known as hOKT3γ1 (Ala-Ala)), or visilizumab.

In one embodiment the anti-TCR antibody is in the form of an antibody fragment (such as an anti-CD3 antibody or binding fragment thereof), for example an scFv form, that is part of a fusion protein with the transmembrane region of another protein, for example the transmembrane domain from the PDGF receptor or from the cell surface form of IgG In one embodiment an antibody inhibitor (antagonistic antibody) is independently selected from the group comprising an inhibitor of an angiogenesis factor, such as an anti-VEGF antibody molecule, and inhibitor of T cell deactivation factors, such as an anti-CTLA-4, anti-PD1 or anti-PDL1 antibody molecule. In one embodiment antibody molecule is an agonist independently selected from the group comprising antibodies to CD40, GITR, OX40, CD27 and 4-1BB.

In one embodiment the additional transgene encodes a cytokine, or soluble variant thereof selected from the group comprising IL-2, IFN-alpha, IFN-beta, IFN-gamma, GM-CSF, IL-15, IL-12 and fms-related tyrosine kinase 3 ligand (FLT3L). Advantageously, one or more of this group of proteins expressed by the virus, in particular as a free protein secreted from the cancer cell, may be particularly suitable for stimulating an immune response in vivo to the cancer cell.

In one embodiment the additional transgene encodes a chemokine, selected from the group comprising MIP1-alpha, RANTES, IL-8, CCL5, CCL17, CCL20, CCL22, CXCL9, CXCL10, CXCL11, CXCL13, CXCL12, CCL2, CCL19 and CCL21. Advantageously, one or more of this group of proteins is expressed by the virus as a free protein which may be secreted from the cancer cell may be particularly suitable for attracting immune cells and stimulating an immune response to the cancer cell in vivo.

In one embodiment the additional transgene encodes a ligand specific for a chemokine receptor, selected from the group comprising CXCR2, CCR2, CCR4, CCR5, CCR6, CCR7, CCR8, CXCR3, CXCR4, CXCR5 and CRTH2.

In one embodiment in addition to at least the anti-TCR antibody or binding fragment thereof (such as an anti-CD3 antibody or binding fragment thereof) expressed on the surface of the infected cancer cell, one or more molecules are also expressed on the surface and/or secreted.

Thus in one embodiment the non-adenovirus encodes B7-1, B7-2 or an active fragment of any one of the same or a combination thereof.

Thus in one embodiment the non-adenovirus encodes B7-1, B7-2 or an active fragment of any one of the same or a combination thereof for expression on the surface of the infected cancer cell and an anti-TCR (agonist, such as CD3 agonist) antibody or antibody fragment (such as a scFv) also for expression on the cancer cell surface, in particular where the proteins are expressed as individual proteins on the cell surface.

Thus in one embodiment the non-adenovirus encodes B7-1, B7-2 or an active fragment of any one of the same or a combination thereof for expression on the surface of the infected cancer cell and an anti-VEGF (antagonist) antibody also for expression on the cancer cell surface or for release from the cancer cell, for example by secretion or after lysis/death of the infected cancer cell.

Thus in one embodiment the non-adenovirus encodes B7-1, B7-2 or an active fragment of any one of the same or a combination thereof for expression on the surface of the infected cancer cell and an antibody, antibody fragment or protein ligand that binds CD3, CD28, CD80, CD86, 4-1BB, GITR, OX40, CD27, CD40 also for expression on the cancer cell surface or for release from the cancer cell, for example by secretion or after lysis/death of the infected cancer cell.

Thus in one embodiment the non-adenovirus encodes B7-1, B7-2 or an active fragment of any one of the same or a combination thereof for expression on the surface of the infected cancer cell and a cytokine selected from IL-2, IFN-alpha, IFN-beta, IFN-gamma, GM-CSF, IL-15, IL-12, and FLT3L, for example for release from the cancer cell, in particular by secretion or after cell lysis/death of the infected cancer cell.

Thus in one embodiment the non-adenovirus encodes B7-1, B7-2 or an active fragment of any one of the same or a combination thereof for expression on the surface of the infected cancer cell and a chemokine selected from MIP1-alpha, RANTES, IL-8, CCL5, CCL17, CCL20, CCL22, CXCL9, CXCL10, CXCL11, CXCL13, CXCL12, CCL2, CCL19, CCL21, for example for release from the cancer cell, in particular by secretion or after cell lysis/death of the infected cancer cell.

Thus in one embodiment the non-adenovirus encodes B7-1, B7-2 or an active fragment of any one of the same or a combination thereof for expression on the surface of the infected cancer cell and an anti-TCR (agonist, such as CD3 agonist) antibody or antibody fragment (such as a ScFv) also for expression on the cancer cell surface (in particular where the proteins are expressed as individual proteins on the cell surface) and further encodes a cytokine or chemokine selected from IL-2, IFN-alpha, IFN-gamma, GM-CSF, IL-15, IL-12, FLT3L, MIP1-alpha, RANTES, IL-8, CCL5, CCL17, CCL20, CCL22, CXCL9, CXCL10, CXCL11, CXCL13, CXCL12, CCL2, CCL19, CCL21 for example for release from the cancer cell, in particular by secretion or after cell lysis/death of the infected cancer cell.

Thus in one embodiment the non-adenovirus encodes B7-1, B7-2 or an active fragment of any one of the same or a combination thereof for expression on the surface of the infected cancer cell and an anti-TCR (agonist) antibody or antibody fragment (such as a ScFv) also for expression on the cancer cell surface (in particular where the proteins are expressed as individual proteins on the cell surface) and further encodes an antibody, antibody fragment or protein ligand that binds CD28, CD80, CD86, 4-1BB, GITR, OX40, CD27, CD40 or an anti-VEGF (antagonist) antibody also for expression on the cancer cell surface or for release from the cancer cell, for example by secretion or after lysis/death of the infected cancer cell.

Thus in one embodiment the non-adenovirus encodes B7-1, B7-2 or an active fragment of any one of the same or a combination thereof for expression on the surface of the infected cancer cell and two different cytokines or chemokines selected from IL-2, IFN-alpha, IFN-beta, IFN-gamma, GM-CSF, IL-15, and IL-12, FLT3L, MIP1-alpha, RANTES, IL-8, CCL5, CCL17, CCL20, CCL22, CXCL9, CXCL10, CXCL11, CXCL13, CXCL12, CCL2, CCL19, CCL21, for example for release from the cancer cell, in particular by secretion of after cell lysis/death of the infected cancer cell.

Thus in one embodiment the non-adenovirus encodes B7-1, B7-2 or an active fragment of any one of the same or a combination thereof for expression on the surface of the infected cancer cell and an anti-TCR (agonist, such as CD3 agonist) antibody or antibody fragment (such as a scFv) also for expression on the cancer cell surface (in particular where the proteins are expressed as individual proteins on the cell surface) and further encodes a cytokine selected from IL-2, IFN-alpha, IFN-gamma, GM-CSF, IL-15, and IL-12, and or a chemokine selected from RANTES (CCL5), MIP1α (LD78α (CCL3) or LD78β (CCL3L1) isoforms), MIP1β which can be released from the cancer cell, in particular by secretion before and after cell lysis/death of the infected cancer cell.

In one embodiment which in particular may be combined with any of the embodiments above the virus further encodes an anti-PD-1 antibody (an antagonist).

In one embodiment the protein or proteins encoded in the transgene cassette for cell membrane expression may also comprise a peptide linker or spacer between the transmembrane domain and the extracellular ligand binding domain. Such linkers or spacers may add flexibility to the cell surface expressed protein that enhances the ability of the protein to interact with its target molecule on an adjacent cell. Such linkers or spacers may also be designed or selected to promote dimerisation or trimerisation of the proteins at the cell surface, via disulphide bond formation or protein-protein interactions. For example the hinge regions of immunoglobulin molecules or CD8 may be employed to enhance both flexibility and dimerisation In one embodiment the protein or proteins encoded in the transgene cassette may also comprise a peptide tag. The peptide tag may include c-myc, poly-histidine, V5 or FLAG tags and can be located on the N-terminus or C-terminus of the polypeptide, either intracellularly or extracellularly, or may be encoded within the protein for example in an extracellular loop or between the transmembrane domain and the extracellular domain. Peptide tags can be used as spacers or linkers between different protein domains, for example the transmembrane and the extracellular domain, and be used for detection or purification of the protein.

In one embodiment the one or more additional transgenes (other than the gene encoding the B7 protein or fragment thereof) is under the control of an exogenous or endogenous promoter, for example an endogenous promoter. In one embodiment a transgene in the E3 region ($B_2$) is under control of an exogenous promoter.

In one embodiment the one or more additional transgenes genes are between the E3 region and the fibre L5 in the adenovirus genome, for example at a position $B_X$ in the construct of formula (I), in particular under the control of an exogenous promoter. In one embodiment a transgene in $B_X$ is under the control of an exogenous.

In one embodiment the one or more additional transgenes genes are between the E4 region and the fibre L5 in the adenovirus genome, for example at a position $B_Y$ in the construct of formula (I) or (Ia), in particular under the control of an endogenous promoter, such as the major late promoter. This may be in addition to the gene encoding the anti-TCR antibody or binding fragment thereof (such as an anti-CD3 antibody or binding fragment thereof) encoded in the region $B_Y$.

In one embodiment there is provided a composition comprising an oncolytic virus or viral vector according to the present disclosure, for example a pharmaceutical composition, in particular comprising a pharmaceutically acceptable excipient, such as a diluent or carrier.

In one embodiment there is provided an oncolytic virus or viral vector according to the present disclosure or a composition comprising the same, for use in treatment, in particular for use in the treatment of cancer.

In one embodiment there is provided a method of treating a patient in need thereof comprising administering a therapeutically effective amount of an oncolytic virus or viral vector according to the present disclosure or a composition, such as a pharmaceutical composition comprising the same.

In one embodiment there is provided use of an oncolytic virus or viral vector according to the present disclosure or a composition comprising the same for the manufacture of a medicament for the treatment of cancer, in particular carcinomas, for example colorectal, lung, bladder, renal, pancreatic, hepatic, head and neck, breast or ovarian cancer.

In one embodiment there is provided a polynucleotide comprising genomic sequence of at least 50% of a virus according to the present disclosure (for example 55, 60, 65, 70, 75, 80, 85, 90, 91, 92, 93, 94, 95, 96, 97, 98, 99 or 100%) and comprising a sequence encoding an anti-TCR antibody or binding fragment thereof (such as an anti-CD3 antibody or binding fragment thereof), for example a sequence disclosed herein. In one embodiment the polynucleotide sequence is in the form of a plasmid.

In one embodiment there is provided a host cell, for example a mammalian cell, such as a HEK293 cell or a derivative thereof, comprising an oncolytic virus or viral vector according to the present disclosure or a polynucleotide sequence according to the present disclosure.

In one embodiment there is provided a process for preparing an oncolytic virus or viral vector according to the present disclosure comprising a step of inserting a polynucleotide encoding an anti-TCR antibody or binding fragment thereof (such as an anti-CD3 antibody or binding fragment thereof) into an oncolytic virus or viral vector.

In one embodiment there is provided a process of replicating a virus or viral according to the present disclosure comprising the step of culture host cells in the presence of the virus under conditions suitable for replication. Generally the method will comprise a further step of harvesting the virus, for example from the supernatant or after lysis of the host cells.

Transgene as employed herein refers to a gene that has been inserted into the genome sequence of the virus or viral vector, wherein the gene is unnatural to the virus (exogenous) or not normally found in that particular location in the virus. Examples of transgenes are given herein. Transgene as employed herein also includes a functional fragment of the gene that is a portion of the gene which when inserted is suitable to perform the function or most of the function of the full-length gene, for example 50% of the function or more.

Transgene and coding sequence are used interchangeably herein in the context of inserts into the viral genome, unless the context indicates otherwise. Coding sequence as employed herein means, for example a DNA sequence encoding a functional RNA, peptide, polypeptide or protein. Typically the coding sequence is cDNA for the transgene that encodes the functional RNA, peptide, polypeptide or protein of interest. Functional RNA, peptides, polypeptide and proteins of interest are described below.

In one embodiment transgene as employed herein refers to a segment of DNA containing a gene or cDNA sequence that has been isolated from one organism and is introduced into a different organism i.e. the virus of the present disclosure. In one embodiment this non-native segment of DNA will generally retain the ability to produce functional RNA, peptide, polypeptide or protein. Transgenes employed may for example encode a chimeric protein or a fusion protein.

Clearly the virus genome contains coding sequences of DNA. Endogenous (naturally occurring genes) in the genomic sequence of the virus are not considered a transgene, within the context of the present specification unless then have been modified by recombinant techniques such as that they are in a non-natural location or in a non-natural environment.

Thus in one embodiment the transgene inserted encodes a human or humanised protein, polypeptide or peptide.

Fusion protein as employed herein refers to at least two proteins or fragments or a combination of at least one protein and at least one fragment fused directly or attached to each other, for example by a linker. In one embodiment fusion proteins of the present disclosure do not comprise a B7 protein or active fragment thereof. Fusion proteins comprising B7 fragments or protein and additional proteins are not referred to as chimeric proteins herein. Only proteins containing fragments from different B7 proteins are referred to as chimeric herein.

The activity of a given protein fragment may be analysed in a relevant in vitro assay, for example using full-length protein as a comparator.

A chimeric fragment as employed herein refers a fragment comprising a sequence from two or more proteins from different origins.

B7 proteins include B7-1 (also known as CD80 uniprot number P33681), B7-2 (also known as CD86 uniprot number P42081). These proteins bind CD28 and CTLA-4.

```
MGHTRRQGTSPSKCPYLNFFQLLVLAGLSHFCSGVIHVTKEVKEVATLSC

GHNVSVEELAQTRIYWQKEKKMVLTMMSGDMNIWPEYKNRTIFDITNNLS

IVILALRPSDEGTYECVVLKYEKDAFKREHLAEVTLSVKADFPTPSISDF

EIPTSNIRRIICSTSGGFPEPHLSWLENGEELNAINTTVSQDPETELYAV

SSKLDFNMTTNHSFMCLIKYGHLRVNQTFNWNTTKQEHFPDNLLPSWAIT

LISVNGIFVICCLTYCFAPRCRERRRNERLRRESVRPV
```

Other B7 proteins include B7-DC (also known as PDCD1LG2 and PD-L2 uniprot number Q9BQ51), B7-H1 (also known as PD-L1 and CD274 uniprot number Q9NZQ7). Both these proteins bind PD-1.

Programmed death-ligand 1 (PD-L1) is a 40 kDa type 1 transmembrane protein that has been speculated to play a major role in suppressing the immune system. It appears that upregulation of PD-L1 may allow cancers to evade the host immune system. An analysis of 196 tumor specimens from patients with renal cell carcinoma found that high tumor expression of PD-L1 was associated with increased tumor aggressiveness and a 4.5-fold increased risk of death. Ovarian cancer patients with higher expression of PD-L1 had a significantly poorer prognosis than those with lower expression. PD-L1 expression correlated inversely with intraepithelial CD8+T-lymphocyte count, suggesting that PD-L1 on tumor cells may suppress antitumor CD8+ T cells. The effect might be tumor type dependent; a study on patients with non-small cell lung cancer showed that greater PD-L1 protein and mRNA expression is associated with increased local lymphocytic infiltrate and longer survival. A number of anti-PDL1 antibodies have been shown to be of interest for treating several cancers in clinical trials.

In one embodiment at least the cytoplasmic (intracellular domain of B7-DC and/or B7-H1 is deleted or non-functional. Whilst not wishing to be bound by theory there is evidence to suggest that removal of the intracellular domain reduces the cancer cells resistance to lysis Blood 2008, April 1; 111(7) 3635-3643.

In one embodiment only the transmembrane domain fragment of B7-DC and/or B7-H1 is employed. In one embodiment the following proteins are not provided as full-length proteins B7-DC and B7-H1.

Other B7 proteins include B7-H2 (also known as ICOSLG, B7RP1, CD275 uniprot number 075144) which binds ICOS, B7-H3 (also known as CD276 uniprot number QSZPR3), B7-H4 (also known as VTCN1 uniprot number Q727D3), B7-H5 (also known as VISTA, Platelet receptor Gi24, SISP1), B7-H6 (also known as NCR3LG1, NR3L1) which binds NKp30, B7-H7 (also known as HHLA2) which binds CD28H.

In one embodiment the fragment only comprises the transmembrane domain of any one B7-H2, B7-H3, B7-H4, B7-H5, B7-H6 and B7-H7.

Individual proteins include single proteins, that is proteins or active fragments thereof that are not part of a fusion protein (including chimeric proteins), and also fusion proteins. In one embodiment the individual proteins are single proteins (including active fragments thereof).

GPI anchor as employed herein refers to is a glycolipid that can be attached to the C-terminus of a protein during posttranslational modification. It is composed of a phosphatidylinositol group linked through a carbohydrate-containing linker (glucosamine and mannose glycosidically bound to the inositol residue) and via an ethanolamine phosphate (EtNP) bridge to the C-terminal amino acid of a mature protein. The two fatty acids within the hydrophobic phosphatidyl-inositol group anchor the protein to the cell membrane.

Glypiated (GPI-linked) proteins contain a signal peptide, thus directing them into the endoplasmic reticulum (ER). The C-terminus is composed of hydrophobic amino acids that stay inserted in the ER membrane. The hydrophobic end is then cleaved off and replaced by the GPI-anchor. As the protein processes through the secretory pathway, it is transferred via vesicles to the Golgi apparatus and finally to the extracellular space where it remains attached to the exterior leaflet of the cell membrane. Since the glypiation is the sole means of attachment of such proteins to the membrane, cleavage of the group by phospholipases will result in controlled release of the protein from the membrane. The latter mechanism is used in vitro; i.e., the membrane proteins released from the membranes in the enzymatic assay are glypiated protein.

Phospholipase C (PLC) is an enzyme that is known to cleave the phospho-glycerol bond found in GPI-anchored proteins. Treatment with PLC will cause release of GPI-linked proteins from the outer cell membrane. The T-cell marker Thy-1 and acetylcholinesterase, as well as both intestinal and placental alkaline phosphatases, are known to be GPI-linked and are released by treatment with PLC. GPI-linked proteins are thought to be preferentially located in lipid rafts, suggesting a high level of organization within plasma membrane microdomains.

A review of GPI anchors written by Ferguson, Kinoshita and Hart is available in Chapter 11 of Essentials of Glycobiology $2^{nd}$ Edition.

Virus as employed herein refers to an oncolytic replication competent virus (or adenovirus) or a replication deficient viral vector (adenoviral vector) unless the context indicates otherwise.

In one embodiment the adenovirus is a human adenovirus. "Adenovirus", "serotype" or adenoviral serotype" as employed herein refers to any adenovirus that can be assigned to any of the over 50 currently known adenoviral serotypes, which are classified into subgroups A-F, and further extends to any, as yet, unidentified or unclassified adenoviral serotypes. See, for example, Strauss, "Adenovirus infections in humans," in The Adenoviruses, Ginsberg, ea., Plenum Press, New York, N.Y., pp. 451-596 (1984) and Shenk, "Adenoviridae: The Viruses and Their Replication," in Fields Virology, Vol. 2, Fourth Edition, Knipe, 35ea., Lippincott Williams & Wilkins, pp. 2265-2267 (2001), as shown:

| SubGroup | Adenoviral Serotype |
| --- | --- |
| A | 12, 18, 31 |
| B | 3, 7, 11, 14, 16, 21, 34, 35,51 |
| C | 1, 2, 5, 6 |
| D | 8-10, 13, 15, 17, 19, 20, 22-30, 32, 33,36-39,42-49, |
| E | 4 |
| F | 40,41 |

In one embodiment the adenovirus is a subgroup B, for example independently selected from the group comprising or consisting of: Ad3, Ad7, Ad11, Ad14, Ad16, Ad21, Ad34 and Ad51, such as Ad11, in particular Ad11p (the Slobitski strain). In one embodiment the adenovirus of the invention has the capsid, such as the hexon and/or fibre of a subgroup B adenovirus, such as Ad11, in particular Ad11p. In one embodiment the adenovirus is Ad11 or has the fibre and/or hexon and/or penton of Ad11, such as Ad11p.

A derivative of Ad11 virus as employed herein refers to a virus with at least the capsid of Ad11.

In one embodiment it is not a group A virus.

Enadenotucirev (EnAd) is a chimeric oncolytic adenovirus, formerly known as EnAd (WO2005/118825), with fibre, penton and hexon from Ad11p, hence it is a subgroup B virus. It has a chimeric E2B region, which comprises DNA from Ad11p and Ad3. Almost all of the E3 region and part of the E4 region is deleted in EnAd. Therefore, it has significant space in the genome to accommodate additional genetic material whilst remaining viable. Furthermore, because EnAd is a subgroup B adenovirus, pre-existing immunity in humans is less common than, for example, Ad5. Other examples of chimeric oncolytic viruses with Ad11 fibre, penton and hexon include OvAd1 and OvAd2 (see WO2006/060314).

EnAd seems to preferentially infect tumour cells, replicates rapidly in these cells and causes cell lysis. This, in turn, can generate inflammatory immune responses thereby stimulating the body to also fight the cancer. Part of the success of EnAd is hypothesised to be related to the fast replication of the virus in vivo.

Importantly, it has been demonstrated clinically that EnAd can be administered systemically (e.g. by intravenous or intraperitoneal injection or infusion) and then subsequently selectively infect and express proteins within tumour cells. This property of EnAd, which may be shared by Ad11p and other group B adenoviruses in particular those expressing the capsid proteins of Ad11p (such as those described herein), makes it possible to express proteins on the surface of cancer cells without having to directly inject the transgenes into the tumour which is not feasible for many cancers.

Whilst EnAd selectively lyses tumour cells, it may be possible to introduce further beneficial properties, for example increasing the therapeutic activity of the virus or reducing side-effects of the virus by arming it with transgenes, such as a transgene which encodes a cell signalling protein or an antibody, or a transgene which encodes an entity which stimulates a cell signalling protein(s).

Advantageously arming a virus, with DNA encoding certain proteins that can be expressed inside the cancer cell, may enable the body's own defenses to be employed to combat tumour cells more effectively, for example by making the cells more visible to the immune system or by delivering a therapeutic gene/protein preferentially to target tumour cells.

In one embodiment the oncolytic virus or viral of the present disclosure stimulates the patient's immune system to fight the tumor, for example the anti-CD3 antibody stimulates T cells in vivo.

In one embodiment the oncolytic virus has a fibre, hexon and penton proteins from the same serotype, for example Ad11, in particular Ad11p, for example found at positions 30812-31789, 18254-21100 and 13682-15367 of the genomic sequence of the latter wherein the nucleotide positions are relative to Genbank ID 217307399 (accession number: GC689208).

In one embodiment the adenovirus is enadenotucirev (also known as EnAd and formerly as ColoAd1). Enadenotucirev as employed herein refers the chimeric adenovirus of SEQ ID NO: 21. It is a replication competent oncolytic chimeric adenovirus which has enhanced therapeutic properties compared to wild type adenoviruses (see WO2005/118825). EnAd has a chimeric E2B region, which features DNA from Ad11p and Ad3, and deletions in E3/E4. The structural changes in enadenotucirev result in a genome that is approximately 3.5 kb smaller than Ad11p thereby providing additional "space" for the insertion of transgenes.

Linkers suitable for use in fusion proteins of the present disclosure include:

- hinge linker sequences shown in SEQ ID NO: 22 to 30 (see associated sequence listing);
- flexible linker sequences GS and also the sequences shown in SEQ ID NO: 31 to 70 (see associated sequence listing);
- linker sequences shown in SEQ ID NO: 73 to 86

Examples of rigid linkers include the peptide sequences GAPAPAAPAPA (SEQ ID NO: 71), PPPP (SEQ ID NO: 72) and PPP.

Definitions Relevant to Formula (I) and (Ia)

A bond refers to a covalent bond connecting the one DNA sequence to another DNA sequence, for example connecting one section of the virus genome to another. Thus when a variable in formula (I) and (Ia) herein represents a bond the feature or element represented by the bond is absent i.e. deleted.

As the structure of adenoviruses is, in general, similar the elements below are discussed in terms of the structural elements and the commonly used nomenclature referring thereto, which are known to the skilled person. When an element is referred to herein then we refer to the DNA sequence encoding the element or a DNA sequence encoding the same structural protein of the element in an adenovirus. The latter is relevant because of the redundancy of the DNA code. The viruses' preference for codon usage may need to be considered for optimised results.

Any structural element from an adenovirus employed in the viruses of the present disclosure may comprise or consist of the natural sequence or may have similarity over the given length of at least 95%, such as 96%, 97%, 98%, 99% or 100%. The original sequence may be modified to omit 10%, 9%, 8%, 7%, 6%, 5%, 4%, 3%, 2% or 1% of the genetic material. The skilled person is aware that when making changes the reading frames of the virus must be not disrupted such that the expression of structural proteins is disrupted.

In one embodiment the given element is a full-length sequence i.e. the full-length gene.

In one embodiment the given element is less than a full-length and retains the same or corresponding function as the full-length sequence.

In one embodiment for a given element which is optional in the constructs of the present disclosure, the DNA sequence may be less than a full-length and have no functionality, for example the E3 region may be totally or partly deleted.

The structural genes encoding structural or functional proteins of the adenovirus are generally linked by non-coding regions of DNA. Thus there is some flexibility about where to "cut" the genomic sequence of the structural element of interest (especially non-coding regions thereof) for the purpose of inserting a transgene into the viruses of the present disclosure. Thus for the purposes of the present specification, the element will be considered a structural element of reference to the extent that it is fit for purpose and does not encode extraneous material. Thus, if appropriate the gene will be associated with suitable non-coding regions, for example as found in the natural structure of the virus.

Thus in one embodiment an insert, such as DNA encoding a restriction site and/or transgene, is inserted into a non-coding region of genomic virus DNA, such as an intron or intergenic sequence. Having said this some non-coding regions of adenovirus may have a function, for example in alternative splicing, transcription regulation or translation regulation, and this may need to be taken into consideration.

The sites identified herein, that are associated with the L5 region, are suitable for accommodating a variety of DNA sequences encoding complex entities such as RNAi, cytokines, single chain or multimeric proteins, such as antibodies.

Gene as employed herein refers to coding and any non-coding sequences associated therewith, for example introns and associated exons. In one embodiment a gene comprises or consists of only essential structural components, for example coding region.

Below follows a discussion relating to specific structural elements of adenoviruses.

The Inverted Terminal Repeat (ITR) sequences are common to all known adenoviruses and were so named because of their symmetry, and are the viral chromosome origins of replication. Another property of these sequences is their ability to form a hairpin.

The 5'ITR as employed herein refers to part or all of an ITR from the 5' end of an adenovirus, which retains the function of the ITR when incorporated into an adenovirus in an appropriate location. In one embodiment the 5'ITR comprises or consists of the sequence from about 1 bp to 138 bp of SEQ ID NO: 82 or a sequence 90, 95, 96, 97, 98 or 99% identical thereto along the whole length, in particular the sequence consisting of from about 1 bp to 138 bp of SEQ ID NO: 21.

The 3'ITR as employed herein refers to part or all of an ITR from 3' end of an adenovirus which retains the function of the ITR when incorporated into an adenovirus in an appropriate location. In one embodiment the 3'ITR comprises or consists of the sequence from about 32189 bp to 32326 bp of SEQ ID NO: 82 or a sequence 90, 95, 96, 97, 98 or 99% identical thereto along the whole length, in particular the sequence consisting of from about 32189 bp to 32326 bp of SEQ ID NO: 21.

B1 as employed herein refers to the DNA sequence encoding: part or all of an E1A from an adenovirus, part or all of the E1B region of an adenovirus, and independently part or all of E1A and E1B region of an adenovirus.

When B1 is a bond then E1A and E1B sequences will be omitted from the virus. In one embodiment B1 is a bond and thus the virus is a vector.

In one embodiment B1 further comprises a transgene. It is known in the art that the E1 region can accommodate a transgene which may be inserted in a disruptive way into the E1 region (i.e. in the "middle" of the sequence) or part or all of the E1 region may be deleted to provide more room to accommodate genetic material.

E1A as employed herein refers to the DNA sequence encoding part or all of an adenovirus E1A region. The latter here is referring to the polypeptide/protein E1A. It may be mutated such that the protein encoded by the E1A gene has conservative or non-conservative amino acid changes, such that it has: the same function as wild-type (i.e. the corresponding non-mutated protein); increased function in comparison to wild-type protein; decreased function, such as no function in comparison to wild-type protein; or has a new function in comparison to wild-type protein or a combination of the same as appropriate.

E1B as employed herein refers to the DNA sequence encoding part or all of an adenovirus E1B region (i.e. polypeptide or protein), it may be mutated such that the protein encoded by the E1B gene/region has conservative or non-conservative amino acid changes, such that it has: the same function as wild-type (i.e. the corresponding non-mutated protein); increased function in comparison to wild-type protein; decreased function, such as no function in comparison to wild-type protein; or has a new function in comparison to wild-type protein or a combination of the same as appropriate.

Thus B1 can be modified or unmodified relative to a wild-type E1 region, such as a wild-type E1A and/or E1B. The skilled person can easily identify whether E1A and/or E1B are present or (part) deleted or mutated.

Wild-type as employed herein refers to a known adenovirus. A known adenovirus is one that has been identified and named, regardless of whether the sequence is available.

In one embodiment B1 has the sequence from 139 bp to 3932 bp of SEQ ID NO: 21.

$B_A$ as employed herein refers to the DNA sequence encoding the E2B-L1-L2-L3-E2A-L4 regions including any non-coding sequences, as appropriate (in particular corresponding to the natural sequence from an adenovirus). Generally this sequence will not comprise a transgene. In one embodiment the sequence is substantially similar or identical to a contiguous sequence from a known adenovirus, for example a serotype shown in Table 1, in particular a group B virus, for example Ad3, Ad7, Ad11, Ad14, Ad16, Ad21, Ad34, Ad35, Ad51 or a combination thereof, such as Ad3, Ad11 or a combination thereof. In one embodiment is E2B-L1-L2-L3-E2A-L4 refers to comprising these elements and other structural elements associated with the region, for example BA will generally include the sequence encoding the protein IV2a, for example as follows: IV2A IV2a-E2B-L1-L2-L3-E2A-L4.

In one embodiment the E2B region is chimeric. That is, comprises DNA sequences from two or more different adenoviral serotypes, for example from Ad3 and Ad11, such as Ad11p. In one embodiment the E2B region has the sequence from 5068 bp to 10355 bp of SEQ ID NO: 21 or a sequence 95%, 96%, 97%, 98% or 99% identical thereto over the whole length.

In one embodiment the E2B in component $B_A$ comprises the sequences shown in SEQ ID NO: 87 (which corresponds to SEQ ID NO: 3 disclosed in WO2005/118825).

In one embodiment BA has the sequence from 3933 bp to 27184 bp of SEQ ID NO: 21.

E3 as employed herein refers to the DNA sequence encoding part or all of an adenovirus E3 region (i.e. protein/polypeptide), it may be mutated such that the protein encoded by the E3 gene has conservative or non-conservative amino acid changes, such that it has the same function as wild-type (the corresponding unmutated protein); increased function in comparison to wild-type protein; decreased function, such as no function in comparison to wild-type protein or has a new function in comparison to wild-type protein or a combination of the same, as appropriate.

In one embodiment the E3 region is form an adenovirus serotype given in Table 1 or a combination thereof, in particular a group B serotype, for example Ad3, Ad7, Ad11 (in particular Ad11p), Ad14, Ad16, Ad21, Ad34, Ad35, Ad51 or a combination thereof, such as Ad3, Ad11 (in particular Ad11p) or a combination thereof.

In one embodiment the E3 region is partially deleted, for example is 95%, 90%, 85%, 80%, 75%, 70%, 65%, 60%, 55%, 50%, 45%, 40%, 35%, 30%, 25%, 20%, 15%, 10%, 5% deleted.

In one embodiment $B_2$ is a bond, wherein the DNA encoding the E3 region is absent.

In one embodiment the DNA encoding the E3 region can be replaced or interrupted by a transgene. As employed herein "E3 region replaced by a transgene as employed herein includes part or all of the E3 region is replaced with a transgene.

In one embodiment the $B_2$ region comprises the sequence from 27185 bp to 28165 bp of SEQ ID NO: 21.

In one embodiment $B_2$ consists of the sequence from 27185 bp to 28165 bp of SEQ ID NO: 21.

$B_X$ as employed herein refers to the DNA sequence in the vicinity of the 5' end of the L5 gene in BB. In the vicinity of or proximal to the 5' end of the L5 gene as employed herein refers to: adjacent (contiguous) to the 5' end of the L5 gene or a non-coding region inherently associated herewith i.e. abutting or contiguous to the 5' prime end of the L5 gene or a non-coding region inherently associated therewith. Alternatively, in the vicinity of or proximal to may refer to being close the L5 gene, such that there are no coding sequences between the BX region and the 5' end of L5 gene.

Thus in one embodiment $B_X$ is joined directly to a base of L5 which represents, for example the start of a coding sequence of the L5 gene.

Thus in one embodiment $B_X$ is joined directly to a base of L5 which represents, for example the start of a non-coding sequence, or joined directly to a non-coding region naturally associated with L5. A non-coding region naturally associated L5 as employed herein refers to part of all of a non-coding regions which is part of the L5 gene or contiguous therewith but not part of another gene.

In one embodiment $B_X$ comprises the sequence of SEQ ID NO: 88. This sequence is an artificial non-coding sequence wherein a DNA sequence, for example comprising a transgene (or transgene cassette), a restriction site or a combination thereof may be inserted therein. This sequence is advantageous because it acts as a buffer in that allows some flexibility on the exact location of the transgene whilst minimising the disruptive effects on virus stability and viability.

The insert(s) can occur anywhere within SEQ ID NO: 82 from the 5' end, the 3' end or at any point between bp 1 to 201, for example between base pairs 1/2, 2/3, 3/4, 4/5, 5/6, 6/7, 7/8, 8/9, 9/10, 10/11, 11/12, 12/13, 13/14, 14/15, 15/16, 16/17, 17/18, 18/19, 19/20, 20/21, 21/22, 22/23, 23/24, 24/25, 25/26, 26/27, 27/28, 28/29, 29/30, 30/31, 31/32, 32/33, 33/34, 34/35, 35/36, 36/37, 37/38, 38/39, 39/40, 40/41, 41/42, 42/43, 43/44, 44/45, 45/46, 46/47, 47/48, 48/49, 49/50, 50/51, 51/52, 52/53, 53/54, 54/55, 55/56, 56/57, 57/58, 58/59, 59/60, 60/61, 61/62, 62/63, 63/64, 64/65, 65/66, 66/67, 67/68, 68/69, 69/70, 70/71, 71/72, 72/73, 73/74, 74/75, 75/76, 76/77, 77/78, 78/79, 79/80, 80/81, 81/82, 82/83, 83/84, 84/85, 85/86, 86/87, 87/88, 88/89, 89/90, 90/91, 91/92, 92/93, 93/94, 94/95, 95/96, 96/97, 97/98, 98/99, 99/100, 100/101, 101/102, 102/103, 103/104, 104/105, 105/106, 106/107, 107/108, 108/109, 109/110, 110/111, 111/112, 112/113, 113/114, 114/115, 115/116, 116/117, 117/118, 118/119, 119/120, 120/121, 121/122, 122/123, 123/124, 124/125, 125/126, 126/127, 127/128, 128/129, 129/130, 130/131, 131/132, 132/133, 133/134, 134/135, 135/136, 136/137, 137/138, 138/139, 139/140, 140/141, 141/142, 142/143, 143/144, 144/145, 145/146, 146/147, 147/148, 148/149, 150/151, 151/152, 152/153, 153/154, 154/155, 155/156, 156/157, 157/158, 158/159, 159/160, 160/161, 161/162, 162/163, 163/164, 164/165, 165/166, 166/167, 167/168, 168/169, 169/170, 170/171, 171/172, 172/173, 173/174, 174/175, 175/176, 176/177, 177/178, 178/179, 179/180, 180/181, 181/182, 182/183, 183/184, 184/185, 185/186, 186/187, 187/188, 189/190, 190/191, 191/192, 192/193, 193/194, 194/195, 195/196, 196/197, 197/198, 198/199, 199/200 or 200/201.

In one embodiment $B_X$ comprises SEQ ID NO: 21 with a DNA sequence inserted between bp 27 and bp 28 or a place corresponding to between positions 28192 bp and 28193 bp of SEQ ID NO: 21.

In one embodiment $B_X$ has the sequence from 28166 bp to 28366 bp of SEQ ID NO: 21. In one embodiment $B_X$ is a bond.

$B_B$ as employed herein refers to the DNA sequence encoding the L5 region. As employed herein the L5 region refers to the DNA sequence containing the gene encoding the fibre polypeptide/protein, as appropriate in the context. The fibre gene/region encodes the fibre protein which is a major capsid component of adenoviruses. The fibre functions in receptor recognition and contributes to the adenovirus' ability to selectively bind and infect cells.

In viruses of the present disclosure the fibre can be from any adenovirus serotype and adenoviruses which are chimeric as result of changing the fibre for one of a different serotype are known. In one embodiment the fibre is from a group B virus, in particular Ad11, such as Ad11p.

DNA sequence in relation to $B_Y$ as employed herein refers to the DNA sequence in the vicinity of the 3' end of the L5 gene of $B_B$. In the vicinity of or proximal to the 3' end of the L5 gene as employed herein refers to: adjacent (contiguous) to the 3' end of the L5 gene or a non-coding region inherently associated therewith i.e. abutting or contiguous to the 3' prime end of the L5 gene or a non-coding region inherently associated therewith (i.e. all or part of an non-coding sequence endogenous to L5). Alternatively, in the vicinity of or proximal to may refer to being close the L5 gene, such that there are no coding sequences between the $B_Y$ region and the 3' end of the L5 gene.

Thus in one embodiment $B_Y$ is joined directly to a base of L5 which represents the "end" of a coding sequence.

Thus in one embodiment $B_Y$ is joined directly to a base of L5 which represents the "end" of a non-coding sequence, or joined directly to a non-coding region naturally associated with L5.

Inherently and naturally are used interchangeably herein. In one embodiment $B_Y$ comprises the sequence of SEQ ID NO: 89. This sequence is a non-coding sequence wherein a DNA sequence, for example comprising a transgene (or transgene cassette), a restriction site or a combination thereof may be inserted. This sequence is advantageous because it acts a buffer in that allows some flexibility on the exact location of the transgene whilst minimising the disruptive effects on virus stability and viability.

The insert(s) can occur anywhere within SEQ ID NO: 88 from the 5' end, the 3' end or at any point between bp 1 to 35, for example between base pairs 1/2, 2/3, 3/4, 4/5, 5/6, 6/7, 7/8, 8/9, 9/10, 10/11, 11/12, 12/13, 13/14, 14/15, 15/16, 16/17, 17/18, 18/19, 19/20, 20/21, 21/22, 22/23, 23/24, 24/25, 25/26, 26/27, 27/28, 28/29, 29/30, 30/31, 31/32, 32/33, 33/34, or 34/35.

In one embodiment $B_Y$ comprises SEQ ID NO: 89 with a DNA sequence inserted between positions bp 12 and 13 or a place corresponding to 29356 bp and 29357 bp in SEQ ID NO: 21. In one embodiment the insert is a restriction site insert. In one embodiment the restriction site insert comprises one or two restriction sites. In one embodiment the restriction site is a 19 bp restriction site insert comprising 2 restriction sites. In one embodiment the restriction site insert is a 9 bp restriction site insert comprising 1 restriction site. In one embodiment the restriction site insert comprises one or two restriction sites and at least one transgene, for example one or two or three transgenes, such as one or two transgenes. In one embodiment the restriction site is a 19 bp restriction site insert comprising 2 restriction sites and at least one transgene, for example one or two transgenes. In one embodiment the restriction site insert is a 9 bp restriction site insert comprising 1 restriction site and at least one transgene, for example one or two transgenes. In one embodiment two restriction sites sandwich one or more, such as two transgenes (for example in a transgene cassette). In one embodiment when BY comprises two restrictions sites the said restriction sites are different from each other. In one embodiment said one or more restrictions sites in $B_Y$ are non-naturally occurring (such as unique) in the particular adenovirus genome into which they have been inserted. In one embodiment said one or more restrictions sites in BY are different to other restrictions sites located elsewhere in the adenovirus genome, for example different to naturally occurring restrictions sites or restriction sites introduced into other parts of the genome, such as BX. Thus in one embodiment the restriction site or sites allow the DNA in the section to be cut specifically.

In one embodiment $B_Y$ has the sequence from 29345 bp to 29379 bp of SEQ ID NO: 21. In one embodiment $B_Y$ is a bond.

In one embodiment the insert is after bp 12 in SEQ ID NO: 89.

In one embodiment the insert is at about position 29356 bp of SEQ ID NO: 21.

In one embodiment the insert is a transgene cassette comprising one or more transgenes, for example 1, 2 or 3, such as 1 or 2.

E4 as employed herein refers to the DNA sequence encoding part or all of an adenovirus E4 region (i.e. polypeptide/protein region), which may be mutated such that the protein encoded by the E4 gene has conservative or non-conservative amino acid changes, and has the same function as wild-type (the corresponding non-mutated protein); increased function in comparison to wild-type protein; decreased function, such as no function in comparison to wild-type protein or has a new function in comparison to wild-type protein or a combination of the same as appropriate.

In one embodiment the E4 region is partially deleted, for example is 95%, 90%, 85%, 80%, 75%, 70%, 65%, 60%, 55%, 50%, 45%, 40%, 35%, 30%, 25%, 20%, 15%, 10% or 5% deleted. In one embodiment the E4 region has the sequence from 32188 bp to 29380 bp of SEQ ID NO: 21.

In one embodiment E4 is present except for the E4orf4 region which is deleted.

In one embodiment $B_3$ is a bond, i.e. wherein E4 is absent.

In one embodiment $B_3$ has the sequence consisting of from 32188 bp to 29380 bp of SEQ ID NO: 21.

As employed herein number ranges are inclusive of the end points.

The skilled person will appreciate that the elements in the formulas herein, such as formula (I), (Ia) are contiguous and may embody non-coding DNA sequences as well as the genes and coding DNA sequences (structural features) mentioned herein. In one or more embodiments the formulas of the present disclosure are attempting to describe a naturally occurring sequence in the adenovirus genome. In this context it will be clear to the skilled person that the formula is referring to the major elements characterising the relevant section of genome and is not intended to be an exhaustive description of the genomic stretch of DNA.

E1A, E1B, E3 and E4 as employed herein each independently refer to the wild-type and equivalents thereof, mutated or partially deleted forms of each region as described herein, in particular a wild-type sequence from a known adenovirus.

"Insert" as employed herein refers to a DNA sequence that is incorporated either at the 5' end, the 3' end or within a given DNA sequence reference segment such that it interrupts the reference sequence. The latter is a reference sequence employed as a reference point relative to which the insert is located. In the context of the present disclosure inserts generally occur within either SEQ ID NO: 88 or SEQ ID NO: 89. An insert can be either a restriction site insert, a transgene cassette or both. When the sequence is interrupted the virus will still comprise the original sequence, but generally it will be as two fragments sandwiching the insert.

In one embodiment the transgene or transgene cassette does not comprise a non-biased inserting transposon, such as a TN7 transposon or part thereof. Tn7 transposon as employed herein refers to a non-biased insertion transposon as described in WO2008/080003.

In one embodiment the transgene or transgene cassette further comprises a regulatory element or sequence.

Other Regulatory Sequences

"Regulator of gene expression" (or regulator/regulatory element) as employed herein refers to a genetic feature, such as a promoter, enhancer or a splice acceptor sequence that plays a role in gene expression, typically by initiating or enhancing transcription or translation.

"Splice acceptor sequence", "splice acceptor" or "splice site" as employed herein refers to a regulatory sequence determining when an mRNA molecule will be recognised by small nuclear ribonucleoproteins of the spliceosome complex. Once assembled the spliceosome catalyses splicing between the splice acceptor site of the mRNA molecule to an upstream splice donor site producing a mature mRNA molecule that can be translated to produce a single polypeptide or protein.

Different sized splice acceptor sequences may be employed in the present invention and these can be described as short splice acceptor (small), splice acceptor (medium) and branched splice acceptor (large).

SSA as employed herein means a short splice acceptor, typically comprising just the splice site, for example 4 bp. SA as employed herein means a splice acceptor, typically comprising the short splice acceptor and the polypyrimidine tract, for example 16 bp. bSA as employed herein means a branched splice acceptor, typically comprising the short splice acceptor, polypyrimidine tract and the branch point, for example 26 bp.

In one embodiment the splice acceptor employed in the constructs of the disclosure are CAGG or SEQ ID NO: 90 or 91. In one embodiment the SSA has the nucleotide sequence CAGG. In one embodiment the SA has the nucleotide sequence of SEQ ID NO: 90. In one embodiment the SA has the nucleotide sequence of SEQ ID NO: 91.

In one embodiment the splice site is immediately proceeded (i.e. followed in a 5' to 3' direction) by a consensus Kozak sequence comprising CCACC. In one embodiment the splice site and the Kozak sequence are interspersed by up to 100 or less bp. In one embodiment the Kozak sequence has the nucleotide sequence of CCACC.

Typically, when under the control of an endogenous or exogenous promoter (such as an endogenous promoter), the coding sequence will be immediately preceded by a Kozak sequence. The start of the coding region is indicated by the initiation codon (AUG), for example is in the context of the sequence (gcc)gccRccAUGg [SEQ ID NO: 92] the start of the start of the coding sequences is indicated by the bases in bold. A lower case letter denotes common bases at this position (which can nevertheless vary) and upper case letters indicate highly-conserved bases, i.e. the 'AUGG' sequence is constant or rarely, if ever, changes; 'R' indicates that a purine (adenine or guanine) is usually observed at this position and the sequence in brackets (gcc) is of uncertain significance. Thus in one embodiment the initiation codon AUG is incorporated into a Kozak sequence.

Internal Ribosome Entry DNA Sequence as employed herein refers to a DNA sequence encoding an Internal Ribosome Entry Sequence (IRES). IRES as employed herein means a nucleotide sequence that allows for initiation of translation a messenger RNA (mRNA) sequence, including initiation starting within an mRNA sequence. This is particularly useful when the cassette encodes polycistronic mRNA. Using an IRES results in a polycistronic mRNA that is translated into multiple individual proteins or peptides. In one embodiment the Internal Ribosome Entry DNA sequence has the nucleotide sequence of SEQ ID NO: 93. In one embodiment a particular IRES is only used once in the genome. This may have benefits with respect to stability of the genome.

"High self-cleavage efficiency 2A peptide" or "2A peptide" as employed herein refers to a peptide which is efficiently cleaved following translation. Suitable 2A peptides include P2A, F2A, E2A and T2A. The present inventors have noted that once a specific DNA sequence encoding a given 2A peptide is used once, the same specific DNA sequence may not be used a second time. However, redundancy in the DNA code may be utilised to generate a DNA sequence that is translated into the same 2A peptide. Using 2A peptides is particularly useful when the cassette encodes polycistronic mRNA. Using 2A peptides results in a single polypeptide chain being translated which is modified post-translation to generate multiple individual proteins or peptides.

In one embodiment the encoded P2A peptide employed has the amino acid sequence of SEQ ID NO: 94. In one embodiment the encoded F2A peptide employed has the amino acid sequence of SEQ ID NO: 95. In one embodiment the encoded E2A peptide employed has the amino acid sequence of SEQ ID NO: 96. In one embodiment the encoded T2A peptide employed has the amino acid sequence of SEQ ID NO: 97.

In one embodiment an mRNA or each mRNA encoded by transgene is/are comprise a polyadenylation signal sequence, such as typically at the end of an mRNA sequence. Thus one embodiment the transgene or the transgene cassette comprises at least one sequence encoding a polyadenylation signal sequence.

“PolyA”, “Polyadenylation signal” or “polyadenylation sequence” as employed herein means a DNA sequence, usually containing an AATAAA site, that once transcribed can be recognised by a multiprotein complex that cleaves and polyadenylates the nascent mRNA molecule.

In one embodiment the construct does not include a polyadenylation sequence. In one embodiment the regulator of gene expression is a splice acceptor sequence.

In one embodiment the sequence encoding a protein/polypeptide/peptide, such as an antibody or antibody fragment further comprises a polyadenylation signal.

In one embodiment there is provided a virus or construct with a sequence disclosed herein.

Antibodies

Antibody molecule as employed herein includes any construct comprising a full length antibody or a binding fragment thereof, multispecific antibody formats. Thus the antibody molecules of the present invention include a complete antibody molecule having full length heavy and light chains or a fragment thereof and may be, but are not limited to Fab, modified Fab, Fab', modified Fab', F(ab')2, Fv, Fab-Fv, Fab-dsFv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g. bispecific or may be monospecific (see for example WO 92/22853 and WO05/113605). Bispecific and multispecific antibody variants are especially considered in this example since the aim is to neutralise two independent target proteins:

Unless the context indicates otherwise antibody will generally refer to a full length antibody.

Antibody binding fragment as employed herein refers to less than a full-length antibody, which retains specificity for the target antigen. Antibody binding fragments may include a Fab, Fab', modified Fab', F(ab')2, Fv, Fab-Fv, Fab-dsFv, single domain antibodies (e.g. VH or VL or VHH), scFv, ds-scFv.

In one embodiment antibodies or binding fragments thereof employed in the technology of the present disclosure are monoclonal.

Monoclonal antibodies for use in the present disclosure may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and International Patent Application number WO2004/106377.

Binding domains employed in antibody molecules of the present disclosure may be humanised. Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

When the CDRs or specificity determining residues are grafted, any appropriate acceptor variable region framework sequence may be used having regard to the class/type of the donor antibody from which the CDRs are derived, including mouse, primate and human framework regions. Suitably, the humanised antibody according to the present invention has a variable domain comprising human acceptor framework regions as well as one or more of the CDRs provided herein.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a humanised antibody of the present invention, the acceptor heavy and light chains do not necessarily need to be derived from the same antibody and may, if desired, comprise composite chains having framework regions derived from different chains.

Also, in a humanised antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply neutralising or agonising an antigen. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705:129-134, 1995).

Formulations

The present disclosure relates also extends to a pharmaceutical formulation of a virus as described herein.

In one embodiment there is provided a liquid parenteral formulation, for example for infusion or injection, of a replication capable oncolytic virus or replication deficient viral vector according to the present disclosure wherein the formulation provides a dose in the range of $1\times10^{10}$ to $1\times10^{14}$ viral particles per volume of dose.

Parenteral formulation means a formulation designed not to be delivered through the GI tract. Typical parenteral delivery routes include injection, implantation or infusion. In one embodiment the formulation is provided in a form for bolus delivery.

In one embodiment the parenteral formulation is in the form of an injection. Injection includes intravenous, subcutaneous, intra-tumoral or intramuscular injection. Injection as employed herein means the insertion of liquid into the body via a syringe. In one embodiment the method of the present disclosure does not involve intra-tumoral injection.

In one embodiment the parenteral formulation is in the form of an infusion.

Infusion as employed herein means the administration of fluids at a slower rate by drip, infusion pump, syringe driver or equivalent device. In one embodiment the infusion is administered over a period in the range of 1.5 minutes to 120 minutes, such as about 3, 4, 5, 6, 7, 8, 9, 10, 11, 12, 13, 14 15, 16, 17, 18, 19 20, 25, 30, 35, 40, 45, 50, 55, 60, 65, 70, 65, 80, 85, 90, 95, 100, 105, 110 or 115 minutes.

In one embodiment one dose of the formulation less than 100 mls, for example 30 mls, such as administered by a syringe driver.

In one embodiment the injection is administered as a slow injection, for example over a period of 1.5 to 30 minutes.

In one embodiment the formulation is for intravenous (i.v.) administration. This route is particularly effective for delivery of oncolytic virus because it allows rapid access to the majority of the organs and tissue and is particular useful for the treatment of metastases, for example established metastases especially those located in highly vascularised regions such as the liver and lungs.

Therapeutic formulations typically will be sterile and stable under the conditions of manufacture and storage. The composition can be formulated as a solution, microemulsion, liposome, or other parenteral formulation suitable for administration to a human and may be formulated as a pre-filled device such as a syringe or vial, particular as a single dose.

The formulation will generally comprise a pharmaceutically acceptable diluent or carrier, for example a non-toxic, isotonic carrier that is compatible with the virus, and in which the virus is stable for the requisite period of time.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a dispersant or surfactant such as lecithin or a non-ionic surfactant such as polysorbate 80 or 40. In dispersions the maintenance of the required particle size may be assisted by the presence of a surfactant. Examples of isotonic agents include sugars, polyalcohols such as mannitol, sorbitol, or sodium chloride in the composition.

In one embodiment parenteral formulations employed may comprise one or more of the following a buffer, for example 4-(2-hydroxyethyl)-1-piperazineethanesulfonic acid, a phosphate buffer and/or a Tris buffer, a sugar for example dextrose, mannose, sucrose or similar, a salt such as sodium chloride, magnesium chloride or potassium chloride, a detergent such as a non-ionic surfactant such as brij, PS-80, PS-40 or similar. The formulation may also comprise a preservative such as EDTA or ethanol or a combination of EDTA and ethanol, which are thought to prevent one or more pathways of possible degradation.

In one embodiment the formulation will comprise purified oncolytic virus according to the present disclosure, for example $1\times10^{18}$ to $1\times10^{14}$ viral particles per dose, such as $1\times10^{18}$ to $1\times10^{12}$ viral particles per dose. In one embodiment the concentration of virus in the formulation is in the range $2\times10^{8}$ to $2\times10^{14}$ vp/mL, such as $2\times10^{12}$ vp/ml.

In one embodiment the parenteral formulation comprises glycerol.

In one embodiment the formulation comprises oncolytic adenovirus as described herein, HEPES (N-2-hydroxyethylpiperazine-N'-2-ethanesulfonic acid), glycerol and buffer. In one embodiment the parenteral formulation consists of virus of the disclosure, HEPES for example 5 mM, glycerol for example 5-20% (v/v), hydrochloric acid, for example to adjust the pH into the range 7-8 and water for injection.

In one embodiment 0.7 mL of virus of the disclosure at a concentration of $2\times10^{12}$ vp/mL is formulated in 5 mM HEPES, 20% glycerol with a final pH of 7.8.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure will generally contain a virus as described herein with a physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the carrying the virus is of primary importance and thus in one embodiment the virus according to the present disclosure may be adsorbed or absorbed onto a particle, such as a lactose particle of the given size.

The propellant gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The above-mentioned propellant gases may be used on their own or in mixtures thereof.

Particularly suitable propellant gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellant gas-containing inhalable aerosols may also contain other ingredients, such as co-solvents, stabilisers, surface-active agents (surfactants), antioxidants, lubricants and means for adjusting the pH. All these ingredients are known in the art.

The propellant gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The virus of the invention can be delivered dispersed in a solvent, e.g. in the form of a solution or a suspension, for example as already described above for parenteral formulations. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution and dispensing of the formulation into sterile receptacles by methods familiar to those of ordinary skill in the art.

Nebulisable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

Treatment

In a further aspect the present disclosure extends to a virus or viral vector or a formulation thereof as described herein for use in treatment, in particular for the treatment of cancer.

In one embodiment the method of treatment is for use in the treatment of a tumour.

Tumour as employed herein is intended to refer to an abnormal mass of tissue that results from excessive cell division that is uncontrolled and progressive, also called a neoplasm. Tumours may be either benign (not cancerous) or malignant. Tumour encompasses all forms of cancer and metastases.

In one embodiment the tumour is a solid tumour. The solid tumour may be localised or metastasised.

In one embodiment the tumour is of epithelial origin.

In one embodiment the tumour is a malignancy, such as colorectal cancer, hepatoma, prostate cancer, pancreatic cancer, breast cancer, ovarian cancer, thyroid cancer, renal cancer, bladder cancer, head and neck cancer or lung cancer.

In one embodiment the tumour is a colorectal malignancy.

Malignancy as employed herein means cancerous cells.

In one embodiment the oncolytic virus or viral vector is employed in the treatment or prevention of metastasis.

In one embodiment the method or formulation herein is employed in the treatment of drug resistant cancers.

In one embodiment the virus or viral vector is administered in combination with the administration of a further cancer treatment or therapy.

In one embodiment there is provided a virus, viral vector or formulation according to the present disclosure for use in the manufacture of a medicament for the treatment of cancer, for example a cancer described above.

In a further aspect there is provide a method of treating cancer comprising administering a therapeutically effective amount of a virus or formulation according to the present disclosure to a patient in need thereof, for example a human patient.

In one embodiment the oncolytic virus or formulation herein is administered in combination with another therapy.

"In combination" as employed herein is intended to encompass where the oncolytic virus or viral vector is administered before, concurrently and/or post cancer treatment or therapy.

Cancer therapy includes surgery, radiation therapy, targeted therapy and/or chemotherapy.

Cancer treatment as employed herein refers to treatment with a therapeutic compound or biological agent, for example an antibody intended to treat the cancer and/or maintenance therapy thereof.

In one embodiment the cancer treatment is selected from any other anti-cancer therapy including a chemotherapeutic agent, a targeted anticancer agent, radiotherapy, radio-isotope therapy or any combination thereof.

In one embodiment the virus or viral vector of the present disclosure ay be used as a pre-treatment to the therapy, such as a surgery (neoadjuvant therapy), to shrink the tumour, to treat metastasis and/or prevent metastasis or further metastasis. The oncolytic virus or viral vector may be used after the therapy, such as a surgery (adjuvant therapy), to treat metastasis and/or prevent metastasis or further metastasis.

Concurrently as employed herein is the administration of the additional cancer treatment at the same time or approximately the same time as the oncolytic virus or viral vector formulation. The treatment may be contained within the same formulation or administered as a separate formulation.

In one embodiment the virus or viral vector is administered in combination with the administration of a chemotherapeutic agent.

Chemotherapeutic agent as employed herein is intended to refer to specific antineoplastic chemical agents or drugs that are selectively destructive to malignant cells and tissues. For example, alkylating agents, antimetabolites, anthracyclines, plant alkaloids, topoisomerase inhibitors, and other antitumour agents. Other examples of chemotherapy include doxorubicin, 5-fluorouracil (5-FU), paclitaxel, capecitabine, irinotecan, and platins such as cisplatin and oxaliplatin. The preferred dose may be chosen by the practitioner based on the nature of the cancer being treated.

In one embodiment the therapeutic agent is ganciclovir, which may assist in controlling immune responses and/or tumour vascularisation.

In one embodiment the therapeutic agent is a check-point inhibitor, such as PD-1 inhibitor, a PD-L1 inhibitor, in particular wherein the inhibitor is a monoclonal antibody or antibody fragment.

In one embodiment one or more therapies employed in the method herein are metronomic, that is a continuous or frequent treatment with low doses of anticancer drugs, often given concomitant with other methods of therapy.

Subgroup B oncolytic adenoviruses, in particular Ad11 and those derived therefrom such as EnAd may be particularly synergistic with chemotherapeutics because they seem to have a mechanism of action that is largely independent of apoptosis, killing cancer cells by a predominantly necrolytic mechanism. Moreover, the immunosuppression that occurs during chemotherapy may allow the oncolytic virus to function with greater efficiency.

Therapeutic dose as employed herein refers to the amount of virus or viral vector that is suitable for achieving the intended therapeutic effect when employed in a suitable treatment regimen, for example ameliorates symptoms or conditions of a disease. A dose may be considered a therapeutic dose in the treatment of cancer or metastases when the number of viral particles may be sufficient to result in the following: tumour or metastatic growth is slowed or stopped, or the tumour or metastasis is found to shrink in size, and/or the life span of the patient is extended. Suitable therapeutic doses are generally a balance between therapeutic effect and tolerable toxicity, for example where the side-effect and toxicity are tolerable given the benefit achieved by the therapy.

In one embodiment there is provided systemically administering multiple doses of a parenteral formulation of an oncolytic adenovirus according to the present disclosure in a single treatment cycle, for example wherein the total dose given in each administration is in the range of $1\times10^{10}$ to $1\times10^{14}$ viral particles per dose.

In one embodiment one or more doses (for example each dose) of virus or viral vector is administered such that the rate of viral particle delivery is in the range of $2\times10^{10}$ particles per minute to $2\times10^{12}$ particles per minute.

In one embodiment a virus or therapeutic construct according to the present disclosure (including a formulation comprising same) is administered weekly, for example one week 1 the dose is administered on day 1, 3, 5, followed by one dose each subsequent week.

In one embodiment a virus or therapeutic construct according to the present disclosure (including a formulation comprising same) is administered bi-weekly or tri-weekly, for example is administered in week 1 one on days 1, 3 and 5, and on week 2 or 3 is also administered on days 1, 3 and 5 thereof. This dosing regimen may be repeated as many times as appropriate.

In one embodiment a virus or therapeutic construct according to the present disclosure (including a formulation comprising same) is administered monthly.

In one embodiment the viruses, viral vectors and constructs of the present disclosure are prepared by recombinant techniques. The skilled person will appreciate that the armed virus or viral vector genome can be manufactured by other technical means, including entirely synthesising the genome or a plasmid comprising part of all of the genome. The skilled person will appreciate that in the event of synthesising the genome the region of insertion may not comprise the restriction site nucleotides as the latter are artefacts following insertion of genes using cloning methods.

In one embodiment the armed virus or viral vector genome is entirely synthetically manufactured, The disclosure herein further extends to a virus of formula (I) or a subformula thereof, obtained or obtainable from inserting a transgene or transgene cassette.

"Is" as employed herein means comprising.

In the context of this specification "comprising" is to be interpreted as "including".

Embodiments of the invention comprising certain features/elements are also intended to extend to alternative embodiments "consisting" or "consisting essentially" of the relevant elements/features.

Where technically appropriate, embodiments of the invention may be combined. Technical references such as patents and applications are incorporated herein by reference.

Any embodiments specifically and explicitly recited herein may form the basis of a disclaimer either alone or in combination with one or more further embodiments.

The present invention is further described by way of illustration only in the following examples.

EXAMPLES

Example 1: Production of EnAd Viruses Expressing the T Cell Activating Antigen CD80 and a Membrane-Anchored Single Chain Fv Fragment Antibody to the ε Chain of the Human CD3 Complex (CD3ε)

Figure 2A:
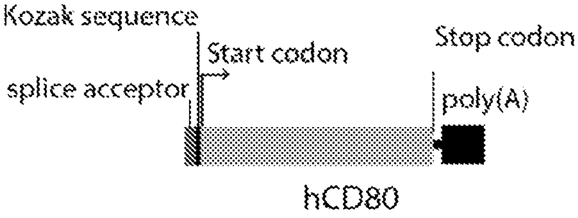
Figure 2B:
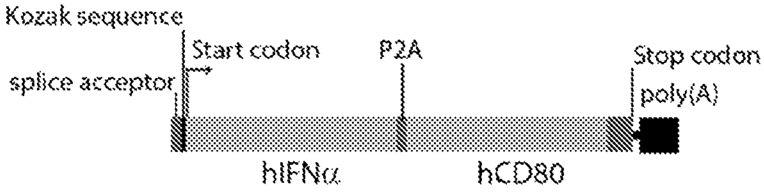
Figure 2C:
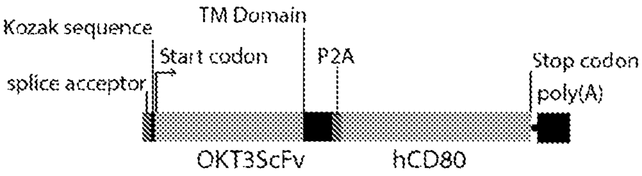
Figure 2D:
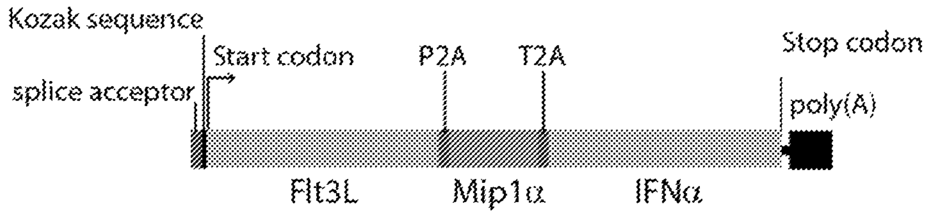
Figure 2E:
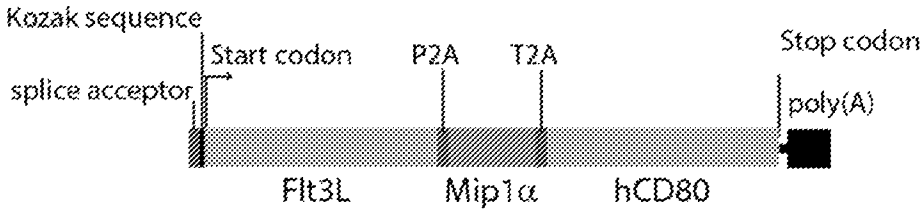
Figure 2F:
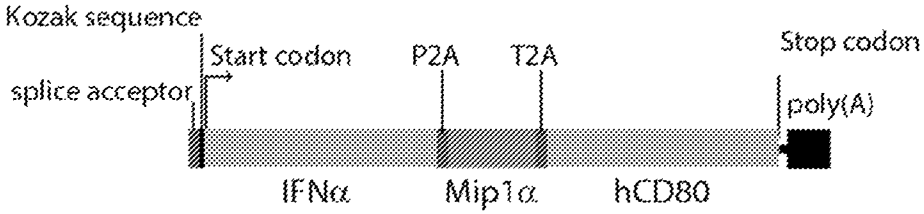
Figure 2F:
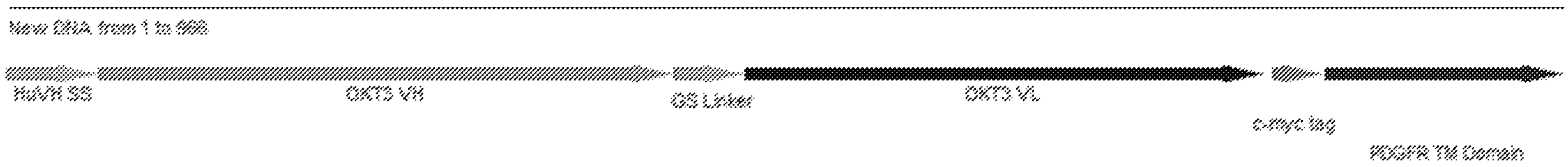

The plasmid pEnAd2.4 was used to generate the plasmids pNG-348 by direct insertion of a cassette encoding the human T cell activating antigen CD80 (SEQ ID NO 98) and a membrane-anchored chimeric form of the single chain Fv anti-human CD3e (SEQ ID NO 4). The pNG-348 cassette contains; a 5' short splice acceptor sequence (CAGG); membrane-anchored anti-human CD3e ScFv cDNA; a high efficiency self-cleavable P2A peptide sequence (SEQ ID NO. 94); human CD80 cDNA sequence and a 3' polyadenylation sequence (SEQ ID NO. 99. A Schematic of the inserted transgene cassette is shown in FIG. 2C. Construction of the plasmid is confirmed by DNA sequencing.

Virus Production and Characterisation

The plasmid pNG-348 is linearised by restriction digest with the enzyme AscI to produce the virus genome NG-348 (SEQ ID NO: 100). The virus NG-348 is amplified and purified according to methods given below.

Digested DNA was purified by phenol/chloroform extraction and precipitated for 16 hrs, −20° C. in 300 µl>95% molecular biology grade ethanol and 10 µl 3M Sodium Acetate. The precipitated DNA was pelleted by centrifuging at 14000 rpm, 5 mins and was washed in 500 µl 70% ethanol, before centrifuging again, 14000 rpm, 5 mins. The clean DNA pellet was air dried, resuspended in 500 µl OptiMEM containing 15 µl lipofectamine transfection reagent and incubated for 30 mins, RT. The transfection mixture was then added drop wise to a T-25 flask containing 293 cells grown to 70% confluency. After incubation of the cells with the transfection mix for 2 hrs at 37° C., 5% $CO_2$ 4 mls of cell media (DMEM high glucose with glutamine supplemented with 2% FBS) was added to the cells and the flasks was incubated 37° C., 5% $CO_2$.

The transfected 293 cells were monitored every 24 hrs and were supplemented with additional media every 48-72 hrs. The production of virus was monitored by observation of a significant cytopathic effect (CPE) in the cell monolayer. Once extensive CPE was observed the virus was harvested from 293 cells by three freeze-thaw cycles. The harvested viruses were used to re-infect 293 cells in order to amplify the virus stocks. Viable virus production during amplification was confirmed by observation of significant CPE in the cell monolayer. Once CPE was observed the virus was harvested from 293 cells by three freeze-thaw cycles. The amplified stock was used for further amplification before the virus was purified by double caesium chloride banding to produce a NG-330 virus stock.

Example 2: Production of EnAd Viruses Expressing the T Cell Activating Antigen CD80 and a Membrane-Anchored Single Chain Fv Fragment Antibody to the ε Chain of the Human CD3 Complex (CD3ε)

Figure 3:
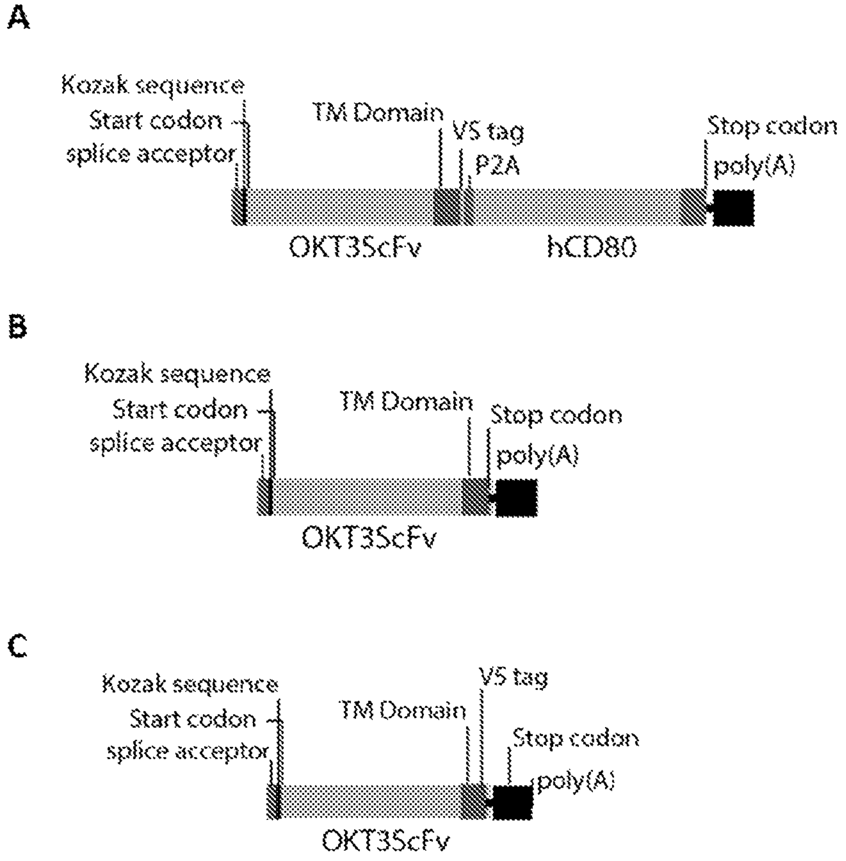
FIG. 3 shows schematics of the NG-348A (A), NG-420 (B) and NG-420A (C) transgene cassettes

The plasmid pEnAd2.4 was used to generate the plasmids pNG-348A by direct insertion of a cassette encoding the human T cell activating antigen CD80 (SEQ ID NO 98) and a membrane-anchored chimeric form of the single chain Fv anti-human CD3e with a C-terminal V5 tag (SEQ ID NO: 5). The pNG-348 cassette contains; a 5' short splice acceptor sequence (CAGG); membrane-anchored anti-human CD3e ScFv cDNA; a C-terminal V5 tag (SEQ ID NO: 101); a high efficiency self-cleavable P2A peptide sequence (SEQ ID NO: 94); human CD80 cDNA sequence and a 3' polyadenylation sequence (SEQ ID NO: 99). A Schematic of the NG-348A transgene cassettes is shown in FIG. 3, panel A. Construction of the plasmid is confirmed by DNA sequencing.

Virus Production and Characterisation

The plasmid pNG-348A is linearised by restriction digest with the enzyme AscI to produce the virus genome NG-348A (SEQ ID NO: 102). The virus NG-348A is amplified and purified according to methods detailed in Example 1.

Example 3: Production of EnAd Viruses Expressing a Membrane-Anchored Single Chain Fv Fragment Antibody to the ε Chain of the Human CD3 Complex (CD3ε)

The plasmid pEnAd2.4 was used to generate the plasmids pNG-420 and pNG-420A by direct insertion of a cassettes encoding a membrane-anchored chimeric form of the single chain Fv anti-human CD3e with a C-terminal V5 tag (SEQ ID NO: 5) or without a V5 tag (SEQ ID NO: 4). The pNG-420 cassette contains; a 5' short splice acceptor sequence (CAGG); membrane-anchored anti-human CD3e ScFv cDNA and a 3' polyadenylation sequence (SEQ ID NO: 99). The pNG-420A cassette contains; a 5' short splice acceptor sequence (CAGG); membrane-anchored anti-human CD3e scFv cDNA; a C-terminal V5 tag (SEQ ID NO: 101) and a 3' polyadenylation sequence (SEQ ID NO: 99). Schematics of the NG-420 and NG-420A transgene cassettes are shown in FIG. 3, panels B and C. Construction of each plasmid is confirmed by DNA sequencing.

Virus Production and Characterisation

The plasmids pNG-420 and pNG-420A are linearised by restriction digest with the enzyme AscI to produce the virus genomes NG-420 (SEQ ID NO: 103) and NG-420A (SEQ ID NO: 104). The viruses NG-420 and NG-420A are amplified and purified according to methods detailed in Example 1.

Figure 43:
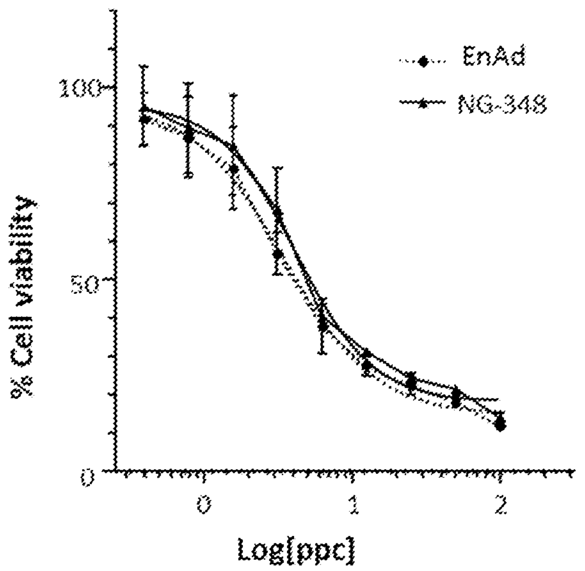
FIG. 43 shows comparable oncolytic potency (left panel) and infectivity (table) of EnAd, and NG-348 viruses in an HT-29 cytotoxicity assay
Figure 44:
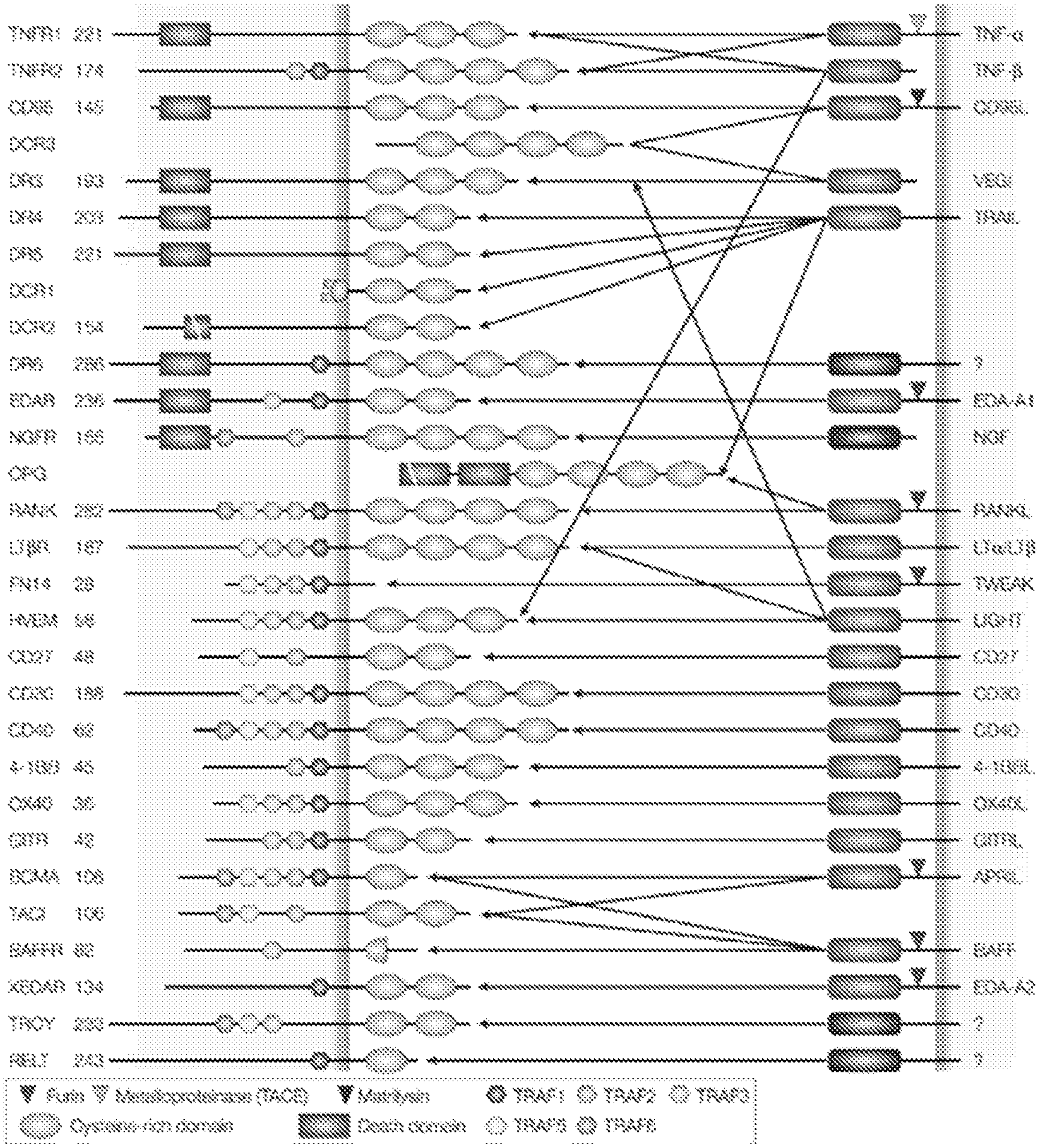
FIG. 44 shows the signalling pathway of the TNF superfamily, from a Nature Reviews Immunology 3, 745-756 (September 2003).

Example 4: Oncolytic Activity and Infectivity of NG-347 and NG-348 Viruses in Colon Carcinoma Cells Virus Oncolytic Potency HT-29 colon carcinoma cells were seeded in 96 well plates at a cell density of 2.5e4 cells/well. Plates were incubated for 4 hrs, 37° C., 5% $CO_2$, before cells were either infected with EnAd, NG-347 or NG-348 virus particles at an infection density range of 100-0.39 particles per cell (ppc). HT-29 cell viability was assessed using Cell Titre 96 MTS Reagent (Promega: G3581) 72 hrs post infection. Quantification of the % cell survival at each infection density demonstrated that NG-348 oncolytic potency was comparable to EnAd (FIG. 43).

Viral Particle Infectivity

HT-29 colon carcinoma cells were seeded in 12 well plates at a cell density of 4e5 cells/well. Plates were incubated for 24 hrs, 37° C., 5% $CO_2$, before cells were either infected with EnAd, NG-347 or NG-348 virus particles at an infection density range of 1.6e7-2e6 vp/mL. Infection of HT-29 cells was detected by antibody staining of the virus protein hexon. Stained cells were quantified by manual counting of 6 fields of view per well, across 6 replicate wells for each dilution tested. The particle to infectivity ratio (P:I) was calculated for each virus from the viral titre and demonstrated NG-348 has similar infectivity ratios to EnAd reference controls (FIG. 43 Table).

Example 5: Cell Surface Expression of the T Cell Activating Antigen, CD80, in NG-347 and NG-348 Infected Carcinoma Cell Lines CD80 transgene expression (assessed by flow cytometry) was compared in NG-348 and EnAd treated colon carcinoma cell line, DLD-1 or lung carcinoma cell line, A549. A549 or DLD-1 carcinoma cell lines were seeded in 12 well plates at cell densities of 7.5e5 cells/well. Plates were incubated for 18 hrs, 37° C., 5% $CO_2$, before cells were either infected with, 10 EnAd, NG-348 virus particles per cell (ppc) or were left uninfected. CD80 protein expression was compared on the surface of A549 or DLD-1 cells at 24, 48, 72 or 96 hrs post-infection. At each time point cells were harvested and stained according to methods detailed below.

For CD80 cell surface expression, cells were then either incubated at 5° C. for 1 hr with buffer, mouse isotype control antibody conjugated to Cy5 or anti-human CD80 antibody conjugated to Cy5 (clone 2D10). All samples were also co-stained with Zombie Aqua live/dead to differentiate viable cells. Samples were washed 3 times with 1% BSA/PBS before analysis by flow cytometry (FACS, Attune) for cell viability and CD80 protein expression on the cell surface. In keeping with the IFNα expression data, CD80 expression could only be detected on HT-29 cells, with no detectable expression on either the fibroblast or bronchial epithelial cell lines.

Figure 4A:
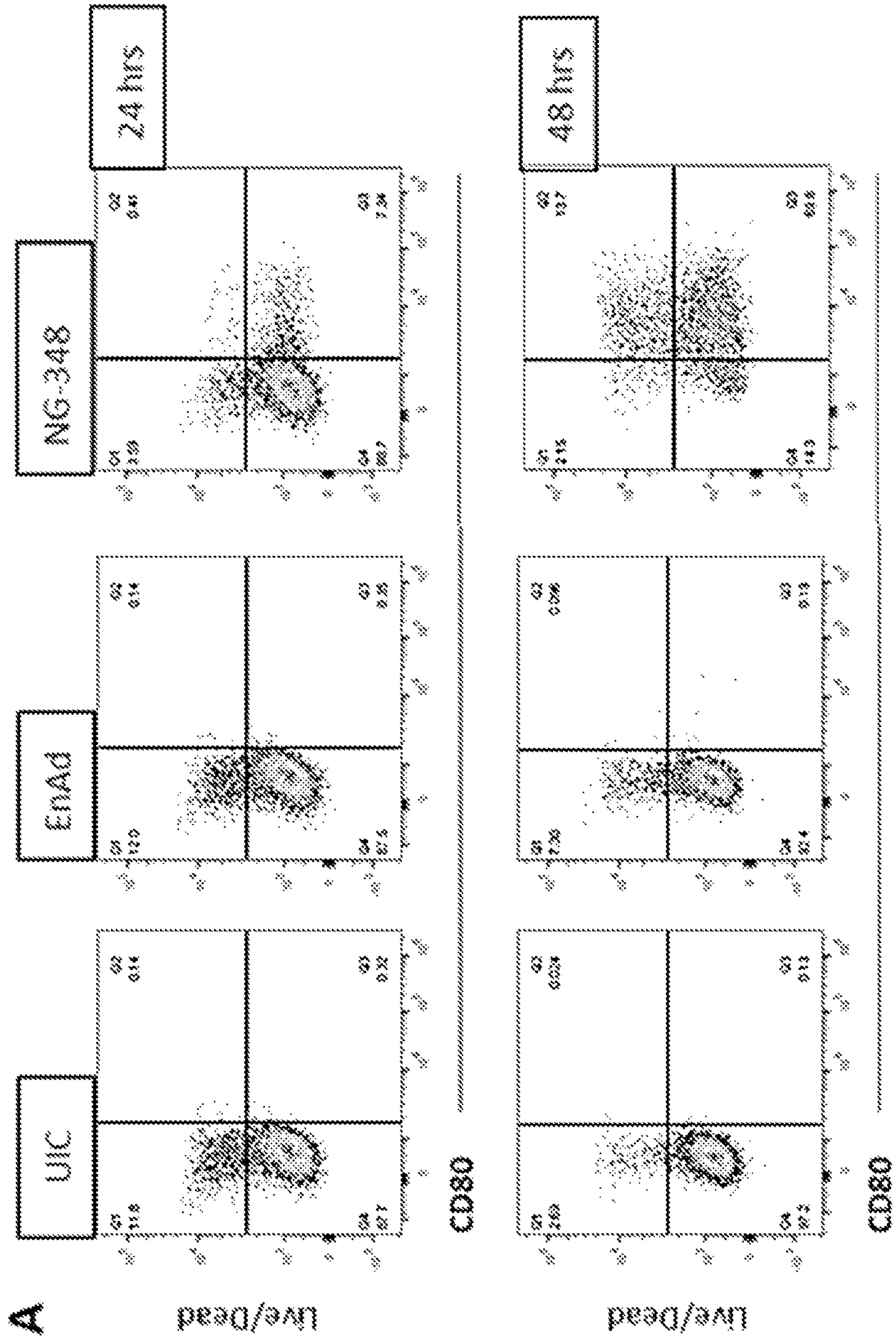
FIGS. 4A-4B show high CD80 expression by 48 hours on the cell surface of A549 tumour cells infected with either NG-347 or NG-348 viruses but little or no CD80 expression following EnAd infection
Figure 4A:
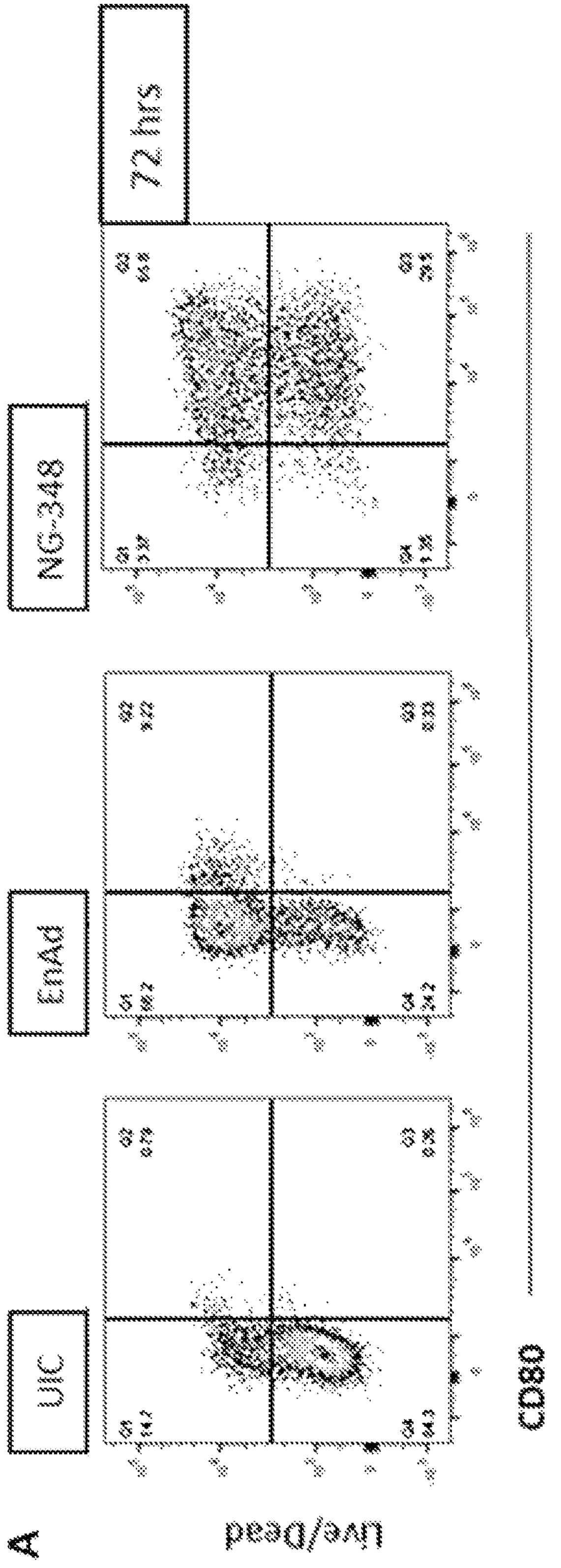
Figure 4B:
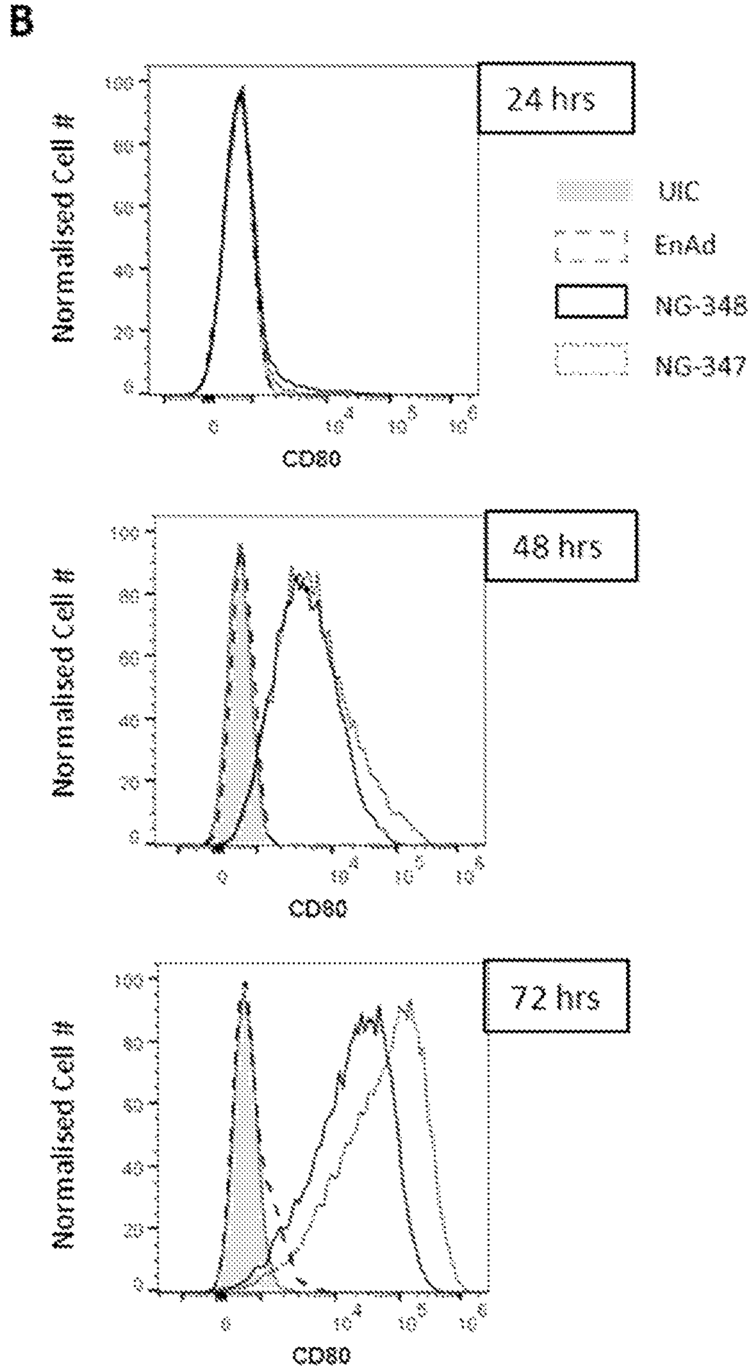
Figure 5A:
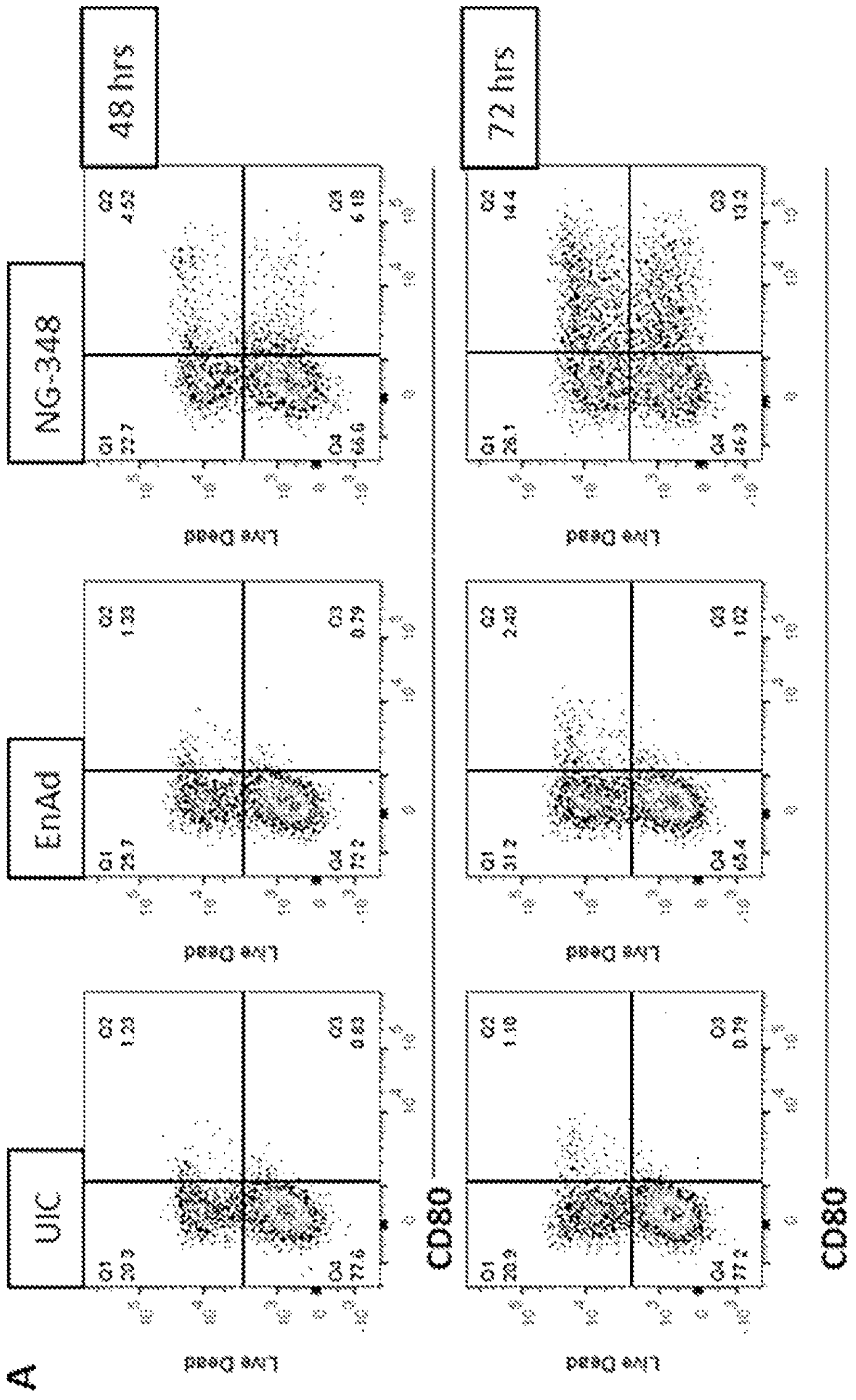
FIGS. 5A-5B show high CD80 expression by 48 hours on the cell surface of DLD-1 tumour cells infected with NG-348 viruses but little or no CD80 expression following EnAd infection
Figure 5A:
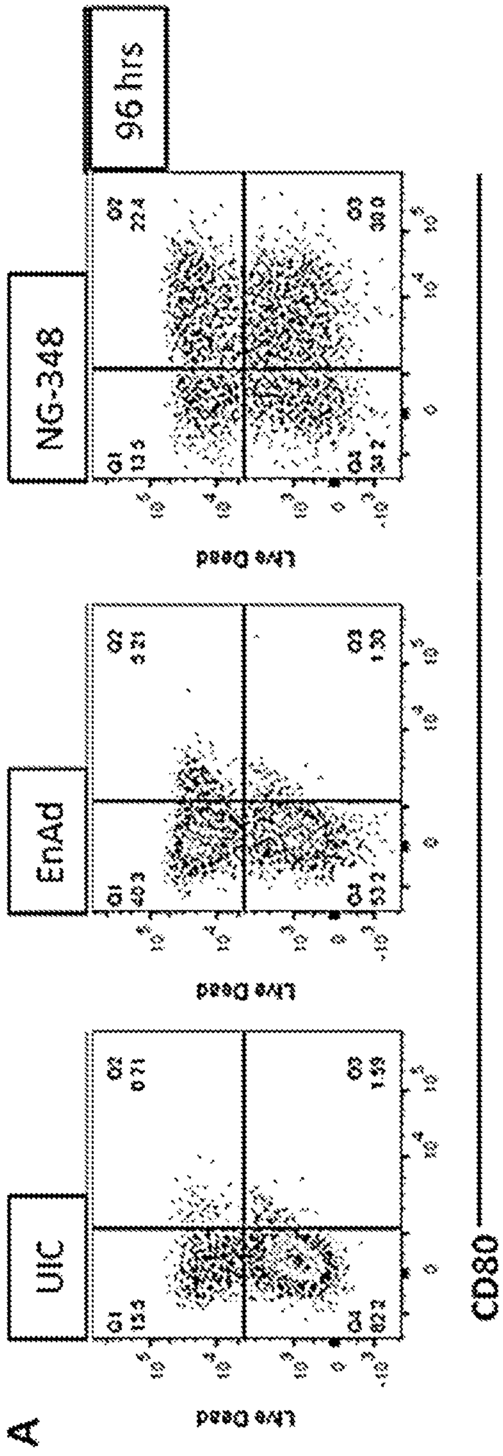
Figure 5B:
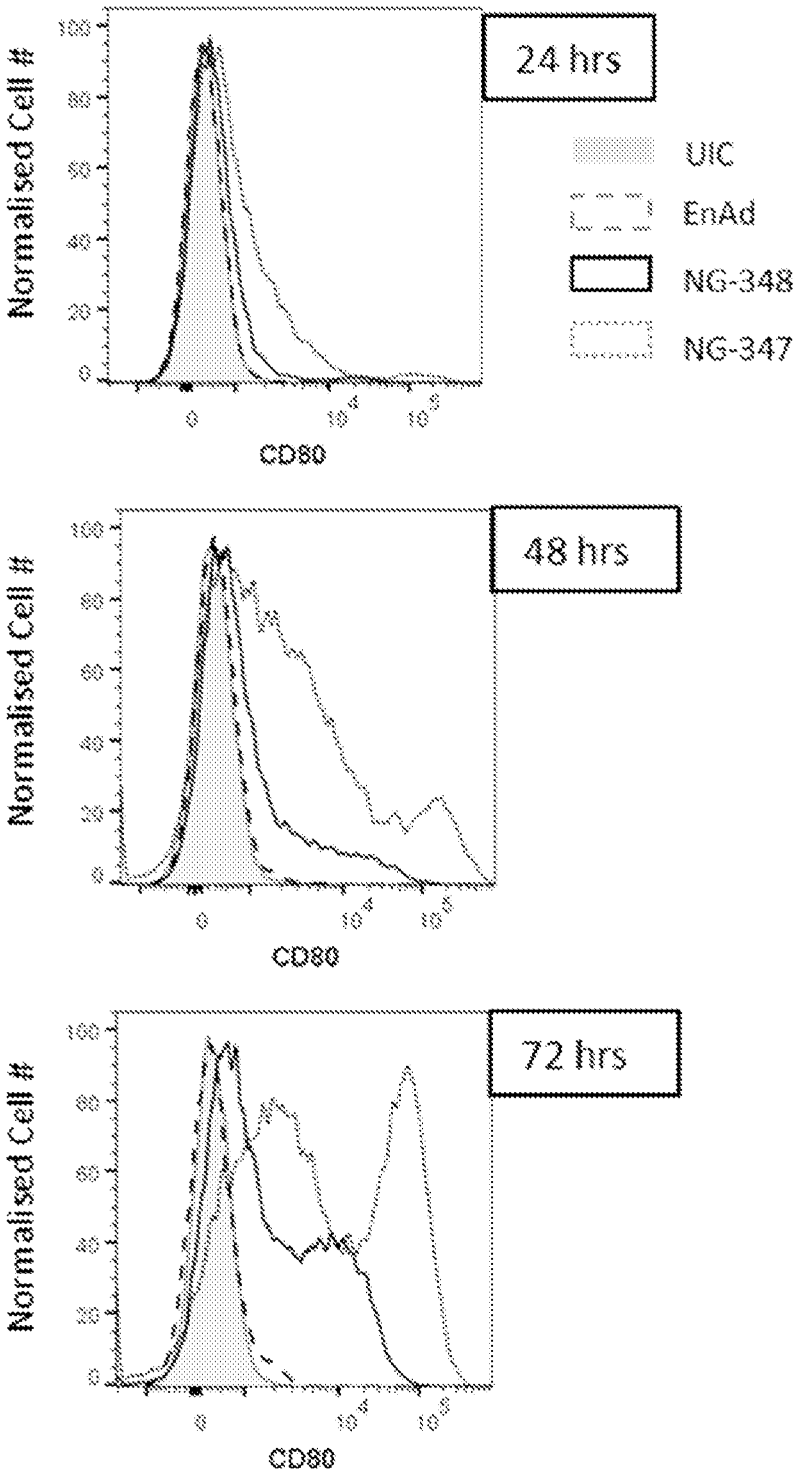

Cells were analysed for cell viability and CD80 protein expression at the cell surface by flow cytometry. Analysis of CD80 expression at 72 hrs post infection in A549 cells showed CD80 could be detected on the surface of >95% of NG-348 treated cells (FIGS. 4A and 4B). At 96 hrs post infection the virus treatments had lysed the majority of A549 cells therefore FACs analysis was not carried out. For DLD-1 cells expression could be detected on >50% of cells by 96 hrs post-treatment with NG-348 (FIGS. 5A and 5B). Staining was not detected on EnAd or untreated controls.

Example 6: T Cell Activation and Degranulation Mediated by NG-348 Infected Carcinoma Cell Lines A549 lung carcinoma cells, either infected with NG-348 or EnAd virus particles or left uninfected, were co-cultured with T cells isolated from human PBMC donors. The selectivity of expression of NG-348 virus encoded CD80 was assessed on the surface of both A549 and T cells by flow cytometry. T cell activation was assessed by analysing cell surface activation markers (by Flow cytometry), CD107a cell surface expression as a marker for degranulation (by Flow cytometry) and secretion of stimulatory cytokines, IL-2 and IFNγ (by ELISA).

A549 cells were seeded into 12 well plates at a density of 5e5 cells/well. Plates were incubated for 18 hrs, 37° C., 5% $CO_2$, before cells were either infected with 10 EnAd or NG-348 virus particles per cell (ppc) or were left uninfected. At 48 hrs post-infection $CD3^+$ T cells, isolated by negative selection from PBMCs (MACs) were added to the A549 cell monolayers at a ratio of 8 T cells:1 tumour cell. The co-culture was carried out for 16 hrs, after which point cellular supernatants were collected for ELISA analysis and tumour cells and T cells harvested for Flow cytometry analysis. Culture media containing non-adherent cells was removed from co-culture wells and centrifuged (300×g). The supernatant was carefully removed, diluted 1 in 2 with PBS 5% BSA and stored for ELISA analysis. The adherent cell monolayers were washed once with PBS and then detached using trypsin. The trypsin was inactivated using complete media and the cells were added to the cell pellets that had been collected from the culture supernatants. The cells were centrifuged (300×g), the supernatant discarded and the cell pellet washed in 200 μL of PBS. The cells were centrifuged again then resuspended in 50 μL of FACs buffer (5% BSA PBS) containing Live/Dead Aqua (Life tech) for 15 minutes at RT. The cells were washed once in FACs buffer before staining with panels of directly conjugated antibodies: anti-CD3 conjugated to BV605; anti-CD25 conjugated to BV421; anti-CD107a conjugated to FITC; anti-EpCam conjugated to PE or anti-CD4 conjugated to PE; and either anti-CD80 conjugated to PE/Cy5 or anti-HLA-DR conjugated to PE/Cy5. A sample of cells from each co-culture condition was also stained with relevant isotype control antibodies. All staining was carried out in FACs buffer in a total volume of 504/well for 15 minutes, 4° C. Cells were then washed with FACs buffer (2004) before resuspension in 2004 of FACs buffer and analysis by Flow cytometry (Attune).

Selective Expression of CD80

Figure 6:
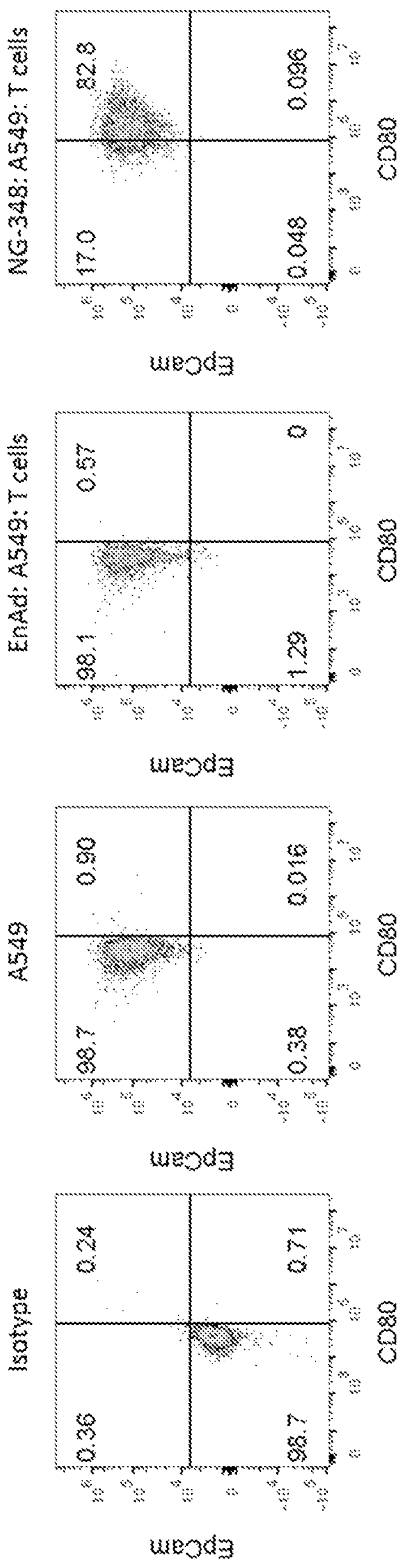
FIG. 6 shows CD80 expression on $EpCam^+$ A549 cells infected with NG-348 and co-cultured with human $CD3^+$ T-cells, but not when infection was with EnAd

Similar to results shown in example 14, CD80 expression was detectable at the surface of >80% of NG-348 infected $EpCam^+$ A549 cells but not EnAd infected or uninfected control cells (FIG. 6). In contrast $CD3^+$ T cells showed no detectable expression of CD80 at the cell surface indicating, at least under these experimental conditions, transgene expression is selective for tumour cells in the co-culture.

Upregulation of T Cell Activation Markers

Figure 7:
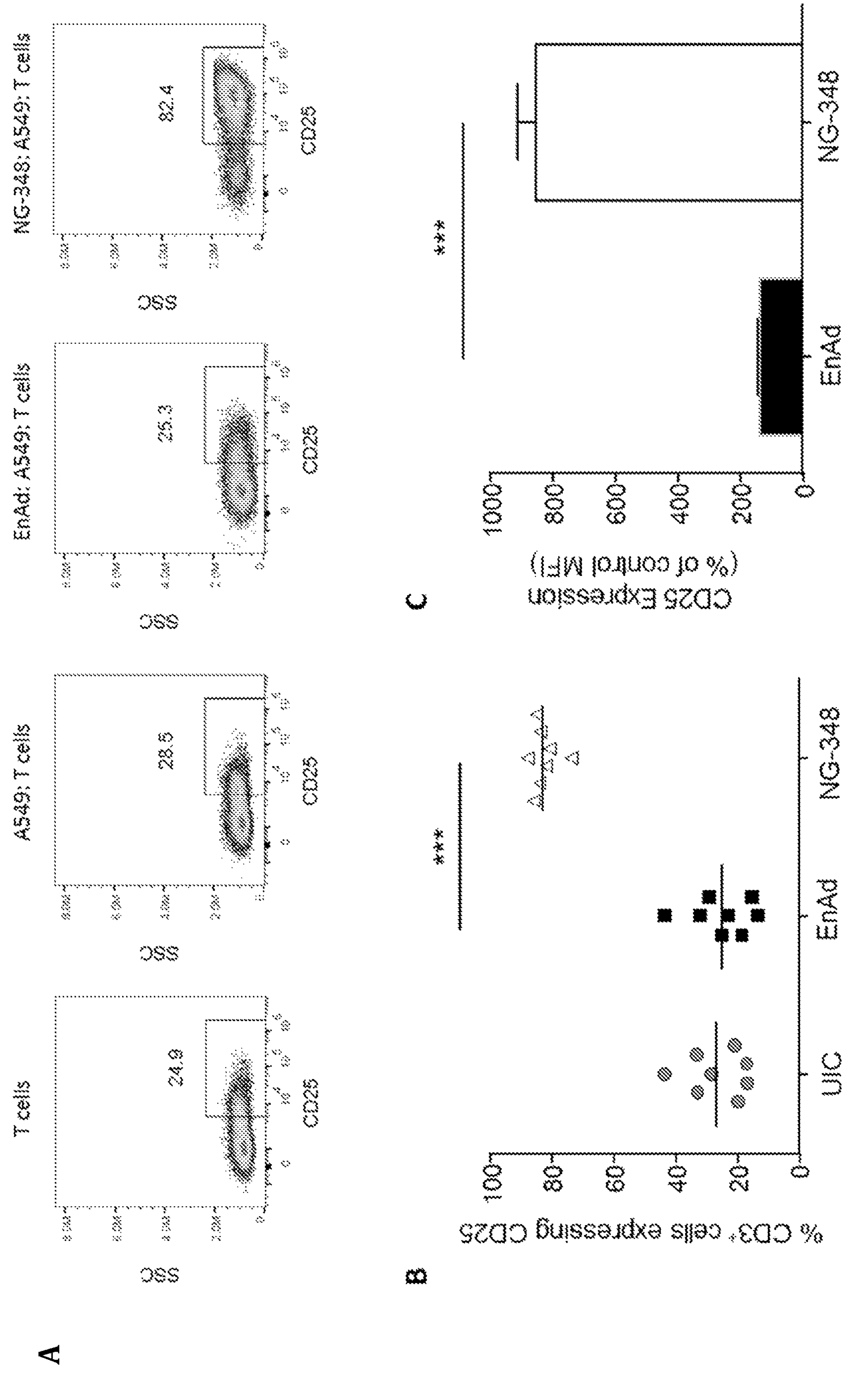
FIG. 7 shows CD25 is upregulated on human $CD3^+$ T-cells following co-culture with NG-348 infected A549 cells, but not when infection was with EnAd (A), with both the percentage of $CD25^+$ cells (B) and the level of CD25 expression per cell (C) was increased.
Figure 8:
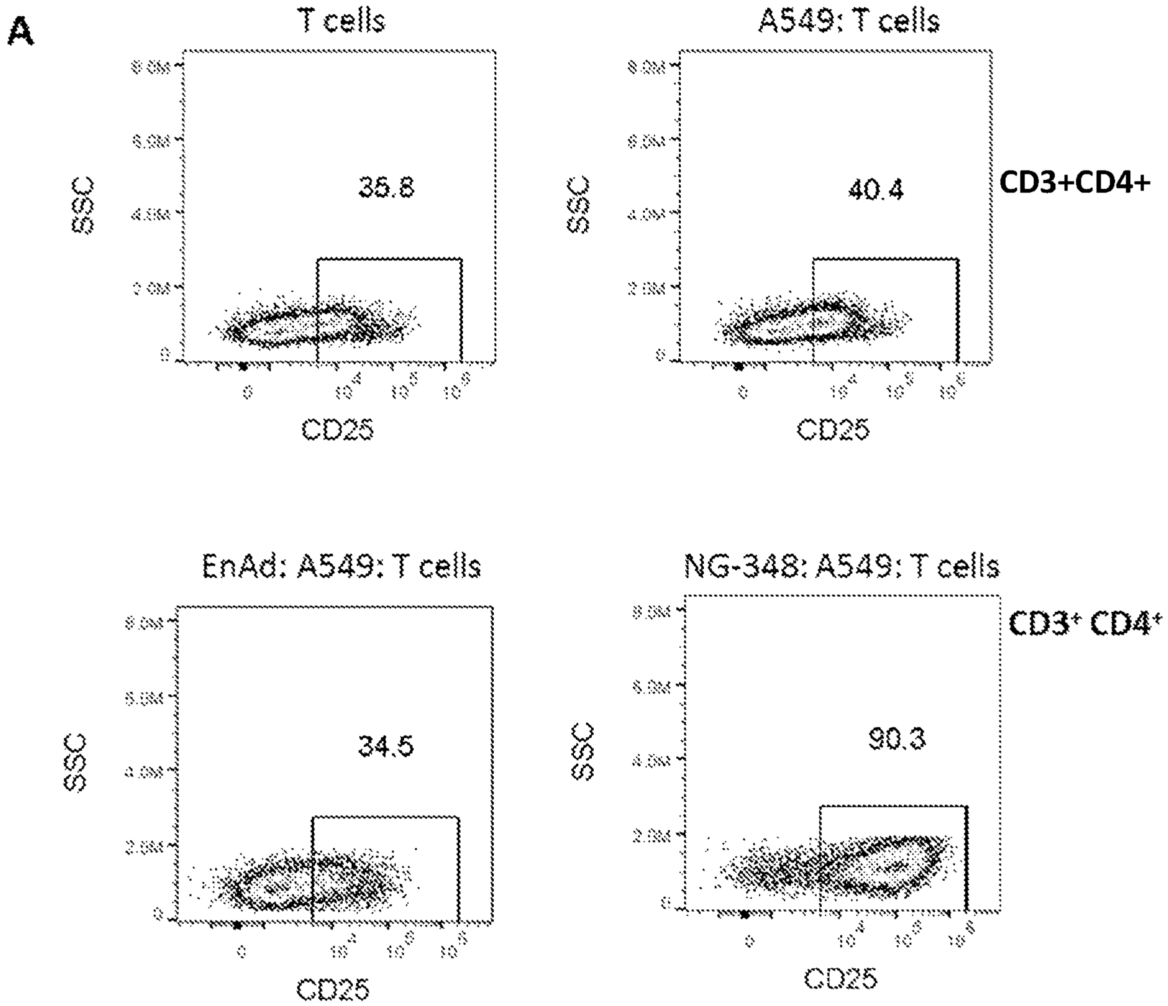
FIG. 8 shows CD25 is upregulated on both $CD4^+$ and $CD4^-$ (primarily CD8) human $CD3^+$ T cell subsets following co-culture with NG-348 infected A549 cells, but not when infection was with EnAd.
Figure 8:
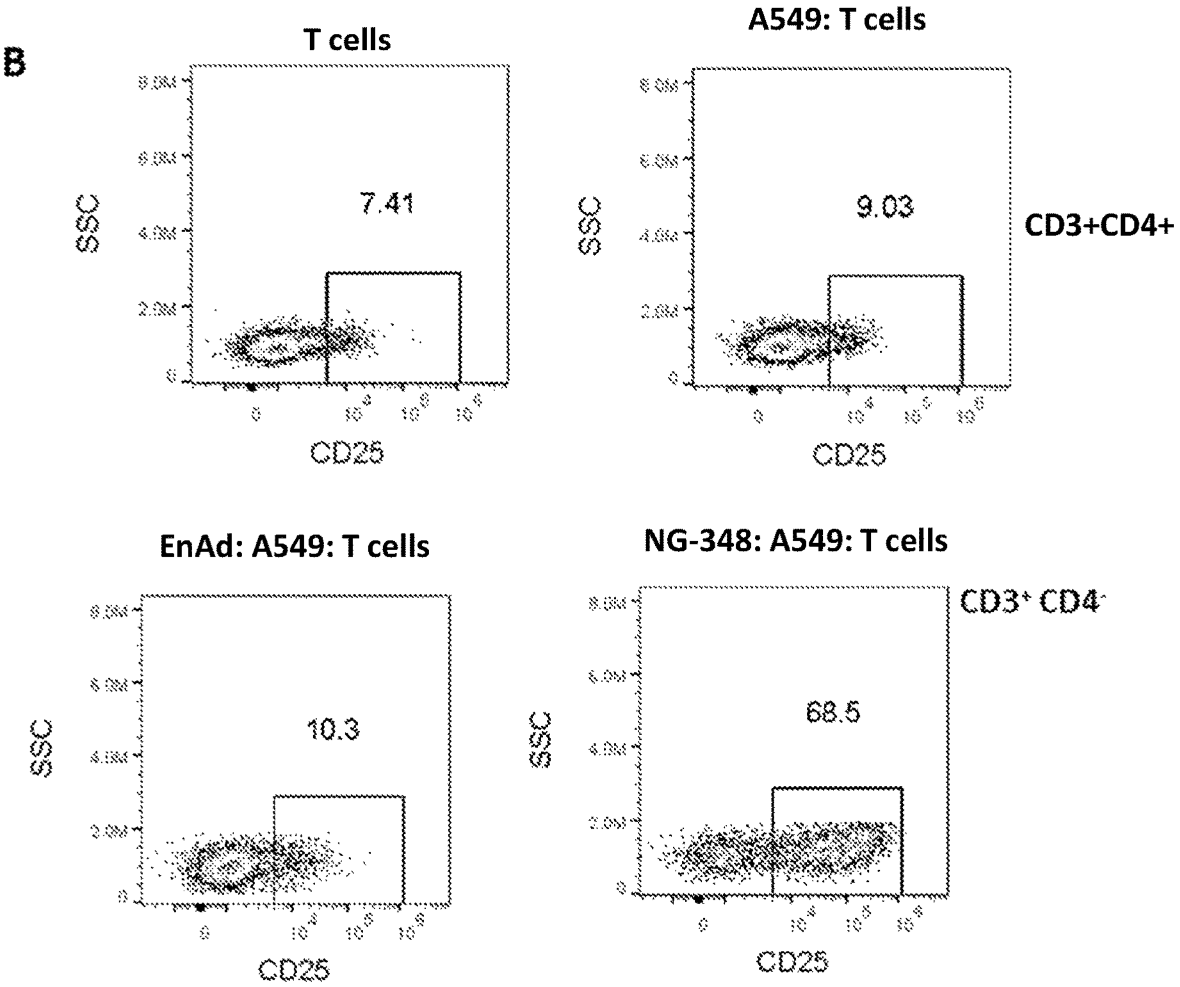
Figure 8:
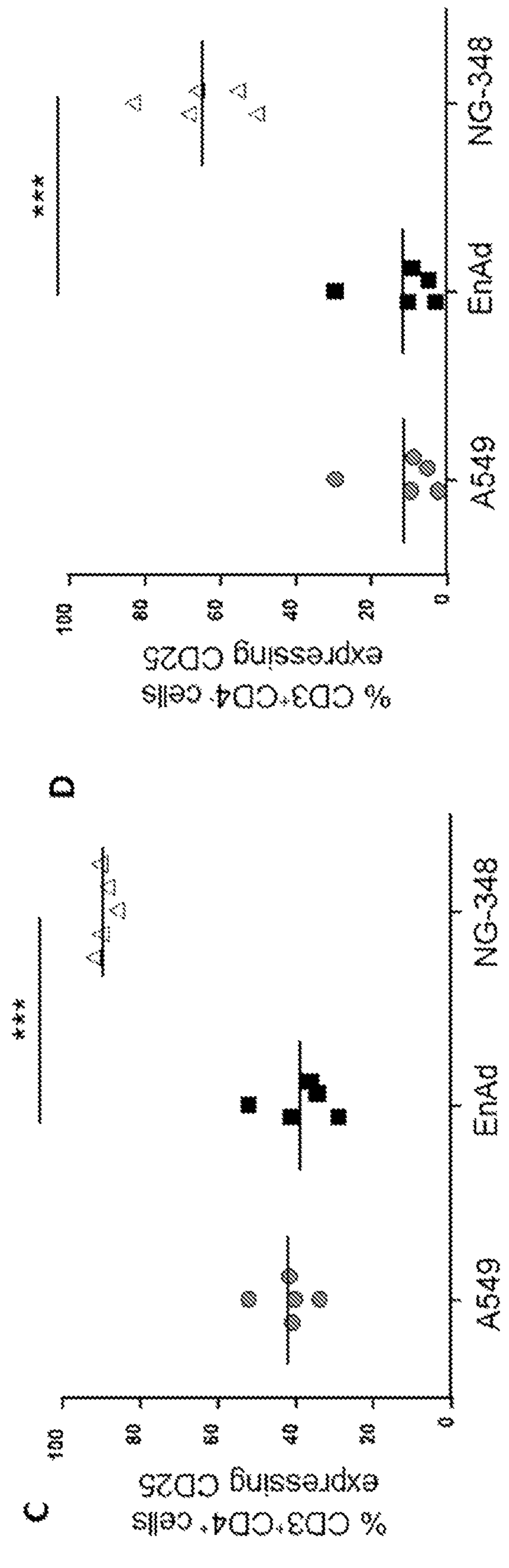

Flow cytometry analysis of T cell activation was assessed by expression of the T cell activation markers CD25 and HLA-DR on live, CD3+, single cells. These data showed that both the number of T cells expressing CD25 (FIG. 7, panels A and B) and the average level of CD25 expression on the T cell surface (FIG. 7, panel C) were significantly higher for T cells cultured with NG-348 infected A549 cells than EnAd or uninfected controls. Specifically, there was no difference in T cell activation status when comparing untreated controls to EnAd (26.9%±3.4% and 25.3±3.5% of T cells expressing CD25, respectively) whereas CD25 was upregulated on the majority of cells co-cultured with NG-348 (83.2±1.5%). CD25 expression was also analysed on CD4 and CD8 T cell subsets by gating the $CD3^+$ T cells based on their expression of CD4. These analyses showed that CD25 expression is significantly upregulated on both CD4+ and CD4− T cell subsets in NG-348 treated co-cultures compared to EnAd and uninfected controls (FIG. 8).

Figure 9:
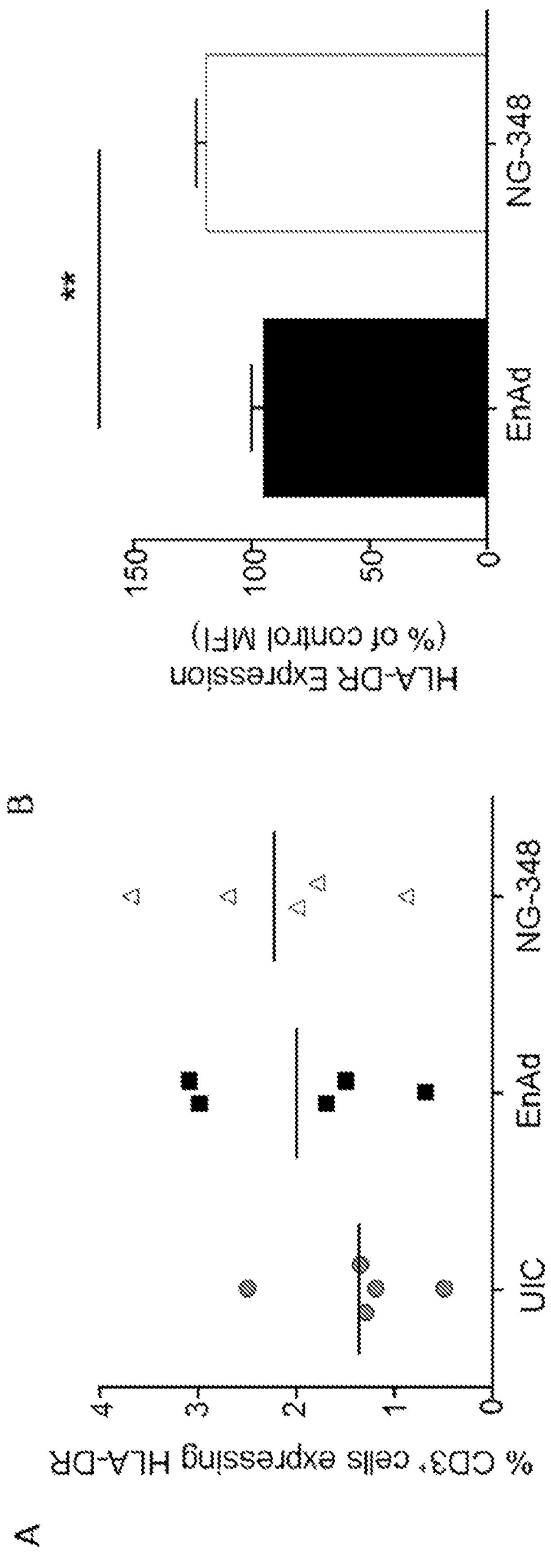
FIG. 9 shows low level of HLA-DR expression on human $CD3^+$ T cells following co-culture with NG-348 or EnAd infected A549 cells

In contrast to CD25 the number of cells expressing HLA-DR was low, <5%, for all conditions tested (FIG. 9, panel A). This is likely due to the early time point after co-culture at which flow cytometry analysis was carried out. However, there was a slight but significant increase in the mean fluorescence intensity of HLA-DR staining $CD3^+$ $HLA\text{-}DR^+$ cells from NG-348 treated co-cultures compared to controls (FIG. 9, panel B).

Stimulation of T Cell Degranulation

Figure 10:
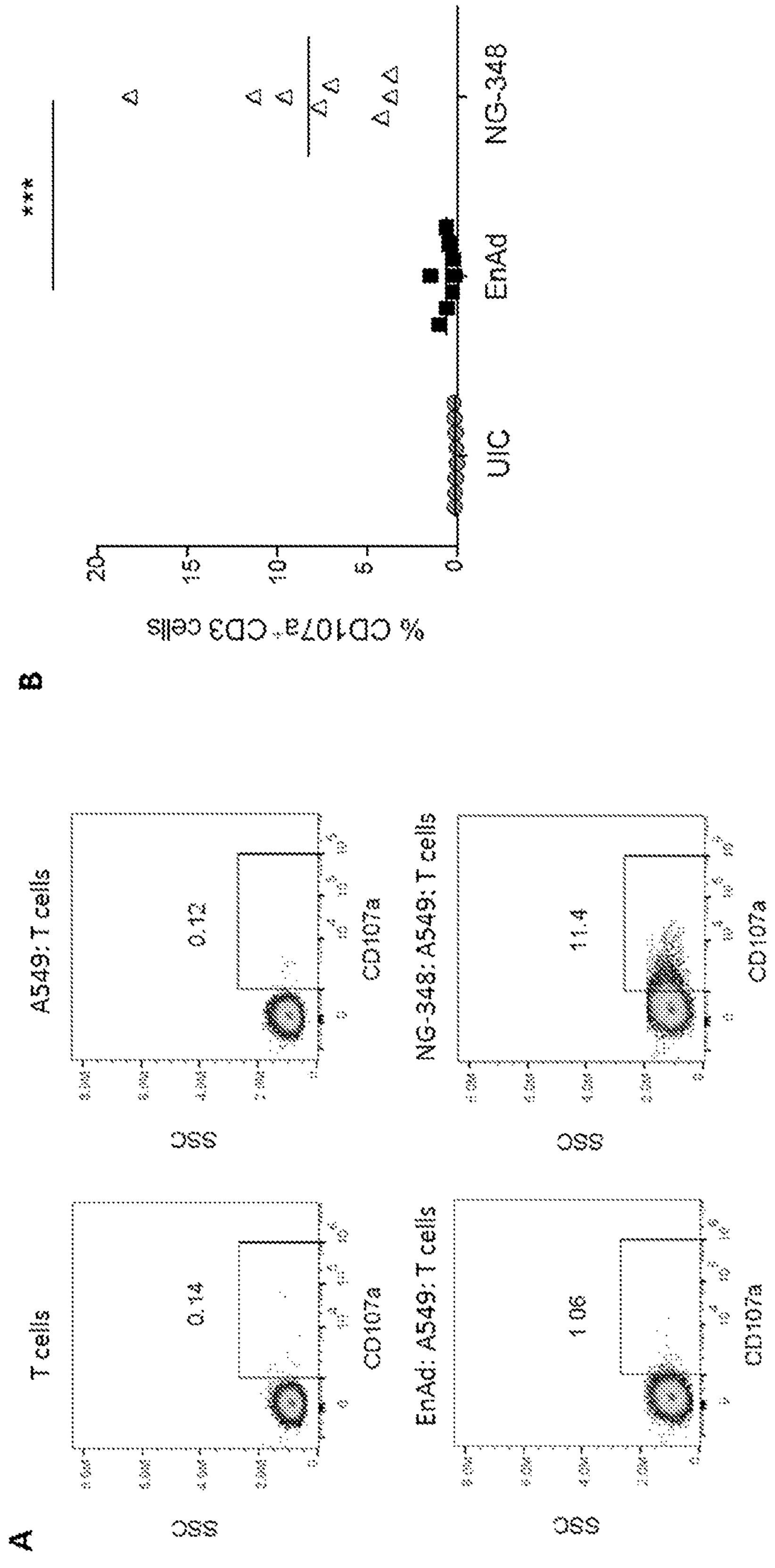
FIG. 10 shows induction of CD107a expression on the surface of live, $CD3^+$ T cells following co-culture with NG-348 infected A549 cells, but not when infection was with EnAd.
Figure 11:
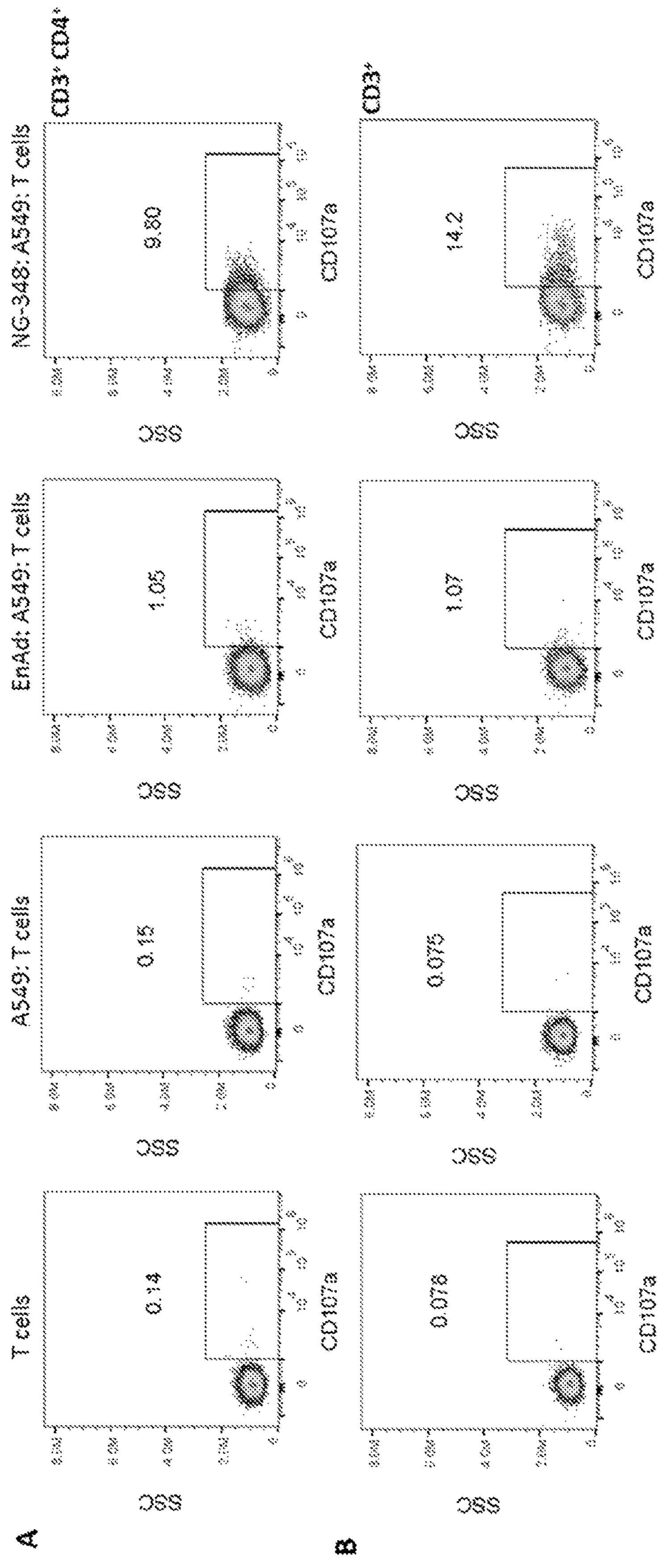
FIG. 11 shows induction of CD107a expression on the surface of both $CD4^+$ and $CD4^-$ $CD3^+$ T cell subsets following co-culture with NG-348 infected A549 cells, but not when infection was with EnAd.
Figure 11:
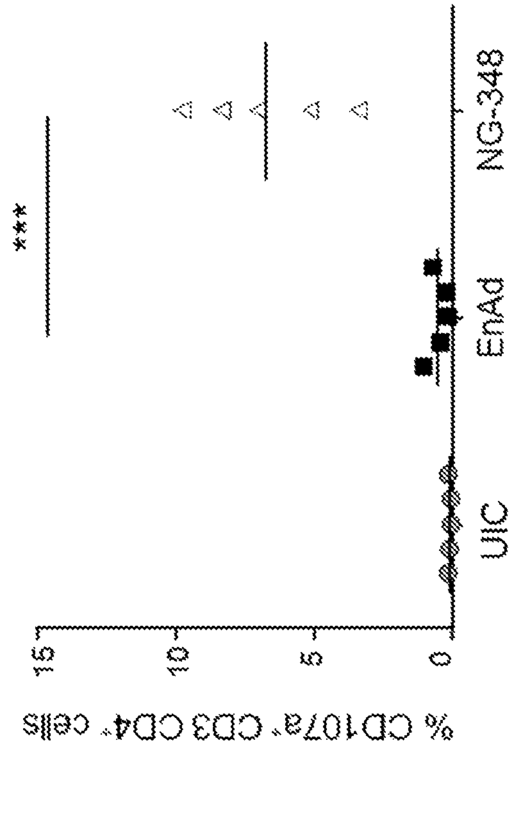
Figure 11:
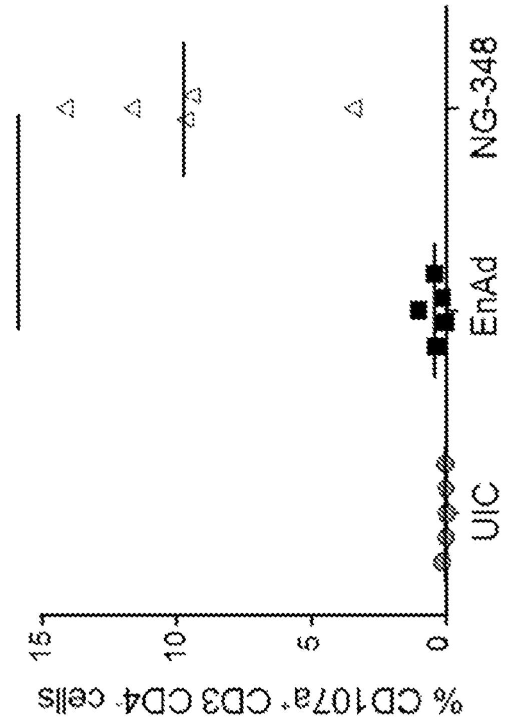

Analysis of CD107a expression on the surface of live, $CD3^+$ T cells showed a significant increase in the number of T cells which had degranulated and were therefore stained with CD107a, when A549 cells were infected with NG-348 (8.3%±1.7% of cells) compared to either EnAd (0.6%±0.2% of cells) or untreated controls (0.1%±0.02% of cells) (FIG. 10). Similar to CD25 upregulation, both $CD4^+$ and CD4− T cell subsets showed significantly increased CD107a expression compared to EnAd or A549 controls (FIG. 11).

Secretion of the Stimulatory Cytokines IL-2 and IFNγ

For detection of IL-2 or IFNγ expression, co-culture supernatants were diluted into 5% BSA/PBS assay buffer (in a range of 1:100 to 1:1000) and ELISA was carried out using the Human IL-2 Ready Set go Kit (Affymetrix) or Human IFN gamma Ready set go kit (Affymetrix) according to the manufacturer's protocol.

Figure 12:
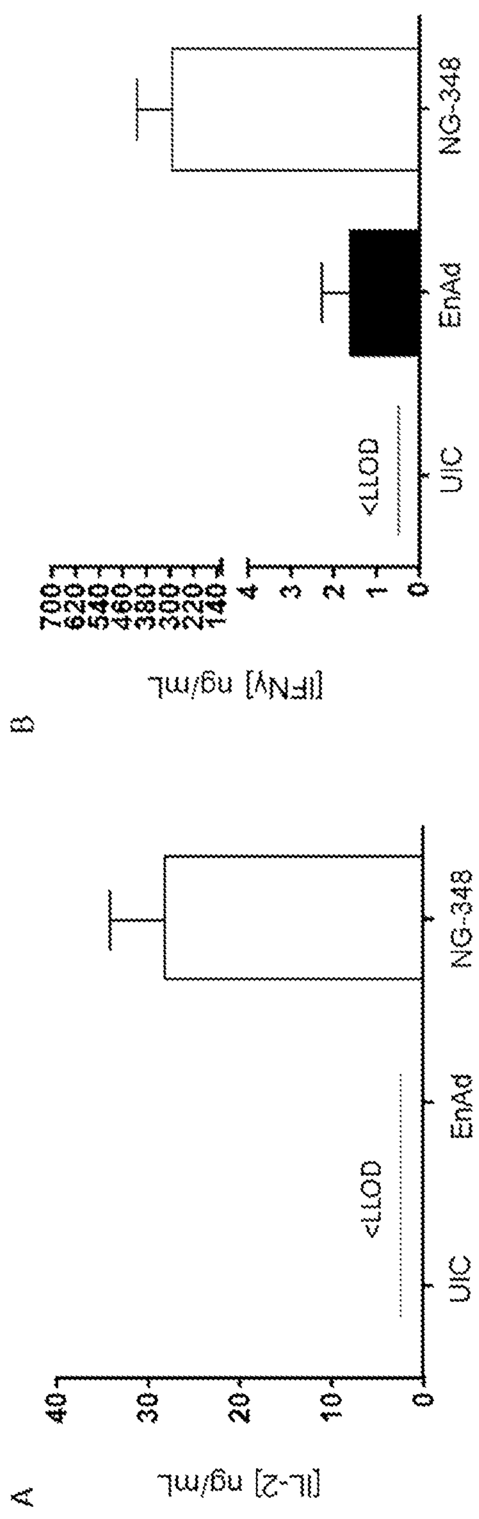
FIG. 12 shows induction of IL-2 (A) and IFNγ (B) production by $CD3^+$ T cells following co-culture with NG-348 infected A549 cells, but no IL-2 and only low levels of IFNγ when infection was with EnAd.

The concentrations of secreted IL-2 or IFNγ were determined by interpolating from the standard curves. Expression of IL-2 could only be detected in the supernatants of co-cultures using NG-348 infected A549 cells and was not detectable in either the EnAd, or untreated controls (FIG. 12, panel A). Expression of IFNγ could also be detected, at very high levels (>300 ng/mL) in supernatants of co-cultures from NG-348 infected A549 cells, which was significantly higher that either EnAd or untreated controls (FIG. 12, panel B).

Example 7: T Cell Activation of CD4 and CD8 T Cells can be Independently Mediated by NG-348 Infected Carcinoma Cell Lines A549 lung carcinoma cells infected with NG-348 or EnAd virus particles or left uninfected, were co-cultured with either $CD4^+$ T cells or $CD8^+$ T cells isolated from human PBMC donors. T cell activation was assessed by the secretion of the stimulatory IFNγ into culture supernatants. A549 cells were seeded and infected with NG-348 or EnAd virus particles or left uninfected according to the methods detailed in Example 14. 48 hrs post infection $CD4^+$ T cells or $CD8^+$ T cells isolated by negative selection from a PBMC donor were added to the A549 cell monolayer at a ratio of 8 T cells to 1 tumour cells. After 16 hrs of co-culture supernatants were harvested and assessed for IFNγ according to the methods detailed.

Analysis of IFNα Expression by ELISA

Supernatants of HT-29 or A549 cell lines infected for 24, 48 or 72 hrs with 10 ppc of EnAd or NG-343 or left uninfected were analysed for expression of secreted IFNα by ELISA.

Culture supernatants were removed from each well and centrifuged for 5 mins, 1200 rpm to remove cell debris. Supernatants were diluted into 5% BSA/PBS assay buffer (1:2 or 1:50 or 1:100) and ELISA was carried out using the Verikine Human IFN alpha Kit (Pbl assay science) according to the manufacturer's protocol.

Figure 13:
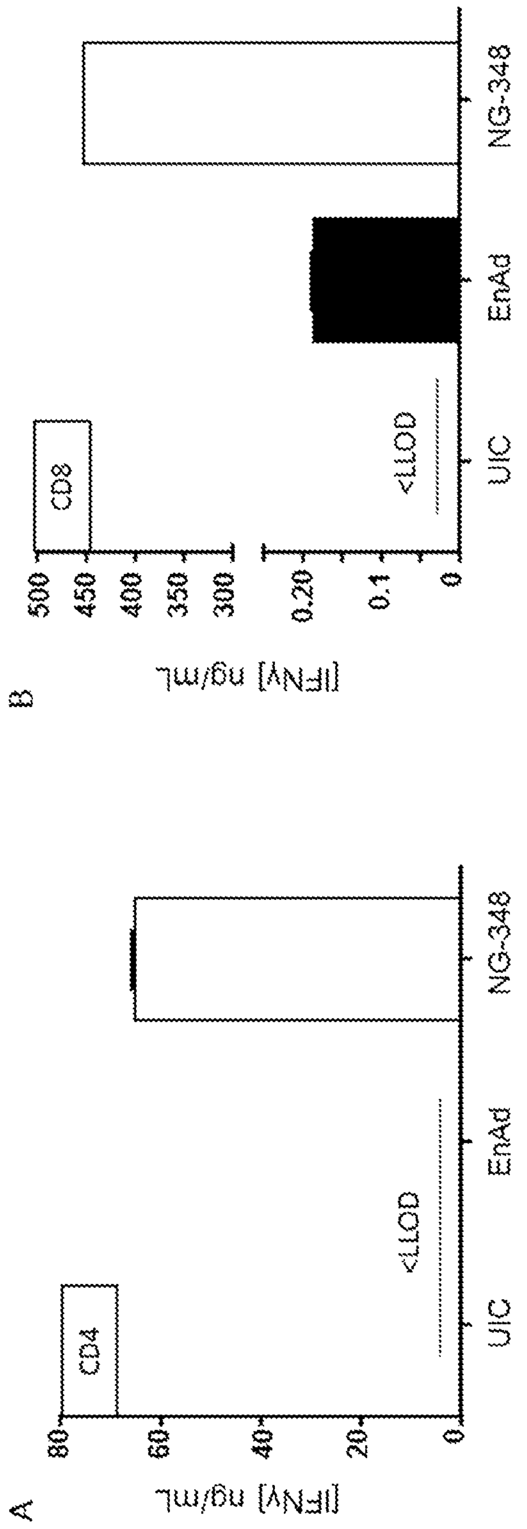
FIG. 13 shows induction of IFNγ production by both CD4+(A) and $CD8^+$ (B) $CD3^+$ T cells following co-culture with NG-348 infected A549 cells, but no ($CD4^+$ cells) or low ($CD8^+$ cells) IFNγ when infection was with EnAd.

The concentrations of secreted IFNα were determined by interpolating from the standard curves. IFNα expression which increased in the cellular supernatants over the course of infection was detected in both HT-29 and A549 cells lines For $CD4^+$ T cells Expression of IFNγ was only detected in supernatants of co-cultures from NG-348 infected A549 cells and was not detectable in either the EnAd or untreated controls (FIG. 13, panel A). For $CD8^+$ T cells expression of IFNγ was detected at significantly higher levels for NG-348 infected A549 cells than for EnAd or untreated controls (FIG. 13, panel B), demonstrating that both CD8 and CD4 cells can be activated to secret IFNγ by NG-348 virus activity in tumour cell lines.

Example 8

A549 human lung carcinoma cells and MRC5 human fibroblast cells were cultured with EnAd, NG-347 or NG-348 viruses (at 10 ppc) to compare virus genome replication, virus hexon and transgene expression by these cell types. After 72 hours culture, cells were either stained for FACS analyses of surface markers or supernatants and cell lysates prepared for virus genome replication (qPCR) or mRNA (RT-qPCR) analyses of hexon or transgene expression.

Figure 14:
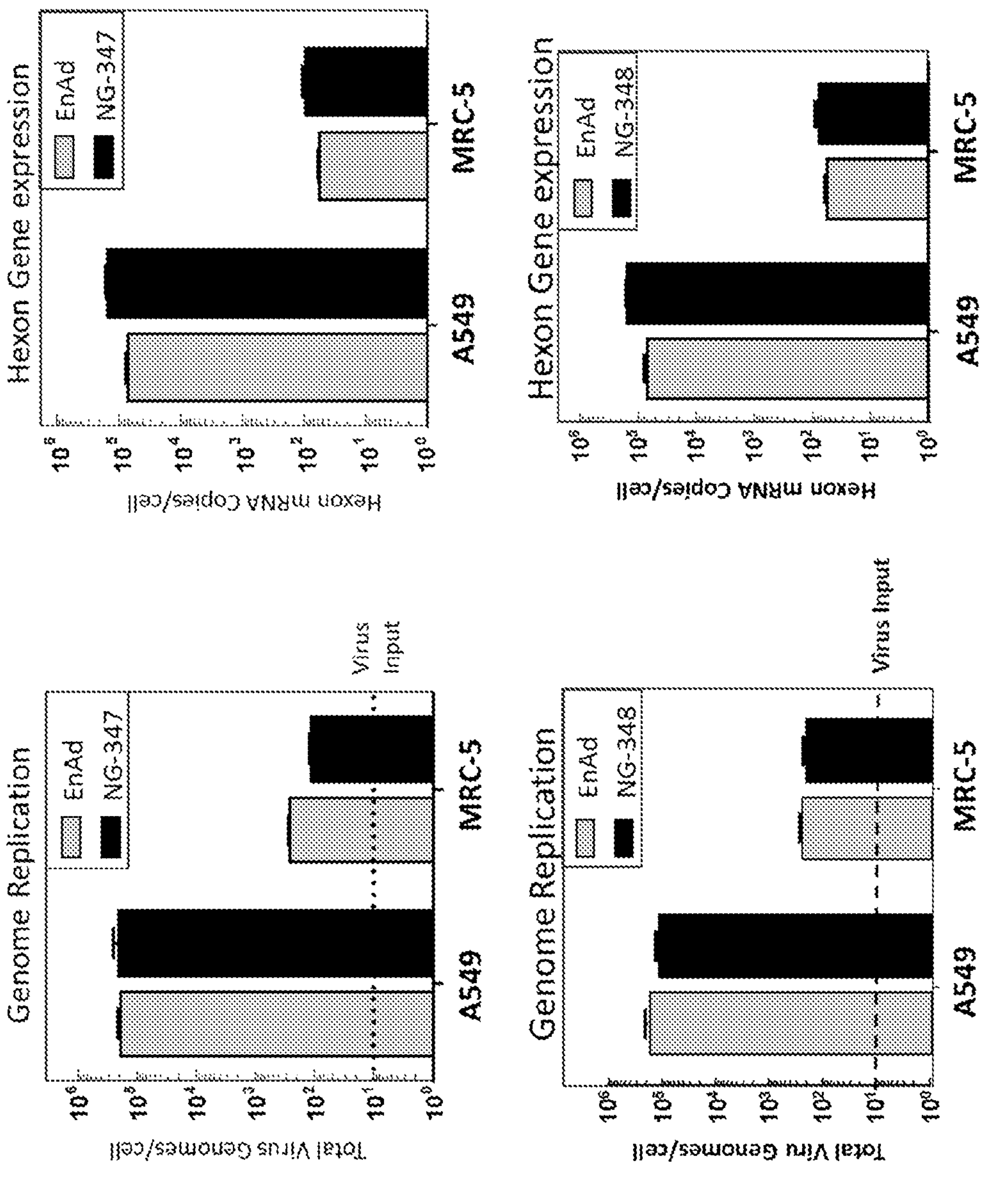
FIG. 14 shows genome replication and hexon gene expression (mRNA levels) for EnAd, NG-347, and NG-348 in MRC-5 fibroblast cells compared to A549 tumour cells

Virus genome replication and hexon mRNA expression for the two transgene bearing viruses, NG-347 and NG-348 were equivalent to those for the parental virus, EnAd (FIG. 14). For NG-348 (FIG. 15), CD80 and anti-human CD3-ScFv transgene mRNA expression levels were high with A549 tumour cells, with only a low level signal for the non-tumour MRC5 cells. CD80 protein expression on the surface of cells assessed by FACS was detected on the majority of NG-348 treated A549 cells but was not detectable on MRC5 cells, with no CD80 detected on either cell type left untreated or treated with EnAd. Similarly, CD80 transgene mRNA and protein expression following NG-347 treatment was selectively detected in A549 tumour cells not MRC5 cells (FIG. 16). For EnAd and NG-347 treated cell cultures, levels of MIP1α and IFNα mRNA in cell lysates and secreted proteins in supernatants were measured by RT-qPCR and specific ELISAs, respectively. Data (FIG. 17) show selective expression of both transgenes by A549 tumour cells, with no detectable MIP1α chemokine or IFNα cytokine in MRC5 supernatants.

Example 9

Figure 18:
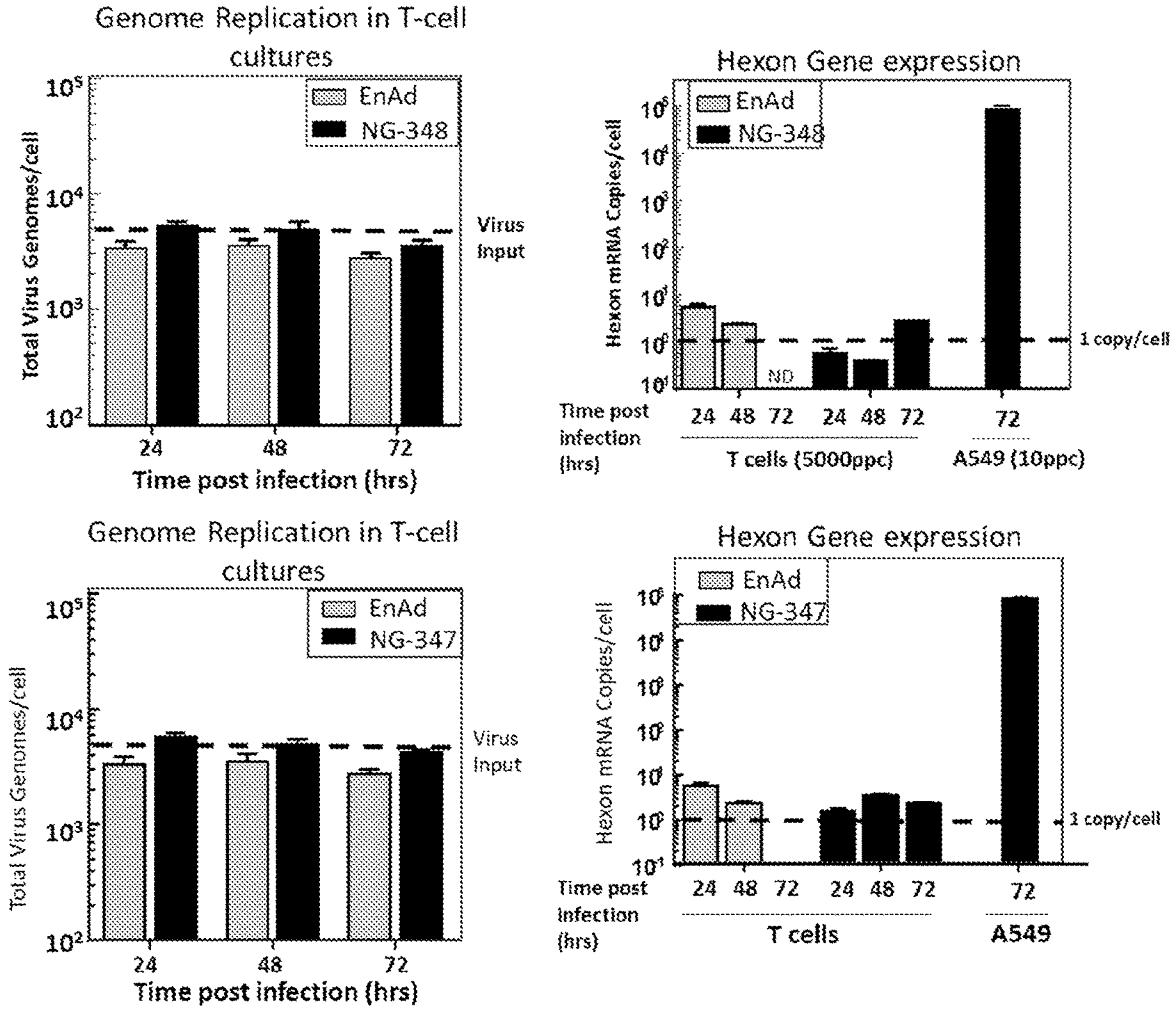
FIG. 18 shows genome replication and hexon gene expression (mRNA levels) for EnAd, NG-347, and NG-348 in purified human T-cell cultures.
Figure 19:
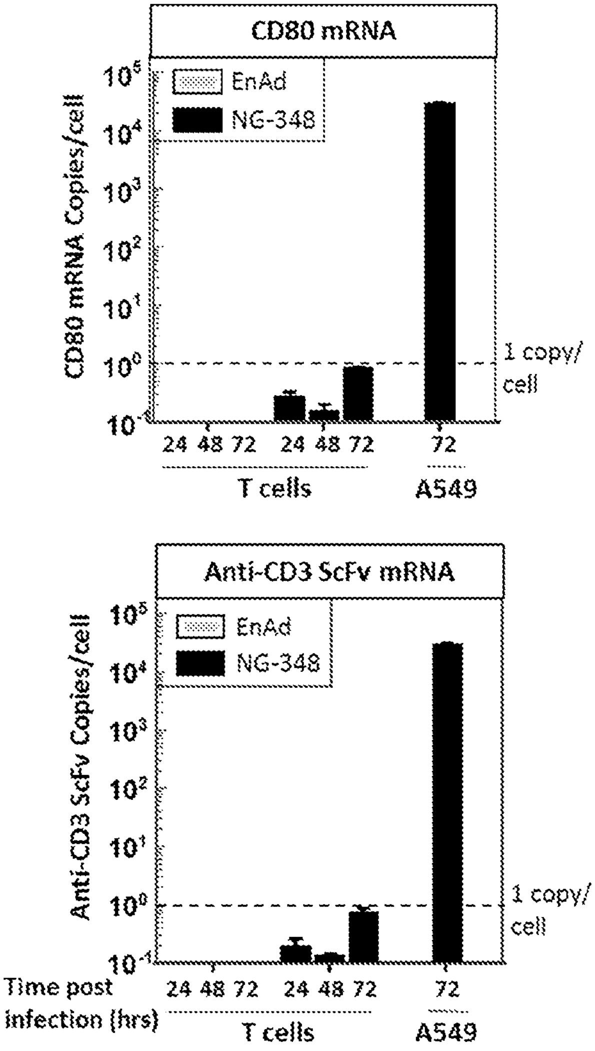
FIG. 19 shows CD80 and anti-CD3 scFv transgene mRNA and protein expression (flow cytometry) for virus NG-348 in human T-cells compared to A549 tumour cells
Figure 19:
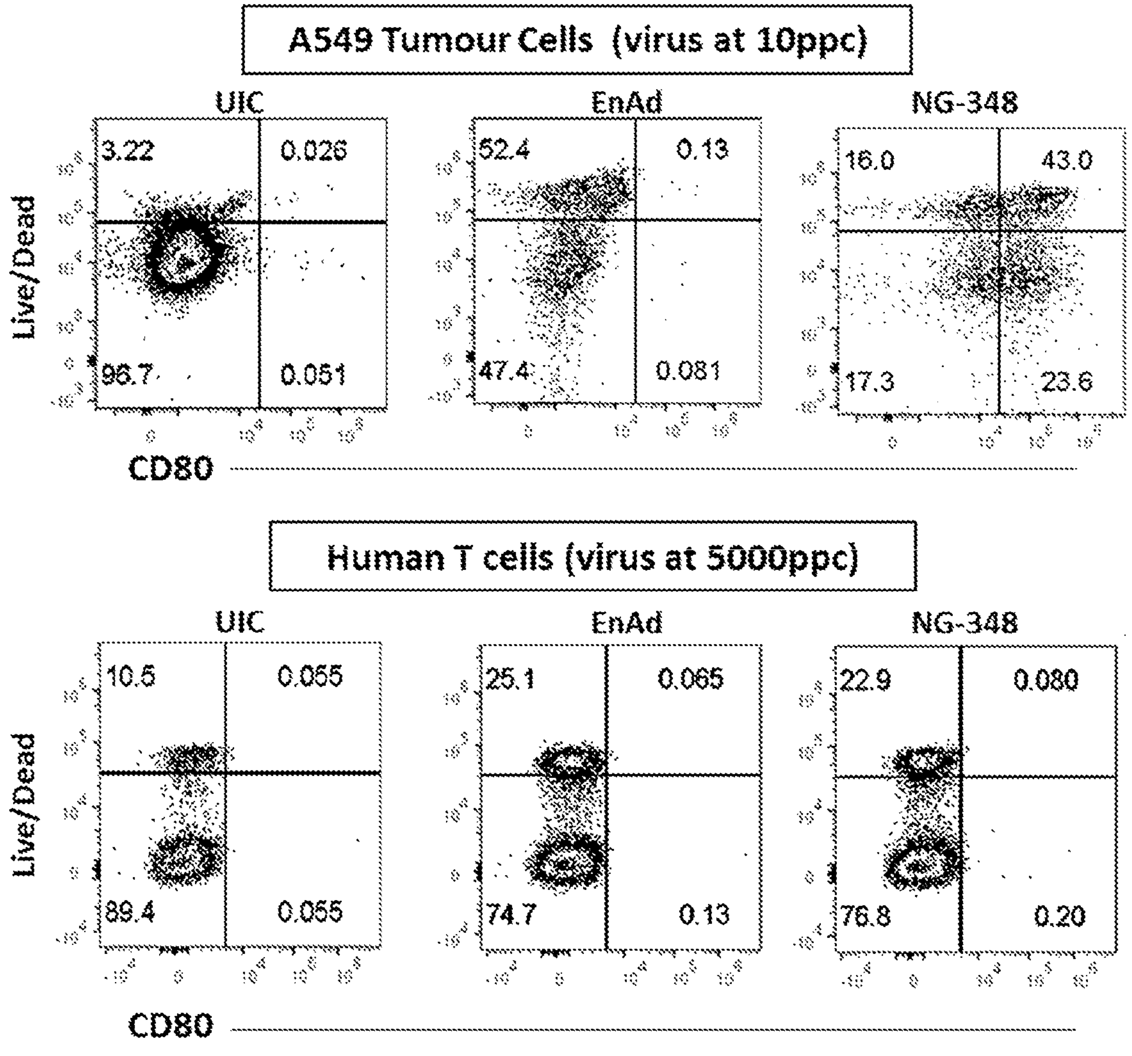
Figure 20:
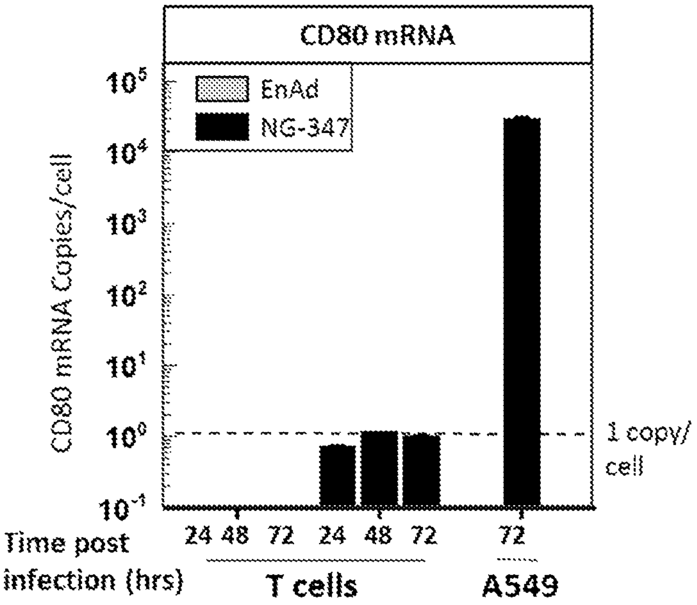
FIG. 20 shows CD80 transgene mRNA and CD80 transgene protein for virus NG-347 in purified human T-cells compared to A549 tumour cells
Figure 20:
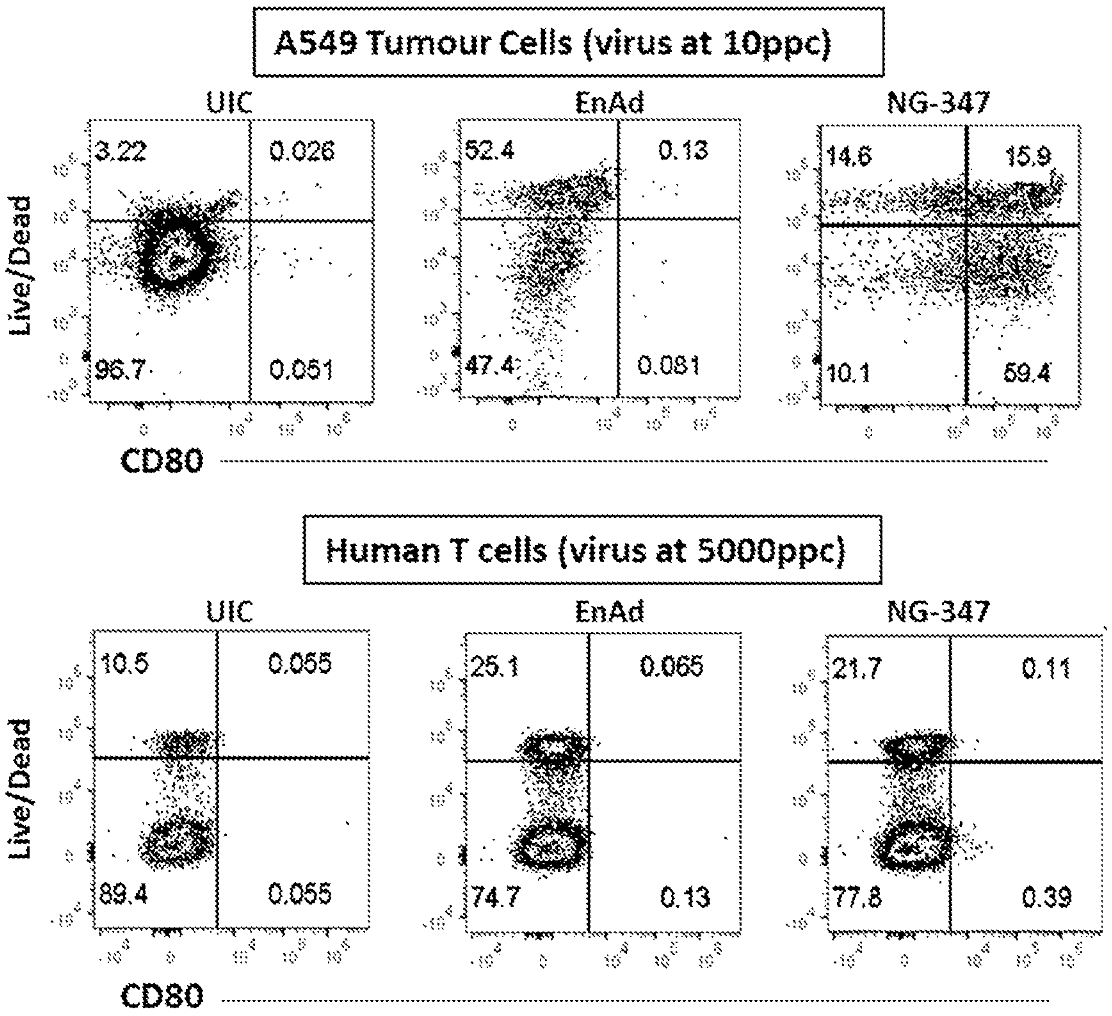
Figure 21:
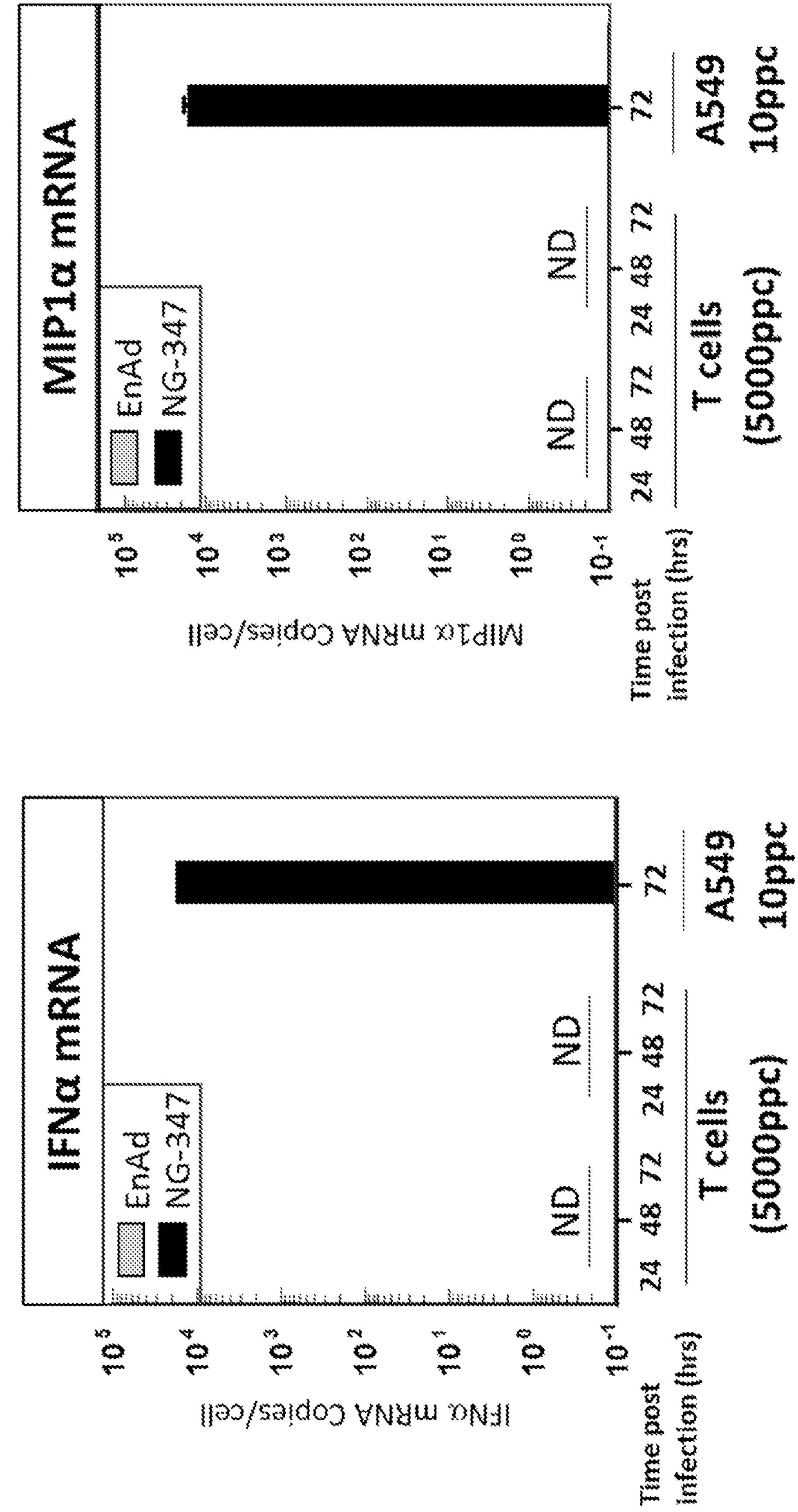
FIG. 21 shows IFNα and MIP1α transgene mRNA generated by virus NG-347 in T cells compared to A549 tumour cells
Figure 22:
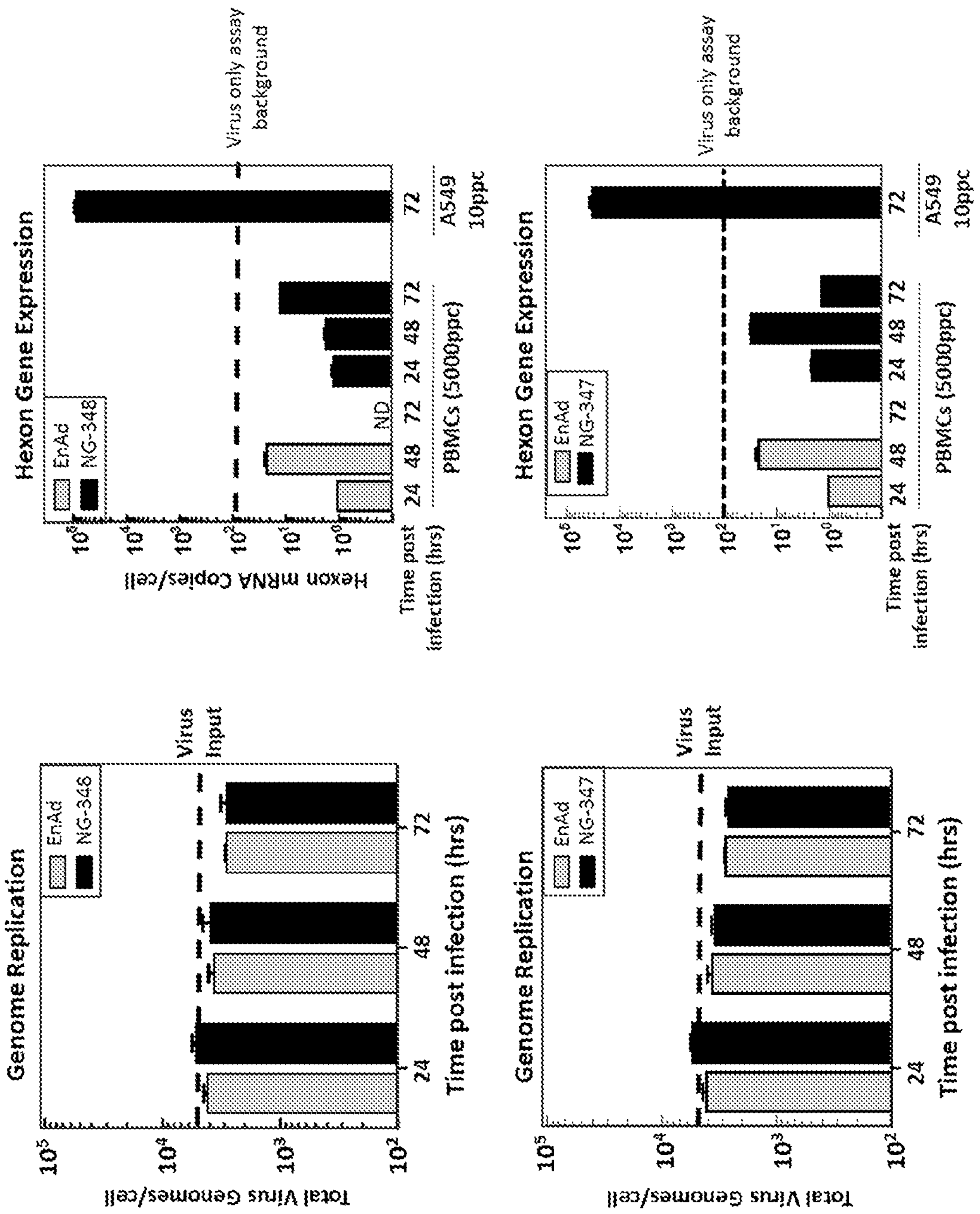
FIG. 22 shows NG-347 and NG-348 genome replication and hexon gene expression by human PBMCs compared to A549 tumour cells
Figure 23:
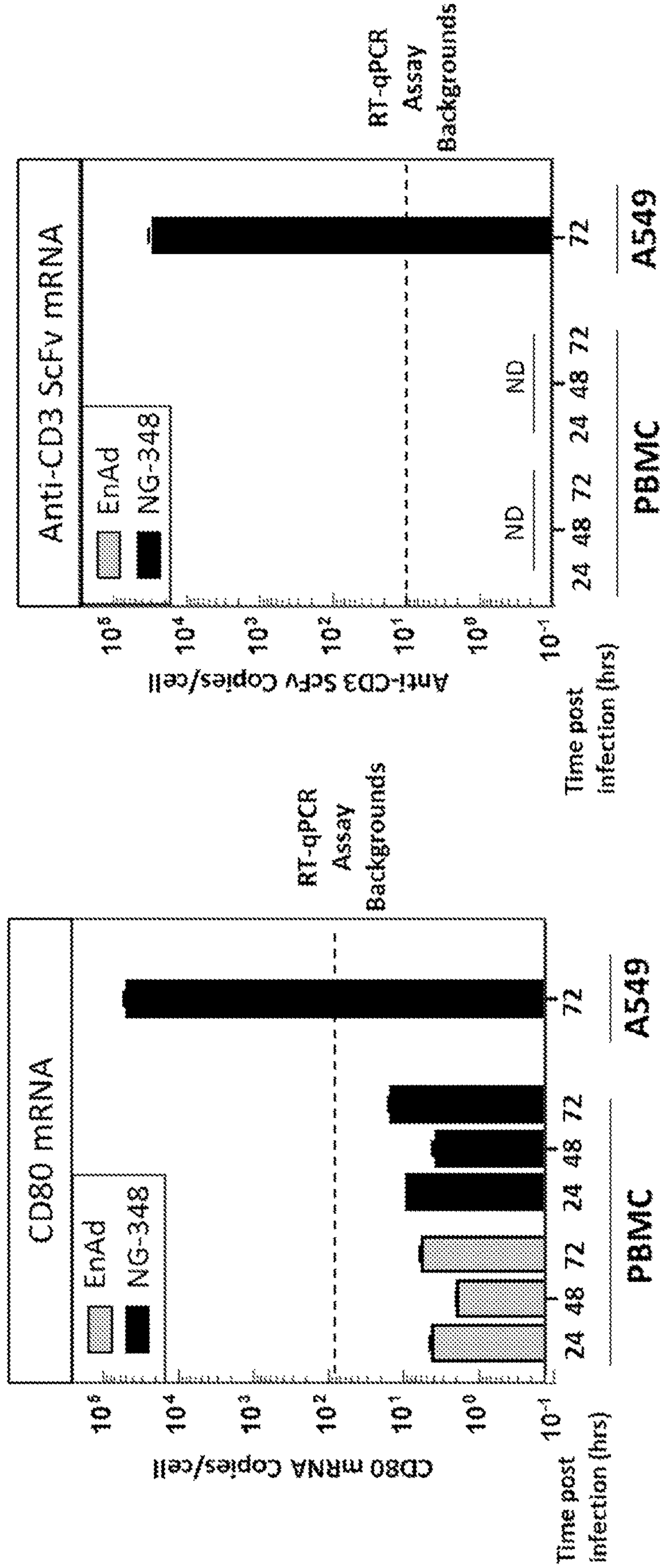
FIG. 23 shows CD80 and anti-CD3 scFv mRNA generated by virus NG-348 by PBMCs compared to A549 tumour cells
Figure 24:
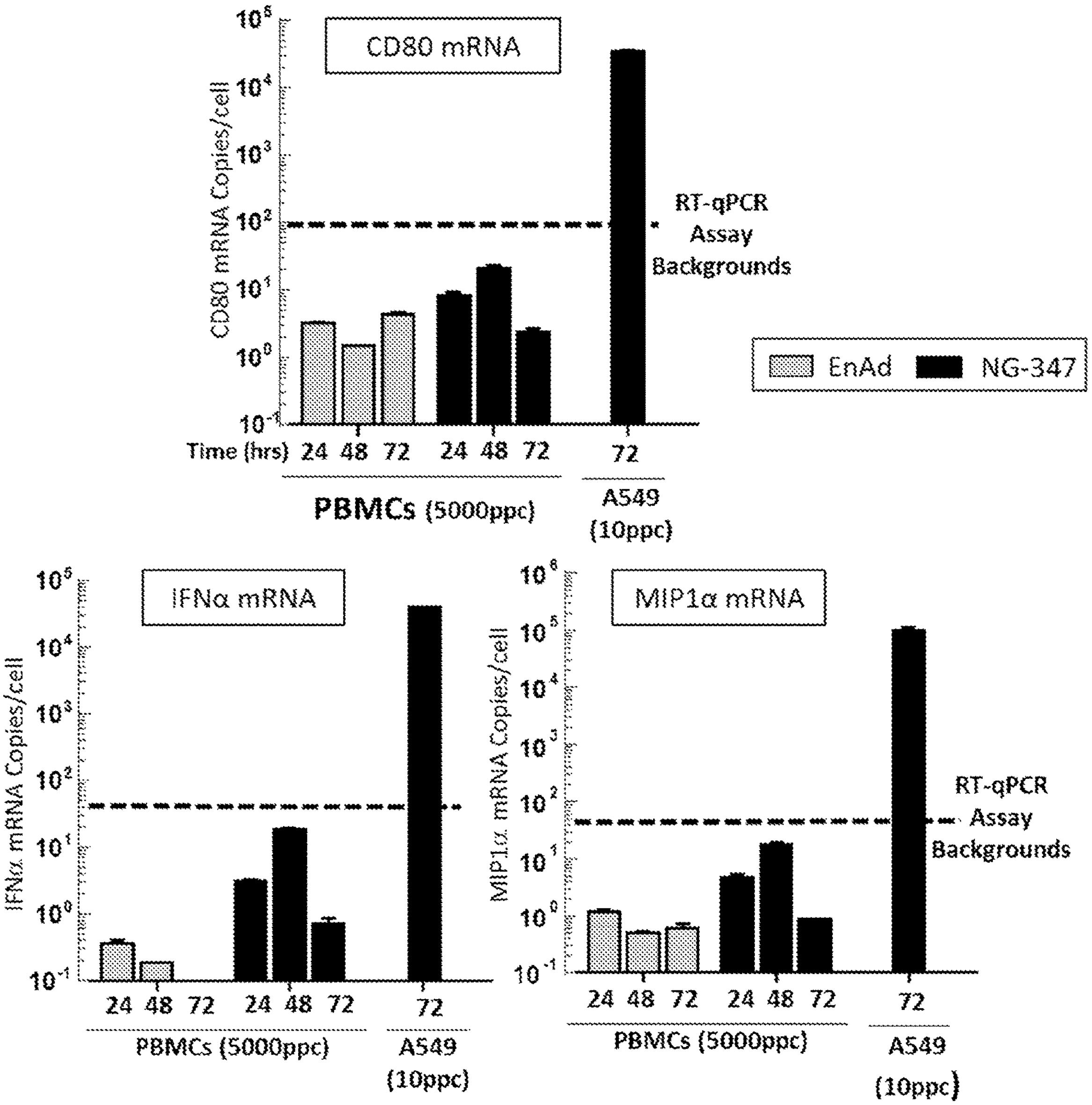
FIG. 24 shows CD80, IFNα and MIP1α mRNA generated by virus NG-347 by PBMCs compared to A549 tumour cells
Figure 25:
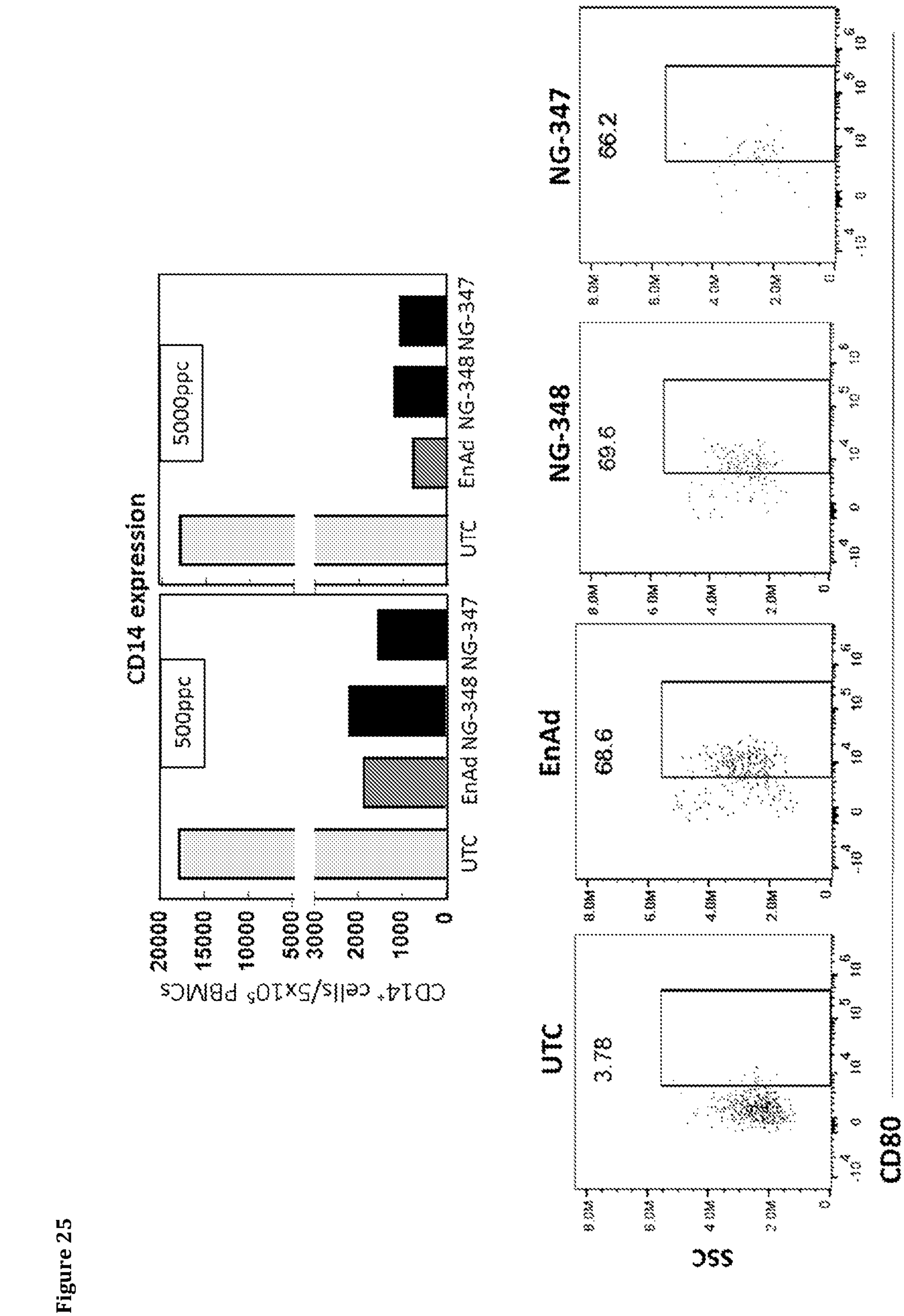
FIG. 25 shows the similar activation of human dendritic cells by EnAd, NG-347 and NG-348 virus particles, as measured by down-regulation of CD14 expression and upregulation of CD80 on the cell surface
Figure 26:
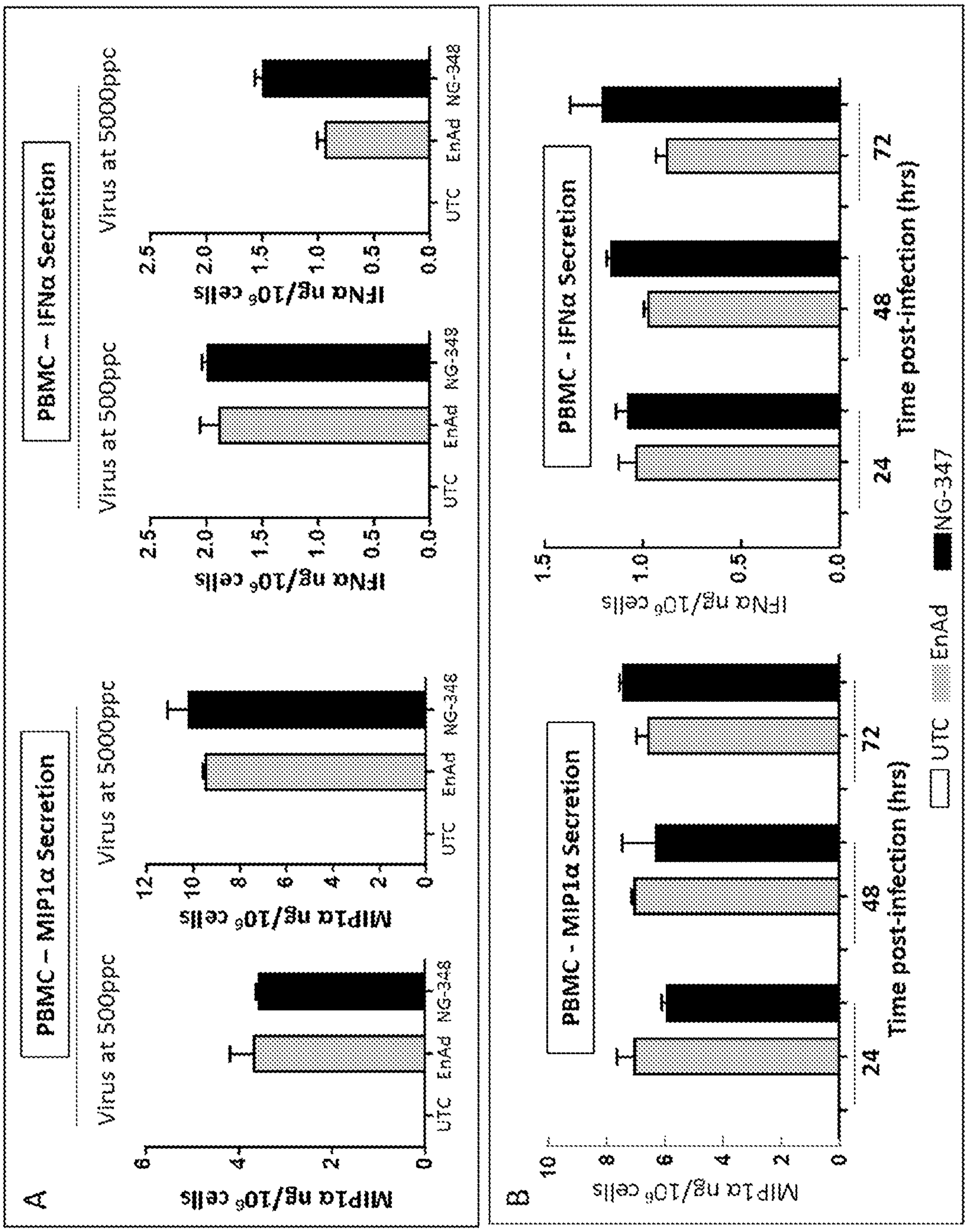
FIG. 26 shows similar particle-mediated MIP1α and IFNα protein secretion from PBMCs cultured with NG-348 (A) or NG-347 (B) compared to EnAd.
Figure 27:
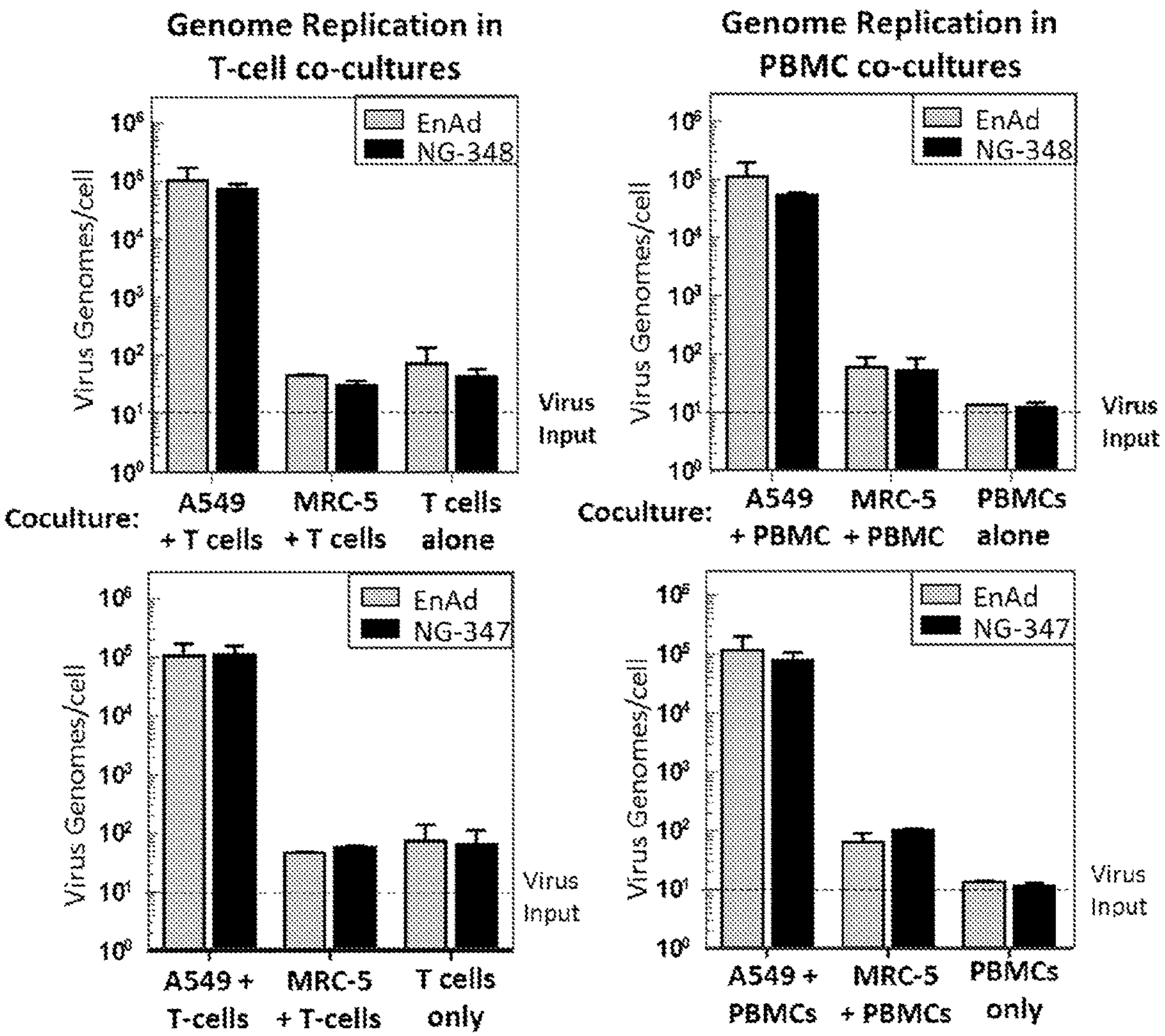
FIG. 27 shows NG-347 or NG-348 genome replication in co-cultures or T-cells or PBMCs with MRC-5 fibroblast cells compared to co-cultures with A549 tumour cells

The selectivity/activity of EnAd, NG-347 and NG-348 viruses with human T-cells was evaluated by culturing isolated $CD3^+$ T cells for 3 days with either 500 ppc or 5000 ppc of each virus. Selectivity/activity was assessed by a) flow cytometry analysis of T cells stained with antibodies targeting CD69, CD4, CD80, CD25 and CD3, b) ELISA analysis of human MIP1α, IFNα and IFNγ protein secretion, c) qPCR analysis of virus replication and d) RT-qPCR analysis of gene expression As shown in FIG. 18, T-cells were not supportive of virus genome replication for any of the viruses tested with only background signals in the virus hexon RT-qPCR assay. A549 tumour cells supported high levels of hexon mRNA expression. RT-qPCR analyses for transgene mRNA expression by T-cells showed only background signals (<1 copy/cell) for CD80 by both NG-347 and NG-348, and a similar lack of significant expression of anti-CD3-ScFv mRNA by NG-348, despite the high virus exposure (5000 ppc). High levels of expression of both transgenes were detected with treated (10 ppc) A549 tumour cells (FIGS. 19 & 20). Expression of IFNα and MIP1α transgene mRNA was also selectively detected by NG-347 (not EnAd) treated A549 tumour cells (at 10 ppc) and not by T-cells treated with 5000 ppc (FIG. 21). In addition, CD80 cell surface protein expression was only detectable with A549 cells not T-cells for both NG-347 and NG-348 (FIGS. 19 & 20). EnAd treatment did not lead to CD80 expression by either cell type, and A549 cell death (as assessed by dye uptake) was similarly high for all three viruses; a low level of non-specific T-cell death was induced by all viruses due to the very high levels of virus particles used in the experiment (FIGS. 19 & 20). Similar transgene mRNA and protein expression data were obtained when viruses were used at 500 ppc (data not shown).

In the absence of tumour cells, purified human T-cells were not activated to upregulate activation markers CD25 or CD69 when cultured with any of the viruses.

Lack of Expression of Activation Markers CD25 and CD69 by Purified Human $CD3^+$ T-Cells Treated with 5000 ppc of Different Viruses

| | Untreated | EnAd | NG-347 | NG-348 |
|---|---|---|---|---|
| $CD25^+$ CD4 T-cells | 30.7 | 24.6 | 23.4 | 23.3 |
| $CD69^+$ CD4 T-cells | 0.1 | 0.4 | 0.3 | 0.7 |
| $CD25^+$ CD8 T-cells | 5.9 | 4.7 | 4.1 | 4.1 |
| $CD69^+$ CD8 T-cells | 0.5 | 1.0 | 0.9 | 1.3 |

Example 10

A similar virus selectivity experiment to that described in Example 9 was carried out using unseparated human PBMCs rather than purified T-cells, including making the same activity assessments. As with human T-cells in example 9, the data from this study collectively demonstrate lack of virus replication and transgene expression by human PBMCs. FIGS. 12-14 show data using 5000 ppc of EnAd, NG-347 or NG-348, but similar data was generated using 500 ppc (not shown). FIG. 12 shows virus genome replication and hexon mRNA expression and FIGS. 13 & 14 show transgene mRNA expression. Assay backgrounds were set according to signals generated in the assay with the respective virus spiked into culture media and then processed in the same way as for the cell lysate samples. There was no detectable expression of CD80 transgene on $CD3^+$ T-cells or CD40+ cells (primarily B-cells) in these PBMC cultures with any of the viruses (not shown).

Figure 15:
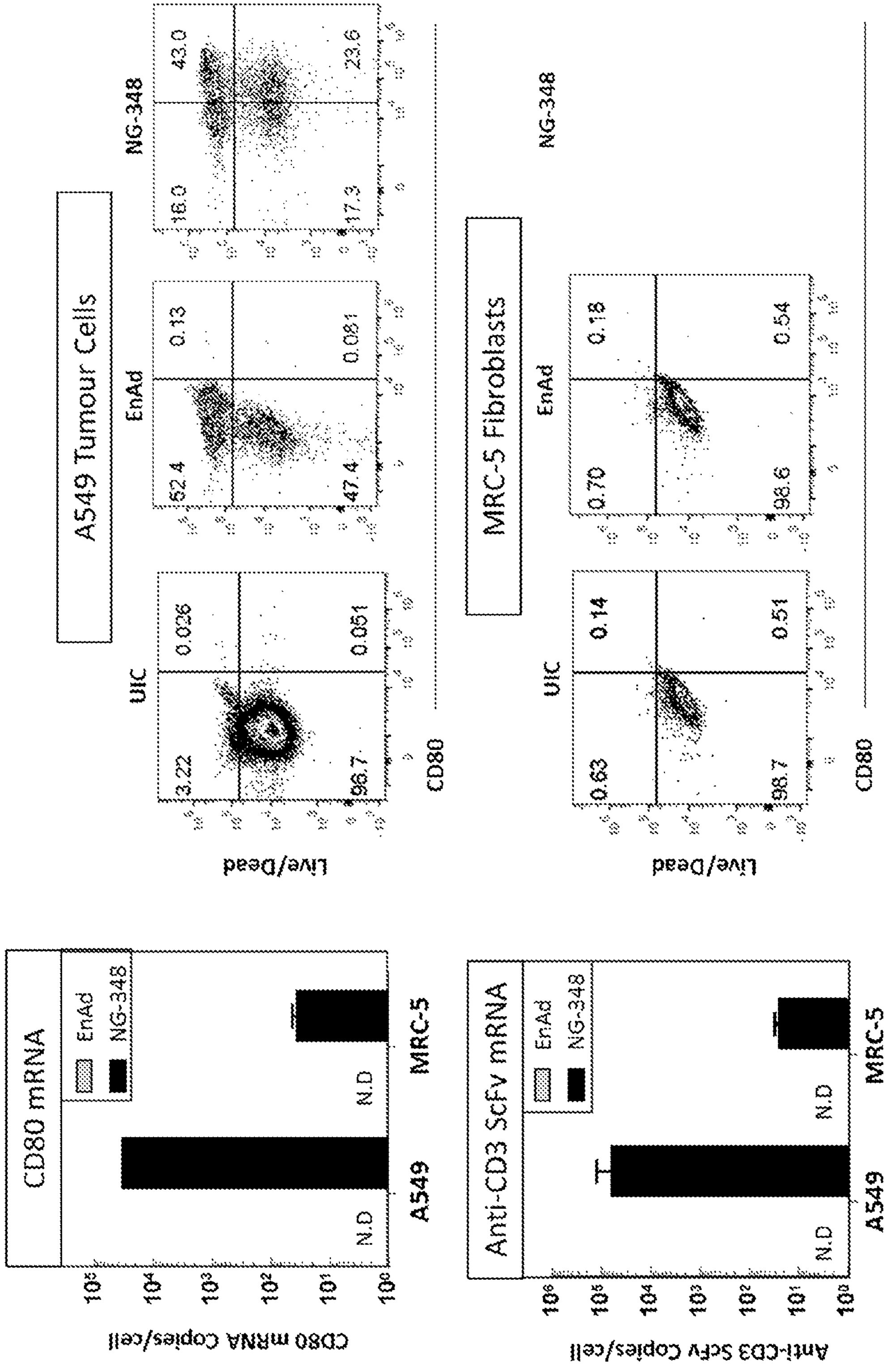
FIG. 15 shows CD80 and anti-CD3-scFv transgene mRNA and CD80 transgene protein (flow cytometry) expression for virus NG-348 in MRC-5 fibroblast cells compared to A549 tumour cells
Figure 16:
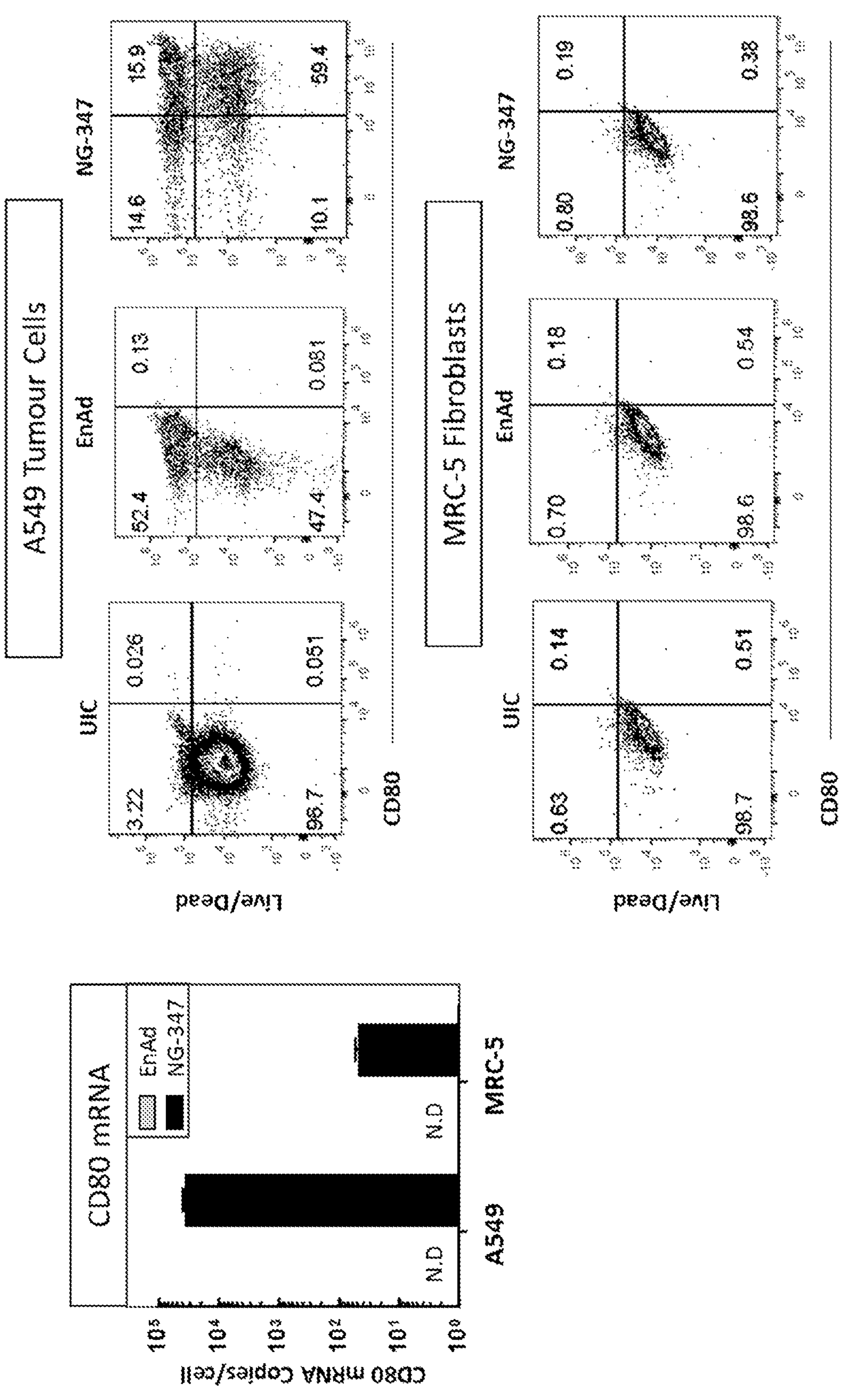
FIG. 16 shows CD80 transgene mRNA and CD80 transgene protein for virus NG-347 in MRC-5 fibroblast cells compared to A549 tumour cells.

NG-347 and NG-348 virus particle-mediated activation of innate immune cells (monocytes, DCs) in the PBMC cultures were similar to those of EnAd, as shown in FIGS. 15 and 16 for downregulation of CD14 expression and upregulation of HLA-DR and endogenous cell surface CD80, as well as secretion of MIP1α and IFNα (note that despite NG-347 encoding both of these molecules in its genome there was no increase in production levels over those for EnAd and NG-348 which do not encode the transgenes).

Example 11

This example is similar in design to experiments in examples 9 and 22 10 in these studies, the human PBMCs or purified T-cells were co-cultured with virus pre-treated (48 hours) A549 tumour cells or MRC5 fibroblasts. A549 or MRC5 cells were treated with 10 ppc of EnAd, NG-347, NG-348 or left untreated (UTC) and cultured for 48 hours to allow sufficient time for virus replication and any transgene expression. PBMCs or T-cells were then added to the cultures and left for 24 or 48 hours to evaluate the ability of virus treated cells to activate T-cells.

Figure 17:
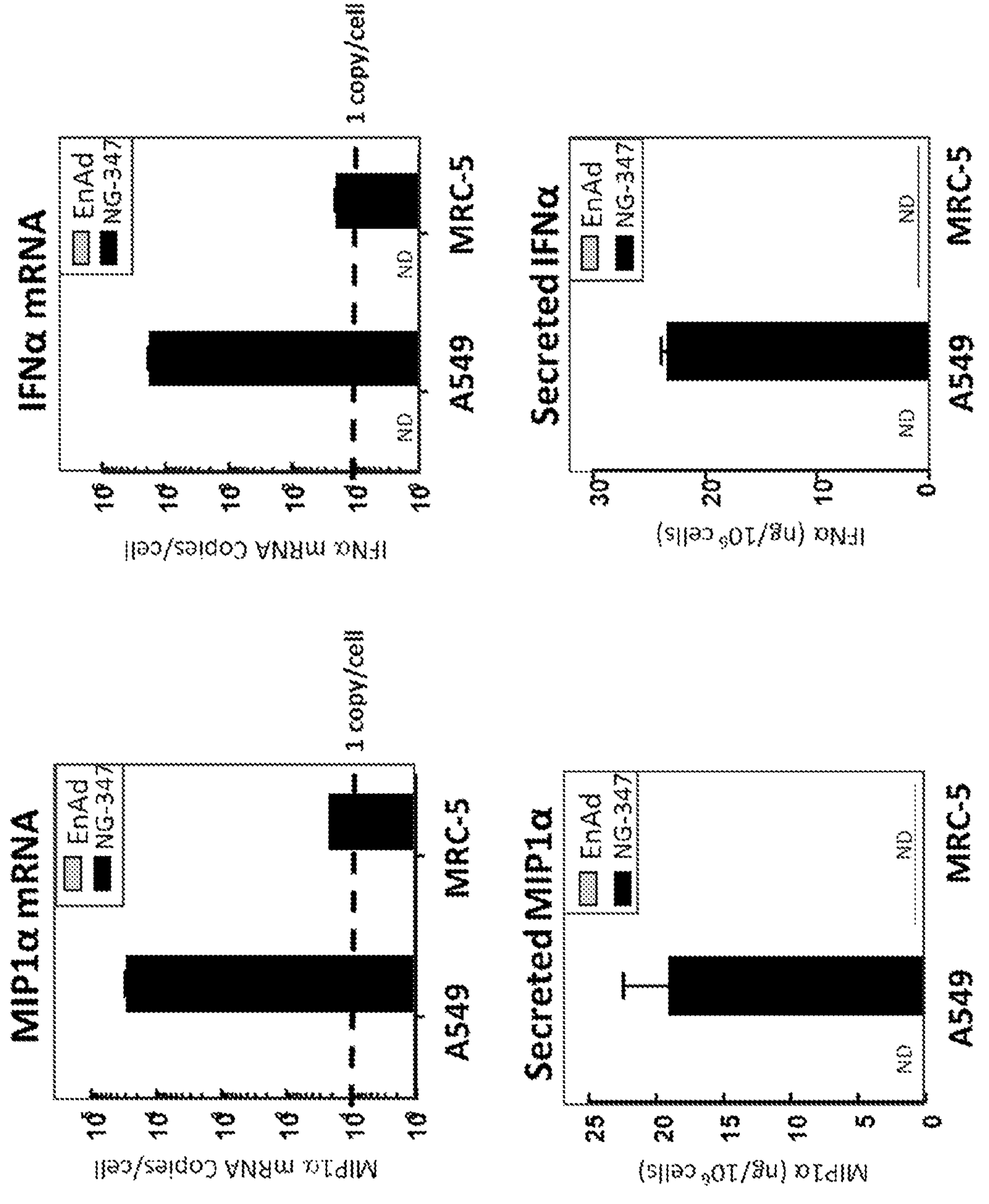
FIG. 17 shows mRNA and secreted protein levels of MIP1α and IFNα generated by virus NG-347 in MRC-5 fibroblast cells compared to A549 tumour cells.

FIG. 17 shows virus genome replication data showing comparable replication of the three viruses in PBMC or T-cell co-cultures with both cell types, replication levels being high with A549 tumour cells and low with MRC5 fibroblasts.

T-cell activation as measured by upregulation of CD25 surface expression and CD8 effector T-cell degranulation, as measured by upregulation of CD107a on the cell surface, and IFNγ production measured by intracellular cytokine staining were all selectively stimulated by NG-348 treated A549 cells compared to EnAd, with no stimulation mediated with MRC co-cultures.

Flow Cytometry Analyses of Activation of Human $CD3^+$ T-Cells in T-Cell and PBMC Co-Cultures with Viruses

| Cells | Treatment | % $CD25^+$ | % $CD8^+CD107a^+$ | % IFN [illegible] |
|---|---|---|---|---|
| A549 + T-cells | Untreated | 37.5 | 0.1 | 0.1 |
| A549 + T-cells | EnAd | 38.4 | 0.1 | 0.2 |
| A549 + T-cells | NG-348 | 88.2 | 17.9 | 12.0 |
| MRC5 + T-cells | Untreated | 38.8 | 0.3 | 0.4 |
| MRC5 + T-cells | EnAd | 38.9 | 0.2 | 0.4 |
| MRC5 + T-cells | NG-348 | 39.1 | 0.3 | 0.3 |
| A549 + PBMCs | Untreated | 28.3 | ND | ND |
| A549 + PBMCs | EnAd | 29.4 | ND | ND |
| A549 + PBMCs | NG-348 | 73.7 | ND | ND |
| MRC5 + PBMCs | Untreated | 23.0 | ND | ND |
| MRC5 + PBMCs | EnAd | 23.3 | ND | ND |
| MRC5 + PBMCs | NG-348 | 21.7 | ND | ND |

ND = Not determined

Figure 28:
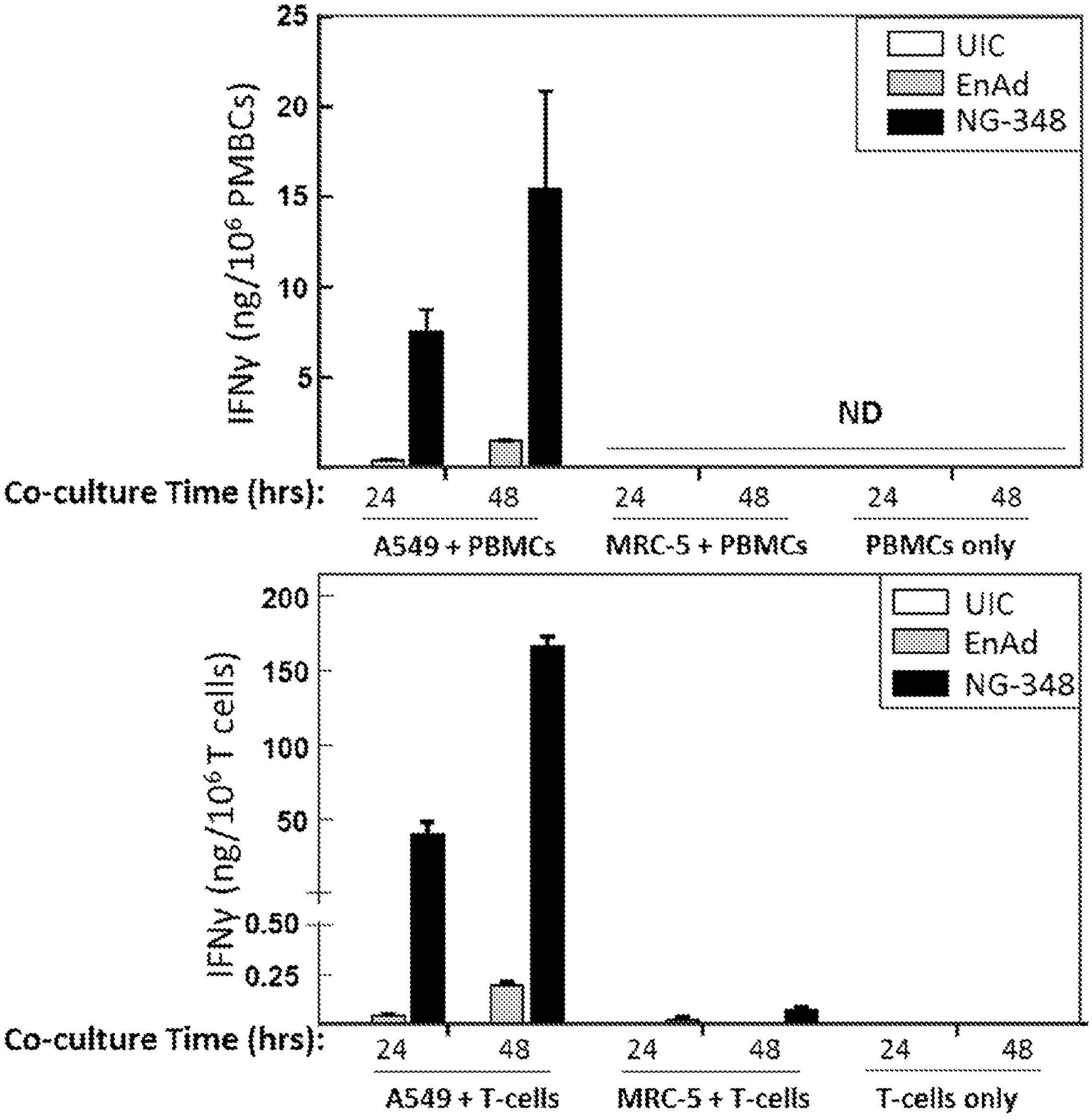
FIG. 28 shows INFγ secreted by PBMCs or T-cells co-cultured with MRC-5 fibroblast cells compared to A549 tumour cells, and treated with EnAd or virus NG-348.

IFNγ secretion into co-culture supernatants was also quantified by ELISA. The data (FIG. 28) similarly demonstrate selective activation of T-cells co-cultured with NG-348 treated A549 tumour cells not MRC5 fibroblasts, with either purified T-cells or PBMCs used in the assays.

Ability of NG-347 to activate T-cells was also assessed by measuring CD69 levels on T-cells from co-cultures of either purified T-cells or PBMCs with A549 tumour cells or MRC5 fibroblasts. As shown in Table 8, a small enhancement in CD69 positive T-cells was seen with NG-347 treatment of A549 tumour cells compared to EnAd, which itself leads to upregulation of this early activation marker. These effects were not seen in MRC5 co-cultures. No CD80 expression was detected on the T-cells (not shown).

CD69 Expression on T-Cells from NG-347 or EnAd Treated Cocultures

| Cells | Treatment | % CD69+ |
|---|---|---|
| A549 + T-cells | Untreated | 2.1 |
| A549 + T-cells | EnAd | 18.7 |
| A549 + T-cells | NG-348 | 35.0 |
| MRC5 + T-cells | Untreated | 3.8 |
| MRC5 + T-cells | EnAd | 3.6 |
| MRC5 + T-cells | NG-348 | 4.4 |
| A549 + PBMCs | Untreated | 1.2 |
| A549 + PBMCs | EnAd | 19.1 |
| A549 + PBMCs | NG-348 | 28.7 |
| MRC5 + PBMCs | Untreated | 2.6 |
| MRC5 + PBMCs | EnAd | 2.7 |
| MRC5 + PBMCs | NG-348 | 3.9 |

Figure 41:
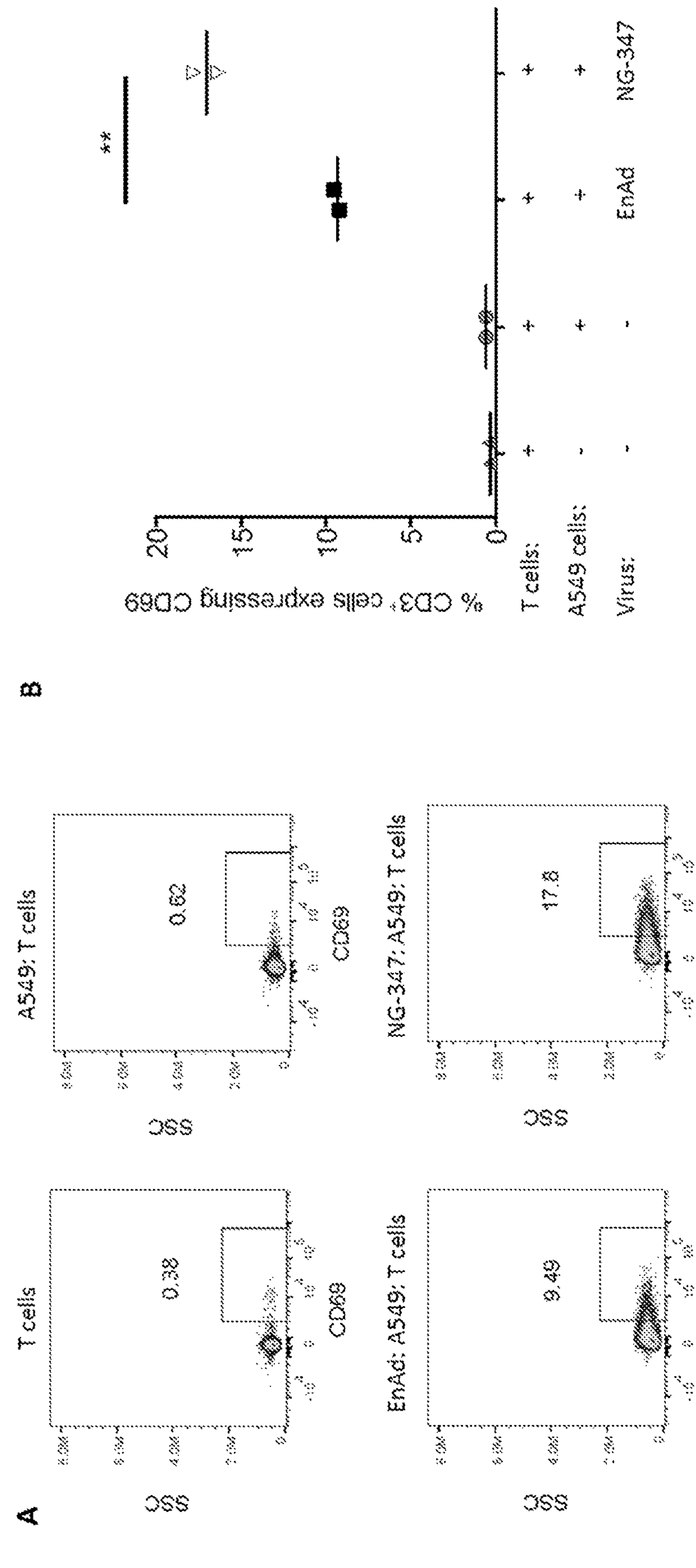
FIG. 41 shows CD69 is upregulated on more human $CD3^+$ T-cells following co-culture with NG-347 infected A549 cells than when infection was with EnAd
Figure 42:
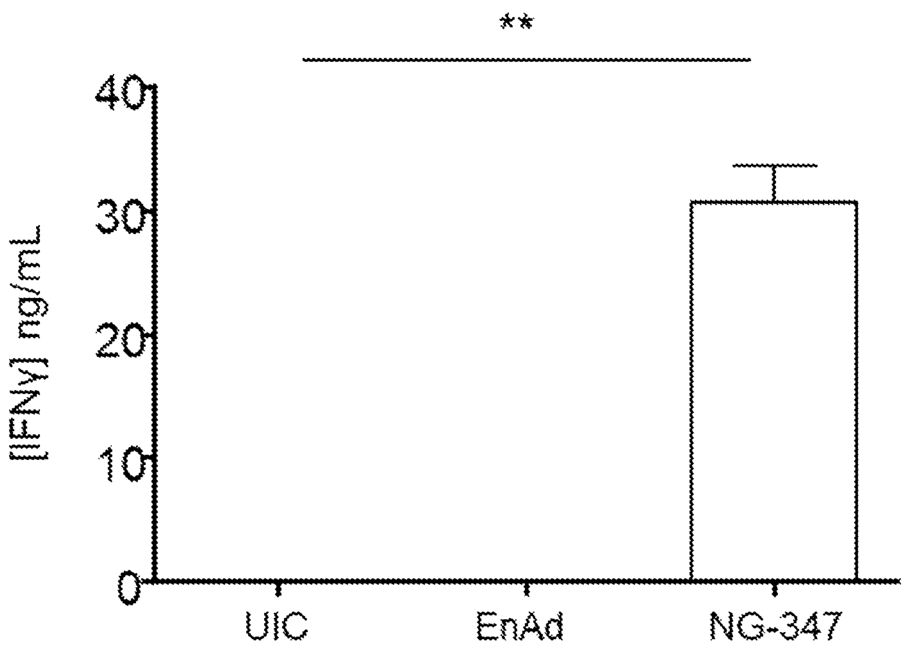
FIG. 42 shows induction of IFNγ production by human $CD3^+$ T cells following co-culture with NG-347 infected A549 cells, but not when infection was with EnAd

In a separate experiment, A549 cells treated with NG-347 and co-cultured with human CD3+ T-cells led to upregulation of CD69 activation marker on the T-cells and secretion of IFNγ (see FIGS. 41 & 42).

Example 12

Figure 29:
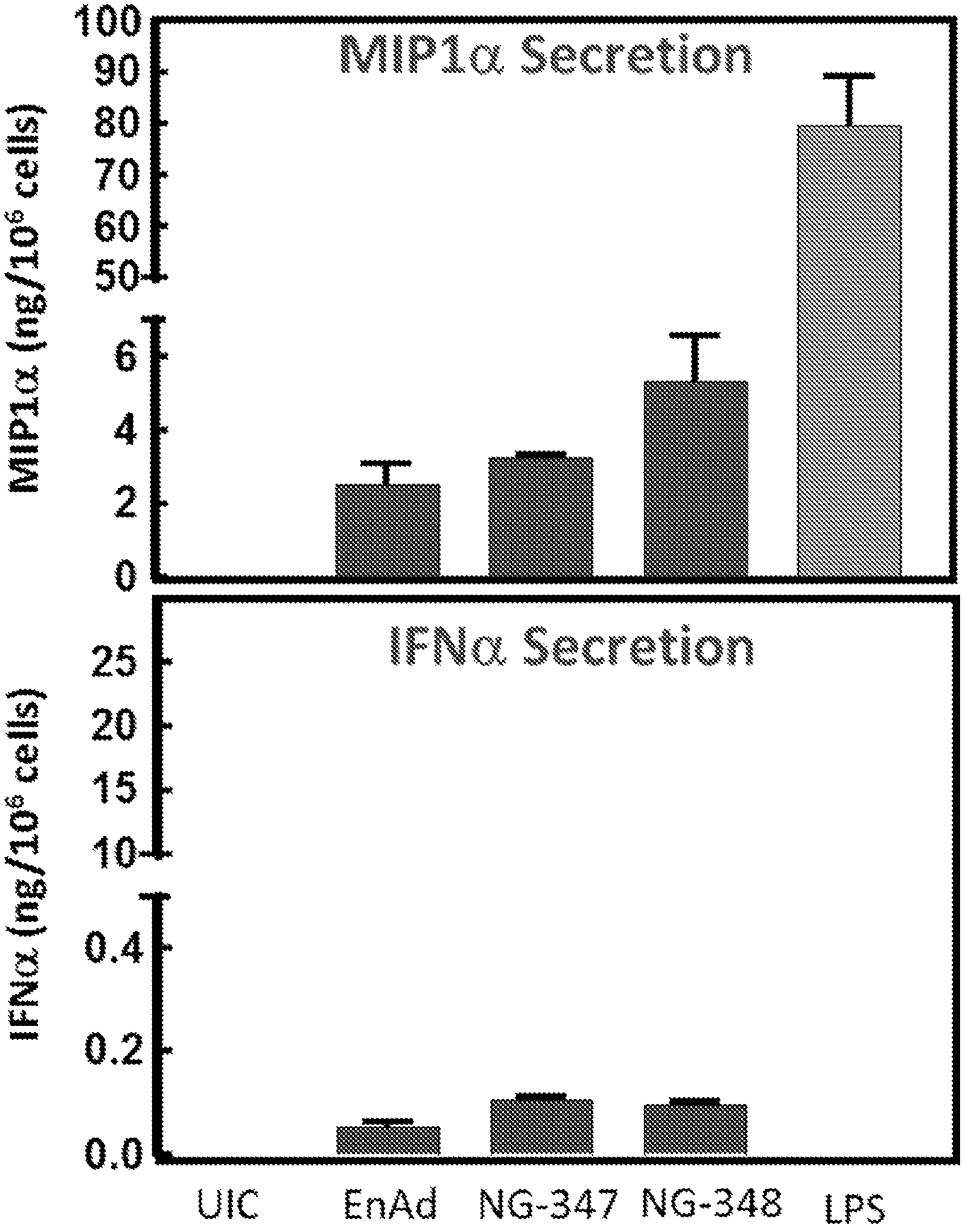
FIG. 29 shows MIP1α and IFNα secreted by human dendritic cells treated with EnAd, NG-347 or NG-348 virus particles
Figure 30:
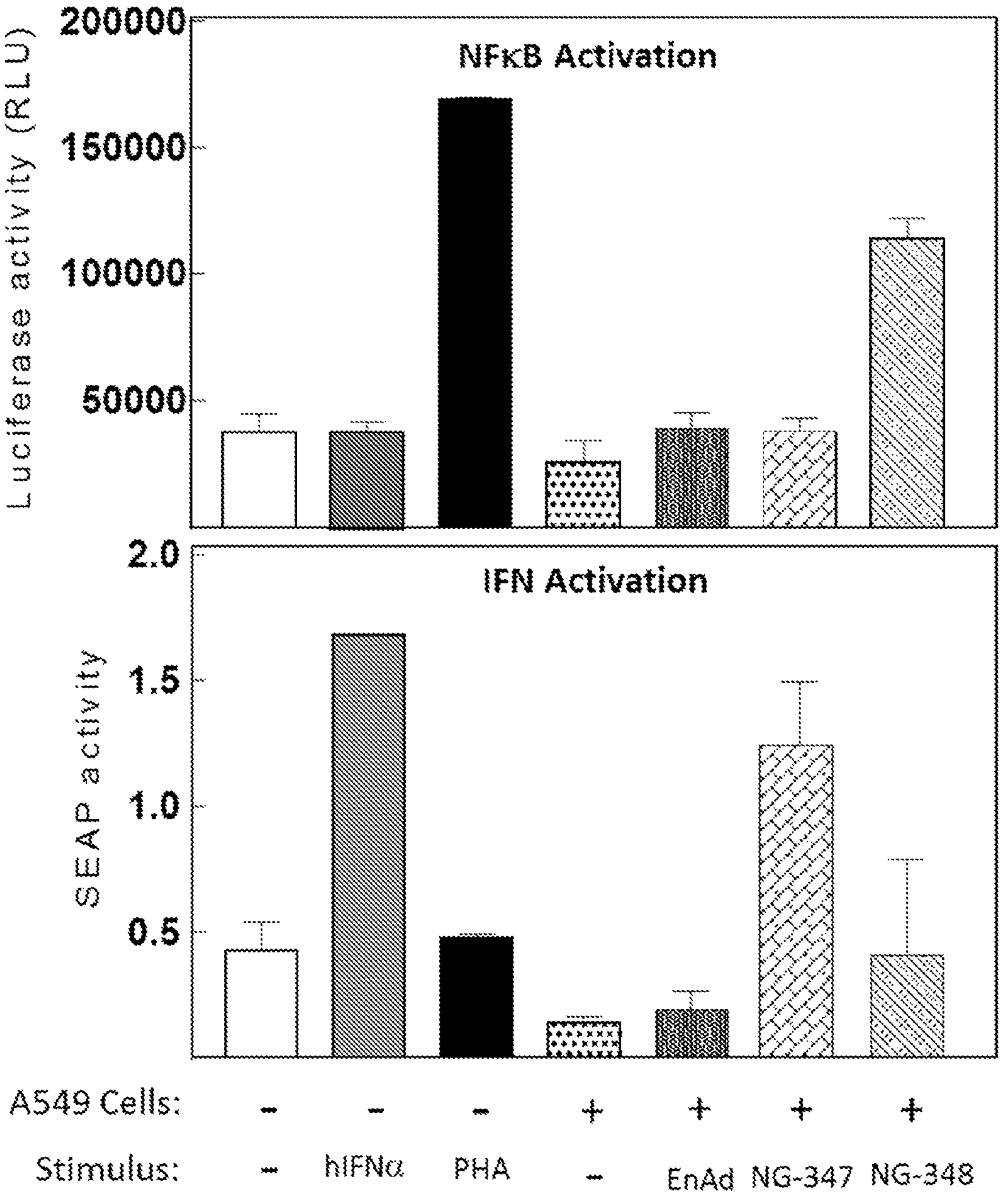
FIG. 30 shows NFκB and IFN reporter gene activation in JurkatDual reporter T-cells co-cultured with EnAd, NG-347 or NG-348 infected A549 tumour cells

CD14+ monocytic cells were isolated from PBMCs by antibody coated magnetic bead separation and cultured with human IL-4 and GM-CSF to differentiate them into dendritic cells. After 3 days of culture, the cells were treated with EnAd, NG-347 or NG-348 at 5000 ppc or left untreated. As a positive activation control, some cells were stimulated with LPS. Two days later supernatants were taken for cytokine ELISAs and cells were stained for surface activation marker expression and analysed by flow cytometry. As shown in table 9, all viruses induced upregulation of the costimulatory molecules CD80 and CD86, indicating that this previously identified particle-mediated innate immune cell activation effect was not altered by the transgene incorporation into the genomes of NG-347 and NG-348. All viruses also stimulated secretion of similar levels of MIP1α and IFNα (FIG. 29).

Particle-Mediated Activation of Human Dendritic Cells by EnAd, NG-347 and NG-348

| DC treatment | % $CD80^+$ | % $CD86^+$ |
|---|---|---|
| Untreated | 3.0 | 10.4 |
| EnAd | 81.6 | 99.3 |
| NG-347 | 82.1 | 99.4 |
| NG-348 | 62.5 | 99.5 |
| LPS positive control | 97.5 | 98.5 |

Example 13

Figure 31:
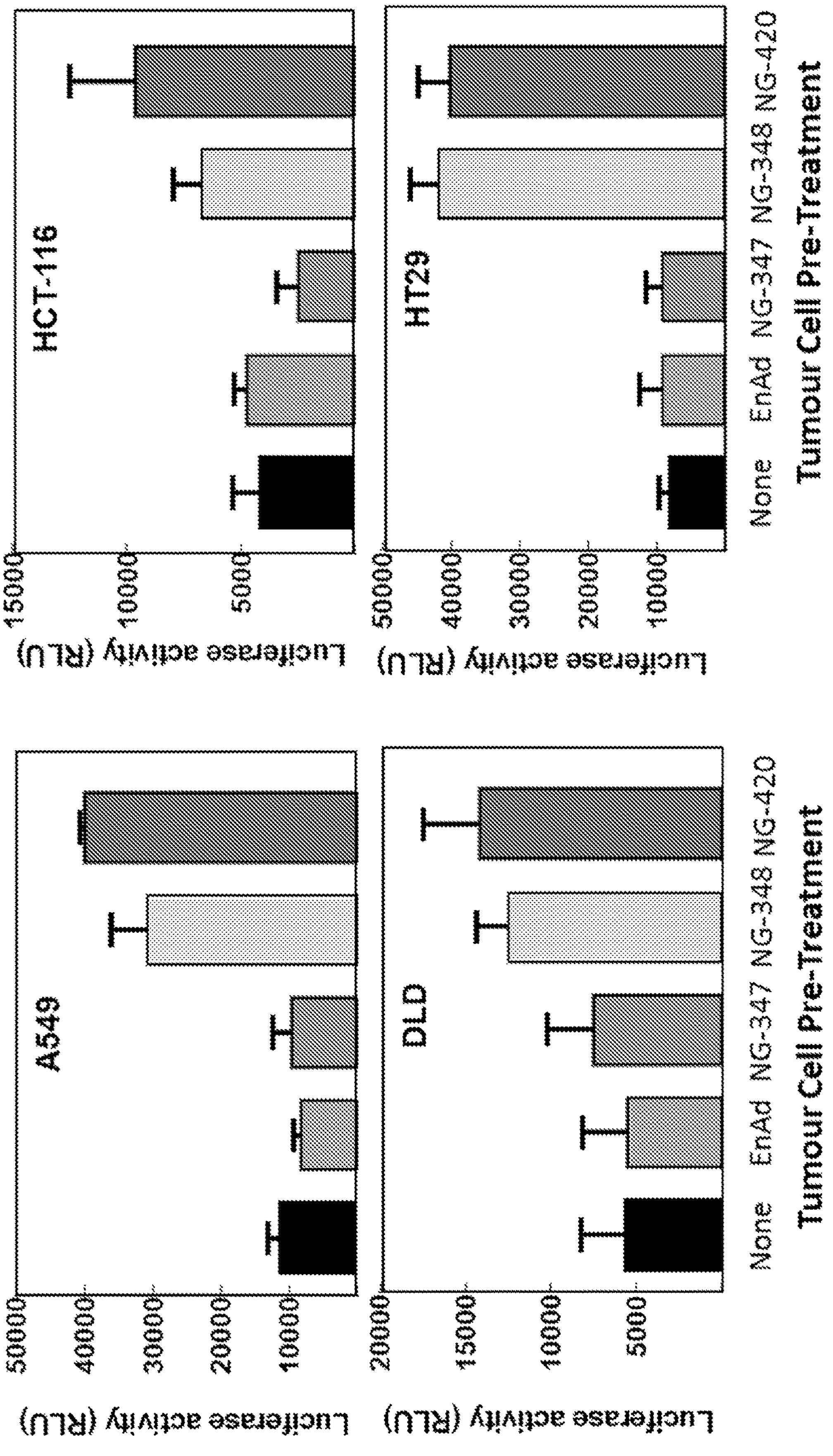
FIG. 31 shows NF-κB-luciferase reporter activity generated by JurkatDual reporter T-cells co-cultured with EnAd, NG-347, NG-348 or NG-420 treated A549 HCT-116, DLD and HT29 tumour cells

In a set of experiments, JurkatDual cells were used in co-cultures with tumour cells as a T-cell activation reporter assay for assessing functionality of transgene expression by NG-347, NG-348 and NG-420 viruses, with EnAd serving as a negative control. JurkatDual cells stably express two different reporter genes: an NFκB reporter gene producing a secreted form of luciferase which is responsive to signalling via the T-cell receptor complex and an IFNα-responsive secreted alkaline phosphatase (SEAP) reporter gene. A549 cells were pre-cultured with viruses at '10 ppc for two days, and then JurkatDual cells were added for overnight co-culture (18-24h) and then supernatants collected for assay of luciferase and SEAP activities. As shown in FIG. 43, NG-347 infected A549 cells selectively induced SEAP production, which aligns with their production of IFNα (see FIG. 7) but did not induce luciferase activity. In contrast, NG-348 which expresses the membrane anti-CD3-ScFv to activate the T-cell receptor complex induced luciferase but not SEAP. In another experiment A549 lung carcinoma cells and HCT-116, HT-29 & DLD colon carcinoma cells were pre-cultured for 48 hours with 10 ppc of EnAd, NG-347, NG-348 or NG-420 viruses before co-culturing with JurkatDual cells overnight, with supernatants tested for levels of luciferase to indicate level of activation induced. As shown in FIG. 31, all four tumour cell types cultured with NG-348 or NG-420 viruses, which encode cell surface anti-CD3-ScFv, activated the JurkatDual cells whereas EnAd and NG-347 did not, with levels of luciferase similar to that of uninfected tumour cell controls (UIC).

Figure 32:
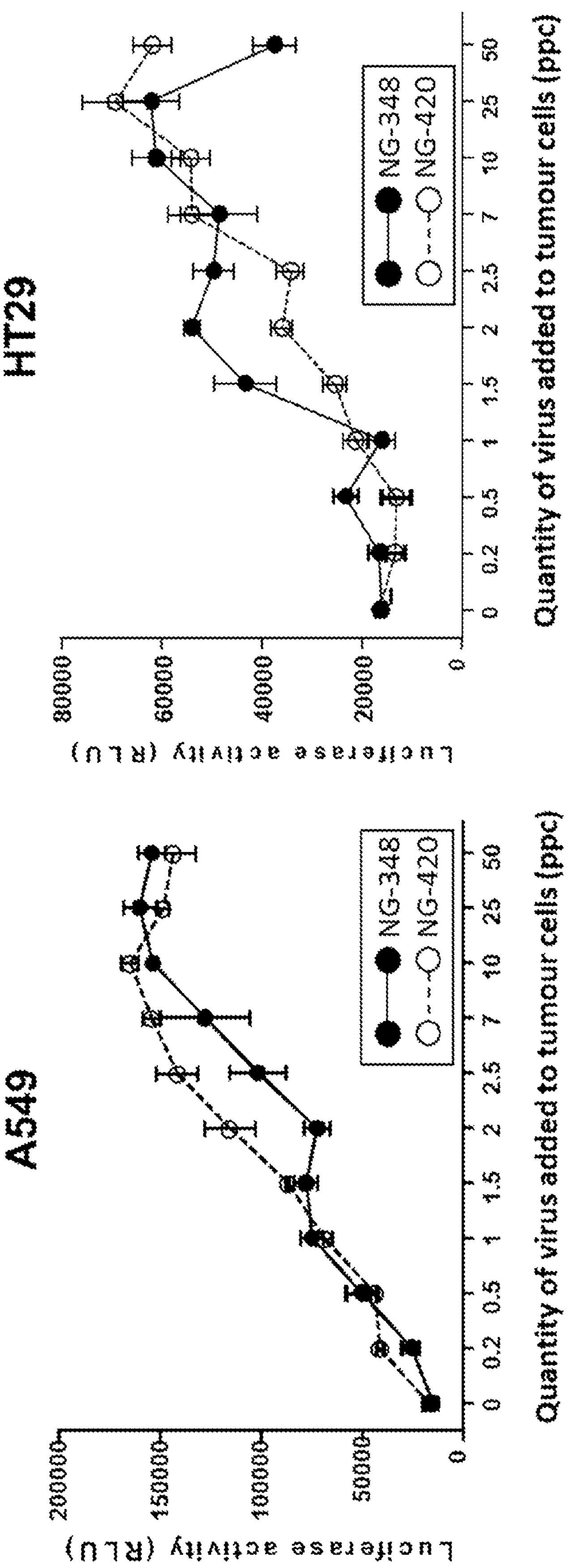
FIG. 32 shows NF-κB-luciferase reporter activity generated by JurkatDual cells co-cultured with either A549 or HT29 tumour cells infected with virus NG-348 and virus NG-420 as a function of virus particles added

In another experiment, A549 or HT-29 tumour cells were pre-cultured with different amounts of either NG-348 or NG-420 before adding the JurkatDual cells and measuring their luciferase secretion. The data in FIG. 32 show that activation of the NFκB activity in JurkatDual cells is dependent on the dose of virus used to treat the tumour cells with.

Example 14

Figure 33:
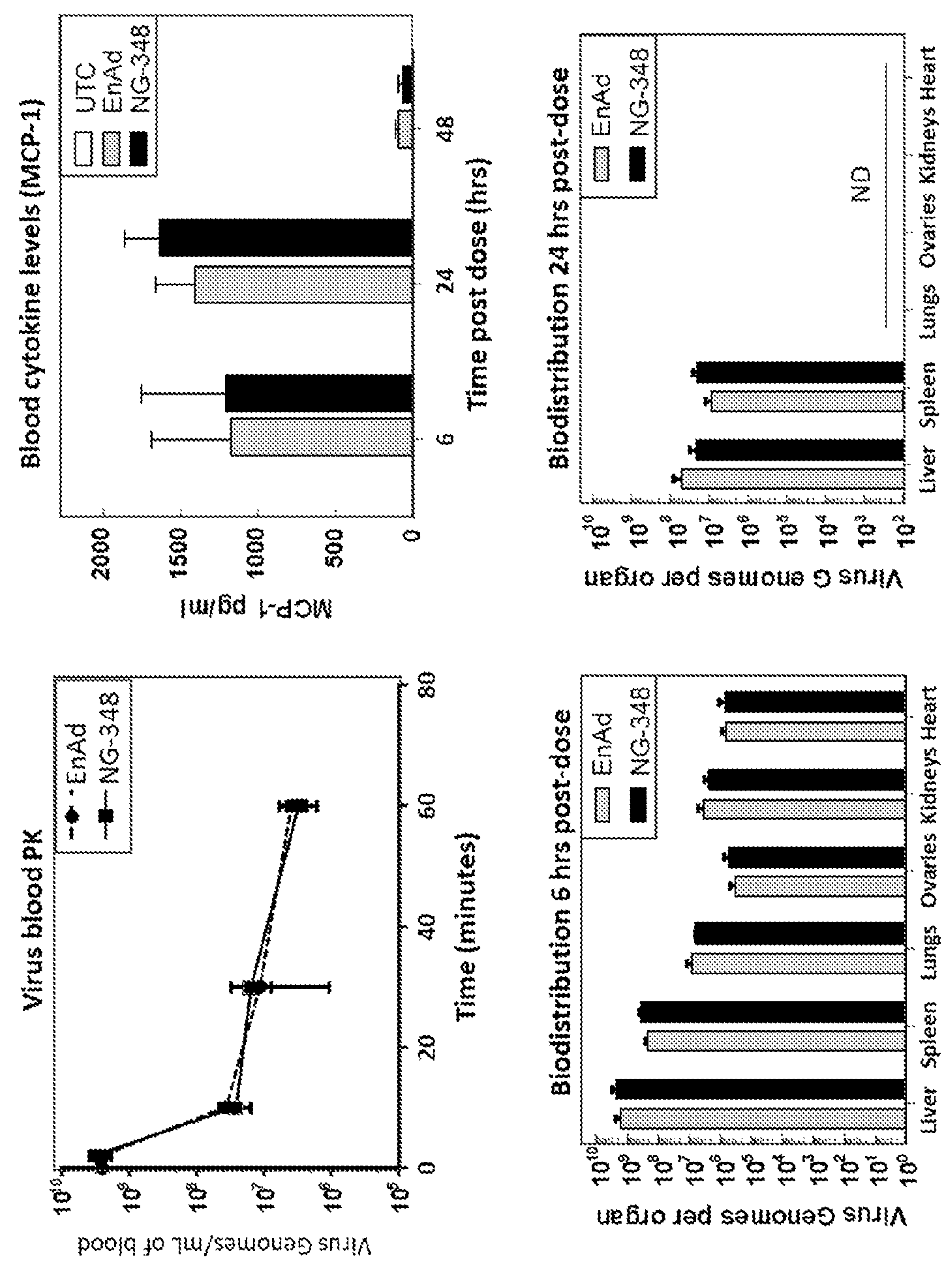
FIG. 33 shows the pharmacokinetics of EnAd and virus NG-348 in blood; blood cytokine levels after exposure to EnAd or virus NG-348; tissue biodistribution of EnAd or NG-348 viruses 6 or 24 hours after IV administration to CD1 mice

The in vivo pharmacokinetic, biodistribution and particle-mediated systemic cytokine induction activities of EnAd and NG-348 following IV dosing in immunocompetent CD1 mice were compared, Mice were dosed intravenously with $5\times10^9$ particles of either EnAd or NG-348 and bled 2, 10, 30, 60 and 120 minutes post dosing. Whole blood was DNA extracted and analysed by qPCR for levels of virus genome (FIG. 33). Clearance of both viruses from the blood followed similar kinetics. Similarly, the induction of MCP-1 cytokine response (a measure of particle-mediated activation of innate immune such as liver Kupffer cells) was also similar for both viruses, as were the tissue biodistribution patterns (FIG. 33).

Example 15

Figure 34:
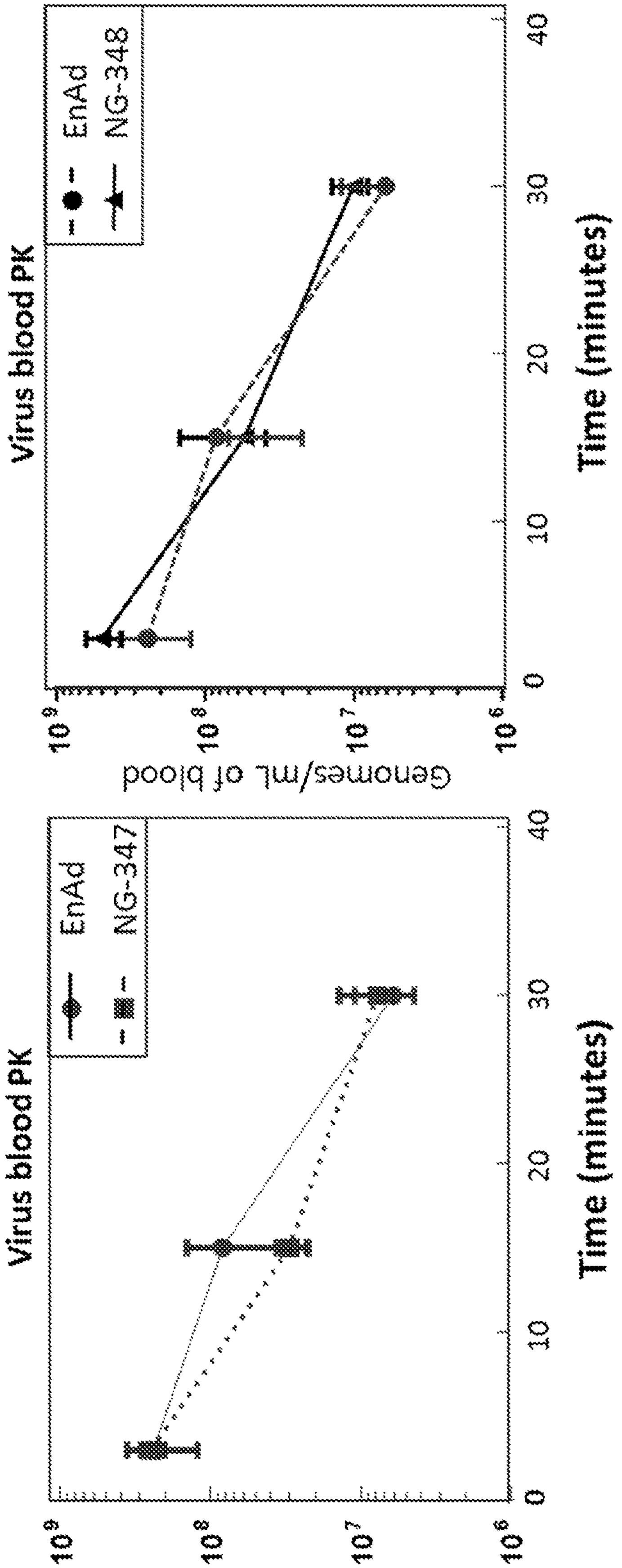
FIG. 34 shows the pharmacokinetics in blood of EnAd, NG-347 and NG-348 viruses following IV administration to CB17-SCID mice bearing a subcutaenous HCT-116 tumour xenograft.
Figure 35:
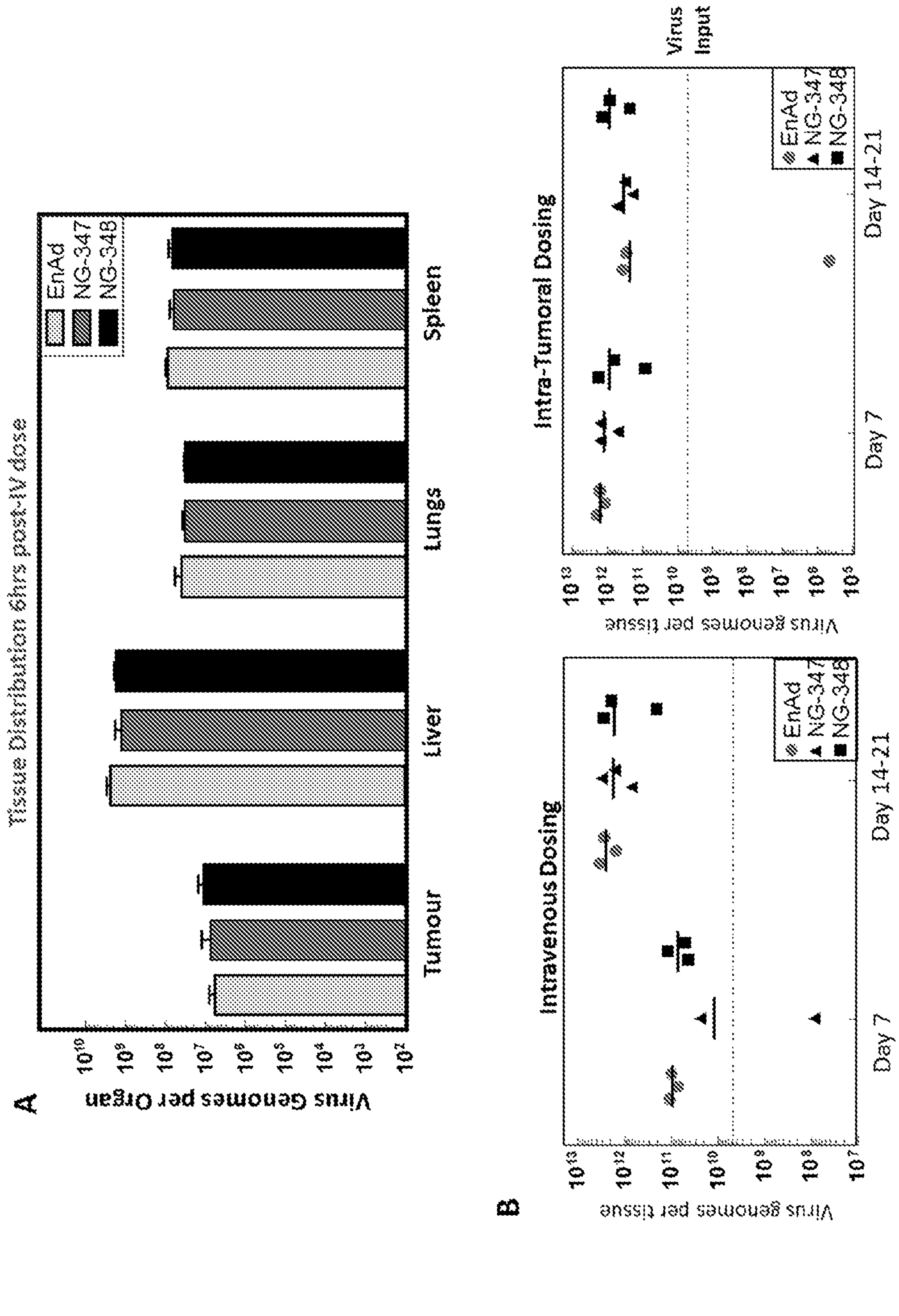
FIG. 35 shows the tissue distribution of EnAd, NG-347 and NG-348 viruses 6 hours post intravenous dosing in tumour-bearing CB17-SCID mice, and virus genomes in HCT-116 tumour xenografts at day 7 and day 14-21 following intravenous or intra-tumoral dosing of EnAd, NG-347 and NG-348

CB17 SCID mice were implanted subcutaneously with HCT116 cells and injected intratumourally (IT) or intravenously (IV) with EnAd, NG-347 or NG-348 viruses ($5\times10^9$ virus particles), or control, once tumours were greater than 70 $mm^3$. For the IV dosed mice, blood samples were taken from three mice from each group 3, 15 and 30 minutes after IV dosing, DNA extracted and the level of virus genomes in the blood assessed by qPCR (pharmacokinetics [PK] analysis). Data (FIG. 34) show that NG-347 and NG-348 have similar PK to EnAd (and to each other). After 6 hours, tumours, livers, lungs and spleens were resected from 3 mice from each group. Homogenised tissues were DNA extracted and analysed for level of virus genomes by qPCR (biodistribution analysis). Data (FIG. 35, panel A) show similar tissue biodistribution for the three viruses. After 7 days or 14-21 days, tumours were excised from three mice from each group and homogenized to produce a tumour lysate which was used to prepare both DNA and RNA. Level of virus genomes in the tumours at the two time points were measured by qPCR analyses of the extracted DNA. Data (FIG. 35, panel B) show that tumours from both IV and IT dosed mice have levels of virus genomes higher than the amount of virus dosed, indicating virus replication in the tissue, with IT dosing giving higher genome levels than IV at day 7, but both being similarly high at the 14-21 day timeframe. All three viruses replicated to similar levels.

Figure 36:
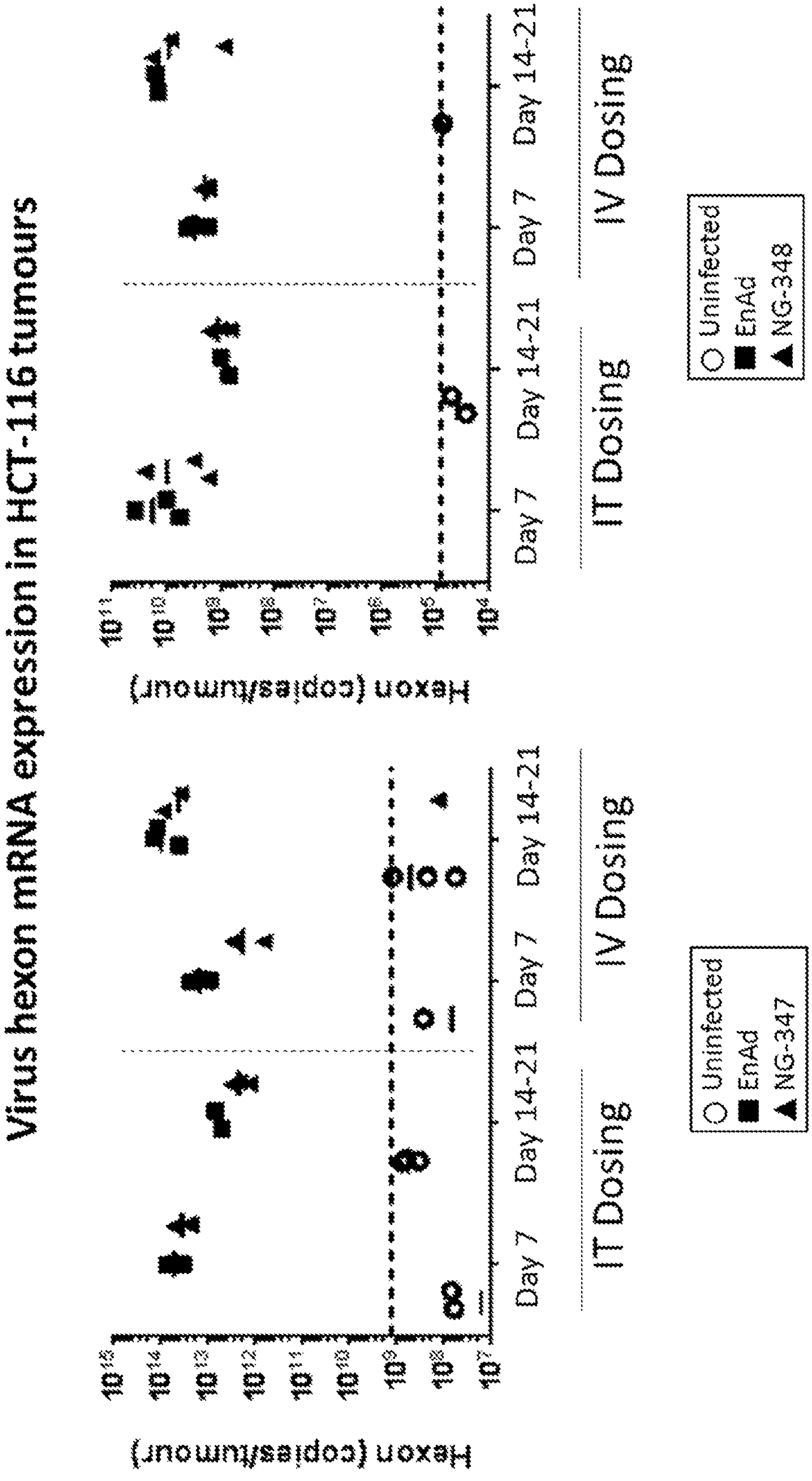
FIG. 36 shows virus hexon mRNA generated in HCT-116 tumour xenografts by EnAd, NG-347 or NG-348 viruses on day 7 or 14-21 following intravenous or intra-tumoral dosing
Figure 37:
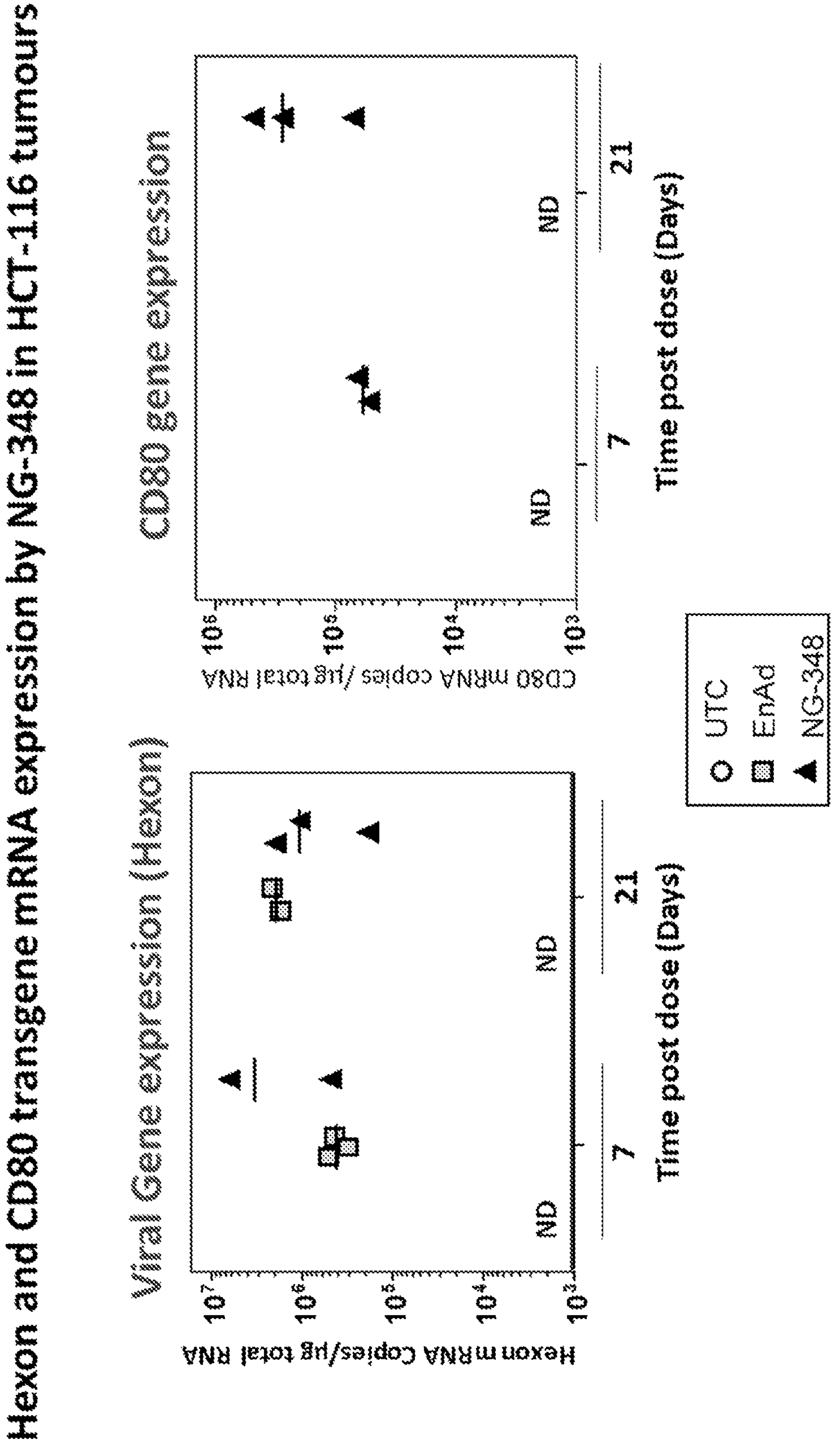
FIG. 37 shows mRNA levels for hexon and CD80 transgene in HCT-116 tumour xenografts 7 or 21 days following intravenous dosing with virus NG-348
Figure 38:
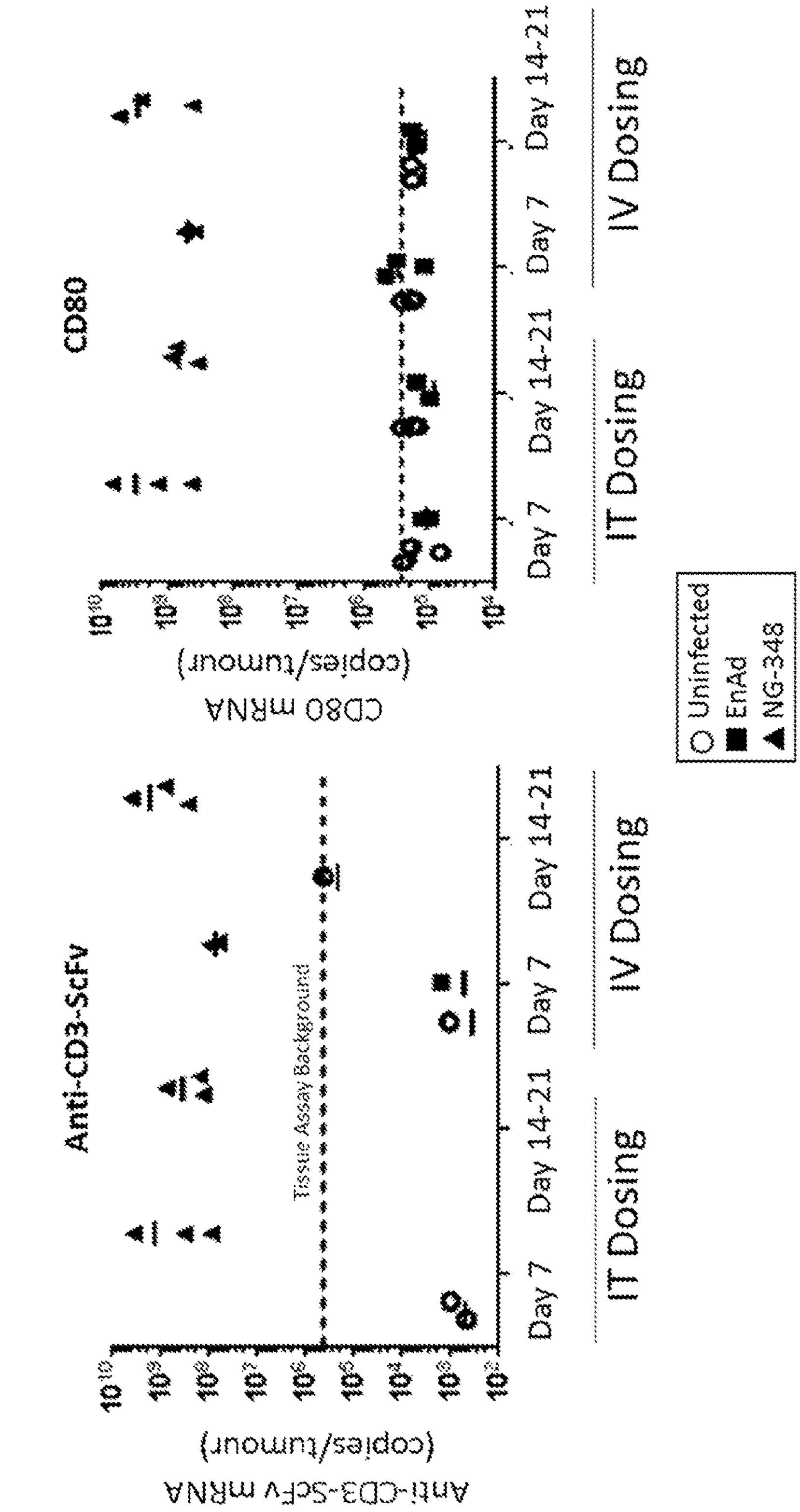
FIG. 38 shows mRNA levels for a transgenes encoding anti-CD3 scFv and CD80 in HCT-116 tumour xenografts 7 or 14-21 days following IV dosing with virus NG-348
Figure 39:
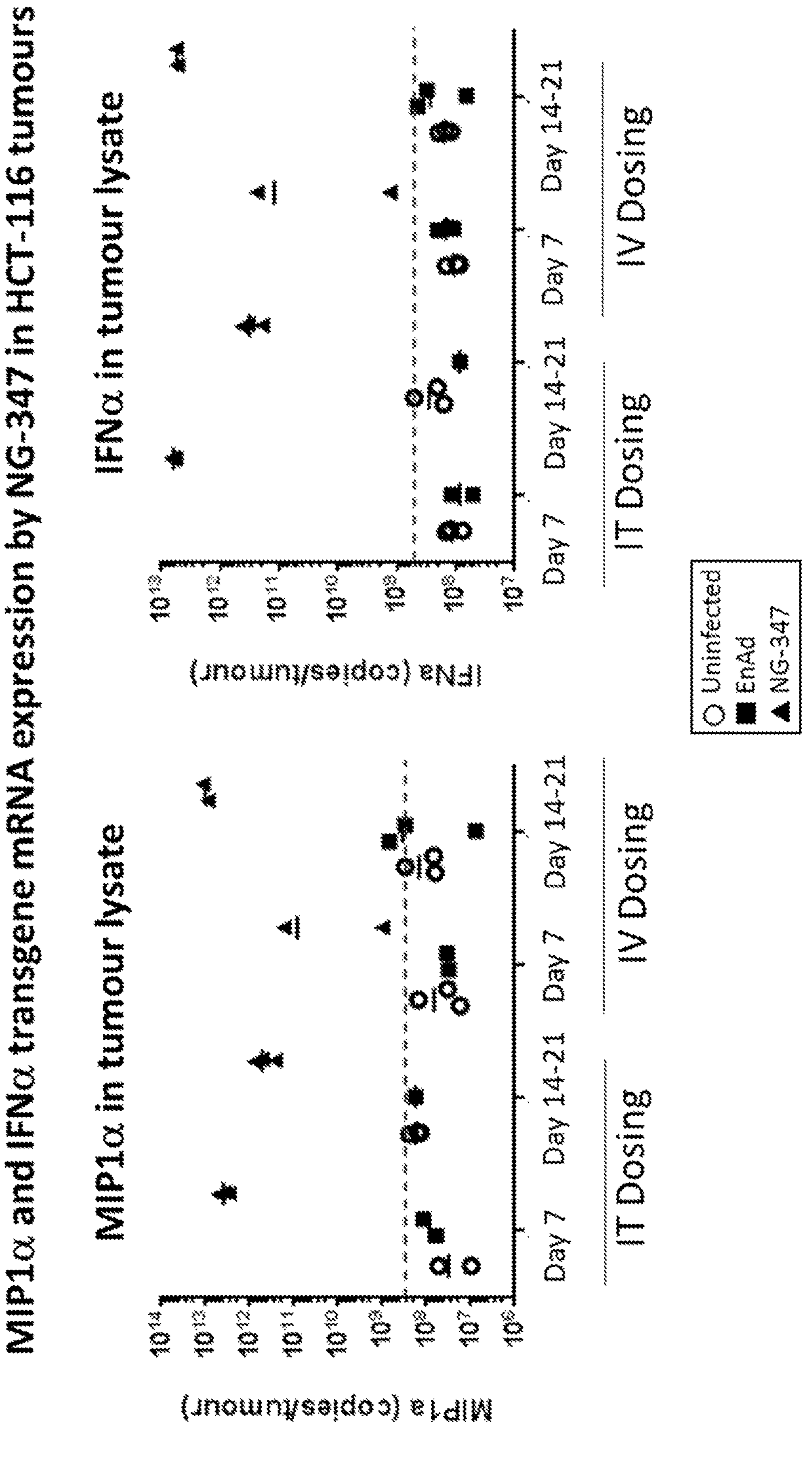
FIG. 39 shows mRNA levels of MIP1α and IFNα transgenes in HCT-116 tumour xenografts 7 or 14-21 days following intravenous dosing with virus NG-347

Similarly, levels of virus hexon mRNA in tumour lysates detected by RT-qPCR were comparable between EnAd, NG-347 and NG-348 at both time points tested (FIGS. 36 and 37). Similar levels of anti-CD3-ScFv and CD80 mRNA were detected at both time points and both dosing routes for NG-348 treatment, with only assay background readings with EnAd dosing (FIGS. 37 & 38). MIP1α and IFNα mRNA levels were also selectively detected following NG-347 dosing, either IT or IV (FIG. 39).

Figure 40:
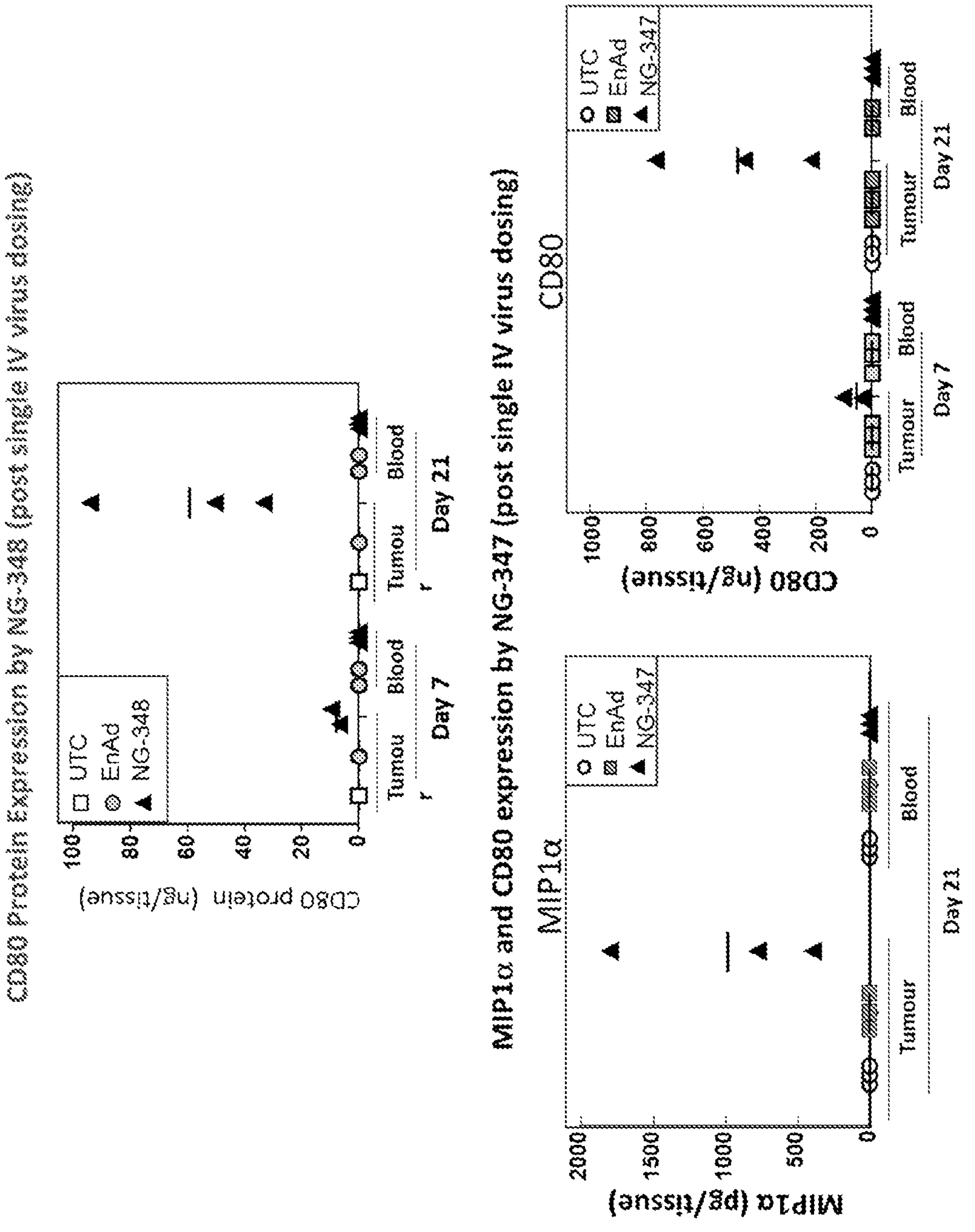
FIG. 40 shows CD80 protein expression in HCT-116 tumour xenografts 7 and 21 days following an intravenous dose of virus NG-348; and shows MIP1α and CD80 protein expression in HCT-116 tumours following an intravenous dose of virus NG-347.

Levels of CD80 protein encoded by both NG-347 and NG-348, and MIP1α protein encoded by NG-347 were measured in tumour lysates using specific ELISAs. The data in FIG. 40 show that following the single IV virus dose, both proteins could also be detected selectively in tumour extracts. Neither protein was detected in blood samples from the same mice.

Example 16

To evaluate the activity and tumour cell dependency of NG-348 virus in vivo, different combination of human PBMCs ($5\times10^7$ cells), A549 human tumour cells ($5\times10^6$) and either EnAd or NG-348 (at $5\times10^9$ ppc) were injected into the peritoneum of immunodeficient SCID-beige mice, with viruses or control (saline) being dosed within 15 minutes after injection of the cells. After 3 days, the peritoneal cavity was lavaged with 5 mL of saline and recovered cells were analysed by flow cytometric analyses with a panel of T-cell activation markers (CD25, CD69 and HLA-DR) to assess levels of T-cell activation, following gating on the $CD3^+$ T-cell population. Data from two separate experiments demonstrate that NG-348 selectively leads to human T-cell activation in vivo in a tumour cell dependent manner.

In Vivo Activation of Human T-Cells in A549 Tumour Bearing Mice by NG-348

| Group | Virus | Tumour | N | % $CD25^+$ | % $CD69^+$ | % $DR^+$ | % $CD25^+$, $CD69^+$ | % $CD25^+$, $DR^+$ |
|---|---|---|---|---|---|---|---|---|
| Experiment 1 | | | | | | | | |
| 1 | EnAd | Saline | 2 | 1.9 | 1.6 | 7.7 | 0.2 | 0.3 |
| | | | | 2.3 | 3.0 | 9.1 | 0.5 | 0.6 |
| 2 | EnAd | $5\times10^6$ | 2 | 4.2 | 6.2 | 8.4 | 0.8 | 1.4 |
| | | A549 cells | | 2.9 | 5.5 | 8.4 | 0.3 | 0.4 |

-continued

| Group | Virus | Tumour | N | % CD25+ | % CD69+ | % DR+ | % CD25+, CD69+ | % CD25+, DR+ |
|---|---|---|---|---|---|---|---|---|
| 3 | NG-348 | Saline | 1 | 3.4 | 2.6 | 9.2 | 0.5 | 0.8 |
| 4 | NG-348 | 5 x $10^6$ | 2 | 35.8, | 50.4 | 26.3 | 22.4 | 16.4 |
| | | A549 cells | | 36.6 | 42.2 | 19.2 | 18.0 | 12.2 |
| | | | | Experiment 2 | | | | |
| 1 | Saline | Saline | 1 | 25.6 | 37.3 | 14.8 | 14.1 | 7.08 |
| 2 | EnAd | Saline | 2 | 6.5 | 17.8 | 5.50 | 3.58 | 1.01 |
| | | | | 7.3 | 18.2 | 6.1 | 3.46 | 1.49 |
| 3 | NG-348 | Saline | 2 | 10.2 | 26.7, | 7.7 | 6.73 | 2.16 |
| | | | | 6.5 | 18.3 | 6.0 | 3.61 | 1.44 |
| 4 | Saline | 5 x $10^6$ | 2 | 28.4 | 54.4, | 13.3 | 22.3 | 8.54 |
| | | A549 cells | | 22.7 | 51.1 | 15.0 | 17.5 | 7.72 |
| 5 | EnAd | 5 x $10^6$ A549 cells | 1 | 13.2 | 29.4 | 5.1 | 7.84 | 1.62 |
| 6 | NG-348 | 5 x $10^6$ | 3 | 34.4 | 58.9, | 12.5 | 27.2 | 9.07 |
| | | A549 cells | | 29.6 | 59.2, | 9.8 | 23.3 | 7.5 |
| | | | | 56.4 | 85.0 | 17.0 | 52.7 | 14.2 |

The invention claimed is:

1. A replication capable group B oncolytic adenovirus selected from the group consisting of Ad 11 and enadenotucirev (EnAd), wherein the adenovirus comprises a transgene encoding an antibody or a binding fragment thereof for expression on the surface of a cancer cell, wherein said antibody or binding fragment is specific to a CD3 protein of a T-cell receptor complex (TCR), and the gene encoding said antibody or binding fragment is located between the adenoviral gene L5 and the gene E4, and the encoded antibody further comprises a transmembrane domain or a GPI anchor, wherein the transgene encoding the anti-CD3 antibody or binding fragment is under the control of the endogenous major late promoter of the adenovirus, wherein the adenovirus encodes at least one further transgene, wherein the further transgene(s) encode(s) a protein independently selected from a cytokine, a chemokine, an antagonistic antibody molecule or binding fragment thereof, an agonistic antibody molecule or binding fragment thereof, and combinations thereof, and said one or more further transgenes are between the gene E4 and the gene L5 under the control of the major late promoter of the adenovirus, and wherein the anti-CD3 antibody or binding fragment thereof and protein encoded by the further transgene are expressed independently anchored at the surface of the cancer cell, wherein the adenovirus does not encode a B7 protein or an active fragment thereof.

2. The adenovirus of claim 1, wherein the virus is Ad11.

3. The adenovirus according to claim 1, wherein the virus is EnAd.

4. The adenovirus of claim 1, wherein the virus is replication competent.

5. The adenovirus of claim 1, wherein the transmembrane domain is selected from a sequence comprising one of SEQ ID NOs: 10 to 15.

6. The adenovirus of claim 1, wherein the antibody or binding fragment is selected from a full-length antibody, a Fab, modified Fab, Fab', modified Fab', F(ab')2, Fv, single domain antibody, scFv, bi, tri or tetra-valent antibody, Bis-scFv, diabody, triabody, tetrabody, humabody, disulfide stabilised forms of any one of the same and epitope-binding fragments thereof.

7. The adenovirus of claim 1, wherein the antibody binding fragment is a single chain Fv.

8. The adenovirus of claim 1, wherein the further transgene or transgenes are independently selected from FLT-3 ligand, IFN-$\alpha$2, OX40, CD27, CD28, CD40, GITR, and 4-1 BB.

9. The adenovirus of claim 1, wherein the at least one further transgene encodes a cytokine.

10. The adenovirus of claim 1, wherein a second further transgene encodes a cytokine.

11. The adenovirus of claim 1, wherein the cytokine is independently selected from IL-2, IFN-alpha, IFN-beta, IFN-gamma, Flt3 ligand, GM-CSF, IL-15, and IL-12.

12. The adenovirus of claim 1, wherein the at least one further transgene encodes a chemokine.

13. The adenovirus of claim 12, wherein the chemokine is independently selected from MIP-1 alpha, RANTES, IL-8, CCL5, CCL17, CCL20, CCL22, CXCL9, CXCL10, CXCL11, CXCL13, CXCL12, CCL2, CCL19 and CCL21.

14. The adenovirus of claim 13, wherein the chemokine encoded is MIP-1 alpha.

15. The adenovirus of claim 14, wherein the adenovirus comprises transgenes encoding a cytokine and chemokine combination selected from i) MIP-1$\alpha$ and Flt3, and ii) MIP-1$\alpha$ and IFN$\alpha$.

16. The adenovirus of claim 1, wherein the anti-CD3 antibody or binding fragment has at least a binding domain comprising a VH and a VL region from muromonab-CD3 (OKT3), otelixizumab, teplizumab or visilizumab.

17. A composition comprising a replication capable group B oncolytic adenovirus of claim 1.

18. A method of treating a cancer patient comprising the step of: administering a therapeutically effective amount of a replication capable group B oncolytic adenovirus of claim 1, wherein the adenovirus selectively infects cancer cells and expresses on the surface of the cells the encoded anti-CD3 antibody or binding fragment thereof.

19. The method of claim 18, wherein the administration of the adenovirus results in in vivo stimulation of T cells to target the cancer cells.

* * * * *